(12) United States Patent
Sooknanan et al.

(10) Patent No.: US 8,540,988 B2
(45) Date of Patent: *Sep. 24, 2013

(54) ANTIBODIES THAT BIND POLYPEPTIDES INVOLVED IN THE PROCESS OF BONE REMODELING

(75) Inventors: Roy Rabindranauth Sooknanan, Beaconsfield (CA); Gilles Bernard Tremblay, La Prairie (CA); Mario Filion, Longueuil (CA)

(73) Assignee: Alethia Biotherapeutics Inc., Montreal, Quebec (CA)

( * ) Notice: Subject to any disclaimer, the term of this patent is extended or adjusted under 35 U.S.C. 154(b) by 0 days.

This patent is subject to a terminal disclaimer.

(21) Appl. No.: 13/152,205

(22) Filed: Jun. 2, 2011

(65) Prior Publication Data
US 2011/0311526 A1 Dec. 22, 2011

Related U.S. Application Data

(62) Division of application No. 12/279,054, filed as application No. PCT/CA2007/000210 on Feb. 13, 2007, now Pat. No. 7,989,160.

(60) Provisional application No. 60/772,585, filed on Feb. 13, 2006, provisional application No. 60/816,858, filed on Jun. 28, 2006.

(51) Int. Cl.
*A61K 39/00* (2006.01)
*A61K 39/395* (2006.01)
*C07K 16/00* (2006.01)
*C07K 16/18* (2006.01)
*C07K 16/22* (2006.01)

(52) U.S. Cl.
USPC .................. 424/130.1; 424/133.1; 424/135.1; 424/139.1; 424/141.1; 424/142.1; 424/145.1; 530/387.1; 530/387.3; 530/387.9; 530/388.1; 530/388.15; 530/388.24; 530/389.1; 530/389.2

(58) Field of Classification Search
None
See application file for complete search history.

(56) References Cited

U.S. PATENT DOCUMENTS

| | | | |
|---|---|---|---|
| 5,712,127 A | 1/1998 | Malek et al. | |
| 6,057,098 A | 5/2000 | Buechler et al. | |
| 6,451,555 B1 | 9/2002 | Duffy | |
| 6,498,024 B1 | 12/2002 | Malek et al. | |
| 6,617,434 B1 | 9/2003 | Duffy | |
| 7,357,929 B2 | 4/2008 | Carmeliet et al. | |
| 7,402,664 B2 | 7/2008 | Wolfgang et al. | |
| 7,407,940 B2 | 8/2008 | Falla et al. | |
| 7,411,051 B2 | 8/2008 | Rosen et al. | |
| 7,417,112 B2 | 8/2008 | Rathore et al. | |
| 7,425,612 B2 | 9/2008 | Nakamura et al. | |
| 7,432,065 B2 | 10/2008 | Lu et al. | |
| 7,449,320 B2 | 11/2008 | Miller et al. | |
| 7,459,539 B2 | 12/2008 | Challita-Eid et al. | |
| 7,485,327 B2 | 2/2009 | Kim et al. | |
| 7,488,590 B2 | 2/2009 | Feige et al. | |
| 7,501,391 B2 | 3/2009 | Khan et al. | |
| 7,501,557 B1 | 3/2009 | Wagner et al. | |
| 7,510,840 B1 | 3/2009 | Challita-Eid et al. | |
| 7,514,224 B2 | 4/2009 | Lu et al. | |
| 7,514,407 B2 | 4/2009 | Averback | |
| 7,517,529 B2 | 4/2009 | Khan et al. | |
| 7,524,513 B2 | 4/2009 | Hai-Quan et al. | |
| 7,528,232 B2 | 5/2009 | Wagner et al. | |
| 7,528,242 B2 | 5/2009 | Anderson et al. | |
| 7,534,579 B2 | 5/2009 | Glucksmann et al. | |
| 7,541,450 B2 | 6/2009 | Liu et al. | |
| 7,547,512 B2 | 6/2009 | Peiris et al. | |
| 7,560,433 B2 | 7/2009 | Khan et al. | |
| 7,566,685 B2 | 7/2009 | Kinsella | |
| 7,569,547 B2 | 8/2009 | Lindberg et al. | |
| 7,572,894 B2 | 8/2009 | Jin et al. | |
| 7,575,876 B2 | 8/2009 | Zhang | |
| 7,585,839 B2 | 9/2009 | Larsen et al. | |
| 7,585,849 B2 | 9/2009 | Liu et al. | |
| 7,585,937 B2 | 9/2009 | Kungl | |
| 7,601,807 B2 | 10/2009 | Kanayama et al. | |
| 7,608,704 B2 | 10/2009 | Yue et al. | |
| 7,625,996 B2 | 12/2009 | Fischer et al. | |
| 7,628,989 B2 | 12/2009 | Jakobovits et al. | |
| 7,635,681 B2 | 12/2009 | Bonny | |
| 7,635,755 B2 | 12/2009 | Kaplan et al. | |
| 7,641,905 B2 | 1/2010 | Jakobovits et al. | |
| 7,662,409 B2 | 2/2010 | Masters | |
| 7,662,776 B2 | 2/2010 | Khan et al. | |
| 7,671,011 B2 | 3/2010 | Shai et al. | |
| 7,691,977 B2 | 4/2010 | Fuh et al. | |

(Continued)

FOREIGN PATENT DOCUMENTS

EP 1369479 12/2003
EP 1369479 A1 12/2003

(Continued)

OTHER PUBLICATIONS

Wells, 1990, Biochemistry 29:8509-8517.*

(Continued)

*Primary Examiner* — Elizabeth C Kemmerer
(74) *Attorney, Agent, or Firm* — Fangli Chen; Robert N. Sahr; Choate, Hall & Stewart LLP

(57) ABSTRACT

This invention relates, in part, to unique and newly identified genetic polynucleotides involved in the process of bone remodeling, variants and derivatives of the polynucleotides and corresponding polypeptides, uses of the polynucleotides, polypeptides, variants and derivatives, and methods and compositions for the amelioration of symptoms caused by bone remodeling disorders. Disclosed in particular are the isolation and identification of polynucleotides, polypeptides variants and derivatives involved in osteoclast activity, validation of the identified polynucleotides for their potential as therapeutic targets and use of the polynucleotides, polypeptides, variants and derivatives for the amelioration of disease states and research purposes.

19 Claims, 39 Drawing Sheets

(56) References Cited

U.S. PATENT DOCUMENTS

| | | |
|---|---|---|
| 7,989,160 B2 | 8/2011 | Sooknanan et al. |
| 8,168,181 B2 | 5/2012 | Sooknanan et al. |
| 2003/0118592 A1 | 6/2003 | Ledbetter et al. |
| 2003/0133939 A1 | 7/2003 | Ledbetter et al. |
| 2004/0023313 A1 | 2/2004 | Boyle et al. |
| 2004/0033535 A1 | 2/2004 | Boyle et al. |
| 2004/0076992 A1* | 4/2004 | Nakamura et al. ............. 435/6 |
| 2004/0082508 A1 | 4/2004 | Yue et al. |
| 2005/0107588 A1 | 5/2005 | Duggan et al. |
| 2005/0118625 A1 | 6/2005 | Mounts |
| 2005/0153333 A1 | 7/2005 | Sooknanan |
| 2005/0170450 A1 | 8/2005 | Durocher et al. |
| 2006/0153867 A1 | 7/2006 | Li |
| 2006/0240516 A1 | 10/2006 | Jalinot et al. |
| 2008/0070232 A1 | 3/2008 | Durocher |
| 2008/0171094 A1 | 7/2008 | Benner et al. |
| 2008/0176243 A1 | 7/2008 | Khan et al. |
| 2008/0176790 A1 | 7/2008 | DeFrees |
| 2008/0178308 A1 | 7/2008 | Afar et al. |
| 2008/0194489 A1 | 8/2008 | Khan et al. |
| 2008/0199939 A1 | 8/2008 | Havenga et al. |
| 2008/0206239 A1 | 8/2008 | Jones et al. |
| 2008/0207502 A1 | 8/2008 | Rastelli et al. |
| 2008/0207522 A1 | 8/2008 | Hancock et al. |
| 2008/0213268 A1 | 9/2008 | Watts et al. |
| 2008/0242618 A1 | 10/2008 | Khan et al. |
| 2008/0242837 A1 | 10/2008 | Khan et al. |
| 2008/0242847 A1 | 10/2008 | Liu et al. |
| 2008/0248527 A1 | 10/2008 | Wolfgang et al. |
| 2008/0254020 A1 | 10/2008 | Walker et al. |
| 2008/0261819 A1 | 10/2008 | Lorens et al. |
| 2008/0274979 A1 | 11/2008 | Ellis-Behnke et al. |
| 2008/0275547 A1 | 11/2008 | Kanamaru et al. |
| 2008/0279908 A1 | 11/2008 | Bertozzi et al. |
| 2008/0286808 A1 | 11/2008 | Schellenberger et al. |
| 2008/0287309 A1 | 11/2008 | Bowdish et al. |
| 2008/0299111 A1 | 12/2008 | Delacourte et al. |
| 2008/0299601 A1 | 12/2008 | Fike et al. |
| 2008/0306001 A1 | 12/2008 | Liik et al. |
| 2008/0306009 A1 | 12/2008 | Khan et al. |
| 2008/0318871 A1 | 12/2008 | Khan et al. |
| 2009/0004210 A1 | 1/2009 | Mattner et al. |
| 2009/0005257 A1 | 1/2009 | Jespers et al. |
| 2009/0005266 A1 | 1/2009 | Ostermeier et al. |
| 2009/0005541 A1 | 1/2009 | Kungl |
| 2009/0010983 A1 | 1/2009 | Melvik et al. |
| 2009/0012032 A1 | 1/2009 | Nakamura et al. |
| 2009/0017460 A1 | 1/2009 | Anderson et al. |
| 2009/0019605 A1 | 1/2009 | Takagi et al. |
| 2009/0023648 A1 | 1/2009 | Stredonsky et al. |
| 2009/0028813 A1 | 1/2009 | Stedronsky et al. |
| 2009/0028856 A1 | 1/2009 | Chen et al. |
| 2009/0041671 A1 | 2/2009 | Young et al. |
| 2009/0042769 A1 | 2/2009 | Maclean |
| 2009/0047335 A1 | 2/2009 | Rastelli et al. |
| 2009/0069259 A1 | 3/2009 | Collingwood |
| 2009/0075377 A1 | 3/2009 | Lu et al. |
| 2009/0081178 A1 | 3/2009 | Murray et al. |
| 2009/0081457 A1 | 3/2009 | Nagarajan et al. |
| 2009/0082551 A1 | 3/2009 | Zuckerman |
| 2009/0088387 A1 | 4/2009 | Castillo et al. |
| 2009/0092582 A1 | 4/2009 | Bogin et al. |
| 2009/0093408 A1 | 4/2009 | Bridon et al. |
| 2009/0093621 A1 | 4/2009 | Ferrari et al. |
| 2009/0099031 A1 | 4/2009 | Stemmer et al. |
| 2009/0099066 A1 | 4/2009 | Moulton et al. |
| 2009/0117578 A1 | 5/2009 | Metz et al. |
| 2009/0123412 A1 | 5/2009 | Healy et al. |
| 2009/0130111 A1 | 5/2009 | Wu et al. |
| 2009/0131265 A1 | 5/2009 | Zhang |
| 2009/0136595 A1 | 5/2009 | Shah et al. |
| 2009/0136912 A1 | 5/2009 | Kurokawa et al. |
| 2009/0142280 A1 | 6/2009 | Zhang et al. |
| 2009/0142828 A1 | 6/2009 | Bucciarelli et al. |
| 2009/0142839 A1 | 6/2009 | Primiano |
| 2009/0143567 A1 | 6/2009 | Rathore et al. |
| 2009/0149339 A1 | 6/2009 | Lu et al. |
| 2009/0169520 A1 | 7/2009 | Soreq et al. |
| 2009/0170191 A1 | 7/2009 | Jakobovits et al. |
| 2009/0175821 A1 | 7/2009 | Bridon et al. |
| 2009/0176664 A1 | 7/2009 | Chu |
| 2009/0180958 A1 | 7/2009 | Koivistoinen et al. |
| 2009/0197812 A1 | 8/2009 | Kim et al. |
| 2009/0214570 A1 | 8/2009 | Mrsny et al. |
| 2009/0214582 A1 | 8/2009 | Dean |
| 2009/0215667 A1 | 8/2009 | Wagner et al. |
| 2009/0221505 A1 | 9/2009 | Kolonin et al. |
| 2009/0226372 A1 | 9/2009 | Ruoslahti et al. |
| 2009/0226374 A1 | 9/2009 | Hugli |
| 2009/0226433 A1 | 9/2009 | Grandea, III et al. |
| 2009/0227505 A1 | 9/2009 | Khan et al. |
| 2009/0234026 A1 | 9/2009 | Kaplan et al. |
| 2009/0252728 A1 | 10/2009 | Jakobovits et al. |
| 2009/0258017 A1 | 10/2009 | Callahan et al. |
| 2009/0264372 A1 | 10/2009 | Dal Farra et al. |
| 2009/0270320 A1 | 10/2009 | Panjwani et al. |
| 2009/0275050 A1 | 11/2009 | Glucksmann et al. |
| 2009/0275503 A1 | 11/2009 | Shai et al. |
| 2009/0281038 A1 | 11/2009 | Wagner et al. |
| 2009/0298707 A1 | 12/2009 | Yarbrough et al. |
| 2009/0304746 A1 | 12/2009 | Sette et al. |
| 2009/0317420 A1 | 12/2009 | Telford et al. |
| 2010/0004172 A1 | 1/2010 | Khan et al. |
| 2010/0015664 A1 | 1/2010 | Kanayama et al. |
| 2010/0016215 A1 | 1/2010 | Moulton et al. |
| 2010/0016220 A1 | 1/2010 | Nakamura et al. |
| 2010/0016697 A1 | 1/2010 | Spinale et al. |
| 2010/0029005 A1 | 2/2010 | Kamiie et al. |
| 2010/0035817 A1 | 2/2010 | Fischer et al. |
| 2010/0041614 A1 | 2/2010 | Bussolino et al. |
| 2010/0047163 A1 | 2/2010 | Forte et al. |
| 2010/0055438 A1 | 3/2010 | Kaplan et al. |
| 2010/0056457 A1 | 3/2010 | Barbas, III et al. |
| 2010/0056459 A1 | 3/2010 | Bonny |
| 2010/0076173 A1 | 3/2010 | Stephanopoulos et al. |
| 2010/0080814 A1 | 4/2010 | Desjarlais et al. |
| 2010/0080824 A1 | 4/2010 | Peiris et al. |
| 2010/0086532 A1 | 4/2010 | Barbas, III et al. |
| 2010/0104575 A1 | 4/2010 | Sooknanan et al. |
| 2010/0209428 A1 | 8/2010 | Hiruma et al. |
| 2011/0268733 A1 | 11/2011 | Hiruma et al. |
| 2011/0311526 A1 | 12/2011 | Sooknanan et al. |

FOREIGN PATENT DOCUMENTS

| | | |
|---|---|---|
| EP | 1544215 | 6/2005 |
| EP | 1544215 A1 | 6/2005 |
| EP | 1580263 | 9/2005 |
| EP | 1580263 A1 | 9/2005 |
| EP | 1715038 A1 | 10/2006 |
| EP | 1751179 | 2/2007 |
| EP | 1751179 A2 | 2/2007 |
| EP | 1874337 | 1/2008 |
| EP | 1874337 A2 | 1/2008 |
| EP | 1931198 | 6/2008 |
| EP | 1931198 A2 | 6/2008 |
| EP | 1934252 | 6/2008 |
| EP | 1934252 A1 | 6/2008 |
| EP | 1950221 | 7/2008 |
| EP | 1950221 A2 | 7/2008 |
| EP | 1953551 | 8/2008 |
| EP | 1953551 A2 | 8/2008 |
| EP | 1963499 | 9/2008 |
| EP | 1963499 A2 | 9/2008 |
| EP | 1970383 | 9/2008 |
| EP | 1970383 A1 | 9/2008 |
| EP | 1996609 | 12/2008 |
| EP | 1996609 A2 | 12/2008 |
| EP | 2002036 | 12/2008 |
| EP | 2002036 A2 | 12/2008 |
| EP | 2021467 | 2/2009 |
| EP | 2021467 A1 | 2/2009 |
| EP | 2032149 | 3/2009 |
| EP | 2032149 A2 | 3/2009 |
| EP | 2041569 | 4/2009 |

| | | | | | | |
|---|---|---|---|---|---|---|
| EP | 2041569 A2 | 4/2009 | | WO | WO-2007/093042 A1 | 8/2007 |
| EP | 2046806 | 4/2009 | | WO | WO-2007/100524 A2 | 9/2007 |
| EP | 2046806 A2 | 4/2009 | | WO | WO-2007/104062 A2 | 9/2007 |
| EP | 2053406 | 4/2009 | | WO | WO2007100524 | 9/2007 |
| EP | 2053406 A2 | 4/2009 | | WO | WO2007104062 | 9/2007 |
| EP | 2057465 | 5/2009 | | WO | WO-2007/111952 A2 | 10/2007 |
| EP | 2057465 A2 | 5/2009 | | WO | WO2007111952 | 10/2007 |
| EP | 2097094 | 9/2009 | | WO | WO-2007/128121 A1 | 11/2007 |
| EP | 2097094 A2 | 9/2009 | | WO | WO2007128121 | 11/2007 |
| EP | 2105141 | 9/2009 | | WO | WO-2007/146319 A2 | 12/2007 |
| EP | 2105141 A1 | 9/2009 | | WO | WO2007146319 | 12/2007 |
| EP | 2129682 | 12/2009 | | WO | WO-2008/006028 A2 | 1/2008 |
| EP | 2129682 A1 | 12/2009 | | WO | WO2008006028 | 1/2008 |
| EP | 2130838 | 12/2009 | | WO | WO-2008/024105 A2 | 2/2008 |
| EP | 2130838 A2 | 12/2009 | | WO | WO2008024105 | 2/2008 |
| EP | 2140005 | 1/2010 | | WO | WO2008116468 | 2/2008 |
| EP | 2140005 A1 | 1/2010 | | WO | WO-2008/063369 A2 | 5/2008 |
| EP | 2168986 | 3/2010 | | WO | WO2008063369 | 5/2008 |
| EP | 2168986 A2 | 3/2010 | | WO | WO-2008/093982 A1 | 8/2008 |
| EP | 2170363 | 4/2010 | | WO | WO-2008/101160 A2 | 8/2008 |
| EP | 2170363 A2 | 4/2010 | | WO | WO2008093982 | 8/2008 |
| JP | 2003169687 | 6/2003 | | WO | WO2008101160 | 8/2008 |
| JP | 2003169687 A | 6/2003 | | WO | WO-2008/113185 A1 | 9/2008 |
| JP | 2003210166 | 7/2003 | | WO | WO2008113185 | 9/2008 |
| JP | 2003210166 A | 7/2003 | | WO | WO-2008/116468 A2 | 10/2008 |
| JP | 2004107352 | 4/2004 | | WO | WO-2008/134544 A1 | 11/2008 |
| JP | 2004107352 A | 4/2004 | | WO | WO2008134544 | 11/2008 |
| JP | 2004189848 | 7/2004 | | WO | WO-2008/148545 A1 | 12/2008 |
| JP | 2004189848 A | 7/2004 | | WO | WO2008148545 | 12/2008 |
| JP | 2004533803 | 11/2004 | | WO | WO-2009/005793 A2 | 1/2009 |
| JP | 2004533803 A | 11/2004 | | WO | WO-2009/008727 A2 | 1/2009 |
| JP | 2004339189 | 12/2004 | | WO | WO2009005793 | 1/2009 |
| JP | 2004339189 A | 12/2004 | | WO | WO2009008727 | 1/2009 |
| JP | 2007020403 | 2/2007 | | WO | WO-2009/020101 A1 | 2/2009 |
| JP | 2007020403 A | 2/2007 | | WO | WO-2009/023125 A1 | 2/2009 |
| JP | 2008500267 | 1/2008 | | WO | WO2009020101 | 2/2009 |
| JP | 2008500267 A | 1/2008 | | WO | WO2009023125 | 2/2009 |
| JP | 2008504221 | 2/2008 | | WO | WO2009039854 | 2/2009 |
| JP | 2008504221 A | 2/2008 | | WO | WO-2009/031835 A2 | 3/2009 |
| JP | 2008094822 | 4/2008 | | WO | WO-2009/031836 A1 | 3/2009 |
| JP | 2008094822 A | 4/2008 | | WO | WO-2009/032158 A2 | 3/2009 |
| JP | 2008111841 | 5/2008 | | WO | WO-2009/038756 A2 | 3/2009 |
| JP | 2008111841 A | 5/2008 | | WO | WO2009031835 | 3/2009 |
| JP | 2008263955 | 11/2008 | | WO | WO2009031836 | 3/2009 |
| JP | 2008263955 A | 11/2008 | | WO | WO2009032158 | 3/2009 |
| JP | 200972081 A | 4/2009 | | WO | WO2009038756 | 3/2009 |
| JP | 2009072081 | 4/2009 | | WO | WO2009146179 | 3/2009 |
| JP | 2009183293 | 8/2009 | | WO | WO-2009/039854 A2 | 4/2009 |
| JP | 2009183293 A | 8/2009 | | WO | WO-2009/048072 A1 | 4/2009 |
| JP | 2009528255 | 8/2009 | | WO | WO-2009/050453 A2 | 4/2009 |
| JP | 2009528255 A | 8/2009 | | WO | WO2009048072 | 4/2009 |
| WO | WO 94/11014 | 5/1994 | | WO | WO2009050453 | 4/2009 |
| WO | WO/94/11014 | 5/1994 | | WO | WO-2009/059379 A1 | 5/2009 |
| WO | WO-94/11014 A1 | 5/1994 | | WO | WO-2009/059972 A2 | 5/2009 |
| WO | WO-02/20723 A2 | 3/2002 | | WO | WO-2009/061130 A2 | 5/2009 |
| WO | WO0220723 | 3/2002 | | WO | WO-2009/061890 A1 | 5/2009 |
| WO | WO0220822 | 3/2002 | | WO | WO2009059379 | 5/2009 |
| WO | WO-0220822 A2 | 3/2002 | | WO | WO2009059972 | 5/2009 |
| WO | WO-03/048305 A2 | 6/2003 | | WO | WO2009061130 | 5/2009 |
| WO | WO03048305 | 6/2003 | | WO | WO2009061890 | 5/2009 |
| WO | WO03104275 | 12/2003 | | WO | WO2009132876 | 5/2009 |
| WO | WO-03104275 A2 | 12/2003 | | WO | WO-2009/090651 A2 | 7/2009 |
| WO | WO-2004/064972 A2 | 8/2004 | | WO | WO2009090651 | 7/2009 |
| WO | WO2004064972 | 8/2004 | | WO | WO-2009/106715 A2 | 9/2009 |
| WO | WO-2005/061546 A1 | 7/2005 | | WO | WO-2009/108261 A2 | 9/2009 |
| WO | WO2005061546 | 7/2005 | | WO | WO-2009/112645 A1 | 9/2009 |
| WO | WO/2005/078087 | 8/2005 | | WO | WO2009106715 | 9/2009 |
| WO | WO-2005/078087 A1 | 8/2005 | | WO | WO2009108261 | 9/2009 |
| WO | WO-2005/081628 A2 | 9/2005 | | WO | WO2009112645 | 9/2009 |
| WO | WO2005081628 | 9/2005 | | WO | WO-2009/132876 A1 | 11/2009 |
| WO | WO2006153867 | 7/2006 | | WO | WO-2009/139599 A2 | 11/2009 |
| WO | WO-2006/113311 A2 | 10/2006 | | WO | WO2009139599 | 11/2009 |
| WO | WO2006113311 | 10/2006 | | WO | WO-2009/146179 A1 | 12/2009 |
| WO | WO-2007/043059 A1 | 4/2007 | | WO | WO-2010/000794 A1 | 1/2010 |
| WO | WO2007043059 | 4/2007 | | WO | WO2010000794 | 1/2010 |
| WO | WO-2007/062422 A2 | 5/2007 | | WO | WO2010035504 | 1/2010 |
| WO | WO2007062422 | 5/2007 | | WO | WO-2010/033736 A1 | 3/2010 |
| WO | WO-2007/063300 A2 | 6/2007 | | WO | WO2010033736 | 3/2010 |
| WO | WO2007063300 | 6/2007 | | WO | WO-2010/035504 A1 | 4/2010 |

| | | |
|---|---|---|
| WO | WO-2010/037395 A2 | 4/2010 |
| WO | WO2010037395 | 4/2010 |
| WO | WO/2011/041894 | 4/2011 |
| WO | WO-2011/041894 A1 | 4/2011 |
| WO | WO/2012/045481 | 4/2012 |
| WO | WO-2012/045481 A2 | 4/2012 |

OTHER PUBLICATIONS

Ngo et al., 1994, The Protein Folding Problem and Tertiary Structure Prediction, Merz et al., Birkhauser, Boston, pp. 492-495.*
Williams et al. (2012, Eur. J. Immunol. 42:2109-2120).*
Li et al. (1980, PNAS USA 77:3211-3214).*
NCBI Reference sequence: NP_998767, Angata T. et al., J. Glycobiology 17 (8), pp. 838-846 (2007).
GenBank accession No. BAD18800, Kawabata A. et al., Direct Submission, submitted (Apr. 22, 2004), Institute of Medical Science.
GenBank accession No. BAF83089, Wakamatsu A. et al., Direct submission, submitted (Oct. 9, 2007) Reverse Proteomics Researach Institute.
GenBank accession No. BAF83091, Wakamatsu A. et al., Direct submission, submitted (Oct. 9, 2007) Reverse Proteomics Researach Institute.
IPI No: IPI00796217.1, Oct. 31, 2006.
GenBank accession No. AAY40743, Angata T. et al., J. Glycobiology 17 (8), pp. 838-846 (2007).
IPI No: IPI00663527.4; sequence update Sep. 10, 2007.
IPI No: IPI00568858.3, Apr. 20, 2010.
UniProtKB/TrEMBL A7E1W8_MOUSE, Sep.-Nov. 2007.
GenBank accession No. AAY40744, Angata,T. et al., J. Glycobiology 17 (8), 838-846 (2007).
ENSEMBL Protein ID: ENSBTAP00000022107, /Jul. 19, 2010.
IPI No: IPI00711850.1. sequence update Jun. 9, 2010.
ENSEMBL Protein ID: ENSMUSP00000112309, Jul. 19, 2010.
Sordillo et al., "RANK-FC": A therapeutic Antagonist of RANK-L in Myeloma Skeletal Complications of Malignancy, Cancer Suppl. vol. 97:3, 802-812 (2003).
Angata, T. et al., (2007) "Siglec-15: An immune system Siglec conserved throughout vertebrate evolution", Glycobiology, vol. 17(8):838-846.
Agrawal, N., et al. (2003). "RNA interference: biology, mechanism, and applications." Microbiol Mol Biol Rev 67(4): 657-85.
Baron R., Primer on the Metabolic Bone Diseases and Disorders of Mineral Metabolism, Fifth Ed. 2003, American Society for Bone and Mineral Research, Washington DC, pp. 1-8.
Biskobing DM, Fan D. Acid pH increases carbonic anhydrase II and calcitonin receptor mRNA expression in mature osteoclasts. Calcif Tissue Int. Aug. 2000;67(2):178-83.
Boyle, W. J., W. S. Simonet, et al. (2003). "Osteoclast differentiation and activation." Nature 423(6937): 337-42.
Brage M, et al., Different cysteine proteinases involved in bone resorption and osteoclast formation. Calcif Tissue Int. Jun. 2005;76(6)439-47. Epub May 19, 2005.
Brandenberger R. et al.Nat. Biotechnol. vol. 22, No. 6, 2004, pp. 707-716.
Brummelkamp, T. R., R. Bernards, et al. (2002). "A system for stable expression of short interfering RNAs in mammalian cells." Science 296(5567): 550-3.
deVernejoul, M. C., "Dynamics of Bone Remodeling: Biochemical and Pathophysiological Basis", Eur J Clin Chem Clin Biochem 34: 729-734 (1996).
Elbahsir, et al. (2001). "Duplexes of 21-nucleotide RNAs mediate RNA interference in cultured mammalian cells." Nature 411(6836): 494-8.
Frost H.M., 1964 Dymanics of Bone Remodeling. In: Bone Biodynamics, Little and Brown, Boston, MA, USA pp. 315.
Gee et al. In: Huber and Carr (1994) Molecular and Immunologic Approaches, Futura Publishing Co., Mt. Kisco N.Y., pp. 163-177.
Hannon, G. J. (2002). "RNA interference." Nature 418(6894): 244-51.
Ishida N. et al.: 'Large scale gene expression analysis of osteoclastogenesis in vitro . . . ' J. Bio. Chem. vol. 277, No. 43, (2002) pp. 41147-41156, XP003017032.

Janssen, E., M. Zhu, et al. (2003). "LAB: a new membrane-associated adaptor molecule in B cell activation." Nat Immunol 4(2): 117-23.
Jilka, R. L. et al., "Increased Osteoclast Development After Esgtrogen Loss: Mediation by Interleukin-6", Science 257: 88-91 (1992).
Kawai, J., A. Shinagawa, et al. (2001). "Functional annotation of a full-length mouse cDNA collection." Nature 409(6821): 685-90.
Kawaida, R.,et al. (2003). "Jun dimerization protein 2 (JDP2), . . . mediates osteoclast differentiation induced by RANKL." J Exp Med 197(8): 1029-1035.
Lee, J. S., Z. Hmama, et al. (2004) J Biol Chem 279(10): 9379-88.
Malkin I, et al., Association of ANKH gene polymorphisms with radiographic hand bone size and geometry in a Chuvasha population. Bone. Feb. 2005;36(2):365-73.
McMAHON C, et al.,Bone marrow transplantation corrects osteopetrosis in the carbonic anhydrase II deficiency syndrome. Blood. Apr. 1, 2001;97(7):1947-50.
Morello, R., et al. (1999). "cDNA cloning, characterization and chromosome mapping of Crtap encoding the mouse cartilage associated protein." Matrix Biol 18(3): 319-324.
Netzel-Arnett, S., et al. (2003). Cancer Metastasis Rev 22(2-3): 237-58.
Nishi, T. et al., (2002). "The vacuolar (H+)-ATPases—nature's most versatile proton pumps." Nat Rev Mol Cell Biol 3(2): 94-103.
Nishi, T., et al. (2003). "Expression and function of the mouse V-ATPase d subunit isoforms." J Biol Chem 278(47): 46396-402.
Poli, V. et al., "Interleukin-6 deficient mice are protected from bone loss caused by estrogen depletion", EMBO J 13: 1189-1196 (1994).
Rubinson, D. A.,et al. (2003). Nat Genet 33(3): 401-406.
Shan, J., et al. (2002). "TSP50, a possible protease in human testes, is activated in breast cancer epithelial cells."CancerRes 62(1): 290-294.
Smith, A. N., et al. (2005). J Am Soc Nephrol 16(5): 1245-56.
Smith, A. N., et al.(2000) Nat Genet 26(1): 71-5.
Srivastava, S. et al., "Estrogen Blocks M-CSF Gene Expression and Osteoclast Formation by Regulating Phosphorylation of Egr-1 . . . ", J Clin Invest 102:1850-1859 (1998).
Stehberger, P. A., N. Schulz, et al. (2003).J Am Soc Nephrol 14(12): 3027-38.
Strausberg, R. L., et al. (2002). "Generation and initial analysis of more than 15,000 full-length human and mouse cDNA sequences." Proc Natl Acad Sci USA 99(26): 16899-16903.
Tonachini, L.,R. et al. (1999) "cDNA cloning, characterization and chromosome mapping of the gene encoding human cartilage associated protein" Cytogenet Cell Genet 87(3-4):191.
Yuan, L., et al. (1999). "Isolation of a novel gene, TSP50, by a hypomethylated DNA fragment in human breast cancer." Cancer Res 59(13): 3215-21.
GenBank Acc. No. NM_001102, GI:194097348, first referenced 1989, updated 2008.
GenBank Acc. No. NM_004794, GI:34485717, first referenced 1993, updated 2005.
Ngo et al., 1994, The Protein Folding Problem and Tertiaty Structure Prediction, Merz et al., eds Birkhauser, Boston, pp. 492-495.
Sooknanan et al., (2004) "Identification of osteoclast-specific gene using subtractive transcription amplification of mRNA (STAR)" J. Bone Min. Res. 19:S415.
Tremblay et al., (2004) "Functional validation of osteoclast-specific genes in RAW264.7 cells by RNA interference" J. Bone Min. Res. 19:S414.
Supplementary Europen Search Report, EP07710624, date of amiling Jul. 10, 2009.
Database Geneseq (Online) Derwent; May 3, 2007, Human Siglec 15, SEQID2" XP002531845, from JP-2007020403 (Nat. Inst. of Adv. Ind. & TEchol.).
Hiruma, Y, et al., (2011) "Siglec-15, a member of the sialic acid-binding lectin, is a novel regulator for osteoclst diffrerentiation" Biochem Biophys Commun 409(3):424-429.
GeneBank Acc. No. NM_00104433, first referenced 2000, updated 2009.
Stuible, M. et al., Sep. 2011, abstract of oral presentation No. 1187, The American Society for Bone and Mineral Research.
Bird, RE et al., "Single-Chain antigen binding proteins" Science 242 (4877): 423-426, 1988.
ENSFCAP Protein ID: ENSFCAP00000009910; Jul. 19, 2010.

Jpn. J. Cancer Chemother. 2004, vol. 31, No. 7, p. 1027-1033 (with English abstract).

Agrawal, N., et al., RNA Interference: Biology, Mechanism, and Applications, Microbiology and Molecular Biology Reviews, 67(4):657-685 (2003).

Angata, T. et al., Siglec-15: an immune system Siglec conserved throughout vertebrate evolution, Glycobiology, 17(8):838-846 (2007).

Baron R., Primer on the Metabolic Bone Diseases and Disorders of Mineral Metabolism, Fifth Ed., American Society for Bone and Mineral Research, Washington DC, pp. 1-8 (2003).

Bird, R.E. et al., Single-Chain Antigen-Binding Proteins, Science, 242(4877):423-426 (1988).

Biskobing, D.M. et al., Acid pH increases Carbonic Anhydrase II and Calcitonin Receptor mRNA Expression in Mature Osteoclasts, Calcified Tissue International, 67(2):178-183 (2000).

Blixt, O. et al., Sialoside Specificity of the Siglec Family Assessed Using Novel Multivalent Probes, The Journal of Bilogical Chemistry, 278:31007-31019 (2003).

Boyle, W.J. et al., Osteoclast differentiation and activation, Nature, 423(6937):337-342 (2003).

Brage, M. et al., Different Cysteine Proteinases Involved in Bone Resorption and Osteoclast Formation, Calcified Tissue International, 76(6)439-447 (2005).

Brandenberger, R. et al., Transcriptome characterization elucidates signaling networks that control human ES cell growth and differentiation, Nature Biotechnology, 22(6):707-716 (2004).

Bregni, M. et al., B-Cell restricted saporin immunotoxins: activity against B-cell lines and chronic lymphocytic leukemia cells, Blood, 73:753-762 (1989).

Brummelkamp, T.R. et al., A System for Stable Expression of Short Interfering RNAs in Mammalian Cells, Science, 296(5567):550-553 (2002).

Clackson, T. et al., Making antibody fragments using phage display libraries, Nature, 352:624-628 (1991).

Crocker, P.R. et al., Siglecs and their roles in the immune system, Nature Reviews Immunology, 7(4):255-266 (2007).

Database Geneseq (Online) Derwent; Human Siglec 15, SEQID2, XP002531845, from JP-2007020403-A (Nat. Inst. of Adv. Ind. & Technol.) May 3, 2007.

Database Geneseq [Online], Human protease/osteoarthritis gene-specific probe—SEQ ID 118248, Database accession No. AFV92822, Oct. 18, 2007.

Database Geneseq [Online], Human protease/osteoarthritis gene-specific probe—SEQ ID 72066, Database accession No. AFV46640, Oct. 18, 2007.

De Vernejoul, M.C., Dynamics of Bone Remodeling: Biochemical and Pathophysiological Basis, European Journal of Clinical Chemistry and Clinical Biochemistry, 34:729-734 (1996).

Elbashir, S.M. et al., Duplexes of 21-nucleotide RNAs mediate RNA interference in cultured mammalian cells, Nature, 411(6836):494-498 (2001).

Ellis, G.K. et al., Randomized Trial of Denosumab in Patients Receiving Adjuvant Aromatase Inhibitors for Nonmetastatic Breast Cancer, Journal of Clinical Oncology, 26(30):4875-4882 (2008).

Ensembl Protein ID: ENSBTAP00000016659, Jul. 19, 2010.
Ensembl Protein ID: ENSBTAP00000022107, Jul. 19, 2010.
Ensembl Protein ID: ENSCAFP00000026052, Jul. 19, 2010.
Ensembl Protein ID: ENSDNOP00000011608; Jul. 19, 2010.
Ensembl Protein ID: ENSECAP00000015632, Jul. 19, 2010.
Ensembl Protein ID: ENSFCAP00000009910, Jul. 19, 2010.
Ensembl Protein ID: ENSMICP00000015938, Jul. 19, 2010.
Ensembl Protein ID: ENSMLUP00000004457, Jul. 19, 2010.
Ensembl Protein ID: ENSMMUP00000004742, Jul. 19, 2010.
Ensembl Protein ID: ENSMUSP00000112309, Jul. 19, 2010
Ensembl Protein ID: ENSOPRP00000004369, Jul. 19, 2010.
Ensembl Protein ID: ENSPPYP00000010254, Jul. 19, 2010.
Ensembl Protein ID: ENSPTRP00000042370, Jul. 19, 2010.
Ensembl Protein ID: ENSPTRP00000049394, Jul. 19, 2010.
Ensembl Protein ID: ENSRNOP00000041280, Jul. 19, 2010.
Ensembl Protein ID: ENSSARP00000011800, Jul. 19, 2010.
Ensembl Protein ID: ENSSTOP00000002285, Jul. 19, 2010.
Ensembl Protein ID:ENSP00000374125, Jul. 6, 2010.

Frost, H.M., Dynamics of Bone Remodeling. In: Bone Biodynamics, Little and Brown, Boston, MA, USA, pp. 315-333 (1964).

Gee, J.E. et al., Potential Therapeutic Usefulness of Intermolecular Triplex DNA. In: Huber BE Cancer Therapy in the Twenty-First Century, vol. 1: Molecular and Immunologic Approaches, Futura Publishing Co., Inc., Mt. Kisco, N.Y., pp. 163-177 (1994).

GenBank Acc. No. AAY40743, Angata T. et al., J. Glycobiology 17 (8), pp. 838-846 (2007).

GenBank Acc. No. AAY40744, Angata, T. et al., J. Glycobiology, 17(8):838-846 (2007).

GenBank Acc. No. AK172835, GI:47077862, 2004.

GenBank Acc. No. AL357873, GI:16972902, 2008.

GenBank Acc. No. AL645465, GI:18476850, 2008.

GenBank Acc. No. BAD18800, Kawabata, A. et al., Direct Submission, submitted (Apr. 22, 2004), Institute of Medical Science.

GenBank Acc. No. BAF83089, Wakamatsu, A. et al., Direct submission, submitted (Oct. 9, 2007) Reverse Proteomics Research Institute.

GenBank Acc. No. BAF83091, Wakamatsu, A. et al., Direct submission, submitted (Oct. 9, 2007) Reverse Proteomics Research Institute.

GenBank Acc. No. NM_000067, GI:157952216, first referenced 1976, updated 2008.

GenBank Acc. No. NM_000099, GI:19882253, first referenced 1990, updated 2008.

GenBank Acc. No. NM_000887, GI:34452172, first referenced 1987, updated 2008.

GenBank Acc. No. NM_001014433, GI:62526019, first referenced 2000, updated 2005.

GenBank Acc. No. NM_00104433, first referenced 2000, updated 2009.

GenBank Acc. No. NM_0010102, GI:194097348, first referenced 1989, updated 2008.

GenBank Acc. No. NM_001690, GI:19913423, first referenced 1993, updated 2007.

GenBank Acc. No. NM_001935, GI:47078262, first referenced 1991, updated 2008.

GenBank Acc. No. NM_002994, GI:41872613, first referenced 1991, updated 2008.

GenBank Acc. No. NM_003341, GI:33359692, first referenced 1993, updated 2008.

GenBank Acc. No. NM_004414, GI:44680111, first referenced 1995, updated 2008.

GenBank Acc. No. NM_004763, GI:115527101, first referenced 1997, updated 2007.

GenBank Acc. No. NM_004794, Gl:34485717, first referenced 1993, updated 2005.

GenBank Acc. No. NM_005410, GI:62530390, first referenced 1991, updated 2008.

GenBank Acc. No. NM_005765, GI:15011917, first referenced 1998, updated 2007.

GenBank Acc. No. NM_006357, GI:33359695, first referenced 1997, updated 2008.

GenBank Acc. No. NM_006555, GI:34304384, first referenced 1997, updated 2007.

GenBank Acc. No. NM_006660, GI:12597621, first referenced 1999, updated 2008.

GenBank Acc. No. NM_013322, GI:23111022, first referenced 2001, updated 2006.

GenBank Acc. No. NM_014358, GI:90577173, first referenced 1999, updated 2003.

GenBank Acc. No. NM_014656, GI:7657258, 2006.

GenBank Acc. No. NM_015973, GI:88853582, first refenced 1990, updated 2008.

GenBank Acc. No. NM_018252, GI:149158718, 2006.

GenBank Acc. No. NM_018482, GI:46094080, first referenced 1998, updated 2008.

GenBank Acc. No. NM_021181, GI:19923571, first referenced 2001, updated 2008.

GenBank Acc. No. NM_030794, GI:13540575, first referenced 2000, updated 2008.

GenBank Acc. No. NM_032565, GI:141802977, first referenced 2003, updated 2007.

GenBank Acc. No. NM_032569, GI:190358483, first referenced 2005, updated 2006.
GenBank Acc. No. NM_032731, GI:153791420, first referenced 2004, updated 2008.
GenBank Acc. No. NM_054027, GI:170671715, first referenced 1995, updated 2008.
GenBank Acc. No. NM_138461, GI:115511027, 2004.
GenBank Acc. No. NM_145280, GI:188528683, 2004.
GenBank Acc. No. NM_178833, GI:196259823, first referenced 2007, updated 2008.
GenBank Acc. No. NM_182488, GI:209954829, first referenced 1998, updated 2004.
GenBank Acc. No. NM_213602, GI:47106068, 2007.
GenBank Acc. No. XM_884636, GI:149270200, 2007.
GeneBank Acc. No. NM_001771.3, first reference 1990.
GeneBank Acc.No. NM_001772.3, first reference 1988.
Ghetie, M.A. et al., Evaluation of Ricin A Chain-containing Immunotoxins Directed Against CD19 and CD22 Antigens on Normal and Malignant Human B-Cells as Potential Reagents for in Vivo Therapy, Cancer Research, 48:2610-2617 (1988).
Hannon, G.J., RNA interference, Nature, 418(6894):244-251 (2002).
Hashimoto, T. et al., Biochemical Markers in Bone Metastasis, Jpn. J. Cancer Chemother, 31(7):1027-1033 (2004).
Hiruma, Y. et al., Siglec-15, a member of the sialic acid-binding lectin, is a novel regulator for osteoclast differentiation, Biochemical and Biophysical Research Communications, 409(3):424-429 (2011).
Huston, J.S. et al., Protein engineering of antibody binding sites: Recovery of specific activity in an anti-digoxin single-chain Fv analogue produced in *Escherichia coli*, Proceedings of the National Academy of Sciences, 85:5879-5883 (1988).
IPI No: IPI00568858.4, sequence update Oct. 12, 2009.
IPI No: IPI00647937.1, Sep. 4, 2005.
IPI No: IPI00663527.4, sequence update Sep. 10, 2007.
IPI No: IPI00711850.4., sequence update Jun. 9, 2010.
IPI No: IPI00716135.2, 2007.
IPI No: IPI00796217.1, sequence update Oct. 31, 2006.
Ishida, N. et al., Large Scale Gene Expression Analysis of Osteoclastogenesis in Vitro and Elucidation of NFAT2 as a Key Regulator, The Journal of Biological Chemistry, 277(43):41147-41156 (2002).
Ishida-Kitagawa, N. et al., Siglec-15 Protein Regulates Formation of Functional Osteoclasts in Concert with Dnax-activating Protein of 12 kDa (DAP12), the Journal of Biological Chemistry, 287(21):17493-17502 (2012).
Janssen, E. et al., LAB: A new membrane-associated adaptor molecule in B cell activation, Nature Immunology, 4(2):117-123 (2003).
Jilka, R.L. et al., Increased Osteoclast Development After Estrogen Loss: Mediation by Interleukin-6, Science 257:88-91 (1992).
Kawai, J. et al., Functional annotation of a full-length mouse cDNA collection, Nature, 409(6821):685-690 (2001).
Kawaida, R. et al., Jun Dimerization Protein 2 (JDP2), a Member of the Ap-1 Family of Transcription Factor, Mediates Osteoclast Differentiation Induced by RANKL, The Journal of Experimental Medicine, 197(8):1029-1035 (2003).
Lacey, D.L. et al., Bench to bedside: elucidation of the OPG-RANK-RANKL pathway and the development of denosumab, Nature Reviews Drug Discovery, 11:401-419 (2012).
Larkin, M.A. et al., Clustal W and Clustal X version 2.0, Bioinformatics, 23(21): 2947-2948 (2007).
Lee, J.S. et al., Stable gene silencing in human monocytic cell lines using lentiviral-delivered small interference RNA. Silencing of the p110α isoform of phosphoinositide 3-kinase reveals differential regulation of adherence induced by 1α,25-dihydroxycholecalciferol and bacterial lipopolysaccharide, the Journal of Biological Chemistry, 279(10):9379-9388 (2004).
Li, C.H. et al., β-Endorphin omission analogs: Dissociation of immunoreactivity from other biological activities, Proceedings of the National Academy of Sciences, 77(6):3211-3214 (1980).
Malkin, I. et al., Association of ANKH gene polymorphisms with radiographic hand bone size and geometry in a Chuvasha population, Bone, 36(2):365-373 (2005).

McMAHON, C. et al. Bone marrow transplantation corrects osteopetrosis in the carbonic anhydrase II deficiency syndrome, Blood, 97(7):1947-1950 (2001).
McMILLAN, S.J. et al., CD33-related sialic-acid-binding immunoglobulin-like lectins in health and disease, Carbohydrate Research, 343(12):2050-2056 (2008).
Morello, R. et al., cDNA cloning, characterization and chromosome mapping of *Crtap* encoding the mouse Cartilage Associated Protein, Matrix Biology, 18(3): 319-324 (1999).
NCBI Accession No. XP_889729; Dec. 1, 2005.
NCBI reference sequence: AAY40743.1, 2005.
NCBI reference sequence: EAX01462.1, first reference 2005.
NCBI Reference sequence: NP_001094508, May 28, 2010.
NCBI reference sequence: NP_001094508.1, 2007.
NCBI Reference sequence: NP_998767, Angata, T. et al., J. Glycobiology, 17(8):838-846 (2007).
NCBI Reference sequence: XP_001056537, Apr. 2, 2010.
NCBI Reference sequence: XP_001089000, Jun. 1, 2010.
NCBI reference sequence: XP_001089000.1, 2010.
NCBI Reference sequence: XP_512109, Sep. 16, 2006.
NCBI reference sequence: XP_512109.2, Oct. 25, 2012.
NCBI Reference sequence: XP_574176, Apr. 2, 2010.
NCBI reference sequence: XP_574176.2, 2006.
NCBI Reference sequence: XP_601064, Jun. 3, 2010.
NCBI reference sequence: XP_601064.4, 2008.
NCBI Reference sequence: XP_855238, Aug. 30, 2005.
NCBI reference sequence: XP_855238.1, 2005.
Netzel-Arnett, S. et al., Member anchored serine proteases: A rapidly expanding group of cell surface proteolytic enzymes with potential roles in cancer, Cancer and Metastasis Reviews, 22(2-3):237-258 (2003).
Ngo, J.T. et al., Computational Complexity, Protein Structure Prediction, and the Levinthal Paradox in The Protein Folding Problem and Tertiary Structure Prediction, Birkhauser, Boston, pp. 491-495 (1994).
Nishi, T. et al., Expression and Function of the Mouse V-ATPase d Subunit Isoforms, The Journal of Biological Chemistry, 278(47): 46396-46402 (2003).
Nishi, T. et al., The vacuolar (H+)-ATPases-nature's most versatile proton pumps. Nature Reviews Molecular Cell Biology, 3(2):94-103 (2002).
O'Reilly, M.K. et al., Siglecs as targets for therapy in immune cell mediated disease, Trends in Pharmacological Sciences, 30(5):240-248 (2009).
Poli, V. et al., Interleukin-6 deficient mice are protected from bone loss caused by estrogen depletion, The EMBO Journal, 13(5):1189-1196 (1994).
Portolano, S. et al., Lack of Promiscuity in Autoantigen-Specific H and L Chain Combinations as Revealed by Human H and L Chain "Roulette", The Journal of Immunology, 150:880-887 (1993).
Rubinson, D.A. et al., A lentivirus-based system to functionally silence genes in primary mammalian cells, stem cells and transgenic mice by RNA interference, Nature Genetics, 33(3):401-406 (2003).
Shan, J. et al., TSP50, a Possible Protease in Human Testes, Is Activated in Breast Cancer Epithelial Cells, Cancer Research, 62(1):290-294 (2002).
Shankavaram, U.T. et al., Transcript and protein expression profiles of the NCI-60 cancer panel: an integromic microarray study, Molecular Cancer Therapies, 6(3):820-832 (2007).
Smith, a.N. et al., Mutations in *ATP6N1B*, encoding a new kidney vacuolar proton pump 116-kD subunit, cause recessive distal renal tubular acidosis with preserved hearing, Nature Genetics, 26(1):71-75 (2000).
Smith, A.N., et al. Vacuolar H+-ATPase d2 Subunit: Molecular Characterization, Development Regulation, and Localization to Specialized Proton Pumps in Kidney and Bone, Journal of the American Society of Nephrology, 16(5):1245-1256 (2005).
Sooknanan, R. et al., Identification of Osteoclast-Specific Genes using Subtractive Transcription Amplification of mRNA (STAR), Journal of Bone and Mineral Research, 19:S415 (2004).
Sordillo, E.M. et al., Rank-FC: A Therapeutic Antagonist for Rank-L in Myeloma, Skeletal Complications of Malignancy, Cancer Supplement, 97(3):802-812 (2003).

Srivastava, S. et al., Estrogen Blocks M-CSF Gene Expression and Osteoclast Formation by Regulating Phosphorylation of Egr-1 and Its Interaction with Sp-1, The Journal of Clinical Investigation, 102(10):1850-1859 (1998).

Stehberger, P.A. et al., Localization and Regulation of the ATP6V0A4 (a4) Vacuolar H+-ATPase Subunit Defective in an Inherited Form of Distal Renal Tubular Acidosis, Journal of the American Society of Nephrology, 14(12):3027-3038 (2003).

Strausberg, R.L. et al., Generation and initial analysis of more than 15,000 full-length human and mouse cDNA sequences, Proceedings of the National Academy of Sciences, 99(26):16899-16903 (2002).

Stuible, M. et al., Abstract of Oral Presentation No. 1187, Targeting of the DAP12-associated, Osteoclast-specific, Receptor Siglec-15 by Antibody 25E9 inhibits Differentiation and Resorption Activity, The American Society for Bone and Mineral Research, San Diego Convention Center, Sep. 19, 2011.

Sugawara, K. et al., A Useful Method to Evaluate Bone Resorption Inhibitors, Using Osteoclast-like Multinucleated Cells, Analytical Biochemistry, 255:204-210 (1998).

Supplementary European Search Report for EP07710624.3, 13 pages (Jul. 10, 2009).

Susa, M. et al., Human primary osteoclasts: in vitro generation and application as pharmacological and clinical assay, Journal of Translational Medicine, 2(6):1-12 (2004).

Takahata, M. et al., Sialylation of cell surface glycoconjugates is essential for osteoclastogenesis, Bone, 41(1):77-86 (2007).

Tatusova, T. et al., Blast 2 sequences, a new tool for comparing protein and nucleotide sequences, FEMS Microbiology Letters, 174:247-250 (1999).

Tonachini, L. et al., cDNA cloning, characterization and chromosome mapping of the gene encoding human cartilage associated protein (CRTAP), Cytogenetics and Cell Genetics, 87(34):191-194 (1999).

Tremblay, G.B. et al., Functional Validation of Osteoclast-Specific Genes in RAW264.7 Cells by RNA Interference, Journal of Bone and Mineral Research, 19:S414 (2004).

UniProtKB/Swiss-Prot A8K2Y5_HUMAN, Jul. 13, 2010.

UniProtKB/Swiss-Prot Q6ZMC9 (SIG15_HUMAN), Jun. 15, 2010.

UniProtKB/TrEMBL A7E1W7_HUMAN, Mar. 2, 2010.

UniProtKB/TrEMBL A7E1W8_MOUSE, Sep. 11, 2007.

Van Der Velden, V.H.J. et al., Targeting of the CD33-calicheamicin immunoconjugate Mylotarg (CMA-676) in acute myeloid leukemia: in vivo saturation and internalization by leukemic and normal myeloid cells, Blood, 97:3197-3204 (2001).

Ward, E.S. et al., Binding activities of a repertoire of single immunoglobulin variable domains secreted from *Escherichia coli*, Nature, 341:544-546 (1989).

Wells, J.A., Additivity of Mutational Effects in Proteins, Biochemistry, 29(37):8509-8517 (1990).

Williams, E.L. et al., Development and characterization of monoclonal antibodies specific for the murine inhibitory FcγRIIB (CD32B), European Journal of Immunology, 42:2109-2120 (2012).

Yuan, L. et al., Isolation of a Novel Gene, *TSP50*, by a Hypomethylated DNA Fragment in Human Breast Cancer, Cancer Research, 59(13):3215-3221 (1999).

Notice of Opposition against European Patent No. 1994155 including references D1-D12 (Jul. 30, 2013).

* cited by examiner

FIG.6
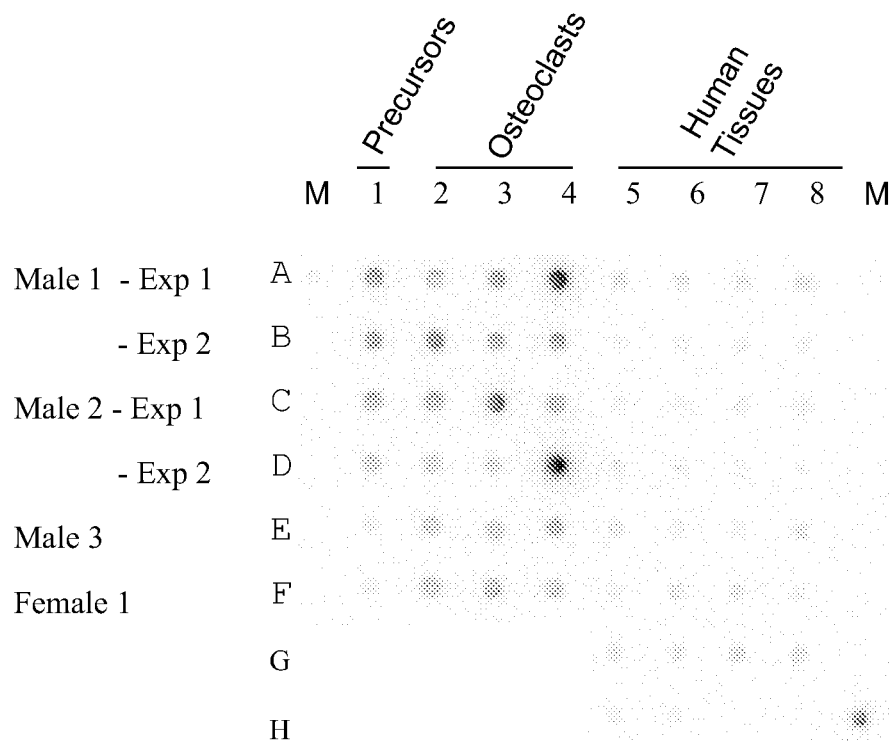
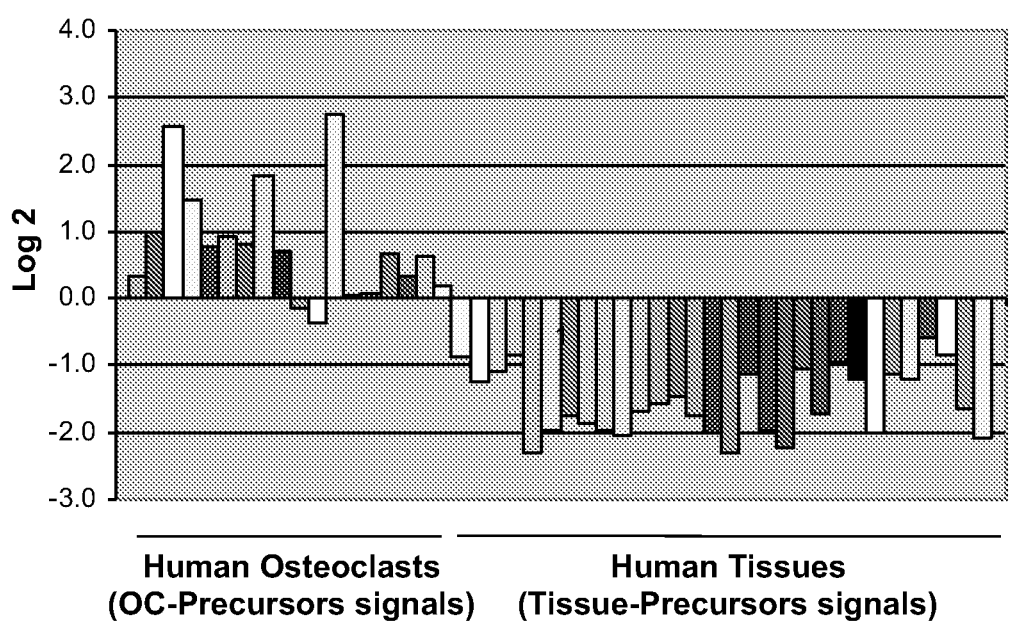

SEQUENCE LISTING

<160> NUMBER OF SEQ ID NOS: 86

<210> SEQ ID NO 1
<211> LENGTH: 1523
<212> TYPE: DNA
<213> ORGANISM: Homo sapiens

<400> SEQUENCE: 1

| | | | | | |
|---|---|---|---|---|---|
| tccggctccc | gcagagccca | cagggacctg | cagatctgag | tgccctgccc | accccgccc | 60 |
| gccttccttc | ccccaccacg | cctgggaggg | ccctcactgg | ggaggtggcc | gagaacgggt | 120 |
| ctggcctggg | gtgttcagat | gctcacagca | tggaaaagtc | catctggctg | ctggcctgct | 180 |
| tggcgtgggt | tctcccgaca | ggctcatttg | tgagaactaa | aatagatact | acggagaact | 240 |
| tgctcaacac | agaggtgcac | agctcgccag | cgcagcgctg | gtccatgcag | gtgccacccg | 300 |
| aggtgagcgc | ggaggcaggc | gacgcggcag | tgctgccctg | caccttcacg | cacccgcacc | 360 |
| gccactacga | cgggccgctg | acggccatct | ggcgcgcggg | cgagccctat | gcgggcccgc | 420 |
| aggtgttccg | ctgcgctgcg | gcgcgggca | gcgagctctg | ccagacggcg | ctgagcctgc | 480 |
| acggccgctt | ccggctgctg | ggcaacccgc | gccgcaacga | cctctcgctg | cgcgtcgagc | 540 |
| gcctcgccct | ggctgacgac | cgccgctact | tctgccgcgt | cgagttcgcc | ggcgacgtcc | 600 |
| atgaccgcta | cgagagccgc | cacggcgtcc | ggctgcacgt | gacagccgcg | ccgcggatcg | 660 |
| tcaacatctc | ggtgctgccc | agtccggctc | acgccttccg | cgcgctctgc | actgccgaag | 720 |
| gggagccgcc | gccgccctc | gcctggtccg | gcccggccct | gggcaacagc | ttggcagccg | 780 |
| tgcggagccc | cgtgagggt | cacgccacc | tagtgaccgc | cgaactgccc | gcactgaccc | 840 |
| atgacggccg | ctacacgtgt | acggccgcca | acagcctggg | ccgctccgag | gccagcgtct | 900 |
| acctgttccg | cttccatggc | gccagcgggg | cctcgacggt | cgccctcctg | ctcggcgctc | 960 |
| tcggcttcaa | ggcgctgctg | ctgctcgggg | tcctggccgc | ccgcgctgcc | cgccgccgcc | 1020 |
| cagagcatct | ggacaccccg | gacaccccac | cacggtccca | ggcccaggag | tccaattatg | 1080 |
| aaaatttgag | ccagatgaac | ccccggagcc | caccagccac | catgtgctca | ccgtgaggag | 1140 |
| tccctcagcc | accaacatcc | atttcagcac | tgtaaagaac | aaaggccagt | gcgaggcttg | 1200 |
| gctggcacag | ccagtcctgg | ttctcgggca | ccttggcagc | cccagctgg | gtggctcctc | 1260 |
| ccctgctcaa | ggtcaagacc | ctgctcaagg | aggctcatct | ggcctcctat | gtggacaacc | 1320 |
| atttcggagc | tccctgatat | ttttgccagc | atttcgtaaa | tgtgcatacg | tctgtgtgtg | 1380 |
| tgtgtgtgtg | tgagagagag | agagagagag | tacacgcatt | agcttgagcg | tgaaacttcc | 1440 |
| agaaatgttc | ccttgcccctt | tcttacctag | aacacctgct | atagtaaagc | agacaggaaa | 1500 |
| ctgttaaaaa | aaaaaaaaaa | aaa | | | | 1523 |

<210> SEQ ID NO 2
<211> LENGTH: 823
<212> TYPE: DNA
<213> ORGANISM: Homo sapiens

<400> SEQUENCE: 2

| | | | | | |
|---|---|---|---|---|---|
| acggaaacgg | gcgtgccatt | tccgcgcacg | tctgcagatg | cggtagtcga | ttggtcaagt | 60 |
| ctcccatggc | tcctccttca | tcaggaggtg | ggcaaaccgc | gccatgatag | ggtcgggatt | 120 |
| ggctggctct | ggaggcgcag | gtggtccttc | ttctactgtc | acatggtgcg | cgctgttttc | 180 |
| taatcacgtg | gctgccaccc | aggcctctct | gctcctgtct | tttgtttgga | tgccggcgct | 240 |

```
gctgcctgtg gcctcccgcc ttttgttgct accccgagtc ttgctgacca tggcctctgg      300 aagcccccg acccagccct cgccggcctc ggattccggc tctggctacg ttccgggctc       360
ggtctctgca gcctttgtta cttgccccaa cgagaaggtc gccaaggaga tcgccagggc      420
cgtggtggag aagcgcctag cagcctgcgt caacctcatc cctcagatta catccatcta      480
tgagtggaaa gggaagatcg aggaagacag tgaggtgctg atgatgatta aacccaaag      540 ttccttggtc ccagctttga cagattttgt tcgttctgtg cacccttacg aagtggccga     600
ggtaattgca ttgcctgtgg aacaggggaa cttttccgtac ctgcagtggg tgcgccaggt    660
cacagagtca gttctgact ctatcacagt cctgccatga tgagcccctgt tcctgctcat     720 catgaagatc cccgcgatac ttcaacgcct tctgacttcc aggtgatgac tgggcccca      780 ataaatcccg tctttgggtc tctctgccaa aaaaaaaaa aaa                        823

<210> SEQ ID NO 3
<211> LENGTH: 2447
<212> TYPE: DNA
<213> ORGANISM: Homo sapiens

<400> SEQUENCE: 3
cggtgtctcg tcatctccgg gaagactcgg cgcctgggtc cgcgctctct gggtaagctt      60
tccgggaagc tttcccggga gctcgctggt cctggcccca gaagcctgcg gacccgccca     120
gggaggataa gcagctgaaa gaccgcgcgg tgccgctccg aggccccggg acgtgggccc     180
atggtcggcc tggcgccacc tttccggggg aagccacgcg caccaggcat cgcacgcggc     240
tctgcacccg cgccgccgga cctgaaaccc ggcggagggc acacgggggct gccgctgcgg    300 gccccggacc aacccatgct tactccggag cctgtaccgg cgccgacggg tcggacctcc     360
ctgcgcggtg tcgcccagcg ggttcgtgcg aaaggcgggg ccgactacac gcggtgccgc    420
gccctgagac cgtttatctg cagtcaacgc agcctcccgg ctcagcctgg gaagatgcgc    480
gaatcgggaa ccccagagcg cggtggctag accgggctcc gccgcctccc ccacagcccc    540
tttcctaatc gttcagacgg agcctggtcg acttcgccgg agactgccag atctcgttcc   600
tcttccctgt gtcatcttct taattataaa taatggggga tgaagataaa agaattacat    660
atgaagattc agaaccatcc acaggaatga attacacgcc ctccatgcat caagaagcac    720
aggaggagac agttatgaag ctcaaaggta tagatgcaaa tgaaccaaca gaaggaagta    780 ttctttttgaa aagcagtgaa aaaaagctac aagaaacacc aactgaagca aatcacgtac    840
aaagactgag acaaatgctg gcttgccctc cacatggttt actggacagg gtcataacaa   900
atgttaccat cattgttctt ctgtgggctg tagtttggtc aattactggc agtgaatgtc   960
ttcctggagg aaacctattt ggaattataa tcctattcta ttgtgccatc attggtggta    1020
aacttttggg gcttattaag ttacctacat tgcctccact gccttctctt cttggcatgc    1080
tgcttgcagg gtttctcatc agaaatatcc cagtcatcaa cgataatgtg cagatcaagc   1140
acaagtggtc ttcctctttg agaagcatag ccctgtctat cattctggtt cgtgctggcc    1200
ttggtctgga ttcaaaggcc ctgaagaagt taaaggcgt ttgtgtaaga ctgtccatgg     1260
gtccctgtat tgtggaggcg tgcacatctg ctcttcttgc ccattacctg ctgggtttac    1320
catggcaatg gggatttata ctgggttttg ttttaggtgc tgtatctcca gctgttgtgg    1380
tgccttcaat gctcctttg cagggaggag gctatggtgt tgagaagggt gtcccaacct     1440
tgctcatggc agctgcagc ttcgatgaca ttctggccat cactggcttc aacacatgct    1500
tgggcatagc cttttccaca ggctctactg tctttaatgt cctcagagga gttttggagg   1560
```

-continued

```
tggtaattgg tgtggcaact ggatctgttc ttggattttt cattcagtac tttccaagcc    1620
gtgaccagga caaacttgtg tgtaagagaa cattccttgt gttggggttg tctgtgctag    1680
ctgtgttcag cagtgtgcat tttggttttcc ctggatcagg aggactgtgc acgttggtca   1740
tggctttcct tgcaggcatg ggatggacca gcgaaaaggc agaggttgaa aagataattg    1800
cagttgcctg ggacattttt cagccccttc ttttggact aattggagca gaggtatcta    1860
ttgcatctct cagaccagaa actgtaggcc tttgtgttgc caccgtaggc attgcagtat   1920
tgatacgaat tttgactaca tttctgatgg tgtgttttgc tggttttaac ttaaaagaaa    1980
agatatttat ttcttttgca tggcttccaa aggccacagt tcaggctgca ataggatctg    2040
tggctttgga cacagcaagg tcacatggag agaaacaatt agaggactat ggaatggatg    2100
tgttgacagt ggcattttg tccatcctca tcacagcccc aattggaagt ctgcttattg     2160
gtttactggg ccccaggctt ctgcagaaag ttgaacatca aaataaagat gaagaagttc    2220
aaggagagac ttctgtgcaa gtttagaggt gaaagagag agtgctgaac ataatgttta    2280
gaaagctgct actttttca agatgcatat tgaaatatgt aatgtttaag cttaaaatgt     2340
aatagaacca aaagtgtagc tgtttcttta aacagcattt ttagcccttg ctctttccat    2400
gtgggtggta atgattctat atccccaaaa aaaaaaaaaa aaaaaaa                  2447

<210> SEQ ID NO 4
<211> LENGTH: 975
<212> TYPE: DNA
<213> ORGANISM: Homo sapiens

<400> SEQUENCE: 4
gacaaccttc aggtccagcc ctggagctgg aggagtggag ccccactctg aagacgcagc      60
ctttctccag gttctgtctc tcccattctg attcttgaca ccagatgcag gatggtgtcc     120
tctccctgca cgccggcaag ctcacggact tgctcccgta tcctgggact gagccttggg     180
actgcagccc tgtttgctgc tggggccaac gtggcactcc tccttcctaa ctgggatgtc     240
acctacctgt tgaggggcct ccttggcagg catgccatgc tgggaactgg gctctgggga    300
ggaggcctca tggtactcac tgcagctatc ctcatctcct tgatgggctg gagatacggc     360
tgcttcagta agagtgggct ctgtcgaagc gtgcttactg ctctgttgtc aggtggcctg     420
gctttacttg gagccctgat ttgctttgtc acttctggag ttgctctgaa agatggtcct     480
ttttgcatgt ttgatgtttc atccttcaat cagacacaag cttggaaata tggttaccca    540
ttcaaagacc tgcatagtag gaattatctg tatgaccgtt cgctctggaa ctccgtctgc    600
ctggagccct ctgcagctgt tgtctggcac gtgtccctct tctccgccct tctgtgcatc    660
agcctgctcc agcttctcct ggtggtcgtt catgtcatca acagcctcct gggccttttc    720
tgcagcctct gcgagaagtg acaggcagaa ccttcacttg caagcatggg tgttttcatc    780
atcggctgtc ttgaatcctt tctacaagga gtgggttcag gccctctgtg gttaaagact    840
gtatccatgc tgtgctcaag gaggaactgg caaatgctga atattctcca gaagaaatgc    900
ctcagcttac aaaacatttta tcagaaaaca ttaaagataa attaaaaggt aatcatggtg    960
aaaaaaaaaa aaaaa                                                     975

<210> SEQ ID NO 5
<211> LENGTH: 1770
<212> TYPE: DNA
<213> ORGANISM: Homo sapiens

<400> SEQUENCE: 5
```

| | |
|---|---:|
| ccacgcgtcc gcacttccag ggtcggggag acggaactgc ggcgaccatg tatttctggt | 60 |
| ttatcaaacc gctaacaccc agtctaaggg caggttctgt cccattgtta tcactatcga | 120 |
| agcagccgat ggaggagggg aggtctgagc agagggcggg gtgcaggcgg aatggccctc | 180 |
| gtgccctatg aggagaccac ggaatttggg ttgcagaaat ccacaagcc tcttgcaact | 240 |
| ttttcctttg caaccacac gatccagatc cggcaggact ggagacacct gggagtcgca | 300 |
| gcggtggttt gggatgcggc catcgttctt tccacatacc tggagatggg agctgtggag | 360 |
| ctcaggggcc gctctgccgt ggagctgggt gctggcacgg gctggtggg catagtggct | 420 |
| gccctgctgg gtgctcatgt gactatcacg gatcgaaaag tagcattaga atttcttaaa | 480 |
| tcaaacgttc aagccaactt acctcctcat atccaaacta aaactgttgt taaggagctg | 540 |
| acttgggac aaaatttggg gagttttct cctggagaat ttgacctgat acttggtgct | 600 |
| gatatcatat atttagaaga aacattcaca gatcttcttc aaacactgga acatctctgt | 660 |
| agcaatcact ctgtgattct tttagcatgc cgaattcgct atgaacggga taacaacttc | 720 |
| ttagcaatgc tggagaggca atttattgtg agaaaggttc actacgatcc tgaaaaagat | 780 |
| gtacatattt acgaagcaca gaagagaaac cagaaggagg acttataatt ggctataatt | 840 |
| tataagaatg ttgtcattga gtgtgtcact taaggtctta gactgcaaat ctaaccatat | 900 |
| ttaatgaaat gtcttactgt acaaaaagtc taagccaaag gttctcaggg gagaaagcac | 960 |
| atgtgcagtt ttaaaacaaa gcagtgcttt gtcccattgc tgtgattttt agtcagactt | 1020 |
| tactcagtct gaaatgcaat taacattaaa ggattaagtg tgagatttcg atttatgcta | 1080 |
| tttgtgtatc ccatactcct ccctttaat aaacagtttc cactgatgat atgaagggcc | 1140 |
| ggtataaaga agtctttaaa tgagtaagct ttcttggtaa gattaaatct tacaaattat | 1200 |
| ttttaaaacc ttgtgatata tacaatgttt agctgagttt tctaatttc tggatgtaaa | 1260 |
| acaaaaggtt taacctatac attccttgag ctgttagtgc tatttaaatc ttttgccctg | 1320 |
| tttaggtcct aaacactttt agttgagtag gatatgagct tttttgggtc tcatatcatg | 1380 |
| cttttttgcct taatttcagg tatatatata tataagtaaa ggaattaagt aaaaataaaa | 1440 |
| tttcagttac tttttaaaag cacctgaaat ctggccggat gcggtggctc atgcctgtaa | 1500 |
| tcccaccact tgggaggcc gaggcgggca gatcacctga ggtcgggagt caagaccag | 1560 |
| cctggccaac atggtgaaac cccatctcta ctaaaaatac aaaaattagc cgggcgtggt | 1620 |
| gtcgggcgcc tgtagtccca gctgctcggg aggctgaggc aggggaatcg cttgaacctg | 1680 |
| ggaggcggag gttgcagtga gctgagattg cgccattgta ctccagcctg ggggacagga | 1740 |
| gcgagactcc atctcaaaaa aaaaaaaaaa | 1770 |

<210> SEQ ID NO 6
<211> LENGTH: 2475
<212> TYPE: DNA
<213> ORGANISM: Homo sapiens

<400> SEQUENCE: 6

| | |
|---|---:|
| gtgcagaagg cacgaggaag ccacagtgct ccggatcctc caatcttcgc tcctccaatc | 60 |
| tccgctcctc cacccagttc aggaacccgc gaccgctcgc agcgctctct tgaccactat | 120 |
| gagcctcctg tccagccgcg cggcccgtgt ccccggtcct tcgagctcct tgtgcgcgct | 180 |
| gttggtgctg ctgctgctgc tgacgcagcc agggcccatc gccagcgctg gtcctgccgc | 240 |
| tgctgtgttg agagagctgc gttgcgtttg tttacagacc acgcaaggag ttcatcccaa | 300 |
| aatgatcagt aatctgcaag tgttcgccat aggcccacag tgctccaagg tggaagtggt | 360 |

-continued

```
agcctccctg aagaacggga aggaaatttg tcttgatcca gaagccccTT ttctaaagaa     420
agtcatccag aaaattttgg acggtggaaa caaggaaaac tgattaagag aaatgagcac     480
gcatggaaaa gtttcccagt cttcagcaga aagttttct ggaggtctct gaacccaggg     540
aagacaagaa ggaaagattt tgttgttgtt tgtttatttg ttttccagt agttagcttt      600
cttcctggat tcctcacttt gaagagtgtg aggaaaacct atgtttgccg cttaagcttt     660
cagctcagct aatgaagtgt ttagcatagt acctctgcta tttgctgtta ttttatctgc     720
tatgctattg aagttttggc aattgactat agtgtgagcc aggaatcact ggctgttaat     780
cttcaaagt gtcttgaatt gtaggtgact attatatttc aagaaatat tccttaagat       840
attaactgag aaggctgtgg atttaatgtg gaaatgatgt tcataagaa ttctgttgat      900
ggaaatacac tgttatcttc acttttataa gaaataggaa atattttaat gtttcttggg    960
gaatatgtta gagaatttcc ttactcttga ttgtgggata ctatttaatt atttcacttt    1020
agaaagctga gtgtttcaca ccttatctat gtagaatata tttccttatt cagaatttct   1080
aaaagtttaa gttctatgag ggctaatatc ttatcttcct ataattttag acattcttta   1140
tcttttagt atggcaaact gccatcattt acttttaaac tttgatttta tatgctattt    1200
attaagtatt ttattaggag taccataatt ctggtagcta aatatatatt ttagatagat   1260
gaagaagcta gaaaacaggc aaattcctga ctgctagttt atatagaaat gtattctttt   1320
agttttaaa gtaaaggcaa acttaacaat gacttgtact ctgaaagttt tggaaacgta    1380
ttcaaacaat ttgaatataa atttatcatt tagttataaa aatatatagc gacatcctcg   1440
aggccctagc atttctcctt ggatagggga ccagagagag cttggaatgt aaaaacaaa    1500
acaaaacaaa aaaaaacaag gagaagttgt ccaagggatg tcaattttt atccctctgt    1560
atgggttaga ttttccaaaa tcataatttg aagaaggcca gcatttatgg tagaatatat   1620
aattatatat aaggtggcca cgctggggca agttccctcc ccactcacag ctttggcccc   1680
tttcacagag tagaacctgg gttagaggat tgcagaagac gagcggcagc ggggagggca   1740
gggaagatgc ctgtcgggtt tttagcacag ttcatttcac tgggattttg aagcatttct   1800
gtctgaatgt aaagcctgtt ctagtcctgg tgggacacac tggggttggg ggtgggggaa   1860
gatgcggtaa tgaaaccggt tagtcagtgt tgtcttaata tccttgataa tgctgtaaag   1920
tttattttta caaatatttc tgtttaagct atttcacctt tgtttggaaa tccttccctt   1980
ttaaagagaa aatgtgacac ttgtgaaaag gcttgtagga aagctcctcc ctttttttct   2040
ttaaacctt aaatgacaaa cctaggtaat taatggttgt gaatttctat ttttgctttg    2100
tttttaatga acatttgtct ttcagaatag gattctgtga taatatttaa atggcaaaaa   2160
caaaacataa ttttgtgcaa ttaacaaagc tactgcaaga aaaataaaac atttcttggt   2220
aaaaacgtat gtatttatat attatatatt tatatataat atatattata tatttagcat   2280
tgctgagctt tttagatgcc tattgtgtat cttttaaagg ttttgaccat tttgttatga   2340
gtaattacat atatattaca ttcactatat taaaattgta cttttttact atgtgtctca   2400
ttggttcata gtctttattt tgtccttga ataaacatta aagatttct aaacttcaaa     2460
aaaaaaaaaa aaaaa                                                    2475
```

<210> SEQ ID NO 7
<211> LENGTH: 2044
<212> TYPE: DNA
<213> ORGANISM: Homo sapiens

<400> SEQUENCE: 7

```
ctggacgagt ccgagcgcgt cacctcctca cgctgcggct gtcgcccgtg tcccgccggc    60
ccgttccgtg tcgccccgca gtgctgcggc cgccgcggca ccatggctgt gtttgtcgtg   120
ctcctggcgt tggtggcggg tgttttgggg aacgagttta gtatattaaa atcaccaggg   180
tctgttgttt tccgaaatgg aaattggcct ataccaggag agcggatccc agacgtggct   240
gcattgtcca tgggcttctc tgtgaaagaa gacctttctt ggccaggact cgcagtgggt   300
aacctgtttc atcgtcctcg ggctaccgtc atggtgatgg tgaagggagt gaacaaactg   360
gctctacccc caggcagtgt catttcgtac cctttggaga atgcagttcc ttttagtctt   420
gacagtgttg caaattccat tcactcctta ttttctgagg aaactcctgt tgttttgcag   480
ttggctccca gtgaggaaag agtgtatatg gtagggaagg caaactcagt gtttgaagac   540
ctttcagtca ccttgcgcca gctccgtaat cgcctgtttc aagaaaactc tgttctcagt   600
tcactccccc tcaattctct gagtaggaac aatgaagttg acctgctctt tctttctgaa   660
ctgcaagtgc tacatgatat ttcaagcttg ctgtctcgtc ataagcatct agccaaggat   720
cattctcctg atttatattc actggagctg gcaggtttgg atgaaattgg aagcgttat   780
ggggaagact ctgaacaatt cagagatgct tctaagatcc ttgttgacgc tctgcaaaag   840
tttgcagatg acatgtacag tctttatggt gggaatgcag tggtagagtt agtcactgtc   900
aagtcatttg acacctccct cattaggaag acaaggacta tccttgaggc aaaacaagcg   960
aagaacccag caagtcccta taaccttgca tataagtata attttgaata ttccgtggtt  1020
ttcaacatgg tactttggat aatgatcgcc ttggccttgg ctgtgattat cacctcttac  1080
aatatttgga acatggatcc tggatatgat agcatcattt ataggatgac aaaccagaag  1140
attcgaatgg attgaatgtt acctgtgcca gaattagaaa aggggttgg aaattggctg  1200
ttttgttaaa atatatcttt tagtgtgctt taaagtagat agtatacttt acatttataa  1260
aaaaaaatca aattttgttc tttattttgt gtgtgcctgt gatgttttc tagagtgaat  1320
tatagtattg acgtgaatcc cactgtggta tagattccat aatatgcttg aatattatga  1380
tatagccatt taataacatt gatttcattc tgtttaatga atttggaaat atgcactgaa  1440
agaaatgtaa aacatttaga atagctcgtg ttatggaaaa aagtgcactg aatttattag  1500
acaaacttac gaatgcttaa cttctttaca cagcataggt gaaaatcata tttgggctat  1560
tgtatactat gaacaatttg taaatgtctt aatttgatgt aaataactct gaacaagag   1620
aaaaggtttt taacttagag tagccctaaa atatggatgt gcttatataa tcgcttagtt  1680
ttggaactgt atctgagtaa cagaggacag ctgtttttta accctcttct gcaagtttgt  1740
tgacctacat gggctaatat ggatactaaa aatactacat tgatctaaga agaaactagc  1800
cttgtggagt atatagatgc ttttcattat acacacaaaa atccctgagg gacattttga  1860
ggcatgaata taaaacattt ttatttcagt aacttttccc cctgtgtaag ttactatggt  1920
ttgtggtaca acttcattct atagaatatt aagtggaagt gggtgaattc tactttttat  1980
gttggagtgg accaatgtct atcaagagtg acaaataaag ttaatgatga ttccaaaaaa  2040
aaaa                                                               2044
```

<210> SEQ ID NO 8
<211> LENGTH: 2392
<212> TYPE: DNA
<213> ORGANISM: Homo sapiens

<400> SEQUENCE: 8

```
agcggggcag cggctgcgcc ctgcgccggg gcggagccgg gggcgggccg gcggccggca    60
```

```
ggcggggget  ggggcccgag  gccgggagtg  cctgagcgcc  ggcggcgacg  acggcagcgg   120
cggcccagcg  ggctcggtgg  ttgggtccgc  ggcggctcgg  ggtccgcccg  cgggctgcgg   180
tgcgagcggg  cggccggct   cccctcctcc  cccgcccgcc  gccgccgctg  tgattgggtg   240
gaagatggcg  ctggccggat  ggaaatccta  atgacagtct  ccaaattcgc  ctccatctgt   300
accatgggcg  ccaatgcttc  ggcattagag  aaagagattg  gtccagaaca  gtttccggtc   360
aatgagcact  attttggatt  agtcaatttt  gggaatacct  gctactgcaa  ttcagttctt   420
caagcacttt  attttgtcg   tccatttcgg  gaaaaagttc  ttgcgtataa  gagtcaacct   480
aggaaaaagg  agagccttct  tacatgctta  gcagatctct  tccatagcat  agccactcag   540
aagaaaaagg  ttggagtaat  accccctaag  aagttcatca  caagattacg  aaagaaaat    600 gagcttttg   acaactacat  gcaacaagat  gcccatgaat  tcttaaatta  cctactaaat   660
acaattgctg  atattttaca  agaagagaga  aagcaggaaa  acaaaatgg   tcgtttacct   720 aatggtaata  ttgataatga  aaataataac  agcacaccag  acccaacgtg  ggttgatgag   780 attttcagg   gaacattaac  taatgaaacc  agatgtctta  cttgtgaaac  tataagcagc   840
aaagatgaag  attttttaga  cctttctgtt  gacgtggaac  aaaatacatc  aattactcac   900
tgcttaaggg  gtttcagcaa  cacagaaact  ctgtgcagtg  aatacaagta  ttactgtgaa   960
gagtgtcgca  gcaaacagga  agcacacaaa  cggatgaaag  ttaaaaaact  gcccatgatt  1020
ctagctctac  acctgaagag  atttaaatat  atggatcaac  ttcatcgata  tacaaaactc  1080
tcttaccggg  tagttttcc   tttagaactt  cgtctgttta  acacttcagg  tgatgccacc  1140
aatccagaca  gaatgtacga  ccttgttgct  gttgtggttc  actgtggaag  tggtcccaat  1200
cgaggccatt  atattgcaat  agttaagagt  catgattttt  ggttgttgtt  tgatgacgac  1260
attgtagaaa  aaatagatgc  acaagctatt  gaagaattct  acgggttgac  atcagatatc  1320
tcaaagaact  ctgagtctgg  ttacatcctt  ttctatcagt  ctcgggactg  agagggaacc  1380
gtgatgaaga  gacactttct  gcctcatttc  ttctctggtt  attttggaaa  ggatcaagca  1440 ctgattttc   aagaaaagag  aaatgcagga  agctcagggg  gcagtagcac  actttgcaca  1500
cgataaagca  aagacgatgg  attgacaagc  ccttccgatc  atggtagttg  atttatttgc  1560
tcaggtatca  tgctgtctgt  acagttccat  acaacaagga  ggtgaaatca  gagataccag  1620 ctcctcttt   aaaacagcct  tccagtcatt  ggcacgcatt  ttctctttat  taattgcacc  1680
aataatgctt  tgaattcctt  gggggtgcag  tagaaagaat  cggaatctgt  gccgtattga  1740
taaggagatg  atgttgaaca  cactgcataa  atttgcctgg  ttcagtatgt  atagaagcat  1800
attcagtggt  cttttcaaga  gtaaaccaga  atactttg    ggcccaacac  ttgcagttgc  1860
cttcctgatg  taaaaactaa  catgctagat  aatccagtgt  cggaagaca   aagatgtttt  1920 gcttctctga  agaagcttat  aataatatac  agtatatgta  tatgtaggga  gcaattggtc  1980
aaaagtggct  ttttgtttcc  ccaaggggaa  agactggctg  tgtaattata  attttttcct  2040
tatttatttt  acttaaaact  ggtagagtct  aagtattata  tgaagtgccc  atgattctgt  2100
cagtaaattt  gaacatattt  ttattagtta  atgtcagttt  aagttgtcct  tttgtttgtt  2160
tctattttta  aggtgaattt  taatttctat  ctgaaatcag  ttaagatacc  ttgagaaaaa  2220
ctgcagtgag  aggagataaa  tatccttttt  caggaggaac  tgatatctct  ggctaaatat  2280
ttgtcctttt  attatggttt  ctaaatcagt  tattttcttc  agctttaatt  tcataaaatt  2340
aaaaaactat  tttaaaaaaa  aaaaaaaaaa  aaaaaaaaaa  aaaaaaaaaa  aa          2392
```

<210> SEQ ID NO 9

```
<211> LENGTH: 1479
<212> TYPE: DNA
<213> ORGANISM: Homo sapiens

<400> SEQUENCE: 9
ggaagccatt gcctgtttaa tagttgctgt tgctgcactt ccgcttctct cccagcgaga      60
gagagacacg agtggccagg cccagccgca gccgcagcag cagccgccgc ggcggcacgg     120
aggagccaga cacaaagaga ggggctgttt gcggggtggg gtgggggggtt cgctatgtcg     180 gatgacgatt cgagggccag caccagctcc tcctcatctt cgtcttccaa ccagcaaacc     240
gagaaagaaa caacaccccc caagaagaag gagagtaaag tcagcatgag caaaaactcc     300
aaactcctct ccaccagcgc caagagaatt cagaaggagc tggcggacat cactttagac     360
cctccaccta attgcagtgc tggtcccaaa ggcgataaca tctatgaatg agatcaacc      420 attctagggc ctccaggatc cgtgtatgag ggtggtgtat tctttctcga tatcactttt     480
acaccagaat atcccttcaa gcctccaaag gttacatttc ggacaagaat ctatcattgt     540
aatattaaca gtcaaggtgt tatttgcttg acatattga  aagataattg gagtccagca     600
ctaaccattt ctaaagtcct cctttctatc tgctcacttc ttacagactg taatcctgcc     660 gacccctttgg tgggaagtat tgccactcag tatatgacca acagagcaga acatgacaga    720
atggccagac agtggaccaa gagatacgct acataaattg gggtttcaca attcttacat     780
tatttgtctg tcacagaaga gagctgctta tgattttgaa ggggtcaggg agggtgggag     840
ttggtaaaga gtagggtatt tctataacag atattattca gtcttatttc ctaagatttt     900
gttgtaactt aaggtatctt gctacagtag acagaattgg taatagcaac ttttaaaatt     960
gtcattagtt ctgcaatatt agctgaaatg tagtacagaa aagaatgtac atttagacat    1020
ttgggttcag ttgcttgtag tctgtaaatt taaaacagct taatttggta caggttacac    1080
atatggccat ttatgtaaag tccctctaag actacatact ttttgtttaa aacaaaattg    1140
gaatttgttt tcccttcttg aagggaaca ttgatattta acagagttt tagagattgt     1200 catctcatat atataaaatg gacacgtggc tataaaacac catataagag atgagtagtg    1260
cgttttattt tatatgccaa tctactttgt ttaaaaaagg tctgaatcag gacttgtgaa    1320
aacctgtagt gaaataccctt aagctgttaa ctaactgtaa ggcgtggaat aggagttgct    1380
cagtggattg gttctatgtt gtggactact taagtctgca tttgttactg tgctaataaa    1440
caatattaaa aaccacctaa taaacaaaaa aaaaaaaaa                           1479

<210> SEQ ID NO 10
<211> LENGTH: 931
<212> TYPE: DNA
<213> ORGANISM: Homo sapiens

<400> SEQUENCE: 10
ttgctttcct ctgccgcatg gtcctgggcc gttggcgtcg gaagcctgaa gcatgggcgc      60
tgagtgggag ctgggggccg aggctggcgg ttcgctgctg ctgtgcgccg cgctgctggc     120
ggcgggctgc gccctgggcc tgcgcctggg ccgcgggcag ggggcggcgg accgcggggc     180
gctcatctgg ctctgctacg acgcgctggt gcacttcgcg ctggaaggcc ttttgtcta     240 cttgtctttta gtaggaaacg ttgcaaattc cgatggcttg attgcttctt tatgaaaga      300 atatggcaaa gctgatgcaa gatgggttta ttttgatcca accattgtgt ctgtggaaat     360
tctgaccgtc gccctggatg ggtctctggc attgttcctc attttatgcca tagtcaaaga     420 aaaatattac cggcatttcc tgcagatcac cctgtgcgtg tgcgagctgt atggctgctg     480
```

| | |
|---|---|
| gatgaccttc ctcccagagt ggctcaccag aagccccaac ctcaacacca gcaactggct | 540 |
| gtactgttgg ctttacctgt ttttttttaa cggtgtgtgg gttctgatcc caggactgct | 600 |
| actgtggcag tcatggctag aactcaagaa aatgcatcag aaagaaacca gttcagtgaa | 660 |
| gaagtttcag tgaactttca aaaccataaa caccattatc taacttcatg aaccagaatg | 720 |
| aatcaaatct ttttgtttgg ccaaaatgta atacattcca gtctacactt tgttttttgta | 780 |
| ttgttgctcc tgaacaacct gtttcaaatt ggttttaagg cgaccagttt tcgttgtatt | 840 |
| gttgttcaat taaatggtga tatagggaaa agagaacaaa tttgaatttg taataataaa | 900 |
| atgtttaatt atacaaaaaa aaaaaaaaaa a | 931 |

<210> SEQ ID NO 11
<211> LENGTH: 6041
<212> TYPE: DNA
<213> ORGANISM: Homo sapiens

<400> SEQUENCE: 11

| | |
|---|---|
| ggtcgttttc tgatgtgacg gctgagacat gagatcttca gcctccaggc tctccagttt | 60 |
| ttcgtcgaga gattcactat ggaatcggat gccggaccag atctctgtct cggagttcat | 120 |
| cgccgagacc accgaggact acaactcgcc caccacgtcc agcttcacca cgcggctgca | 180 |
| caactgcagg aacaccgtca cgctgctgga ggaggctcta gaccaagata aacagccct | 240 |
| tcagaaagtg aagaagtctg taaaagcaat atataattct ggtcaagatc atgtacaaaa | 300 |
| tgaagaaaac tatgcacaag ttcttgataa gtttgggagt aatttttaa gtcgagacaa | 360 |
| ccccgacctt ggcaccgcgt tgtcaagtt ttctactctt acaaaggaac tgtccacact | 420 |
| gctgaaaaat ctgctccagg gtttgagcca caatgtgatc ttcaccttgg attctttgtt | 480 |
| aaaaggagac ctaaagggag tcaaaggaga tctcaagaag ccatttgaca aagcctggaa | 540 |
| agattatgag acaaagttta caaaaattga gaaagagaaa agagagcacg caaaacaaca | 600 |
| tgggatgatc cgcacagaga taacaggagc tgagattgcg gaagaaatgg agaaggaaag | 660 |
| gcgcctcttt cagctccaaa tgtgtgaata tctcattaaa gttaatgaaa tcaagaccaa | 720 |
| aaagggtgtg gatctgctgc agaatcttat aaagtattac catgcacagt gcaatttctt | 780 |
| tcaagatggc ttgaaaacag ctgataagtt gaaacagtac attgaaaaac tggctgctga | 840 |
| tttatataat ataaaacaga cccaggatga agaaagaaa cagctaactg cactccgaga | 900 |
| cttaataaaa tcctctcttc aactggatca gaaagaagat tctcagagcc ggcaaggagg | 960 |
| atacagcatg catcagctcc agggcaataa ggaatatggc agtgaaaaga aggggtacct | 1020 |
| gctaaagaaa agtgacggga tccggaaagt atggcagagg aggaagtgtt cagtcaagaa | 1080 |
| tgggattctg accatctcac atgccacatc taacaggcaa ccagccaagt tgaaccttct | 1140 |
| cacctgccaa gtaaaaccta atgccgaaga caaaaaatct tttgacctga tatcacataa | 1200 |
| tagaacatat cactttcagg cagaagatga gcaggattat gtagcatgga tatcagtatt | 1260 |
| gacaaatagc aaagaagagg ccctaaccat ggccttccgt ggagagcaga gtgcgggaga | 1320 |
| gaacagcctg aagacctga caaaagccat tattggaggat gtccagcggc tcccaggaa | 1380 |
| tgacatttgc tgcgattgtg gctcatcaga acccacctgg ctttcaacca acttgggtat | 1440 |
| tttgacctgt atagaatgtt ctggcatcca tagggaaatg ggggttcata tttctcgcat | 1500 |
| tcagtctttg gaactagaca aattaggaac ttctgaactc ttgctggcca agaatgtagg | 1560 |
| aaacaatagt tttaatgata ttatggaagc aaatttaccc agcccctcac caaaaccccac | 1620 |
| cccttcaagt gatatgactg tacgaaaaga atatatcact gcaaagtatg tagatcatag | 1680 |

```
gttttcaagg aagacctgtt caacttcatc agctaaacta aatgaattgc ttgaggccat   1740
caaatccagg gatttacttg cactaattca agtctatgca gaaggggtag agctaatgga   1800
accactgctg gaacctgggc aggagcttgg ggagacagcc cttcaccttg ccgtccgaac   1860
tgcagatcag acatctctcc atttggttga cttccttgta caaaactgtg gaacctgga    1920 taagcagacg gccctgggaa acacagttct acactactgt agtatgtaca gtaaacctga   1980
gtgtttgaag cttttgctca ggagcaagcc cactgtggat atagttaacc aggctggaga   2040
aactgcccta gacatagcaa agagactaaa agctacccag tgtgaagatc tgctttccca   2100
ggctaaatct ggaaagttca atccacacgt ccacgtagaa tatgagtgga atcttcgaca   2160
ggaggagata gatgagagcg atgatgatct ggatgacaaa ccaagcccta tcaagaaaga   2220
gcgctcaccc agacctcaga gcttctgcca ctcctccagc atctcccccc aggacaagct   2280
ggcactgcca ggattcagca ctccaaggga caaacagcgg ctctcctatg gagccttcac   2340
caaccagatc ttcgtttcca caagcacaga ctcgcccaca tcaccaacca cggaggctcc   2400
ccctctgcct cctaggaacg ccgggaaagg tccaactggc ccaccttcaa cactccctct   2460
aagcacccag acctctagtg gcagctccac cctatccaag aagaggcctc ctcccccacc   2520 accccggacac aagagaaccc tatccgaccc tcccagccca ctacctcatg gcccccaaa   2580 caaaggcgca gttccttggg gtaacgatgg gggtccatcc tcttcaagta agactacaaa   2640
caagtttgag ggactatccc agcagtcgag caccagttct gcaaagactg cccttggccc   2700
aagagttctt cctaaactac ctcagaaagt ggcactaagg aaaacagatc atctctccct   2760
agacaaagcc accatcccgc ccgaaatctt tcagaaatca tcacagttgg cagagttgcc   2820
acaaaagcca ccacctggag acctgccccc aaagcccaca gaactggccc ccaagcccca   2880
aattggagat ttgccgccta agccaggaga actgccccccc aaaccacagc tggggggacct   2940 gccacccaaa ccccaactct cagacttacc tcccaaacca cagatgaagg acctgccccc   3000
caaaccacag ctgggagacc tgctagcaaa atcccagact ggagatgtct cacccaaggc   3060
tcagcaaccc tctgaggtca cactgaagtc acacccattg gatctatccc caaatgtgca   3120
gtccagagac gccatccaaa agcaagcatc tgaagactcc aacgacctca cgcctactct   3180
gccagagacg cccgtaccac tgcccagaaa aatcaatacg gggaaaaata aagtgaggcg   3240
agtgaagacc atttatgact gccaggcaga caacgatgac gagctcacat tcatcgaggg   3300
agaagtgatt atcgtcacag gggaagagga ccaggagtgg tggattggcc acatcgaagg   3360
acagcctgaa aggaagggg tctttccagt gtcctttgtt catatcctgt ctgactagca    3420
aaacgcagaa ccttaagatt gtccacatcc ttcatgcaag actgctgcct tcatgtaacc   3480
ctgggcacag tgtgtatata gctgctgtta cagagtaaga aactcatgga agggccacct   3540
caggaggggg atataatgtg tgttgtaaat atcctgtggt tttctgcctt caccagtatg   3600
agggtagcct cggacccggc gcgccttact ggtttgccaa agccatcctt ggcatctagc   3660
acttacatct ctctatgctg ttctacaagc aaacaaacaa aaataggagt ataggaactg   3720
ctggctttgc aaatagaagt ggtctccagc aaccgttgaa aggcatagaa ttgactctgt   3780
tcctaacaat gcagtattct caattgtgtt actgaaaatg caacattagc aaagaggtgg   3840
gttctgtttt ccaggtgaaa cttttagctc catgacagac cagcctgtag ttatctgtgt   3900
acacagttta cagctacaaa aacctacttt ggtatttatt acagaaaagt gctcagttaa   3960
tgtaagtgtt attccttcag caaaatattc actgacccaa aactctttat ggcattttac   4020
aatgcacaca gcctcatgca agtttagaca agtggattta tactgtctta tgagtgcccg   4080
```

```
ccctgatat attacctcat tatgcaaaaa taacatatct ttcatgacta ttttgacaaa    4140
agtttaaaac acatatgaag ttcaaatttc aggaaccaag gactgccaga aaatattagc    4200
ctctacatta cgcatgcatt tagaagctta cctgaaatct gccttttata aaggaatagt    4260
atggataagt ggaattgtac attttttaaa cttgattgcc attaaagcag aaattataag    4320
gttgcaacaa tatttgtttc taatcactgg cttttctcaag agtatggatt gacatattgt    4380
gttatgaatg cacatctctc agatgtgttg aagcatccat tgcatccatt ttttattatt    4440
ttcttagttt tgttcttgga caaatttaaa cttttaaaag attattcaag atgaatttaa    4500
aagtcaaccc ttcacacagt ttccctactg tatgtagaat ccaggtgctg aaaccaagtg    4560 tttctttttcc catgctcttt gttaaacccc aattatagat aattttttcca gtcttaagct    4620 ctgtccacct tcaagtcaat tcataaccaa gttttttgaac gctgctatga attgcactgt    4680
gaaaagcact cttccctctc agttttcttt tcatcccagc catgtttatc agatccttaa    4740
gaacattgta tttcagtctt ttacatcagt ctgaattttg gaaagaatg caatagttgt    4800 actccacagt cagtggaact gttccctgag tccgaggctc atgtgtcatt ctggcactac    4860
atttgcttaa attgctattt tggcaacagc acagaaaact aatatttta agcagagaat    4920 cttggcaatg agtgagagat gttaatttca cagaagcaca actcccaacc caaccccttag    4980 gaaaagccct cttccatcgt tacagtgctc agtgaatatt aatttagttc tgcttaagtg    5040
gttgctatac aaactttgaa tagccaccta ataaataaac cttgcatgac aaacctgcaa    5100 aatatttttat cagctgttat tggaaagtga ttttaagcaa ttgcttcctc agtgtcaggg    5160
cacatgtgaa tttccacacc aaacagagca tgaggaacca gttgacatgc tgggttgtga    5220
ctggcagctt tagcagcctc ggtactgaag ccacaccagt gtccggatgg aagtctgcat    5280
ctgaggttgc tcagtgtccc ggtcattcat ttacacattt taacttgcat taagagctg    5340 ttcttttctg tggcctagac tcttttcact gatctcaaaa taaactggtt tttttcaaaa    5400 aaaaaaaaa aacaaaaaca aaaaaaaac acaaaagctg catgtctaaa attacatgga    5460
gttagtgtct attcttttc cccttttgca gcaacttaca cagcattttt aacacctttt    5520
ttttctagtt tttttgttcg gttttgtttt ccatcaggaa tttgagttct ctctaaccca    5580
gcttactgtg ggacatagga aaactcagta gaaataccttt tggtgatctt gttgagttta    5640
agtctgatct tgatcttaaa ctcagtaagc cactatctgc aattttgtac attatatagt    5700
attttgaaga tatggaacct tatgaaaaaa aaatagcaaa ttagttcttt ttcccccaga    5760
ggggaaagtt atgttctgca aatagtgtgt gtcttatttt actgttgaac agcaattgct    5820
atttattttt ttattgccta gaacttcaac atgttgtata ggaatcctgt agtgccacta    5880
gttaaatgcc gaattctcat ctggatgtta ccatcaaaca tcagtacact tgtcatttca    5940
catgtgttta atgtgacagt ttttcagtac tgtatgtgtt aatttctact ttttttaata    6000
tttaaaattg cttttaaata aacatattct cagttgatcc c                        6041
```

<210> SEQ ID NO 12
<211> LENGTH: 2672
<212> TYPE: DNA
<213> ORGANISM: Homo sapiens

<400> SEQUENCE: 12

```
cttccagaga gcaatatggc tggttcccca acatgcctca ccctcatcta tatcctttgg      60
cagctcacag ggtcagcagc ctctggaccc gtgaaagagc tggtcggttc cgttggtggg     120
gccgtgactt tccccctgaa gtccaaagta aagcaagttg actctattgt ctggaccttc     180
```

```
aacacaaccc ctcttgtcac catacagcca gaagggggca ctatcatagt gacccaaaat    240
cgtaataggg agagagtaga cttcccagat ggaggctact ccctgaagct cagcaaactg    300
aagaagaatg actcagggat ctactatgtg gggatataca gctcatcact ccagcagccc    360
tccacccagg agtacgtgct gcatgtctac gagcacctgt caaagcctaa agtcaccatg    420
ggtctgcaga gcaataagaa tggcacctgt gtgaccaatc tgacatgctg catggaacat    480
ggggaagagg atgtgattta tacctggaag gccctggggc aagcagccaa tgagtcccat    540
aatgggtcca tcctccccat ctcctggaga tggggagaaa gtgatatgac cttcatctgc    600
gttgccagga accctgtcag cagaaacttc tcaagcccca tccttgccag gaagctctgt    660
gaaggtgctg ctgatgaccc agattcctcc atggtcctcc tgtgtctcct gttggtgccc    720
ctcctgctca gtctctttgt actggggcta tttctttggt ttctgaagag agagagacaa    780
gaagagtaca ttgaagagaa gagagagtg acatttgtc gggaaactcc taacatatgc     840
ccccattctg gagagaacac agagtacgac acaatccctc acactaatag aacaatccta    900
aaggaagatc cagcaaatac ggtttactcc actgtggaaa taccgaaaaa gatggaaaat    960
ccccactcac tgctcacgat gccagacaca ccaaggctat ttgcctatga gaatgttatc   1020
tagacagcag tgcactcccc taagtctctg ctcaaaaaaa aaacaattct cggcccaaag   1080
aaaacaatca gaagaattca ctgatttgac tagaaacatc aaggaagaat gaagaacgtt   1140
gacttttttc caggataaat tatctctgat gcttctttag atttaagagt tcataattcc   1200
atccactgct gagaaatctc ctcaaaccca gaaggtttaa tcacttcatc ccaaaaatgg   1260
gattgtgaat gtcagcaaac cataaaaaaa gtgcttagaa gtattcctat agaaatgtaa   1320
atgcaaggtc acacatatta atgacagcct gttgtattaa tgatggctcc aggtcagtgt   1380
ctggagtttc attccatccc agggcttgga tgtaaggatt ataccaagag tcttgctacc   1440
aggagggcaa gaagaccaaa acagacagac aagtccagca gaagcagatg cacctgacaa   1500
aaatggatgt attaattggc tctataaact atgtgcccag cactatgctg agcttacact   1560
aattggtcag acgtgctgtc tgccctcatg aaattggctc caaatgaatg aactactttc   1620
atgagcagtt gtagcaggcc tgaccacaga ttcccagagg gccaggtgtg gatccacagg   1680
acttgaaggt caaagttcac aaagatgaag aatcagggta gctgaccatg tttggcagat   1740
actataatgg agacacagaa gtgtgcatgg cccaaggaca aggacctcca gccaggcttc   1800
atttatgcac ttgtgctgca aaagaaaagt ctaggtttta aggctgtgcc agaacccatc   1860
ccaataaaga gaccgagtct gaagtcacat tgtaaatcta gtgtaggaga cttggagtca   1920
ggcagtgaga ctggtggggc acggggggca gtgggtactt gtaaaccttt aaagatggtt   1980
aattcattca atagatattt attaagaacc tatgcggccc ggcatggtgg ctcacacctg   2040
taatcccagc actttgggag gccaaggtgg gtgggtcatc tgaggtcagg agttcaagac   2100
cagcctggcc aacatggtga aacccatct ctactaaaga tacaaaaatt tgctgagcgt    2160
ggtggtgtgc acctgtaatc ccagctactc gagaggccaa ggcatgagaa tcgcttgaac   2220 ctggaggtg gaggttgcag tgagctgaga tggcaccact gcactccggc ctaggcaacg    2280
agagcaaaac tccaatacaa acaaacaaac aaacacctgt gctaggtcag tctggcacgt   2340
aagatgaaca tccctaccaa cacagagctc accatctctt atacttaagt gaaaaacatg   2400
gggaagggga aaggggaatg gctgcttttg atatgttccc tgacacatat cttgaatgga   2460
gacctcccta ccaagtgatg aaagtgttga aaaacttaat aacaaatgct tgttgggcaa   2520
gaatgggatt gaggattatc ttctctcaga aaggcattgt gaaggaattg agccagatct   2580
```

```
ctctccctac tgcaaaaccc tattgtagta aaaaagtctt ctttactatc ttaataaaac    2640
agatattgtg agattcaaaa aaaaaaaaaa aa                                   2672

<210> SEQ ID NO 13
<211> LENGTH: 1559
<212> TYPE: DNA
<213> ORGANISM: Homo sapiens

<400> SEQUENCE: 13
gactgcgcgg ccgggaggag ccgagccggg cggcggcggc gggaggctac agcgcgcggg     60
ggtctcccgc gtcccctccg cctcgccggg agctcgcgcc ctcgcccagc cgagctccca    120
cccccgcttt tttccgaagg cgctgggcgg cgccaccctc cggccggagc ccggcactgc    180 acaacccccct ccgactttca atgttccaca ctccccggcc agagcctcct cggcttcttt    240
ttttccctcc ccccccttcc ccccccaca gctgcctcca tttccttaag gaagggtttt     300
tttctctctc cctcccccac accgtagcgg cgcgcgagcg ggccgggcgg gcggccgagt    360
tttccaagag ataacttcac caagatgtcc agtgataggc aaaggtccga tgatgagagc    420
cccagcacca gcagtggcag ttcagatgcg gaccagcgag acccagccgc tccagagcct    480
gaagaacaag aggaaagaaa accttctgcc acccagcaga gaaaaacac caaactctct    540 agcaaaacca ctgctaagtt atccactagt gctaaaagaa ttcagaagga gctagctgaa    600
ataacccttg atcctcctcc taattgcagt gctgggccta aaggagataa catttatgaa    660
tggagatcaa ctatacttgg tccaccgggt tctgtatatg aagtggtgt gttttttctg    720 gatatcacat tttcatcaga ttatccattt aagccaccaa aggttacttt ccgcaccaga    780
atctatcact gcaacatcaa cagtcaggga gtcatctgtc tggacatcct taaagacaac    840
tggagtcccg ctttgactat ttcaaaggtt ttgctgtcta tttgttccct tttgacagac    900
tgcaaccctg cggatcctct ggttggaagc atagccactc agtatttgac aacagagca    960 gaacacgaca ggatagccag acagtggacc aagagatacg caacataatt cacataattt   1020
gtatgcagtg tgaaggagca gaaggcatct tctcactgtg ctgcaaatct ttatagcctt   1080
tacaatacgg acttctgtgt atatgttata ctgattctac tctgcttttta tccttttggag  1140 cctgggagac tccccaaaaa ggtaaatgct atcaagagta gaactttgta gctgtagatt   1200
agttatgttt aaaacgccta cttgcaagtc ttgcttcttt gggatatcaa aatgtatttt   1260
gtgatgtact aaggatactg gtcctgaagt ctaccaaata ttatagtgca ttttagccta   1320
attcattatc tgtatgaagt tataaaagta gctgtagatg gctaggaatt atgtcatttg   1380
tattaaaccc agatctattt ctgagtatgt ggttcatgct gttgtgaaaa atgttttacc   1440 ttttacctttt gtcagtttgt aatgagagga tttcctttta ccctttgtag ctcagagagc   1500
acctgatgta tcatctcaaa cacaataaac atgctcctga aggaaaaaaa aaaaaaaaa    1559

<210> SEQ ID NO 14
<211> LENGTH: 765
<212> TYPE: DNA
<213> ORGANISM: Homo sapiens

<400> SEQUENCE: 14
ccacgcgtcc gggaccccggc ccgcgccttc tgcccctgct gccggccgcg ccatgcggtg     60
agcgccccag gccgccagag cccacccgac ccggcccgac gccgggacct gccgcccaga    120
cccgccaccg cacccggacc ccgacgctcc gaacccgggc gcagccgcag ctcaagatgg    180
cccgaggcag cgccctcctt ctcgcctccc tcctcctcgc gcggccctt tctgcctctg    240
```

| | |
|---|---|
| cggggctctg gtcgccggcc aaggaaaaac gaggctggac cctgaacagc gcgggctacc | 300 |
| tgctgggccc acatgccgtt ggcaaccaca ggtcattcag cgacaagaat ggcctcacca | 360 |
| gcaagcggga gctgcggccc gaagatgaca tgaaaccagg aagctttgac aggtccatac | 420 |
| ctgaaaacaa tatcatgcgc acaatcattg agtttctgtc tttcttgcat ctcaaagagg | 480 |
| ccggtgccct cgaccgcctc ctggatctcc ccgccgcagc ctcctcagaa gacatcgagc | 540 |
| ggtcctgaga gcctcctggg catgtttgtc tgtgtgctgt aacctgaagt caaaccttaa | 600 |
| gataatggat aatcttcggc caatttatgc agagtcagcc attcctgttc tctttgcctt | 660 |
| gatgttgtgt tgttatcatt taagatttt ttttttggt aattattttg agtggcaaaa | 720 |
| taaagaatag caattaaaaa aaaaaaaca aaaaaaaaa aaaaa | 765 |

<210> SEQ ID NO 15
<211> LENGTH: 3732
<212> TYPE: DNA
<213> ORGANISM: Homo sapiens

<400> SEQUENCE: 15

| | |
|---|---|
| cggtggttgg gtggtaagat ggcggctgtg agtctgcggc tcggcgactt ggtgtggggg | 60 |
| aaactcggcc gatatcctcc ttggccagga aagattgtta atccaccaaa ggacttgaag | 120 |
| aaacctcgcg gaaagaaatg cttctttgtg aaatttttg gaacagaaga tcatgcctgg | 180 |
| atcaaagtgg aacagctgaa gccatatcat gctcataaag aggaaatgat aaaaattaac | 240 |
| aagggtaaac gattccagca agcggtagat gctgtcgaag agttcctcag gagagccaaa | 300 |
| gggaaagacc agacgtcatc ccacaattct tctgatgaca agaatcgacg taattccagt | 360 |
| gaggagagaa gtaggccaaa ctcaggtgat gagaagcgca aacttagcct gtctgaaggg | 420 |
| aaggtgaaga agaacatggg agaaggaaag aagagggtgt cttcaggctc ttcagagaga | 480 |
| ggctccaaat cccctctgaa aagagcccaa gagcaaagtc cccggaagcg ggtcggcccc | 540 |
| ccaaaggatg agaaggatct caccatcccg gagtctagta ccgtgaaggg gatgatggcc | 600 |
| ggaccgatgg ccgcgtttaa atggcagcca accgcaagcg agcctgttaa agatgcagat | 660 |
| cctcatttcc atcatttcct gctaagccaa acagagaagc cagctgtctg ttaccaggca | 720 |
| atcacgaaga agttgaaaat atgtgaagag gaaactggct ccacctccat ccaggcagct | 780 |
| gacagcacag ccgtgaatgg cagcatcaca cccacagaca aaaagatagg attttttggc | 840 |
| cttggtctca tgggaagtgg aatcgtctcc aacttgctaa aaatgggtca cacagtgact | 900 |
| gtctggaacc gcactgcaga gaatgtgat ttgttcatcc aggaggggc ccgtctggga | 960 |
| agaaccccg ctgaagtcgt ctcaacctgc gacatcactt tcgcctgcgt gtcggatccc | 1020 |
| aaggcggcca aggacctggt gctgggcccc agtggtgtgc tgcaagggat ccgccctggg | 1080 |
| aagtgctacg tggacatgtc aacagtggac gctgacaccg tcactgagct ggcccaggtg | 1140 |
| attgtgtcca gggggggcg ctttctggaa gccccgtct cagggaatca gcagctgtct | 1200 |
| aatgacggga tgttggtgat cttagcggct ggagacaggg gcttatatga ggactgcagc | 1260 |
| agctgcttcc aggcgatggg gaagacctcc ttcttcctag gtgaagtggg caatgcagcc | 1320 |
| aagatgatgc tgatcgtgaa catggtccaa gggagcttca tggccactat tgccgagggg | 1380 |
| ctgaccctgg cccaggtgac aggccagtcc cagcagacac tcttggacat cctcaatcag | 1440 |
| ggacagttgg ccagcatctt cctggaccag aagtgccaaa atatcctgca aggaaacttt | 1500 |
| aagcctgatt tctacctgaa atacattcag aaggatctcc gcttagccat tgcgctgggt | 1560 |
| gatgcggtca accatccgac tcccatggca gctgcagcaa atgaggtgta caaaagagcc | 1620 |

| | |
|---|---|
| aaggcgctgg accagtccga caacgatatg tccgccgtgt accgagccta catacactaa | 1680 |
| gctgtcgaca ccccgccctc acccctccaa tccccctct gacccctct tcctcacatg | 1740 |
| gggtcggggg cctgggagtt cattctggac cagcccacct atctccattt ccttttatac | 1800 |
| agactttgag acttgccatc agcacagcac acagcagcac ccttcccctg aggccggtgg | 1860 |
| ggaggggaca agtgtcagca ggattggcgt gtgggaaagc tcttgagctg ggcactggcc | 1920 |
| ccccggacga ggtggctgtg tgttcacaca cacacacaca cacacacaca cacacacaca | 1980 |
| caggctctcg ccccaggata gaagctgccc agaaactgct gcctggcttt ttttcttccg | 2040 |
| agcttgtctt atctcaaacc ccttccagtc aaggaactag aatcagcaac gagagttgga | 2100 |
| agccttccca cagcttcccc cagagcgaag aggctgtagt catgtcccca tcccccactg | 2160 |
| gattccctac aaggagaggc cttgggccca gatgagccag tacagactcc agacagaggg | 2220 |
| gcccttgggg ccctccaacc tcaggtgatg agctgagaaa gatgttcacg tctaagcgtc | 2280 |
| cagtgtgcac ccagcgctcc atagacgcct ttgtgaactg aaaagagact ggcagagtcc | 2340 |
| cgagaagatg gggccctggc tttccaggga gtgcagcaag cagccggcct gcaggtgagc | 2400 |
| atggaggccc ggccctcacc gcctcgaagc catgccccag atgccactgc cacagcgggc | 2460 |
| gctcgctcct ccctaggctg ttttagtatt tggatttgca ttccatccct tgggagggag | 2520 |
| tcctcagggc cactagtgat gagccaagag gagtgggggt tggggcgct cctttctgtt | 2580 |
| tccgttaggc cacagactct tcacctggct ctgaagagcc actcttacct cggtcccctc | 2640 |
| ccagtggtcc caccttctcc accctgccct gccaagtccc ctgcatgccc accgctctcc | 2700 |
| atcctccctc ctctccctct tcctcccgtg gagacagtat ttctttctgt ctgtcccttt | 2760 |
| ggcccagacc cagcctgacc aacgatgagc atttcttagg ctcagctctt gatacggaaa | 2820 |
| cgagtgtctt cactccagcc agcatcatgg tcttcggtgc ttcccgggcc ggggtctgt | 2880 |
| cgggagggaa gagaactggg cctgacctac ctgaactgac tggccctccg aggtgggtct | 2940 |
| gggacatcct agaggcccta catttgtcct tggatagggg accggggggg gcttggaatg | 3000 |
| ttgcaaaaaa aaagttaccc aagggatgtc agttttttat ccctctgcat gggttggatt | 3060 |
| ttccaaaatc ataatttgca gaaggaaggc cagcatttac gatgcaatat gtaattatat | 3120 |
| atagggtggc cacactaggg cggggtcctt ccccccctaca cagctttggc cccttcaga | 3180 |
| gattagaaac tgggttagag gattgcagaa gacgagtggg gggagggcag ggaagatgcc | 3240 |
| tgtcgggttt ttagcacagt tcatttcact gggattttga agcatttctg tctgaacaca | 3300 |
| agcctgttct agtcctggcg gaacacactg ggggtggggg cggggaaga tgcggtaatg | 3360 |
| aaaccggtta gtcaattttg tcttaatatt gttgacaatt ctgtaaagtt cctttttatg | 3420 |
| aatatttctg tttaagctat ttcaccttc ttttgaaatc cttccctttt aaggagaaaa | 3480 |
| tgtgacactt gtgaaaaagc ttgtaagaaa gcccctccct ttttttcttt aaacctttaa | 3540 |
| atgacaaatc taggtaatta aggttgtgaa tttttatttt tgctttgttt ttaatgaaca | 3600 |
| tttgtctttc agaataggat tgtgtgataa tgtttaaatg gcaaaacaa aacatgattt | 3660 |
| tgtgcaatta acaaagctac tgcaagaaaa ataaaacact tcttggtaac acaaaaaaaa | 3720 |
| aaaaaaaaaa aa | 3732 |

```
<210> SEQ ID NO 16
<211> LENGTH: 4666
<212> TYPE: DNA
<213> ORGANISM: Homo sapiens

<400> SEQUENCE: 16
```

```
agtaccttgg tccagctctt cctgcaacgg cccaggagct cagagctcca catctgacct      60
tctagtcatg accaggacca gggcagcact cctcctgttc acagccttag caacttctct     120
aggtttcaac ttggacacag aggagctgac agccttccgt gtggacagcg ctgggtttgg     180
agacagcgtg gtccagtatg ccaactcctg ggtggtggtt ggagccccccc aaaagataac    240
agctgccaac caaacgggtg gcctctacca gtgtggctac agcactggtg cctgtgagcc     300
catcggcctg caggtgcccc cggaggccgt gaacatgtcc ctgggcctgt ccctggcgtc     360
taccaccagc ccttcccagc tgctggcctg cggccccacc gtgcaccacg agtgcgggag     420
gaacatgtac ctcaccggac tctgcttcct cctgggcccc acccagctca cccagaggct     480
cccggtgtcc aggcaggagt gcccaagaca ggagcaggac attgtgttcc tgatcgatgg     540
ctcaggcagc atctcctccc gcaactttgc cacgatgatg aacttcgtga gagctgtgat     600
aagccagttc cagagaccca gcacccagtt ttccctgatg cagttctcca acaaattcca     660
aacacacttc actttcgagg aattcaggcg cagctcaaac cccctcagcc tgttggcttc     720
tgttcaccag ctgcaagggt ttacatacac ggccaccgcc atccaaaatg tcgtgcaccg     780
attgttccat gcctcatatg gggcccgtag ggatgccgcc aaaattctca ttgtcatcac     840
tgatgggaag aaagaaggcg acagcctgga ttataaggat gtcatcccca tggctgatgc     900
agcaggcatc atccgctatg caattggggt tggattagct tttcaaaaca gaaattcttg     960
gaaagaatta aatgacattg catcgaagcc ctcccaggaa cacatattta agtggaggaa    1020
ctttgatgct ctgaaagata ttcaaaaacca actgaaggag aagatctttg ccattgaggg   1080
tacggagacc acaagcagta gctccttcga attggagatg gcacaggagg gcttcagcgc    1140
tgtgttcaca cctgatggcc ccgttctggg ggctgtgggg agcttcacct ggtctggagg    1200
tgccttcctg tacccccccaa atatgagccc taccttcatc aacatgtctc aggagaatgt    1260
ggacatgagg gactcttacc tgggttactc caccgagctg gccctctgga aaggggtgca    1320
gagcctggtc ctgggggccc cccgctacca gcacaccggg aaggctgtca tcttcaccca    1380
ggtgtccagg caatggagga tgaaggccga agtcacgggg actcagatcg gctcctactt    1440
cggggcctcc ctctgctccg tggacgtaga cagcgacggc agcaccgacc tggtcctcat    1500
cggggccccc cattactacg agcagacccg agggggccag gtgtctgtgt gtcccttgcc    1560
caggggggtgg agaaggtggt ggtgtgatgc tgttctctac ggggagcagg gccacccctg    1620
gggtcgcttt ggggcggctc tgacagtgct ggggggatgtg aatgggggaca agctgacaga   1680
cgtggtcatc ggggccccag gagaggagga gaaccggggt gctgtctacc tgtttcacgg    1740
agtcttggga cccagcatca gcccctccca cagccagcgg atcgcgggct cccagctctc    1800
ctccaggctg cagtattttg gcaggcact gagcgggggt caagacctca cccaggatgg    1860
actggtggac ctggctgtgg gggcccgggg ccaggtgctc ctgctcagga ccagacctgt    1920
gctctgggtg ggggtgagca tgcagttcat acctgccgag atccccaggt ctgcgtttga    1980
gtgtcgggag caggtggtct ctgagcagac cctggtacag tccaacatct gcctttacat    2040
tgacaaacgt tctaagaacc tgcttgggag ccgtgacctc caaagctctg tgaccttgga    2100
cctggccctc gaccctggcc gcctgagtcc ccgtgccacc ttccaggaaa caaagaaccg    2160
gagtctgagc cgagtccgag tcctcgggct gaaggcacac tgtgaaaact tcaacctgct    2220
gctcccgagc tgcgtggagg actctgtgac ccccattacc ttgcgtctga acttcacgct    2280
ggtgggcaag cccctccttg ccttcagaaa cctgcggcct atgctggccg ccgatgctca    2340
gagatacttc acggcctccc taccctttga gaagaactgt ggagccgacc atatctgcca    2400
```

```
ggacaatctc ggcatctcct tcagcttccc aggcttgaag tccctgctgg tggggagtaa    2460
cctggagctg aacgcagaag tgatggtgtg aatgacggg gaagactcct acggaaccac     2520
catcaccttc tcccaccccg caggactgtc ctaccgctac gtggcagagg ccagaaaca     2580 agggcagctg cgttccctgc acctgacatg tgacagcgcc ccagttggga gccagggcac    2640
ctggagcacc agctgcagaa tcaaccacct catcttccgt ggcggcgccc agatcacctt    2700
cttggctacc tttgacgtct cccccaaggc tgtcctggga accggctgc ttctgacagc     2760 caatgtgagc agtgagaaca cactcccag gaccagcaag accaccttcc agctggagct     2820
cccggtgaag tatgctgtct acactgtggt tagcagccac gaacaattca ccaaatacct    2880
caacttctca gagtctgagg agaaggaaag ccatgtggcc atgcacagat accaggtcaa    2940
taacctggga cagagggacc tgcctgtcag catcaacttc tgggtgcctg tggagctgaa    3000
ccaggaggct gtgtggatgg atgtggaggt ctcccacccc cagaacccat cccttcggtg    3060
ctcctcagag aaaatcgcac ccccagcatc tgacttcctg gcgcacattc agaagaatcc    3120
cgtgctggac tgctccattg ctggctgcct gcggttccgc tgtgacgtcc cctccttcag    3180
cgtccaggag gagctggatt tcaccctgaa gggcaacctc agctttggct gggtccgcca    3240
gatattgcag aagaaggtgt cggtcgtgag tgtggctgaa attacgttcg acacatccgt    3300
gtactcccag cttccaggac aggaggcatt tatgagagct cagacgacaa cggtgctgga    3360
gaagtacaag gtccacaacc ccaccccccct catcgtaggc agctccattg ggggtctgtt    3420
gctgctggca ctcatcacag cggtactgta caagttggc ttcttcaagc gtcagtacaa     3480
ggaaatgatg gaggaggcaa atggacaaat tgccccagaa acgggacac agaccccag      3540 cccgcccagt gagaaatgat cccctctttg ccttggactt cttctccccc gcgagttttc    3600
cccacttact taccctcacc tgtcaggcct gacgggagg aaccactgca ccaccgagag     3660
aggctgggat gggcctgctt cctgtctttg ggagaaaacg tcttgcttgg aaggggcct    3720 ttgtcttgtc aaggttccaa ctggaaaccc ttaggacagg gtccctgctg tgttccccaa    3780
aggacttgac ttgcaatttc tacctagaaa tacatggaca atacccccag gcctcagtct    3840
cccttctccc atgaggcacg aatgatcttt cttcctttc tttttttttt ttttctttt     3900 ctttttttt ttttgagac ggagtctcgc tctgtcaccc aggctggagt gcaatggcgt      3960
gatctcggct cactgcaacc tccgcctccc gggttcaagt aattctgctg tctcagcctc    4020
ctgagtagct gggactacag gcacacgcca cctcgcccgg cccgatcttt ctaaaataca    4080
gttctgaata tgctgctcat ccccacctgt cttcaacagc tccccattac cctcaggaca    4140
atgtctgaac tctccagctt cgcgtgagaa gtccccttcc atcccagagg gtgggcttca    4200
gggcgcacag catgagaggc tctgtgcccc catcaccctc gtttccagtg aattagtgtc    4260
atgtcagcat cagctcaggg cttcatcgtg gggctctcag ttccgatttc ccaggctgaa    4320
ttgggagtga gatgcctgca tgctgggttc tgcacagctg gcctcccgcg ttgggcaaca    4380
ttgctggctg aagggagga gcgccctcta gggagggaca tggccccggt gcggctgcag     4440
ctcacccagc ccaggggca gaagagaccc aaccacttct attttttgag gctatgaata     4500
tagtacctga aaaatgcca agacatgatt attttttaa aaagcgtact ttaaatgttt      4560
gtgttaataa attaaaacat gcacaaaaag atgcatctac cgctcttggg aaatatgtca    4620
aaggtctaaa aataaaaaag ccttctgtga aaaaaaaaa aaaaa                     4666
```

<210> SEQ ID NO 17  
<211> LENGTH: 4086  
<212> TYPE: DNA

<213> ORGANISM: Homo sapiens

<400> SEQUENCE: 17

```
aatggagccg ctgtcagcag aaccttctgc cgccgccgcc gccgccgccg tccctcctct    60
ttttttccc ggcagatctt tgttgtgtgg gagggcagca gggatggact tgagcttgcg   120
gatcccctgc tagagcagcc gcgctcggag aaggcgccgc agccgcgagg aggagccgcc   180
gccgccgcgc ccgaggcccc gccgcccgcg gcctctgtcg gccgcgccc cgctcgcccc   240
gtcgccccgt cgcccctcgc ctccccgcag agtcccctcg cggcagcaga tgtgtgtggg   300
gtcagcccac ggcggggact atggtgaaat tcccggcgct cacgcactac tggcccctga   360
tccggttctt ggtgcccctg ggcatcacca acatagccat cgacttcggg gagcaggcct   420
tgaaccgggg cattgctgct gtcaaggagg atgcagtcga gatgctggcc agctacgggc   480
tggcgtactc cctcatgaag ttcttcacgg gtcccatgag tgacttcaaa aatgtgggcc   540
tggtgtttgt gaacagcaag agagacagga ccaaagccgt cctgtgtatg gtggtggcag   600
gggccatcgc tgccgtcttt cacacactga tagcttatag tgatttagga tactacatta   660
tcaataaact gcaccatgtg gacgagtcgg tggggagcaa gacgagaagg gccttcctgt   720
acctcgccgc cttcctttc atggacgcaa tggcatggac ccatgctggc attctcttaa   780
aacacaaata cagtttcctg gtgggatgtg cctcaatctc agatgtcata gctcaggttg   840
ttttgtagc cattttgctt cacagtcacc tggaatgccg ggagcccctg ctcatcccga   900
tcctctcctt gtacatgggc gcacttgtgc gctgcaccac cctgtgcctg gctactaca   960
agaacattca cgacatcatc cctgacagaa gtggcccgga gctgggggga gatgcaacaa  1020
taagaaagat gctgagcttc tggtggcctt tggctctaat tctggccaca cagagaatca  1080
gtcggcctat tgtcaacctc tttgtttccc gggaccttgg tggcagttct gcagccacag  1140
aggcagtggc gattttgaca gccacatacc ctgtgggtca catgccatac ggctggttga  1200
cggaaatccg tgctgtgtat cctgctttcg acaagaataa cccagcaac aaactggtga  1260
gcacgagcaa cacagtcacg gcagcccaca tcaagaagtt caccttcgtc tgcatggctc  1320
tgtcactcac gctctgtttc gtgatgtttt ggacacccaa cgtgtctgag aaaatcttga  1380
tagacatcat cggagtggac tttgcctttg cagaactctg tgttgttcct ttgcggatct  1440
tctccttctt cccagttcca gtcacagtga gggcgcatct caccgggtgg ctgatgacac  1500
tgaagaaaac cttcgtcctt gccccagct ctgtgctgcg gatcatcgtc ctcatcgcca  1560
gcctcgtggt cctaccctac ctgggggtgc acggtcgac cctgggcgtg gctccctcc   1620
tggcgggctt tgtgggagaa tccaccatgg tcgccatcgc tgcgtgctat gtctaccgga  1680
agcagaaaaa gaagatggag aatgagtcgg ccacggaggg ggaagactct gccatgacag  1740
acatgcctcc gacagaggag gtgacagaca tcgtggaaat gagagaggag aatgaataag  1800
gcacgggacg ccatgggcac tgcagggaca gtcagtcagg atgacacttc ggcatcatct  1860
cttccctctc ccatcgtatt tgttcccctt tttttgttt tgttttggta atgaaagagg  1920
ccttgattta aaggtttcgt gtcaattctc tagcatactg ggtatgctca cactgacggg  1980
gggacctagt gaatggtctt tactgttgct atgtaaaaac aaacgaaaca actgacttca  2040
taccctgcc tcacgaaaac ccaaaagaca cagctgcctc acggttgacg ttgtgtcctc  2100
ctcccctgga caatctcctc ttggaaccaa aggactgcag ctgtgccatc gcgcctcggt  2160
caccctgcac agcaggccac agactctcct gtccccttc atcgctctta agaatcaaca  2220
ggttaaaact cggcttcctt tgatttgctt cccagtcaca tggccgtaca aagagatgga  2280
```

```
gccccggtgg cctcttaaat ttcccttccg ccacggagtt cgaaaccatc tactccacac    2340
atgcaggagg cgggtggcac gctgcagccc ggagtccccg ttcacactga ggaacggaga    2400
cctgtgacca cagcaggctg acagatggac agaatctccc gtagaaaggt ttggtttgaa    2460
atgcccaggg ggcagcaaac tgacatggtt gaatgatagc atttcactct gcgttctcct    2520
agatctgagc aagctgtcag ttctcacccc caccgtgtat atacatgagc taactttttt    2580
aaattgtcac aaaagcgcat ctccagattc cagaccctgc cgcatgactt ttcctgaagg    2640
cttgcttttc cctcgccttt cctgaaggtc gcattagagc gagtcacatg gagcatccta    2700
actttgcatt ttagttttta cagtgaactg aagctttaag tctcatccag cattctaatg    2760
ccaggttgct gtagggtaac ttttgaagta gatatattac ctggttctgc tatccttagt    2820
cataactctg cggtacaggt aattgagaat gtactacggt acttccctcc cacaccatac    2880
gataaagcaa gacattttat aacgatacca gagtcactat gtggtcctcc ctgaaataac    2940
gcattcgaaa tccatgcagt gcagtatatt tttctaagtt ttggaaagca ggttttttcc    3000
tttaaaaaaa ttatagacac ggttcactaa attgatttag tcagaattcc tagactgaaa    3060
gaacctaaac aaaaaaatat tttaaagata taaatatatg ctgtatatgt tatgtaatt    3120 attttaggct ataatacatt tcctattttc gcattttcaa taaaatgtct ctaatacaat    3180
acggtgattg cttgtgtgct caacatacct gcagttgaaa cgtattgtat caatgaacat    3240
tgtaccttat tggcagcagt tttataaagt ccgtcatttg catttgaatg taaggctcag    3300
taaatgacag aactatttt cattatgggt aactggggaa taaatgggtc actggagtag    3360
gaatagaagt gcaagctgga aaggcaaaaa tgagaaagaa aaaggcaggc cctttgtgtc    3420
taccgttttc agtgctgtgt gatcatattg ttcctcacag caaaaaagaa tgcaagggca    3480
taatgttagc tgtgaacatg ccagggttgc attcacattc ctgggtaccc agtgctgatg    3540
gggtgtgccc acgtggggac atgtccttgg cgtgcttcct cagagtggct tttcctccat    3600
taatacatat atgagtactg aaaaattaag ttgcatagct gctttgcagt ggtttcagag    3660
gcagatctga aagagattaaa aaaaaatctc aatgtatcag ctttttttaa aggacattac    3720
tagaaaatta aacagtattt tttaacatgt gtgactttca tgcttctggg gttggagctt    3780
aaagatccaa actgagaaag caggccgggc atggtggctc atgcctgtaa tcccaacact    3840
ttgggaggcc aaggagggtg gatcacttaa ggtcaggagt tgagaccag cctggccaac    3900 atggcaaaac cctgtctcta ctaaaaacat aaaaattagc tgggggtggt agcacatacc    3960
tgtaatccca gctactcagg aggctgaggc aggagaattt gcttgatcct gggaggcaga    4020
ggttgtagtg agccgagatc gcgccatcgc actccagcct gggtgacaag agcaaaactc    4080
catctc                                                              4086

<210> SEQ ID NO 18
<211> LENGTH: 4567
<212> TYPE: DNA
<213> ORGANISM: Homo sapiens

<400> SEQUENCE: 18
gacagcctct gggtcctcgg tcggtacagt ctctgcacct cgcgccccag caggtaaact      60
aacattatgg attttccaa gctacccaaa atactcgatg aagataaaga agcacatt       120 ggttatgtgc atgggtctc aggacctgtg gttacagcct gtgacatggc gggtgcagcc     180
atgtatgagc tggtgagagt gggccacagc gaattggttg gagagattat tcgattggag    240
ggtgacatgg ctactattca ggtgtatgaa gaaacttctg gtgtgtctgt tggagatcct    300
```

```
gtacttcgca ctggtaaacc cctctctgta gagcttggtc ctggcattat gggagccatt     360
tttgatggta ttcaaagacc tttgtcggat atcagcagtc agacccaaag catctacatc     420
cccagaggag taaacgtgtc tgctcttagc agagatatca aatgggactt tacaccttgc     480
aaaaacctac gggttggtag tcatatcact ggcggagaca tttatggaat tgtcagtgag     540
aactcgctta tcaaacacaa aatcatgtta cccccacgaa acagaggaac tgtaacttac     600
attgctccac ctgggaatta tgatacctct gatgttgtct tggagcttga atttgaaggt     660
gtaaaggaga agttcaccat ggtgcaagta tggcctgtac gtcaagttcg acctgtcact     720
gagaagctgc cagccaatca tcctctgttg actggccaga gagtccttga tgcccttttt     780
ccgtgtgtcc agggaggaac tactgctatc cctggagcct ttggctgtgg aaagacagtg     840
atatcacagt ctctatccaa gtattctaac agtgatgtaa tcatctatgt aggatgtggt     900
gaaagaggaa atgagatgtc tgaagtcctc cgggacttcc cagagctcac aatggaggtt     960
gatggtaagg tagagtcaat tatgaagagg acagctttgg tagccaatac ctccaatatg    1020
cctgttgctg ctagagaagc ctctatttat actggaatca cactgtcaga gtacttccgt    1080
gacatgggct atcatgtcag tatgatggct gactctacct ctagatgggc tgaggccctt    1140
agagaaatct ctggtcgttt agctgaaatg cctgcagata gtggatatcc agcctatctt    1200
ggtgcccgtc tggcctcgtt ttatgaacga gcaggcaggg tgaaatgtct tggaaatcct    1260
gaaagagaag ggagtgtcag cattgtagga gcagtttctc cacctggtgg tgattttcct    1320
gatccagtta catctgccac tcttggtatc gttcaggtgt tctggggctt agataagaaa    1380
ctagctcaac gtaagcattt cccctctgtc aattggctca tcagctacag caagtatatg    1440
cgtgccttgg atgaatacta tgacaaaaac ttcacagagt tcgttcctct gaggacgaaa    1500
gctaaggaaa ttctgcagga agaagaagac ctggcagaaa ttgtacagct tgtgggaaag    1560
gcttctttgg cagaaacaga taaaatcact ctggaggtag caaaacttat caaagatgat    1620
ttcctacaac aaaatggata tactccttat gacaggttct gcccattcta caagacagta    1680
gggatgctgt ccaacatgat tgcattttat gatatggctc gtagagctgt tgaaaccact    1740
gcccagagtg acaataaaat cacatggtcc attattcgtg agcacatggg agacatcctc    1800
tataaacttt cctccatgaa attcaaggat ccactgaaag atggtgaggc aaagatcaaa    1860
agcgactatg cacaacttct tgaagacatg cagaatgcat tccgtagcct tgaagattag    1920
aagccttgaa gattacaact gtgatttcct tttcctcagc aagctcctat gtgtatattt    1980
tcctgaattt ctcatctcaa acccttcgct tctttattgt gcagctttga gactagtgcc    2040
tatgtgtgtt atttgtttcc ctgtttttttt ggtaggtctt atataaaaca aacattcctt    2100
tgttctagtg ttgtgaaggg cctccctctt cctttatctg aagtggtgaa tatagtaaat    2160
atacattctg gttacactac tgtaaacttg tatgtagggt gatgaccctc tttgtcctag    2220
gtgtaccctt tcctcatctc tattaaattg taaacaggac tactgcatgt actctctttg    2280
cagtgaattt ggaatggaag gccaggtttc tataacttt gaacaggtac tttgtgaaat    2340
gactcaattt ctattgtggt aagctcattg gcagcttagc attttgcaaa ggaattgctt    2400
tgcaggaaat atttaatttt caaaaacata atgattaatg ttccaattat gcatcacttc    2460
ccccagtata aatcaggaat gtttgtgaga aaccattggg aactatactc ttttatttt    2520 tattttttat tttttttatt attttttttt tggggacgga gtgtccctct tgttgcccag    2580
gctggagtgc aatggcgtga tcttggctca ctgcagcctt cgcctccggg ttcaagtga    2640 ttctcctgcc tcagcctccc gagtagctgg gattacaggc atgctccacc atgcccagct    2700
```

| | |
|---|---|
| aattttgtat ttttagtaga aacggggttt caccatattg gtcaggctgg tctcgaactc | 2760 |
| cagacctcag gtgatccgcc cacctcggcc tcccaaactg ctgggattac aggcgtgagc | 2820 |
| caccgcgcct ggccagggac tatactcttt ttaaaataga catttgtggg gctcacacaa | 2880 |
| tatatgaaat agtaccctct aaaaaagaga aaaaaaaat caggcggtca aacttagagc | 2940 |
| aacattgtct tattaaagca tagtttattt cactagaaaa aatttaatat caaggactat | 3000 |
| tacatacttc attactagga agttcttttt aaaatgacac ttaaaacaat cactgaaaac | 3060 |
| ttgatccaca tcacaccctg tttatttttcc ttaaacatct tggaagccta agcttctgag | 3120 |
| aatcatgtgg caagtgtgat gggcagtaaa ataccagaga agatgtttag tagcaattaa | 3180 |
| aggctgtttg cacctttaag gaccagctgg gctgtagtga ttcctggggc cagagtggca | 3240 |
| ttatgttttt acaaaataat gacatatgtc acatgtttgc atgtttgttt gcttgttgaa | 3300 |
| tttttgaaca gccagttgac caatcataga aagtattact ttctttcata tggttttttgg | 3360 |
| ttcactggct taagaggttt ctcagaatat ctatggccac agcagcatac cagtttccat | 3420 |
| cctaatagga atgaaattaa ttttgtatct actgataaca gaatctgggt cacatgaaaa | 3480 |
| aaaatcattt tatccgtctt ttaagtatat gtttaaaata ataatttatg tgtctgcata | 3540 |
| ttgcagaaca gctctgagag caacagtttc ccattaactc tttctgacca atagtgctgg | 3600 |
| caccgttgct tcctctttgg gaagaggaaa gggtgtgtga acatggctaa caatcttcaa | 3660 |
| atacccaaat tgtgatagca taaataaagt atttatttta tgcctcagta tattattatt | 3720 |
| taattttta ggtaatgcct atctcttggt ctattaagga aagaagcaat cagtagagaa | 3780 |
| ttcaggatag ttttgtttaa attcttgcag attacatgtt tttacagtgg cctgctattg | 3840 |
| aggaaaggta ttcttctata caacttgttt taacctttga gaacattgac agaaattatg | 3900 |
| caatggtttg ttgagatacg gacttgatgg tgctgtttaa tcagtttgct tccaaagtgg | 3960 |
| cctactcaag aggccctaag actggtagaa attaaaagga tttcaaaaac tttctattcc | 4020 |
| tttcttaaac ctaccagcaa actaggattg tgatagcaat gaatggtatg atgaagaaag | 4080 |
| tttgaccaaa tttgttttttt tgttgttgtt gttgttttga atttgaaatc attcttattc | 4140 |
| cctttaagaa tgtttatgta tgagtgtgaa gatgctagcg aacctatgct cagatattca | 4200 |
| tcgtaagtct cccttcacct gttacagagt ttcagatcgg tcactgatag tatgtatttc | 4260 |
| tttagtaaga atgtgttaaa attacaatga tcttttaaaa agatgatgca gttctgtatt | 4320 |
| tattgtgctg tgtctggtcc taagtggagc caattaaaca agtttcatat gtatttttcc | 4380 |
| agtgttgaat ctcacacact gtactttgaa aatttccttc catcctgaat aacgaataga | 4440 |
| agaggccata tatattgcct ccttatcctt gagatttcac taccttatg ttaaaagttg | 4500 |
| tgtataattg ttaaaatctg tgaaagaata aaaagtggat ttaaattaaa aaaaaaaaa | 4560 |
| aaaaaaa | 4567 |

<210> SEQ ID NO 19
<211> LENGTH: 2475
<212> TYPE: DNA
<213> ORGANISM: Homo sapiens

<400> SEQUENCE: 19

| | |
|---|---|
| acgcctggtc tctgggacgc ccctccggac ccgtttcgcc tcgcggagcc ggtaggtcca | 60 |
| ggtgcagcgg ccgcagtgct gcgtccgtgc gccgcgggct ggggcggtct caggtgtgcc | 120 |
| gaagctctgg tcagtgccat gatccggcag gagcgctcca catcctacca ggagctgagt | 180 |
| gaggagttgg tccaggtggt tgagagctca gagctggcag acgagcagga caaggagacg | 240 |

```
gtcagagtcc aaggtccggg tatcttacca ggcctggaca gcgagtccgc ctccagcagc      300
atccgcttca gcaaggcctg cctgaagaac gtcttctcgg tcctactcat cttcatctac      360
ctgctgctca tggctgtggc cgtcttcctg gtctaccgga ccatcacaga ctttcgtgag      420
aaactcaagc accctgtcat gtctgtgtct tacaaggaag tggatcgcta tgatgcccca      480
ggtattgcct tgtaccccgg tcaggccag ttgctcagct gtaagcacca ttacgaggtc       540
attcctcctc tgacaagccc tggccagccg ggtgacatga attgcaccac ccagaggatc      600
aactacacgg acccctctc caatcagact gtgaaatctg ccctgattgt caggggccc        660 cgggaagtga aaagcggga gctggtcttc ctccagttcc gcctgaacaa gagtagtgag       720
gacttcagcg ccattgatta cctcctcttc tcttcttcc aggagttcct gcaaagccca       780
aacagggtag gcttcatgca ggcctgtgag agtgcctgtt ccagctggaa gttctctggg      840
ggcttccgca cctgggtcaa gatgtcactg gtaaagacca aggaggagga tgggcgggaa      900
gcagtggagt tccggcagga gacaagtgtg gttaactaca ttgaccagag gccagctgcc      960 aaaaaagtg ctcaattgtt ttttgtggtc tttgaatgga agatccttt catccagaaa       1020 gtccaagata tagtcactgc caatccttgg aacacaattg ctcttctctg tggcgccttc     1080
ttggcattat ttaaagcagc agagtttgcc aaactgagta taaaatggat gatcaaaatt     1140
agaaagagat accttaaaag aagaggtcag gcaacgagcc acataagctg aagtcacctc     1200
gcgttgttta gagaactgtc cacatcaatg ggagctgtca tcacttccac tttgtaaacg     1260
gagctatcaa caatcctgta ctcacttgaa gaaatggggc cttgctggga ggaacagcat     1320
gtaaaactgg aacttctaac cccgtcccaa agaggcggt gtagagccta atagaagaga     1380
ctaatggata aacctacaag ttatttaaat atttaaatta ttaataaact tttaaagag     1440 ctggccaatg acttttgaat agggtttgta gaagatgcct ttcttcctgt ttggttcatt    1500
gtattgtatt aggttaagct ctactagggt aatgaaggct ctacttttca cttttaaaa    1560 gtggacaaaa gagtgtgatt tcttttcc aaaaattcct gagtatcaag acgtgcaggt     1620
catgctttgg agcctatgca ctgtacacaa tggcaaaacc ctatgacttt ggcatcatct     1680
gccattgatg tccagcctct gacatgctct ttgatttgtt aaatgttaaa tgagacttta    1740
aggctactag aaactagtaa ttaagttct taatggactg agtagccacc tacttgtccg      1800
gctagaatgt ttgttgatgt atgagtttag attaacactc aaaagcacta ggacagatgt     1860
acatagaagg tgcctactca ttgtatttg atgatttcat taacaggtaa ataaaagtta    1920
atacaaaagg aacgagtgtg acaatatgaa tatctgctca atcatcgggc acaattactt     1980
tcatttggtg acttccaagg acaaaaggt agtatgagtc tggactccca agatggatct     2040
aactctcaag gtatgttcta actgcttcca gggaaggggt tgttaggcat ggcaactgat     2100
ggcaggtgtc cagaaagagt gacctggtgt ccccgaggaa gctgggttaa ctctttactg     2160
tgtccacaaa actaccatc atatgaggaa ggggtatacg cagtgtgacc ctcaaaaagc      2220
ttttagccta gcctttgaca gaaatgagta tgcattaaaa aaagtctat ttttcacatt     2280 aaggttctaa aaattgtttc cagagtttta aattatttat gtgcctgttg cttcaaagag     2340
gacttggtag catttcctaa attttgtaat ctggcttccg ataatccaaa gggaataact     2400
caaatgtatg aataggcatt ttaaatggga agaaactgtt ttttggatga atgattaaaa     2460
gtgaactgta taaag                                                       2475

<210> SEQ ID NO 20
<211> LENGTH: 1425
<212> TYPE: DNA
```

<213> ORGANISM: Homo sapiens

<400> SEQUENCE: 20

```
gcggacgtgg gcaggagggc tggaaaagcc ggcgctggag cgggaacggg agtagctgcc      60
tgggcgccaa aggccgcggc actcccacgc ggacccgaa gtccgcaacc cggggatggg     120
cccgcggctg cgagggatc ttctctggat caagcaatgg tggtgaaaaa tgtttcgcaa     180
gggcaaaaaa cgacacagta gtagcagttc ccaaagtagc gaaatcagta ctaagagcaa     240
gtctgtggat tctagccttg ggggtctttc acgatccagc actgtggcca gcctcgacac     300
agattccacc aaaagctcag acaaagcaa caataattca gatacctgtg cagaatttcg     360
aataaaatat gttggtgcca ttgagaaact gaaactctcc gagggaaaag gccttgaagg     420
gccattagac ctgataaatt atatagacgt tgcccagcaa gatggaaagt tgccttttgt     480
tcctccggag gaagaattta ttatgggagt ttccaagtat ggcataaaag tatcaacatc     540
agatcaatat gatgttttgc acaggcatgc tctctactta ataatccgga tggtgtgtta     600
cgatgacggt ctggggcgg gaaaaagctt actggctctg aagaccacag atgcaagcaa     660
tgaggaatac agcctgtggg tttatcagtg caacagcctg gaacaagcac aagccatttg     720
caaggtttta tccaccgctt ttgactctgt attaacatct gagaaccct gaatcctgca     780
atcaagtaga agtcaacttc atctgaaagt tcagctgttt tcaaactgca atgctgaaat     840
gttatgcaaa taatgaagtt atcccttgct ctagattttc tgaagaaaat ggattgtgta     900
aaatgctgat catttgttta ttaaaatgtg tcctattaca cagtgagtta actctcaatg     960
aagtcatcta tttctgggc taaaaaactt catttgtctt tttcaacttc taataagctt    1020
aacctaagtg tcacgaagac gagatgtcac agaggtccac tcagtgacaa acacacactg    1080
aaggcctgag ggaagactga ggacatgggc tcagtggtgg cttcccagtc atggtatcac    1140
tggcatggac ctctgtccgg cagaggtgtg gactggagac caggattcat gctggtctgg    1200
aacaatgaca ttgccaactt aagacacaca aagcagattt tcagaagtgt ctggtcaaga    1260
taacatgctg gccaaccaca attcctagag ttaagagaac cttaaaagat taccgctcat    1320
gctaaaagta tgtaaagatc ccatgtacag tatgatagtg tacttttttt aaaggactgt    1380
caatatacaa aactttaaag attaaaaaca ttaaaaataa aaaaa                    1425
```

<210> SEQ ID NO 21
<211> LENGTH: 728
<212> TYPE: DNA
<213> ORGANISM: Homo sapiens

<400> SEQUENCE: 21

```
cctcgccccg cctacgcggg aacccaaccg cggcgaccgg acgtgcactc ctccagtagc      60
ggctgcacgt cgtgcaatgg cccgctatga ggaggtgagc gtgtccggct tcgaggagtt     120
ccaccgggcc gtggaacagc acaatggcaa gaccattttc gcctacttta cgggttctaa     180
ggacgccggg gggaaaagct ggtgccccga ctgcgtgcag gctgaaccag tcgtacgaga     240
ggggctgaag cacattagtg aaggatgtgt gttcatctac tgccaagtag agaaaaagcc     300
ttattggaaa gatccaaata tgacttcag aaaaaacttg aaagtaacag cagtgcctac     360
actacttaag tatggaacac ctcaaaaaact ggtagaatct gagtgtcttc aggccaacct     420
ggtggaaatg ttgttctctg aagattaaga ttttaggatg gcaatcatgt cttgatgtcc     480
tgatttgttc tagtatcaat aaactgtata cttgctttga attcatgtta gcaataaatg     540
atgttaaaaa aactggcatg tgtctaaaca atagagtgct attaaaatgc ccatgaacct     600
```

| | |
|---|---|
| ttagtttgcc tgtaatacat ggatattttt aagatataaa gaagtcttca gaaatagcag | 660 |
| taaaggctca aaggaacgtg attcttgaag gtgacggtaa tacctaaaaa ctcctaaagg | 720 |
| tgcagagc | 728 |

<210> SEQ ID NO 22
<211> LENGTH: 2143
<212> TYPE: DNA
<213> ORGANISM: Homo sapiens

<400> SEQUENCE: 22

| | |
|---|---|
| tcggagctga acttcctaaa agacaaagtg tttatctttc aagattcatt ctccctgaat | 60 |
| cttaccaaca aaacactcct gaggagaaag aaagagaggg agggagagaa aaagagagag | 120 |
| agagaaacaa aaaaccaaag agagagaaaa aatgaattca tctaaatcat ctgaaacaca | 180 |
| atgcacagag agaggatgct tctcttccca aatgttctta tggactgttg ctgggatccc | 240 |
| catcctattt ctcagtgcct gtttcatcac cagatgtgtt gtgacatttc gcatctttca | 300 |
| aacctgtgat gagaaaaagt ttcagctacc tgagaatttc acagagctct cctgctacaa | 360 |
| ttatggatca ggttcagtca agaattgttg tccattgaac tgggaatatt ttcaatccag | 420 |
| ctgctacttc tttttctactg acaccatttc ctgggcgtta agtttaaaga actgctcagc | 480 |
| catgggggct cacctggtgg ttatcaactc acaggaggag caggaattcc tttcctacaa | 540 |
| gaaacctaaa atgagagagt tttttattgg actgtcagac caggttgtcg agggtcagtg | 600 |
| gcaatgggtg gacggcacac ctttgacaaa gtctctgagc ttctgggatg taggggagcc | 660 |
| caacaacata gctaccctgg aggactgtgc caccatgaga gactcttcaa acccaaggca | 720 |
| aaattggaat gatgtaacct gtttcctcaa ttattttcgg atttgtgaaa tggtaggaat | 780 |
| aaatcctttg aacaaaggaa aatctcttta agaacagaag gcacaactca aatgtgtaaa | 840 |
| gaaggaagag caagaacatg gccacaccca ccgccccaca cgagaaattt gtgcgctgaa | 900 |
| cttcaaagga cttcataagt atttgttact ctgatataaa taaaaataag tagttttaaa | 960 |
| tgttataatt catgttactg gctgaagtgc attttctctc tacgttagtc tcaggtcctc | 1020 |
| ttcccagaat ttacaaagca attcatacct tttgctacat ttgcctcatt ttttagtgtt | 1080 |
| cgtatgaaag tacagggaca cggagccaag acagagtcta gcaaagaagg ggattttgga | 1140 |
| aggtgccttc caaaaatctc ctgaatccgg gctctgtagc aggtcctctt ctttctagct | 1200 |
| tctgacaagt ctgtcttctc ttcttggttt cataccgttc ttatctcctg cccaagcata | 1260 |
| tatcgtctct ttactcccct gtataatgag taagaagctt cttcaagtca tgaaacttat | 1320 |
| tcctgctcag aataccggtg tggccttttct ggctacaggc ctccactgca ccttcttagg | 1380 |
| gaagggcatg ccagccatca gctccaaaca ggctgtaacc aagtccaccc atccctgggg | 1440 |
| cttcctttgc tctgccttat tttcaattga ctgaatggat ctcaccagat tttgtatcta | 1500 |
| ttgctcagct aggacccgag tccaatagtc aatttattct aagcgaacat tcatctccac | 1560 |
| actttcctgt ctcaagccca tccattattt cttaactttt attttagctt tcgggggtac | 1620 |
| atgttaaagg cttttatat aggtaaactc atgtcgtgga ggtttgttgt acagattatt | 1680 |
| tcatcaccca ggtattaagc ccagtgccta atattgtttt tttcggctcc tctccctcct | 1740 |
| cctaccttcc gccctcaagt agactccagt gtctgttatt cccttctttg tgtttatgaa | 1800 |
| ttctcatcat ttagctccca cttataagtg aggacatgca gtatttggtt ttctgttccc | 1860 |
| atgtttgcta aggataatgg tttccagttc taccgatgtt cccacaaaag acataatttt | 1920 |
| cttttttaag gctgcttagt attccatggt atctatgtat cacattttct ctatccaatc | 1980 |

| | |
|---|---:|
| tattgttgac tcacatttag attgattcca tgttttgct attgtgaata gtgctgcaat | 2040 |
| gaacattcgt gtgcatgtgt ctttatggta gaaagattta tatttctctg agtatgtatc | 2100 |
| cagtaatagc ccattcattt attgcataaa attctaccaa tac | 2143 |

<210> SEQ ID NO 23
<211> LENGTH: 1128
<212> TYPE: DNA
<213> ORGANISM: Homo sapiens

<400> SEQUENCE: 23

| | |
|---|---:|
| cctcctctcc ctggcttttg tgttggtgcc tccgagctgc aaggagggtg cgctggagga | 60 |
| ggaggagggg ggcccggagt gagaggcacc cccttcacgc gcgcgcgcgc acacggtgcc | 120 |
| ggcgcacgca cacgggcg gacacacaca cgcgcgca cacacacacg cacagagctc | 180 |
| gctcgcctcg agcgcacgaa cgtggacgtt ctctttgtgt ggagccctca aggggggttg | 240 |
| gggcccggt tcggtccggg ggagatggcg cagcccatcc tgggccatgg gagcctgcag | 300 |
| cccgcctcgg ccgctggcct ggcgtccctg gagctcgact cgtcgctgga ccagtacgtg | 360 |
| cagattcgca tcttcaaaat aatcgtgatt ggggactcca acgtgggcaa gacctgcctg | 420 |
| accttccgct tctgcggggg taccttccca gacaagactg aagccaccat cggcgtggac | 480 |
| ttcagggaga gaccgtgga atcgagggc gagaagatca aggttcaggt gtgggacaca | 540 |
| gcaggtcagg aacgtttccg caaaagcatg gtcgagcatt actaccgcaa cgtacatgcc | 600 |
| gtggtcttcg tctatgacgt caccaagatg acatctttca ccaacctcaa aatgtggatc | 660 |
| caagaatgca atgggcatgc tgtgccccca ctagtcccca aagtgcttgt gggcaacaag | 720 |
| tgtgacttga gggaacagat ccaggtgccc tccaacttag ccctgaaatt tgctgatgcc | 780 |
| cacaacatgc tcttgtttga acatcggcc aaggacccca agagagcca gaacgtggag | 840 |
| tcgattttca tgtgcttggc ttgccgattg aaggcccaga atccctgct gtatcgtgat | 900 |
| gctgagaggc agcaggggaa ggtgcagaaa ctggagttcc cacaggaagc taacagtaaa | 960 |
| acttcctgtc cttgttgaaa ccaaacgata taaatacaag ataaattatc actggagttt | 1020 |
| tttcttttccc ttttttctgt gcctgcataa tgctgacacc tgcttgtttc catacaaatt | 1080 |
| gatatcaaaa taaaatttgt atagattaaa aaaaaaaaa aaaaaaaa | 1128 |

<210> SEQ ID NO 24
<211> LENGTH: 2457
<212> TYPE: DNA
<213> ORGANISM: Homo sapiens

<400> SEQUENCE: 24

| | |
|---|---:|
| ggagcgcgtg aggctccggc gcgcaagccc ggagcagccc gctggggcgc acagggtcgc | 60 |
| gcgggcgcgg ggatggagga cggcgtggcc ggtccccagc tcggggccgc ggcggaggcg | 120 |
| gcggaggcgg ccgagcgcgc agcgcggccc ggggtgacgc tgcggccctt cgcgcccctc | 180 |
| tcggggggcgg ccgaggcgga cgagggcggc ggcgactgga gcttcattga ctgcgagatg | 240 |
| gaggaggtgg acctgcagga cctgcccagc gccaccatcg cctgtcacct ggacccgcgc | 300 |
| gtgttcgtgg acggcctgtg ccgggccaaa tttgagtccc tctttaggac gtatgacaag | 360 |
| gacatcacct ttcagtattt taagagcttc aaacgagtca gaataaactt cagcaacccc | 420 |
| ttctccgcag cagatgccag gctccagctg cataagactg agtttctggg aaaggaaatg | 480 |
| aagttatatt ttgctcagac cttacacata ggaagctcac acctggctcc gccaaatcca | 540 |
| gacaagcagt ttctgatctc ccctcccgcc tctccgccag tgggatggaa acaagtggaa | 600 |

-continued

| | |
|---|---|
| gatgcgaccc cagtcataaa ctatgatctc ttatatgcca tctccaagct ggggccaggg | 660 |
| gaaaagtatg aattgcacgc agcgactgac accactccca gcgtggtggt ccatgtatgt | 720 |
| gagagtgatc aagagaagga ggaagaagag gaaatggaaa gaatgaggag acctaagcca | 780 |
| aaaattatcc agaccaggag gccggagtac acgccgatcc acctcagctg aactggcacg | 840 |
| cgacgaggac gcattccaaa tcatactcac gggaggaatc ttttactgtg gaggtggctg | 900 |
| gtcacgactt cttcggaggt ggcagccgag atcggggtgg cagaaatccc agttcatgtt | 960 |
| gctcagaaga gaatcaaggc cgtgtcccct tgttctaatg ctgcacacca gttactgttc | 1020 |
| atggcacccg ggaatgactt gggccaatca ctgagtttgt ggtgatcgca caaggacatt | 1080 |
| tgggactgtc ttgagaaaac agataatgat agtgttttgt acttgttctt ttctggtagg | 1140 |
| ttctgtctgt gccaagggca ggttgatcag tgagctcagg agagagcttc ctgtttctaa | 1200 |
| gtggcctgca ggggccactc tctactggta ggaagaggta ccacaggaag ccgcctagtg | 1260 |
| cagagaggtt gtgaaaacag cagcaatgca atgtggaaat tgtagcgttt cctttcttcc | 1320 |
| ctcatgttct catgtttgtg catgtatatt actgatttac aagactaacc tttgttcgta | 1380 |
| tataaagtta caccgttgtt gttttacatc ttttgggaag ccaggaaagc gtttggaaaa | 1440 |
| cgtatcacct ttcccagatt ctcggattct cgactctttg caacagcact tgcttgcgga | 1500 |
| actcttcctg gaatgcattc actcagcatc cccaaccgtg caacgtgtaa cttgtgcttt | 1560 |
| tgcaaaagaa gttgatctga aattcctctg tagaatttag cttatacaat tcagagaata | 1620 |
| gcagtttcac tgccaacttt tagtgggtga gaaattttag tttaggtgtt tgggatcgga | 1680 |
| cctcagtttc tgttgtttct tttatgtggt ggtttctata catgaatcat agccaaaaac | 1740 |
| ttttttggaa actgttggtt gagatagttg gttcttttac cccacgaaga catcaagata | 1800 |
| cacttgtaaa taaagctgat agcatatatt catacctgtt gtacacttgg gtgaaaagta | 1860 |
| tggcagtggg agactaagat gtattaacct acctgtgaat catatgttgt aggaaaagct | 1920 |
| gttcccatgt ctaacaggac ttgaattcaa agcatgtcaa gtggatagta gatctgtggc | 1980 |
| gatatgagag ggatgcagtg cctttcccca ttcattcctg atggaattgt tatactaggt | 2040 |
| taacatttgt aattttttc tagttgtaat gtgtatgtct ggtaaatagg tattatattt | 2100 |
| tggccttaca ataccgtaac aatgtttgtc attttgaaat acttaatgcc aagtaacaat | 2160 |
| gcatgctttg gaaatttgga agatggtttt attctttgag aagcaaatat gtttgcatta | 2220 |
| aatgctttga ttgttcatat caagaaattg attgaacgtt ctcaaaccct gtttacggta | 2280 |
| cttggtaaga gggagccggt ttgggagaga ccattgcatc gctgtccaag tgtttcttgt | 2340 |
| taagtgctttt taaactggag aggctaacct caaaatattt tttttaactg cattctataa | 2400 |
| taaatgggca cagtatgctc cttacagaaa aaaaaaaaa aaaaaaaaa aaaaaaa | 2457 |

<210> SEQ ID NO 25
<211> LENGTH: 2783
<212> TYPE: DNA
<213> ORGANISM: Homo sapiens

<400> SEQUENCE: 25

| | |
|---|---|
| gattgcgagc caggaggagg aagccggcgg tggccccgtc agcagccggc tgctgagagg | 60 |
| ccggtaggcg gcggcggtcc cgaggggcgg cggccgcgct gctccctgag aacgggtccc | 120 |
| gcagctgggc aggcgggcgg cctgagggcg cggagccatg aagctgtaca gcctcagcgt | 180 |
| cctctacaaa ggcaggccaa aggtggtgct gctcaaagcc gcatacgatg tgtcttcctt | 240 |
| cagcttttc cagagatcca gcgttcagga attcatgacc ttcacgagtc aactgattgt | 300 |

| | |
|---|---|
| ggagcgctca tcgaaaggca ctagagcttc tgtcaaagaa caagactatc tgtgccacgt | 360 |
| ctacgtccgg aatgatagtc ttgcaggtgt ggtcattgct gacaatgaat acccatcccg | 420 |
| ggtggccttt accttgctgg agaaggtact agatgaattc tccaagcaag tcgacaggat | 480 |
| agactggcca gtaggatccc ctgctacaat ccattaccca gccctggatg gtcacctcag | 540 |
| tagataccag aacccacgag aagctgatcc catgactaaa gtgcaggccg aactagatga | 600 |
| gaccaaaatc attctgcaca acaccatgga gtctctgtta gagcgaggtg agaagctaga | 660 |
| tgacttggtg tccaaatccg aggtgctggg aacacagtct aaagccttct ataaaactgc | 720 |
| ccggaaacaa aactcatgct gtgccatcat gtgatgcagc ctgccagagg cccaatgctg | 780 |
| gaatggcacc atcattcaca tcagaactgc agcccctgga aaagaagaga cagccataga | 840 |
| cgaggagcca gagtggggc agactggcca ttttattt gaagttcctg cgagaaatgg | 900 |
| atggtggaag ggtggcgaat gttcaaattc atatgtgtgg tagtgattct tggaaagaat | 960 |
| ttgaggtccc caaaggtgta ttttgggca aatgaaacca taaactccga ctggcttctg | 1020 |
| tagatgccaa agggctcttt ttcagctaac cctgggaagg ctctgtggga gggaggtcgg | 1080 |
| agccagctgt ttctcgatct ttggtatatc tttggatctt atttgtacat taatgatatt | 1140 |
| aacactccag tgggggtgg ggagtccctg atgctagggc tggggtgggt ggagtttgaa | 1200 |
| gactcttggg aaagcctctc ctggggccac tgttgggggt gggagtgagc ccaccacaga | 1260 |
| ggccacaggc aggcccccac ttcaggccca aggcctgggg cgggggaac agtcactggg | 1320 |
| tctcagattc tgagactgtt gtttagctta cctttctgct aggattggct ccccgcagag | 1380 |
| ggcagggccc atcctaagca gcttccaagt cccacaaagg tggcttgtgg gaggatttgg | 1440 |
| aaggagctgc attgtgggcg gggagtgtgt gggttgggtt cgtaccagca agtagactag | 1500 |
| gaactgagcc caggaaaggg ggatgttttc ctggtgtttg gatggtcagc tgggagtgtc | 1560 |
| catcatcagg ggaagatcaa acacaggtgc actcagctgc ccaggcctc tgggacactt | 1620 |
| gccttgactt gcaacttgcc ttgaacatca cgatcaaagc agcaggtgct gtggtctctc | 1680 |
| aaaattgatt tttatttgac tctgtggctc taagactgcc ttgaaccgcc tgaggcctat | 1740 |
| gcatctgaac aagtgggtct ctcccttgag caccaggagt gggtgccagc cggccccgag | 1800 |
| gattcccagc accccaccta tggtcttgcc agcataggct tgctagttcc ttcttggtca | 1860 |
| gaggtagctg cagagggggg aggccaaggg tttggtctaa gctgtgccct gccacctggc | 1920 |
| aggaggccca ctcactgccc aagtcatggc aacaggctgg agcagcccag gagatgggcc | 1980 |
| taaaatgttc tggatccctt gggtcctagt gttatgttcc agtctgccca cctgtgctca | 2040 |
| ggatgcagcc ctgggatcca gcacccatgg aagcttctgc tgggatggtg tcacctatgg | 2100 |
| gttttgaacc agtgtggtat ggtccttggg agctctgctc tgagcttgcc acactgctga | 2160 |
| gagcacccac tgtcctgacc agagtctcag tggtcctgac ccccaatgtg gcaggggct | 2220 |
| gggcaggagg gtgggtctg ctgtgggttc agaggactcc acctcctggc tggtttacct | 2280 |
| gctgctgccc attttctctg ggtactgctg ccagaggac tttagcctac ccctgaagag | 2340 |
| cctgtccatg tcatttcct actgccatag atacctaag cccagggccc cttgaggccc | 2400 |
| agactcagcc tgcccactgg tgccggagac ggagtggagt gggcctggat ccgagggatg | 2460 |
| ctacctctcc ctttcccact tgaggaccct ggggagagat gggggcgggg aaaatggagg | 2520 |
| tatgaatttg gggtaagagg aagtgagatc tccgcttgca ggtcagcccc tgccttgcag | 2580 |
| ggcgggctgg cttgactcag gccctgtgag atagagggcc cagcccagcc ccacccacag | 2640 |
| atcccctgct cctgttgtgt tctgttgtaa atcatttggc gagactgtat tttagtaact | 2700 |

-continued

| | |
|---|---|
| gctgcctaac ttccctgtgt tctatttgag aggcgcctgt ctggataaag ttgtcttgaa | 2760 |
| atttcaaaaa aaaaaaaaaa aaa | 2783 |

<210> SEQ ID NO 26
<211> LENGTH: 3398
<212> TYPE: DNA
<213> ORGANISM: Homo sapiens

<400> SEQUENCE: 26

| | |
|---|---|
| cgctgtcgcc gccagtagca gccttcgcca gcagcgccgc ggcggaaccg ggcgcagggg | 60 |
| agcgagcccg gccccgccag cccagcccag cccagcccta ctccctcccc acgccagggc | 120 |
| agcagccgtt gctcagagag aaggtggagg aagaaatcca gaccctagca cgcgcgcacc | 180 |
| atcatggacc attatgattc tcagcaaacc aacgattaca tgcagccaga gaggactgg | 240 |
| gaccgggacc tgctcctgga cccggcctgg gagaagcagc agagaaagac attcacggca | 300 |
| tggtgtaact cccacctccg gaaggcgggg acacagatcg agaacatcga gaggacttc | 360 |
| cgggatggcc tgaagctcat gctgctgctg gaggtcatct caggtgaacg cttggccaag | 420 |
| ccagagcgag gcaagatgag agtgcacaag atctccaacg tcaacaaggc cctggatttc | 480 |
| atagccagca aaggcgtcaa actggtgtcc atcggagccg aagaaatcgt ggatgggaat | 540 |
| gtgaagatga ccctgggcat gatctggacc atcatcctgc gctttgccat ccaggacatc | 600 |
| tccgtggaag agacttcagc caaggaaggg ctgctcctgt ggtgtcagag aaagacagcc | 660 |
| ccttacaaaa atgtcaacat ccagaacttc acataagct ggaaggatgg cctcggcttc | 720 |
| tgtgctttga tccaccgaca ccggcccgag ctgattgact acgggaagct gcggaaggat | 780 |
| gatccactca caaatctgaa tacggctttt gacgtggcag agaagtacct ggacatcccc | 840 |
| aagatgctgg atgccgaaga catcgttgga actgcccgac cggatgagaa agccatcatg | 900 |
| acttacgtgt ctagcttcta ccacgccttc tctggagccc agaaggcgga cagcagcc | 960 |
| aatcgcatct gcaaggtgtt ggccgtcaac caggagaacg agcagcttat ggaagactac | 1020 |
| gagaagctgg ccagtgatct gttggagtgg atccgccgca caatcccgtg gctggagaac | 1080 |
| cgggtgcccg agaacaccat gcatgccatg caacagaagc tggaggactt ccgggactac | 1140 |
| cggcgcctgc acaagccgcc caaggtgcag gagaagtgcc agctggagat caacttcaac | 1200 |
| acgctgcaga ccaagctgcg gctcagcaac cggcctgcct tcatgccctc tgagggcagg | 1260 |
| atggtctcgg acatcaacaa tgcctggggc tgcctggagc aggtggagaa gggctatgag | 1320 |
| gagtggttgc tgaatgagat ccggaggctg gagcgactgg accacctggc agagaagttc | 1380 |
| cggcagaagg cctccatcca cgaggcctgg actgacggca agaggccat gctgcgacag | 1440 |
| aaggactatg agaccgccac cctctcggag atcaaggccc tgctcaagaa gcatgaggcc | 1500 |
| ttcgagagtg acctggctgc ccaccaggac cgtgtggagc agattgccgc catcgcacag | 1560 |
| gagctcaatg gctggacta ttatgactca cccagtgtca cgcccgttg ccaaaagatc | 1620 |
| tgtgaccagt gggacaatct gggggcccta actcagaagc gaagggaagc tctggagcgg | 1680 |
| accgagaaac tgctggagac cattgaccag ctgtacttgg agtatgccaa gcgggctgca | 1740 |
| cccttcaaca actggatgga gggggccatg gaggacctgc aggacacctt cattgtgcac | 1800 |
| accattgagg agatccaggg actgaccaca gcccatgagc agttcaaggc caccctccct | 1860 |
| gatgccgaca aggagcgcct ggccatcctg ggcatccaca tgaggtgtc caagattgtc | 1920 |
| cagacctacc acgtcaatat ggcgggcacc aaccccctaca caaccatcac gcctcaggag | 1980 |
| atcaatggca aatgggacca cgtgcggcag ctggtgcctc ggagggacca agctctgacg | 2040 |

-continued

| | |
|---|---|
| gaggagcatg cccgacagca gcacaatgag aggctacgca agcagtttgg agcccaggcc | 2100 |
| aatgtcatcg ggccctggat ccagaccaag atggaggaga tcggggaggat ctccattgag | 2160 |
| atgcatggga ccctggagga ccagctcagc cacctgcggc agtatgagaa gagcatcgtc | 2220 |
| aactacaagc caaagattga tcagctggag ggcgaccacc agctcatcca ggaggcgctc | 2280 |
| atcttcgaca caagcacac caactacacc atggagcaca tccgtgtggg ctgggagcag | 2340 |
| ctgctcacca ccatcgccag gaccatcaat gaggtagaga accagatcct gacccgggat | 2400 |
| gccaagggca tcagccagga gcagatgaat gagttccggg cctccttcaa ccactttgac | 2460 |
| cgggatcact ccggcacact gggtcccgag gagttcaaag cctgcctcat cagcttgggt | 2520 |
| tatgatattg caacgaccc ccagggagaa gcagaatttg cccgcatcat gagcattgtg | 2580 |
| gaccccaacc gcctggggt agtgacattc caggccttca ttgacttcat gtcccgcgag | 2640 |
| acagccgaca cagatacagc agaccaagtc atggcttcct tcaagatcct ggctggggac | 2700 |
| aagaactaca ttaccatgga cgagctgcgc cgcgagctgc cacccgacca ggctgagtac | 2760 |
| tgcatcgcgc ggatggcccc ctacaccggc cccgactccg tgccaggtgc tctggactac | 2820 |
| atgtcctttct ccacggcgct gtacggcgag agtgacctct aatccacccc gcccggccgc | 2880 |
| cctcgtcttg tgcgccgtgc cctgccttgc acctccgccg tcgcccatct cctgcctggg | 2940 |
| ttcggtttca gctcccagcc tccacccggg tgagctgggg cccacgtggc atcgatcctc | 3000 |
| cctgcccgcg aagtgacagt ttacaaaatt atttttctgca aaaagaaaa aaagttacg | 3060 |
| ttaaaaacca aaaactaca tattttatta tagaaaaagt atttttttctc caccagacaa | 3120 |
| atggaaaaaa agaggaaaga ttaactattt gcaccgaaat gtcttgtttt gttgcgacat | 3180 |
| aggaaaataa ccaagcacaa agttatattc catccttttt actgattttt ttttcttcta | 3240 |
| tctgttccat ctgctgtatt catttctcca atctcatgtc catttggtg tgggagtcgg | 3300 |
| ggtaggggt actcttgtca aaaggcacat tggtgcgtgt gtgtttgcta gctcacttgt | 3360 |
| ccatgaaaat attttatgat attaaagaaa atcttttg | 3398 |

<210> SEQ ID NO 27
<211> LENGTH: 2351
<212> TYPE: DNA
<213> ORGANISM: Homo sapiens

<400> SEQUENCE: 27

| | |
|---|---|
| tgcgggcagg attcacgccg ctgtgacccg gaggtcctca gggggcgaag ccccggccta | 60 |
| ggcctcgcgg agatgcccag ctgcggtgct tgtacttgcg gcgcggcggc cgtccggctc | 120 |
| atcacctcct cactcgcctc cgcgcagaga ggtatttctg gtggtcgcat tcatatgtca | 180 |
| gttttaggaa ggcttgggac atttgaaact cagattctgc aaagagctcc tcttagatcc | 240 |
| tttacagaaa caccagcata ctttgcctca aaagatggga taagtaaaga tggttctgga | 300 |
| gatggaaata gaaatcagc aagtgaggga agtagtaaga atcaggctc tgggaattct | 360 |
| gggaaaggtg gaaaccagct gcgctgtcct aaatgtggcg acttgtgcac acatgtagag | 420 |
| acctttgtat catccacccg ttttgtcaag tgtgaaaagt gtcatcattt ttttgttgtg | 480 |
| ctatctgaag cagactcaaa gaaaagcata attaagaac ctgaatcagc agcagaagct | 540 |
| gtaaaattgg cattccaaca gaaaccacca cctcccccta agaagattta taactacctc | 600 |
| gacaagtatg ttgttggcca gtcatttgct aagaaggtgc tttcagttgc tgtgtacaat | 660 |
| cattataaga gaatatataa taatatccca gctaatctga gacagcaagc agaggttgag | 720 |
| aagcagacat cattaacacc aagagagtta gaaataagaa gacgggagga tgagtacaga | 780 |

-continued

| | |
|---|---|
| tttacaaaat tgcttcagat tgctggaatt agcccacatg gtaatgcttt aggagcatca | 840 |
| atgcagcaac aggtaaatca acaaatacct caggaaaaac gaggaggtga agtattggat | 900 |
| tcttctcatg atgacataaa acttgaaaaa agtaatattt tgctgcttgg accaactggg | 960 |
| tcaggtaaaa ctctgctggc acaaacccta gctaaatgcc ttgatgtccc ttttgctatc | 1020 |
| tgtgactgta caactttgac tcaggctgga tatgtaggcg aagatattga atctgtgatt | 1080 |
| gcaaaactac tccaagatgc caattataat gtggaaaaag cacaacaagg aattgtcttt | 1140 |
| ctggatgaag tagataagat tggcagtgtg ccaggcattc atcaattacg ggatgtaggt | 1200 |
| ggagaaggcg ttcagcaagg cttattaaaa ctactagaag gcacaatagt caatgttcca | 1260 |
| gaaaagaatt cccgaaagct ccgtggagaa acagttcaag ttgatacaac aaacatcctg | 1320 |
| tttgtggcat ctggtgcttt caatggttta gacagaatca tcagcaggag gaaaaatgaa | 1380 |
| aagtatcttg gatttggaac accatctaat ctgggaaaag gcagaagggc tgcagctgct | 1440 |
| gcagaccttg ctaatcgaag tggggaatcg aatactcacc aagacattga agaaaaagat | 1500 |
| cggttattgc gtcatgtgga agccagagat ctgattgagt ttggcatgat tcctgagttt | 1560 |
| gtgggacggt tgcctgtggt ggttccattg catagcctag atgagaaaac acttgtacaa | 1620 |
| atattaactg agccacgaaa tgctgttatt cctcagtacc aggccttatt cagcatggat | 1680 |
| aagtgtgaac tgaatgttac tgaggatgct ttgaaagcta tagccagatt ggcactagaa | 1740 |
| cgaaaaacag gtgcacgagg ccttcggtcc ataatggaaa agctgttact agaaccaatg | 1800 |
| tttgaagtcc ctaattctga tatcgtatgt gtggaggttg acaaagaagt agtagaagga | 1860 |
| aaaaaggaac caggatacat ccgggctcca acaaaagaat cctctgaaga ggagtatgac | 1920 |
| tctggagttg aagaagaagg atggccccgc caagcagatg ctgcaaacag ctaaactgtc | 1980 |
| atattgctgt cttgtatata cagctttttcc ttcttttgtt taggatcata attgtctcta | 2040 |
| cagtctgata ttaaaggcat tggatctatc ttggatatca tacatggtca gagaagcctt | 2100 |
| taggagaaga atcagatcat gtatataatt gtaacatcac attgattta cggaagatgt | 2160 |
| tatatggact ttaatgacac aatgtttaga gataaaatgt acattatttt ggttcagttt | 2220 |
| tttaaaaaaa atatgcttta acaaaattct taggaattct tttaagcaat gcaggtattg | 2280 |
| cgataactgt agattttaca ataatgttac tctacaaatg ggaaaataaa ttctttaaaa | 2340 |
| ttgaatattg a | 2351 |

<210> SEQ ID NO 28
<211> LENGTH: 1551
<212> TYPE: DNA
<213> ORGANISM: Homo sapiens

<400> SEQUENCE: 28

| | |
|---|---|
| ggcgcccaag ccgccgccgc cagatcggtg ccgattcctg ccctgccccg accgccagcg | 60 |
| cgaccatgtc ccatcactgg gggtacggca aacacaacgg acctgagcac tggcataagg | 120 |
| acttccccat tgccaaggga gagcgccagt cccctgttga catcgacact catacagcca | 180 |
| agtatgaccc ttccctgaag cccctgtctg tttcctatga tcaagcaact tccctgagga | 240 |
| tcctcaacaa tggtcatgct ttcaacgtgg agtttgatga ctctcaggac aaagcagtgc | 300 |
| tcaagggagg acccctggat ggcacttaca gattgattca gtttcacttt cactggggtt | 360 |
| cacttgatgg acaaggttca gagcatactg tggataaaaa gaaatatgct gcagaacttc | 420 |
| acttggttca ctggaacacc aaatatgggg attttgggaa agctgtgcag caacctgatg | 480 |
| gactggccgt tctaggtatt ttttttgaagg ttggcagcgc taaaccgggc cttcagaaag | 540 |

-continued

```
ttgttgatgt gctggattcc attaaaacaa agggcaagag tgctgacttc actaacttcg    600
atcctcgtgg cctccttcct gaatccctgg attactggac ctacccaggc tcactgacca    660
cccctcctct tctggaatgt gtgacctgga ttgtgctcaa ggaacccatc agcgtcagca    720
gcgagcaggt gttgaaattc cgtaaactta acttcaatgg ggagggtgaa cccgaagaac    780
tgatggtgga caactggcgc ccagctcagc cactgaagaa caggcaaatc aaagcttcct    840
tcaaataaga tggtcccata gtctgtatcc aaataatgaa tcttcgggtg tttcccttta    900
gctaagcaca gatctacctt ggtgatttgg accctggttg cttt gtgtct agttttctag    960 acccttcatc tcttacttga tagacttact aataaaatgt gaagactaga ccaattgtca   1020
tgcttgacac aactgctgtg gctggttggt gctttgttta tggtagtagt ttttctgtaa   1080
cacagaatat aggataagaa ataagaataa agtaccttga ctttgttcac agcatgtagg   1140
gtgatgagca ctcacaattg ttgactaaaa tgctgctttt aaaacatagg aaagtagaat   1200
ggttgagtgc aaatccatag cacaagataa attgagctag ttaaggcaaa tcaggtaaaa   1260
tagtcatgat tctatgtaat gtaaaccaga aaaataaat gttcatgatt tcaagatgtt    1320
atattaaaga aaactttaa aaattattat atatttatag caaagttatc ttaaatatga    1380
attctgttgt aatttaatga cttttgaatt acagagatat aaatgaagta ttatctgtaa   1440
aaattgttat aattagagtt gtgatacaga gtatatttcc attcagacaa tatatcataa   1500
cttaataaat attgtatttt agatatattc tctaataaaa ttcagaattc t            1551
```

<210> SEQ ID NO 29
<211> LENGTH: 2591
<212> TYPE: DNA
<213> ORGANISM: Homo sapiens

<400> SEQUENCE: 29

```
gctgagcgcg ggcgcggggc cgctacgtgc gcggggagcg cggggagcgc ggggagcgcg     60
gggctgcgct cgtgtgcgct cctgggcgct cgccgccgcc gctgccgccg cgcgcctttg    120
agtcagcaaa ctccgcggcc cgcaagcccg gctcggcccg gccctgctct gttctgcccg    180
gaggagccgc ccattgatcg tgtcctgtgc tgaagatgtt tccggaacaa cagaaagagg    240
aatttgtaag tgtctgggtt cgagatccta ggattcagaa ggaggacttc tggcattctt    300
acattgacta tgagatatgt attcatacta atagcatgtg ttttacaatg aaacatcct    360 gtgtacgaag aagatataga gaattcgtgt ggctgaggca gagactccaa agtaatgcgt    420
tgctggtaca actgccagaa cttccatcta aaaacctgtt tttcaacatg aacaatcgcc    480
agcacgtgga tcagcgtcgc cagggtctgg aagatttcct cagaaaagtc ctacagaatg    540
cacttttgct ttcagatagc agccttcacc tcttcttaca gagccatctg aattcagaag    600
acattgaggc gtgtgtttct gggcagacta agtactctgt ggaagaagca attcacaagt    660
ttgccttaat gaatagacgt ttccctgaag aagatgaaga aggaaaaaaa gaaaatgata    720
tagattatga ttcagaaagt tcatcctctg ggcttggaca cagtagtgat gacagcagtt    780
cacatggatg taaagtaaat acagctccgc aggaatcctg aaaaataatt ctaatgttac    840
tatcttagga atagcaaatt atgtccagtc atagagaaga aagcttcata ataatacatt    900
cttacctaaa gctcactgtc atgatgttag gtatttaaat tcttaaagat gttgggttgt    960
ttattagtgg tattttatg ttgtcttatt ttaggtaagc ttctgtgtaa agctaaaaat   1020
cctgtgaata caatactatc ctttacaggc agacattatt ggtaaacaag atcttgccct   1080
ccaatgaaat gacttacatg ttttaaaaaa ccgagttggt tttattgaat ttaaaaagat   1140
```

```
aggtaactaa gtagcattta aaatcaagat agagcattcc ttcttgtatc agtggggcag    1200
tgttaccata aacacggtgt atatgttgtt aaacccatg aagagtaaca gtgtagacca     1260
gactgcctct ctcagatatg tgcctgatat tttgtggata cctcccctgc actggcaaaa    1320
cactatgctt ttgggtgtta gactgaaata ttttaagagt atttaacctt tccagtattc    1380
tgtttcacgc ttagatggaa atgtatctta tgaatagaga catattaaaa taatgtttac    1440
atcttagaaa aaacatagat agtgctagta atattactta taactgtaat atatagattc    1500
agaaatacat tttcattatc caaaatcagc ttcaacaaat ggtttctgga gacaaataat    1560
ttgttttcat tatcattgta taatcaggtt aatgatttat tttttgacta aatgtgcaat    1620
ttcttatcac tagataactt tcagtatcag tggtggttac ttattactta aatcagagga    1680
aggattttat aaagattaat aaatttaatt ttaccaataa atattcccat aatttagaaa    1740
aggatgtcga cttgctaatt tcagaaataa ttattcattt ttaaaaagcc ccttttaaag    1800
catctacttg aagattggta taattttcat aaaatgtctt ttttttttagt gtcccaaaga    1860 tatcttagat aaactatttt gaagttcaga tttcagatga ggcaacattt tcttgagata    1920
attacccaag tttcatccat gttgaatggt acaaaatatt tctgtgaaac taacaggaag    1980
atattttcag ataactagga taacttgttg ctttgttacc cagcctaatt gaagagtggc    2040
agaggctact acaaaaagca accttttcat tttcactaag agtttaaaag ctattgtatt    2100
attaaaaagt ctttacaatg cttgtttcaa agaaccaaca gaaaaaaaag ctaagaaaac    2160
tgagaactaa cattaaaaaa attaaattta gaataagaat gatttcttta atttgtcctt    2220 ttttctttg gtctaaaaca ttattaaatt tttgtaaata ttttgattta atgtgtctta    2280
gatcctcatt attttaatac aggaaaagaa aagatttagt aatttcttac catgctaata    2340
tgtaaagttc atgccatcca ggcatttaag agcgatcctc atcccttcag caatatgtat    2400
ttgagttcac actatttctg ttttacagca gttttgaaaa acacatacta tgccaccaat    2460
tgtcatatta tttttagatg atgtaacata gccatcaaaa ttaatattat gtaatgccta    2520
atacttagta tgtaaatgtc acgagatcat ttttacatta aacgtgaaaa aaaatcaaaa    2580
aaaaaaaaaa a                                                        2591
```

<210> SEQ ID NO 30
<211> LENGTH: 2501
<212> TYPE: DNA
<213> ORGANISM: Homo sapiens

<400> SEQUENCE: 30

```
gaacctcctc gcgactttcc aaggtatctt tcagatgaag gcattgaagc ttgcacaagc     60
tctccagaca aagtcaatgt aaatgacatc atcctgattg ctctcaatat ctgagaacaa    120
ttggcaagaa attcctcccc agtgacatca atagtggaaa ggtagaaaag ctcgaaggtc    180
catgtgtttt gcaaattcaa aaaattcgca atgttgctgc accaaggat aatgaagaat     240 ctcaggctgc accaaggatg ctgcgattac agatgactga tggtcatata agttgcacag    300
cagtagaatt tagttatatg tcaaaaataa gcctgaacac accacctgga actaaagtta    360
agctctcagg cattgttgac ataaaaaatg gattcctgct cttgaatgac tctaacacca    420
cagttcttgg tggtgaagtg gaacacctta ttgagaaatg ggagttacag agaagcttat    480
caaaacacaa tagaagcaat attggaactg aaggtggacc accgcctttt gtgccttttg    540
gacagaagtg tgtatctcat gtccaagtgg atagcagaga acttgatcga agaaaaacat    600
tgcaagttac aatgcctgtc aaacctacaa atgataatga tgaatttgaa aagcaaagga    660
```

```
cggctgctat tgctgaagtt gcaaagagca aggaaaccaa gacatttgga ggaggtggtg    720
gtggtgctag aagtaatctc aatatgaatg ctgctggtaa ccgaaatagg gaagttttac    780
agaaagaaaa gtcaaccaaa tcagagggaa acatgaagg  tgtctataga gaactggttg    840
atgagaaagc tctgaagcac ataacggaaa tgggcttcag taaggaagca tcgaggcaag    900
ctcttatgga taatggcaac aacttagaag cagcactgaa cgtacttctt acaagcaata    960
aacagaaacc tgttatgggt cctcctctga gaggtagagg aaaaggcagg gggcgaataa   1020
gatctgaaga tgaagaggac ctgggaaatg caaggccatc agcaccaagc acattatttg   1080
atttcttgga atctaaaatg ggaactttga atgtggaaga acctaaatca cagccacagc   1140
agcttcatca gggacaatac agatcatcaa atactgagca aaatggagta aagataata   1200 atcatctgag acatcctcct cgaaatgata ccaggcagcc aagaaatgaa aaaccgcctc   1260
gttttcaaag agactcccaa aattcaaagt cagttttaga aggcagtgga ttacctagaa   1320
atagaggttc tgaaagacca agtacttctt cagtatctga agtatgggct gaagacagaa   1380
tcaaatgtga tagaccgtat tctagatatg acagaactaa agatacttca tatcctttag   1440
gttctcagca tagtgatggt gcttttaaaa aagagataa  ctctatgcaa agcagatcag   1500
gaaaaggtcc ctcctttgca gaggcaaaag aaaatccact tcctcaagga tctgtagatt   1560
ataataatca aaaacgtgga aaaagagaaa gccaaacatc tattcctgac tattttatg   1620 acaggaaatc acaaacaata aataatgaag ctttcagtgg tataaaaatt gaaaaacatt   1680
ttaatgtaaa tactgattat cagaatccag ttcgaagtaa tagtttcatt ggtgttccaa   1740
atggagaagt agaaatgcca ctgaaaggaa gacgaatagg acctattaag ccagcaggac   1800
ctgtcacagc tgtaccctgt gatgataaaa tattttacaa tagtgggccc aaacgaagat   1860
ctgggccaat taagccagaa aaaatactag aatcatctat tcctatggag tatgcaaaaa   1920
tgtggaaacc tggagatgaa tgttttgcac tttattggga agacaacaag ttttaccggg   1980
cagaagttga agccctccat tcttcgggta tgacagcagt tgttaaattc attgactacg   2040
gaaactatga agaggtgcta ctgagcaata tcaagcccat tcaaacagag gcatgggagg   2100
aagaaggcac ctacgatcaa actctggagt tccgtagggg aggtgatggc cagccaagac   2160
gatccactcg gccaacccaa cagttttacc aaccaccccg ggctcggaac taataggaaa   2220
agactctttg tgaagaaacg agccagtgac tgaaacaccc tggtggaaac ctgttgacag   2280
accttccact ttctcttcag aataagtagc tgtggtggat attattattt gaagaaagaa   2340
aaaacagatt ttagggtgga aaaaacagtc aactcacaca aagaatggaa aaaaatactg   2400
agttaaatta agcaaatacc ttttacaagt gaaaggaaga attttctctc tgccgtcaat   2460
aaaaccattg tgctattatt gtttaaaaaa aaaaaaaaaa a                       2501
```

<210> SEQ ID NO 31
<211> LENGTH: 2164
<212> TYPE: DNA
<213> ORGANISM: Homo sapiens

<400> SEQUENCE: 31

```
ataaatatca gagtgtgctg ctgtggcttt gtggagctgc cagagtaaag caaagagaaa     60
ggaagcaggc ccgttggaag tggttgtgac aaccccagca atgtggagaa gcctggggct    120
tgccctggct ctctgtctcc tcccatcggg aggaacagag agccaggacc aaagctcctt    180
atgtaagcaa cccccagcct ggagcataag agatcaagat ccaatgctaa actccaatgg    240
ttcagtgact gtggttgctc ttcttcaagc cagctgatac ctgtgcatac tgcaggcatc    300
```

| | |
|---|---|
| taaattagaa gacctgcgag taaaactgaa gaaagaagga tattctaata tttcttatat | 360 |
| tgttgttaat catcaaggaa tctcttctcg attaaaatac acacatctta agaataaggt | 420 |
| ttcagagcat attcctgttt atcaacaaga agaaaaccaa acagatgtct ggactctttt | 480 |
| aaatggaagc aaagatgact tcctcatata tgatagatgt ggccgtcttg tatatcatct | 540 |
| tggtttgcct ttttccttcc taactttccc atatgtagaa gaagccatta agattgctta | 600 |
| ctgtgaaaag aaatgtggaa actgctctct cacgactctc aaagatgaag acttttgtaa | 660 |
| acgtgtatct ttggctactg tggataaaac agttgaaact ccatcgcctc attaccatca | 720 |
| tgagcatcat cacaatcatg gacatcagca ccttggcagc agtgagcttt cagagaatca | 780 |
| gcaaccagga gcaccaaatg ctcctactca tcctgctcct ccaggccttc atcaccacca | 840 |
| taagcacaag ggtcagcata ggcagggtca cccagagaac cgagatatgc cagcaagtga | 900 |
| agatttacaa gatttacaaa agaagctctg tcgaaagaga tgtataaatc aattactctg | 960 |
| taaattgccc acagattcag agttggctcc taggagctga tgctgccatt gtcgacatct | 1020 |
| gatatttgaa aaacagggt ctgcaatcac ctgacagtgt aaagaaaacc tcccatcttt | 1080 |
| atgtagctga cagggacttc gggcagagga aacataact gaatcttgtc agtgacgttt | 1140 |
| gcctccagct gcctgacaaa taagtcagca gcttataccc acagaagcca gtgccagttg | 1200 |
| acgctgaaag aatcaggcaa aaaagtgaga atgaccttca aactaaatat ttaaaatagg | 1260 |
| acatactccc caatttagtc tagacacaat ttcatttcca gcatttttat aaactaccaa | 1320 |
| attagtgaac caaaaataga aattagattt gtgcaaacat ggagaaatct actgaattgg | 1380 |
| cttccagatt ttaaatttta tgtcatagaa atattgactc aaaccatatt ttttatgatg | 1440 |
| gagcaactga aaggtgattg cagcttttgg ttaatatgtc tttttttttc tttttccagt | 1500 |
| gttctatttg ctttaatgag aatagaaacg taaactatga cctaggggtt tctgttggat | 1560 |
| aattagcagt ttagaatgga ggaagaacaa caaagacatg ctttccattt ttttctttac | 1620 |
| ttatctctca aaacaatatt actttgtctt ttcaatcttc tacttttaac taataaaata | 1680 |
| agtggatttt gtattttaag atccagaaat acttaacacg tgaatatttt gctaaaaaag | 1740 |
| catatataac tattttaaat atccatttat cttttgtata tctaagactc atcctgattt | 1800 |
| ttactatcac acatgaataa agcctttgta tctttctttc tctaatgttg tatcatactc | 1860 |
| ttctaaaact tgagtggctg tcttaaaaga tataagggga aagataatat tgtctgtctc | 1920 |
| tatattgctt agtaagtatt tccatagtca atgatggttt aataggtaaa ccaaacccta | 1980 |
| taaacctgac ctcctttatg gttaatacta ttaagcaaga atgcagtaca gaattggata | 2040 |
| cagtacggat ttgtccaaat aaattcaata aaaaccttaa agctgaaaaa aaaaaaaaa | 2100 |
| aaaaaaaaa aaaaaaaaa aaaaaaaaa aaaaaaaaa aaaaaaaaa aaaaaaaaa | 2160 |
| aaaa | 2164 |

```
<210> SEQ ID NO 32
<211> LENGTH: 4564
<212> TYPE: DNA
<213> ORGANISM: Homo sapiens

<400> SEQUENCE: 32
```

| | |
|---|---|
| ccggggccct acacgccaga cctggctcgg ggtgggagtg cagaggcaac caaaaaggaa | 60 |
| cccacacctc cctccagggc ccggggcgct gtcagacggg gcagcaacca ggagattccc | 120 |
| tgggcctgca ggaagccctt ccgcggaccg aaagattgtt ccccattttg gagatgaaga | 180 |
| aactgagact caaagcagct gagtgacctt cccaaggaca cacactgaac tgggcggtga | 240 |

-continued

```
tcaggatctg aatgcacagg gcgggtgttc agcgattgtt tactacgttg aacgtgacct    300
ccaggaaagc agttctggcc gagatccct gacaacgcaa agcaagaagt aacgtggaag     360
gaggctcccc aagctggctg ccatttttgc tgctgtgtgt ggaggtgctg ccagtggcat    420
gcccaaaccc aaagctggaa gaggaataaa ttacaagtgg tcaaggttgc atccttttga    480
gcccaggacc tgcttgtaag ccgagagggt tctctggccc taatctagcc aagcaccatg    540
gagagaatca gtgccttctt cagctctatc tgggacacca tcttgaccaa acaccaagaa    600
ggcatctaca acaccatctg cctgggagtc ctcctgggcc tgccactctt ggtgatcatc    660
acactcctct tcatctgttg ccattgctgc tggagcccac caggcaagag gggccagcag    720
ccagagaaga acaagaagaa gaagaagaag aagaagaaga aggatgaaga agacctctgg    780
atctctgctc aacccaagct tctccagatg gagaagagac catcactgcc tgtttagtta    840
ggcaggaagc agaggtgttt cctttctggg gctaagcctc cttctgacca cacacagaca    900
tttcaggaac ccctgaaata atgcactatg tccatgtcca cagagtaact actcaaccaa    960
ggaacaaacc tcagactaag tgtcccagtg gagggcagtc ccagggacca cgtggacaat   1020
tcttggatac tgtcttggca gctatgtgtc caatagcaat gctccttact gcagacccag   1080
gcatgcctcc cacctgtctc tggcataccc cacatgcaaa gcacaaagaa catttatcca   1140
tacatctcaa tatggttccc aagtgtgtgc acatgcacgt aacacacaca cacacaaatt   1200
caggtagcag gtacgtgggc aagtatattc tgctcatcaa atggtcattg gctatgtact   1260
ttgtgcaggg aagtacatta tctacagtca caaaaatgtc tcatgggaaa gccttgccag   1320
attcagacac atatatacaa tttcctaacc agcaaggccc ccatacacca tctattccat   1380
aaaccactca ggttacagat gcatgctttc ctatttctaa ctctacacat aaacttttac   1440
tggaagtact cataattgga cattccagca acctgctaca gtccccaccc ttgtgtgtct   1500
tgatacagac acaccaagtt tctgtgcctc tgacccctca cctgtgccaa gatgtttaaa   1560
gtgtgatggt tcaaaattca ttgaaagctc ttttcttgta actcatgaca aagtccgtcc   1620
tcattgccac tgagaggtgt ttaatgtgat ccaagacctc tctgtgaaac attaccccg    1680 caaaccactc agcaaagtgc ctttctccaa gcaagaacaa agagctcttg gtggtgactg   1740
ctagaaaatt atggaagccc actcatttat gtcagtggac tgcaactgtg tacctgtgca   1800
atgtttacag atggaaaggg tgaggagatg ctacacctga gctaggtatc tcctatataa   1860
ccaaagtttc cagcagggaa ggaactagac aatcatcagt gcagtctcac agaaggcaac   1920
actggaagtg atgtcataag gttgtgatgt gtgcacggta tggcacaggt gggatgcaga   1980
ggtaacagag tttaaatgaa agtaggatga agctataaag aggtttattt atatttatat   2040
tgaagctcag gcaagtgcct tgcacacagt aggtacttat aactaactgt ggttactgtt   2100
ggatatgtga tgttgttaag ggtaagcttg taatacctca ccagttctcc ccgagtgatc   2160
ttctcttcta agtgagccca ctaattgctg caatggatga aattgggtgt taatgctgg    2220 agagcacatg taggtgacac atgtgccttg aggtatgtga ggacatgtaa attagatcca   2280
cagtgagctg aggagggctt cccccgccag agtgaggttg ggaagcagag ttaatccact   2340
tataggatga actgcttggt atttttattg tattgtgact gtattacaaa gatggacaat   2400
tcactccttg ggagcaagtt atgctctaga agtttattta caaatatgct gggcagctct   2460
cttgaaatat tttcccaagg aagctattct acacagtggc aaaattgcta tctaattaat   2520
aatgtagcta aactatgata tttatagtag caaaaaacta aattctataa gattgcatta   2580
aaggaaagat atattctatt tgctcacttg ggctgcttgg tactcacctg ccctccaggt   2640
```

```
gtactttagg cctgtggagg gtgggcattt agtggtgacc cttgcaccag ggttttctaa    2700
cagatgaccc tgtgaatcat aatttaaacc tgcatatatt ttatagccag tcacatttgc    2760
cctctcaccc tatatggcca taaactgcct aagcactcag gcctcccact catcaacccc    2820
tttgaccaga gaaagaagca ctctggttct ctatcccctt gtcacataga gagtttgtca    2880
tggggcctct ggctgtgccc ttcacataac agaatgactt gccatctgcc tgcaccaaac    2940
ccagggatgt ggaagacatc tccccacaac tgccactgct caccaggaca agctgccctt    3000
cctgtctcca cctctcagtc ccctagaat ggatggctgg ggagaggtgg aggctgacag    3060
ctgagacgta gtgtcagata tgatctagga gggcggatca ccgggatccg ggaccataca    3120
agtaacatgg tttccatggc aactgcttgc tcctttgaat taagacagca gtcagttgtc    3180
attgccatga caaggcctct atctccaggc acaatgtccc tgctgtctcc taatccaatg    3240
gacttgctct cacccaggg atgaaacacc cagaaactca cttctcagtc acttccacag    3300
ccgatgactc agaagagcca aacccagaat ggggcctctc ttttccccat cacagactcc    3360
cctgacaacc tttcctggcg taactagagg agtcccagtg caggataggc cctaaacgtt    3420
ttgttaaata aacaggtgca tgaaaggagc ctaaggccat tgttgatatc cactctcttc    3480
tttccacttc cttctcatct ttttctccat gtttttatgct tctctgattc cctcttctgc    3540
ctgcaccaga ccagccccag ccctttattc ctctccattt tcactccttc agcctctgt    3600 ccctgaactg ccactggcaa cccatgggac ctcaggacca gagactgctt gactcatctg    3660
gggagggtaa gttcacgggg acaaaaaaa tgattcctaa agaagaggct tcctagacca    3720
gcacaggctc gagaaagaca tcccctaggc ctggacttct gagcagcttt agccaggctc    3780
cggacggcag ccagaggagg ccttttcccca ttgctccttt ccccattgct caatggattc    3840
catgtttctt tttcttgggg ggagcaggga gggagaaagg tagaaaaatg gcagccacct    3900
ttccaagaaa aatataaagg gtccaagctg tatagtattt gtcagtattt ttttctgtaa    3960
aattcaaaca cacacaaaag aaaaatttat ttaaataaaa tactttgaaa atgaaaagtc    4020
ttgatgtagt cagatggtta ctctcttaac attaggtatt accccactc agacatcact    4080 cagaaatgat caatgcaggg actctttctg tgacacaaat gtcccagccc tccctggtca    4140
ccgccttcgc catggtagag tcataggtct gaggatgagg aatgtggctg tctcacccctt    4200 gcttgcaaaa cagatggcct tggagaccag actccctcaa aggtgccagc tacaggaaaa    4260
atatactgat gttccttggc aacacttaca gaacttttcca tcaatgaggt ccatcaatgg    4320
cttcttaaag gaaaagggg gaaatagcaa aaacctaagg aagaatggac ctttgagtta    4380
aatccagtgt ttgttgggaa aggagggatc aaaaacctct atagtagcca ctagggcaaa    4440
aactgtgtgt atgtgtgtgt gtaagtgtgt gtacactgtt caatatggtt caatatggta    4500
ccaatagcca catgtgacta tttaaattca ttgcaatgaa ataaaattaa aggtatacta    4560
gctc                                                                4564

<210> SEQ ID NO 33
<211> LENGTH: 3913
<212> TYPE: DNA
<213> ORGANISM: Homo sapiens

<400> SEQUENCE: 33
ctttcactgg caagagacgg agtcctgggt ttcagttcca gttgcctgcg gtgggctgtg      60
tgagtttgcc aaagtcccct gccctctctg ggtctcggtt ccctcgcctg tccacgtgag     120
gttggaggag ctgaacgccg acgtcatttt tagctaagag ggagcagggt ccccgagtcg     180
```

```
ccggcccagg gtctgcgcat ccgaggccgc gcgcccttc ccctccccca cggctcctcc    240
gggccccgca ctctgcgccc cggctgccgc ccagcgccct acaccgccct caggggggccc    300 tcgcgggctc cccccggccg ggatgccagt gccccgcgcc acgcgcgcct gctcccgcgc    360
cgcctgccct gcagcctgcc cgcggcgcct ttatacccag cgggctcggc gctcactaat    420
gtttaactcg gggccgaaac ttgccagcgg cgagtgactc caccgcccgg agcagcggtg    480
caggacgcgc gtctccgccg cccgcggtga cttctgcctg cgctccttct ctgaacgctc    540
acttccgagg agacgccgac gatgaagaca ccgtggaagg ttcttctggg actgctgggt    600
gctgctgcgc ttgtcaccat catcaccgtg cccgtggttc tgctgaacaa aggcacagat    660
gatgctacag ctgacagtcg caaaacttac actctaactg attacttaaa aaatacttat    720
agactgaagt tatactcctt aagatggatt tcagatcatg aatatctcta caaacaagaa    780 ataatatct tggtattcaa tgctgaatat ggaaacagct cagttttctt ggagaacagt    840
acatttgatg agtttggaca ttctatcaat gattattcaa tatctcctga tgggcagttt    900
attctcttag aatacaacta cgtgaagcaa tggaggcatt cctacacagc ttcatatgac    960
atttatgatt taaataaaag gcagctgatt acagaagaga ggattccaaa caacacacag   1020
tgggtcacat ggtcaccagt gggtcataaa ttggcatatg tttggaacaa tgacatttat   1080
gttaaaattg aaccaaattt accaagttac agaatcacat ggacggggaa agaagatata   1140
atatataatg gaataactga ctgggtttat gaagaggaag tcttcagtgc ctactctgct   1200
ctgtggtggt ctccaaacgg cacttttta gcatatgccc aatttaacga cacagaagtc   1260
ccacttattg aatactcctt ctactctgat gagtcactgc agtacccaaa gactgtacgg   1320
gttccatatc caaaggcagg agctgtgaat ccaactgtaa agttctttgt tgtaaataca   1380
gactctctca gctcagtcac caatgcaact tccatacaaa tcactgctcc tgcttctatg   1440
ttgatagggg atcactactt gtgtgatgtg acatgggcaa cacaagaaag aatttctttg   1500
cagtggctca ggaggattca gaactattcg gtcatggata tttgtgacta tgatgaatcc   1560
agtggaagat ggaactgctt agtggcacgg caacacattg aaatgagtac tactggctgg   1620
gttggaagat ttaggccttc agaacctcat tttacccttg atggtaatag cttctacaag   1680
atcatcagca atgaagaagg ttacagacac atttgctatt ccaaataga taaaaaagac   1740 tgcacattta ttacaaaagg cacctgggaa gtcatcggga tagaagctct aaccagtgat   1800
tatctatact acattagtaa tgaatataaa ggaatgccag gaggaaggaa tctttataaa   1860
atccaactta gtgactatac aaaagtgaca tgcctcagtt gtgagctgaa tccggaaagg   1920
tgtcagtact attctgtgtc attcagtaaa gaggcgaagt attatcagct gagatgttcc   1980
ggtcctggtc tgcccctcta tactctacac agcagcgtga atgataaagg gctgagagtc   2040
ctggaagaca attcagcttt ggataaaatg ctgcagaatg tccagatgcc ctccaaaaaa   2100
ctggacttca ttattttgaa tgaaacaaaa ttttggtatc agatgatctt gcctcctcat   2160
tttgataaat ccaagaaata tcctctacta ttagatgtgt atgcaggccc atgtagtcaa   2220
aaagcagaca ctgtcttcag actgaactgg gccacttacc ttgcaagcac agaaaacatt   2280
atagtagcta gctttgatgg cagaggaagt ggttaccaag gagataagat catgcatgca   2340
atcaacagaa gactgggaac atttgaagtt gaagatcaaa ttgaagcagc cagacaattt   2400
tcaaaaatgg gatttgtgga caacaaacga attgcaattt ggggctggtc atatggaggg   2460
tacgtaacct caatggtcct gggatcggga agtggcgtgt tcaagtgtgg aatagccgtg   2520
gcgcctgtat cccggtggga gtactatgac tcagtgtaca cagaacgtta catgggtctc   2580
```

```
ccaactccag aagacaacct tgaccattac agaaattcaa cagtcatgag cagagctgaa    2640
aattttaaac aagttgagta cctccttatt catggaacag cagatgataa cgttcacttt    2700
cagcagtcag ctcagatctc caaagccctg gtcgatgttg gagtggattt ccaggcaatg    2760
tggtatactg atgaagacca tggaatagct agcagcacag cacaccaaca tatatatacc    2820
cacatgagcc acttcataaa acaatgtttc tctttacctt agcacctcaa aataccatgc    2880
catttaaagc ttattaaaac tcattttgt tttcattatc tcaaaactgc actgtcaaga    2940
tgatgatgat cttaaaata cacactcaaa tcaagaaact taaggttacc tttgttccca    3000
aatttcatac ctatcatctt aagtaggggac ttctgtcttc acaacagatt attaccttac    3060
agaagtttga attatccggt cgggttttat tgtttaaaat catttctgca tcagctgctg    3120
aaacaacaaa taggaattgt ttttatggag gctttgcata gattccctga gcaggatttt    3180
aatctttttc taactggact ggttcaaatg ttgttctctt ctttaaaggg atggcaagat    3240
gtgggcagtg atgtcactag gcagggaca ggataagagg gattagggag agaagatagc    3300
agggcatggc tgggaaccca agtccaagca taccaacacg agcaggctac tgtcagctcc    3360
cctcggagaa gagctgttca cagccagact ggcacagttt tctgagaaag actattcaaa    3420
cagtctcagg aaatcaaata tgcaaagcac tgacttctaa gtaaaaccac agcagttgaa    3480
aagactccaa agaaatgtaa gggaaactgc cagcaacgca ggcccccagg tgccagttat    3540
ggctataggt gctacaaaaa cacagcaagg gtgatgggaa agcattgtaa atgtgctttt    3600
aaaaaaaaat actgatgttc ctagtgaaag aggcagcttg aaactgagat gtgaacacat    3660
cagcttgccc tgttaaaaga tgaaaatatt tgtatcacaa atcttaactt gaaggagtcc    3720
ttgcatcaat ttttcttatt tcatttcttt gagtgtctta attaaaagaa tattttaact    3780
tccttggact cattttaaaa aatggaacat aaaatacaat gttatgtatt attattccca    3840
ttctacatac tatggaattt ctcccagtca tttaataaat gtgccttcat tttttcagaa    3900
aaaaaaaaaa aaa                                                        3913
```

<210> SEQ ID NO 34
<211> LENGTH: 818
<212> TYPE: DNA
<213> ORGANISM: Homo sapiens

<400> SEQUENCE: 34

```
cgcagcgggt cctctctatc tagctccagc ctctcgcctg cgccccactc cccgcgtccc      60
gcgtcctagc cgaccatggc cggggcccctg cgcgccccgc tgctcctgct ggccatcctg     120
gccgtggccc tggccgtgag ccccgcggcc ggctccagtc ccggcaagcc gccgcgcctg     180
gtgggaggcc ccatggacgc cagcgtggag gaggagggtg tgcggcgtgc actggacttt     240
gccgtcggcg agtacaacaa agccagcaac gacatgtacc acagccgcgc gctgcaggtg     300
gtgcgcgccc gcaagcagat cgtagctggg gtgaactact tcttggacgt ggagctgggc     360
cgaaccacgt gtaccaagac ccagcccaac ttggacaact gccccttcca tgaccagcca     420
catctgaaaa ggaaagcatt ctgctctttc cagatctacg ctgtgccttg cagggcaca     480 atgaccttgt cgaaatccac ctgtcaggac gcctaggggt ctgtaccggg ctggcctgtg     540
cctatcacct cttatgcaca cctcccaccc cctgtattcc caccccctgga ctggtggccc     600 ctgccttggg gaaggtctcc ccatgtgcct gcaccaggag acagacagag aaggcagcag     660
gcggcctttg ttgctcagca aggggctctg ccctccctcc ttccttcttg cttctcatag     720
ccccggtgtg cggtgcatac accccccacct cctgcaataa aatagtagca tcggcaaaaa     780
```

| aaaaaaaaaa aaaaaaaaaa aaaaaaaaaa aaaaaaaa | 818 |

<210> SEQ ID NO 35
<211> LENGTH: 1102
<212> TYPE: DNA
<213> ORGANISM: Mus musculus

<400> SEQUENCE: 35

| cccagcggcc ctgcagactt ggcacagagc acacccacct gcctttgtca cagcacacta | 60 |
| agaaggttct ctgtggtgac caggctgggt agagggctgc tgggtctgca ggcgtcagag | 120 |
| catggagggg tccctccaac tcctggcctg cttggcctgt gtgctccaga tgggatccct | 180 |
| tgtgaaaact agaagagacg cttcggggga tctgctcaac acagaggcgc acagtgcccc | 240 |
| ggcgcagcgc tggtccatgc aggtgcccgc ggaggtgaac gcggaggctg gcgacgcggc | 300 |
| ggtgctgccc tgcaccttca cgcacccgca ccgccactac gacgggccgc tgacggccat | 360 |
| ctggcgctcg ggcgagccgt acgcgggccc gcaggtgttc cgctgcaccg cggcgccggg | 420 |
| cagcgagctg tgccagacgg cgctgagcct gcacggccgc ttccgcctgc tgggcaaccc | 480 |
| gcgccgcaac gacctgtccc tgcgcgtcga gcgcctcgcc ctggcggaca gcggccgcta | 540 |
| cttctgccgc gtggagttca ccggcgacgc ccacgatcgc tatgagagtc gccatggggt | 600 |
| ccgtctgcgc gtgactgctg cgccgcggat cgtcaacatc tcggtgctgc cgggccccgc | 660 |
| gcacgccttc cgcgcgctct gcaccgccga ggggagccc ccgccgccc tcgcctggtc | 720 |
| gggtcccgcc ccaggcaaca gctccgctgc cctgcagggc cagggtcacg gctaccaggt | 780 |
| gaccgccgag ttgcccgcgc tgaccgcga cggccgctac acgtgcacgg cggccaatag | 840 |
| cctgggccgc gccgaggcca gcgtctacct gttccgcttc cacggcgccc ccggaacctc | 900 |
| gaccctagcg ctcctgctgg gcgcgctggg cctcaaggcc ttgctgctgc ttggcattct | 960 |
| gggagcgcgt gccacccgac gccgactaga tcacctggtc ccccaggaca cccctccacg | 1020 |
| tgcggaccag gacacttcac ctatctgggg ctcagctgaa gaaatagaag atctgaaaga | 1080 |
| cctgcataaa ctccaacgct ag | 1102 |

<210> SEQ ID NO 36
<211> LENGTH: 2996
<212> TYPE: DNA
<213> ORGANISM: Artificial
<220> FEATURE:
<223> OTHER INFORMATION: p14 vector

<400> SEQUENCE: 36

| ttttcccagt cacgacgttg taaaacgacg gccagtgaat tctaatacga ctcactatag | 60 |
| ggagacgaga gcacctggat aggttcgcgt ggcgcgccgc atgcgtcgac ggatcctgag | 120 |
| aacttcaggc tcctgggcaa cgtgctggtt attgtgctgt ctcatcattt tggcaaagaa | 180 |
| ttcactcctc aggtgcaggc tgcctatcag aaggtggtgg ctggtgtggc caatgccctg | 240 |
| gctcacaaat accactgaga tcttttttccc tctgccaaaa attatgggga catcatgaag | 300 |
| ccccttgagc atctgacttc tggctaataa aggaaattta ttttcattgc aaaaaaaaaa | 360 |
| agcggccgct aactgttggt gcaggcgctc ggaccgctag cttggcgtaa tcatggtcat | 420 |
| agctgtttcc tgtgtgaaat tgttatccgc tcacaattcc acacaacata cgagccggaa | 480 |
| gcataaagtg taaagcctgg ggtgcctaat gagtgagcta actcacatta attgcgttgc | 540 |
| gctcactgcc cgctttccag tcgggaaacc tgtcgtgcca gctgcattaa tgaatcggcc | 600 |
| aacgcgcggg gagaggcggt ttgcgtattg ggcgctcttc cgcttcctcg ctcactgact | 660 |

```
cgctgcgctc ggtcgttcgg ctgcggcgag cggtatcagc tcactcaaag gcggtaatac      720
ggttatccac agaatcaggg gataacgcag gaaagaacat gtgagcaaaa ggccagcaaa      780
aggccaggaa ccgtaaaaag gccgcgttgc tggcgttttt ccataggctc cgcccccctg      840
acgagcatca caaaaatcga cgctcaagtc agaggtggcg aaacccgaca ggactataaa      900
gataccaggc gtttccccct ggaagctccc tcgtgcgctc tcctgttccg accctgccgc      960
ttaccggata cctgtccgcc tttctccctt cgggaagcgt ggcgctttct caatgctcac     1020
gctgtaggta tctcagttcg gtgtaggtcg ttcgctccaa gctgggctgt gtgcacgaac     1080 ccccgttca gcccgaccgc tgcgccttat ccggtaacta tcgtcttgag tccaacccgg      1140
taagacacga cttatcgcca ctggcagcag ccactggtaa caggattagc agagcgaggt     1200 atgtaggcg tgctacagag ttcttgaagt ggtggcctaa ctacggctac actagaagga      1260
cagtatttgg tatctgcgct ctgctgaagc cagttacctt cggaaaaaga gttggtagct     1320
cttgatccgg caaacaaacc accgctggta gcggtggttt ttttgtttgc aagcagcaga     1380
ttacgcgcag aaaaaaagga tctcaagaag atcctttgat cttttctacg gggtctgacg     1440
ctcagtggaa cgaaaactca cgttaaggga ttttggtcat gagattatca aaaaggatct     1500
tcacctagat ccttttaaat taaaaatgaa gttttaaatc aatctaaagt atatatgagt     1560
aaacttggtc tgacagttac caatgcttaa tcagtgaggc acctatctca gcgatctgtc     1620
tatttcgttc atccatagtt gcctgactcc ccgtcgtgta gataactacg atacgggagg     1680
gcttaccatc tggccccagt gctgcaatga taccgcgaga cccacgctca ccggctccag     1740
atttatcagc aataaaccag ccagccggaa gggccgagcg cagaagtggt cctgcaactt     1800
tatccgcctc catccagtct attaattgtt gccgggaagc tagagtaagt agttcgccag     1860
ttaatagttt gcgcaacgtt gttgccattg ctacaggcat cgtggtgtca cgctcgtcgt     1920
ttggtatggc ttcattcagc tccggttccc aacgatcaag gcgagttaca tgatccccca     1980
tgttgtgcaa aaaagcggtt agctccttcg gtcctccgat cgttgtcaga agtaagttgg     2040
ccgcagtgtt atcactcatg gttatggcag cactgcataa ttctcttact gtcatgccat     2100
ccgtaagatg cttttctgtg actggtgagt actcaaccaa gtcattctga atagtgta      2160 tgcggcgacc gagttgctct tgcccggcgt caatacggga taataccgcg ccacatagca     2220
gaactttaaa agtgctcatc attggaaaac gttcttcggg gcgaaaactc tcaaggatct     2280
taccgctgtt gagatccagt tcgatgtaac ccactcgtgc acccaactga tcttcagcat     2340
cttttacttt caccagcgtt tctgggtgag caaaaacagg aaggcaaaat gccgcaaaaa     2400
agggaataag ggcgacacgg aaatgttgaa tactcatact cttccttttt caatattatt     2460
gaagcattta tcagggttat tgtctcatga gcggatacat atttgaatgt atttagaaaa     2520
ataaacaaat aggggttccg cgcacatttc cccgaaaagt gccacctgac gtctaagaaa     2580
ccattattat catgacatta acctataaaa ataggcgtat cacgaggccc tttcgtctcg     2640
cgcgtttcgg tgatgacggt gaaaacctct gacacatgca gctcccggag acggtcacag     2700
cttgtctgta agcggatgcc gggagcagac aagcccgtca gggcgcgtca gcgggtgttg     2760
gcgggtgtcg ggctggctt aactatgcgg catcagagca gattgtactg agagtgcacc      2820
atatgcggtg tgaaataccg cacagatgcg taaggagaaa ataccgcatc aggcgccatt     2880
cgccattcag gctgcgcaac tgttgggaag ggcgatcggt gcgggcctct tcgctattac     2940
gccagctggc gaaaggggga tgtgctgcaa ggcgattaag ttgggtaacg ccaggg         2996
```

<210> SEQ ID NO 37

<211> LENGTH: 2992
<212> TYPE: DNA
<213> ORGANISM: Artificial
<220> FEATURE:
<223> OTHER INFORMATION: p17+ vector

<400> SEQUENCE: 37

| | | | | | |
|---|---|---|---|---|---|
| ttttcccagt | cacgacgttg | taaaacgacg | gccagtgaat | tcgagctcac | atacgattta | 60 |
| ggtgacacta | taggcctgca | ccaacagtta | acacggcgcg | ccgcatgcgt | cgacggatcc | 120 |
| tgagaacttc | aggctcctgg | caacgtgct | ggttattgtg | ctgtctcatc | attttggcaa | 180 |
| agaattcact | cctcaggtgc | aggctgccta | tcagaaggtg | gtggctggtg | tggccaatgc | 240 |
| cctggctcac | aaataccact | gagatctttt | tccctctgcc | aaaaattatg | gggacatcat | 300 |
| gaagcccctt | gagcatctga | cttctggcta | ataaaggaaa | tttattttca | ttgcaaaaaa | 360 |
| aaaaagcggc | cgctagagtc | ggccgcagcg | gccgagcttg | gcgtaatcat | ggtcatagct | 420 |
| gtttcctgtg | tgaaattgtt | atccgctcac | aattccacac | aacatacgag | ccggaagcat | 480 |
| aaagtgtaaa | gcctggggtg | cctaatgagt | gagctaactc | acattaattg | cgttgcgctc | 540 |
| actgcccgct | ttccagtcgg | gaaacctgtc | gtgccagctg | cattaatgaa | tcggccaacg | 600 |
| cgcggggaga | ggcggtttgc | gtattgggcg | ctcttccgct | tcctcgctca | ctgactcgct | 660 |
| gcgctcggtc | gttcggctgc | ggcgagcggt | atcagctcac | tcaaaggcgg | taatacggtt | 720 |
| atccacagaa | tcagggata | acgcaggaaa | gaacatgtga | gcaaaaggcc | agcaaaaggc | 780 |
| caggaaccgt | aaaaaggccg | cgttgctggc | gtttttccat | aggctccgcc | ccctgacga | 840 |
| gcatcacaaa | aatcgacgct | caagtcagag | gtggcgaaac | ccgacaggac | tataaagata | 900 |
| ccaggcgttt | cccctggaa | gctccctcgt | gcgctctcct | gttccgaccc | tgccgcttac | 960 |
| cggatacctg | tccgcctttc | tcccttcggg | aagcgtggcg | ctttctcaaa | gctcacgctg | 1020 |
| taggtatctc | agttcggtgt | aggtcgttcg | ctccaagctg | ggctgtgtgc | acgaaccccc | 1080 |
| cgttcagccc | gaccgctgcg | ccttatccgg | taactatcgt | cttgagtcca | acccggtaag | 1140 |
| acacgactta | tcgccactgg | cagcagccac | tggtaacagg | attagcagag | cgaggtatgt | 1200 |
| aggcggtgct | acagagttct | tgaagtggtg | gcctaactac | ggctacacta | gaagaacagt | 1260 |
| atttggtatc | tgcgctctgc | tgaagccagt | taccttcgga | aaaagagttg | gtagctcttg | 1320 |
| atccggcaaa | caaaccaccg | ctggtagcgg | tggttttttt | gtttgcaagc | agcagattac | 1380 |
| gcgcagaaaa | aaaggatctc | aagaagatcc | tttgatcttt | tctacggggt | ctgacgctca | 1440 |
| gtggaacgaa | aactcacgtt | aagggatttt | ggtcatgaga | ttatcaaaaa | ggatcttcac | 1500 |
| ctagatcctt | ttaaattaaa | aatgaagttt | taaatcaatc | taaagtatat | atgagtaaac | 1560 |
| ttggtctgac | agttaccaat | gcttaatcag | tgaggcacct | atctcagcga | tctgtctatt | 1620 |
| tcgttcatcc | atagttgcct | gactccccgt | cgtgtagata | actacgatac | gggagggctt | 1680 |
| accatctggc | cccagtgctg | caatgatacc | gcgagaccca | cgctcaccgg | ctccagattt | 1740 |
| atcagcaata | aaccagccag | ccggaagggc | cgagcgcaga | agtggtcctg | caactttatc | 1800 |
| cgcctccatc | cagtctatta | attgttgccg | ggaagctaga | gtaagtagtt | cgccagttaa | 1860 |
| tagtttgcgc | aacgttgttg | ccattgctac | aggcatcgtg | gtgtcacgct | cgtcgtttgg | 1920 |
| tatggcttca | ttcagctccg | gttcccaacg | atcaaggcga | gttacatgat | cccccatgtt | 1980 |
| gtgcaaaaaa | gcggttagct | ccttcggtcc | tccgatcgtt | gtcagaagta | agttggccgc | 2040 |
| agtgttatca | ctcatggtta | tggcagcact | gcataattct | cttactgtca | tgccatccgt | 2100 |
| aagatgcttt | tctgtgactg | gtgagtactc | aaccaagtca | ttctgagaat | agtgtatgcg | 2160 |

```
gcgaccgagt tgctcttgcc cggcgtcaat acgggataat accgcgccac atagcagaac    2220
tttaaaagtg ctcatcattg gaaaacgttc ttcggggcga aaactctcaa ggatcttacc    2280
gctgttgaga tccagttcga tgtaacccac tcgtgcaccc aactgatctt cagcatcttt    2340
tactttcacc agcgtttctg ggtgagcaaa aacaggaagg caaaatgccg caaaaagggg    2400
aataagggcg acacggaaat gttgaatact catactcttc cttttcaat attattgaag    2460 catttatcag ggttattgtc tcatgagcgg atacatattt gaatgtattt agaaaaataa    2520
acaaataggg gttccgcgca catttccccg aaaagtgcca cctgacgtct aagaaaccat    2580
tattatcatg acattaacct ataaaaatag gcgtatcacg aggccctttc gtctcgcgcg    2640
tttcggtgat gacggtgaaa acctctgaca catgcagctc ccggagacgg tcacagcttg    2700
tctgtaagcg gatgccggga gcagacaagc ccgtcagggc gcgtcagcgg gtgttggcgg    2760
gtgtcggggc tggcttaact atgcggcatc agagcagatt gtactgagag tgcaccatat    2820
gcggtgtgaa ataccgcaca gatgcgtaag agaaaatac cgcatcaggc gccattcgcc    2880
attcaggctg cgcaactgtt gggaagggcg atcggtgcgg gcctcttcgc tattacgcca    2940
gctggcgaaa gggggatgtg ctgcaaggcg attaagttgg gtaacgccag gg            2992
```

<210> SEQ ID NO 38
<211> LENGTH: 2757
<212> TYPE: DNA
<213> ORGANISM: Artificial
<220> FEATURE:
<223> OTHER INFORMATION: pCATRMAN vector

<400> SEQUENCE: 38

```
ttttcccagt cacgacgttg taaaacgacg gccagtgaat tctaatacga ctcactatag      60
ggagatggag aaaaaaatca ctggacgcgt ggcgcgccat taattaatgc ggccgctagc     120
tcgagtgata taagcggat gaatggctgc aggcatgcaa gcttggcgta atcatggtca     180
tagctgtttc ctgtgtgaaa ttgttatccg ctcacaattc cacacaacat acgagccgga     240
agcataaagt gtaaagcctg gggtgcctaa tgagtgagct aactcacatt aattgcgttg     300
cgctcactgc ccgcttccca gtcgggaaac ctgtcgtgcc agctgcatta atgaatcggc     360
caacgcgcgg ggagaggcgg tttgcgtatt gggcgctctt ccgcttcctc gctcactgac     420
tcgctgcgct cggtcgttcg gctgcggcga gcggtatcag ctcactcaaa ggcggtaata     480
cggttatcca cagaatcagg ggataacgca ggaaagaaca tgtgagcaaa aggccagcaa     540
aaggccagga accgtaaaaa ggccgcgttg ctggcgtttt tccataggct ccgcccccct     600
gacgagcatc acaaaaatcg acgctcaagt cagaggtggc gaaacccgac aggactataa     660
agataccagg cgtttccccc tggaagctcc ctcgtgcgct ctcctgttcc gaccctgccg     720
cttaccggat acctgtccgc ctttctccct tcgggaagcg tggcgctttc tcaatgctca     780
cgctgtaggt atctcagttc ggtgtaggtc gttcgctcca agctgggctg tgtgcacgaa     840
ccccccgttc agcccgaccg ctgcgcctta tccggtaact atcgtcttga gtccaacccg     900
gtaagacacg acttatcgcc actggcagca gccactggta acaggattag cagagcgagg     960
tatgtaggcg gtgctacaga gttcttgaag tggtggccta actacggcta cactagaagg    1020
acagtatttg gtatctgcgc tctgctgaag ccagttacct tcggaaaaag agttggtagc    1080
tcttgatccg gcaaacaaac caccgctggt agcggtggtt ttttttgtttg caagcagcag    1140 attacgcgca gaaaaaaagg atctcaagaa gatcctttga tcttttctac ggggtctgac    1200
gctcagtgga acgaaaactc acgttaaggg attttggtca tgagattatc aaaaaggatc    1260
```

-continued

| | |
|---|---|
| ttcacctaga tcctttaaa ttaaaaatga agttttaaat caatctaaag tatatatgag | 1320 |
| taaacttggt ctgacagtta ccaatgctta atcagtgagg cacctatctc agcgatctgt | 1380 |
| ctatttcgtt catccatagt tgcctgactc cccgtcgtgt agataactac gatacgggag | 1440 |
| ggcttaccat ctggccccag tgctgcaatg ataccgcgag acccacgctc accggctcca | 1500 |
| gatttatcag caataaacca gccagccgga agggccgagc gcagaagtgg tcctgcaact | 1560 |
| ttatccgcct ccatccagtc tattaattgt tgccgggaag ctagagtaag tagttcgcca | 1620 |
| gttaatagtt tgcgcaacgt tgttgccatt gctacaggca tcgtggtgtc acgctcgtcg | 1680 |
| tttggtatgg cttcattcag ctccggttcc caacgatcaa ggcgagttac atgatccccc | 1740 |
| atgttgtgca aaaaagcggt tagctccttc ggtcctccga tcgttgtcag aagtaagttg | 1800 |
| gccgcagtgt tatcactcat ggttatggca gcactgcata attctcttac tgtcatgcca | 1860 |
| tccgtaagat gcttttctgt gactggtgag tactcaacca agtcattctg agaatagtgt | 1920 |
| atgcggcgac cgagttgctc ttgcccggcg tcaatacggg ataataccgc gccacatagc | 1980 |
| agaactttaa aagtgctcat cattggaaaa cgttcttcgg ggcgaaaact ctcaaggatc | 2040 |
| ttaccgctgt tgagatccag ttcgatgtaa ccccactcgt gcacccaactg atcttcagca | 2100 |
| tcttttactt tcaccagcgt ttctgggtga gcaaaaacag gaaggcaaaa tgccgcaaaa | 2160 |
| aagggaataa gggcgacacg gaaatgttga atactcatac tcttcctttt tcaatattat | 2220 |
| tgaagcattt atcagggtta ttgtctcatg agcggataca tatttgaatg tatttagaaa | 2280 |
| aataaacaaa taggggttcc gcgcacattt ccccgaaaag tgccacctga cgtctaagaa | 2340 |
| accattatta tcatgacatt aacctataaa aataggcgta tcacgaggcc ctttcgtctc | 2400 |
| gcgcgtttcg gtgatgacgg tgaaaacctc tgacacatgc agctcccgga cggtcaca | 2460 |
| gcttgtctgt aagcggatgc cgggagcaga caagcccgtc agggcgcgtc agcgggtgtt | 2520 |
| ggcgggtgtc ggggctggct taactatgcg gcatcagagc agattgtact gagagtgcac | 2580 |
| catatgcggt gtgaaatacc gcacagatgc gtaaggagaa aataccgcat caggcgccat | 2640 |
| tcgccattca ggctgcgcaa ctgttgggaa gggcgatcgg tgcgggcctc ttcgctatta | 2700 |
| cgccagctgg cgaaaggggg atgtgctgca aggcgattaa gttgggtaac gccaggg | 2757 |

<210> SEQ ID NO 39
<211> LENGTH: 2995
<212> TYPE: DNA
<213> ORGANISM: Artificial
<220> FEATURE:
<223> OTHER INFORMATION: p20 vector

<400> SEQUENCE: 39

| | |
|---|---|
| ttttcccagt cacgacgttg taaaacgacg gccagtgaat tcaattaacc ctcactaaag | 60 |
| ggagacttgt tccaaatgtg ttaggcgcgc cgcatgcgtc gacggatcct gagaacttca | 120 |
| ggctcctggg caacgtgctg gttattgtgc tgtctcatca ttttggcaaa gaattcactc | 180 |
| ctcaggtgca ggctgcctat cagaaggtgg tggctggtgt ggccaatgcc ctggctcaca | 240 |
| aataccactg agatcttttt ccctctgcca aaaattatgg ggacatcatg aagcccttg | 300 |
| agcatctgac ttctggctaa taaaggaaat ttattttcat tgcaaaaaaa aaaagcggcc | 360 |
| gctcttctat agtgtcacct aaatggccca gcggccgagc ttggcgtaat catggtcata | 420 |
| gctgtttcct gtgtgaaatt gttatccgct cacaattcca cacaacatac gagccggaag | 480 |
| cataaagtgt aaagcctggg gtgcctaatg agtgagctaa ctcacattaa ttgcgttgcg | 540 |
| ctcactgccc gctttccagt cgggaaacct gtcgtgccag ctgcattaat gaatcggcca | 600 |

```
acgcgcgggg agaggcggtt tgcgtattgg gcgctcttcc gcttcctcgc tcactgactc    660
gctgcgctcg gtcgttcggc tgcggcgagc ggtatcagct cactcaaagg cggtaatacg    720
gttatccaca gaatcagggg ataacgcagg aaagaacatg tgagcaaaag gccagcaaaa    780
ggccaggaac cgtaaaaagg ccgcgttgct ggcgtttttc cataggctcc gcccccctga    840
cgagcatcac aaaaatcgac gctcaagtca gaggtggcga aacccgacag gactataaag    900
ataccaggcg tttccccctg gaagctccct cgtgcgctct cctgttccga ccctgccgct    960
taccggatac ctgtccgcct ttctcccttc gggaagcgtg gcgctttctc aaagctcacg   1020
ctgtaggtat ctcagttcgg tgtaggtcgt tcgctccaag ctgggctgtg tgcacgaacc   1080
ccccgttcag cccgaccgct gcgccttatc cggtaactat cgtcttgagt ccaacccggt   1140
aagacacgac ttatcgccac tggcagcagc cactggtaac aggattagca gagcgaggta   1200
tgtaggcggt gctacagagt tcttgaagtg gtggcctaac tacggctaca ctagaagaac   1260
agtatttggt atctgcgctc tgctgaagcc agttaccttc ggaaaaagag ttggtagctc   1320
ttgatccggc aaacaaacca ccgctggtag cggtggtttt tttgtttgca agcagcagat   1380
tacgcgcaga aaaaaggatc tcaagaaga tcctttgatc ttttctacgg ggtctgacgc   1440
tcagtggaac gaaaactcac gttaagggat tttggtcatg agattatcaa aaaggatctt   1500
cacctagatc cttttaaatt aaaaatgaag ttttaaatca atctaaagta tatatgagta   1560
aacttggtct gacagttacc aatgcttaat cagtgaggca cctatctcag cgatctgtct   1620
atttcgttca tccatagttg cctgactccc cgtcgtgtag ataactacga tacgggaggg   1680
cttaccatct ggccccagtg ctgcaatgat accgcgagac ccacgctcac cggctccaga   1740
tttatcagca ataaccagc cagccggaag ggccgagcgc agaagtggtc ctgcaacttt   1800
atccgcctcc atccagtcta ttaattgttg ccgggaagct agagtaagta gttcgccagt   1860
taatagtttg cgcaacgttg ttgccattgc tacaggcatc gtggtgtcac gctcgtcgtt   1920
tggtatggct tcattcagct ccggttccca acgatcaagg cgagttacat gatcccccat   1980
gttgtgcaaa aaagcggtta gctccttcgg tcctccgatc gttgtcagaa gtaagttggc   2040
cgcagtgtta tcactcatgg ttatggcagc actgcataat tctcttactg tcatgccatc   2100
cgtaagatgc ttttctgtga ctggtgagta ctcaaccaag tcattctgag aatagtgtat   2160
gcggcgaccg agttgctctt gcccggcgtc aatacgggat aataccgcgc cacatagcag   2220
aactttaaaa gtgctcatca ttggaaaacg ttcttcgggg cgaaaactct caaggatctt   2280
accgctgttg agatccagtt cgatgtaacc cactcgtgca cccaactgat cttcagcatc   2340
ttttactttc accagcgttt ctgggtgagc aaaaacagga aggcaaaatg ccgcaaaaaa   2400
gggaataagg gcgacacgga aatgttgaat actcatactc ttcctttttc aatattattg   2460
aagcatttat cagggttatt gtctcatgag cggatacata tttgaatgta tttagaaaaa   2520
taaacaaata ggggttccgc gcacatttcc ccgaaaagtg ccacctgacg tctaagaaac   2580
cattattatc atgacattaa cctataaaaa taggcgtatc acgaggccct ttcgtctcgc   2640
gcgtttcggt gatgacggtg aaaacctctg acacatgcag ctcccggaga cggtcacagc   2700
ttgtctgtaa gcggatgccg ggagcagaca agcccgtcag ggcgcgtcag cgggtgttgg   2760
cgggtgtcgg gctggctta actatgcggc atcagagcag attgtactga gagtgcacca   2820
tatgcggtgt gaaataccgc acagatgcgt aaggagaaaa taccgcatca ggcgccattc   2880
gccattcagg ctgcgcaact gttgggaagg gcgatcggtg cgggcctctt cgctattacg   2940
ccagctggcg aaagggggat gtgctgcaag gcgattaagt tgggtaacgc caggg         2995
```

```
<210> SEQ ID NO 40
<211> LENGTH: 48
<212> TYPE: DNA
<213> ORGANISM: Artificial
<220> FEATURE:
<223> OTHER INFORMATION: OGS77 primer

<400> SEQUENCE: 40
aattctaata cgactcacta tagggagacg agagcacctg gataggtt              48

<210> SEQ ID NO 41
<211> LENGTH: 20
<212> TYPE: DNA
<213> ORGANISM: Artificial
<220> FEATURE:
<223> OTHER INFORMATION: OGS302 primer

<400> SEQUENCE: 41
gcctgcacca acagttaaca                                             20

<210> SEQ ID NO 42
<211> LENGTH: 19
<212> TYPE: DNA
<213> ORGANISM: Artificial
<220> FEATURE:
<223> OTHER INFORMATION: human 0326.1 siRNA for SEQ ID NO.:1

<400> SEQUENCE: 42
caggcccagg agtccaatt                                              19

<210> SEQ ID NO 43
<211> LENGTH: 19
<212> TYPE: DNA
<213> ORGANISM: Artificial
<220> FEATURE:
<223> OTHER INFORMATION: human 0369.1 shRNA for SEQ ID NO.:2

<400> SEQUENCE: 43
tcccgtcttt gggtcaaaa                                              19

<210> SEQ ID NO 44
<211> LENGTH: 19
<212> TYPE: DNA
<213> ORGANISM: Artificial
<220> FEATURE:
<223> OTHER INFORMATION: mouse 0326.1 shRNA for SEQ ID NO.:35

<400> SEQUENCE: 44
gcgccgcgga tcgtcaaca                                              19

<210> SEQ ID NO 45
<211> LENGTH: 19
<212> TYPE: DNA
<213> ORGANISM: Artificial
<220> FEATURE:
<223> OTHER INFORMATION: mouse 0326.2 shRNA for SEQ ID NO.:35

<400> SEQUENCE: 45
acacgtgcac ggcggccaa                                              19

<210> SEQ ID NO 46
<211> LENGTH: 4455
<212> TYPE: DNA
<213> ORGANISM: Artificial
<220> FEATURE:
<223> OTHER INFORMATION: pSilencer 2.0 vector
```

<400> SEQUENCE: 46

```
tcgcgcgttt cggtgatgac ggtgaaaacc tctgacacat gcagctcccg gagacggtca      60
cagcttgtct gtaagcggat gccgggagca gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgccaa gcttttccaa aaaactaccg     420
ttgttatagg tgtctcttga acacctataa caacggtagt ggatcccgcg tcctttccac     480
aagatatata aacccaagaa atcgaaatac tttcaagtta cggtaagcat atgatagtcc     540
attttaaaac ataattttaa aactgcaaac tacccaagaa attattactt tctacgtcac     600
gtattttgta ctaatatctt tgtgtttaca gtcaaattaa ttctaattat ctctctaaca     660
gccttgtatc gtatatgcaa atatgaagga atcatgggaa ataggccctc ttcctgcccg     720
accttggcgc gcgctcggcg cgcggtcacg ctccgtcacg tggtgcgttt tgcctgcgcg     780
tctttccact ggggaattca tgcttctcct ccctttagtg agggtaattc tctctctctc     840
cctatagtga gtcgtattaa ttccttctct tctatagtgt cacctaaatc gttgcaattc     900
gtaatcatgt catagctgtt tcctgtgtga aattgttatc cgctcacaat tccacacaac     960
atacgagccg gaagcataaa gtgtaaagcc tggggtgcct aatgagtgag ctaactcaca    1020
ttaattgcgt tgcgctcact gcccgctttc cagtcgggaa acctgtcgtg ccagctgcat    1080
taatgaatcg gccaacgcgc ggggagaggc ggtttgcgta ttgggcgctc ttccgcttcc    1140
tcgctcactg actcgctgcg ctcggtcgtt cggctgcggc gagcggtatc agctcactca    1200
aaggcggtaa tacggttatc cacagaatca ggggataacg caggaaagaa catgtgagca    1260
aaaggccagc aaaaggccag gaaccgtaaa aaggccgcgt tgctggcgtt tttccatagg    1320
ctccgccccc ctgacgagca tcacaaaaat cgacgctcaa gtcagaggtg gcgaaacccg    1380
acaggactat aaagatacca ggcgtttccc cctggaagct ccctcgtgcg ctctcctgtt    1440
ccgaccctgc cgcttaccgg atacctgtcc gcctttctcc cttcgggaag cgtggcgctt    1500
tctcatagct cacgctgtag gtatctcagt tcggtgtagg tcgttcgctc caagctgggc    1560
tgtgtgcacg aaccccccgt tcagcccgac cgctgcgcct tatccggtaa ctatcgtctt    1620
gagtccaacc cggtaagaca cgacttatcg ccactggcag cagccactgg taacaggatt    1680
agcagagcga ggtatgtagg cggtgctaca gagttcttga agtggtggcc taactacggc    1740
tacactagaa gaacagtatt tggtatctgc gctctgctga gccagttac cttcggaaaa     1800
agagttggta gctcttgatc cggcaaaaaa accaccgctg gtagcggtgg tttttttgtt    1860
tgcaagcagc agattacgcg cagaaaaaaa ggatctcaag aagatccttt gatcttttct    1920
acggggtctg acgctcagtg gaacgaaaac tcacgttaag ggattttggt catgagatta    1980
tcaaaaagga tcttcaccta gatccttta aattaaaaat gaagttttaa atcaatctaa    2040
agtatatatg agtaaacttg gtctgacagt taccaatgct taatcagtga ggcacctatc    2100
tcagcgatct gtctatttcg ttcatccata gttgcctgac tccccgtcgt gtagataact    2160
acgatacggg agggcttacc atctggcccc agtgctgcaa tgataccgcg agacccacgc    2220
tcaccggctc cagatttatc agcaataaac cagccagccg aagggccga gcgcagaagt     2280
ggtcctgcaa ctttatccgc ctccatccag tctattaatt gttgccggga agctagagta    2340
```

```
agtagttcgc cagttaatag tttgcgcaac gttgttgcca ttgctacagg catcgtggtg    2400
tcacgctcgt cgtttggtat ggcttcattc agctccggtt cccaacgatc aaggcgagtt    2460
acatgatccc ccatgttgtg caaaaaagcg gttagctcct tcggtcctcc gatcgttgtc    2520
agaagtaagt tggccgcagt gttatcactc atggttatgg cagcactgca taattctctt    2580
actgtcatgc catccgtaag atgctttttct gtgactggtg agtactcaac caagtcattc    2640
tgagaatagt gtatgcggcg accgagttgc tcttgcccgg cgtcaatacg ggataatacc    2700
gcgccacata gcagaacttt aaaagtgctc atcattggaa aacgttcttc ggggcgaaaa    2760
ctctcaagga tcttaccgct gttgagatcc agttcgatgt aacccactcg tgcacccaac    2820
tgatcttcag catcttttac tttcaccagc gtttctgggt gagcaaaaac aggaaggcaa    2880
aatgccgcaa aaaagggaat aagggcgaca cggaaatgtt gaatactcat actcttcctt    2940
tttcaatatt attgaagcat ttatcagggt tattgtctca tgagcggata catatttgaa    3000
tgtatttaga aaaataaaca aataggggtt ccgcgcacat ttccccgaaa agtgccacct    3060
attggtgtgg aaagtcccca ggctccccag caggcagaag tatgcaaagc atgcatctca    3120
attagtcagc aaccaggtgt ggaaagtccc caggctcccc agcaggcaga agtatgcaaa    3180
gcatgcatct caattagtca gcaaccatag tcccgcccct aactccgccc atcccgcccc    3240
taactccgcc cagttccgcc cattctccgc cccatggctg actaatttttt tttatttatg    3300 cagaggccga ggccgcctcg gcctctgagc tattccagaa gtagtgagga ggcttttttg    3360
gaggcctagg cttttgcaaa aagctagctt gcatgcctgc aggtcggccg ccacgaccgg    3420
tgccgccacc atccctgac ccacgcccct gaccctcac aaggagacga ccttccatga    3480
ccgagtacaa gcccacggtg cgcctcgcca cccgcgacga cgtccccgg gccgtacgca    3540 ccctcgccgc cgcgttcgcc gactaccccg ccacgcgcca caccgtcgac ccggaccgcc    3600
acatcgagcg ggtcaccgag ctgcaagaac tcttcctcac gcgcgtcggg ctcgacatcg    3660
gcaaggtgtg ggtcgcggac gacggcgccg cggtggcggt ctggaccacg ccggagagcg    3720
tcgaagcggg ggcggtgttc gccgagatcg gcccgcgcat ggccgagttg agcggttccc    3780
ggctggccgc gcagcaacag atggaaggcc tcctggcgcc gcaccggccc aaggagcccg    3840
cgtggttcct ggccaccgtc ggcgtctcgc ccgaccacca gggcaagggt ctgggcagcg    3900
ccgtcgtgct ccccggagtg gaggcggccg agcgcgccgg ggtgcccgcc ttcctggaga    3960
cctccgcgcc ccgcaacctc cccttctacg agcggctcgg cttcaccgtc accgccgacg    4020
tcgaggtgcc cgaaggaccg cgcacctggt gcatgacccg caagcccggt gcctgacgcc    4080
cgccccacga cccgcagcgc ccgaccgaaa ggagcgcacg accccatggc tccgaccgaa    4140
gccaccgggg gcgcccccgc cgaccccgca cccgccccccg aggcccaccg actctagagg    4200
atcataatca gccataccac atttgtagag gttttacttg cttaaaaaa cctcccacac    4260 ctccccctga acctgaaaca taaaatgaat gcaattgttg ttgttaactt gtttattgca    4320
gcttataatg gttacaaata aagcaatagc atcacaaatt tcacaaataa agcatttttt    4380
tcactgcaat ctaagaaacc attattatca tgacattaac ctataaaaat aggcgtatca    4440
cgaggccctt tcgtc                                                    4455
```

<210> SEQ ID NO 47
<211> LENGTH: 4002
<212> TYPE: DNA
<213> ORGANISM: Artificial
<220> FEATURE:
<223> OTHER INFORMATION: pd2 vector

<400> SEQUENCE: 47

```
tagttattaa tagtaatcaa ttacggggtc attagttcat agcccatata tggagttccg    60
cgttacataa cttacggtaa atggcccgcc tggctgaccg cccaacgacc cccgcccatt   120
gacgtcaata atgacgtatg ttcccatagt aacgccaata gggactttcc attgacgtca   180
atgggtggag tatttacggt aaactgccca cttggcagta catcaagtgt atcatatgcc   240
aagtacgccc cctattgacg tcaatgacgg taaatggccc gcctggcatt atgcccagta   300
catgacctta tgggactttc ctacttggca gtacatctac gtattagtca tcgctattac   360
catggtgatg cggttttggc agtacatcaa tgggcgtgga tagcggtttg actcacgggg   420
atttccaagt ctccacccca ttgacgtcaa tgggagtttg ttttggcacc aaaatcaacg   480
ggactttcca aaatgtcgta caactccgcc ccattgacg caaatgggcg gtaggcgtgt   540
acggtgggag gtctatataa gcagagctgg tttagtgaac cgtcagatcc gctagcgcta   600
ccggactcag atctcgagct caagcttcga attctgcagt cgacggtacc gcgggcccgg   660
gatccaccgg ggccgcgact ctagatcata atcagccata ccacatttgt agaggtttta   720
cttgctttaa aaaacctccc acacctcccc ctgaacctga acataaaat gaatgcaatt   780
gttgttgtta acttgtttat tgcagcttat aatggttaca aataaagcaa tagcatcaca   840
aatttcacaa ataaagcatt ttttcactg cattctagtt gtggtttgtc caaactcatc   900
aatgtatctt aaggcgtaaa ttgtaagcgt taatattttg ttaaaattcg cgttaaattt   960
ttgttaaatc agctcatttt ttaaccaata ggccgaaatc ggcaaaatcc cttataaatc  1020
aaaagaatag accgagatag ggttgagtgt tgttccagtt tggaacaaga gtccactatt  1080
aaagaacgtg gactccaacg tcaaagggcg aaaaaccgtc tatcagggcg atggcccact  1140
acgtgaacca tcaccctaat caagtttttt ggggtcgagg tgccgtaaag cactaaatcg  1200
gaaccctaaa gggagccccc gatttagagc ttgacgggga agccggcga acgtggcgag  1260
aaaggaaggg aagaaagcga aaggagcggg cgctaggggcg ctggcaagtg tagcggtcac  1320
gctgcgcgta accaccacac ccgccgcgct taatgcgccg ctacagggcg cgtcaggtgg  1380
cacttttcgg ggaaatgtgc gcggaacccc tatttgttta ttttttctaaa tacattcaaa  1440
tatgtatccg ctcatgagac aataaccctg ataaatgctt caataatatt gaaaaaggaa  1500
gagtcctgag gcggaaagaa ccagctgtgg aatgtgtgtc agttagggtg tggaaagtcc  1560
ccaggctccc cagcaggcag aagtatgcaa agcatgcatc tcaattagtc agcaaccagg  1620
tgtggaaagt cccaggctc cccagcaggc agaagtatgc aaagcatgca tctcaattag  1680
tcagcaacca tagtcccgcc cctaactccg cccatcccgc cctaactccg cccagttcc  1740
gcccattctc cgccccatgg ctgactaatt ttttttattt atgcagaggc cgaggccgcc  1800
tcggcctctg agctattcca gaagtagtga ggaggctttt ttggaggcct aggcttttgc  1860
aaagatcgat caagacag gatgaggatc gtttcgcatg attgaacaag atggattgca  1920
cgcaggttct ccggccgctt gggtggagag gctattcggc tatgactggg cacaacagac  1980
aatcggctgc tctgatgccg ccgtgttccg gctgtcagcg caggggcgcc cggttctttt  2040
tgtcaagacc gacctgtccg gtgccctgaa tgaactgcaa gacgaggcag cgcggctatc  2100
gtggctggcc acgacgggcg ttccttgcgc agctgtgctc gacgttgtca ctgaagcggg  2160
aagggactgg ctgctattgg gcgaagtgcc ggggcaggat ctcctgtcat ctcaccttgc  2220
tcctgccgag aaagtatcca tcatggctga tgcaatgcgg cggctgcata cgcttgatcc  2280
ggctacctgc ccattcgacc accaagcgaa acatcgcatc gagcgagcac gtactcggat  2340
```

```
ggaagccggt cttgtcgatc aggatgatct ggacgaagag catcaggggc tcgcgccagc    2400
cgaactgttc gccaggctca aggcgagcat gcccgacggc gaggatctcg tcgtgaccca    2460
tggcgatgcc tgcttgccga atatcatggt ggaaaatggc cgcttttctg gattcatcga    2520
ctgtggccgg ctgggtgtgg cggaccgcta tcaggacata gcgttggcta cccgtgatat    2580
tgctgaagag cttggcggcg aatgggctga ccgcttcctc gtgctttacg gtatcgccgc    2640
tcccgattcg cagcgcatcg ccttctatcg ccttcttgac gagttcttct gagcgggact    2700
ctggggttcg aaatgaccga ccaagcgacg cccaacctgc catcacgaga tttcgattcc    2760
accgccgcct tctatgaaag gttgggcttc ggaatcgttt ccgggacgc cggctggatg     2820 atcctccagc gcggggatct catgctggag ttcttcgccc accctagggg gaggctaact    2880
gaaacacgga aggagacaat accggaagga acccgcgcta tgacggcaat aaaaagacag    2940
aataaaacgc acggtgttgg gtcgtttgtt cataaacgcg gggttcggtc ccagggctgg    3000
cactctgtcg ataccccacc gagacccat tgggccaat acgccgcgt tcttccttt       3060 tccccacccc acccccaag ttcgggtgaa ggcccagggc tcgcagccaa cgtcggggcg     3120
gcaggccctg ccatagcctc aggttactca tatatacttt agattgattt aaaacttcat    3180
ttttaattta aaaggatcta ggtgaagatc ctttttgata atctcatgac caaaatccct    3240
taacgtgagt tttcgttcca ctgagcgtca gaccccgtag aaaagatcaa aggatcttct    3300
tgagatcctt ttttctgcg cgtaatctgc tgcttgcaaa caaaaaaacc accgctacca    3360
gcggtggttt gtttgccgga tcaagagcta ccaactcttt ttccgaaggt aactggcttc    3420
agcagagcgc agataccaaa tactgtcctt ctagtgtagc cgtagttagg ccaccacttc    3480
aagaactctg tagcaccgcc tacatacctc gctctgctaa tcctgttacc agtggctgct    3540
gccagtggcg ataagtcgtg tcttaccggg ttggactcaa gacgatagtt accggataag    3600
gcgcagcggt cgggctgaac ggggggttcg tgcacacagc ccagcttgga gcgaacgacc    3660
tacaccgaac tgagatacct acagcgtgag ctatgagaaa gcgccacgct tcccgaaggg    3720
agaaaggcgg acaggtatcc ggtaagcggc agggtcggaa caggagagcg cacgagggag    3780
cttccagggg gaaacgcctg gtatctttat agtcctgtcg gtttcgcca cctctgactt     3840 gagcgtcgat ttttgtgatg ctcgtcaggg gggcggagcc tatggaaaaa cgccagcaac    3900
gcggcctttt tacggttcct ggccttttgc tggccttttg ctcacatgtt ctttcctgcg    3960
ttatcccctg attctgtgga taaccgtatt accgccatgc at                       4002
```

<210> SEQ ID NO 48
<211> LENGTH: 328
<212> TYPE: PRT
<213> ORGANISM: Homo sapiens

<400> SEQUENCE: 48

Met Glu Lys Ser Ile Trp Leu Leu Ala Cys Leu Ala Trp Val Leu Pro
1               5                   10                  15

Thr Gly Ser Phe Val Arg Thr Lys Ile Asp Thr Thr Glu Asn Leu Leu
            20                  25                  30

Asn Thr Glu Val His Ser Ser Pro Ala Gln Arg Trp Ser Met Gln Val
        35                  40                  45

Pro Pro Glu Val Ser Ala Glu Ala Gly Asp Ala Ala Val Leu Pro Cys
    50                  55                  60

Thr Phe Thr His Pro His Arg His Tyr Asp Gly Pro Leu Thr Ala Ile
65                  70                  75                  80

Trp Arg Ala Gly Glu Pro Tyr Ala Gly Pro Gln Val Phe Arg Cys Ala

```
                    85                  90                  95
Ala Ala Arg Gly Ser Glu Leu Cys Gln Thr Ala Leu Ser Leu His Gly
            100                 105                 110

Arg Phe Arg Leu Leu Gly Asn Pro Arg Asn Asp Leu Ser Leu Arg
            115                 120                 125

Val Glu Arg Leu Ala Leu Ala Asp Asp Arg Tyr Phe Cys Arg Val
            130                 135                 140

Glu Phe Ala Gly Asp Val His Asp Arg Tyr Ser Arg His Gly Val
145                 150                 155                 160

Arg Leu His Val Thr Ala Ala Pro Arg Ile Val Asn Ile Ser Val Leu
                165                 170                 175

Pro Ser Pro Ala His Ala Phe Arg Ala Leu Cys Thr Ala Glu Gly Glu
                180                 185                 190

Pro Pro Pro Ala Leu Ala Trp Ser Gly Pro Ala Leu Gly Asn Ser Leu
            195                 200                 205

Ala Ala Val Arg Ser Pro Arg Glu Gly His Gly His Leu Val Thr Ala
            210                 215                 220

Glu Leu Pro Ala Leu Thr His Asp Gly Arg Tyr Thr Cys Thr Ala Ala
225                 230                 235                 240

Asn Ser Leu Gly Arg Ser Glu Ala Ser Val Tyr Leu Phe Arg Phe His
                245                 250                 255

Gly Ala Ser Gly Ala Ser Thr Val Ala Leu Leu Leu Gly Ala Leu Gly
                260                 265                 270

Phe Lys Ala Leu Leu Leu Leu Gly Val Leu Ala Ala Arg Ala Ala Arg
            275                 280                 285

Arg Arg Pro Glu His Leu Asp Thr Pro Asp Thr Pro Pro Arg Ser Gln
            290                 295                 300

Ala Gln Glu Ser Asn Tyr Glu Asn Leu Ser Gln Met Asn Pro Arg Ser
305                 310                 315                 320

Pro Pro Ala Thr Met Cys Ser Pro
                325

<210> SEQ ID NO 49
<211> LENGTH: 198
<212> TYPE: PRT
<213> ORGANISM: Homo sapiens

<400> SEQUENCE: 49

Met Ile Gly Ser Gly Leu Ala Gly Ser Gly Ala Gly Gly Pro Ser
1               5                   10                  15

Ser Thr Val Thr Trp Cys Ala Leu Phe Ser Asn His Val Ala Ala Thr
                20                  25                  30

Gln Ala Ser Leu Leu Leu Ser Phe Val Trp Met Pro Ala Leu Leu Pro
            35                  40                  45

Val Ala Ser Arg Leu Leu Leu Pro Arg Val Leu Leu Thr Met Ala
            50                  55                  60

Ser Gly Ser Pro Pro Thr Gln Pro Ser Pro Ala Ser Asp Ser Gly Ser
65                  70                  75                  80

Gly Tyr Val Pro Gly Ser Val Ser Ala Ala Phe Val Thr Cys Pro Asn
                85                  90                  95

Glu Lys Val Ala Lys Glu Ile Ala Arg Ala Val Val Glu Lys Arg Leu
            100                 105                 110

Ala Ala Cys Val Asn Leu Ile Pro Gln Ile Thr Ser Ile Tyr Glu Trp
            115                 120                 125

Lys Gly Lys Ile Glu Glu Asp Ser Glu Val Leu Met Met Ile Lys Thr
```

-continued

```
                130                 135                 140
Gln Ser Ser Leu Val Pro Ala Leu Thr Asp Phe Val Arg Ser Val His
145                 150                 155                 160

Pro Tyr Glu Val Ala Glu Val Ile Ala Leu Pro Val Glu Gln Gly Asn
                165                 170                 175

Phe Pro Tyr Leu Gln Trp Val Arg Gln Val Thr Glu Ser Val Ser Asp
                180                 185                 190

Ser Ile Thr Val Leu Pro
                195

<210> SEQ ID NO 50
<211> LENGTH: 537
<212> TYPE: PRT
<213> ORGANISM: Homo sapiens

<400> SEQUENCE: 50

Met Gly Asp Glu Asp Lys Arg Ile Thr Tyr Glu Asp Ser Pro Ser
1               5                   10                  15

Thr Gly Met Asn Tyr Thr Pro Ser Met His Gln Glu Ala Gln Glu Glu
                20                  25                  30

Thr Val Met Lys Leu Lys Gly Ile Asp Ala Asn Glu Pro Thr Glu Gly
                35                  40                  45

Ser Ile Leu Leu Lys Ser Ser Glu Lys Lys Leu Gln Glu Thr Pro Thr
50                  55                  60

Glu Ala Asn His Val Gln Arg Leu Arg Gln Met Leu Ala Cys Pro Pro
65                  70                  75                  80

His Gly Leu Leu Asp Arg Val Ile Thr Asn Val Thr Ile Ile Val Leu
                85                  90                  95

Leu Trp Ala Val Val Trp Ser Ile Thr Gly Ser Glu Cys Leu Pro Gly
                100                 105                 110

Gly Asn Leu Phe Gly Ile Ile Ile Leu Phe Tyr Cys Ala Ile Ile Gly
                115                 120                 125

Gly Lys Leu Leu Gly Leu Ile Lys Leu Pro Thr Leu Pro Pro Leu Pro
                130                 135                 140

Ser Leu Leu Gly Met Leu Leu Ala Gly Phe Leu Ile Arg Asn Ile Pro
145                 150                 155                 160

Val Ile Asn Asp Asn Val Gln Ile Lys His Lys Trp Ser Ser Ser Leu
                165                 170                 175

Arg Ser Ile Ala Leu Ser Ile Ile Leu Val Arg Ala Gly Leu Gly Leu
                180                 185                 190

Asp Ser Lys Ala Leu Lys Lys Leu Lys Gly Val Cys Val Arg Leu Ser
                195                 200                 205

Met Gly Pro Cys Ile Val Glu Ala Cys Thr Ser Ala Leu Leu Ala His
                210                 215                 220

Tyr Leu Leu Gly Leu Pro Trp Gln Trp Gly Phe Ile Leu Gly Phe Val
225                 230                 235                 240

Leu Gly Ala Val Ser Pro Ala Val Val Pro Ser Met Leu Leu Leu
                245                 250                 255

Gln Gly Gly Gly Tyr Gly Val Glu Lys Gly Val Pro Thr Leu Leu Met
                260                 265                 270

Ala Ala Gly Ser Phe Asp Asp Ile Leu Ala Ile Thr Gly Phe Asn Thr
                275                 280                 285

Cys Leu Gly Ile Ala Phe Ser Thr Gly Ser Thr Val Phe Asn Val Leu
                290                 295                 300

Arg Gly Val Leu Glu Val Val Ile Gly Val Ala Thr Gly Ser Val Leu
```

```
              305                 310                 315                 320
Gly Phe Phe Ile Gln Tyr Phe Pro Ser Arg Asp Gln Asp Lys Leu Val
                        325                 330                 335

Cys Lys Arg Thr Phe Leu Val Leu Gly Leu Ser Val Leu Ala Val Phe
                        340                 345                 350

Ser Ser Val His Phe Gly Phe Pro Gly Ser Gly Gly Leu Cys Thr Leu
                        355                 360                 365

Val Met Ala Phe Leu Ala Gly Met Gly Trp Thr Ser Glu Lys Ala Glu
            370                 375                 380

Val Glu Lys Ile Ile Ala Val Ala Trp Asp Ile Phe Gln Pro Leu Leu
385                 390                 395                 400

Phe Gly Leu Ile Gly Ala Glu Val Ser Ile Ala Ser Leu Arg Pro Glu
                        405                 410                 415

Thr Val Gly Leu Cys Val Ala Thr Val Gly Ile Ala Val Leu Ile Arg
                        420                 425                 430

Ile Leu Thr Thr Phe Leu Met Val Cys Phe Ala Gly Phe Asn Leu Lys
                        435                 440                 445

Glu Lys Ile Phe Ile Ser Phe Ala Trp Leu Pro Lys Ala Thr Val Gln
            450                 455                 460

Ala Ala Ile Gly Ser Val Ala Leu Asp Thr Ala Arg Ser His Gly Glu
465                 470                 475                 480

Lys Gln Leu Glu Asp Tyr Gly Met Asp Val Leu Thr Val Ala Phe Leu
                        485                 490                 495

Ser Ile Leu Ile Thr Ala Pro Ile Gly Ser Leu Leu Ile Gly Leu Leu
                        500                 505                 510

Gly Pro Arg Leu Leu Gln Lys Val Glu His Gln Asn Lys Asp Glu Glu
                        515                 520                 525

Val Gln Gly Glu Thr Ser Val Gln Val
            530                 535

<210> SEQ ID NO 51
<211> LENGTH: 209
<212> TYPE: PRT
<213> ORGANISM: Homo sapiens

<400> SEQUENCE: 51

Met Val Ser Ser Pro Cys Thr Pro Ala Ser Ser Arg Thr Cys Ser Arg
1               5                   10                  15

Ile Leu Gly Leu Ser Leu Gly Thr Ala Ala Leu Phe Ala Ala Gly Ala
                20                  25                  30

Asn Val Ala Leu Leu Leu Pro Asn Trp Asp Val Thr Tyr Leu Leu Arg
            35                  40                  45

Gly Leu Leu Gly Arg His Ala Met Leu Gly Thr Gly Leu Trp Gly Gly
        50                  55                  60

Gly Leu Met Val Leu Thr Ala Ala Ile Leu Ile Ser Leu Met Gly Trp
65                  70                  75                  80

Arg Tyr Gly Cys Phe Ser Lys Ser Gly Leu Cys Arg Ser Val Leu Thr
                85                  90                  95

Ala Leu Leu Ser Gly Gly Leu Ala Leu Leu Gly Ala Leu Ile Cys Phe
                100                 105                 110

Val Thr Ser Gly Val Ala Leu Lys Asp Gly Pro Phe Cys Met Phe Asp
            115                 120                 125

Val Ser Ser Phe Asn Gln Thr Gln Ala Trp Lys Tyr Gly Tyr Pro Phe
        130                 135                 140

Lys Asp Leu His Ser Arg Asn Tyr Leu Tyr Asp Arg Ser Leu Trp Asn
```

```
            145                 150                 155                 160
Ser Val Cys Leu Glu Pro Ser Ala Ala Val Val Trp His Val Ser Leu
                    165                 170                 175

Phe Ser Ala Leu Leu Cys Ile Ser Leu Leu Gln Leu Leu Leu Val Val
                180                 185                 190

Val His Val Ile Asn Ser Leu Leu Gly Leu Phe Cys Ser Leu Cys Glu
                195                 200                 205

Lys

<210> SEQ ID NO 52
<211> LENGTH: 218
<212> TYPE: PRT
<213> ORGANISM: Homo sapiens

<400> SEQUENCE: 52

Met Ala Leu Val Pro Tyr Glu Glu Thr Thr Glu Phe Gly Leu Gln Lys
1               5                   10                  15

Phe His Lys Pro Leu Ala Thr Phe Ser Phe Ala Asn His Thr Ile Gln
                20                  25                  30

Ile Arg Gln Asp Trp Arg His Leu Gly Val Ala Ala Val Val Trp Asp
            35                  40                  45

Ala Ala Ile Val Leu Ser Thr Tyr Leu Glu Met Gly Ala Val Glu Leu
        50                  55                  60

Arg Gly Arg Ser Ala Val Glu Leu Gly Ala Gly Thr Gly Leu Val Gly
65                  70                  75                  80

Ile Val Ala Ala Leu Leu Gly Ala His Val Thr Ile Thr Asp Arg Lys
                85                  90                  95

Val Ala Leu Glu Phe Leu Lys Ser Asn Val Gln Ala Asn Leu Pro Pro
                100                 105                 110

His Ile Gln Thr Lys Thr Val Val Lys Glu Leu Thr Trp Gly Gln Asn
            115                 120                 125

Leu Gly Ser Phe Ser Pro Gly Glu Phe Asp Leu Ile Leu Gly Ala Asp
        130                 135                 140

Ile Ile Tyr Leu Glu Glu Thr Phe Thr Asp Leu Leu Gln Thr Leu Glu
145                 150                 155                 160

His Leu Cys Ser Asn His Ser Val Ile Leu Leu Ala Cys Arg Ile Arg
                165                 170                 175

Tyr Glu Arg Asp Asn Asn Phe Leu Ala Met Leu Glu Arg Gln Phe Ile
                180                 185                 190

Val Arg Lys Val His Tyr Asp Pro Glu Lys Asp Val His Ile Tyr Glu
            195                 200                 205

Ala Gln Lys Arg Asn Gln Lys Glu Asp Leu
        210                 215

<210> SEQ ID NO 53
<211> LENGTH: 114
<212> TYPE: PRT
<213> ORGANISM: Homo sapiens

<400> SEQUENCE: 53

Met Ser Leu Leu Ser Ser Arg Ala Ala Arg Val Pro Gly Pro Ser Ser
1               5                   10                  15

Ser Leu Cys Ala Leu Leu Val Leu Leu Leu Leu Thr Gln Pro Gly Gly
                20                  25                  30

Pro Ile Ala Ser Ala Gly Pro Ala Ala Ala Val Leu Arg Glu Leu Arg
            35                  40                  45
```

```
Cys Val Cys Leu Gln Thr Thr Gln Gly Val His Pro Lys Met Ile Ser
     50                  55                  60

Asn Leu Gln Val Phe Ala Ile Gly Pro Gln Cys Ser Lys Val Glu Val
 65                  70                  75                  80

Val Ala Ser Leu Lys Asn Gly Lys Glu Ile Cys Leu Asp Pro Glu Ala
                 85                  90                  95

Pro Phe Leu Lys Lys Val Ile Gln Lys Ile Leu Asp Gly Gly Asn Lys
                100                 105                 110

Glu Asn

<210> SEQ ID NO 54
<211> LENGTH: 350
<212> TYPE: PRT
<213> ORGANISM: Homo sapiens

<400> SEQUENCE: 54

Met Ala Val Phe Val Leu Leu Ala Leu Val Ala Gly Val Leu Gly
 1               5                  10                  15

Asn Glu Phe Ser Ile Leu Lys Ser Pro Gly Ser Val Val Phe Arg Asn
                 20                  25                  30

Gly Asn Trp Pro Ile Pro Gly Glu Arg Ile Pro Asp Val Ala Ala Leu
                 35                  40                  45

Ser Met Gly Phe Ser Val Lys Glu Asp Leu Ser Trp Pro Gly Leu Ala
     50                  55                  60

Val Gly Asn Leu Phe His Arg Pro Arg Ala Thr Val Met Val Met Val
 65                  70                  75                  80

Lys Gly Val Asn Lys Leu Ala Leu Pro Pro Gly Ser Val Ile Ser Tyr
                 85                  90                  95

Pro Leu Glu Asn Ala Val Pro Phe Ser Leu Asp Ser Val Ala Asn Ser
                100                 105                 110

Ile His Ser Leu Phe Ser Glu Glu Thr Pro Val Val Leu Gln Leu Ala
                115                 120                 125

Pro Ser Glu Glu Arg Val Tyr Met Val Gly Lys Ala Asn Ser Val Phe
                130                 135                 140

Glu Asp Leu Ser Val Thr Leu Arg Gln Leu Arg Asn Arg Leu Phe Gln
145                 150                 155                 160

Glu Asn Ser Val Leu Ser Ser Leu Pro Leu Asn Ser Leu Ser Arg Asn
                165                 170                 175

Asn Glu Val Asp Leu Leu Phe Leu Ser Glu Leu Gln Val Leu His Asp
                180                 185                 190

Ile Ser Ser Leu Leu Ser Arg His Lys His Leu Ala Lys Asp His Ser
                195                 200                 205

Pro Asp Leu Tyr Ser Leu Glu Leu Ala Gly Leu Asp Glu Ile Gly Lys
                210                 215                 220

Arg Tyr Gly Glu Asp Ser Glu Gln Phe Arg Asp Ala Ser Lys Ile Leu
225                 230                 235                 240

Val Asp Ala Leu Gln Lys Phe Ala Asp Met Tyr Ser Leu Tyr Gly
                245                 250                 255

Gly Asn Ala Val Val Glu Leu Val Thr Val Lys Ser Phe Asp Thr Ser
                260                 265                 270

Leu Ile Arg Lys Thr Arg Thr Ile Leu Glu Ala Lys Gln Ala Lys Asn
                275                 280                 285

Pro Ala Ser Pro Tyr Asn Leu Ala Tyr Lys Tyr Asn Phe Glu Tyr Ser
                290                 295                 300

Val Val Phe Asn Met Val Leu Trp Ile Met Ile Ala Leu Ala Leu Ala
```

```
                 305                 310                 315                 320
Val Ile Ile Thr Ser Tyr Asn Ile Trp Asn Met Asp Pro Gly Tyr Asp
                325                 330                 335

Ser Ile Ile Tyr Arg Met Thr Asn Gln Lys Ile Arg Met Asp
                340                 345                 350

<210> SEQ ID NO 55
<211> LENGTH: 370
<212> TYPE: PRT
<213> ORGANISM: Homo sapiens

<400> SEQUENCE: 55

Met Glu Ile Leu Met Thr Val Ser Lys Phe Ala Ser Ile Cys Thr Met
1               5                   10                  15

Gly Ala Asn Ala Ser Ala Leu Glu Lys Glu Ile Gly Pro Glu Gln Phe
                20                  25                  30

Pro Val Asn Glu His Tyr Phe Gly Leu Val Asn Phe Gly Asn Thr Cys
            35                  40                  45

Tyr Cys Asn Ser Val Leu Gln Ala Leu Tyr Phe Cys Arg Pro Phe Arg
        50                  55                  60

Glu Lys Val Leu Ala Tyr Lys Ser Gln Pro Arg Lys Lys Glu Ser Leu
65                  70                  75                  80

Leu Thr Cys Leu Ala Asp Leu Phe His Ser Ile Ala Thr Gln Lys Lys
                85                  90                  95

Lys Val Gly Val Ile Pro Pro Lys Lys Phe Ile Thr Arg Leu Arg Lys
                100                 105                 110

Glu Asn Glu Leu Phe Asp Asn Tyr Met Gln Gln Asp Ala His Glu Phe
            115                 120                 125

Leu Asn Tyr Leu Leu Asn Thr Ile Ala Asp Ile Leu Gln Glu Glu Arg
        130                 135                 140

Lys Gln Glu Lys Gln Asn Gly Arg Leu Pro Asn Gly Asn Ile Asp Asn
145                 150                 155                 160

Glu Asn Asn Asn Ser Thr Pro Asp Pro Thr Trp Val Asp Glu Ile Phe
                165                 170                 175

Gln Gly Thr Leu Thr Asn Glu Thr Arg Cys Leu Thr Cys Glu Thr Ile
                180                 185                 190

Ser Ser Lys Asp Glu Asp Phe Leu Asp Leu Ser Val Asp Val Glu Gln
            195                 200                 205

Asn Thr Ser Ile Thr His Cys Leu Arg Gly Phe Ser Asn Thr Glu Thr
        210                 215                 220

Leu Cys Ser Glu Tyr Lys Tyr Cys Glu Glu Cys Arg Ser Lys Gln
225                 230                 235                 240

Glu Ala His Lys Arg Met Lys Val Lys Lys Leu Pro Met Ile Leu Ala
                245                 250                 255

Leu His Leu Lys Arg Phe Lys Tyr Met Asp Gln Leu His Arg Tyr Thr
                260                 265                 270

Lys Leu Ser Tyr Arg Val Val Phe Pro Leu Glu Leu Arg Leu Phe Asn
            275                 280                 285

Thr Ser Gly Asp Ala Thr Asn Pro Asp Arg Met Tyr Asp Leu Val Ala
        290                 295                 300

Val Val Val His Cys Gly Ser Gly Pro Asn Arg Gly His Tyr Ile Ala
305                 310                 315                 320

Ile Val Lys Ser His Asp Phe Trp Leu Leu Phe Asp Asp Ile Val
                325                 330                 335

Glu Lys Ile Asp Ala Gln Ala Ile Glu Glu Phe Tyr Gly Leu Thr Ser
```

```
                    340             345             350
Asp Ile Ser Lys Asn Ser Glu Ser Gly Tyr Ile Leu Phe Tyr Gln Ser
            355                 360                 365

Arg Asp
    370

<210> SEQ ID NO 56
<211> LENGTH: 193
<212> TYPE: PRT
<213> ORGANISM: Homo sapiens

<400> SEQUENCE: 56

Met Ser Asp Asp Ser Arg Ala Ser Thr Ser Ser Ser Ser Ser Ser Ser
1               5                   10                  15

Ser Ser Asn Gln Gln Thr Glu Lys Glu Thr Asn Thr Pro Lys Lys Lys
            20                  25                  30

Glu Ser Lys Val Ser Met Ser Lys Asn Ser Lys Leu Leu Ser Thr Ser
        35                  40                  45

Ala Lys Arg Ile Gln Lys Glu Leu Ala Asp Ile Thr Leu Asp Pro Pro
    50                  55                  60

Pro Asn Cys Ser Ala Gly Pro Lys Gly Asp Asn Ile Tyr Glu Trp Arg
65                  70                  75                  80

Ser Thr Ile Leu Gly Pro Pro Gly Ser Val Tyr Glu Gly Gly Val Phe
                85                  90                  95

Phe Leu Asp Ile Thr Phe Thr Pro Glu Tyr Pro Phe Lys Pro Pro Lys
            100                 105                 110

Val Thr Phe Arg Thr Arg Ile Tyr His Cys Asn Ile Asn Ser Gln Gly
        115                 120                 125

Val Ile Cys Leu Asp Ile Leu Lys Asp Asn Trp Ser Pro Ala Leu Thr
    130                 135                 140

Ile Ser Lys Val Leu Leu Ser Ile Cys Ser Leu Leu Thr Asp Cys Asn
145                 150                 155                 160

Pro Ala Asp Pro Leu Val Gly Ser Ile Ala Thr Gln Tyr Met Thr Asn
                165                 170                 175

Arg Ala Glu His Asp Arg Met Ala Arg Gln Trp Thr Lys Arg Tyr Ala
            180                 185                 190

Thr

<210> SEQ ID NO 57
<211> LENGTH: 206
<212> TYPE: PRT
<213> ORGANISM: Homo sapiens

<400> SEQUENCE: 57

Met Gly Ala Glu Trp Glu Leu Gly Ala Glu Ala Gly Gly Ser Leu Leu
1               5                   10                  15

Leu Cys Ala Ala Leu Leu Ala Ala Gly Cys Ala Leu Gly Leu Arg Leu
            20                  25                  30

Gly Arg Gly Gln Gly Ala Ala Asp Arg Gly Ala Leu Ile Trp Leu Cys
        35                  40                  45

Tyr Asp Ala Leu Val His Phe Ala Leu Glu Gly Pro Phe Val Tyr Leu
    50                  55                  60

Ser Leu Val Gly Asn Val Ala Asn Ser Asp Gly Leu Ile Ala Ser Leu
65                  70                  75                  80

Trp Lys Glu Tyr Gly Lys Ala Asp Ala Arg Trp Val Tyr Phe Asp Pro
                85                  90                  95
```

```
Thr Ile Val Ser Val Glu Ile Leu Thr Val Ala Leu Asp Gly Ser Leu
                100                 105                 110

Ala Leu Phe Leu Ile Tyr Ala Ile Val Lys Glu Lys Tyr Arg His
            115                 120                 125

Phe Leu Gln Ile Thr Leu Cys Val Cys Glu Leu Tyr Gly Cys Trp Met
            130                 135                 140

Thr Phe Leu Pro Glu Trp Leu Thr Arg Ser Pro Asn Leu Asn Thr Ser
145                 150                 155                 160

Asn Trp Leu Tyr Cys Trp Leu Tyr Leu Phe Phe Asn Gly Val Trp
                165                 170                 175

Val Leu Ile Pro Gly Leu Leu Leu Trp Gln Ser Trp Leu Glu Leu Lys
                180                 185                 190

Lys Met His Gln Lys Glu Thr Ser Ser Val Lys Lys Phe Gln
                195                 200                 205

<210> SEQ ID NO 58
<211> LENGTH: 1129
<212> TYPE: PRT
<213> ORGANISM: Homo sapiens

<400> SEQUENCE: 58

Met Arg Ser Ser Ala Ser Arg Leu Ser Ser Phe Ser Ser Arg Asp Ser
1               5                   10                  15

Leu Trp Asn Arg Met Pro Asp Gln Ile Ser Val Ser Glu Phe Ile Ala
                20                  25                  30

Glu Thr Thr Glu Asp Tyr Asn Ser Pro Thr Thr Ser Ser Phe Thr Thr
            35                  40                  45

Arg Leu His Asn Cys Arg Asn Thr Val Thr Leu Leu Glu Glu Ala Leu
50                  55                  60

Asp Gln Asp Arg Thr Ala Leu Gln Lys Val Lys Lys Ser Val Lys Ala
65                  70                  75                  80

Ile Tyr Asn Ser Gly Gln Asp His Val Gln Asn Glu Gly Asn Tyr Ala
                85                  90                  95

Gln Val Leu Asp Lys Phe Gly Ser Asn Phe Leu Ser Arg Asp Asn Pro
            100                 105                 110

Asp Leu Gly Thr Ala Phe Val Lys Phe Ser Thr Leu Thr Lys Glu Leu
            115                 120                 125

Ser Thr Leu Leu Lys Asn Leu Leu Gln Gly Leu Ser His Asn Val Ile
130                 135                 140

Phe Thr Leu Asp Ser Leu Leu Lys Gly Asp Leu Lys Gly Val Lys Gly
145                 150                 155                 160

Asp Leu Lys Lys Pro Phe Asp Lys Ala Trp Lys Asp Tyr Glu Thr Lys
                165                 170                 175

Phe Thr Lys Ile Glu Lys Glu Lys Arg Glu His Ala Lys Gln His Gly
            180                 185                 190

Met Ile Arg Thr Glu Ile Thr Gly Ala Glu Ile Ala Glu Glu Met Glu
            195                 200                 205

Lys Glu Arg Arg Leu Phe Gln Leu Gln Met Cys Glu Tyr Leu Ile Lys
210                 215                 220

Val Asn Glu Ile Lys Thr Lys Lys Gly Val Asp Leu Leu Gln Asn Leu
225                 230                 235                 240

Ile Lys Tyr Tyr His Ala Gln Cys Asn Phe Phe Gln Asp Gly Leu Lys
                245                 250                 255

Thr Ala Asp Lys Leu Lys Gln Tyr Ile Glu Lys Leu Ala Ala Asp Leu
            260                 265                 270
```

-continued

```
Tyr Asn Ile Lys Gln Thr Gln Asp Glu Glu Lys Lys Gln Leu Thr Ala
    275                 280                 285
Leu Arg Asp Leu Ile Lys Ser Ser Leu Gln Leu Gln Lys Glu Asp
    290                 295                 300
Ser Gln Ser Arg Gln Gly Gly Tyr Ser Met His Gln Leu Gln Gly Asn
305                 310                 315                 320
Lys Glu Tyr Gly Ser Glu Lys Lys Gly Tyr Leu Leu Lys Lys Ser Asp
                325                 330                 335
Gly Ile Arg Lys Val Trp Gln Arg Arg Lys Cys Ser Val Lys Asn Gly
                340                 345                 350
Ile Leu Thr Ile Ser His Ala Thr Ser Asn Arg Gln Pro Ala Lys Leu
            355                 360                 365
Asn Leu Leu Thr Cys Gln Val Lys Pro Asn Ala Glu Asp Lys Lys Ser
    370                 375                 380
Phe Asp Leu Ile Ser His Asn Arg Thr Tyr His Phe Gln Ala Glu Asp
385                 390                 395                 400
Glu Gln Asp Tyr Val Ala Trp Ile Ser Val Leu Thr Asn Ser Lys Glu
                405                 410                 415
Glu Ala Leu Thr Met Ala Phe Arg Gly Glu Gln Ser Ala Gly Glu Asn
                420                 425                 430
Ser Leu Glu Asp Leu Thr Lys Ala Ile Ile Glu Asp Val Gln Arg Leu
            435                 440                 445
Pro Gly Asn Asp Ile Cys Cys Asp Cys Gly Ser Ser Glu Pro Thr Trp
    450                 455                 460
Leu Ser Thr Asn Leu Gly Ile Leu Thr Cys Ile Glu Cys Ser Gly Ile
465                 470                 475                 480
His Arg Glu Met Gly Val His Ile Ser Arg Ile Gln Ser Leu Glu Leu
                485                 490                 495
Asp Lys Leu Gly Thr Ser Glu Leu Leu Leu Ala Lys Asn Val Gly Asn
            500                 505                 510
Asn Ser Phe Asn Asp Ile Met Glu Ala Asn Leu Pro Ser Pro Ser Pro
    515                 520                 525
Lys Pro Thr Pro Ser Ser Asp Met Thr Val Arg Lys Glu Tyr Ile Thr
530                 535                 540
Ala Lys Tyr Val Asp His Arg Phe Ser Arg Lys Thr Cys Ser Thr Ser
545                 550                 555                 560
Ser Ala Lys Leu Asn Glu Leu Leu Glu Ala Ile Lys Ser Arg Asp Leu
                565                 570                 575
Leu Ala Leu Ile Gln Val Tyr Ala Glu Gly Val Glu Leu Met Glu Pro
            580                 585                 590
Leu Leu Glu Pro Gly Gln Glu Leu Gly Glu Thr Ala Leu His Leu Ala
    595                 600                 605
Val Arg Thr Ala Asp Gln Thr Ser Leu His Leu Val Asp Phe Leu Val
    610                 615                 620
Gln Asn Cys Gly Asn Leu Asp Lys Gln Thr Ala Leu Gly Asn Thr Val
625                 630                 635                 640
Leu His Tyr Cys Ser Met Tyr Ser Lys Pro Glu Cys Leu Lys Leu Leu
                645                 650                 655
Leu Arg Ser Lys Pro Thr Val Asp Ile Val Asn Gln Ala Gly Glu Thr
            660                 665                 670
Ala Leu Asp Ile Ala Lys Arg Leu Lys Ala Thr Gln Cys Glu Asp Leu
    675                 680                 685
Leu Ser Gln Ala Lys Ser Gly Lys Phe Asn Pro His Val His Val Glu
    690                 695                 700
```

```
Tyr Glu Trp Asn Leu Arg Gln Glu Ile Asp Glu Ser Asp Asp Asp
705                 710                 715                 720

Leu Asp Asp Lys Pro Ser Pro Ile Lys Lys Glu Arg Ser Pro Arg Pro
            725                 730                 735

Gln Ser Phe Cys His Ser Ser Ile Ser Pro Gln Asp Lys Leu Ala
            740                 745                 750

Leu Pro Gly Phe Ser Thr Pro Arg Asp Lys Gln Arg Leu Ser Tyr Gly
            755                 760                 765

Ala Phe Thr Asn Gln Ile Phe Val Ser Thr Ser Thr Asp Ser Pro Thr
            770                 775                 780

Ser Pro Thr Thr Glu Ala Pro Pro Leu Pro Pro Arg Asn Ala Gly Lys
785                 790                 795                 800

Gly Pro Thr Gly Pro Pro Ser Thr Leu Pro Leu Ser Thr Gln Thr Ser
                805                 810                 815

Ser Gly Ser Ser Thr Leu Ser Lys Lys Arg Pro Pro Pro Pro Pro
                820                 825                 830

Gly His Lys Arg Thr Leu Ser Asp Pro Pro Ser Pro Leu Pro His Gly
                835                 840                 845

Pro Pro Asn Lys Gly Ala Val Pro Trp Gly Asn Asp Gly Gly Pro Ser
850                 855                 860

Ser Ser Ser Lys Thr Thr Asn Lys Phe Glu Gly Leu Ser Gln Gln Ser
865                 870                 875                 880

Ser Thr Ser Ser Ala Lys Thr Ala Leu Gly Pro Arg Val Leu Pro Lys
                885                 890                 895

Leu Pro Gln Lys Val Ala Leu Arg Lys Thr Asp His Leu Ser Leu Asp
                900                 905                 910

Lys Ala Thr Ile Pro Pro Glu Ile Phe Gln Lys Ser Ser Gln Leu Ala
                915                 920                 925

Glu Leu Pro Gln Lys Pro Pro Pro Gly Asp Leu Pro Pro Lys Pro Thr
                930                 935                 940

Glu Leu Ala Pro Lys Pro Gln Ile Gly Asp Leu Pro Pro Lys Pro Gly
945                 950                 955                 960

Glu Leu Pro Pro Lys Pro Gln Leu Gly Asp Leu Pro Pro Lys Pro Gln
                965                 970                 975

Leu Ser Asp Leu Pro Pro Lys Pro Gln Met Lys Asp Leu Pro Pro Lys
                980                 985                 990

Pro Gln Leu Gly Asp Leu Leu Ala Lys Ser Gln Thr Gly Asp Val Ser
                995                 1000                1005

Pro Lys Ala Gln Gln Pro Ser Glu Val Thr Leu Lys Ser His Pro
    1010                1015                1020

Leu Asp Leu Ser Pro Asn Val Gln Ser Arg Asp Ala Ile Gln Lys
    1025                1030                1035

Gln Ala Ser Glu Asp Ser Asn Asp Leu Thr Pro Thr Leu Pro Glu
    1040                1045                1050

Thr Pro Val Pro Leu Pro Arg Lys Ile Asn Thr Gly Lys Asn Lys
    1055                1060                1065

Val Arg Arg Val Lys Thr Ile Tyr Asp Cys Gln Ala Asp Asn Asp
    1070                1075                1080

Asp Glu Leu Thr Phe Ile Glu Gly Glu Val Ile Ile Val Thr Gly
    1085                1090                1095

Glu Glu Asp Gln Glu Trp Trp Ile Gly His Ile Glu Gly Gln Pro
    1100                1105                1110

Glu Arg Lys Gly Val Phe Pro Val Ser Phe Val His Ile Leu Ser
```

Asp

<210> SEQ ID NO 59
<211> LENGTH: 335
<212> TYPE: PRT
<213> ORGANISM: Homo sapiens

<400> SEQUENCE: 59

Met Ala Gly Ser Pro Thr Cys Leu Thr Leu Ile Tyr Ile Leu Trp Gln
1               5                   10                  15

Leu Thr Gly Ser Ala Ala Ser Gly Pro Val Lys Glu Leu Val Gly Ser
            20                  25                  30

Val Gly Gly Ala Val Thr Phe Pro Leu Lys Ser Lys Val Lys Gln Val
        35                  40                  45

Asp Ser Ile Val Trp Thr Phe Asn Thr Thr Pro Leu Val Thr Ile Gln
    50                  55                  60

Pro Glu Gly Gly Thr Ile Ile Val Thr Gln Asn Arg Asn Arg Glu Arg
65                  70                  75                  80

Val Asp Phe Pro Asp Gly Gly Tyr Ser Leu Lys Leu Ser Lys Leu Lys
                85                  90                  95

Lys Asn Asp Ser Gly Ile Tyr Tyr Val Gly Ile Tyr Ser Ser Ser Leu
            100                 105                 110

Gln Gln Pro Ser Thr Gln Glu Tyr Val Leu His Val Tyr Glu His Leu
        115                 120                 125

Ser Lys Pro Lys Val Thr Met Gly Leu Gln Ser Asn Lys Asn Gly Thr
    130                 135                 140

Cys Val Thr Asn Leu Thr Cys Cys Met Glu His Gly Glu Glu Asp Val
145                 150                 155                 160

Ile Tyr Thr Trp Lys Ala Leu Gly Gln Ala Ala Asn Glu Ser His Asn
                165                 170                 175

Gly Ser Ile Leu Pro Ile Ser Trp Arg Trp Gly Glu Ser Asp Met Thr
            180                 185                 190

Phe Ile Cys Val Ala Arg Asn Pro Val Ser Arg Asn Phe Ser Ser Pro
        195                 200                 205

Ile Leu Ala Arg Lys Leu Cys Glu Gly Ala Ala Asp Asp Pro Asp Ser
    210                 215                 220

Ser Met Val Leu Leu Cys Leu Leu Val Pro Leu Leu Leu Ser Leu
225                 230                 235                 240

Phe Val Leu Gly Leu Phe Leu Trp Phe Leu Lys Arg Glu Arg Gln Glu
                245                 250                 255

Glu Tyr Ile Glu Glu Lys Lys Arg Val Asp Ile Cys Arg Glu Thr Pro
            260                 265                 270

Asn Ile Cys Pro His Ser Gly Glu Asn Thr Glu Tyr Asp Thr Ile Pro
        275                 280                 285

His Thr Asn Arg Thr Ile Leu Lys Glu Asp Pro Ala Asn Thr Val Tyr
    290                 295                 300

Ser Thr Val Glu Ile Pro Lys Lys Met Glu Asn Pro His Ser Leu Leu
305                 310                 315                 320

Thr Met Pro Asp Thr Pro Arg Leu Phe Ala Tyr Glu Asn Val Ile
                325                 330                 335

<210> SEQ ID NO 60
<211> LENGTH: 207
<212> TYPE: PRT
<213> ORGANISM: Homo sapiens

<400> SEQUENCE: 60

| Met | Ser | Ser | Asp | Arg | Gln | Arg | Ser | Asp | Asp | Glu | Ser | Pro | Ser | Thr | Ser |
|---|---|---|---|---|---|---|---|---|---|---|---|---|---|---|---|
| 1 | | | | 5 | | | | | 10 | | | | | 15 | |

Ser Gly Ser Ser Asp Ala Asp Gln Arg Asp Pro Ala Ala Pro Glu Pro
          20               25              30

Glu Glu Gln Glu Glu Arg Lys Pro Ser Ala Thr Gln Gln Lys Lys Asn
        35             40               45

Thr Lys Leu Ser Ser Lys Thr Thr Ala Lys Leu Ser Thr Ser Ala Lys
50               55               60

Arg Ile Gln Lys Glu Leu Ala Glu Ile Thr Leu Asp Pro Pro Pro Asn
65             70              75            80

Cys Ser Ala Gly Pro Lys Gly Asp Asn Ile Tyr Glu Trp Arg Ser Thr
          85               90              95

Ile Leu Gly Pro Pro Gly Ser Val Tyr Glu Gly Gly Val Phe Phe Leu
         100           105            110

Asp Ile Thr Phe Ser Ser Asp Tyr Pro Phe Lys Pro Pro Lys Val Thr
        115          120            125

Phe Arg Thr Arg Ile Tyr His Cys Asn Ile Asn Ser Gln Gly Val Ile
130             135              140

Cys Leu Asp Ile Leu Lys Asp Asn Trp Ser Pro Ala Leu Thr Ile Ser
145            150            155           160

Lys Val Leu Leu Ser Ile Cys Ser Leu Leu Thr Asp Cys Asn Pro Ala
         165           170            175

Asp Pro Leu Val Gly Ser Ile Ala Thr Gln Tyr Leu Thr Asn Arg Ala
        180          185            190

Glu His Asp Arg Ile Ala Arg Gln Trp Thr Lys Arg Tyr Ala Thr
        195          200            205

<210> SEQ ID NO 61
<211> LENGTH: 123
<212> TYPE: PRT
<213> ORGANISM: Homo sapiens

<400> SEQUENCE: 61

Met Ala Arg Gly Ser Ala Leu Leu Ala Ser Leu Leu Leu Ala Ala
1             5              10             15

Ala Leu Ser Ala Ser Ala Gly Leu Trp Ser Pro Ala Lys Glu Lys Arg
         20           25            30

Gly Trp Thr Leu Asn Ser Ala Gly Tyr Leu Leu Gly Pro His Ala Val
        35          40            45

Gly Asn His Arg Ser Phe Ser Asp Lys Asn Gly Leu Thr Ser Lys Arg
50             55              60

Glu Leu Arg Pro Glu Asp Asp Met Lys Pro Gly Ser Phe Asp Arg Ser
65             70              75           80

Ile Pro Glu Asn Asn Ile Met Arg Thr Ile Glu Phe Leu Ser Phe
        85          90            95

Leu His Leu Lys Glu Ala Gly Ala Leu Asp Arg Leu Leu Asp Leu Pro
        100          105            110

Ala Ala Ala Ser Ser Glu Asp Ile Glu Arg Ser
        115          120

<210> SEQ ID NO 62
<211> LENGTH: 553
<212> TYPE: PRT
<213> ORGANISM: Homo sapiens

<400> SEQUENCE: 62

Met Ala Ala Val Ser Leu Arg Leu Gly Asp Leu Val Trp Gly Lys Leu
1               5                   10                  15

Gly Arg Tyr Pro Pro Trp Pro Gly Lys Ile Val Asn Pro Pro Lys Asp
            20                  25                  30

Leu Lys Lys Pro Arg Gly Lys Lys Cys Phe Phe Val Lys Phe Phe Gly
        35                  40                  45

Thr Glu Asp His Ala Trp Ile Lys Val Glu Gln Leu Lys Pro Tyr His
50                  55                  60

Ala His Lys Glu Glu Met Ile Lys Ile Asn Lys Gly Lys Arg Phe Gln
65                  70                  75                  80

Gln Ala Val Asp Ala Val Glu Glu Phe Leu Arg Arg Ala Lys Gly Lys
                85                  90                  95

Asp Gln Thr Ser Ser His Asn Ser Ser Asp Lys Asn Arg Arg Asn
            100                 105                 110

Ser Ser Glu Glu Arg Ser Arg Pro Asn Ser Gly Asp Glu Lys Arg Lys
        115                 120                 125

Leu Ser Leu Ser Glu Gly Lys Val Lys Lys Asn Met Gly Glu Gly Lys
130                 135                 140

Lys Arg Val Ser Ser Gly Ser Ser Glu Arg Gly Ser Lys Ser Pro Leu
145                 150                 155                 160

Lys Arg Ala Gln Glu Gln Ser Pro Arg Lys Arg Gly Arg Pro Pro Lys
                165                 170                 175

Asp Glu Lys Asp Leu Thr Ile Pro Glu Ser Ser Thr Val Lys Gly Met
            180                 185                 190

Met Ala Gly Pro Met Ala Ala Phe Lys Trp Gln Pro Thr Ala Ser Glu
        195                 200                 205

Pro Val Lys Asp Ala Asp Pro His Phe His His Phe Leu Leu Ser Gln
210                 215                 220

Thr Glu Lys Pro Ala Val Cys Tyr Gln Ala Ile Thr Lys Lys Leu Lys
225                 230                 235                 240

Ile Cys Glu Glu Glu Thr Gly Ser Thr Ser Ile Gln Ala Ala Asp Ser
                245                 250                 255

Thr Ala Val Asn Gly Ser Ile Thr Pro Thr Asp Lys Lys Ile Gly Phe
            260                 265                 270

Leu Gly Leu Gly Leu Met Gly Ser Gly Ile Val Ser Asn Leu Leu Lys
        275                 280                 285

Met Gly His Thr Val Thr Val Trp Asn Arg Thr Ala Glu Lys Cys Asp
290                 295                 300

Leu Phe Ile Gln Glu Gly Ala Arg Leu Gly Arg Thr Pro Ala Glu Val
305                 310                 315                 320

Val Ser Thr Cys Asp Ile Thr Phe Ala Cys Val Ser Asp Pro Lys Ala
                325                 330                 335

Ala Lys Asp Leu Val Leu Gly Pro Ser Gly Val Leu Gln Gly Ile Arg
            340                 345                 350

Pro Gly Lys Cys Tyr Val Asp Met Ser Thr Val Asp Ala Asp Thr Val
        355                 360                 365

Thr Glu Leu Ala Gln Val Ile Val Ser Arg Gly Gly Arg Phe Leu Glu
370                 375                 380

Ala Pro Val Ser Gly Asn Gln Gln Leu Ser Asn Asp Gly Met Leu Val
385                 390                 395                 400

Ile Leu Ala Ala Gly Asp Arg Gly Leu Tyr Glu Asp Cys Ser Ser Cys
                405                 410                 415

-continued

```
Phe Gln Ala Met Gly Lys Thr Ser Phe Leu Gly Glu Val Gly Asn
            420                 425                 430

Ala Ala Lys Met Met Leu Ile Val Asn Met Val Gln Gly Ser Phe Met
                435                 440                 445

Ala Thr Ile Ala Glu Gly Leu Thr Leu Ala Gln Val Thr Gly Gln Ser
        450                 455                 460

Gln Gln Thr Leu Leu Asp Ile Leu Asn Gln Gly Gln Leu Ala Ser Ile
465                 470                 475                 480

Phe Leu Asp Gln Lys Cys Gln Asn Ile Leu Gln Gly Asn Phe Lys Pro
                485                 490                 495

Asp Phe Tyr Leu Lys Tyr Ile Gln Lys Asp Leu Arg Leu Ala Ile Ala
            500                 505                 510

Leu Gly Asp Ala Val Asn His Pro Thr Pro Met Ala Ala Ala Asn
        515                 520                 525

Glu Val Tyr Lys Arg Ala Lys Ala Leu Asp Gln Ser Asp Asn Asp Met
530                 535                 540

Ser Ala Val Tyr Arg Ala Tyr Ile His
545                 550
```

<210> SEQ ID NO 63
<211> LENGTH: 1163
<212> TYPE: PRT
<213> ORGANISM: Homo sapiens

<400> SEQUENCE: 63

```
Met Thr Arg Thr Arg Ala Ala Leu Leu Leu Phe Thr Ala Leu Ala Thr
1               5                   10                  15

Ser Leu Gly Phe Asn Leu Asp Thr Glu Glu Leu Thr Ala Phe Arg Val
                20                  25                  30

Asp Ser Ala Gly Phe Gly Asp Ser Val Val Gln Tyr Ala Asn Ser Trp
            35                  40                  45

Val Val Val Gly Ala Pro Gln Lys Ile Thr Ala Ala Asn Gln Thr Gly
        50                  55                  60

Gly Leu Tyr Gln Cys Gly Tyr Ser Thr Gly Ala Cys Glu Pro Ile Gly
65                  70                  75                  80

Leu Gln Val Pro Pro Glu Ala Val Asn Met Ser Leu Gly Leu Ser Leu
                85                  90                  95

Ala Ser Thr Thr Ser Pro Ser Gln Leu Leu Ala Cys Gly Pro Thr Val
                100                 105                 110

His His Glu Cys Gly Arg Asn Met Tyr Leu Thr Gly Leu Cys Phe Leu
            115                 120                 125

Leu Gly Pro Thr Gln Leu Thr Gln Arg Leu Pro Val Ser Arg Gln Glu
        130                 135                 140

Cys Pro Arg Gln Glu Gln Asp Ile Val Phe Leu Ile Asp Gly Ser Gly
145                 150                 155                 160

Ser Ile Ser Ser Arg Asn Phe Ala Thr Met Met Asn Phe Val Arg Ala
                165                 170                 175

Val Ile Ser Gln Phe Gln Arg Pro Ser Thr Gln Phe Ser Leu Met Gln
                180                 185                 190

Phe Ser Asn Lys Phe Gln Thr His Phe Thr Phe Glu Glu Phe Arg Arg
            195                 200                 205

Ser Ser Asn Pro Leu Ser Leu Leu Ala Ser Val His Gln Leu Gln Gly
        210                 215                 220

Phe Thr Tyr Thr Ala Thr Ala Ile Gln Asn Val Val His Arg Leu Phe
225                 230                 235                 240
```

-continued

```
His Ala Ser Tyr Gly Ala Arg Arg Asp Ala Ala Lys Ile Leu Ile Val
            245                 250                 255

Ile Thr Asp Gly Lys Lys Glu Gly Asp Ser Leu Asp Tyr Lys Asp Val
        260                 265                 270

Ile Pro Met Ala Asp Ala Ala Gly Ile Ile Arg Tyr Ala Ile Gly Val
    275                 280                 285

Gly Leu Ala Phe Gln Asn Arg Asn Ser Trp Lys Glu Leu Asn Asp Ile
290                 295                 300

Ala Ser Lys Pro Ser Gln Glu His Ile Phe Lys Val Glu Asp Phe Asp
305                 310                 315                 320

Ala Leu Lys Asp Ile Gln Asn Gln Leu Lys Glu Lys Ile Phe Ala Ile
                325                 330                 335

Glu Gly Thr Glu Thr Thr Ser Ser Ser Phe Glu Leu Glu Met Ala
            340                 345                 350

Gln Glu Gly Phe Ser Ala Val Phe Thr Pro Asp Gly Pro Val Leu Gly
        355                 360                 365

Ala Val Gly Ser Phe Thr Trp Ser Gly Gly Ala Phe Leu Tyr Pro Pro
    370                 375                 380

Asn Met Ser Pro Thr Phe Ile Asn Met Ser Gln Glu Asn Val Asp Met
385                 390                 395                 400

Arg Asp Ser Tyr Leu Gly Tyr Ser Thr Glu Leu Ala Leu Trp Lys Gly
                405                 410                 415

Val Gln Ser Leu Val Leu Gly Ala Pro Arg Tyr Gln His Thr Gly Lys
            420                 425                 430

Ala Val Ile Phe Thr Gln Val Ser Arg Gln Trp Arg Met Lys Ala Glu
        435                 440                 445

Val Thr Gly Thr Gln Ile Gly Ser Tyr Phe Gly Ala Ser Leu Cys Ser
    450                 455                 460

Val Asp Val Asp Ser Asp Gly Ser Thr Asp Leu Val Leu Ile Gly Ala
465                 470                 475                 480

Pro His Tyr Tyr Glu Gln Thr Arg Gly Gly Gln Val Ser Val Cys Pro
                485                 490                 495

Leu Pro Arg Gly Trp Arg Arg Trp Trp Cys Asp Ala Val Leu Tyr Gly
            500                 505                 510

Glu Gln Gly His Pro Trp Gly Arg Phe Gly Ala Ala Leu Thr Val Leu
        515                 520                 525

Gly Asp Val Asn Gly Asp Lys Leu Thr Asp Val Val Ile Gly Ala Pro
    530                 535                 540

Gly Glu Glu Glu Asn Arg Gly Ala Val Tyr Leu Phe His Gly Val Leu
545                 550                 555                 560

Gly Pro Ser Ile Ser Pro Ser His Ser Gln Arg Ile Ala Gly Ser Gln
                565                 570                 575

Leu Ser Ser Arg Leu Gln Tyr Phe Gly Gln Ala Leu Ser Gly Gly Gln
            580                 585                 590

Asp Leu Thr Gln Asp Gly Leu Val Asp Leu Ala Val Gly Ala Arg Gly
        595                 600                 605

Gln Val Leu Leu Leu Arg Thr Arg Pro Val Leu Trp Val Gly Val Ser
    610                 615                 620

Met Gln Phe Ile Pro Ala Glu Ile Pro Arg Ser Ala Phe Glu Cys Arg
625                 630                 635                 640

Glu Gln Val Val Ser Glu Gln Thr Leu Val Gln Ser Asn Ile Cys Leu
                645                 650                 655

Tyr Ile Asp Lys Arg Ser Lys Asn Leu Leu Gly Ser Arg Asp Leu Gln
            660                 665                 670
```

```
Ser Ser Val Thr Leu Asp Leu Ala Leu Asp Pro Gly Arg Leu Ser Pro
        675                 680                 685

Arg Ala Thr Phe Gln Glu Thr Lys Asn Arg Ser Leu Ser Arg Val Arg
690                 695                 700

Val Leu Gly Leu Lys Ala His Cys Glu Asn Phe Asn Leu Leu Leu Pro
705                 710                 715                 720

Ser Cys Val Glu Asp Ser Val Thr Pro Ile Thr Leu Arg Leu Asn Phe
                725                 730                 735

Thr Leu Val Gly Lys Pro Leu Leu Ala Phe Arg Asn Leu Arg Pro Met
            740                 745                 750

Leu Ala Ala Asp Ala Gln Arg Tyr Phe Thr Ala Ser Leu Pro Phe Glu
        755                 760                 765

Lys Asn Cys Gly Ala Asp His Ile Cys Gln Asp Asn Leu Gly Ile Ser
770                 775                 780

Phe Ser Phe Pro Gly Leu Lys Ser Leu Leu Val Gly Ser Asn Leu Glu
785                 790                 795                 800

Leu Asn Ala Glu Val Met Val Trp Asn Asp Gly Glu Asp Ser Tyr Gly
                805                 810                 815

Thr Thr Ile Thr Phe Ser His Pro Ala Gly Leu Ser Tyr Arg Tyr Val
            820                 825                 830

Ala Glu Gly Gln Lys Gln Gly Gln Leu Arg Ser Leu His Leu Thr Cys
        835                 840                 845

Asp Ser Ala Pro Val Gly Ser Gln Gly Thr Trp Ser Thr Ser Cys Arg
850                 855                 860

Ile Asn His Leu Ile Phe Arg Gly Gly Ala Gln Ile Thr Phe Leu Ala
865                 870                 875                 880

Thr Phe Asp Val Ser Pro Lys Ala Val Leu Gly Asp Arg Leu Leu Leu
                885                 890                 895

Thr Ala Asn Val Ser Ser Glu Asn Asn Thr Pro Arg Thr Ser Lys Thr
            900                 905                 910

Thr Phe Gln Leu Glu Leu Pro Val Lys Tyr Ala Val Tyr Thr Val Val
        915                 920                 925

Ser Ser His Glu Gln Phe Thr Lys Tyr Leu Asn Phe Ser Glu Ser Glu
930                 935                 940

Glu Lys Glu Ser His Val Ala Met His Arg Tyr Gln Val Asn Asn Leu
945                 950                 955                 960

Gly Gln Arg Asp Leu Pro Val Ser Ile Asn Phe Trp Val Pro Val Glu
                965                 970                 975

Leu Asn Gln Glu Ala Val Trp Met Asp Val Glu Val Ser His Pro Gln
            980                 985                 990

Asn Pro Ser Leu Arg Cys Ser Ser Glu Lys Ile Ala Pro Pro Ala Ser
        995                 1000                1005

Asp Phe Leu Ala His Ile Gln Lys Asn Pro Val Leu Asp Cys Ser
    1010                1015                1020

Ile Ala Gly Cys Leu Arg Phe Arg Cys Asp Val Pro Ser Phe Ser
    1025                1030                1035

Val Gln Glu Glu Leu Asp Phe Thr Leu Lys Gly Asn Leu Ser Phe
    1040                1045                1050

Gly Trp Val Arg Gln Ile Leu Gln Lys Lys Val Ser Val Val Ser
    1055                1060                1065

Val Ala Glu Ile Thr Phe Asp Thr Ser Val Tyr Ser Gln Leu Pro
    1070                1075                1080

Gly Gln Glu Ala Phe Met Arg Ala Gln Thr Thr Thr Val Leu Glu
```

```
                    1085                1090                1095
Lys Tyr Lys Val His Asn Pro Thr Pro Leu Ile Val Gly Ser Ser
        1100                1105                1110

Ile Gly Gly Leu Leu Leu Ala Leu Ile Thr Ala Val Leu Tyr
        1115                1120                1125

Lys Val Gly Phe Phe Lys Arg Gln Tyr Lys Glu Met Met Glu Glu
        1130                1135                1140

Ala Asn Gly Gln Ile Ala Pro Glu Asn Gly Thr Gln Thr Pro Ser
        1145                1150                1155

Pro Pro Ser Glu Lys
        1160

<210> SEQ ID NO 64
<211> LENGTH: 492
<212> TYPE: PRT
<213> ORGANISM: Homo sapiens

<400> SEQUENCE: 64

Met Val Lys Phe Pro Ala Leu Thr His Tyr Trp Pro Leu Ile Arg Phe
1               5                   10                  15

Leu Val Pro Leu Gly Ile Thr Asn Ile Ala Ile Asp Phe Gly Glu Gln
            20                  25                  30

Ala Leu Asn Arg Gly Ile Ala Ala Val Lys Glu Asp Ala Val Glu Met
        35                  40                  45

Leu Ala Ser Tyr Gly Leu Ala Tyr Ser Leu Met Lys Phe Phe Thr Gly
    50                  55                  60

Pro Met Ser Asp Phe Lys Asn Val Gly Leu Val Phe Val Asn Ser Lys
65                  70                  75                  80

Arg Asp Arg Thr Lys Ala Val Leu Cys Met Val Ala Gly Ala Ile
                85                  90                  95

Ala Ala Val Phe His Thr Leu Ile Ala Tyr Ser Asp Leu Gly Tyr Tyr
            100                 105                 110

Ile Ile Asn Lys Leu His His Val Asp Glu Ser Val Gly Ser Lys Thr
        115                 120                 125

Arg Arg Ala Phe Leu Tyr Leu Ala Ala Phe Pro Phe Met Asp Ala Met
    130                 135                 140

Ala Trp Thr His Ala Gly Ile Leu Leu Lys His Lys Tyr Ser Phe Leu
145                 150                 155                 160

Val Gly Cys Ala Ser Ile Ser Asp Val Ile Ala Gln Val Val Phe Val
                165                 170                 175

Ala Ile Leu Leu His Ser His Leu Glu Cys Arg Glu Pro Leu Leu Ile
            180                 185                 190

Pro Ile Leu Ser Leu Tyr Met Gly Ala Leu Val Arg Cys Thr Thr Leu
        195                 200                 205

Cys Leu Gly Tyr Tyr Lys Asn Ile His Asp Ile Ile Pro Asp Arg Ser
    210                 215                 220

Gly Pro Glu Leu Gly Gly Asp Ala Thr Ile Arg Lys Met Leu Ser Phe
225                 230                 235                 240

Trp Trp Pro Leu Ala Leu Ile Leu Ala Thr Gln Arg Ile Ser Arg Pro
                245                 250                 255

Ile Val Asn Leu Phe Val Ser Arg Asp Leu Gly Gly Ser Ser Ala Ala
            260                 265                 270

Thr Glu Ala Val Ala Ile Leu Thr Ala Thr Tyr Pro Val Gly His Met
        275                 280                 285

Pro Tyr Gly Trp Leu Thr Glu Ile Arg Ala Val Tyr Pro Ala Phe Asp
```

```
                    290                 295                 300
Lys Asn Asn Pro Ser Asn Lys Leu Val Ser Thr Ser Asn Thr Val Thr
305                 310                 315                 320

Ala Ala His Ile Lys Lys Phe Thr Phe Val Cys Met Ala Leu Ser Leu
                325                 330                 335

Thr Leu Cys Phe Val Met Phe Trp Thr Pro Asn Val Ser Glu Lys Ile
            340                 345                 350

Leu Ile Asp Ile Ile Gly Val Asp Phe Ala Phe Ala Glu Leu Cys Val
        355                 360                 365

Val Pro Leu Arg Ile Phe Ser Phe Phe Pro Val Pro Val Thr Val Arg
    370                 375                 380

Ala His Leu Thr Gly Trp Leu Met Thr Leu Lys Lys Thr Phe Val Leu
385                 390                 395                 400

Ala Pro Ser Ser Val Leu Arg Ile Ile Val Leu Ile Ala Ser Leu Val
                405                 410                 415

Val Leu Pro Tyr Leu Gly Val His Gly Ala Thr Leu Gly Val Gly Ser
            420                 425                 430

Leu Leu Ala Gly Phe Val Gly Glu Ser Thr Met Val Ala Ile Ala Ala
        435                 440                 445

Cys Tyr Val Tyr Arg Lys Gln Lys Lys Met Glu Asn Glu Ser Ala
    450                 455                 460

Thr Glu Gly Glu Asp Ser Ala Met Thr Asp Met Pro Thr Glu Glu
465                 470                 475                 480

Val Thr Asp Ile Val Glu Met Arg Glu Glu Asn Glu
                485                 490

<210> SEQ ID NO 65
<211> LENGTH: 617
<212> TYPE: PRT
<213> ORGANISM: Homo sapiens

<400> SEQUENCE: 65

Met Asp Phe Ser Lys Leu Pro Lys Ile Leu Asp Glu Asp Lys Glu Ser
1               5                   10                  15

Thr Phe Gly Tyr Val His Gly Val Ser Gly Pro Val Val Thr Ala Cys
                20                  25                  30

Asp Met Ala Gly Ala Ala Met Tyr Glu Leu Val Arg Val Gly His Ser
            35                  40                  45

Glu Leu Val Gly Glu Ile Ile Arg Leu Glu Gly Asp Met Ala Thr Ile
        50                  55                  60

Gln Val Tyr Glu Glu Thr Ser Gly Val Ser Val Gly Asp Pro Val Leu
65                  70                  75                  80

Arg Thr Gly Lys Pro Leu Ser Val Glu Leu Gly Pro Gly Ile Met Gly
                85                  90                  95

Ala Ile Phe Asp Gly Ile Gln Arg Pro Leu Ser Asp Ile Ser Ser Gln
            100                 105                 110

Thr Gln Ser Ile Tyr Ile Pro Arg Gly Val Asn Val Ser Ala Leu Ser
        115                 120                 125

Arg Asp Ile Lys Trp Asp Phe Thr Pro Cys Lys Asn Leu Arg Val Gly
    130                 135                 140

Ser His Ile Thr Gly Gly Asp Ile Tyr Gly Ile Val Ser Glu Asn Ser
145                 150                 155                 160

Leu Ile Lys His Lys Ile Met Leu Pro Pro Arg Asn Arg Gly Thr Val
                165                 170                 175

Thr Tyr Ile Ala Pro Pro Gly Asn Tyr Asp Thr Ser Asp Val Val Leu
```

```
                180                 185                 190
Glu Leu Glu Phe Glu Gly Val Lys Glu Lys Phe Thr Met Val Gln Val
            195                 200                 205
Trp Pro Val Arg Gln Val Arg Pro Val Thr Glu Lys Leu Pro Ala Asn
210                 215                 220
His Pro Leu Leu Thr Gly Gln Arg Val Leu Asp Ala Leu Phe Pro Cys
225                 230                 235                 240
Val Gln Gly Gly Thr Thr Ala Ile Pro Gly Ala Phe Gly Cys Gly Lys
                245                 250                 255
Thr Val Ile Ser Gln Ser Leu Ser Lys Tyr Ser Asn Ser Asp Val Ile
            260                 265                 270
Ile Tyr Val Gly Cys Gly Glu Arg Gly Asn Glu Met Ser Glu Val Leu
        275                 280                 285
Arg Asp Phe Pro Glu Leu Thr Met Glu Val Asp Gly Lys Val Glu Ser
    290                 295                 300
Ile Met Lys Arg Thr Ala Leu Val Ala Asn Thr Ser Asn Met Pro Val
305                 310                 315                 320
Ala Ala Arg Glu Ala Ser Ile Tyr Thr Gly Ile Thr Leu Ser Glu Tyr
                325                 330                 335
Phe Arg Asp Met Gly Tyr His Val Ser Met Met Ala Asp Ser Thr Ser
            340                 345                 350
Arg Trp Ala Glu Ala Leu Arg Glu Ile Ser Gly Arg Leu Ala Glu Met
        355                 360                 365
Pro Ala Asp Ser Gly Tyr Pro Ala Tyr Leu Gly Ala Arg Leu Ala Ser
    370                 375                 380
Phe Tyr Glu Arg Ala Gly Arg Val Lys Cys Leu Gly Asn Pro Glu Arg
385                 390                 395                 400
Glu Gly Ser Val Ser Ile Val Gly Ala Val Ser Pro Pro Gly Gly Asp
                405                 410                 415
Phe Ser Asp Pro Val Thr Ser Ala Thr Leu Gly Ile Val Gln Val Phe
            420                 425                 430
Trp Gly Leu Asp Lys Lys Leu Ala Gln Arg Lys His Phe Pro Ser Val
        435                 440                 445
Asn Trp Leu Ile Ser Tyr Ser Lys Tyr Met Arg Ala Leu Asp Glu Tyr
    450                 455                 460
Tyr Asp Lys His Phe Thr Glu Phe Val Pro Leu Arg Thr Lys Ala Lys
465                 470                 475                 480
Glu Ile Leu Gln Glu Glu Asp Leu Ala Glu Ile Val Gln Leu Val
                485                 490                 495
Gly Lys Ala Ser Leu Ala Glu Thr Asp Lys Ile Thr Leu Glu Val Ala
            500                 505                 510
Lys Leu Ile Lys Asp Asp Phe Leu Gln Gln Asn Gly Tyr Thr Pro Tyr
        515                 520                 525
Asp Arg Phe Cys Pro Phe Tyr Lys Thr Val Gly Met Leu Ser Asn Met
    530                 535                 540
Ile Ala Phe Tyr Asp Met Ala Arg Arg Ala Val Glu Thr Thr Ala Gln
545                 550                 555                 560
Ser Asp Asn Lys Ile Thr Trp Ser Ile Ile Arg Glu His Met Gly Asp
                565                 570                 575
Ile Leu Tyr Lys Leu Ser Ser Met Lys Phe Lys Asp Pro Leu Lys Asp
            580                 585                 590
Gly Glu Ala Lys Ile Lys Ser Asp Tyr Ala Gln Leu Leu Glu Asp Met
        595                 600                 605
```

Gln Asn Ala Phe Arg Ser Leu Glu Asp
    610             615

<210> SEQ ID NO 66
<211> LENGTH: 350
<212> TYPE: PRT
<213> ORGANISM: Homo sapiens

<400> SEQUENCE: 66

Met Ile Arg Gln Glu Arg Ser Thr Ser Tyr Gln Glu Leu Ser Glu Glu
1               5                   10                  15

Leu Val Gln Val Val Glu Ser Ser Glu Leu Ala Asp Glu Gln Asp Lys
            20                  25                  30

Glu Thr Val Arg Val Gln Gly Pro Gly Ile Leu Pro Gly Leu Asp Ser
        35                  40                  45

Glu Ser Ala Ser Ser Ile Arg Phe Ser Lys Ala Cys Leu Lys Asn
    50                  55                  60

Val Phe Ser Val Leu Leu Ile Phe Ile Tyr Leu Leu Met Ala Val
65                  70                  75                  80

Ala Val Phe Leu Val Tyr Arg Thr Ile Thr Asp Phe Arg Glu Lys Leu
                85                  90                  95

Lys His Pro Val Met Ser Val Ser Tyr Lys Glu Val Asp Arg Tyr Asp
            100                 105                 110

Ala Pro Gly Ile Ala Leu Tyr Pro Gly Gln Ala Gln Leu Leu Ser Cys
        115                 120                 125

Lys His His Tyr Glu Val Ile Pro Pro Leu Thr Ser Pro Gly Gln Pro
    130                 135                 140

Gly Asp Met Asn Cys Thr Thr Gln Arg Ile Asn Tyr Thr Asp Pro Phe
145                 150                 155                 160

Ser Asn Gln Thr Val Lys Ser Ala Leu Ile Val Gln Gly Pro Arg Glu
                165                 170                 175

Val Lys Lys Arg Glu Leu Val Phe Leu Gln Phe Arg Leu Asn Lys Ser
            180                 185                 190

Ser Glu Asp Phe Ser Ala Ile Asp Tyr Leu Leu Phe Ser Ser Phe Gln
        195                 200                 205

Glu Phe Leu Gln Ser Pro Asn Arg Val Gly Phe Met Gln Ala Cys Glu
    210                 215                 220

Ser Ala Cys Ser Ser Trp Lys Phe Ser Gly Gly Phe Arg Thr Trp Val
225                 230                 235                 240

Lys Met Ser Leu Val Lys Thr Lys Glu Glu Asp Gly Arg Glu Ala Val
                245                 250                 255

Glu Phe Arg Gln Glu Thr Ser Val Val Asn Tyr Ile Asp Gln Arg Pro
            260                 265                 270

Ala Ala Lys Lys Ser Ala Gln Leu Phe Phe Val Phe Glu Trp Lys
        275                 280                 285

Asp Pro Phe Ile Gln Lys Val Gln Asp Ile Val Thr Ala Asn Pro Trp
    290                 295                 300

Asn Thr Ile Ala Leu Leu Cys Gly Ala Phe Leu Ala Leu Phe Lys Ala
305                 310                 315                 320

Ala Glu Phe Ala Lys Leu Ser Ile Lys Trp Met Ile Lys Ile Arg Lys
                325                 330                 335

Arg Tyr Leu Lys Arg Arg Gly Gln Ala Thr Ser His Ile Ser
            340                 345                 350

<210> SEQ ID NO 67
<211> LENGTH: 200

```
<212> TYPE: PRT
<213> ORGANISM: Homo sapiens

<400> SEQUENCE: 67

Met Phe Arg Lys Gly Lys Arg His Ser Ser Ser Ser Gln Ser
1               5                   10                  15

Ser Glu Ile Ser Thr Lys Ser Lys Ser Val Asp Ser Ser Leu Gly Gly
            20                  25                  30

Leu Ser Arg Ser Ser Thr Val Ala Ser Leu Asp Thr Asp Ser Thr Lys
        35                  40                  45

Ser Ser Gly Gln Ser Asn Asn Asn Ser Asp Thr Cys Ala Glu Phe Arg
    50                  55                  60

Ile Lys Tyr Val Gly Ala Ile Glu Lys Leu Lys Leu Ser Glu Gly Lys
65              70                  75                  80

Gly Leu Glu Gly Pro Leu Asp Leu Ile Asn Tyr Ile Asp Val Ala Gln
                85                  90                  95

Gln Asp Gly Lys Leu Pro Phe Val Pro Pro Glu Glu Phe Ile Met
            100                 105                 110

Gly Val Ser Lys Tyr Gly Ile Lys Val Ser Thr Ser Asp Gln Tyr Asp
        115                 120                 125

Val Leu His Arg His Ala Leu Tyr Leu Ile Arg Met Val Cys Tyr
    130                 135                 140

Asp Asp Gly Leu Gly Ala Gly Lys Ser Leu Leu Ala Leu Lys Thr Thr
145                 150                 155                 160

Asp Ala Ser Asn Glu Glu Tyr Ser Leu Trp Val Tyr Gln Cys Asn Ser
                165                 170                 175

Leu Glu Gln Ala Gln Ala Ile Cys Lys Val Leu Ser Thr Ala Phe Asp
            180                 185                 190

Ser Val Leu Thr Ser Glu Lys Pro
            195                 200

<210> SEQ ID NO 68
<211> LENGTH: 123
<212> TYPE: PRT
<213> ORGANISM: Homo sapiens

<400> SEQUENCE: 68

Met Ala Arg Tyr Glu Glu Val Ser Val Ser Gly Phe Glu Glu Phe His
1               5                   10                  15

Arg Ala Val Glu Gln His Asn Gly Lys Thr Ile Phe Ala Tyr Phe Thr
            20                  25                  30

Gly Ser Lys Asp Ala Gly Gly Lys Ser Trp Cys Pro Asp Cys Val Gln
        35                  40                  45

Ala Glu Pro Val Val Arg Glu Gly Leu Lys His Ile Ser Glu Gly Cys
    50                  55                  60

Val Phe Ile Tyr Cys Gln Val Gly Glu Lys Pro Tyr Trp Lys Asp Pro
65              70                  75                  80

Asn Asn Asp Phe Arg Lys Asn Leu Lys Val Thr Ala Val Pro Thr Leu
                85                  90                  95

Leu Lys Tyr Gly Thr Pro Gln Lys Leu Val Glu Ser Glu Cys Leu Gln
            100                 105                 110

Ala Asn Leu Val Glu Met Leu Phe Ser Glu Asp
        115                 120

<210> SEQ ID NO 69
<211> LENGTH: 219
<212> TYPE: PRT
```

<213> ORGANISM: Homo sapiens

<400> SEQUENCE: 69

```
Met Asn Ser Ser Lys Ser Ser Glu Thr Gln Cys Thr Glu Arg Gly Cys
1               5                   10                  15

Phe Ser Ser Gln Met Phe Leu Trp Thr Val Ala Gly Ile Pro Ile Leu
            20                  25                  30

Phe Leu Ser Ala Cys Phe Ile Thr Arg Cys Val Val Thr Phe Arg Ile
        35                  40                  45

Phe Gln Thr Cys Asp Glu Lys Lys Phe Gln Leu Pro Glu Asn Phe Thr
    50                  55                  60

Glu Leu Ser Cys Tyr Asn Tyr Gly Gly Ser Val Lys Asn Cys Cys
65                  70                  75                  80

Pro Leu Asn Trp Glu Tyr Phe Gln Ser Ser Cys Tyr Phe Phe Ser Thr
                85                  90                  95

Asp Thr Ile Ser Trp Ala Leu Ser Leu Lys Asn Cys Ser Ala Met Gly
            100                 105                 110

Ala His Leu Val Val Ile Asn Ser Gln Glu Glu Gln Glu Phe Leu Ser
        115                 120                 125

Tyr Lys Lys Pro Lys Met Arg Glu Phe Phe Ile Gly Leu Ser Asp Gln
    130                 135                 140

Val Val Glu Gly Gln Trp Gln Trp Val Asp Gly Thr Pro Leu Thr Lys
145                 150                 155                 160

Ser Leu Ser Phe Trp Asp Val Gly Glu Pro Asn Asn Ile Ala Thr Leu
                165                 170                 175

Glu Asp Cys Ala Thr Met Arg Asp Ser Ser Asn Pro Arg Gln Asn Trp
            180                 185                 190

Asn Asp Val Thr Cys Phe Leu Asn Tyr Phe Arg Ile Cys Glu Met Val
        195                 200                 205

Gly Ile Asn Pro Leu Asn Lys Gly Lys Ser Leu
    210                 215
```

<210> SEQ ID NO 70
<211> LENGTH: 237
<212> TYPE: PRT
<213> ORGANISM: Homo sapiens

<400> SEQUENCE: 70

```
Met Ala Gln Pro Ile Leu Gly His Gly Ser Leu Gln Pro Ala Ser Ala
1               5                   10                  15

Ala Gly Leu Ala Ser Leu Glu Leu Asp Ser Ser Leu Asp Gln Tyr Val
            20                  25                  30

Gln Ile Arg Ile Phe Lys Ile Ile Val Ile Gly Asp Ser Asn Val Gly
        35                  40                  45

Lys Thr Cys Leu Thr Phe Arg Phe Cys Gly Gly Thr Phe Pro Asp Lys
    50                  55                  60

Thr Glu Ala Thr Ile Gly Val Asp Phe Arg Glu Lys Thr Val Glu Ile
65                  70                  75                  80

Glu Gly Glu Lys Ile Lys Val Gln Val Trp Asp Thr Ala Gly Gln Glu
                85                  90                  95

Arg Phe Arg Lys Ser Met Val Glu His Tyr Tyr Arg Asn Val His Ala
            100                 105                 110

Val Val Phe Val Tyr Asp Val Thr Lys Met Thr Ser Phe Thr Asn Leu
        115                 120                 125

Lys Met Trp Ile Gln Glu Cys Asn Gly His Ala Val Pro Pro Leu Val
    130                 135                 140
```

-continued

```
Pro Lys Val Leu Val Gly Asn Lys Cys Asp Leu Arg Glu Gln Ile Gln
145                 150                 155                 160

Val Pro Ser Asn Leu Ala Leu Lys Phe Ala Asp Ala His Asn Met Leu
            165                 170                 175

Leu Phe Glu Thr Ser Ala Lys Asp Pro Lys Glu Ser Gln Asn Val Glu
        180                 185                 190

Ser Ile Phe Met Cys Leu Ala Cys Arg Leu Lys Ala Gln Lys Ser Leu
    195                 200                 205

Leu Tyr Arg Asp Ala Glu Arg Gln Gln Gly Lys Val Gln Lys Leu Glu
210                 215                 220

Phe Pro Gln Glu Ala Asn Ser Lys Thr Ser Cys Pro Cys
225                 230                 235

<210> SEQ ID NO 71
<211> LENGTH: 252
<212> TYPE: PRT
<213> ORGANISM: Homo sapiens

<400> SEQUENCE: 71

Met Glu Asp Gly Val Ala Gly Pro Gln Leu Gly Ala Ala Glu Ala
1               5                   10                  15

Ala Glu Ala Ala Glu Ala Arg Ala Arg Pro Gly Val Thr Leu Arg Pro
            20                  25                  30

Phe Ala Pro Leu Ser Gly Ala Ala Glu Ala Asp Glu Gly Gly Gly Asp
        35                  40                  45

Trp Ser Phe Ile Asp Cys Glu Met Glu Glu Val Asp Leu Gln Asp Leu
    50                  55                  60

Pro Ser Ala Thr Ile Ala Cys His Leu Asp Pro Arg Val Phe Val Asp
65                  70                  75                  80

Gly Leu Cys Arg Ala Lys Phe Glu Ser Leu Phe Arg Thr Tyr Asp Lys
                85                  90                  95

Asp Ile Thr Phe Gln Tyr Phe Lys Ser Phe Lys Arg Val Arg Ile Asn
            100                 105                 110

Phe Ser Asn Pro Phe Ser Ala Ala Asp Ala Arg Leu Gln Leu His Lys
        115                 120                 125

Thr Glu Phe Leu Gly Lys Glu Met Lys Leu Tyr Phe Ala Gln Thr Leu
130                 135                 140

His Ile Gly Ser Ser His Leu Ala Pro Pro Asn Pro Asp Lys Gln Phe
145                 150                 155                 160

Leu Ile Ser Pro Pro Ala Ser Pro Pro Val Gly Trp Lys Gln Val Glu
            165                 170                 175

Asp Ala Thr Pro Val Ile Asn Tyr Asp Leu Leu Tyr Ala Ile Ser Lys
        180                 185                 190

Leu Gly Pro Gly Glu Lys Tyr Glu Leu His Ala Ala Thr Asp Thr Thr
    195                 200                 205

Pro Ser Val Val Val His Val Cys Glu Ser Asp Gln Glu Lys Glu Glu
210                 215                 220

Glu Glu Glu Met Glu Arg Met Arg Arg Pro Lys Pro Lys Ile Ile Gln
225                 230                 235                 240

Thr Arg Arg Pro Glu Tyr Thr Pro Ile His Leu Ser
                245                 250

<210> SEQ ID NO 72
<211> LENGTH: 198
<212> TYPE: PRT
<213> ORGANISM: Homo sapiens
```

```
<400> SEQUENCE: 72

Met Lys Leu Tyr Ser Leu Ser Val Leu Tyr Lys Gly Glu Ala Lys Val
1               5                   10                  15

Val Leu Leu Lys Ala Ala Tyr Asp Val Ser Ser Phe Ser Phe Phe Gln
            20                  25                  30

Arg Ser Ser Val Gln Glu Phe Met Thr Phe Thr Ser Gln Leu Ile Val
        35                  40                  45

Glu Arg Ser Ser Lys Gly Thr Arg Ala Ser Val Lys Glu Gln Asp Tyr
50                  55                  60

Leu Cys His Val Tyr Val Arg Asn Asp Ser Leu Ala Gly Val Val Ile
65                  70                  75                  80

Ala Asp Asn Glu Tyr Pro Ser Arg Val Ala Phe Thr Leu Leu Glu Lys
                85                  90                  95

Val Leu Asp Glu Phe Ser Lys Gln Val Asp Arg Ile Asp Trp Pro Val
            100                 105                 110

Gly Ser Pro Ala Thr Ile His Tyr Pro Ala Leu Asp Gly His Leu Ser
        115                 120                 125

Arg Tyr Gln Asn Pro Arg Glu Ala Asp Pro Met Thr Lys Val Gln Ala
130                 135                 140

Glu Leu Asp Glu Thr Lys Ile Ile Leu His Asn Thr Met Glu Ser Leu
145                 150                 155                 160

Leu Glu Arg Gly Glu Lys Leu Asp Asp Leu Val Ser Lys Ser Glu Val
                165                 170                 175

Leu Gly Thr Gln Ser Lys Ala Phe Tyr Lys Thr Ala Arg Lys Gln Asn
            180                 185                 190

Ser Cys Cys Ala Ile Met
        195

<210> SEQ ID NO 73
<211> LENGTH: 892
<212> TYPE: PRT
<213> ORGANISM: Homo sapiens

<400> SEQUENCE: 73

Met Asp His Tyr Asp Ser Gln Gln Thr Asn Asp Tyr Met Gln Pro Glu
1               5                   10                  15

Glu Asp Trp Asp Arg Asp Leu Leu Leu Asp Pro Ala Trp Glu Lys Gln
            20                  25                  30

Gln Arg Lys Thr Phe Thr Ala Trp Cys Asn Ser His Leu Arg Lys Ala
        35                  40                  45

Gly Thr Gln Ile Glu Asn Ile Glu Glu Asp Phe Arg Asp Gly Leu Lys
50                  55                  60

Leu Met Leu Leu Leu Glu Val Ile Ser Gly Glu Arg Leu Ala Lys Pro
65                  70                  75                  80

Glu Arg Gly Lys Met Arg Val His Lys Ile Ser Asn Val Asn Lys Ala
                85                  90                  95

Leu Asp Phe Ile Ala Ser Lys Gly Val Lys Leu Val Ser Ile Gly Ala
            100                 105                 110

Glu Glu Ile Val Asp Gly Asn Val Lys Met Thr Leu Gly Met Ile Trp
        115                 120                 125

Thr Ile Ile Leu Arg Phe Ala Ile Gln Asp Ile Ser Val Glu Glu Thr
130                 135                 140

Ser Ala Lys Glu Gly Leu Leu Leu Trp Cys Gln Arg Lys Thr Ala Pro
145                 150                 155                 160
```

-continued

```
Tyr Lys Asn Val Asn Ile Gln Asn Phe His Ile Ser Trp Lys Asp Gly
            165                 170                 175

Leu Gly Phe Cys Ala Leu Ile His Arg His Arg Pro Glu Leu Ile Asp
        180                 185                 190

Tyr Gly Lys Leu Arg Lys Asp Asp Pro Leu Thr Asn Leu Asn Thr Ala
    195                 200                 205

Phe Asp Val Ala Glu Lys Tyr Leu Asp Ile Pro Lys Met Leu Asp Ala
210                 215                 220

Glu Asp Ile Val Gly Thr Ala Arg Pro Asp Glu Lys Ala Ile Met Thr
225                 230                 235                 240

Tyr Val Ser Ser Phe Tyr His Ala Phe Ser Gly Ala Gln Lys Ala Glu
                245                 250                 255

Thr Ala Ala Asn Arg Ile Cys Lys Val Leu Ala Val Asn Gln Glu Asn
            260                 265                 270

Glu Gln Leu Met Glu Asp Tyr Glu Lys Leu Ala Ser Asp Leu Leu Glu
        275                 280                 285

Trp Ile Arg Arg Thr Ile Pro Trp Leu Glu Asn Arg Val Pro Glu Asn
    290                 295                 300

Thr Met His Ala Met Gln Gln Lys Leu Glu Asp Phe Arg Asp Tyr Arg
305                 310                 315                 320

Arg Leu His Lys Pro Pro Lys Val Gln Glu Lys Cys Gln Leu Glu Ile
                325                 330                 335

Asn Phe Asn Thr Leu Gln Thr Lys Leu Arg Leu Ser Asn Arg Pro Ala
            340                 345                 350

Phe Met Pro Ser Glu Gly Arg Met Val Ser Asp Ile Asn Asn Ala Trp
        355                 360                 365

Gly Cys Leu Glu Gln Val Glu Lys Gly Tyr Glu Glu Trp Leu Leu Asn
    370                 375                 380

Glu Ile Arg Arg Leu Glu Arg Leu Asp His Leu Ala Glu Lys Phe Arg
385                 390                 395                 400

Gln Lys Ala Ser Ile His Glu Ala Trp Thr Asp Gly Lys Glu Ala Met
                405                 410                 415

Leu Arg Gln Lys Asp Tyr Glu Thr Ala Thr Leu Ser Glu Ile Lys Ala
            420                 425                 430

Leu Leu Lys Lys His Glu Ala Phe Glu Ser Asp Leu Ala Ala His Gln
        435                 440                 445

Asp Arg Val Glu Gln Ile Ala Ala Ile Ala Gln Glu Leu Asn Glu Leu
    450                 455                 460

Asp Tyr Tyr Asp Ser Pro Ser Val Asn Ala Arg Cys Gln Lys Ile Cys
465                 470                 475                 480

Asp Gln Trp Asp Asn Leu Gly Ala Leu Thr Gln Lys Arg Arg Glu Ala
                485                 490                 495

Leu Glu Arg Thr Glu Lys Leu Leu Glu Thr Ile Asp Gln Leu Tyr Leu
            500                 505                 510

Glu Tyr Ala Lys Arg Ala Ala Pro Phe Asn Asn Trp Met Glu Gly Ala
        515                 520                 525

Met Glu Asp Leu Gln Asp Thr Phe Ile Val His Thr Ile Glu Glu Ile
    530                 535                 540

Gln Gly Leu Thr Thr Ala His Glu Gln Phe Lys Ala Thr Leu Pro Asp
545                 550                 555                 560

Ala Asp Lys Glu Arg Leu Ala Ile Leu Gly Ile His Asn Glu Val Ser
                565                 570                 575

Lys Ile Val Gln Thr Tyr His Val Asn Met Ala Gly Thr Asn Pro Tyr
            580                 585                 590
```

```
Thr Thr Ile Thr Pro Gln Glu Ile Asn Gly Lys Trp Asp His Val Arg
        595                 600                 605
Gln Leu Val Pro Arg Arg Asp Gln Ala Leu Thr Glu Glu His Ala Arg
    610                 615                 620
Gln Gln His Asn Glu Arg Leu Arg Lys Gln Phe Gly Ala Gln Ala Asn
625                 630                 635                 640
Val Ile Gly Pro Trp Ile Gln Thr Lys Met Glu Glu Ile Gly Arg Ile
            645                 650                 655
Ser Ile Glu Met His Gly Thr Leu Glu Asp Gln Leu Ser His Leu Arg
            660                 665                 670
Gln Tyr Glu Lys Ser Ile Val Asn Tyr Lys Pro Lys Ile Asp Gln Leu
        675                 680                 685
Glu Gly Asp His Gln Leu Ile Gln Glu Ala Leu Ile Phe Asp Asn Lys
    690                 695                 700
His Thr Asn Tyr Thr Met Glu His Ile Arg Val Gly Trp Glu Gln Leu
705                 710                 715                 720
Leu Thr Thr Ile Ala Arg Thr Ile Asn Glu Val Glu Asn Gln Ile Leu
            725                 730                 735
Thr Arg Asp Ala Lys Gly Ile Ser Gln Glu Gln Met Asn Glu Phe Arg
        740                 745                 750
Ala Ser Phe Asn His Phe Asp Arg Asp His Ser Gly Thr Leu Gly Pro
    755                 760                 765
Glu Glu Phe Lys Ala Cys Leu Ile Ser Leu Gly Tyr Asp Ile Gly Asn
770                 775                 780
Asp Pro Gln Gly Glu Ala Glu Phe Ala Arg Ile Met Ser Ile Val Asp
785                 790                 795                 800
Pro Asn Arg Leu Gly Val Val Thr Phe Gln Ala Phe Ile Asp Phe Met
            805                 810                 815
Ser Arg Glu Thr Ala Asp Thr Asp Thr Ala Asp Gln Val Met Ala Ser
        820                 825                 830
Phe Lys Ile Leu Ala Gly Asp Lys Asn Tyr Ile Thr Met Asp Glu Leu
    835                 840                 845
Arg Arg Glu Leu Pro Pro Asp Gln Ala Glu Tyr Cys Ile Ala Arg Met
850                 855                 860
Ala Pro Tyr Thr Gly Pro Asp Ser Val Pro Gly Ala Leu Asp Tyr Met
865                 870                 875                 880
Ser Phe Ser Thr Ala Leu Tyr Gly Glu Ser Asp Leu
            885                 890

<210> SEQ ID NO 74
<211> LENGTH: 633
<212> TYPE: PRT
<213> ORGANISM: Homo sapiens

<400> SEQUENCE: 74

Met Pro Ser Cys Gly Ala Cys Thr Cys Gly Ala Ala Ala Val Arg Leu
1               5                   10                  15
Ile Thr Ser Ser Leu Ala Ser Ala Gln Arg Gly Ile Ser Gly Gly Arg
            20                  25                  30
Ile His Met Ser Val Leu Gly Arg Leu Gly Thr Phe Glu Thr Gln Ile
        35                  40                  45
Leu Gln Arg Ala Pro Leu Arg Ser Phe Thr Glu Thr Pro Ala Tyr Phe
    50                  55                  60
Ala Ser Lys Asp Gly Ile Ser Lys Asp Gly Ser Gly Asp Gly Asn Lys
65                  70                  75                  80
```

```
Lys Ser Ala Ser Glu Gly Ser Ser Lys Lys Ser Gly Ser Gly Asn Ser
                85                  90                  95

Gly Lys Gly Gly Asn Gln Leu Arg Cys Pro Lys Cys Gly Asp Leu Cys
            100                 105                 110

Thr His Val Glu Thr Phe Val Ser Ser Thr Arg Phe Val Lys Cys Glu
        115                 120                 125

Lys Cys His His Phe Val Val Leu Ser Glu Ala Asp Ser Lys Lys
    130                 135                 140

Ser Ile Ile Lys Glu Pro Glu Ser Ala Ala Glu Ala Val Lys Leu Ala
145                 150                 155                 160

Phe Gln Gln Lys Pro Pro Pro Pro Lys Lys Ile Tyr Asn Tyr Leu
            165                 170                 175

Asp Lys Tyr Val Val Gly Gln Ser Phe Ala Lys Lys Val Leu Ser Val
            180                 185                 190

Ala Val Tyr Asn His Tyr Lys Arg Ile Tyr Asn Asn Ile Pro Ala Asn
        195                 200                 205

Leu Arg Gln Gln Ala Glu Val Glu Lys Gln Thr Ser Leu Thr Pro Arg
        210                 215                 220

Glu Leu Glu Ile Arg Arg Glu Asp Glu Tyr Arg Phe Thr Lys Leu
225                 230                 235                 240

Leu Gln Ile Ala Gly Ile Ser Pro His Gly Asn Ala Leu Gly Ala Ser
                245                 250                 255

Met Gln Gln Val Asn Gln Ile Pro Gln Glu Lys Arg Gly Gly
        260                 265                 270

Glu Val Leu Asp Ser Ser His Asp Asp Ile Lys Leu Glu Lys Ser Asn
        275                 280                 285

Ile Leu Leu Leu Gly Pro Thr Gly Ser Gly Lys Thr Leu Leu Ala Gln
        290                 295                 300

Thr Leu Ala Lys Cys Leu Asp Val Pro Phe Ala Ile Cys Asp Cys Thr
305                 310                 315                 320

Thr Leu Thr Gln Ala Gly Tyr Val Gly Glu Asp Ile Glu Ser Val Ile
            325                 330                 335

Ala Lys Leu Leu Gln Asp Ala Asn Tyr Asn Val Glu Lys Ala Gln Gln
                340                 345                 350

Gly Ile Val Phe Leu Asp Glu Val Asp Lys Ile Gly Ser Val Pro Gly
            355                 360                 365

Ile His Gln Leu Arg Asp Val Gly Gly Glu Gly Val Gln Gln Gly Leu
    370                 375                 380

Leu Lys Leu Leu Glu Gly Thr Ile Val Asn Val Pro Glu Lys Asn Ser
385                 390                 395                 400

Arg Lys Leu Arg Gly Glu Thr Val Gln Val Asp Thr Thr Asn Ile Leu
                405                 410                 415

Phe Val Ala Ser Gly Ala Phe Asn Gly Leu Asp Arg Ile Ile Ser Arg
            420                 425                 430

Arg Lys Asn Glu Lys Tyr Leu Gly Phe Gly Thr Pro Ser Asn Leu Gly
        435                 440                 445

Lys Gly Arg Arg Ala Ala Ala Ala Asp Leu Ala Asn Arg Ser Gly
    450                 455                 460

Glu Ser Asn Thr His Gln Asp Ile Glu Glu Lys Asp Arg Leu Leu Arg
465                 470                 475                 480

His Val Glu Ala Arg Asp Leu Ile Glu Phe Gly Met Ile Pro Glu Phe
            485                 490                 495

Val Gly Arg Leu Pro Val Val Val Pro Leu His Ser Leu Asp Glu Lys
```

```
                500             505             510
Thr Leu Val Gln Ile Leu Thr Glu Pro Arg Asn Ala Val Ile Pro Gln
            515                 520                 525
Tyr Gln Ala Leu Phe Ser Met Asp Lys Cys Glu Leu Asn Val Thr Glu
        530                 535                 540
Asp Ala Leu Lys Ala Ile Ala Arg Leu Ala Leu Glu Arg Lys Thr Gly
545                 550                 555                 560
Ala Arg Gly Leu Arg Ser Ile Met Glu Lys Leu Leu Leu Glu Pro Met
                565                 570                 575
Phe Glu Val Pro Asn Ser Asp Ile Val Cys Val Glu Val Asp Lys Glu
            580                 585                 590
Val Val Glu Gly Lys Lys Glu Pro Gly Tyr Ile Arg Ala Pro Thr Lys
        595                 600                 605
Glu Ser Ser Glu Glu Glu Tyr Asp Ser Gly Val Glu Glu Gly Trp
            610                 615                 620
Pro Arg Gln Ala Asp Ala Ala Asn Ser
625                 630

<210> SEQ ID NO 75
<211> LENGTH: 260
<212> TYPE: PRT
<213> ORGANISM: Homo sapiens

<400> SEQUENCE: 75

Met Ser His His Trp Gly Tyr Gly Lys His Asn Gly Pro Glu His Trp
1               5                   10                  15
His Lys Asp Phe Pro Ile Ala Lys Gly Glu Arg Gln Ser Pro Val Asp
                20                  25                  30
Ile Asp Thr His Thr Ala Lys Tyr Asp Pro Ser Leu Lys Pro Leu Ser
            35                  40                  45
Val Ser Tyr Asp Gln Ala Thr Ser Leu Arg Ile Leu Asn Asn Gly His
        50                  55                  60
Ala Phe Asn Val Glu Phe Asp Asp Ser Gln Asp Lys Ala Val Leu Lys
65                  70                  75                  80
Gly Gly Pro Leu Asp Gly Thr Tyr Arg Leu Ile Gln Phe His Phe His
                85                  90                  95
Trp Gly Ser Leu Asp Gly Gln Gly Ser Glu His Thr Val Asp Lys Lys
                100                 105                 110
Lys Tyr Ala Ala Glu Leu His Leu Val His Trp Asn Thr Lys Tyr Gly
            115                 120                 125
Asp Phe Gly Lys Ala Val Gln Gln Pro Asp Gly Leu Ala Val Leu Gly
        130                 135                 140
Ile Phe Leu Lys Val Gly Ser Ala Lys Pro Gly Leu Gln Lys Val Val
145                 150                 155                 160
Asp Val Leu Asp Ser Ile Lys Thr Lys Gly Lys Ser Ala Asp Phe Thr
                165                 170                 175
Asn Phe Asp Pro Arg Gly Leu Leu Pro Glu Ser Leu Asp Tyr Trp Thr
                180                 185                 190
Tyr Pro Gly Ser Leu Thr Thr Pro Pro Leu Leu Glu Cys Val Thr Trp
            195                 200                 205
Ile Val Leu Lys Glu Pro Ile Ser Val Ser Ser Glu Gln Val Leu Lys
        210                 215                 220
Phe Arg Lys Leu Asn Phe Asn Gly Glu Gly Glu Pro Glu Glu Leu Met
225                 230                 235                 240
Val Asp Asn Trp Arg Pro Ala Gln Pro Leu Lys Asn Arg Gln Ile Lys
```

Ala Ser Phe Lys
            260

<210> SEQ ID NO 76
<211> LENGTH: 201
<212> TYPE: PRT
<213> ORGANISM: Homo sapiens

<400> SEQUENCE: 76

Met Phe Pro Glu Gln Gln Lys Glu Glu Phe Val Ser Val Trp Val Arg
1               5                   10                  15

Asp Pro Arg Ile Gln Lys Glu Asp Phe Trp His Ser Tyr Ile Asp Tyr
            20                  25                  30

Glu Ile Cys Ile His Thr Asn Ser Met Cys Phe Thr Met Lys Thr Ser
        35                  40                  45

Cys Val Arg Arg Arg Tyr Arg Glu Phe Val Trp Leu Arg Gln Arg Leu
    50                  55                  60

Gln Ser Asn Ala Leu Leu Val Gln Leu Pro Glu Leu Pro Ser Lys Asn
65                  70                  75                  80

Leu Phe Phe Asn Met Asn Asn Arg Gln His Val Asp Gln Arg Arg Gln
                85                  90                  95

Gly Leu Glu Asp Phe Leu Arg Lys Val Leu Gln Asn Ala Leu Leu Leu
            100                 105                 110

Ser Asp Ser Ser Leu His Leu Phe Leu Gln Ser His Leu Asn Ser Glu
        115                 120                 125

Asp Ile Glu Ala Cys Val Ser Gly Gln Thr Lys Tyr Ser Val Glu Glu
    130                 135                 140

Ala Ile His Lys Phe Ala Leu Met Asn Arg Arg Phe Pro Glu Glu Asp
145                 150                 155                 160

Glu Glu Gly Lys Lys Glu Asn Asp Ile Asp Tyr Asp Ser Glu Ser Ser
                165                 170                 175

Ser Ser Gly Leu Gly His Ser Ser Asp Asp Ser Ser Ser His Gly Cys
            180                 185                 190

Lys Val Asn Thr Ala Pro Gln Glu Ser
        195                 200

<210> SEQ ID NO 77
<211> LENGTH: 651
<212> TYPE: PRT
<213> ORGANISM: Homo sapiens

<400> SEQUENCE: 77

Met Leu Arg Leu Gln Met Thr Asp Gly His Ile Ser Cys Thr Ala Val
1               5                   10                  15

Glu Phe Ser Tyr Met Ser Lys Ile Ser Leu Asn Thr Pro Pro Gly Thr
            20                  25                  30

Lys Val Lys Leu Ser Gly Ile Val Asp Ile Lys Asn Gly Phe Leu Leu
        35                  40                  45

Leu Asn Asp Ser Asn Thr Thr Val Leu Gly Gly Glu Val Glu His Leu
    50                  55                  60

Ile Glu Lys Trp Glu Leu Gln Arg Ser Leu Ser Lys His Asn Arg Ser
65                  70                  75                  80

Asn Ile Gly Thr Glu Gly Gly Pro Pro Phe Val Pro Phe Gly Gln
                85                  90                  95

Lys Cys Val Ser His Val Gln Val Asp Ser Arg Glu Leu Asp Arg Arg
            100                 105                 110

-continued

```
Lys Thr Leu Gln Val Thr Met Pro Val Lys Pro Thr Asn Asp Asn Asp
            115                 120                 125

Glu Phe Glu Lys Gln Arg Thr Ala Ala Ile Ala Glu Val Ala Lys Ser
        130                 135                 140

Lys Glu Thr Lys Thr Phe Gly Gly Gly Gly Gly Ala Arg Ser Asn
145                 150                 155                 160

Leu Asn Met Asn Ala Ala Gly Asn Arg Asn Arg Glu Val Leu Gln Lys
                165                 170                 175

Glu Lys Ser Thr Lys Ser Glu Gly Lys His Glu Gly Val Tyr Arg Glu
            180                 185                 190

Leu Val Asp Glu Lys Ala Leu Lys His Ile Thr Glu Met Gly Phe Ser
        195                 200                 205

Lys Glu Ala Ser Arg Gln Ala Leu Met Asp Asn Gly Asn Asn Leu Glu
    210                 215                 220

Ala Ala Leu Asn Val Leu Leu Thr Ser Asn Lys Gln Lys Pro Val Met
225                 230                 235                 240

Gly Pro Pro Leu Arg Gly Arg Gly Lys Gly Arg Gly Arg Ile Arg Ser
                245                 250                 255

Glu Asp Glu Glu Asp Leu Gly Asn Ala Arg Pro Ser Ala Pro Ser Thr
            260                 265                 270

Leu Phe Asp Phe Leu Glu Ser Lys Met Gly Thr Leu Asn Val Glu Glu
        275                 280                 285

Pro Lys Ser Gln Pro Gln Gln Leu His Gln Gly Gln Tyr Arg Ser Ser
    290                 295                 300

Asn Thr Glu Gln Asn Gly Val Lys Asp Asn Asn His Leu Arg His Pro
305                 310                 315                 320

Pro Arg Asn Asp Thr Arg Gln Pro Arg Asn Glu Lys Pro Pro Arg Phe
                325                 330                 335

Gln Arg Asp Ser Gln Asn Ser Lys Ser Val Leu Glu Gly Ser Gly Leu
            340                 345                 350

Pro Arg Asn Arg Gly Ser Glu Arg Pro Ser Thr Ser Ser Val Ser Glu
        355                 360                 365

Val Trp Ala Glu Asp Arg Ile Lys Cys Asp Arg Pro Tyr Ser Arg Tyr
    370                 375                 380

Asp Arg Thr Lys Asp Thr Ser Tyr Pro Leu Gly Ser Gln His Ser Asp
385                 390                 395                 400

Gly Ala Phe Lys Lys Arg Asp Asn Ser Met Gln Ser Arg Ser Gly Lys
                405                 410                 415

Gly Pro Ser Phe Ala Glu Ala Lys Glu Asn Pro Leu Pro Gln Gly Ser
            420                 425                 430

Val Asp Tyr Asn Asn Gln Lys Arg Gly Lys Arg Glu Ser Gln Thr Ser
        435                 440                 445

Ile Pro Asp Tyr Phe Tyr Asp Arg Lys Ser Gln Thr Ile Asn Asn Glu
    450                 455                 460

Ala Phe Ser Gly Ile Lys Ile Glu Lys His Phe Asn Val Asn Thr Asp
465                 470                 475                 480

Tyr Gln Asn Pro Val Arg Ser Asn Ser Phe Ile Gly Val Pro Asn Gly
                485                 490                 495

Glu Val Glu Met Pro Leu Lys Gly Arg Arg Ile Gly Pro Ile Lys Pro
            500                 505                 510

Ala Gly Pro Val Thr Ala Val Pro Cys Asp Asp Lys Ile Phe Tyr Asn
        515                 520                 525

Ser Gly Pro Lys Arg Arg Ser Gly Pro Ile Lys Pro Glu Lys Ile Leu
```

```
            530                 535                 540
Glu Ser Ser Ile Pro Met Glu Tyr Ala Lys Met Trp Lys Pro Gly Asp
545                 550                 555                 560

Glu Cys Phe Ala Leu Tyr Trp Glu Asp Asn Lys Phe Tyr Arg Ala Glu
                565                 570                 575

Val Glu Ala Leu His Ser Ser Gly Met Thr Ala Val Val Lys Phe Ile
                580                 585                 590

Asp Tyr Gly Asn Tyr Glu Glu Val Leu Leu Ser Asn Ile Lys Pro Ile
                595                 600                 605

Gln Thr Glu Ala Trp Glu Glu Gly Thr Tyr Asp Gln Thr Leu Glu
        610                 615                 620

Phe Arg Arg Gly Gly Asp Gly Gln Pro Arg Arg Ser Thr Arg Pro Thr
625                 630                 635                 640

Gln Gln Phe Tyr Gln Pro Pro Arg Ala Arg Asn
                645                 650

<210> SEQ ID NO 78
<211> LENGTH: 381
<212> TYPE: PRT
<213> ORGANISM: Homo sapiens
<220> FEATURE:
<221> NAME/KEY: Xaa
<222> LOCATION: (59)..(59)
<223> OTHER INFORMATION: Xaa is a selenocysteine
<220> FEATURE:
<221> NAME/KEY: Xaa
<222> LOCATION: (300)..(300)
<223> OTHER INFORMATION: Xaa is a selenocysteine
<220> FEATURE:
<221> NAME/KEY: Xaa
<222> LOCATION: (318)..(318)
<223> OTHER INFORMATION: Xaa is a selenocysteine
<220> FEATURE:
<221> NAME/KEY: Xaa
<222> LOCATION: (330)..(330)
<223> OTHER INFORMATION: Xaa is a selenocysteine
<220> FEATURE:
<221> NAME/KEY: Xaa
<222> LOCATION: (345)..(345)
<223> OTHER INFORMATION: Xaa is a selenocysteine
<220> FEATURE:
<221> NAME/KEY: Xaa
<222> LOCATION: (352)..(352)
<223> OTHER INFORMATION: Xaa is a selenocysteine
<220> FEATURE:
<221> NAME/KEY: Xaa
<222> LOCATION: (367)..(367)
<223> OTHER INFORMATION: Xaa is a selenocysteine
<220> FEATURE:
<221> NAME/KEY: Xaa
<222> LOCATION: (369)..(369)
<223> OTHER INFORMATION: Xaa is a selenocysteine
<220> FEATURE:
<221> NAME/KEY: Xaa
<222> LOCATION: (376)..(376)
<223> OTHER INFORMATION: Xaa is a selenocysteine
<220> FEATURE:
<221> NAME/KEY: Xaa
<222> LOCATION: (378)..(378)
<223> OTHER INFORMATION: Xaa is a selenocysteine

<400> SEQUENCE: 78

Met Trp Arg Ser Leu Gly Leu Ala Leu Ala Leu Cys Leu Leu Pro Ser
1               5                   10                  15

Gly Gly Thr Glu Ser Gln Asp Gln Ser Ser Leu Cys Lys Gln Pro Pro
                20                  25                  30

Ala Trp Ser Ile Arg Asp Gln Asp Pro Met Leu Asn Ser Asn Gly Ser
            35                  40                  45
```

```
Val Thr Val Val Ala Leu Leu Gln Ala Ser Xaa Tyr Leu Cys Ile Leu
     50                  55                  60

Gln Ala Ser Lys Leu Glu Asp Leu Arg Val Lys Leu Lys Glu Gly
 65                  70                  75                  80

Tyr Ser Asn Ile Ser Tyr Ile Val Val Asn His Gln Gly Ile Ser Ser
                 85                  90                  95

Arg Leu Lys Tyr Thr His Leu Lys Asn Lys Val Ser Glu His Ile Pro
            100                 105                 110

Val Tyr Gln Gln Glu Glu Asn Gln Thr Asp Val Trp Thr Leu Leu Asn
            115                 120                 125

Gly Ser Lys Asp Asp Phe Leu Ile Tyr Asp Arg Cys Gly Arg Leu Val
    130                 135                 140

Tyr His Leu Gly Leu Pro Phe Ser Phe Leu Thr Phe Pro Tyr Val Glu
145                 150                 155                 160

Glu Ala Ile Lys Ile Ala Tyr Cys Glu Lys Lys Cys Gly Asn Cys Ser
                165                 170                 175

Leu Thr Thr Leu Lys Asp Glu Asp Phe Cys Lys Arg Val Ser Leu Ala
            180                 185                 190

Thr Val Asp Lys Thr Val Glu Thr Pro Ser Pro His Tyr His His Glu
            195                 200                 205

His His His Asn His Gly His Gln His Leu Gly Ser Ser Glu Leu Ser
            210                 215                 220

Glu Asn Gln Gln Pro Gly Ala Pro Asn Ala Pro Thr His Pro Ala Pro
225                 230                 235                 240

Pro Gly Leu His His His His Lys His Lys Gly Gln His Arg Gln Gly
                245                 250                 255

His Pro Glu Asn Arg Asp Met Pro Ala Ser Glu Asp Leu Gln Asp Leu
            260                 265                 270

Gln Lys Lys Leu Cys Arg Lys Arg Cys Ile Asn Gln Leu Leu Cys Lys
            275                 280                 285

Leu Pro Thr Asp Ser Glu Leu Ala Pro Arg Ser Xaa Cys Cys His Cys
            290                 295                 300

Arg His Leu Ile Phe Glu Lys Thr Gly Ser Ala Ile Thr Xaa Gln Cys
305                 310                 315                 320

Lys Glu Asn Leu Pro Ser Leu Cys Ser Xaa Gln Gly Leu Arg Ala Glu
                325                 330                 335

Glu Asn Ile Thr Glu Ser Cys Gln Xaa Arg Leu Pro Pro Ala Ala Xaa
            340                 345                 350

Gln Ile Ser Gln Gln Leu Ile Pro Thr Glu Ala Ser Ala Ser Xaa Arg
            355                 360                 365

Xaa Lys Asn Gln Ala Lys Lys Xaa Glu Xaa Pro Ser Asn
    370                 375                 380

<210> SEQ ID NO 79
<211> LENGTH: 153
<212> TYPE: PRT
<213> ORGANISM: Homo sapiens

<400> SEQUENCE: 79

Met His Tyr Val His Val His Arg Val Thr Thr Gln Pro Arg Asn Lys
 1               5                  10                  15

Pro Gln Thr Lys Cys Pro Ser Gly Gly Gln Ser Gln Gly Pro Arg Gly
            20                  25                  30

Gln Phe Leu Asp Thr Val Leu Ala Ala Met Cys Pro Ile Ala Met Leu
        35                  40                  45
```

Leu Thr Ala Asp Pro Gly Met Pro Pro Thr Cys Leu Trp His Thr Pro
 50                  55                  60

His Ala Lys His Lys Glu His Leu Ser Ile His Leu Asn Met Val Pro
 65                  70                  75                  80

Lys Cys Val His Met His Val Thr His Thr His Thr Asn Ser Gly Ser
                 85                  90                  95

Arg Tyr Val Gly Lys Tyr Ile Leu Leu Ile Lys Trp Ser Leu Ala Met
            100                 105                 110

Tyr Phe Val Gln Gly Ser Thr Leu Ser Thr Val Thr Lys Met Ser His
        115                 120                 125

Gly Lys Ala Leu Pro Asp Ser Asp Thr Tyr Ile Gln Phe Pro Asn Gln
130                 135                 140

Gln Gly Pro His Thr Pro Ser Ile Pro
145                 150

<210> SEQ ID NO 80
<211> LENGTH: 766
<212> TYPE: PRT
<213> ORGANISM: Homo sapiens

<400> SEQUENCE: 80

Met Lys Thr Pro Trp Lys Val Leu Leu Gly Leu Leu Ala Ala Ala
 1               5                  10                  15

Leu Val Thr Ile Ile Thr Val Pro Val Val Leu Leu Asn Lys Gly Thr
            20                  25                  30

Asp Asp Ala Thr Ala Asp Ser Arg Lys Thr Tyr Thr Leu Thr Asp Tyr
        35                  40                  45

Leu Lys Asn Thr Tyr Arg Leu Lys Leu Tyr Ser Leu Arg Trp Ile Ser
 50                  55                  60

Asp His Glu Tyr Leu Tyr Lys Gln Glu Asn Asn Ile Leu Val Phe Asn
 65                  70                  75                  80

Ala Glu Tyr Gly Asn Ser Ser Val Phe Leu Glu Asn Ser Thr Phe Asp
                 85                  90                  95

Glu Phe Gly His Ser Ile Asn Asp Tyr Ser Ile Ser Pro Asp Gly Gln
            100                 105                 110

Phe Ile Leu Leu Glu Tyr Asn Tyr Val Lys Gln Trp Arg His Ser Tyr
        115                 120                 125

Thr Ala Ser Tyr Asp Ile Tyr Asp Leu Asn Lys Arg Gln Leu Ile Thr
130                 135                 140

Glu Glu Arg Ile Pro Asn Asn Thr Gln Trp Val Thr Trp Ser Pro Val
145                 150                 155                 160

Gly His Lys Leu Ala Tyr Val Trp Asn Asn Asp Ile Tyr Val Lys Ile
                165                 170                 175

Glu Pro Asn Leu Pro Ser Tyr Arg Ile Thr Trp Thr Gly Lys Glu Asp
            180                 185                 190

Ile Ile Tyr Asn Gly Ile Thr Asp Trp Val Tyr Glu Glu Glu Val Phe
        195                 200                 205

Ser Ala Tyr Ser Ala Leu Trp Trp Ser Pro Asn Gly Thr Phe Leu Ala
210                 215                 220

Tyr Ala Gln Phe Asn Asp Thr Glu Val Pro Leu Ile Glu Tyr Ser Phe
225                 230                 235                 240

Tyr Ser Asp Glu Ser Leu Gln Tyr Pro Lys Thr Val Arg Val Pro Tyr
                245                 250                 255

Pro Lys Ala Gly Ala Val Asn Pro Thr Val Lys Phe Phe Val Val Asn
            260                 265                 270

```
Thr Asp Ser Leu Ser Ser Val Thr Asn Ala Thr Ser Ile Gln Ile Thr
        275                 280                 285

Ala Pro Ala Ser Met Leu Ile Gly Asp His Tyr Leu Cys Asp Val Thr
290                 295                 300

Trp Ala Thr Gln Glu Arg Ile Ser Leu Gln Trp Leu Arg Arg Ile Gln
305                 310                 315                 320

Asn Tyr Ser Val Met Asp Ile Cys Asp Tyr Asp Glu Ser Ser Gly Arg
                325                 330                 335

Trp Asn Cys Leu Val Ala Arg Gln His Ile Glu Met Ser Thr Thr Gly
                340                 345                 350

Trp Val Gly Arg Phe Arg Pro Ser Glu Pro His Phe Thr Leu Asp Gly
            355                 360                 365

Asn Ser Phe Tyr Lys Ile Ile Ser Asn Glu Gly Tyr Arg His Ile
370                 375                 380

Cys Tyr Phe Gln Ile Asp Lys Lys Asp Cys Thr Phe Ile Thr Lys Gly
385                 390                 395                 400

Thr Trp Glu Val Ile Gly Ile Glu Ala Leu Thr Ser Asp Tyr Leu Tyr
                405                 410                 415

Tyr Ile Ser Asn Glu Tyr Lys Gly Met Pro Gly Gly Arg Asn Leu Tyr
            420                 425                 430

Lys Ile Gln Leu Ser Asp Tyr Thr Lys Val Thr Cys Leu Ser Cys Glu
                435                 440                 445

Leu Asn Pro Glu Arg Cys Gln Tyr Tyr Ser Val Ser Phe Ser Lys Glu
450                 455                 460

Ala Lys Tyr Tyr Gln Leu Arg Cys Ser Gly Pro Gly Leu Pro Leu Tyr
465                 470                 475                 480

Thr Leu His Ser Ser Val Asn Asp Lys Gly Leu Arg Val Leu Glu Asp
                485                 490                 495

Asn Ser Ala Leu Asp Lys Met Leu Gln Asn Val Gln Met Pro Ser Lys
            500                 505                 510

Lys Leu Asp Phe Ile Ile Leu Asn Glu Thr Lys Phe Trp Tyr Gln Met
                515                 520                 525

Ile Leu Pro Pro His Phe Asp Lys Ser Lys Lys Tyr Pro Leu Leu Leu
530                 535                 540

Asp Val Tyr Ala Gly Pro Cys Ser Gln Lys Ala Asp Thr Val Phe Arg
545                 550                 555                 560

Leu Asn Trp Ala Thr Tyr Leu Ala Ser Thr Glu Asn Ile Ile Val Ala
                565                 570                 575

Ser Phe Asp Gly Arg Gly Ser Gly Tyr Gln Gly Asp Lys Ile Met His
            580                 585                 590

Ala Ile Asn Arg Arg Leu Gly Thr Phe Glu Val Glu Asp Gln Ile Glu
                595                 600                 605

Ala Ala Arg Gln Phe Ser Lys Met Gly Phe Val Asp Asn Lys Arg Ile
610                 615                 620

Ala Ile Trp Gly Trp Ser Tyr Gly Gly Tyr Val Thr Ser Met Val Leu
625                 630                 635                 640

Gly Ser Gly Ser Gly Val Phe Lys Cys Gly Ile Ala Val Ala Pro Val
                645                 650                 655

Ser Arg Trp Glu Tyr Tyr Asp Ser Val Tyr Thr Glu Arg Tyr Met Gly
            660                 665                 670

Leu Pro Thr Pro Glu Asp Asn Leu Asp His Tyr Arg Asn Ser Thr Val
                675                 680                 685

Met Ser Arg Ala Glu Asn Phe Lys Gln Val Glu Tyr Leu Leu Ile His
690                 695                 700
```

```
Gly Thr Ala Asp Asp Asn Val His Phe Gln Gln Ser Ala Gln Ile Ser
705                 710                 715                 720

Lys Ala Leu Val Asp Val Gly Val Asp Phe Gln Ala Met Trp Tyr Thr
                725                 730                 735

Asp Glu Asp His Gly Ile Ala Ser Ser Thr Ala His Gln His Ile Tyr
            740                 745                 750

Thr His Met Ser His Phe Ile Lys Gln Cys Phe Ser Leu Pro
        755                 760                 765
```

<210> SEQ ID NO 81
<211> LENGTH: 146
<212> TYPE: PRT
<213> ORGANISM: Homo sapiens

<400> SEQUENCE: 81

```
Met Ala Gly Pro Leu Arg Ala Pro Leu Leu Leu Ala Ile Leu Ala
1               5                   10                  15

Val Ala Leu Ala Val Ser Pro Ala Ala Gly Ser Ser Pro Gly Lys Pro
                20                  25                  30

Pro Arg Leu Val Gly Gly Pro Met Asp Ala Ser Val Glu Glu Glu Gly
            35                  40                  45

Val Arg Arg Ala Leu Asp Phe Ala Val Gly Glu Tyr Asn Lys Ala Ser
50                  55                  60

Asn Asp Met Tyr His Ser Arg Ala Leu Gln Val Val Arg Ala Arg Lys
65                  70                  75                  80

Gln Ile Val Ala Gly Val Asn Tyr Phe Leu Asp Val Glu Leu Gly Arg
                85                  90                  95

Thr Thr Cys Thr Lys Thr Gln Pro Asn Leu Asp Asn Cys Pro Phe His
            100                 105                 110

Asp Gln Pro His Leu Lys Arg Lys Ala Phe Cys Ser Phe Gln Ile Tyr
        115                 120                 125

Ala Val Pro Trp Gln Gly Thr Met Thr Leu Ser Lys Ser Thr Cys Gln
130                 135                 140

Asp Ala
145
```

<210> SEQ ID NO 82
<211> LENGTH: 326
<212> TYPE: PRT
<213> ORGANISM: Mus musculus

<400> SEQUENCE: 82

```
Met Glu Gly Ser Leu Gln Leu Leu Ala Cys Leu Ala Cys Val Leu Gln
1               5                   10                  15

Met Gly Ser Leu Val Lys Thr Arg Arg Asp Ala Ser Gly Asp Leu Leu
                20                  25                  30

Asn Thr Glu Ala His Ser Ala Pro Ala Gln Arg Trp Ser Met Gln Val
            35                  40                  45

Pro Ala Glu Val Asn Ala Glu Ala Gly Asp Ala Ala Val Leu Pro Cys
50                  55                  60

Thr Phe Thr His Pro His Arg His Tyr Asp Gly Pro Leu Thr Ala Ile
65                  70                  75                  80

Trp Arg Ser Gly Glu Pro Tyr Ala Gly Pro Gln Val Phe Arg Cys Thr
                85                  90                  95

Ala Ala Pro Gly Ser Glu Leu Cys Gln Thr Ala Leu Ser Leu His Gly
            100                 105                 110
```

```
Arg Phe Arg Leu Leu Gly Asn Pro Arg Arg Asn Asp Leu Ser Leu Arg
        115                 120                 125
Val Glu Arg Leu Ala Leu Ala Asp Ser Gly Arg Tyr Phe Cys Arg Val
    130                 135                 140
Glu Phe Thr Gly Asp Ala His Asp Arg Tyr Glu Ser Arg His Gly Val
145                 150                 155                 160
Arg Leu Arg Val Thr Ala Ala Pro Arg Ile Val Asn Ile Ser Val Leu
                165                 170                 175
Pro Gly Pro Ala His Ala Phe Arg Ala Leu Cys Thr Ala Glu Gly Glu
            180                 185                 190
Pro Pro Pro Ala Leu Ala Trp Ser Gly Pro Ala Pro Gly Asn Ser Ser
        195                 200                 205
Ala Ala Leu Gln Gly Gln Gly His Gly Tyr Gln Val Thr Ala Glu Leu
    210                 215                 220
Pro Ala Leu Thr Arg Asp Gly Arg Tyr Thr Cys Thr Ala Ala Asn Ser
225                 230                 235                 240
Leu Gly Arg Ala Glu Ala Ser Val Tyr Leu Phe Arg Phe His Gly Ala
                245                 250                 255
Pro Gly Thr Ser Thr Leu Ala Leu Leu Leu Gly Ala Leu Gly Leu Lys
            260                 265                 270
Ala Leu Leu Leu Gly Ile Leu Gly Ala Arg Ala Thr Arg Arg Arg
        275                 280                 285
Leu Asp His Leu Val Pro Gln Asp Thr Pro Pro Arg Ala Asp Gln Asp
    290                 295                 300
Thr Ser Pro Ile Trp Gly Ser Ala Glu Glu Ile Glu Asp Leu Lys Asp
305                 310                 315                 320
Leu His Lys Leu Gln Arg
                325

<210> SEQ ID NO 83
<211> LENGTH: 987
<212> TYPE: DNA
<213> ORGANISM: Homo sapiens

<400> SEQUENCE: 83
atggaaaagt ccatctggct gctggcctgc ttggcgtggg ttctccccgac aggctcattt      60
gtgagaacta aaatagatac tacggagaac ttgctcaaca cagaggtgca cagctcgcca     120
gcgcagcgct ggtccatgca ggtgccaccc gaggtgagcg cggaggcagg cgacgcggca     180
gtgctgccct gcaccttcac gcacccgcac cgccactacg acgggccgct gacggccatc     240
tggcgcgcgg gcgagcccta tgcgggcccg caggtgttcc gctgcgctgc ggcgcggggc     300
agcgagctct gccagacggc gctgagcctg cacggccgct tccggctgct gggcaacccg     360
cgccgcaacg acctctcgct gcgcgtcgag cgcctcgccc tggctgacga ccgccgctac     420
ttctgccgcg tcgagttcgc cggcgacgtc catgaccgct acgagagccg ccacggcgtc     480
cggctgcacg tgacagccgc gccgcggatc gtcaacatct cggtgctgcc cagtccggct     540
cacgccttcc gcgcgctctg cactgccgaa ggggagccgc cgcccgccct cgcctggtcc     600
ggcccggccc tgggcaacag cttggcagcc gtgcggagcc cgcgtgaggg tcacggccac     660
ctagtgaccg ccgaactgcc cgcactgacc catgacggcc gctacacgtg tacggccgcc     720
aacagcctgg gccgctccga ggccagcgtc tacctgttcc gcttccatgg cgccagcggg     780
gcctcgacgg tcgccctcct gctcggcgct ctcggcttca aggcgctgct gctgctcggg     840
gtcctggccg cccgcgctgc ccgccgccgc ccagagcatc tggacacccc ggacacccca     900
```

```
ccacggtccc aggcccagga gtccaattat gaaaatttga gccagatgaa cccccggagc    960
ccaccagcca ccatgtgctc accgtga                                        987
```

<210> SEQ ID NO 84
<211> LENGTH: 471
<212> TYPE: DNA
<213> ORGANISM: Homo sapiens

<400> SEQUENCE: 84

```
atgccggcgc tgctgcctgt ggcctcccgc cttttgttgc taccccgagt cttgctgacc     60
atggcctctg gaagccctcc gacccagccc tcgccggcct cggattccgg ctctggctac    120
gttccgggct cggtctctgc agcctttgtt acttgcccca acgagaaggt cgccaaggag    180
atcgccaggg ccgtggtgga gaagcgccta gcagcctgcg tcaacctcat ccctcagatt    240
acatccatct atgagtggaa agggaagatc gaggaagaca gtgaggtgct gatgatgatt    300
aaaacccaaa gttccttggt cccagctttg acagattttg ttcgttctgt gccccttac    360 gaagtggccg aggtaattgc attgcctgtg aacagggga actttccgta cctgcagtgg    420
gtgcgccagg tcacagagtc agtttctgac tctatcacag tcctgccatg a            471
```

<210> SEQ ID NO 85
<211> LENGTH: 437
<212> TYPE: DNA
<213> ORGANISM: Homo sapiens
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (177)..(177)
<223> OTHER INFORMATION: n is a, c, g, or t
<220> FEATURE:
<221> NAME/KEY: misc_feature
<222> LOCATION: (185)..(185)
<223> OTHER INFORMATION: n is a, c, g, or t
<220> FEATURE:
<221> NAME/KEY: misc_feature
<222> LOCATION: (319)..(319)
<223> OTHER INFORMATION: n is a, c, g, or t
<220> FEATURE:
<221> NAME/KEY: misc_feature
<222> LOCATION: (321)..(321)
<223> OTHER INFORMATION: n is a, c, g, or t
<220> FEATURE:
<221> NAME/KEY: misc_feature
<222> LOCATION: (350)..(350)
<223> OTHER INFORMATION: n is a, c, g, or t
<220> FEATURE:
<221> NAME/KEY: misc_feature
<222> LOCATION: (386)..(386)
<223> OTHER INFORMATION: n is a, c, g, or t
<220> FEATURE:
<221> NAME/KEY: misc_feature
<222> LOCATION: (389)..(389)
<223> OTHER INFORMATION: n is a, c, g, or t

<400> SEQUENCE: 85

```
catgtgccaa catgcaggtt tgctcatatn tatactttg ccatgttggt gtgctgcacc     60
cattaactcg tcatttagca ttaggtatat ttcttaatgc tatccctccc ccctccctcc    120
accccacaac agtcccgcct ggtgtgtgat gttcccaaat tttttttttc tcatcancat    180
tatcnctaaa caacattgaa tgaaacaaca ttgaggatct gctatatttg aaaataaaaa    240
tataactaaa aataatacaa attttaaaaa tacagtgtaa caactattta catagaattt    300
acattgtatt aggtattgna ngtaatctag agttgattta aaggaggggn gtccaaactt    360
```

-continued

```
ttggcttccc tgggccacac tggaanaana attgtcttgg gctacccata aaatacacta      420
acaatagctg ataacga                                                    437
```

<210> SEQ ID NO 86
<211> LENGTH: 98
<212> TYPE: DNA
<213> ORGANISM: Homo sapiens

<400> SEQUENCE: 86

```
gctgatttac agagtttcct ccttataata ttcaaatgtc cattttcaat aacagcaaca      60
aactacaaag aaacaggaaa gtatggtcta ctcacaga                             98
```

ANTIBODIES THAT BIND POLYPEPTIDES INVOLVED IN THE PROCESS OF BONE REMODELING

This patent application is a divisional of U.S. Ser. No. 12/279,054 filed on Feb. 13, 2007, now U.S. Pat. No. 7,989,160, which is a national stage filing under 35 U.S.C. §371 of international application No. PCT/CA2007/000210 filed on Feb. 13, 2007 which claimed priority to U.S. provisional application No. 60/772,585 filed on Feb. 13, 2006 and U.S. provisional application No. 60/816,858 filed Jun. 28, 2006. The entire contents of each of these priority applications are incorporated herein by reference.

FIELD OF THE INVENTION

The present specification makes reference to a Sequence Listing (submitted electronically as a .txt file named "Sequence Listing.txt" on Jun. 2, 2011). The .txt file was generated on Aug. 28, 2008 and is 251 kb in size. The entire contents of the Sequence Listing are herein incorporated by reference.

This invention relates, in part, to unique and newly identified genetic polynucleotides involved in the process of bone remodeling; variants and derivatives of the polynucleotides and corresponding polypeptides, uses of the polynucleotides, polypeptides, variants and derivatives; methods and compositions for the amelioration of symptoms caused by bone remodeling disorders, including but not limited to osteoporosis, osteopenia, osteomalacia, hyperparathyroidism, hypothyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Tumer syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

In particular, this invention relates to polynucleotide expression profiles of active osteoclasts, the isolation and identification of polynucleotides, polypeptides, variants and derivatives involved in osteoclast activity, validation of the identified polynucleotides for their potential as therapeutic targets and use of the polynucleotides, polypeptides, variants and derivatives for the amelioration of disease states and research purposes, as well as in diagnosis of disease states or in the predisposition to develop same.

BACKGROUND OF THE INVENTION

Bone is a dynamic connective tissue comprised of functionally distinct cell populations required to support the structural, mechanical and biochemical integrity of bone and the human body's mineral homeostasis. The principal cell types involved include, osteoblasts responsible for bone formation and maintaining bone mass, and osteoclasts responsible for bone resorption. Osteoblasts and osteoclasts function in a dynamic process termed bone remodeling. The development and proliferation of these cells from their progenitors is governed by networks of growth factors and cytokines produced in the bone microenvironment as well as by systemic hormones. Bone remodeling is ongoing throughout the lifetime of the individual and is necessary for the maintenance of healthy bone tissue and mineral homeostasis. The process remains largely in equilibrium and is governed by a complex interplay of systemic hormones, peptides and downstream signalling pathway proteins, local transcription factors, cytokines, growth factors and matrix remodeling genes.

Any interference or imbalance arising in the bone remodeling process can produce skeletal disease, with the most common skeletal disorders characterized by a net decrease in bone mass. A primary cause of this reduction in bone mass is an increase in osteoclast number and/or activity. The most common of such disease, and perhaps the best known, is osteoporosis occurring particularly in women after the onset of menopause. In fact osteoporosis is the most significant underlying cause of skeletal fractures in late middle-aged and elderly women. While estrogen deficiency has been strongly implicated as a factor in postmenopausal osteoporosis, there is longstanding evidence that remodeling is a locally controlled process being that it takes place in discrete packets throughout the skeleton as first described by Frost over forty years ago (Frost H. M. 1964).

Since bone remodeling takes place in discrete packets, locally produced hormones and enzymes may be more important than systemic hormones for the initiation of bone resorption and the normal remodeling process. Such local control is mediated by osteoblasts and osteoclasts in the microenvironment in which they operate. For example, osteoclasts attach to the bone matrix and form a separate compartment between themselves and the bone surface delimited by a sealing zone formed by a ring of actin surrounding the ruffled border. Multiple small vesicles transport enzymes toward the bone matrix and internalize partially digested bone matrix. The microenvironment within the sealing zone is rich with the presence of lysosomal enzymes and is highly acidic compared to the normal physiological pH of the body. The ruffled border membrane also expresses RANK, the receptor for RANKL, and macrophage-colony stimulating factor (M-CSF) receptor, both of which are responsible for osteoclast differentiation, as well as the calcitonin receptor capable of rapidly inactivating the osteoclast (Baron, R. 2003).

In a complex pattern of inhibition and stimulation not yet fully understood, growth hormone, insulin-like growth factor-1, the sex steroids, thyroid hormone, calciotrophic hormones such as PTH and prostaglandin E2, various cytokines, such as interleukin-1 beta, interleukin-6, and tumour necrosis factor-alpha, and 1,25-dihydroxyvitamin D (calcitriol) act coordinately in the bone remodeling process (Jilka et al. 1992; Poli et al. 1994; Srivastava et al. 1998; de Vernejoul 1996).

Thus, it stands to reason that the unique local environments created by these specialized cells is due to the expression of either unique genetic sequences not expressed in other tissues and/or splice variants of polynucleotides and polypeptides expressed in other tissues. The isolation and identification of polynucleotides, polypeptides and their variants and derivatives specific to osteoclast activity will permit a clearer understanding of the remodeling process and offer tissue specific therapeutic targets for the treatment of disease states related to bone remodeling.

Many diseases linked to bone remodeling are poorly understood, generally untreatable or treatable only to a limited extent. For example, osteoarthritis is difficult to treat as there is no cure and treatment focuses on relieving pain and preventing the affected joint from becoming deformed. Non-steroidal anti-inflammatory drugs (NSAIDs) are generally used to relieve pain.

Another example is osteoporosis where the only current medications approved by the FDA for use in the United States are the anti-resorptive agents that prevent bone breakdown. Estrogen replacement therapy is one example of an anti-resorptive agent. Others include alendronate (Fosamax—a biphosphonate anti-resorptive), risedronate (Actonel—a bisphosphonate anti-resorptive), raloxifene (Evista—selective estrogen receptor modulator (SERM)), calcitonin (Calcimar—a hormone), and parathyroid hormone/teriparatide (Forteo—a synthetic version of the human hormone, parathyroid hormone, which helps to regulate calcium metabolism).

Bisphosphonates such as alendronate and risedronate bind permanently to the surface of bone and interfere with osteoclast activity. This allows the osteoblasts to outpace the rate of resorption. The most common side effects are nausea, abdominal pain and loose bowel movements. However, alendronate is reported to also cause irritation and inflammation of the esophagus, and in some cases, ulcers of the esophagus. Risedronate is chemically different from alendronate and has less likelihood of causing esophagus irritation. However, certain foods, calcium, iron supplements, vitamins and minerals, or antacids containing calcium, magnesium, or aluminum can reduce the absorption of risedronate, thereby resulting in loss of effectiveness.

The most common side effect of Raloxifen and other SERMS (such as Tamoxifen) are hot flashes. However, Raloxifene and other hormone replacement therapies have been shown to increase the risk of blood clots, including deep vein thrombosis and pulmonary embolism, cardiovascular disease and cancer.

Calcitonin is not as effective in increasing bone density and strengthening bone as estrogen and the other anti-resorptive agents. Common side effects of either injected or nasal spray calcitonin are nausea and flushing. Patients can develop nasal irritations, a runny nose, or nosebleeds. Injectable calcitonin can cause local skin redness at the site of injection, skin rash, and flushing.

A situation demonstrative of the link between several disorders or disease states involving bone remodeling is that of the use of etidronate (Didronel) first approved by the FDA to treat Paget's disease. Paget's disease is a bone disease characterized by a disorderly and accelerated remodeling of the bone, leading to bone weakness and pain. Didronel has been used 'off-label' and in some studies shown to increase bone density in postmenopausal women with established osteoporosis. It has also been found effective in preventing bone loss in patients requiring long-term steroid medications (such as Prednisone or Cortisone). However, high dose or continuous use of Didronel can cause another bone disease called osteomalacia. Like osteoporosis, osteomalacia can lead to weak bones with increased risk of fractures. Because of osteomalacia concerns and lack of enough studies yet regarding reduction in the rate of bone fractures, the United States FDA has not approved Didronel for the treatment of osteoporosis.

Osteoporosis therapy has been largely focused on antiresorptive drugs that reduce the rate of bone loss but emerging therapies show promise in increasing bone mineral density instead of merely maintaining it or slowing its deterioration. The osteoporosis early stage pipeline consists largely of drug candidates in new therapeutic classes, in particular cathepsin K inhibitors, osteoprotegerin and calcilytics as well as novel bisphosphonates. Some of these are examples where novel drugs exploiting genomics programs are being developed based on a deeper understanding of bone biology and have the potential to change the face of treatment of bone disorders in the long term.

There thus remains a need to better understand the bone remodeling process and to provide new compositions that are useful for the diagnosis, prognosis, treatment, prevention and evaluation of therapies for bone remodeling and associated disorders. A method for analysing polynucleotide expression patterns has been developed and applied to identify polynucleotides, polypeptides, variants and derivatives specifically involved in bone remodeling.

The present invention seeks to meet these and other needs.

The present description refers to a number of documents, the content of which is herein incorporated by reference in their entirety.

SUMMARY OF THE INVENTION

The present invention relates to polynucleotides comprising sequences involved in the process of bone remodeling, the open reading frame of such sequences, substantially identical sequences (e.g., variants (e.g., allelic variant), non human orthologs), substantially complementary sequences and fragments of any one of the above thereof.

The present invention relates to polypeptide comprising sequences involved in the process of bone remodeling including biologically active analogs and biologically active fragments thereof. The present invention also relates to compositions that are useful for the diagnosis, prognosis, treatment, prevention and/or evaluation of therapies for bone remodeling and associated disorders.

In addition, the present invention relates to a method for analyzing polynucleotide expression patterns, and applied in the identification of polynucleotides, polypeptides, variants and derivatives specifically involved in bone remodeling.

The present invention relates to polynucleotide expression profiles of osteoclasts, the isolation and identification of polynucleotides, their corresponding polypeptides, variants and derivatives involved in osteoclast activity, validation of these identified elements for their potential as therapeutic targets and use of said polynucleotides, polypeptides, variants and derivatives for the amelioration of disease states.

It is an object of the present invention to provide polynucleotides and/or related polypeptides that have been isolated and identified. More specifically, the invention provides (isolated or substantially purified) polynucleotides comprising or consisting of any one of SEQ. ID. NOs:1 to 33, SEQ ID NO.:85 or SEQ ID NO.:86 their coding sequence (open reading frame) substantially identical sequence (e.g., variants, orthologs (e.g., SEQ ID NO.:35)), substantially complementary sequences and related polypeptides comprising any one of SEQ ID NO.: 48-80 and polypeptides encoded by SEQ ID NO.:85 or SEQ ID NO.:86 which have been shown to be upregulated in a highly specific fashion in osteoclasts. The present invention also relates to polypeptide analogs, variants (e.g., SEQ ID NO.:81) and fragments thereof.

NSEQ refers generally to polynucleotide sequences of the present invention and includes for example, SEQ. ID. NOs:1 to 33, SEQ ID NO.:85 or SEQ ID NO.:86 whereas PSEQ refers generally to polypeptide sequences of the present invention and includes, for example, SEQ ID NO.:48 to 82 and polypeptides encoded by SEQ ID NO.:85 or SEQ ID NO.:86. Of course it will be understood that NSEQ also encompasses polynucleotide sequences which are designed or derived from SEQ. ID. NOs:1 to 33 SEQ ID NO.:85 or SEQ ID NO.:86 for example, their coding sequence, complementary sequences. Non-limiting examples of such sequences are disclosed herein (e.g. SEQ ID Nos 42-45).

As used herein the term "NSEQ" refers generally to polynucleotides sequences comprising or consisting of any one of SEQ. ID. NOs:1 to 33, 85 or 86 (e.g., an isolated form) or comprising or consisting of a fragment of any one of SEQ. ID.

NOs:1 to 33, 85 or 86. The term "NSEQ" more particularly refers to a polynucleotide sequence comprising or consisting of a transcribed portion of any one of SEQ. ID. NOs:1 to 33, 85 or 86, which may be, for example, free of untranslated or untranslatable portion(s) (i.e., a coding portion of any one of SEQ ID Nos.: 1 to 33, 85 or 86). The term "NSEQ" additionally refers to a sequence substantially identical to any one of the above and more particularly substantially identical to polynucleotide sequence comprising or consisting of a transcribed portion of any one of SEQ. ID. Nos1 to 33, 85 or 86, which may be, for example, free of untranslated or untranslatable portion(s). The term "NSEQ" additionally refers to a polynucleotide sequence region of any one of SEQ. ID. NOs:1 to 33, 85 or 86 which encodes or is able to encode a polypeptide. The term "NSEQ" also refers to a polynucleotide sequence able of encoding any one of the polypeptides described herein or a polypeptide fragment of any one of the above. Finally, the term "NSEQ" also comprise a sequence substantially complementary to any one of the above.

The term "inhibitory NSEQ" generally refers to a sequence substantially complementary to any one of SEQ. ID. Nos: 1 to 33, 85 or 86, substantially complementary to a fragment of any one of SEQ. ID. Nos: 1 to 33, 85 or 86, substantially complementary to a sequence substantially identical to SEQ. ID. NOs:1 to 33, 85 or 86 and more particularly, substantially complementary to a transcribed portion of any one of SEQ. ID. NOs:1 to 33, 85 or 86 (e.g., which may be free of unstranslated or untranslatable portion) and which may have attenuating or even inhibitory action against the transcription of a mRNA or against expression of a polypeptide encoded by a corresponding SEQ ID NOs.:1 to 33, 85 or 86. Suitable "inhibitory NSEQ" may have for example and without limitation from about 10 to about 30 nucleotides, from about 10 to about 25 nucleotides or from about 15 to about 20 nucleotides. As used herein the term "nucleotide" means deoxyribonucleotide or ribonucleotide. In an exemplary embodiment, the use of nucleotide analogues is also encompassed in the present invention.

The present invention relates in one aspect thereof to an isolated polynucleotide sequence having at least from about 80% to about 100% (e.g., 80%, 90%, 95%, etc.) sequence identity to a polynucleotide sequence selected from the group consisting of polynucleotides comprising (a) any one of a SEQ. ID. NOs:1 to 33 or SEQ ID NO.:85 or SEQ ID NO.:86; (b) an open reading frame of (a); (c) a full complement of (a) or (b), and; (d) a fragment of any one of (a) to (c).

As used herein the term "unstranscribable region" may include for example, a promoter region (or portion thereof), silencer region, enhancer region etc. of a polynucleotide sequence.

As used herein the term "unstranslatable region" may include for example, an initiator portion of a polynucleotide sequence (upstream of an initiator codon, e.g., AUG), intronic regions, stop codon and/or region downstream of a stop codon (including polyA tail, etc.).

Complements of the isolated polynucleotide sequence encompassed by the present invention may be those, for example, which hybridize under high stringency conditions to any of the nucleotide sequences in (a), or (b). The high stringency conditions may comprise, for example, a hybridization reaction at 65° C. in 5×SSC, 5×Denhardt's solution, 1% SDS, and 100 µg/ml denatured salmon sperm DNA.

In accordance with the present invention, the polynucleotide sequence may be used, for example, in the treatment of diseases or disorders involving bone remodeling.

Fragments of polynucleotides may be used, for example, as probes for determining the presence of the isolated polynucleotide (or its complement or fragments thereof) in a sample, cell, tissue, etc. for experimental purposes or for the purpose of diagnostic of a diseases or disorders involving bone remodeling.

The present invention also relates to a combination comprising a plurality of polynucleotides (substantially purified and/or isolated). The polynucleotides may be co-expressed with one or more genes known to be involved in bone remodeling. Furthermore, the plurality of polynucleotides may be selected, for example, from the group consisting of a polynucleotide comprising (a) any one of SEQ. ID. NOs:1 to 33, SEQ ID NO.:85 or SEQ ID NO.:86; (b) an open reading frame (a); (c) a polynucleotide sequence comprising or consisting of a transcribed portion of any one of SEQ. ID. NOs:1 to 33, 85 or 86, which may be, for example, free of untranslated or untranslatable portion(s) (d) a complementary sequence of any one of (a) to (c); (e) a sequence that hybridizes under high stringency conditions to any one of the nucleotide sequences of (a) to (d) and; (f) fragments of any one of (a) to (e).

The present invention further relates to a polynucleotide encoding any one of the polypeptides described herein. In accordance with the present invention, the polynucleotide (RNA, DNA, etc.) may encode a polypeptide which may be selected from the group consisting of any one of SEQ ID NO.:48 to 80, polypeptides encoded by SEQ ID NO.:85 or 86, analogs or fragments thereof (e.g., biologically active fragments, immunologically active fragments, etc.).

The present invention also relates to an isolated nucleic acid molecule comprising the polynucleotides of the present invention, operatively linked to a nucleotide sequence encoding a heterologous polypeptide thereby encoding a fusion polypeptide.

The invention further relates to a polypeptide encoded by a polynucleotide of SEQ. ID. NOs:1 to 33, SEQ ID NO.:85 or SEQ ID NO.:86 or more particularly from the open reading frame of any one of SEQ. ID. NOs:1 to 33, SEQ ID NO.:85 or SEQ ID NO.:86, or a portion thereof. The invention also comprise the product of a gene that is co-expressed with one or more genes known to be involved in bone remodeling.

Isolated naturally occurring allelic variant are also encompassed by the present invention as well as synthetic variants (e.g., made by recombinant DNA technology or by chemical synthesis, etc.) such as biologically active variant which may comprise one or more amino acid substitutions (compared to a naturally occurring polypeptide), such as conservative or non conservative amino acid substitution.

The present invention, further provides a vector (mammalian, bacterial, viral, etc.) comprising the polynucleotides described herein or fragments thereof, such as an expression vector. The vector may further comprise a nucleic acid sequence which may help in the regulation of expression of the polynucleotide and/or a nucleotide sequence encoding a tag (e.g., affinity tag; HA, GST, H is etc.).

In accordance with the present invention, an expression vector may comprise, for example, the following operatively linked elements:
  a) a transcription promoter;
  b) a polynucleotide segment (which may comprise an open reading frame of any one of SEQ ID NOs.:1-33, 85 or 86); and
  c) a transcription terminator.

The invention also relates to an expression vector comprising a polynucleotide described herein, a host cell transformed with the expression vector and a method for producing a polypeptide of the present invention.

The invention further relates to a vector comprising a polynucleotide or polynucleotide fragment. Vectors which may comprise a sequence substantially complementary to the polynucleotides of the present invention (e.g., siRNA, shRNA) are thus encompassed by the present invention. The vector may comprise sequences enabling transcription of the polynucleotide or polynucleotide fragment.

More particularly, the present invention therefore provides a cell which may be genetically engineered to contain and/or to express the polynucleotide (including complements and fragments) and/or polypeptides of the present invention. The cell may be, for example, a mammalian cell, an insect cell, a bacteria cell, etc.

The present invention, therefore provides a host cell which may comprise a vector as described herein. The cell may be, for example, a mammalian cell, an insect cell, a bacteria, etc. The cell may be able to express or expresses a polypeptide encoded by the polynucleotide described herein.

Methods of producing the polypeptides of the present invention encompassed herewith includes for example, culturing the cell in conditions allowing the transcription of a gene or expression of the polypeptide. The polypeptide may be recovered, for example, from cell lysate or from the cell supernatant.

The invention relates to the use of at least one polynucleotide comprising any one of SEQ. ID. NOs:1 to 33, SEQ ID NO.:85 or SEQ ID NO.:86 their coding sequence, substantially identical sequences, substantially complementary sequences or fragments thereof on an array. The array may be used in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder. Of course, the use of a polynucleotide of the present invention in a diagnosis method is not dependent exclusively by way of a specific assay. The sequence or sequences may be used in conventionally used diagnosis methods known in the art.

The present invention also relates to a method of ameliorating bone remodeling disease or disorder symptoms, or for inhibiting or delaying bone disease or disorder, the method may comprise: contacting a compound capable of specifically inhibiting activity or expression of a polynucleotide sequence described herein or a polypeptide described herein, in osteoclasts so that symptoms of the bone remodeling disease or disorder may be ameliorated, or the disease or disorder may be prevented, delayed or lowered.

The present invention further relates to a method for ameliorating bone remodeling disease or disorder symptoms, or for inhibiting or delaying bone disease or disorder, the method may comprise: contacting a compound capable of specifically promoting activity or expression of a polynucleotide sequence described herein or a polypeptide described herein, in osteoclasts so that symptoms of the bone remodeling disease or disorder may be ameliorated, or the disease or disorder may be prevented, delayed or lowered.

The present invention also relates to a method of treating a condition in a mammal characterized by a deficiency in, or need for, bone growth or replacement and/or an undesirable level of bone resorption, which method may comprise administering to a mammalian subject in need of such treatment an effective amount of a suitable compound described herein.

The present invention further relates to a method of using a polynucleotide sequence described herein, a polypeptide described herein on an array and for the use of the array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample may indicate the presence of a bone remodeling disease or disorder.

In accordance with the present invention, the polynucleotide sequence described herein may be used for somatic cell gene therapy or for stem cell gene therapy.

The invention also relates to a pharmaceutical composition comprising a polynucleotide described herein or a polypeptide encoded by the selected polynucleotide or portion thereof and a suitable pharmaceutical carrier.

Additionally, the invention relates to products, compositions, processes and methods that comprises a polynucleotide described herein, a polypeptide encoded by the polynucleotides, a portion thereof, their variants or derivatives, for research, biological, clinical and therapeutic purposes.

The NSEQs and PSEQs may be used in diagnosis, prognosis, treatment, prevention, and selection and evaluation of therapies for diseases and disorders involving bone remodeling including, but not limited to, osteoporosis, osteopenia, osteomalacia, hyperparathyroidism, hyperthyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes.

Use of NSEQ as a Screening Tool

The polynucleotides obtained by the present invention may be used to detect and isolate expression products, for example, mRNA, complementary DNAs (cDNAs) and proteins derived from or homologous to the NSEQs. In one embodiment, the expression of mRNAs homologous to the NSEQs of the present invention may be detected, for example, by hybridization analysis, reverse transcription and in vitro nucleic acid amplification methods. Such procedures permit detection of mRNAs in a variety of tissue types or at different stages of development. The subject nucleic acids which are expressed in a tissue-specific or a developmental-stage-specific manner are useful as tissue-specific markers or for defining the developmental stage of a sample of cells or tissues that may define a particular disease state. One of skill in the art may readily adapt the NSEQs for these purposes.

Those skilled in the art will also recognize that the NSEQs, and its expression products such as cDNA nucleic acids and genomic DNA may be used to prepare short oligonucleotides sequences. For example, oligonucleotides having ten to twelve nucleotides or more may be prepared which hybridize specifically to the present NSEQs and cDNAs and allow detection, identification and isolation of unique nucleic sequences by hybridization. Sequences of for example, at least 15-20 nucleotides may be used and selected from regions that lack homology to other known sequences. Sequences of 20 or more nucleotides that lack such homology show an increased specificity toward the target sequence. Useful hybridization conditions for probes and primers are readily determinable by those of skill in the art. Stringent hybridization conditions encompassed herewith are those that may allow hybridization of nucleic acids that are greater than 90% homologous but which may prevent hybridization of nucleic acids that are less than 70% homologous. The specificity of a probe may be determined by whether it is made from a unique region, a regulatory region, or from a conserved motif. Both probe specificity and the stringency of diagnostic hybridization or amplification (maximal, high, intermediate, or low) reactions may be determined whether the probe identifies exactly complementary sequences, allelic variants, or related sequences. Probes designed to detect related sequences may have at least 50% sequence identity to any of the selected polynucleotides.

It is to be understood herein that the NSEQs (substantially identical sequences and fragments thereof) may hybridize to a substantially complementary sequence found in a test sample. Additionally, a sequence substantially complementary to NSEQ may bind a NSEQ found in a test sample.

Furthermore, a probe may be labelled by any procedure known in the art, for example by incorporation of nucleotides linked to a "reporter molecule". A "reporter molecule", as used herein, may be a molecule that provides an analytically identifiable signal allowing detection of a hybridized probe. Detection may be either qualitative or quantitative. Commonly used reporter molecules include fluorophores, enzymes, biotin, chemiluminescent molecules, bioluminescent molecules, digoxigenin, avidin, streptavidin or radioisotopes. Commonly used enzymes include horseradish peroxidase, alkaline phosphatase, glucose oxidase and β-galactosidase, among others. Enzymes may be conjugated to avidin or streptavidin for use with a biotinylated probe. Similarly, probes may be conjugated to avidin or streptavidin for use with a biotinylated enzyme. Incorporation of a reporter molecule into a DNA probe may be by any method known to the skilled artisan, for example by nick translation, primer extension, random oligo priming, by 3' or 5' end labeling or by other means. In addition, hybridization probes include the cloning of nucleic acid sequences into vectors for the production of mRNA probes. Such vectors are known in the art, are commercially available, and may be used to synthesize RNA probes in vitro. The labelled polynucleotide sequences may be used in Southern or northern analysis, dot blot, or other membrane-based technologies; in PCR technologies; and in micro arrays utilizing samples from subjects to detect altered expression. Oligonucleotides useful as probes for screening of samples by hybridization assays or as primers for amplification may be packaged into kits. Such kits may contain the probes or primers in a pre-measured or pre-determined amount, as well as other suitably packaged reagents and materials needed for the particular hybridization or amplification protocol. In another embodiment, the invention entails a substantially purified polypeptide encoded by the polynucleotides of NSEQs, polypeptide analogs or polypeptide fragments thereof. The polypeptides whether in a premature, mature or fused form, may be isolated from lysed cells, or from the culture medium, and purified to the extent needed for the intended use. One of skill in the art may readily purify these proteins, polypeptides and peptides by any available procedure. For example, purification may be accomplished by salt fractionation, size exclusion chromatography, ion exchange chromatography, reverse phase chromatography, affinity chromatography and the like.

Use of NSEQ for Development of an Expression System

In order to express a biologically active polypeptide, NSEQ, or derivatives thereof, may be inserted into an expression vector, i.e., a vector that contains the elements for transcriptional and translational control of the inserted coding sequence in a particular host. These elements may include regulatory sequences, such as enhancers, constitutive and inducible promoters, and 5' and 3' un-translated regions. Methods that are well known to those skilled in the art may be used to construct such expression vectors. These methods include in vitro recombinant DNA techniques, synthetic techniques, and in vivo genetic recombination.

A variety of expression vector/host cell systems known to those of skill in the art may be utilized to express NSEQ. These include, but are not limited to, microorganisms such as bacteria transformed with recombinant bacteriophage, plasmid, or cosmid DNA expression vectors; yeast transformed with yeast expression vectors; insect cell systems infected with baculovirus vectors; plant cell systems transformed with viral or bacterial expression vectors; or animal cell systems. For long-term production of recombinant proteins in mammalian systems, stable expression in cell lines may be effected. For example, NSEQ may be transformed into cell lines using expression vectors that may contain viral origins of replication and/or endogenous expression elements and a selectable or visible marker gene on the same or on a separate vector. The invention is not to be limited by the vector or host cell employed.

In general, host cells that contain NSEQ and that express a polypeptide encoded by the NSEQ, or a portion thereof, may be identified by a variety of procedures known to those of skill in the art. These procedures include, but are not limited to, DNA-DNA or DNA-RNA hybridizations, PCR amplification, and protein bioassay or immunoassay techniques that include membrane, solution, or chip based technologies for the detection and/or quantification of nucleic acid or amino acid sequences. Immunological methods for detecting and measuring the expression of polypeptides using either specific polyclonal or monoclonal antibodies are known in the art. Examples of such techniques include enzyme-linked immunosorbent assays (ELISAs), radioimmunoassays (RIAs), and fluorescence activated cell sorting (FACS). Those of skill in the art may readily adapt these methodologies to the present invention.

The present invention additionally relates to a bioassay for evaluating compounds as potential antagonists of the polypeptide described herein, the bioassay may comprise:

a) culturing test cells in culture medium containing increasing concentrations of at least one compound whose ability to inhibit the action of a polypeptide described herein is sought to be determined, wherein the test cells may contain a polynucleotide sequence described herein (for example, in a form having improved trans-activation transcription activity, relative to wild-type polynucleotide, and comprising a response element operatively linked to a reporter gene); and thereafter b) monitoring in the cells the level of expression of the product of the reporter gene as a function of the concentration of the potential antagonist compound in the culture medium, thereby indicating the ability of the potential antagonist compound to inhibit activation of the polypeptide encoded by, the polynucleotide sequence described herein.

The present invention further relates to a bioassay for evaluating compounds as potential agonists for a polypeptide encoded by the polynucleotide sequence described herein, the bioassay may comprise:

a) culturing test cells in culture medium containing increasing concentrations of at least one compound whose ability to promote the action of the polypeptide encoded by the polynucleotide sequence described herein is sought to be determined, wherein the test cells may contain a polynucleotide sequence described herein (for example, in a form having improved trans-activation transcription activity, relative to wild-type polynucleotide, and comprising a response element operatively linked to a reporter gene); and thereafter b) monitoring in the cells the level of expression of the product of the reporter gene as a function of the concentration of the potential agonist compound in the culture medium, thereby indicating the ability of the potential agonist compound to promote activation of a polypeptide encoded by the polynucleotide sequence described herein.

Host cells transformed with NSEQ may be cultured under conditions for the expression and recovery of the polypeptide from cell culture. The polypeptide produced by a transgenic cell may be secreted or retained intracellularly depending on the sequence and/or the vector used. As will be understood by those of skill in the art, expression vectors containing NSEQ may be designed to contain signal sequences that direct secretion of the polypeptide through a prokaryotic or eukaryotic cell membrane. Due to the inherent degeneracy of the genetic code, other DNA sequences that encode substantially the same or a functionally equivalent amino acid sequence may be produced and used to express the polypeptide encoded by NSEQ. The nucleotide sequences of the present invention may be engineered using methods generally known in the art in order to alter the nucleotide sequences for a variety of purposes including, but not limited to, modification of the cloning, processing, and/or expression of the gene product. DNA shuffling by random fragmentation and PCR reassembly of gene fragments and synthetic oligonucleotides may be used to engineer the nucleotide sequences. For example, oligonucleotide-mediated site-directed mutagenesis may be used to introduce mutations that create new restriction sites, alter glycosylation patterns, change codon preference, produce splice variants, and so forth.

In addition, a host cell strain may be chosen for its ability to modulate expression of the inserted sequences or to process the expressed polypeptide in the desired fashion. Such modifications of the polypeptide include, but are not limited to, acetylation, carboxylation, glycosylation, phosphorylation, lipidation, and acylation. Post-translational processing, which cleaves a "prepro" form of the polypeptide, may also be used to specify protein targeting, folding, and/or activity. Different host cells that have specific cellular machinery and characteristic mechanisms for post-translational activities (e.g., CHO, HeLa, MDCK, HEK293, and W138) are available commercially and from the American Type Culture Collection (ATCC) and may be chosen to ensure the correct modification and processing of the expressed polypeptide.

Those of skill in the art will readily appreciate that natural, modified, or recombinant nucleic acid sequences may be ligated to a heterologous sequence resulting in translation of a fusion polypeptide containing heterologous polypeptide moieties in any of the aforementioned host systems. Such heterologous polypeptide moieties may facilitate purification of fusion polypeptides using commercially available affinity matrices. Such moieties include, but are not limited to, glutathione S-transferase (GST), maltose binding protein, thioredoxin, calmodulin binding peptide, 6-His (His), FLAG, c-myc, hemaglutinin (HA), and monoclonal antibody epitopes.

In yet a further aspect, the present invention relates to an isolated polynucleotide which may comprise a nucleotide sequence encoding a fusion protein, the fusion protein may comprise a fusion partner fused to a peptide fragment of a protein encoded by, or a naturally occurring allelic variant polypeptide encoded by, the polynucleotide sequence described herein.

Those of skill in the art will also readily recognize that the nucleic acid and polypeptide sequences may be synthesized, in whole or in part, using chemical or enzymatic methods well known in the art. For example, peptide synthesis may be performed using various solid-phase techniques and machines such as the ABI 431A Peptide synthesizer (PE Biosystems) may be used to automate synthesis. If desired, the amino acid sequence may be altered during synthesis and/or combined with sequences from other proteins to produce a variant protein.

Use of NSEQ as a Diagnostic Screening Tool

The skilled artisan will readily recognize that NSEQ may be used for diagnostic purposes to determine the absence, presence, or altered expression (i.e. increased or decreased compared to normal) of the gene. The polynucleotides may be at least 10 nucleotides long or at least 12 nucleotides long, or at least 15 nucleotides long up to any desired length and may comprise complementary RNA and DNA molecules, branched nucleic acids, and/or peptide nucleic acids (PNAs). In one alternative, the polynucleotides may be used to detect and quantify gene expression in samples in which expression of NSEQ is correlated with disease. In another alternative, NSEQ may be used to detect genetic polymorphisms associated with a disease. These polymorphisms may be detected in the transcript cDNA.

The invention provides for the use of at least one polynucleotide comprising NSEQ (e.g., an open reading frame of NSEQ, a substantially complementary sequence, a substantially identical sequence, and fragments thereof) on an array and for the use of that array in a method for diagnosing a bone remodeling disease or disorder by hybridizing the array with a patient sample under conditions to allow complex formation, detecting complex formation, and comparing the amount of complex formation in the patient sample to that of standards for normal and diseased tissues wherein the complex formation in the patient sample indicates the presence of a bone remodeling disease or disorder.

In another embodiment, the present invention provides one or more compartmentalized kits for detection of bone resorption disease states. A first kit may have a receptacle containing at least one isolated probe. Such a probe may be a nucleic acid fragment which is present/absent in the genomic DNA of normal cells but which is absent/present in the genomic DNA of affected cells. Such a probe may be specific for a DNA site that is normally active/inactive but which may be inactive/active in certain cell types. Similarly, such a probe may be specific for a DNA site that may be abnormally expressed in certain cell types. Finally, such a probe may identify a specific DNA mutation. By specific for a DNA site is meant that the probe may be capable of hybridizing to the DNA sequence which is mutated, or may be capable of hybridizing to DNA sequences adjacent to the mutated DNA sequences. The probes provided in the present kits may have a covalently attached reporter molecule. Probes and reporter molecules may be readily prepared as described above by those of skill in the art.

Use of NSEQ as a Therapeutic

One of skill in the art will readily appreciate that the expression systems and assays discussed above may also be used to evaluate the efficacy of a particular therapeutic treatment regimen, in animal studies, in clinical trials, or to monitor the treatment of an individual subject. Once the presence of disease is established and a treatment protocol is initiated, hybridization or amplification assays may be repeated on a regular basis to determine if the level of expression in the patient begins to approximate the level observed in a healthy subject. The results obtained from successive assays may be used to show the efficacy of treatment over a period ranging from several days to many years.

In yet another aspect of the invention, an NSEQ, a portion thereof, or its complement, may be used therapeutically for the purpose of expressing mRNA and polypeptide, or conversely to block transcription or translation of the mRNA. Expression vectors may be constructed using elements from retroviruses, adenoviruses, herpes or vaccinia viruses, or bacterial plasmids, and the like. These vectors may be used for delivery of nucleotide sequences to a particular target organ, tissue, or cell population. Methods well known to those skilled in the art may be used to construct vectors to express nucleic acid sequences or their complements.

Alternatively, NSEQ, a portion thereof, or its complement, may be used for somatic cell or stem cell gene therapy. Vectors may be introduced in vivo, in vitro, and ex vivo. For ex vivo therapy, vectors are introduced into stem cells taken from the subject, and the resulting transgenic cells are clonally propagated for autologous transplant back into that same subject. Delivery of NSEQ by transfection, liposome injections, or polycationic amino polymers may be achieved using methods that are well known in the art. Additionally, endogenous NSEQ expression may be inactivated using homologous recombination methods that insert an inactive gene sequence into the coding region or other targeted region of NSEQ.

Depending on the specific goal to be achieved, vectors containing NSEQ may be introduced into a cell or tissue to express a missing polypeptide or to replace a non-functional polypeptide. Of course, when one wishes to express PSEQ in a cell or tissue, one may use a NSEQ able to encode such PSEQ for that purpose or may directly administer PSEQ to that cell or tissue.

On the other hand, when one wishes to attenuate or inhibit the expression of PSEQ, one may use a NSEQ (e.g., an inhibitory NSEQ) which is substantially complementary to at least a portion of a NSEQ able to encode such PSEQ.

The expression of an inhibitory NSEQ may be done by cloning the inhibitory NSEQ into a vector and introducing the vector into a cell to down-regulate the expression of a polypeptide encoded by the target NSEQ.

Vectors containing NSEQ (e.g., including inhibitory NSEQ) may be transformed into a cell or tissue to express a missing polypeptide or to replace a non-functional polypeptide. Similarly a vector constructed to express the complement of NSEQ may be transformed into a cell to down-regulate the over-expression of a polypeptide encoded by the polynucleotides of NSEQ, or a portion thereof. Complementary or anti-sense sequences may consist of an oligonucleotide derived from the transcription initiation site; nucleotides between about positions −10 and +10 from the ATG are preferred. Similarly, inhibition may be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee et al. 1994)

Ribozymes, enzymatic RNA molecules, may also be used to catalyze the cleavage of mRNA and decrease the levels of particular mRNAs, such as those comprising the polynucleotide sequences of the invention. Ribozymes may cleave mRNA at specific cleavage sites. Alternatively, ribozymes may cleave mRNAs at locations dictated by flanking regions that form complementary base pairs with the target mRNA. The construction and production of ribozymes is well known in the art.

RNA molecules may be modified to increase intracellular stability and half-life. Possible modifications include, but are not limited to, the addition of flanking sequences at the 5' and/or 3' ends of the molecule, or the use of phosphorothioate or 2' O-methyl rather than phosphodiester linkages within the backbone of the molecule. Alternatively, nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases, may be included.

In addition to the active ingredients, a pharmaceutical composition may contain pharmaceutically acceptable carriers comprising excipients and auxiliaries that facilitate processing of the active compounds into preparations that may be used pharmaceutically.

For any compound, the therapeutically effective dose may be estimated initially either in cell culture assays or in animal models such as mice, rats, rabbits, dogs, or pigs. An animal model may also be used to determine the concentration range and route of administration. Such information may then be used to determine useful doses and routes for administration in humans. These techniques are well known to one skilled in the art and a therapeutically effective dose refers to that amount of active ingredient that ameliorates the symptoms or condition. Therapeutic efficacy and toxicity may be determined by standard pharmaceutical procedures in cell cultures or with experimental animals, such as by calculating and contrasting the $ED_{50}$ (the dose therapeutically effective in 50% of the population) and $LD_{50}$ (the dose lethal to 50% of the population) statistics. Any of the therapeutic compositions described above may be applied to any subject in need of such therapy, including, but not limited to mammals such as dogs, cats, cows, horses, rabbits, monkeys, and most preferably, humans.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

The term "Treatment" for purposes of this disclosure refers to both therapeutic treatment and prophylactic or preventative measures, wherein the object is to prevent or slow down (lessen) the targeted pathologic condition or disorder. Those in need of treatment include those already with the disorder as well as those prone to have the disorder or those in whom the disorder is to be prevented.

Use of NSEQ in General Research

The invention finally provides products, compositions, processes and methods that utilize an NSEQ, their open reading frame, or a polypeptide encoded by the polynucleotides of NSEQ or their open reading frame, or a portion thereof, their variants, analogs, derivatives and fragments for research, biological, clinical and therapeutic purposes. For example, to identify splice variants, mutations, and polymorphisms NSEQ may be extended utilizing a partial nucleotide sequence and employing various PCR-based methods known in the art to detect upstream sequences such as promoters and other regulatory elements. Additionally, one may use an XL-PCR kit (PE Biosystems, Foster City Calif.), nested primers, and commercially available cDNA libraries (Life Technologies, Rockville Md.) or genomic libraries (Clontech, Palo Alto Calif.) to extend the sequence.

The polynucleotides may also be used as targets in a micro-array. The micro-array may be used to monitor the expression patterns of large numbers of genes simultaneously and to identify splice variants, mutations, and polymorphisms. Information derived from analyses of the expression patterns may be used to determine gene function, to understand the genetic basis of a disease, to diagnose a disease, and to develop and monitor the activities of therapeutic agents used to treat a disease. Microarrays may also be used to detect genetic diversity, single nucleotide polymorphisms which may characterize a particular population, at the genomic level.

In yet another embodiment, polynucleotides may be used to generate hybridization probes useful in mapping the naturally occurring genomic sequence. Fluorescent in situ hybridization (FISH) may be correlated with other physical chromosome mapping techniques and genetic map data.

The present invention more particularly relates in one aspect thereof to a method of representatively identifying an endogenously differentially expressed sequence involved in osteoclast differentiation. The sequence may be, for example, differentially expressed in a differentiated osteoclast cell compared to an undifferentiated osteoclast precursor cell.

The method of the present invention may comprise;
a) separately providing total messenger RNA from (mature or intermediately) differentiated human osteoclast cell and undifferentiated human osteoclast precursor cell, the total messenger RNA may comprise, for example, at least one endogenously differentially expressed sequence,
b) generating single-stranded cDNA from each messenger RNA of differentiated human osteoclast cell and (e.g., randomly) tagging the 3'-end of the single-stranded cDNA with a RNA polymerase promoter sequence and a first sequence tag;
c) generating single-stranded cDNA from each messenger RNA of undifferentiated human osteoclast precursor cell and (e.g., randomly) tagging the 3'-end of the single-stranded cDNA with a RNA polymerase promoter sequence and a second sequence tag;
d) separately generating partially or completely double-stranded 5'-tagged-DNA from each of b) and c), the double-stranded 5'-tagged-DNA may thus comprise in a 5' to 3' direction, a double-stranded RNA polymerase promoter, a first or second sequence tag and an endogenously expressed sequence,
e) separately linearly amplifying a first and second tagged sense RNA from each of d) with a RNA polymerase enzyme (which may be selected based on the promoter used for tagging),
f) generating single-stranded complementary first or second tagged DNA from one of e),
g) hybridizing the single-stranded complementary first or second tagged DNA of f) with the other linearly amplified sense RNA of e),
h) recovering unhybridized RNA with the help of the first or second sequence tag (for example by PCR or hybridization), and;
i) identifying (determining) the nucleotide sequence of unhybridized RNA.

Steps b) and/or c), may comprise generating a single copy of a single-stranded cDNA.

The method may further comprise the step of comparatively determining the presence of the identified endogenously and differentially expressed sequence in a differentiated osteoclast cell relative to an undifferentiated osteoclast precursor cell.

A sequence which is substantially absent (e.g., totally absent or present in very low quantity) from one of differentiated osteoclast cell or an undifferentiated osteoclast precursor cell and present in the other of differentiated osteoclast cell or an undifferentiated osteoclast precursor cell may therefore be selected.

The sequence thus selected may be a positive regulator of osteoclast differentiation and therefore may represent an attractive target which may advantageously be used to promote bone resorption or alternatively such target may be inhibited to lower or prevent bone resorption.

Alternatively, the sequence selected using the above method may be a negative regulator of osteoclast differentiation and may therefore represent an attractive target which may advantageously be induced (e.g., at the level of transcription, translation, activity etc.) or provided to a cell to lower or prevent bone resorption. Also such negative regulator may, upon its inhibition, serve as a target to promote bone resorption.

In accordance with the present invention, the sequence may be further selected based on a reduced or substantially absent expression in other normal tissue, therefore representing a candidate sequence specifically involved in osteoclast differentiation and bone remodeling.

The method may also further comprise a step of determining the complete sequence of the nucleotide sequence and may also comprise determining the coding sequence of the nucleotide sequence.

The present invention also relates in a further aspect, to the isolated endogenously and differentially expressed sequence (polynucleotide and polypeptide) identified by the method of the present invention.

More particularly, the present invention encompasses a polynucleotide which may comprise the identified polynucleotide sequence, a polynucleotide which may comprise the open reading frame of the identified polynucleotide sequence, a polynucleotide which may comprise a nucleotide sequence substantially identical to the polynucleotide identified by the method of the present invention, a polynucleotide which may comprise a nucleotide sequence substantially complementary to the polynucleotide identified by the method of the present invention, fragments and splice variant thereof, provided that the sequence does not consist in or comprise SEQ ID NO.:34.

In accordance with the present invention, the isolated endogenously and differentially expressed sequence of the present invention may be a complete or partial RNA molecule.

Isolated DNA molecule able to be transcribed into the RNA molecule of the present invention are also encompassed herewith as well as vectors (including expression vectors) comprising the such DNA or RNA molecule.

The present invention also relates to libraries comprising at least one isolated endogenously and differentially expressed sequence identified herein (e.g., partial or complete RNA or DNA, substantially identical sequences or substantially complementary sequences (e.g., probes) and fragments thereof (e.g., oligonucleotides)).

In accordance with the present invention, the isolated endogenously and differentially expressed sequence may be selected, for example, from the group consisting of a polynucleotide which may consist in or comprise;
a) any one of SEQ ID NO.:1 to 33, SEQ ID NO.:85 or SEQ ID NO.:86,
b) the open reading frame of any one of SEQ ID NO.:1 to 33, SEQ ID NO.:85 or SEQ ID NO.:86, c) a polynucleotide which may comprise a nucleotide sequence substantially identical to a) or b), and;
d) a polynucleotide which may comprise a nucleotide sequence substantially complementary to any one of a) to c),
e) fragments of any one of a) to d).

In a further aspect the present invention relates to a polypeptide which may be encoded by the isolated endogenously and differentially expressed sequence of the present invention.

In yet a further aspect the present invention relates to a polynucleotide able to encode a polypeptide of the present invention. Due to the degeneracy of the genetic code, it is to be understood herein that a multiplicity of polynucleotide sequence may encode the same polypeptide sequence and thus are encompassed by the present invention.

Exemplary polypeptides may comprise a sequence selected from the group consisting of any one of SEQ ID NO.: 48 to 80, a polypeptide encoded by SEQ ID NO.:85 or SEQ ID NO.:86.

The present invention also relates to an isolated non-human ortholog polynucleotide sequence (involved in bone remodeling), the open reading frame of the non-human ortholog, substantially identical sequences, substantially complementary sequences, fragments and splice variants thereof.

The present invention as well relates to an isolated polypeptide encoded by the non-human ortholog polynucleotide as well as biologically active analogs and biologically active fragments thereof.

Exemplary embodiments of non-human (e.g., mouse) ortholog polynucleotides encompassed herewith include, for example, SEQ ID NO.:35.

Exemplary embodiments of isolated polypeptide encoded by some non-human orthologs identified herein include for example, a polypeptide such as SEQ ID NO.:82.

The present invention also more particularly relates, in an additional aspect thereof, to an isolated polynucleotide which may be differentially expressed in differentiated osteoclast cell compared to undifferentiated human osteoclast precursor cell.

The isolated polynucleotide may comprise a member selected from the group consisting of;
a) a polynucleotide which may comprise any one of SEQ ID NO.:1 to SEQ ID NO.33, SEQ ID NO.:85 or SEQ ID NO.:86
b) a polynucleotide which may comprise the open reading frame of any one of SEQ ID NO.:1 to SEQ ID NO.33, SEQ ID NO.:85 or SEQ ID NO.:86;
c) a polynucleotide which may comprise a transcribed or transcribable portion of any one of SEQ. ID. NOs:1 to SEQ ID NO.33, SEQ ID NO.:85 or SEQ ID NO.:86, which may be, for example, free of untranslated or untranslatable portion(s);
d) a polynucleotide which may comprise a translated or translatable portion of any one of SEQ. ID. NOs:1 to SEQ ID NO.33, SEQ ID NO.:85 or SEQ ID NO.:86 (e.g., coding portion),
e) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a), b) c) or d),
f) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c) or d) and;
g) a fragment of any one of a) to f)
h) including polynucleotides which consist in the above.

Exemplary polynucleotides fragments of those listed above comprises polynucleotides of at least 10 nucleic acids which may be substantially complementary to the nucleic acid sequence of any one of SEQ ID NO.: 1 to 33, SEQ ID NO.:85 or SEQ ID NO.:86, for example, fragments selected from the group consisting of any one of SEQ ID NO.: 42-45.

The present invention also relates to an isolated polynucleotide involved in osteoclast differentiation, the isolated polynucleotide may be selected, for example, from the group consisting of;
a) a polynucleotide comprising any one of SEQ ID NO.: 1 to 33, SEQ ID NO.:85 or SEQ ID NO.:86,
b) a polynucleotide comprising the open reading frame of any one of SEQ ID NO.: 1 to 33, SEQ ID NO.:85 or SEQ ID NO.:86,
c) a polynucleotide which may comprise a transcribed or transcribable portion of any one of SEQ. ID. NOs:1 to SEQ ID NO.33, SEQ ID NO.:85 or SEQ ID NO.:86, which may be, for example, free of untranslated or untranslatable portion(s);
d) a polynucleotide which may comprise a translated or translatable portion of any one of SEQ. ID. NOs:1 to SEQ ID NO.33, SEQ ID NO.:85 or SEQ ID NO.:86 (e.g., coding portion),
e) a polynucleotide substantially identical to a), b), c) or d), and;
f) a sequence of at least 10 nucleic acids which may be substantially complementary to the nucleic acid sequence of any one of SEQ ID NO.:1 to 33, SEQ ID NO.:85 or SEQ ID NO.:86 or more particularly of a), b), c) or d).

In accordance with the present invention the isolated polynucleotide may be able to promote osteoclast differentiation (e.g., in a mammal or mammalian cell thereof), i.e, a positive regulator of osteoclast differentiation.

Further in accordance with the present invention, the isolated polynucleotide may be able to inhibit, prevent or lower osteoclast differentiation (e.g., in a mammal or mammalian cell thereof), i.e, a negative regulator of osteoclast differentiation.

In yet a further aspect, the present invention relates to an isolated polynucleotide which may be able to inhibit osteoclast differentiation (e.g., in a mammal or mammalian cell thereof). The polynucleotide may be selected, for example, from the group consisting of polynucleotides which may comprise a sequence of at least 10 nucleic acids which is complementary to the nucleic acid sequence of any one of NSEQ described herein.

Suitable polynucleotides include, for example, a polynucleotide having or comprising those which are selected from the group consisting of SEQ ID NO. 42 to 45.

Suitable polynucleotides may be those which may be able to inhibit osteoclast differentiation which has been induced by an inducer of osteoclast differentiation such as those listed herein.

In accordance with the present invention, the polynucleotide may be, for example, a RNA molecule, a DNA molecule, including those which are partial or complete, single-stranded or double-stranded, hybrids, etc.

The present invention also relates to a vector (e.g., an expression vector) comprising the polynucleotide of the present invention.

The present invention additionally relates in an aspect thereof to a library of polynucleotide sequences which may be differentially expressed in a differentiated osteoclast cell compared to an undifferentiated osteoclast precursor cell. The library may comprise, for example, at least one member selected from the group consisting of
  a) a polynucleotide which may comprise any one of SEQ ID NO.:1 to 33, SEQ ID NO.:85 or SEQ ID NO.:86,
  b) a polynucleotide which may comprise the open reading frame of any one of SEQ ID NO.:1 to 33, SEQ ID NO.:85 or SEQ ID NO.:86,
  c) a polynucleotide which may comprise a transcribed or transcribable portion of any one of SEQ. ID. NOs:1 to SEQ ID NO.33, SEQ ID NO.:85 or SEQ ID NO.:86, which may be, for example, free of untranslated or untranslatable portion(s);
  d) a polynucleotide which may comprise a translated or translatable portion of any one of SEQ. ID. NOs:1 to SEQ ID NO.33, SEQ ID NO.:85 or SEQ ID NO.:86 (e.g., coding portion),
  e) a polynucleotide which may comprise a sequence substantially identical (e.g., from about 50 to 100%, or about 60 to 100% or about 70 to 100% or about 80 to 100% or about 85, 90, 95 to 100% identical over the entire sequence or portion of sequences) to a), b), c) or d);
  f) a polynucleotide which may comprise a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c) or d) and;
  g) a fragment of any one of a) to d).

The present invention also relates to an expression library which may comprise a library of polynucleotides described herein. In accordance with the present invention, each of the polynucleotide may be contained within an expression vector.

Arrays and kits comprising a library of polynucleotide sequences (comprising at least one polynucleotide such as complementary sequences) of the present invention are also encompassed herewith.

The present invention also provides in an additional aspect, a pharmaceutical composition for inhibiting osteoclast differentiation (bone resorption and bone resorption related diseases or disorders), the pharmaceutical composition may comprise, for example;
  a) an isolated polynucleotide as defined herein (e.g., able to inhibit osteoclast differentiation) and;
  b) a pharmaceutically acceptable carrier.

The present invention also provides in yet an additional aspect, a method for inhibiting osteoclast differentiation (e.g., for inhibiting bone resorption or for ameliorating bone resorption) in a mammal (individual) in need thereof (or in a mammalian cell), the method may comprise administering an isolated polynucleotide (e.g., able to inhibit osteoclast differentiation) or a suitable pharmaceutical composition comprising such suitable polynucleotide.

In accordance with the present invention, the mammal in need may suffer, for example and without limitation, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In a further aspect, the present invention relates to the use of an isolated polynucleotide (e.g., able to inhibit osteoclast differentiation) for the preparation of a medicament for the treatment of a bone resorption disease.

The present invention in another aspect thereof, provides a pharmaceutical composition for promoting osteoclast differentiation in a mammal in need thereof. The pharmaceutical composition may comprise, for example;
  a. an isolated polynucleotide (e.g., able to promote osteoclast differentiation) and;
  b. a pharmaceutically acceptable carrier.

The present invention also further provides a method for promoting osteoclast differentiation in a mammal in need thereof (or in a mammalian cell), the method may comprise, for example, administering an isolated polynucleotide (e.g., able to promote osteoclast differentiation) or a suitable pharmaceutical composition as described above.

The present invention additionally relates to the use of an isolated polynucleotide (e.g., able to promote osteoclast differentiation) for the preparation of a medicament for the treatment of a disease associated with insufficient bone resorption (e.g., hyperostosis) or excessive bone growth.

The present invention also relates to the use of at least one polynucleotide which may be selected from the group consisting of;
  a) a polynucleotide comprising any one of SEQ ID NO.:1 to 33, SEQ ID NO.:85 or SEQ ID NO.:86,
  b) a polynucleotide comprising the open reading frame of any one of SEQ ID NO.:1 to 33, SEQ ID NO.:85 or SEQ ID NO.:86,
  c) a polynucleotide which may comprise a transcribed or transcribable portion of any one of SEQ. ID. NOs:1 to SEQ ID NO.33, SEQ ID NO.:85 or SEQ ID NO.:86, which may be, for example, free of untranslated or untranslatable portion(s);
  d) a polynucleotide which may comprise a translated or translatable portion of any one of SEQ. ID. NOs:1 to SEQ ID NO.33, SEQ ID NO.:85 or SEQ ID NO.:86 (e.g., coding portion),
  e) a polynucleotide comprising a sequence substantially identical (e.g., from about 50 to 100%, or about 60 to 100% or about 70 to 100% or about 80 to 100% or about 85, 90, 95 to 100% identical over the entire sequence or portion of sequences) to a), b), c) or d);
  f) a polynucleotide comprising a sequence substantially complementary (e.g., from about 50 to 100%, or about 60 to 100% or about 70 to 100% or about 80 to 100% or about 85, 90, 95 to 100% complementarity over the entire sequence or portion of sequences) to a), b), c) or d);
  g) a fragment of any one of a) to f) and;
  h) a library comprising any one of a) to g)
in the diagnosis of a condition related to bone remodeling (a bone disease).

Also encompassed by the present invention are kits for the diagnosis of a condition related to bone remodeling. The kit may comprise a polynucleotide as described herein.

The present invention also provides in an additional aspect, an isolated polypeptide (polypeptide sequence) involved in osteoclast differentiation (in a mammal or a mammalian cell thereof). The polypeptide may comprise (or consist in) a sequence selected from the group consisting of;
 a) any one of SEQ ID NO.: 48 to 80,
 b) a polypeptide able to be encoded and/or encoded by any one of SEQ ID NO.:1 to 33, SEQ ID NO.:85 or SEQ ID NO.:86 (their coding portion)
 c) a biologically active fragment of any one of a) or b),
 d) a biologically active analog of any one of a) or b).

In accordance with the present invention, the biologically active analog may comprise, for example, at least one amino acid substitution (conservative or non conservative) compared to the original sequence. In accordance with the present invention, the analog may comprise, for example, at least one amino acid substitution, deletion or insertion in its amino acid sequence.

The substitution may be conservative or non-conservative. The polypeptide analog may be a biologically active analog or an immunogenic analog which may comprise, for example, at least one amino acid substitution (conservative or non conservative), for example, 1 to 5, 1 to 10, 1 to 15, 1 to 20, 1 to 50 etc. (including any number there between) compared to the original sequence. An immunogenic analog may comprise, for example, at least one amino acid substitution compared to the original sequence and may still be bound by an antibody specific for the original sequence.

In accordance with the present invention, a polypeptide fragment may comprise, for example, at least 6 consecutive amino acids, at least 8 consecutive amino acids or more of an amino acid sequence described herein.

In yet a further aspect, the present invention provides a pharmaceutical composition which may comprise, for example a polypeptide as described herein and a pharmaceutically acceptable carrier.

Methods for modulating osteoclast differentiation in a mammal in need thereof (or in a mammalian cell) are also provided by the present invention, which methods may comprise administering an isolated polypeptide (e.g., able to promote osteoclast differentiation) or suitable pharmaceutical composition described herein.

In additional aspects, the present invention relates to the use of an isolated polypeptide (e.g., able to promote osteoclast differentiation) for the preparation of a medicament for the treatment of a disease associated with insufficient bone resorption.

Methods for ameliorating bone resorption in an individual in need thereof are also encompassed herewith, which method may comprise, for example, administering an isolated polypeptide (e.g., able to inhibit osteoclast differentiation) or suitable pharmaceutical compositions which may comprise such polypeptide.

In accordance with the present invention, the mammal may suffer, for example, from a condition selected from the group consisting of osteoporosis, osteopenia, osteomalacia, hyperparathyroidism, hyperthyroidism, hypogonadism, thyrotoxicosis, systemic mastocytosis, adult hypophosphatasia, hyperadrenocorticism, osteogenesis imperfecta, Paget's disease, Cushing's disease/syndrome, Turner syndrome, Gaucher disease, Ehlers-Danlos syndrome, Marfan's syndrome, Menkes' syndrome, Fanconi's syndrome, multiple myeloma, hypercalcemia, hypocalcemia, arthritides, periodontal disease, rickets (including vitamin D dependent, type I and II, and x-linked hypophosphatemic rickets), fibrogenesis imperfecta ossium, osteosclerotic disorders such as pycnodysostosis and damage caused by macrophage-mediated inflammatory processes, etc.

In yet a further aspect, the present invention relates to the use of a polypeptide able to inhibit osteoclast differentiation in the preparation of a medicament for the treatment of a bone resorption disease in an individual in need thereof.

The present invention also relates to a compound and the use of a compound able to inhibit (e.g., in an osteoclast precursor cell) the activity or expression of a polypeptide which may be selected, for example, from the group consisting of SEQ ID NO.: 48 to 80 or a polypeptide encoded by SEQ ID NO.:85 or SEQ ID NO.:86, in the preparation of a medicament for the treatment of a bone disease in an individual in need thereof.

In yet an additional aspect, the present invention relates to a method of diagnosing a condition related to a bone resorption disorder or disease in an individual in need thereof. The method may comprise, for example, quantifying a polynucleotide described herein, such as, for example, polynucleotide selected from the group consisting of those comprising or consisting of (a) SEQ ID NO.:1 to 33, SEQ ID NO.:85 or SEQ ID NO.:86, (b) a polynucleotide which may comprise the open reading frame of SEQ ID NO.: 1 to 33, SEQ ID NO.:85 or SEQ ID NO.:86, (c) a polynucleotide which may comprise a transcribed or transcribable portion of any one of SEQ. ID. NOs:1 to SEQ ID NO.33, SEQ ID NO.:85 or SEQ ID NO.:86 (d) a polynucleotide which may comprise a translated or translatable portion of any one of SEQ. ID. NOs:1 to SEQ ID NO.33, SEQ ID NO.:85 or SEQ ID NO.:86; (e) substantially identical sequences of any one of (a) to (d); (f) substantially complementary sequences of any one of (a) to (e), or a polypeptide sequence which may be selected, for example, from the group consisting of SEQ ID NO.: 48 to 80 or a polypeptide encoded by SEQ ID NO.:85 or SEQ ID NO.:86, and analogs thereof in a sample from the individual compared to a standard or normal value.

The present invention also relates to an assay and method for identifying a gene and/or protein involved in bone remodeling. The assay and method may comprise silencing an endogenous gene of an osteoclast cell and providing the cell with a candidate gene (or protein). A candidate gene (or protein) positively involved in bone remodeling may be identified by its ability to complement the silenced endogenous gene. For example, a candidate gene involved in osteoclast differentiation provided to a cell for which an endogenous gene has been silenced, may enable the cell to differentiate in the presence of an inducer such as, for example, RANKL.

The present invention further relates to a cell expressing an exogenous form of any one of the polypeptide (including variants, analogs etc.) or polynucleotide of the present invention (including substantially identical sequences, substantially complementary sequences, fragments, variants, orthologs, etc).

In accordance with the present invention, the cell may be for example, a bone cell. Also in accordance with the present invention, the cell may be an osteoclast (at any level of differentiation).

As used herein the term "exogenous form" is to be understood herein as a form which is not naturally expressed by the cell in question.

In a further aspect, the present invention relates to an antibody (e.g., isolated antibody), or antigen-binding fragment thereof, that may specifically bind to a protein or polypeptide described herein. The antibody may be, for example, a monoclonal antibody, a polyclonal antibody an antibody generated using recombinant DNA technologies. The antibody may originate for example, from a mouse, rat or any other mammal.

The antibody may also be a human antibody which may be obtained, for example, from a transgenic non-human mammal capable of expressing human Ig genes. The antibody may also be a humanised antibody which may comprise, for example, one or more complementarity determining regions of non-human origin. It may also comprise a surface residue of a human antibody and/or framework regions of a human antibody. The antibody may also be a chimeric antibody which may comprise, for example, variable domains of a non-human antibody and constant domains of a human antibody.

Suitable antibodies may also include, for example, an antigen-binding fragment, an Fab fragment; an F(ab')$_2$ fragment, and Fv fragment; or a single-chain antibody comprising an antigen-binding fragment (e.g., a single chain Fv).

The antibody of the present invention may be mutated and selected based on an increased affinity and/or specificity for one of a polypeptide described herein and/or based on a reduced immunogenicity in a desired host.

The antibody may further comprise a detectable label attached thereto.

The present invention further relates to a method of producing antibodies able to bind to one of a polypeptide, polypeptide fragments, or polypeptide analogs described herein, the method may comprise:
  a) immunizing a mammal (e.g., mouse, a transgenic mammal capable of producing human Ig, etc.) with a suitable amount of a PSEQ described herein including, for example, a polypeptide fragment comprising at least 6 consecutive amino acids of a PSEQ;
  b) collecting the serum from the mammal, and
  c) isolating the polypeptide-specific antibodies from the serum of the mammal.

The method may further comprise the step of administering a second dose to the animal.

The present invention also relates to a method of producing a hybridoma which secretes an antibody that binds to a polypeptide described herein, the method may comprise:
  a) immunizing a mammal (e.g., mouse, a transgenic mammal capable of producing human Ig, etc.) with a suitable amount of a PSEQ thereof;
  b) obtaining lymphoid cells from the immunized animal obtained from (a);
  c) fusing the lymphoid cells with an immortalizing cell to produce hybrid cells; and
  d) selecting hybrid cells which produce antibody that specifically binds to a PSEQ thereof.

The present invention further relates to a method of producing an antibody that binds to one of the polypeptide described herein, the method may comprise:
  a) synthesizing a library of antibodies (antigen binding fragment) on phage or ribosomes;
  b) panning the library against a sample by bringing the phage or ribosomes into contact with a composition comprising a polypeptide or polypeptide fragment described herein;
  c) isolating phage which binds to the polypeptide or polypeptide fragment, and;
  d) obtaining an antibody from the phage or ribosomes.

The antibody of the present invention may thus be obtained, for example, from a library (e.g., bacteriophage library) which may be prepared, for example, by
  a) extracting cells which are responsible for production of antibodies from a host mammal;
  b) isolating RNA from the cells of (a);
  c) reverse transcribing mRNA to produce cDNA;
  d) amplifying the cDNA using a (antibody-specific) primer; and
  e) inserting the cDNA of (d) into a phage display vector or ribosome display cassette such that antibodies are expressed on the phage or ribosomes.

The host animal may be immunized with polypeptide and/or a polypeptide fragment and/or analog described herein to induce an immune response prior to extracting the cells which are responsible for production of antibodies.

The present invention also relates to a kit for specifically assaying a polypeptide described herein, the kit may comprise, for example, an antibody or antibody fragment capable of binding specifically to the polypeptide described herein.

The present invention further contemplates antibodies that may bind to PSEQ. Suitable antibodies may bind to unique antigenic regions or epitopes in the polypeptides, or a portion thereof. Epitopes and antigenic regions useful for generating antibodies may be found within the proteins, polypeptides or peptides by procedures available to one of skill in the art. For example, short, unique peptide sequences may be identified in the proteins and polypeptides that have little or no homology to known amino acid sequences. Preferably the region of a protein selected to act as a peptide epitope or antigen is not entirely hydrophobic; hydrophilic regions are preferred because those regions likely constitute surface epitopes rather than internal regions of the proteins and polypeptides. These surface epitopes are more readily detected in samples tested for the presence of the proteins and polypeptides. Such antibodies may include, but are not limited to, polyclonal, monoclonal, chimeric, and single chain antibodies, Fab fragments, and fragments produced by a Fab expression library. The production of antibodies is well known to one of skill in the art.

Peptides may be made by any procedure known to one of skill in the art, for example, by using in vitro translation or chemical synthesis procedures. Short peptides which provide an antigenic epitope but which by themselves are too small to induce an immune response may be conjugated to a suitable carrier. Suitable carriers and methods of linkage are well known in the art. Suitable carriers are typically large macromolecules such as proteins, polysaccharides and polymeric amino acids. Examples include serum albumins, keyhole limpet hemocyanin, ovalbumin, polylysine and the like. One of skill in the art may use available procedures and coupling reagents to link the desired peptide epitope to such a carrier. For example, coupling reagents may be used to form disulfide linkages or thioether linkages from the carrier to the peptide of interest. If the peptide lacks a disulfide group, one may be provided by the addition of a cysteine residue. Alternatively, coupling may be accomplished by activation of carboxyl groups.

The minimum size of peptides useful for obtaining antigen specific antibodies may vary widely. The minimum size must be sufficient to provide an antigenic epitope that is specific to the protein or polypeptide. The maximum size is not critical unless it is desired to obtain antibodies to one particular epitope. For example, a large polypeptide may comprise multiple epitopes, one epitope being particularly useful and a second epitope being immunodominant. Typically, antigenic peptides selected from the present proteins and polypeptides will range from 5 to about 100 amino acids in length. More typically, however, such an antigenic peptide will be a maximum of about 50 amino acids in length, and preferably a maximum of about 30 amino acids. It is usually desirable to select a sequence of about 6, 8, 10, 12 or 15 amino acids, up to about 20 or 25 amino acids.

Amino acid sequences comprising useful epitopes may be identified in a number of ways. For example, preparing a series of short peptides that taken together span the entire protein sequence may be used to screen the entire protein sequence. One of skill in the art may routinely test a few large polypeptides for the presence of an epitope showing a desired reactivity and also test progressively smaller and overlapping fragments to identify a preferred epitope with the desired specificity and reactivity.

Antigenic polypeptides and peptides are useful for the production of monoclonal and polyclonal antibodies. Antibodies to a polypeptide encoded by the polynucleotides of NSEQ, polypeptide analogs or portions thereof, may be generated using methods that are well known in the art. Such antibodies may include, but are not limited to, polyclonal, monoclonal, chimeric, and single chain antibodies, Fab fragments, and fragments produced by a Fab expression library. Neutralizing antibodies, such as those that inhibit dimer formation, are especially preferred for therapeutic use. Monoclonal antibodies may be prepared using any technique that provides for the production of antibody molecules by continuous cell lines in culture. These include, but are not limited to, the hybridoma, the human B-cell hybridoma, and the EBV-hybridoma techniques. In addition, techniques developed for the production of chimeric antibodies may be used. Alternatively, techniques described for the production of single chain antibodies may be employed. Fabs that may contain specific binding sites for a polypeptide encoded by the polynucleotides of NSEQ, or a portion thereof, may also be generated. Various immunoassays may be used to identify antibodies having the desired specificity. Numerous protocols for competitive binding or immunoradiometric assays using either polyclonal or monoclonal antibodies with established specificities are well known in the art.

To obtain polyclonal antibodies, a selected animal may be immunized with a protein or polypeptide. Serum from the animal may be collected and treated according to known procedures. Polyclonal antibodies to the protein or polypeptide of interest may then be purified by affinity chromatography. Techniques for producing polyclonal antisera are well known in the art.

Monoclonal antibodies (MAbs) may be made by one of several procedures available to one of skill in the art, for example, by fusing antibody producing cells with immortalized cells and thereby making a hybridoma. The general methodology for fusion of antibody producing B cells to an immortal cell line is well within the province of one skilled in the art. Another example is the generation of MAbs from mRNA extracted from bone marrow and spleen cells of immunized animals using combinatorial antibody library technology.

One drawback of MAbs derived from animals or from derived cell lines is that although they may be administered to a patient for diagnostic or therapeutic purposes, they are often recognized as foreign antigens by the immune system and are unsuitable for continued use. Antibodies that are not recognized as foreign antigens by the human immune system have greater potential for both diagnosis and treatment. Methods for generating human and humanized antibodies are now well known in the art.

Chimeric antibodies may be constructed in which regions of a non-human MAb are replaced by their human counterparts. A preferred chimeric antibody is one that has amino acid sequences that comprise one or more complementarity determining regions (CDRs) of a non-human Mab that binds to a polypeptide encoded by the polynucleotides of NSEQ, or a portion thereof, grafted to human framework (FW) regions. Methods for producing such antibodies are well known in the art. Amino acid residues corresponding to CDRs and FWs are known to one of average skill in the art.

A variety of methods have been developed to preserve or to enhance affinity for antigen of antibodies comprising grafted CDRs. One way is to include in the chimeric antibody the foreign framework residues that influence the conformation of the CDR regions. A second way is to graft the foreign CDRs onto human variable domains with the closest homology to the foreign variable region. Thus, grafting of one or more non-human CDRs onto a human antibody may also involve the substitution of amino acid residues which are adjacent to a particular CDR sequence or which are not contiguous with the CDR sequence but which are packed against the CDR in the overall antibody variable domain structure and which affect the conformation of the CDR. Humanized antibodies of the invention therefore include human antibodies which comprise one or more non-human CDRs as well as such antibodies in which additional substitutions or replacements have been made to preserve or enhance binding characteristics.

Chimeric antibodies of the invention also include antibodies that have been humanized by replacing surface-exposed residues to make the MAb appear human. Because the internal packing of amino acid residues in the vicinity of the antigen-binding site remains unchanged, affinity is preserved. Substitution of surface-exposed residues of a polypeptide encoded by the polynucleotides of NSEQ (or a portion thereof)-antibody according to the invention for the purpose of humanization does not mean substitution of CDR residues or adjacent residues that influence affinity for a polypeptide encoded by the polynucleotides of NSEQ, or a portion thereof.

Chimeric antibodies may also include antibodies where some or all non-human constant domains have been replaced with human counterparts. This approach has the advantage that the antigen-binding site remains unaffected. However, significant amounts of non-human sequences may be present where variable domains are derived entirely from non-human antibodies.

Antibodies of the invention include human antibodies (e.g., humanized) that are antibodies consisting essentially of human sequences. Human antibodies may be obtained from phage display libraries wherein combinations of human heavy and light chain variable domains are displayed on the surface of filamentous phage. Combinations of variable domains are typically displayed on filamentous phage in the form of Fab's or scFvs. The library may be screened for phage bearing combinations of variable domains having desired antigen-binding characteristics. Preferred variable domain combinations are characterized by high affinity for a polypeptide encoded by the polynucleotides of NSEQ, or a portion thereof. Preferred variable domain combinations may also be characterized by high specificity for a polypeptide encoded by the polynucleotides of NSEQ, or a portion thereof, and little cross-reactivity to other related antigens. By screening from very large repertoires of antibody fragments, (2–10× $10^{10}$) a good diversity of high affinity Mabs may be isolated, with many expected to have sub-nanomolar affinities for a polypeptide encoded by the polynucleotides of NSEQ, or a portion thereof.

Alternatively, human antibodies may be obtained from transgenic animals into which un-rearranged human Ig gene segments have been introduced and in which the endogenous mouse Ig genes have been inactivated. Preferred transgenic animals contain very large contiguous Ig gene fragments that are over 1 Mb in size but human polypeptide-specific Mabs of moderate affinity may be raised from transgenic animals containing smaller gene loci. Transgenic animals capable of expressing only human Ig genes may also be used to raise polyclonal antiserum comprising antibodies solely of human origin.

Antibodies of the invention may include those for which binding characteristics have been improved by direct mutation or by methods of affinity maturation. Affinity and specificity may be modified or improved by mutating CDRs and screening for antigen binding sites having the desired characteristics. CDRs may be mutated in a variety of ways. One way is to randomize individual residues or combinations of residues so that in a population of otherwise identical antigen binding sites, all twenty amino acids may be found at particular positions. Alternatively, mutations may be induced over a range of CDR residues by error prone PCR methods. Phage display vectors containing heavy and light chain variable region gene may be propagated in mutator strains of E. coli. These methods of mutagenesis are illustrative of the many methods known to one of skill in the art.

Antibodies of the invention may include complete anti-polypeptide antibodies as well as antibody fragments and derivatives that comprise a binding site for a polypeptide encoded by the polynucleotides of NSEQ, or a portion thereof. Derivatives are macromolecules that comprise a binding site linked to a functional domain. Functional domains may include, but are not limited to signalling domains, toxins, enzymes and cytokines.

The antibodies obtained by the means described herein may be useful for detecting proteins, variant and derivative polypeptides in specific tissues or in body fluids. Moreover, detection of aberrantly expressed proteins or protein fragments is probative of a disease state. For example, expression of the present polypeptides encoded by the polynucleotides of NSEQ, or a portion thereof, may indicate that the protein is being expressed at an inappropriate rate or at an inappropriate developmental stage. Hence, the present antibodies may be useful for detecting diseases associated with protein expression from NSEQs disclosed herein.

A variety of protocols for measuring polypeptides, including ELISAs, RIAs, and FACS, are well known in the art and provide a basis for diagnosing altered or abnormal levels of expression. Standard values for polypeptide expression are established by combining samples taken from healthy subjects, preferably human, with antibody to the polypeptide under conditions for complex formation. The amount of complex formation may be quantified by various methods, such as photometric means. Quantities of polypeptide expressed in disease samples may be compared with standard values. Deviation between standard and subject values may establish the parameters for diagnosing or monitoring disease.

Design of immunoassays is subject to a great deal of variation and a variety of these are known in the art. Immunoassays may use a monoclonal or polyclonal antibody reagent that is directed against one epitope of the antigen being assayed. Alternatively, a combination of monoclonal or polyclonal antibodies may be used which are directed against more than one epitope. Protocols may be based, for example, upon competition where one may use competitive drug screening assays in which neutralizing antibodies capable of binding a polypeptide encoded by the polynucleotides of NSEQ, or a portion thereof, specifically compete with a test compound for binding the polypeptide. Alternatively one may use, direct antigen-antibody reactions or sandwich type assays and protocols may, for example, make use of solid supports or immunoprecipitation. Furthermore, antibodies may be labelled with a reporter molecule for easy detection. Assays that amplify the signal from a bound reagent are also known. Examples include immunoassays that utilize avidin and biotin, or which utilize enzyme-labelled antibody or antigen conjugates, such as ELISA assays.

Kits suitable for immunodiagnosis and containing the appropriate labelled reagents include antibodies directed against the polypeptide protein epitopes or antigenic regions, packaged appropriately with the remaining reagents and materials required for the conduct of the assay, as well as a suitable set of assay instructions.

The present invention therefore provides a kit for specifically assaying a polypeptide described herein, the kit may comprise, for example, an antibody or antibody fragment capable of binding specifically to the polypeptide described herein.

In accordance with the present invention, the kit may be a diagnostic kit, which may comprise:
  a) one or more antibodies described herein; and
  b) a detection reagent which may comprise a reporter group.

In accordance with the present invention, the antibodies may be immobilized on a solid support. The detection reagent may comprise, for example, an anti-immunoglobulin, protein G, protein A or lectin etc. The reporter group may be selected, without limitation, from the group consisting of radioisotopes, fluorescent groups, luminescent groups, enzymes, biotin and dye particles.

In an additional aspect, the present invention provides a method for identifying an inhibitory compound (inhibitor, antagonist) which may be able to impair the function (activity) or expression of a polypeptide described herein, such as, for example, those which may be selected from the group consisting of SEQ ID NO.: 48 to 80 or a polypeptide encoded by SEQ ID NO.:85 or SEQ ID NO.:86, and analogs thereof. The method may comprise contacting the polypeptide or a cell expressing the polypeptide with a candidate compound and measuring the function (activity) or expression of the polypeptide. A reduction in the function or activity of the polypeptide (compared to the absence of the candidate compound) may positively identify a suitable inhibitory compound.

In accordance with the present invention, the impaired function or activity may be associated with a reduced ability of the polypeptide to promote osteoclast differentiation, such as osteoclast differentiation induced by an inducer described herein or known in the art.

In accordance with the present invention the cell may not naturally (endogenously) express (polypeptide may substantially be unexpressed in a cell) the polypeptide or analog or alternatively, the expression of a naturally expressed polypeptide analog may be repressed.

For example, suitable method of screening for an inhibitor of SEQ ID NO.:1, may comprise repressing the expression of the mouse ortholog SEQ ID NO.:35 in a mouse osteoclast cell and evaluating differentiation of the osteoclast cell comprising SEQ ID NO.:1 in the presence or absence of a candidate inhibitor and for example, an inducer of osteoclast differentiation (e.g., RANKL).

The present invention also provides a method for identifying an inhibitory compound (inhibitor, antagonist) able to impair the function (activity) or expression of a polypeptide such as, for example SEQ ID NO.: 1 or SEQ ID NO.:2. The method may comprise, for example, contacting the (isolated) polypeptide or a cell expressing the polypeptide with a candidate compound and measuring the function (activity) or expression of the polypeptide. A reduction in the function or activity of the polypeptide (compared to the absence of the candidate compound) may thus positively identify a suitable inhibitory compound.

In accordance with the present invention, the impaired function or activity may be associated, for example, with a reduced ability of the polypeptide to inhibit or promote osteoclast differentiation.

The cell used to carry the screening test may not naturally (endogenously) express the polypeptide or analogs, or alternatively the expression of a naturally expressed polypeptide analog may be repressed.

The present invention also relates to a method of identifying a positive or a negative regulator of osteoclast differentiation. The method may comprise, for example, performing a knockdown effect as described herein. The method may more particularly comprise a) providing an osteoclast cell with a compound (e.g., siRNA) able to specifically inhibit a target sequence (e.g., a polynucleotide or polypeptide as described herein), b) inducing differentiation (e.g., with an inducer such as, for example, RANKL) and c) determining the level of differentiation of the osteoclast cell (e.g., measuring the number of differentiated cells, their rate of differentiation, specific marker of differentiation etc).

Upon inhibition of a positive regulator, the levels of osteoclast differentiation will appear lowered. Upon inhibition of a negative regulator, the level of osteoclast differentiation will appear increased.

Another method of identifying a positive or a negative regulator of osteoclast differentiation is to a) provide a cell with one of a target sequence described herein (polypeptide or polynucleotide able to express a polypeptide) b) to induce differentiation (e.g., with an inducer such as, for example, RANKL) and c) to determine the level of differentiation of the osteoclast cell (e.g., measuring the number of differentiated cells, their rate of differentiation, specific marker of differentiation etc).

A cell provided with a positive regulator of osteoclast differentiation may have an increased level of differentiation. A cell provided with a negative regulator of osteoclast differentiation may have a decreased level of differentiation.

The present invention also provides a method of identifying a compound capable of interfering with osteoclast differentiation, the method may comprise contacting a cell including therein a non-endogenous polynucleotide sequence comprising any one of SEQ ID NO.:1 to 33, 85 or 86 (a coding portion) and quantifying (e.g. the number of) differentiated osteoclasts. A reduction in osteoclast differentiation in the presence of the compound in comparison to the absence of the compound may be indicative of an antagonist of osteoclast differentiation, while an increase in osteoclast differentiation in the presence of the compound in comparison to the absence of the compound may be indicative of an agonist of osteoclast differentiation.

In accordance with the present invention, the cell may also comprise an endogenous form of a polynucleotide.

As used herein the term "endogenous" means a substance that naturally originates from within an organism, tissue or cell. The term "endogenous polynucleotide" refers to a chromosomal form of a polynucleotide or RNA version (hnRNA, mRNA) produced by the chromosomal form of the polynucleotide. The term "endogenous polypeptide" refers to the form of the protein encoded by an "endogenous polynucleotide".

As used herein the term "non-endogenous" or "exogenous" is used in opposition to "endogenous" in that the substance is provided from an external source although it may be introduced within the cell. The term "non-endogenous polynucleotide" refers to a synthetic polynucleotide introduced within the cell and include for example and without limitation, a vector comprising a sequence of interest, a synthetic mRNA, an oligonucleotide comprising a NSEQ etc. The term "non-endogenous polypeptide" refers to the form of the protein encoded by an "non-endogenous polynucleotide".

The present invention also relate to a method of identifying a compound capable of interfering with osteoclast differentiation, the method may comprise contacting a cell including therein a non-endogenous polypeptide sequence comprising any one of SEQ ID NO.: 48 to 80 and quantifying (e.g. the number of) differentiated osteoclasts. A reduction in osteoclast differentiation in the presence of the compound in comparison to the absence of the compound may be indicative of an antagonist of osteoclast differentiation while an increase in osteoclast differentiation in the presence of the compound in comparison to the absence of the compound may be indicative of an agonist of osteoclast differentiation.

As used herein the term "sequence identity" relates to (consecutive) nucleotides of a nucleotide sequence which with reference to an original nucleotide sequence. The identity may be compared over a region or over the total sequence of a nucleic acid sequence.

Thus, "identity" may be compared, for example, over a region of 3, 4, 5, 10, 19, 20 nucleotides or more (and any number there between). It is to be understood herein that gaps of non-identical nucleotides may be found between identical nucleic acids. For example, a polynucleotide may have 100% identity with another polynucleotide over a portion thereof. However, when the entire sequence of both polynucleotides is compared, the two polynucleotides may have 50% of their overall (total) sequence identical to one another.

Polynucleotides of the present invention or portion thereof having from about 50 to about 100%, or about 60 to about 100% or about 70 to about 100% or about 80 to about 100% or about 85%, about 90%, about 95% to about 100% sequence identity with an original polynucleotide are encompassed herewith. It is known by those of skill in the art, that a polynucleotide having from about 50% to 100% identity may function (e.g., anneal to a substantially complementary sequence) in a manner similar to an original polynucleotide and therefore may be used in replacement of an original polynucleotide. For example a polynucleotide (a nucleic acid sequence) may comprise or have from about 50% to 100% identity with an original polynucleotide over a defined region and may still work as efficiently or sufficiently to achieve the present invention.

Percent identity may be determined, for example, with an algorithm GAP, BESTFIT, or FASTA in the Wisconsin Genetics Software Package Release 7.0, using default gap weights.

As used herein the terms "sequence complementarity" refers to (consecutive) nucleotides of a nucleotide sequence which are complementary to a reference (original) nucleotide sequence. The complementarity may be compared over a region or over the total sequence of a nucleic acid sequence.

Polynucleotides of the present invention or portion thereof having from about 50 to about 100%, or about 60 to about 100% or about 70 to about 100% or about 80 to about 100% or about 85%, about 90%, about 95% to about 100% sequence complementarity with an original polynucleotide are thus encompassed herewith. It is known by those of skill in the art, that an polynucleotide having from about 50% to 100% complementarity with an original sequence may anneal to that sequence in a manner sufficient to carry out the present invention (e.g., inhibit expression of the original polynucleotide).

An "analogue" is to be understood herein as a molecule having a biological activity and chemical structure similar to that of a polypeptide described herein. An "analogue" may have sequence similarity with that of an original sequence or a portion of an original sequence and may also have a modification of its structure as discussed herein. For example, an "analogue" may have at least 90% sequence similarity with an original sequence or a portion of an original sequence. An "analogue" may also have, for example; at least 70% or even 50% sequence similarity (or less, i.e., at least 40%) with an original sequence or a portion of an original sequence.

Also, an "analogue" with reference to a polypeptide may have, for example, at least 50% sequence similarity to an original sequence with a combination of one or more modification in a backbone or side-chain of an amino acid, or an addition of a group or another molecule, etc.

"Polynucleotide" generally refers to any polyribonucleotide or polydeoxyribonucleotide, which may be unmodified RNA or DNA, or modified RNA or DNA. "Polynucleotides" include, without limitation single- and double-stranded DNA, DNA that is a mixture of single- and double-stranded regions, single- and double-stranded RNA, and RNA that is a mixture of single- and double-stranded regions, hybrid molecules comprising DNA and RNA that may be single-stranded or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications may be made to DNA and RNA; thus "polynucleotide" embraces chemically, enzymatically or metabolically modified forms of polynucleotides as typically found in nature, as well as the chemical forms of DNA and RNA characteristic of viruses and cells. "Polynucleotide" includes but is not limited to linear and end-closed molecules. "Polynucleotide" also embraces relatively short polynucleotides, often referred to as oligonucleotides.

"Polypeptides" refers to any peptide or protein comprising two or more amino acids joined to each other by peptide bonds or modified peptide bonds (i.e., peptide isosteres). "Polypeptide" refers to both short chains, commonly referred as peptides, oligopeptides or oligomers, and to longer chains generally referred to as proteins. As described above, polypeptides may contain amino acids other than the 20 gene-encoded amino acids.

As used herein the term "polypeptide analog" relates to mutants, variants, chimeras, fusions, deletions, additions and any other type of modifications made relative to a given polypeptide.

As used herein the term "biologically active" refers to a variant or fragment which retains some or all of the biological activity of the natural polypeptide, i.e., to be able to promote or inhibit osteoclast differentiation. Polypeptides or fragments of the present invention may also include "immunologically active" polypeptides or fragments. "Immunologically active polypeptides or fragments may be useful for immunization purposes (e.g. in the generation of antibodies).

Thus, biologically active polypeptides in the form of the original polypeptides, fragments (modified or not), analogues (modified or not), derivatives (modified or not), homologues, (modified or not) of the polypeptides described herein are encompassed by the present invention.

Therefore, any polypeptide having a modification compared to an original polypeptide which does not destroy significantly a desired biological activity is encompassed herein. It is well known in the art, that a number of modifications may be made to the polypeptides of the present invention without deleteriously affecting their biological activity. These modifications may, on the other hand, keep or increase the biological activity of the original polypeptide or may optimize one or more of the particularity (e.g. stability, bioavailability, etc.) of the polypeptides of the present invention which, in some instance might be desirable. Polypeptides of the present invention may comprise for example, those containing amino acid sequences modified either by natural processes, such as posttranslational processing, or by chemical modification techniques which are known in the art. Modifications may occur anywhere in a polypeptide including the polypeptide backbone, the amino acid side-chains and the amino- or carboxy-terminus. It will be appreciated that the same type of modification may be present in the same or varying degrees at several sites in a given polypeptide. Also, a given polypeptide may contain many types of modifications. It is to be understood herein that more than one modification to the polypeptides described herein are encompassed by the present invention to the extent that the biological activity is similar to the original (parent) polypeptide.

As discussed above, polypeptide modification may comprise, for example, amino acid insertion (i.e., addition), deletion and substitution (i.e., replacement), either conservative or non-conservative (e.g., D-amino acids, desamino acids) in the polypeptide sequence where such changes do not substantially alter the overall biological activity of the polypeptide.

Example of substitutions may be those, which are conservative (i.e., wherein a residue is replaced by another of the same general type or group) or when wanted, non-conservative (i.e., wherein a residue is replaced by an amino acid of another type). In addition, a non-naturally occurring amino acid may substitute for a naturally occurring amino acid (i.e., non-naturally occurring conservative amino acid substitution or a non-naturally occurring non-conservative amino acid substitution).

As is understood, naturally occurring amino acids may be sub-classified as acidic, basic, neutral and polar, or neutral and non-polar. Furthermore, three of the encoded amino acids are aromatic. It may be of use that encoded polypeptides differing from the determined polypeptide of the present invention contain substituted codons for amino acids, which are from the same type or group as that of the amino acid to be replaced. Thus, in some cases, the basic amino acids Lys, Arg and His may be interchangeable; the acidic amino acids Asp and Glu may be interchangeable; the neutral polar amino acids Ser, Thr, Cys, Gln, and Asn may be interchangeable; the non-polar aliphatic amino acids Gly, Ala, Val, Ile, and Leu are interchangeable but because of size Gly and Ala are more closely related and Val, Ile and Leu are more closely related to each other, and the aromatic amino acids Phe, Trp and Tyr may be interchangeable.

It should be further noted that if the polypeptides are made synthetically, substitutions by amino acids, which are not naturally encoded by DNA (non-naturally occurring or unnatural amino acid) may also be made.

A non-naturally occurring amino acid is to be understood herein as an amino acid which is not naturally produced or found in a mammal. A non-naturally occurring amino acid comprises a D-amino acid, an amino acid having an acetylaminomethyl group attached to a sulfur atom of a cysteine, a pegylated amino acid, etc. The inclusion of a non-naturally occurring amino acid in a defined polypeptide sequence will therefore generate a derivative of the original polypeptide. Non-naturally occurring amino acids (residues) include also the omega amino acids of the formula $NH_2(CH_2)_nCOOH$ wherein n is 2-6, neutral nonpolar amino acids, such as sarcosine, t-butyl alanine, t-butyl glycine, N-methyl isoleucine, norleucine, etc. Phenylglycine may substitute for Trp, Tyr or Phe; citrulline and methionine sulfoxide are neutral nonpolar, cysteic acid is acidic, and ornithine is basic. Proline may be substituted with hydroxyproline and retain the conformation conferring properties.

It is known in the art that analogues may be generated by substitutional mutagenesis and retain the biological activity of the polypeptides of the present invention. These analogues have at least one amino acid residue in the protein molecule removed and a different residue inserted in its place. For example, one site of interest for substitutional mutagenesis may include but are not restricted to sites identified as the active site(s), or immunological site(s). Other sites of interest may be those, for example, in which particular residues obtained from various species are identical. These positions may be important for biological activity. Examples of substitutions identified as "conservative substitutions" are shown in Table A. If such substitutions result in a change not desired, then other type of substitutions, denominated "exemplary substitutions" in Table A, or as further described herein in reference to amino acid classes, are introduced and the products screened.

In some cases it may be of interest to modify the biological activity of a polypeptide by amino acid substitution, insertion, or deletion. For example, modification of a polypeptide may result in an increase in the polypeptide's biological activity, may modulate its toxicity, may result in changes in bioavailability or in stability, or may modulate its immunological activity or immunological identity. Substantial modifications in function or immunological identity are accomplished by selecting substitutions that differ significantly in their effect on maintaining (a) the structure of the polypeptide backbone in the area of the substitution, for example, as a sheet or helical conformation. (b) the charge or hydrophobicity of the molecule at the target site, or (c) the bulk of the side chain. Naturally occurring residues are divided into groups based on common side chain properties:

(1) hydrophobic: norleucine, methionine (Met), Alanine (Ala), Valine (Val), Leucine (Leu), Isoleucine (Ile)
(2) neutral hydrophilic: Cysteine (Cys), Serine (Ser), Threonine (Thr)
(3) acidic: Aspartic acid (Asp), Glutamic acid (Glu)
(4) basic: Asparagine (Asn), Glutamine (Gln), Histidine (His), Lysine (Lys), Arginine (Arg)
(5) residues that influence chain orientation: Glycine (Gly), Proline (Pro); and aromatic: Tryptophan (Trp), Tyrosine (Tyr), Phenylalanine (Phe)

Non-conservative substitutions will entail exchanging a member of one of these classes for another.

TABLE A

Examplary amino acid substitution

| Original residue | Exemplary substitution | Conservative substitution |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro | Pro |
| His (H) | Asn, Gln, Lys, Arg | Arg |
| Ile (I) | Leu, Val, Met, Ala, Phe, norleucine | Leu |

TABLE A-continued

Examplary amino acid substitution

| Original residue | Exemplary substitution | Conservative substitution |
|---|---|---|
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala | Leu |
| Pro (P) | Gly | Gly |
| Ser (S) | Thr | Thr |
| Thr (T) | Ser | Ser |
| Trp (W) | Tyr | Tyr |
| Tyr (Y) | Trp, Phe, Thr, Ser | Phe |
| Val (V) | Ile, Leu, Met, Phe, Ala, norleucine | Leu |

It is to be understood herein, that if a "range" or "group" of substances (e.g. amino acids), substituents" or the like is mentioned or if other types of a particular characteristic (e.g. temperature, pressure, chemical structure, time, etc.) is mentioned, the present invention relates to and explicitly incorporates herein each and every specific member and combination of sub-ranges or sub-groups therein whatsoever. Thus, any specified range or group is to be understood as a shorthand way of referring to each and every member of a range or group individually as well as each and every possible sub-ranges or sub-groups encompassed therein; and similarly with respect to any sub-ranges or sub-groups therein. Thus, for example, with respect to a percentage (%) of identity of from about 80 to 100%, it is to be understood as specifically incorporating herein each and every individual %, as well as sub-range, such as for example 80%, 81%, 84.78%, 93%, 99% etc.; and similarly with respect to other parameters such as, concentrations, elements, etc.

It is in particular to be understood herein that the methods of the present invention each include each and every individual steps described thereby as well as those defined as positively including particular steps or excluding particular steps or a combination thereof; for example an exclusionary definition for a method of the present invention, may read as follows: "provided that said polynucleotide does not comprise or consist in SEQ ID NO.:34 or the open reading frame of SEQ ID NO.:34" or "provided that said polypeptide does not comprise or consist in SEQ ID NO.:82" or "provided that said polynucleotide fragment or said polypeptide fragment is less than X unit (e.g., nucleotides or amino acids) long or more than X unit (e.g., nucleotides or amino acids) long".

Other objects, features, advantages, and aspects of the present invention will become apparent to those skilled in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

In the appended drawings:

For each of FIGS. 1 to 34 and 38-39 macroarrays were prepared using RAMP amplified RNA from human precursor cells (A-F 1), and differentiated intermediate (A-F 2-3) and mature osteoclasts for four human donors (A-F 4), and 30 different normal human tissues (adrenal (A5), liver (B5), lung (C5), ovary (D5), skeletal muscle (E5), heart (F5), cervix (G5), thyroid (H5), breast (A6), placenta (B6), adrenal cortex (C6), kidney (D6), vena cava (E6), fallopian tube (F6), pancreas (G6), testicle (H6), jejunum (A7), aorta (B7), esophagus (C7), prostate (D7), stomach (E7), spleen (F7), ileum (G7), trachea (A8), brain (B8), colon (C8), thymus (D8), small intestine (E8), bladder (F8) and duodenum (G8)). The STAR dsDNA clone representing the respective SEQ ID NOs. was labeled with $^{32}$P and hybridized to the macroarray. The probe labeling reaction was also spiked with a dsDNA sequence for *Arabidopsis*, which hybridizes to the same sequence spotted on the macroarray (M) in order to serve as a control for the labeling reaction. Quantitation of the hybridization signal at each spot was performed using a STORM 820 phosphorimager and the ImageQuant TL software (Amersham Biosciences, Piscataway, N.J.). A $log_2$ value representing the average of the signals for the precursors (A-F 1) was used as the baseline and was subtracted from the $log_2$ value obtained for each of the remaining samples in order to determine their relative abundances compared to the precursors and plotted as a bar graph (right panel).

FIG. 6 is a picture of the macroarray hybridization results (upper panel) and quantitation of the signal intensities illustrated by a bar graph (lower panel) showing the differential expression data for STAR selected osteoclast-specific human SEQ. ID. NO. 6 (0210-SL86-1). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8);

DESCRIPTION OF ILLUSTRATIVE EMBODIMENTS

Figure 1:
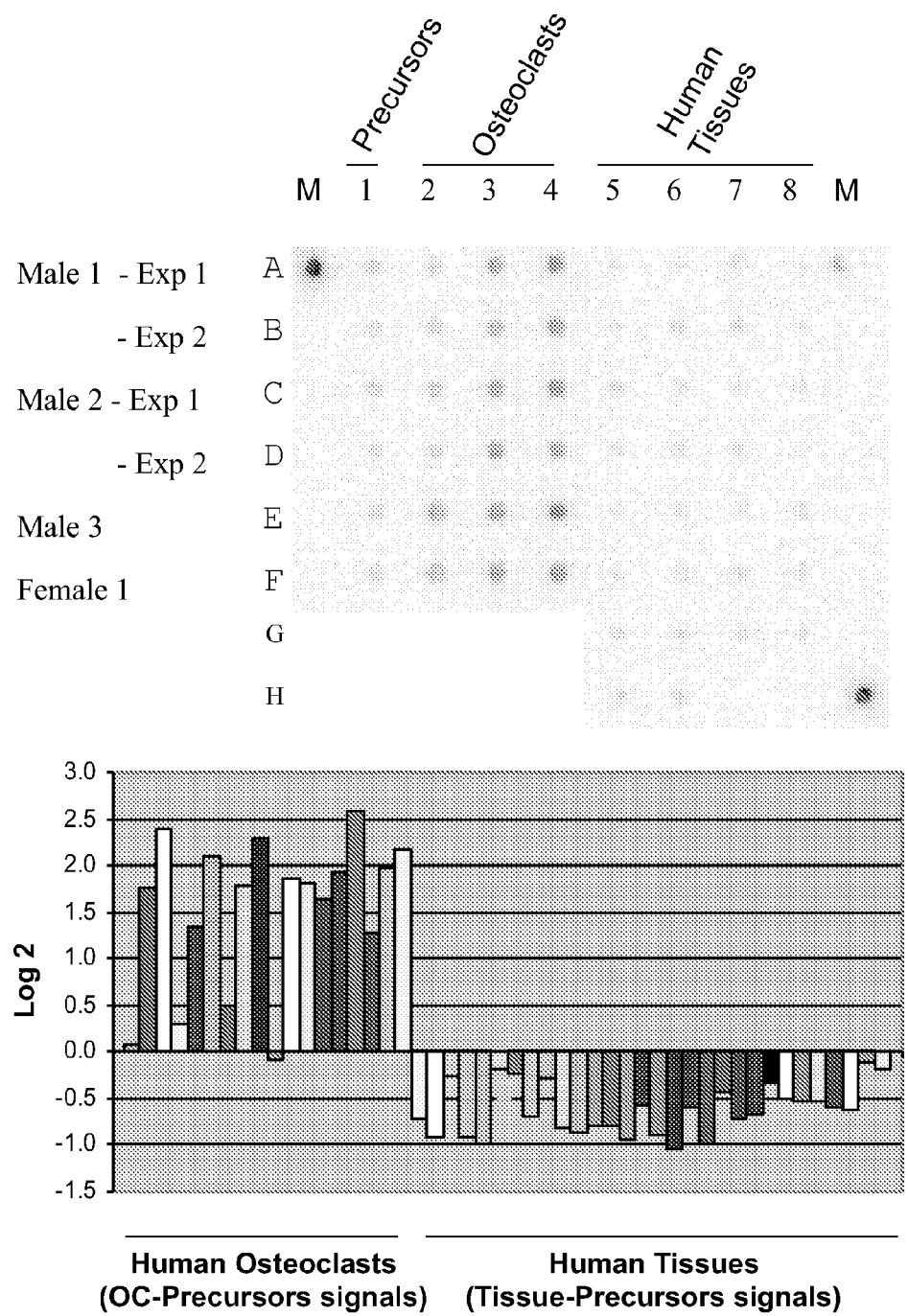
FIG. 1 is a picture of the macroarray hybridization results (upper panel) and quantitation of the signal intensities illustrated by a bar graph (lower panel) showing the differential expression data for STAR selected osteoclast-specific human SEQ. ID. NO. 1 (0326-SL109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 2:
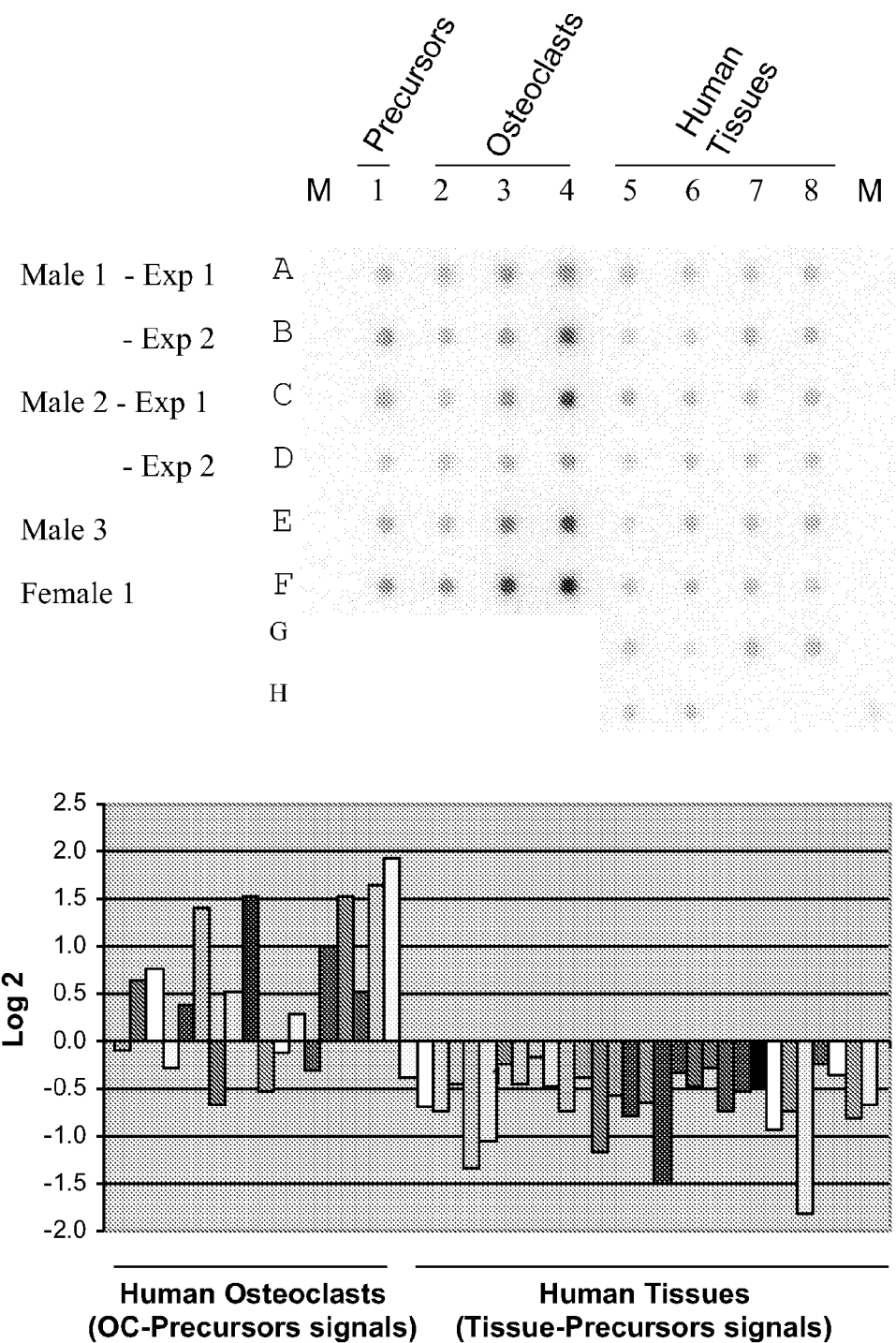
FIG. 2 is a picture of the macroarray hybridization results (upper panel) and quantitation of the signal intensities illustrated by a bar graph (lower panel) showing the differential expression data for STAR selected osteoclast-specific human SEQ. ID. NO. 2 (0369-SL91-1). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 3:
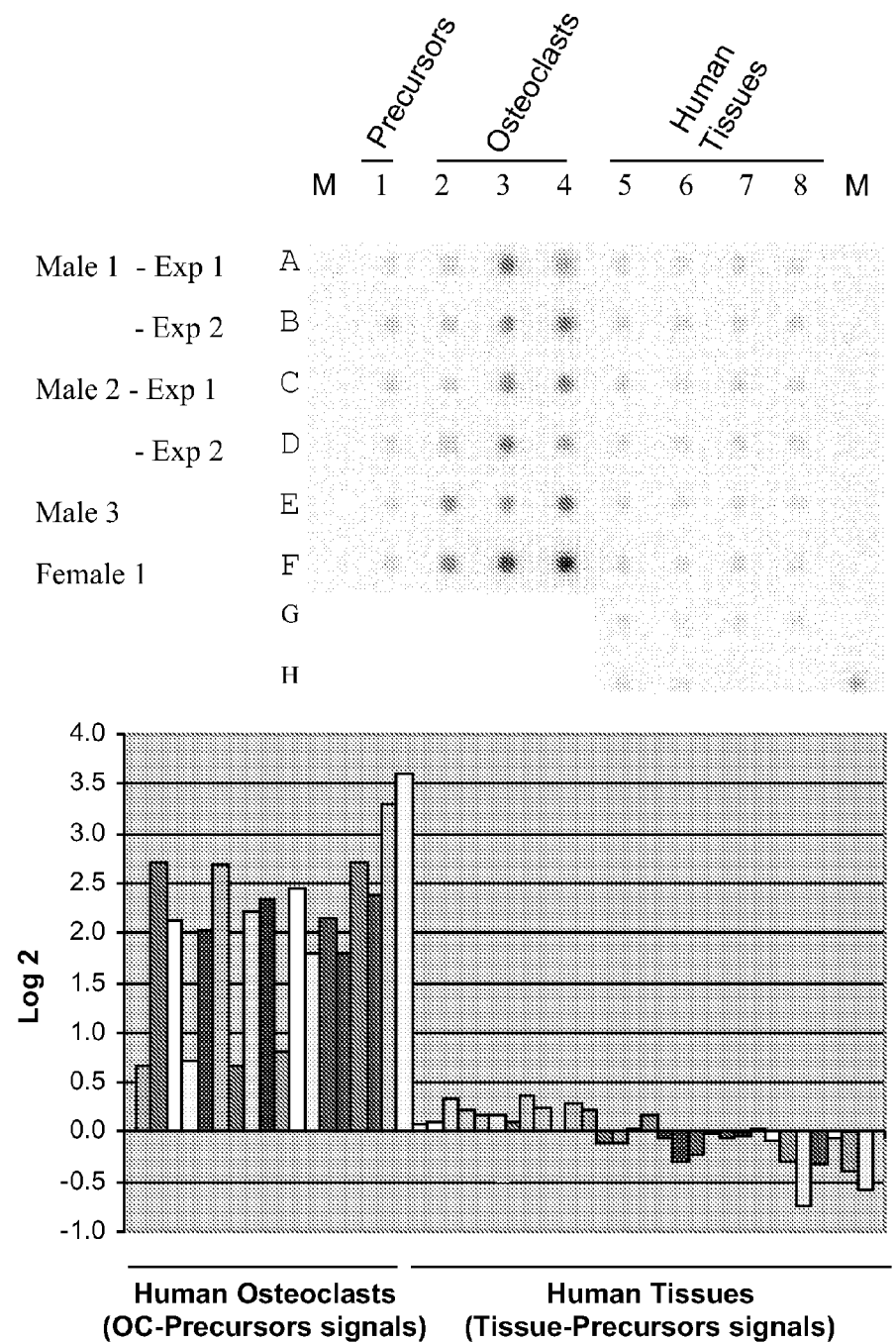
FIG. 3 is a picture of the macroarray hybridization results (upper panel) and quantitation of the signal intensities illustrated by a bar graph (lower panel) showing the differential expression data for STAR selected osteoclast-specific human SEQ. ID. NO. 3 (0027-SL92-1). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 4:
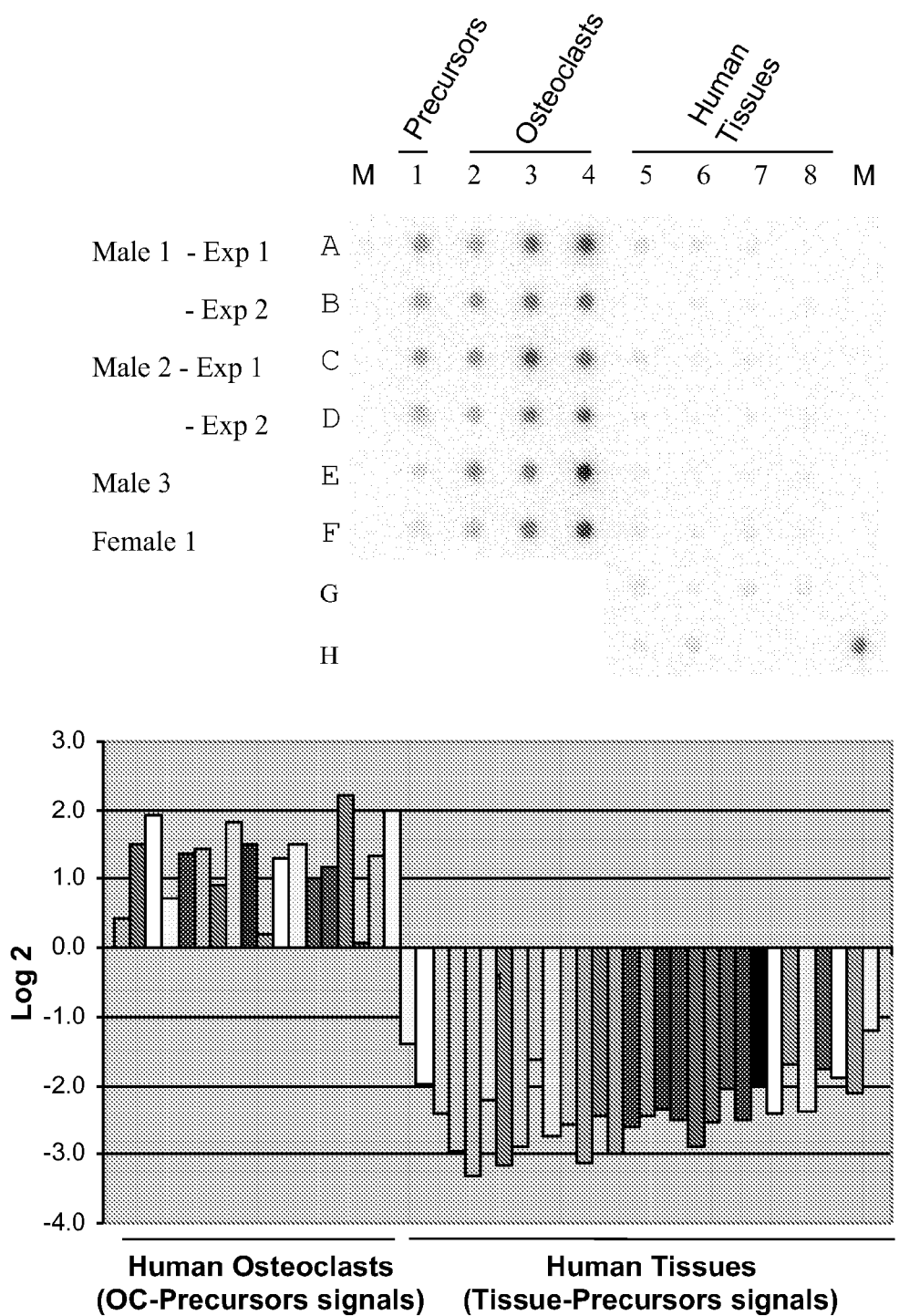
FIG. 4 is a picture of the macroarray hybridization results (upper panel) and quantitation of the signal intensities illustrated by a bar graph (lower panel) showing the differential expression data for STAR selected osteoclast-specific human SEQ. ID. NO. 4 (0199-SL85-2). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 5:
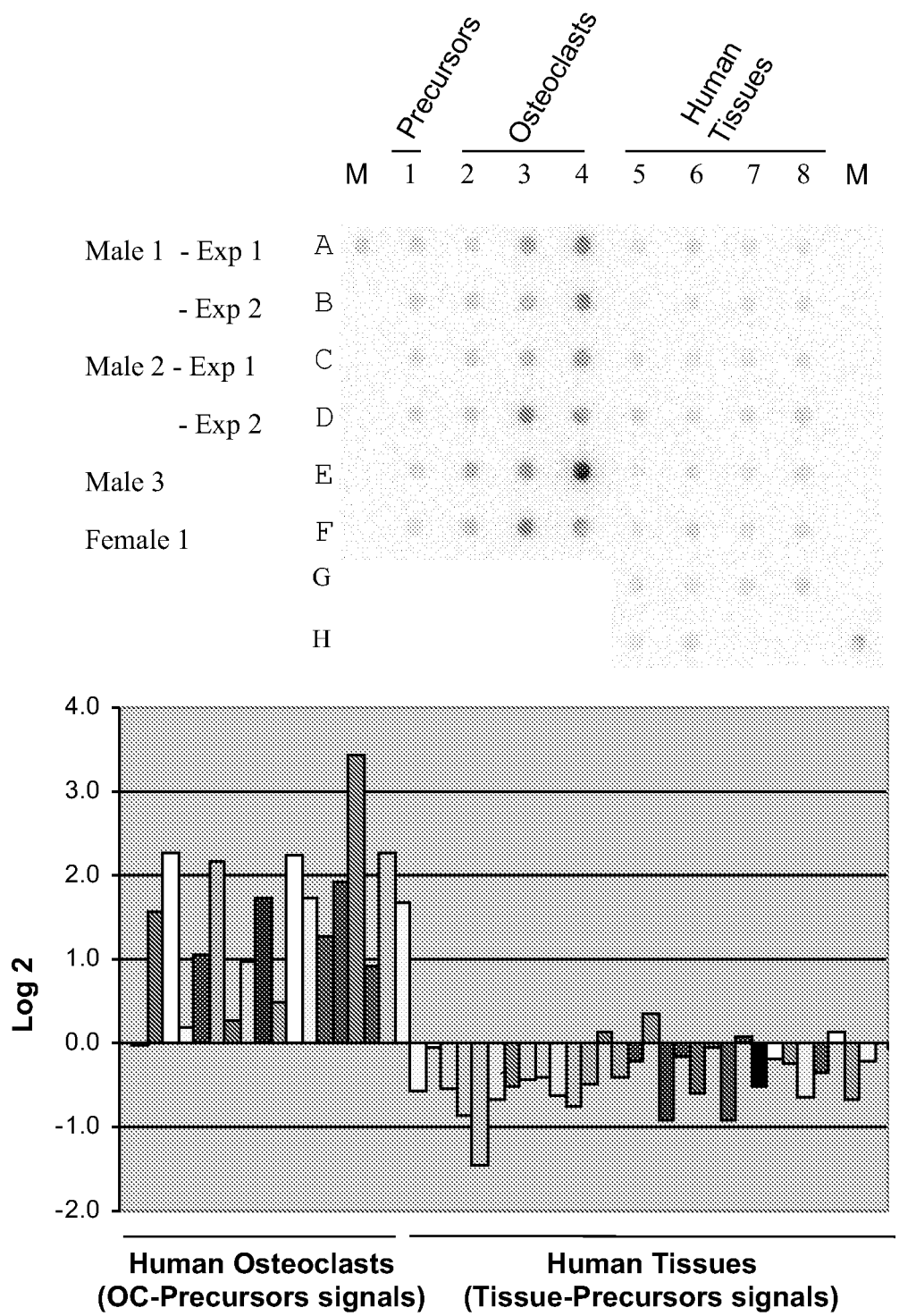
FIG. 5 is a picture of the macroarray hybridization results (upper panel) and quantitation of the signal intensities illustrated by a bar graph (lower panel) showing the differential expression data for STAR selected osteoclast-specific human SEQ. ID. NO. 5 (0571-SL109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 7:
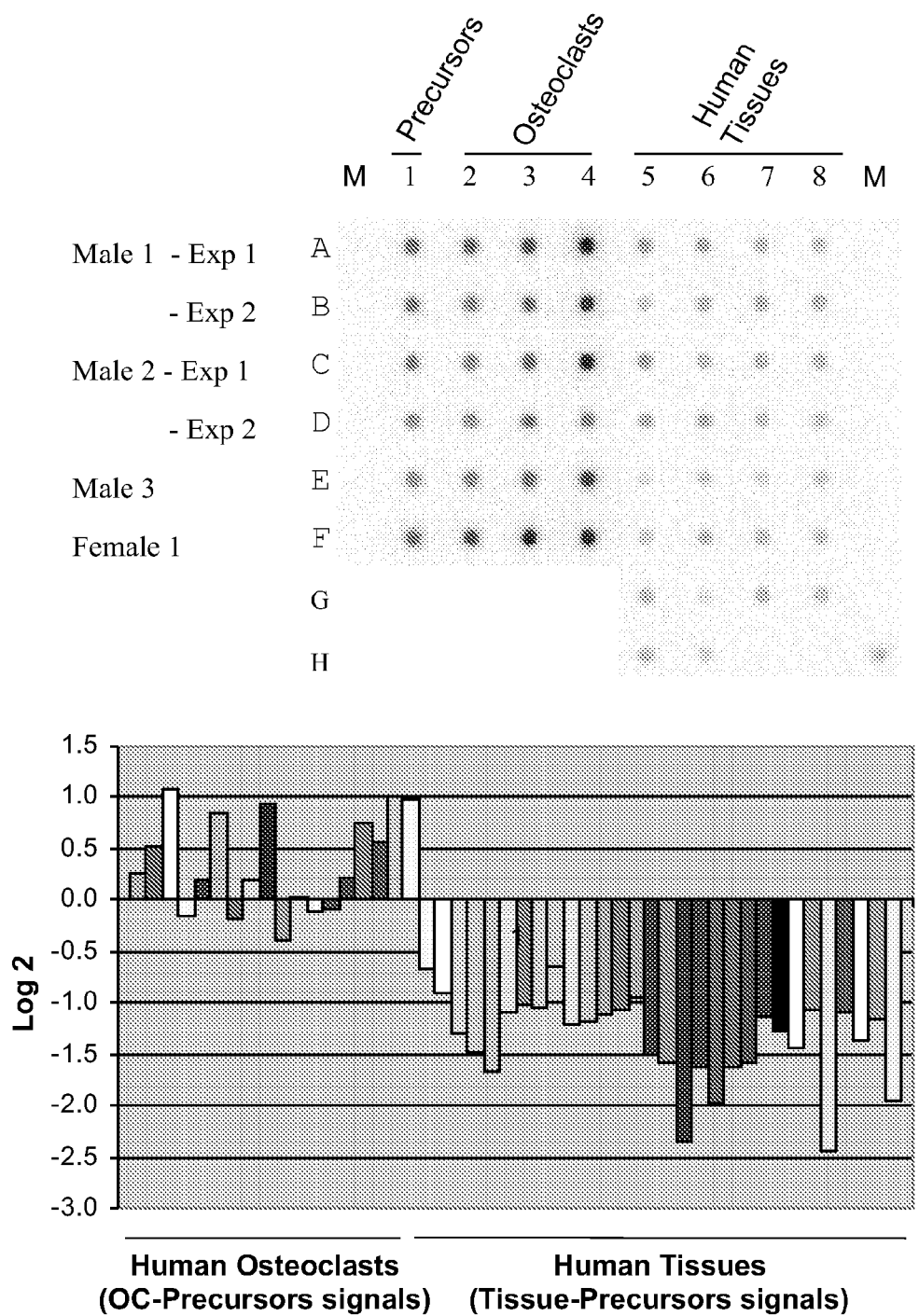
FIG. 7 is a picture of the macroarray hybridization results (upper panel) and quantitation of the signal intensities illustrated by a bar graph (lower panel) showing the differential expression data for STAR selected osteoclast-specific human SEQ. ID. NO. 7 (0238-SL92-1). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 8:
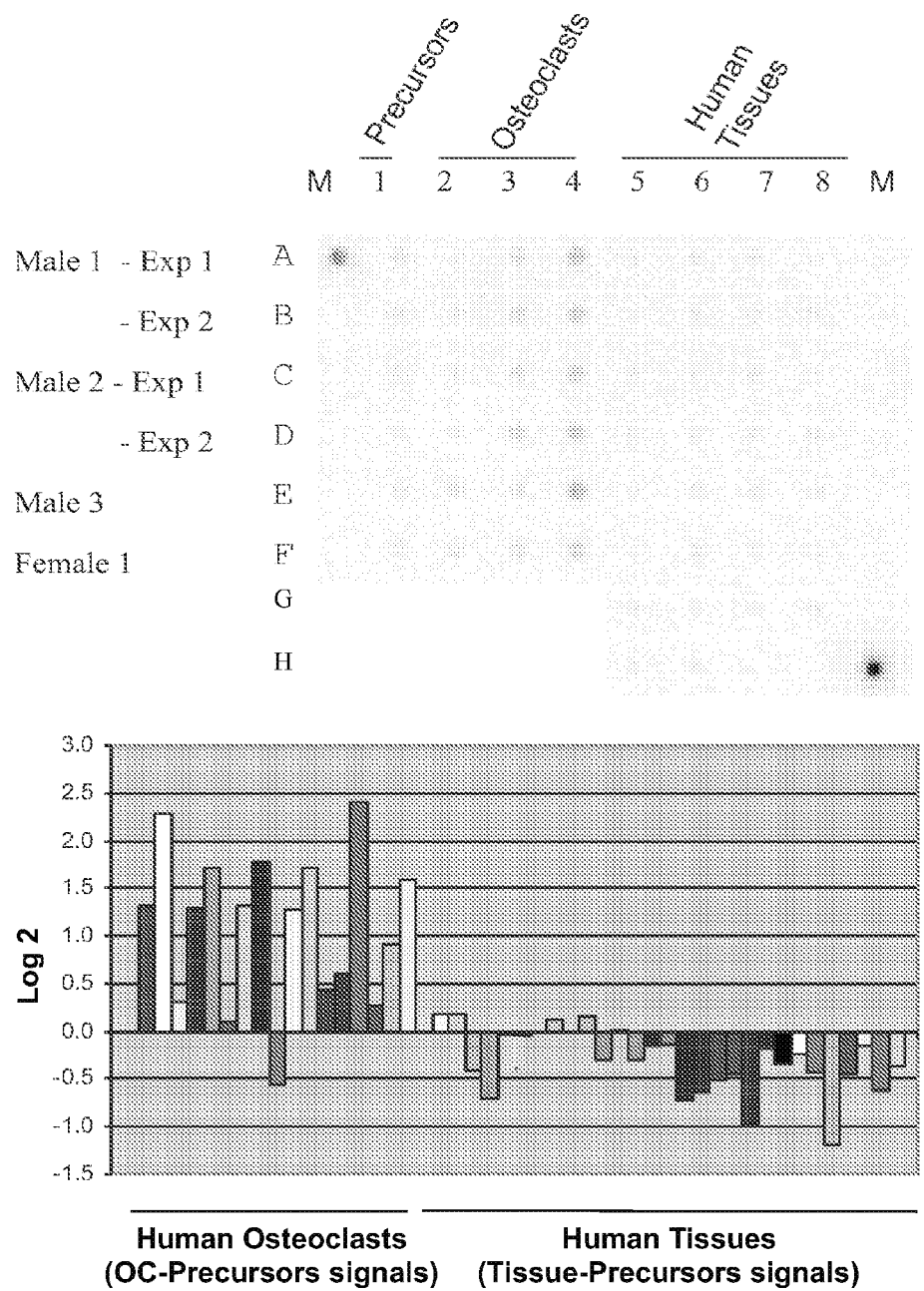
FIG. 8 is a picture of the macroarray hybridization results (upper panel) and quantitation of the signal intensities illustrated by a bar graph (lower panel) showing the differential expression data for STAR selected osteoclast-specific human SEQ. ID. NO. 8 (0380-SL-109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 9:
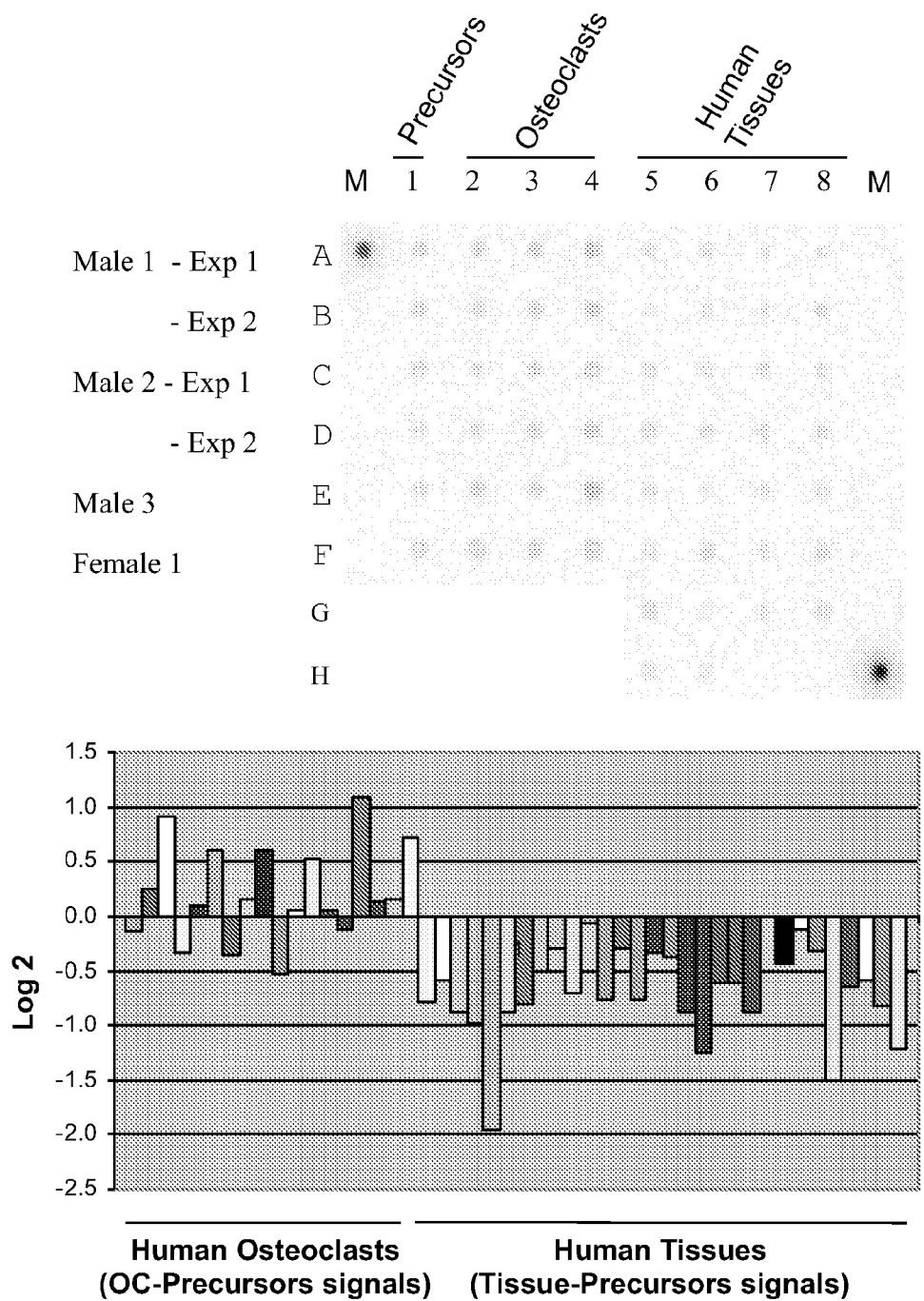
FIG. 9 is a picture of the macroarray hybridization results (upper panel) and quantitation of the signal intensities illustrated by a bar graph (lower panel) showing the differential expression data for STAR selected osteoclast-specific human SEQ. ID. NO. 9 (0381-SL109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 10:
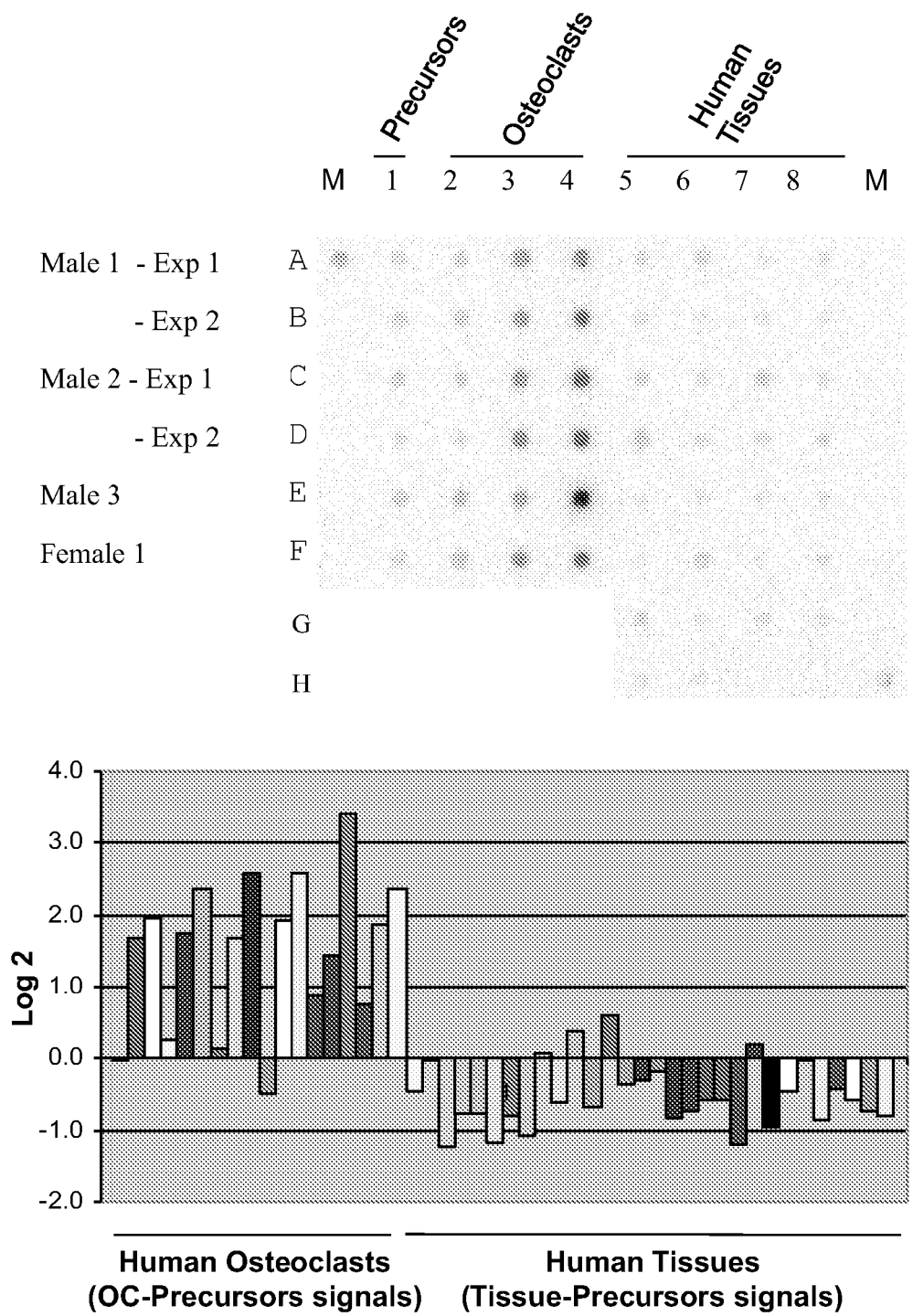
FIG. 10 is a picture of the macroarray hybridization results (upper panel) and quantitation of the signal intensities illustrated by a bar graph (lower panel) showing the differential expression data for STAR selected osteoclast-specific human SEQ. ID. NO. 10 (0424-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 11:
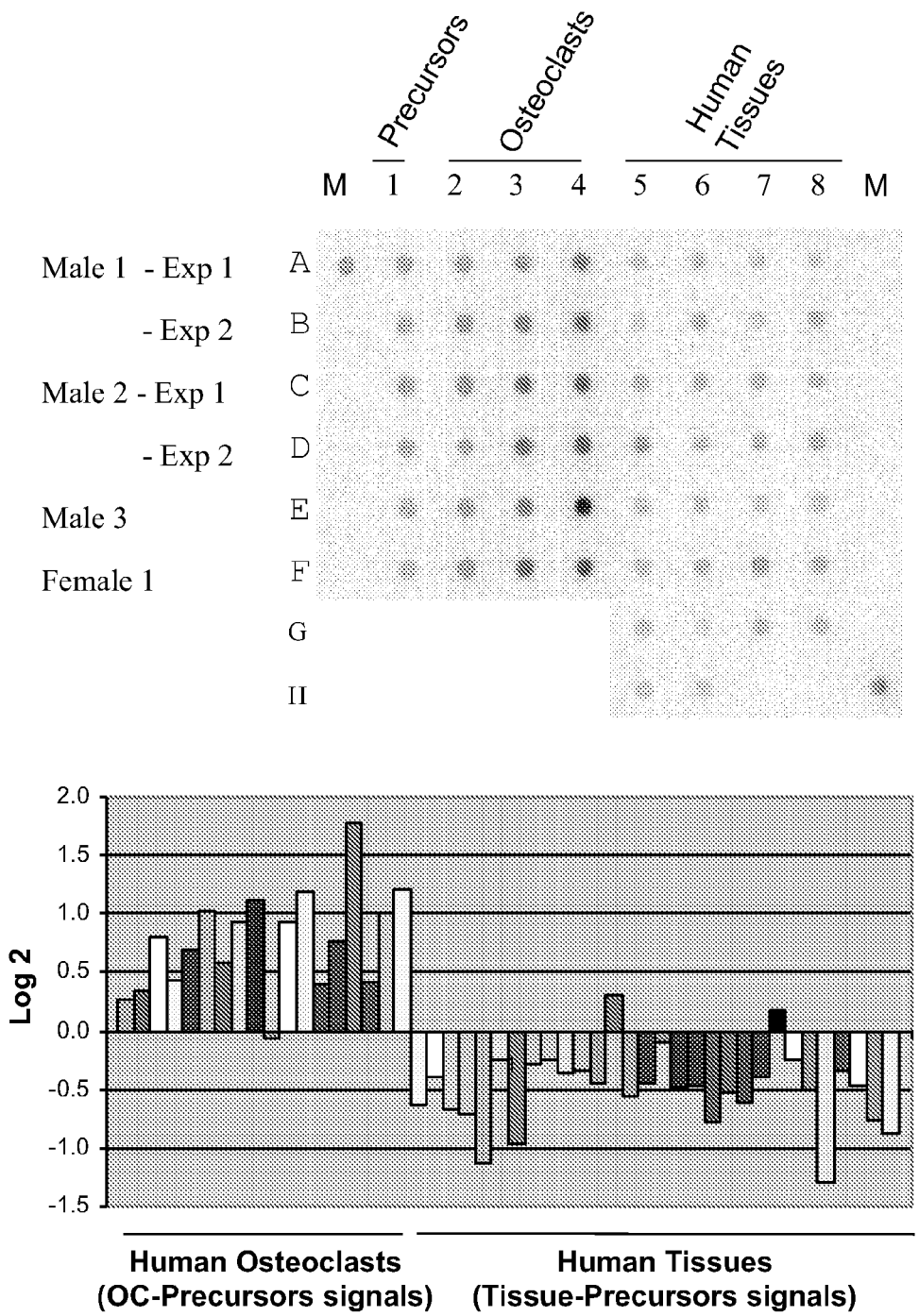
FIG. 11 is a picture of the macroarray hybridization results (upper panel) and quantitation of the signal intensities illustrated by a bar graph (lower panel) showing the differential expression data for STAR selected osteoclast-specific human SEQ. ID. NO. 11 (0434-SL109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 12:
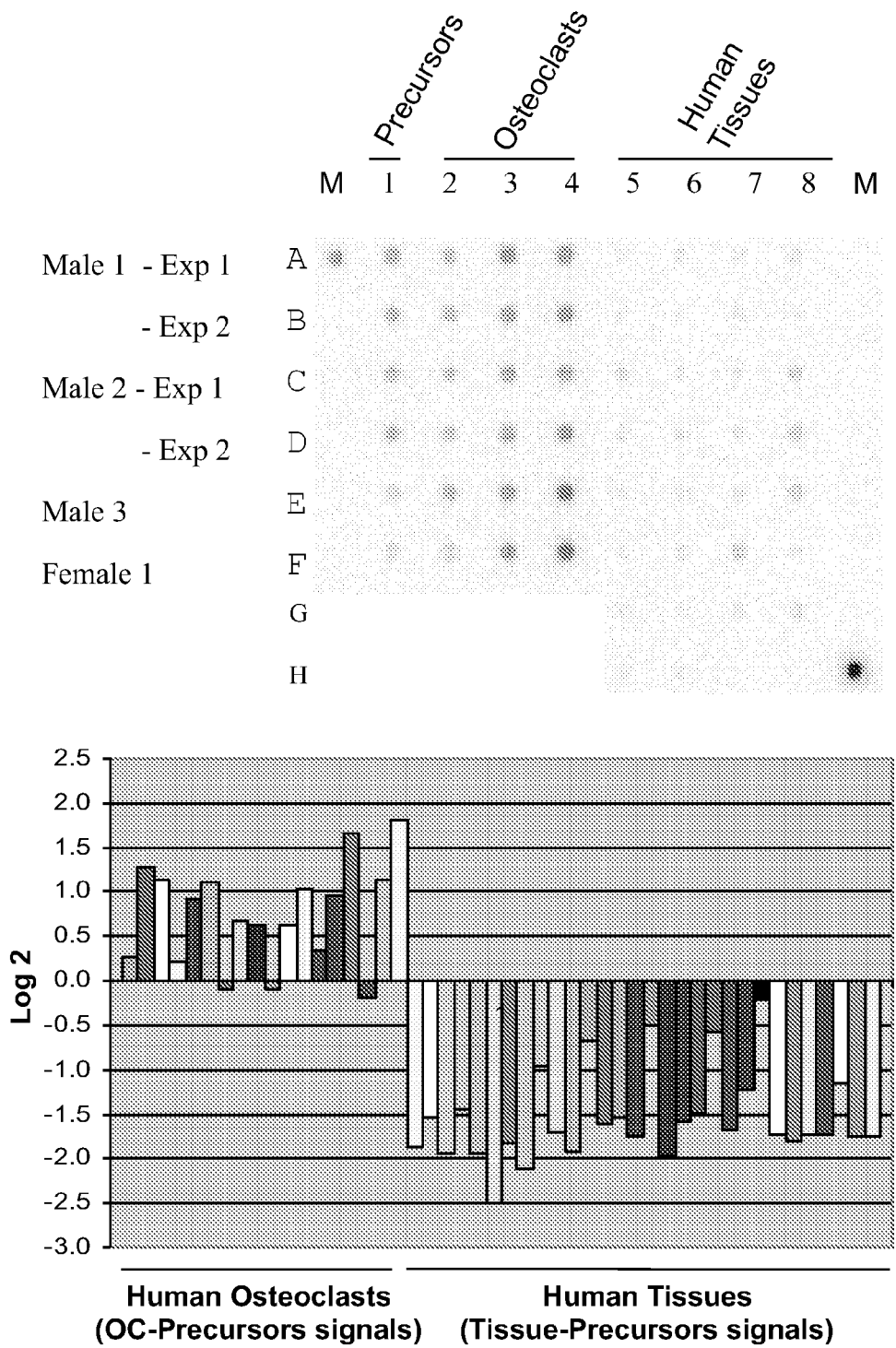
FIG. 12 is a picture of the macroarray hybridization results (upper panel) and quantitation of the signal intensities illustrated by a bar graph (lower panel) showing the differential expression data for STAR selected osteoclast-specific human SEQ. ID. NO. 12 (0613-SL109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8.
Figure 13:
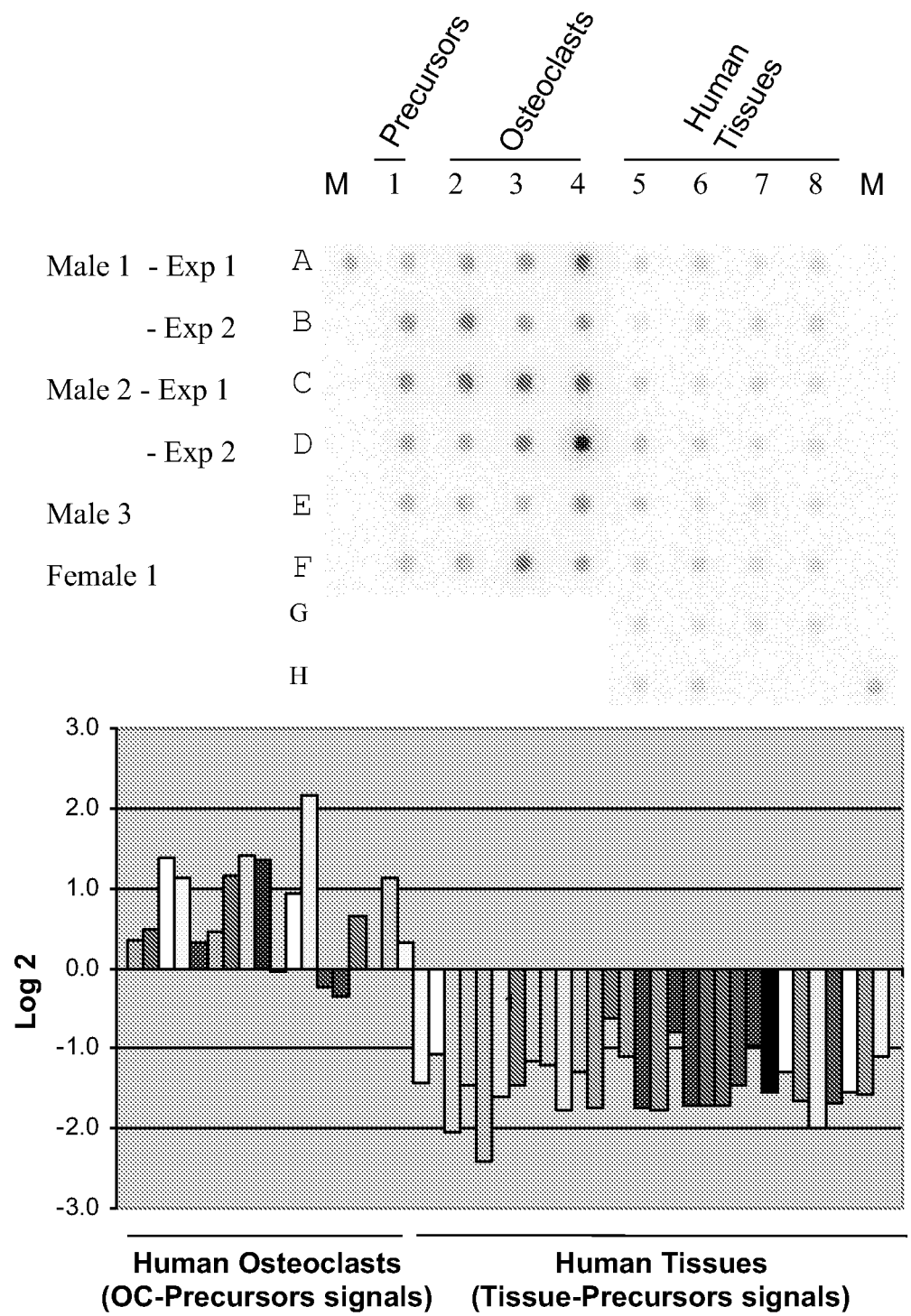
FIG. 13 is a picture of the macroarray hybridization results (upper panel) and quantitation of the signal intensities illustrated by a bar graph (lower panel) showing the differential expression data for STAR selected osteoclast-specific human SEQ. ID. NO. 13 (0697-SL108). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 14:
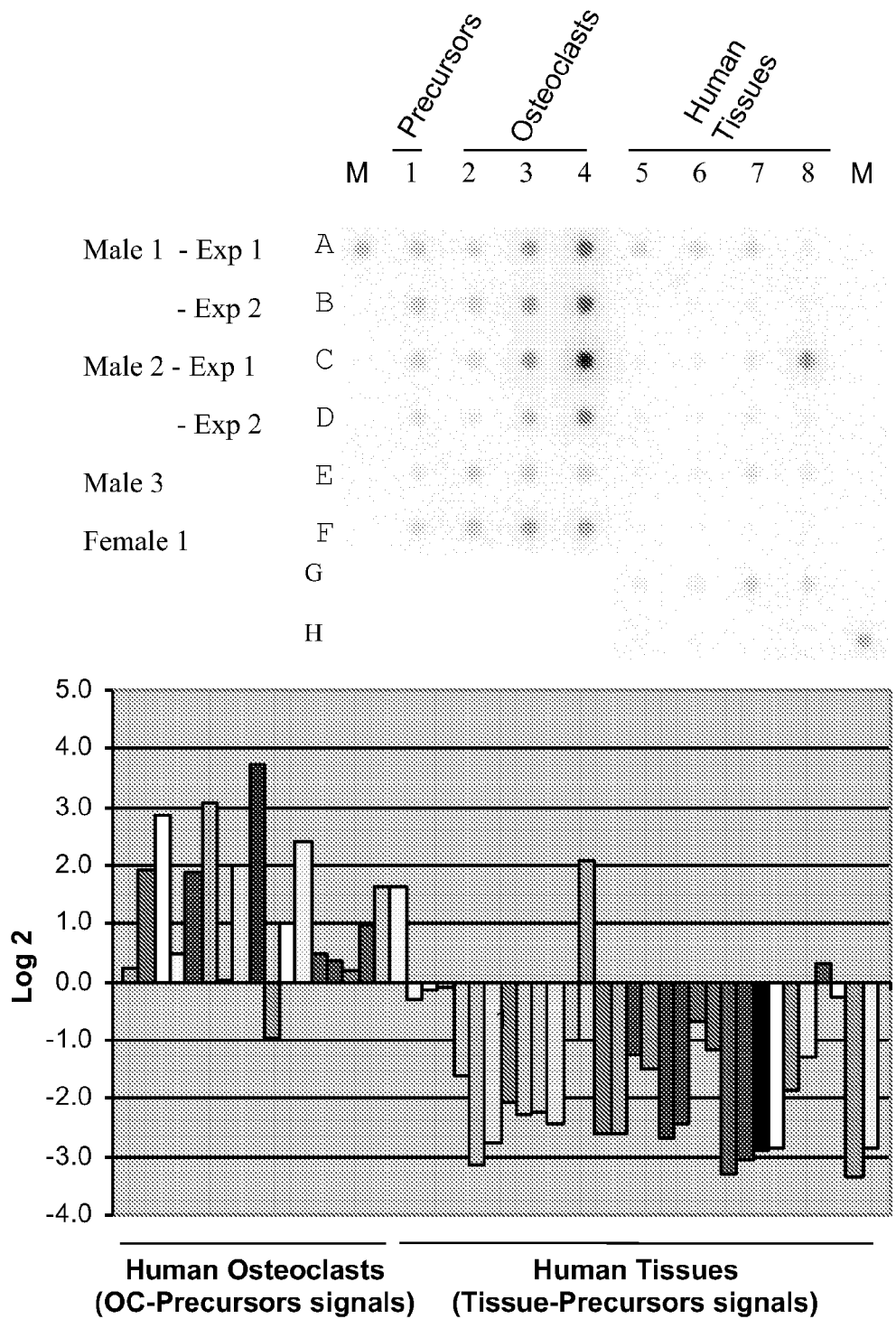
FIG. 14 is a picture of the macroarray hybridization results (upper panel) and quantitation of the signal intensities illustrated by a bar graph (lower panel) showing the differential expression data for STAR selected osteoclast-specific human SEQ. ID. NO. 14 (0103-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 15:
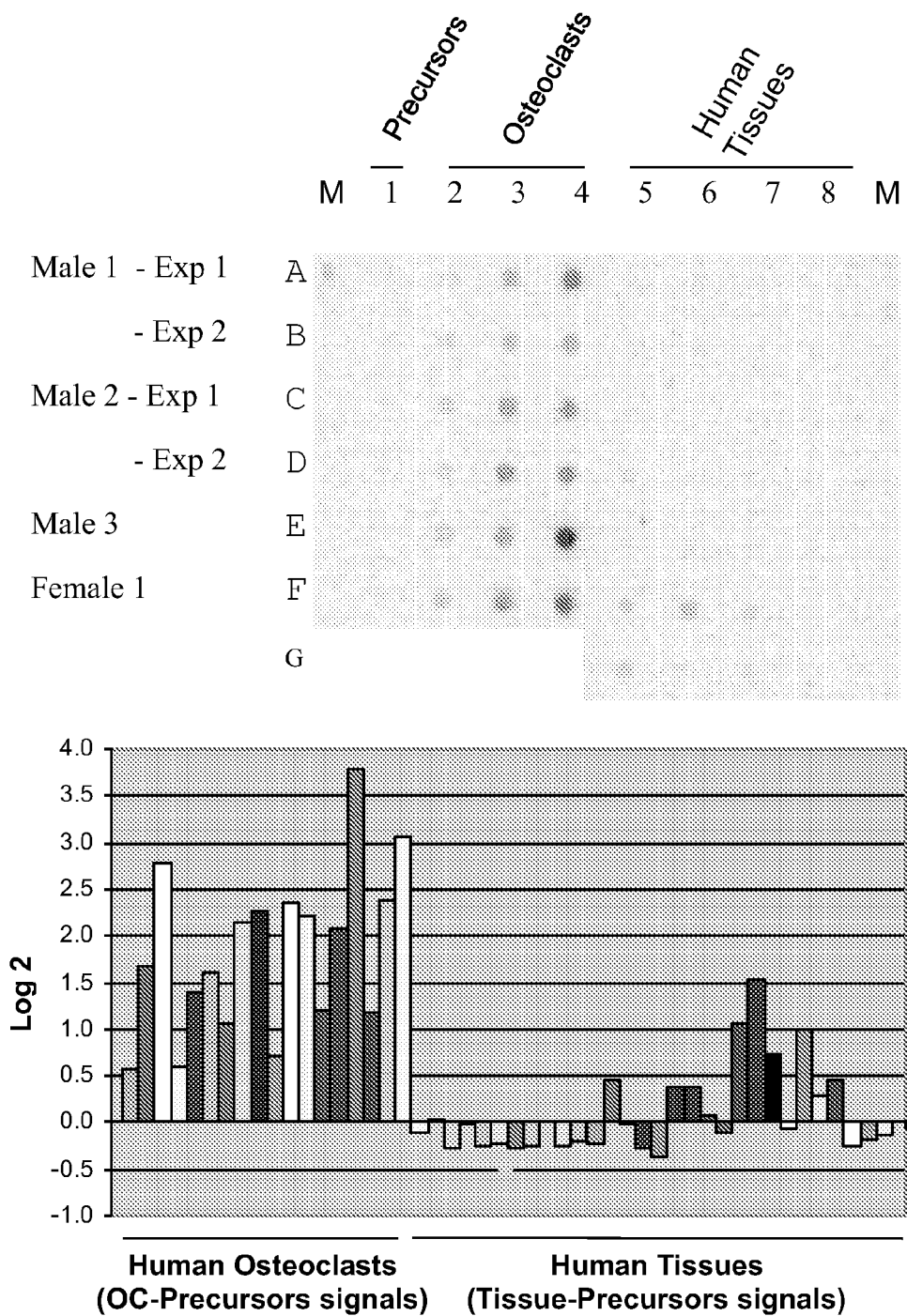
FIG. 15 is a picture of the macroarray hybridization results (upper panel) and quantitation of the signal intensities illustrated by a bar graph (lower panel) showing the differential expression data for STAR selected osteoclast-specific human SEQ. ID. NO. 15 (0047-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 16:
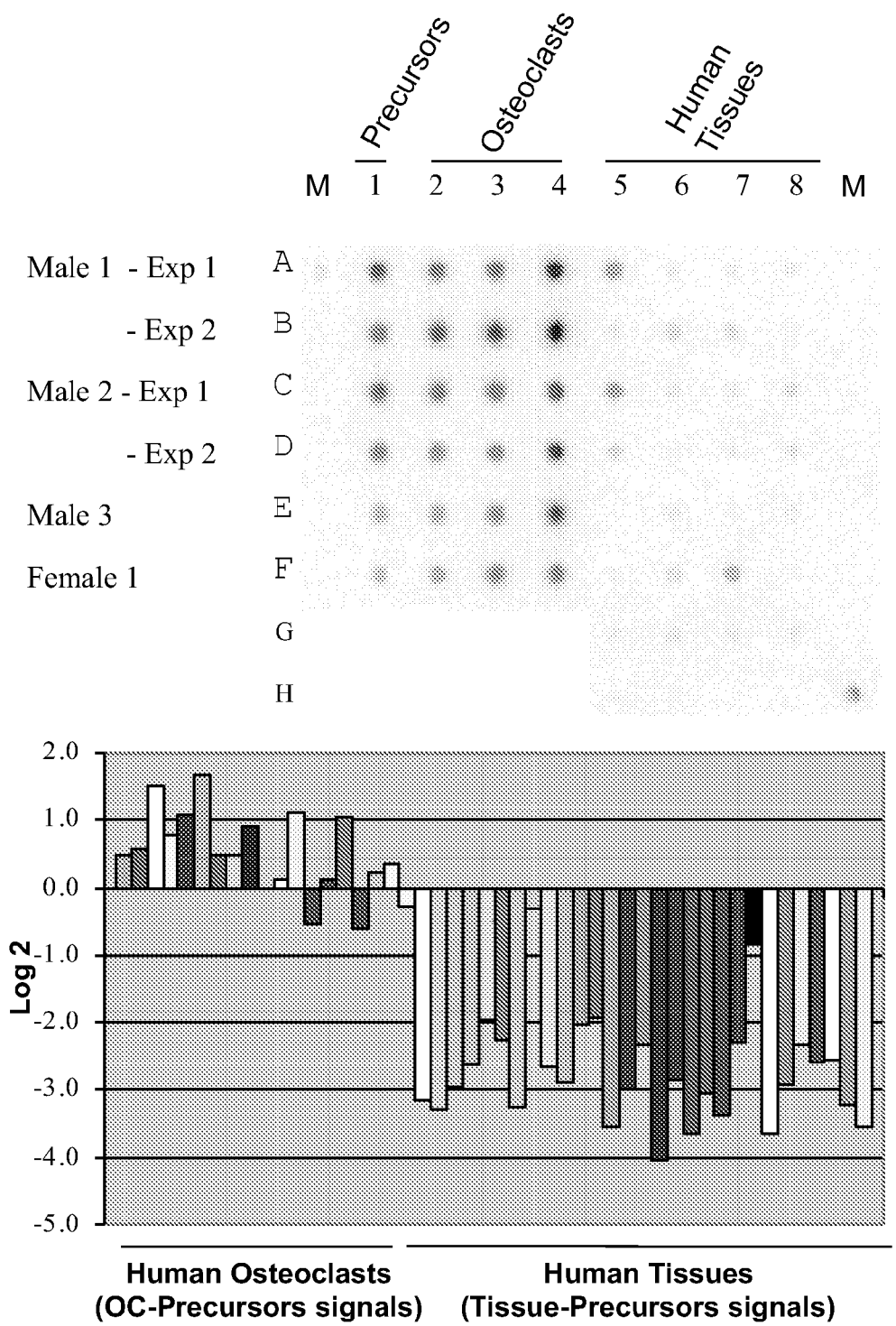
FIG. 16 is a picture of the macroarray hybridization results (upper panel) and quantitation of the signal intensities illustrated by a bar graph (lower panel) showing the differential expression data for STAR selected osteoclast-specific human SEQ. ID. NO. 16 (0120-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 17:
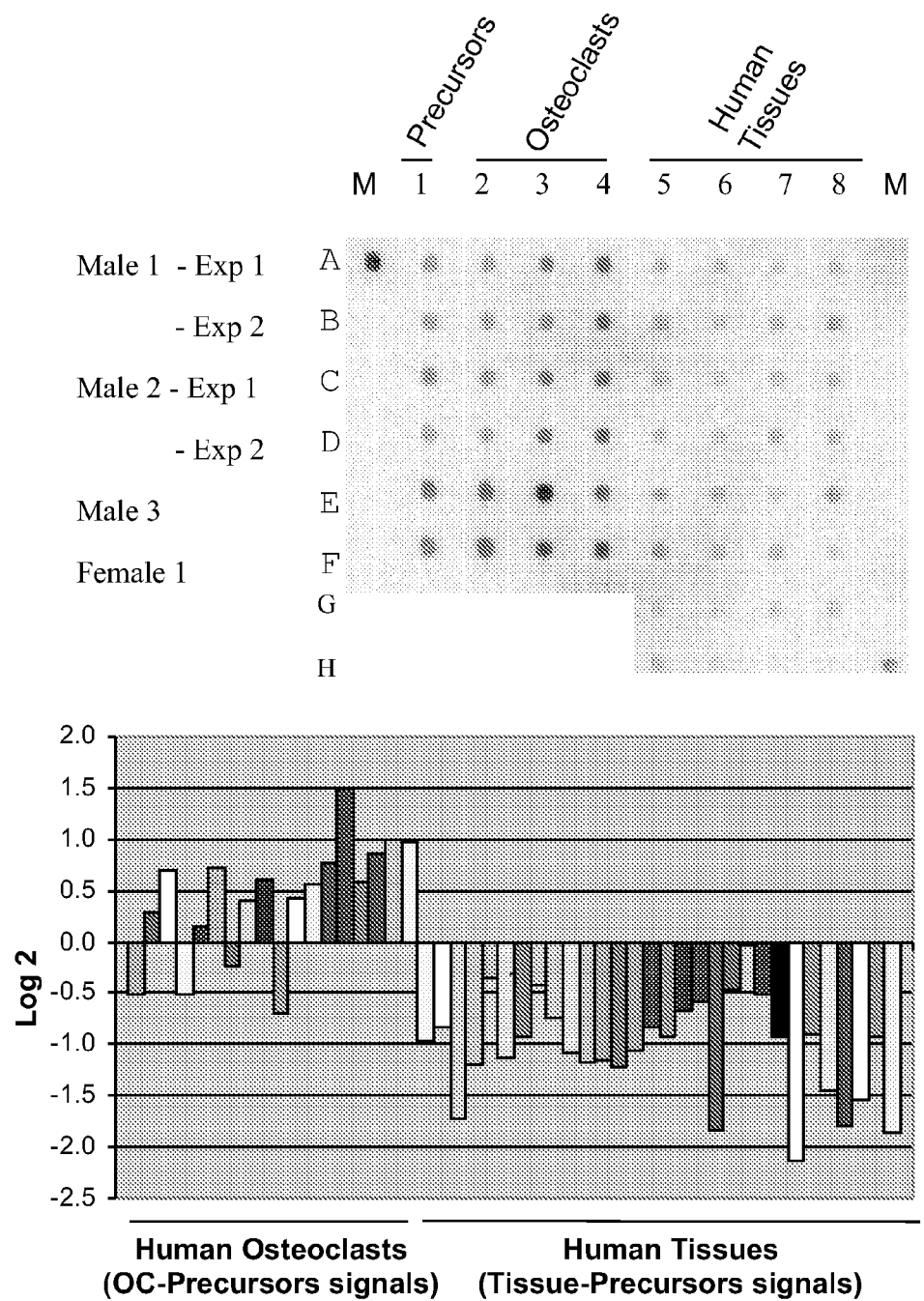
FIG. 17 is a picture of the macroarray hybridization results (upper panel) and quantitation of the signal intensities illustrated by a bar graph (lower panel) showing the differential expression data for STAR selected osteoclast-specific human SEQ. ID. NO. 17 (0314-SL108). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8.
Figure 18:
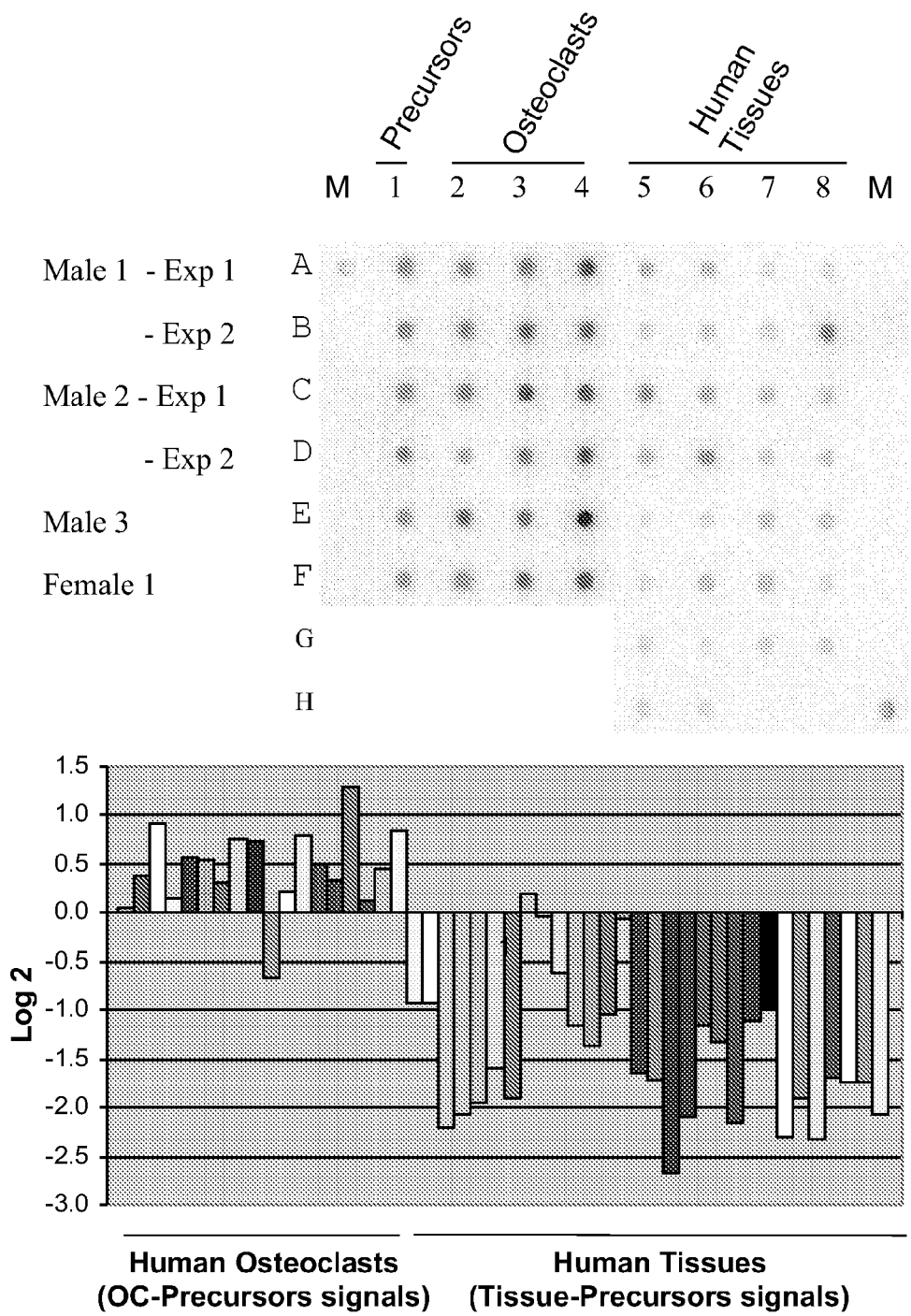
FIG. 18 is a picture of the macroarray hybridization results (upper panel) and quantitation of the signal intensities illustrated by a bar graph (lower panel) showing the differential expression data for STAR selected osteoclast-specific human SEQ. ID. NO. 18 (0421-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 19:
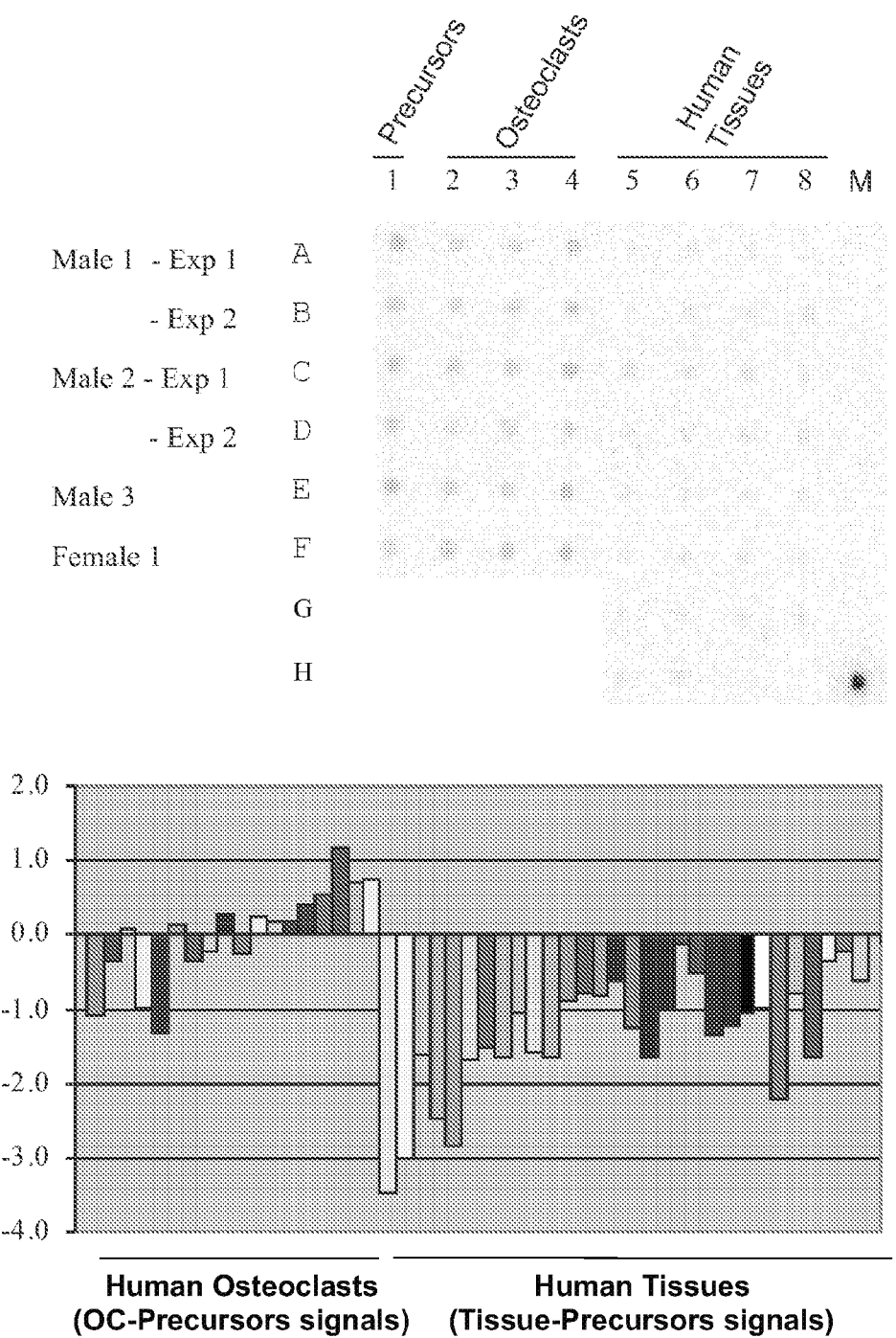
FIG. 19 is a picture of the macroarray hybridization results (upper panel) and quantitation of the signal intensities illustrated by a bar graph (lower panel) showing the differential expression data for STAR selected osteoclast-specific human SEQ. ID. NO. 19 (0619-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 20:
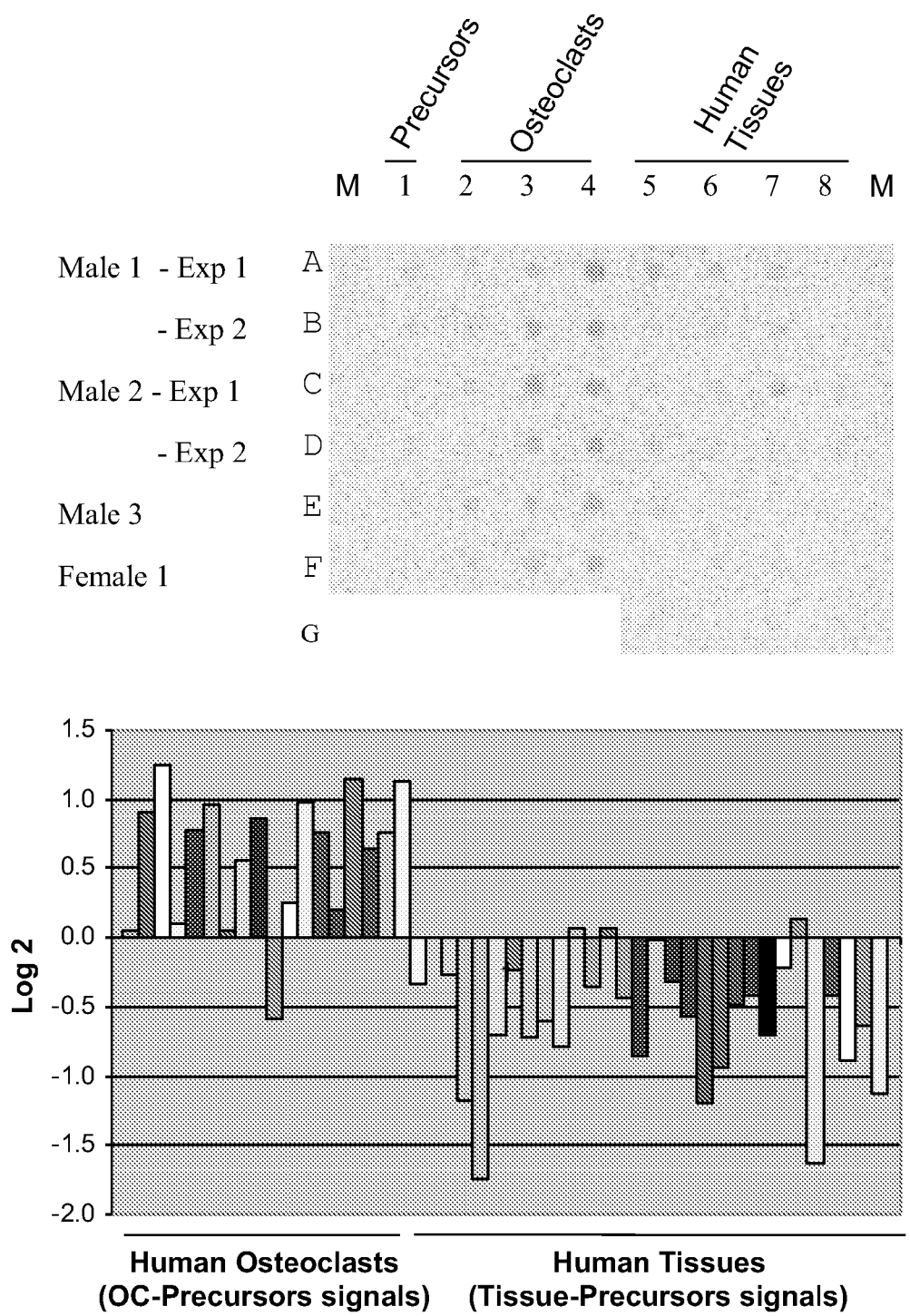
FIG. 20 is a picture of the macroarray hybridization results (upper panel) and quantitation of the signal intensities illustrated by a bar graph (lower panel) showing the differential expression data for STAR selected osteoclast-specific human SEQ. ID. NO. 20 (0621-SL108). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 21:
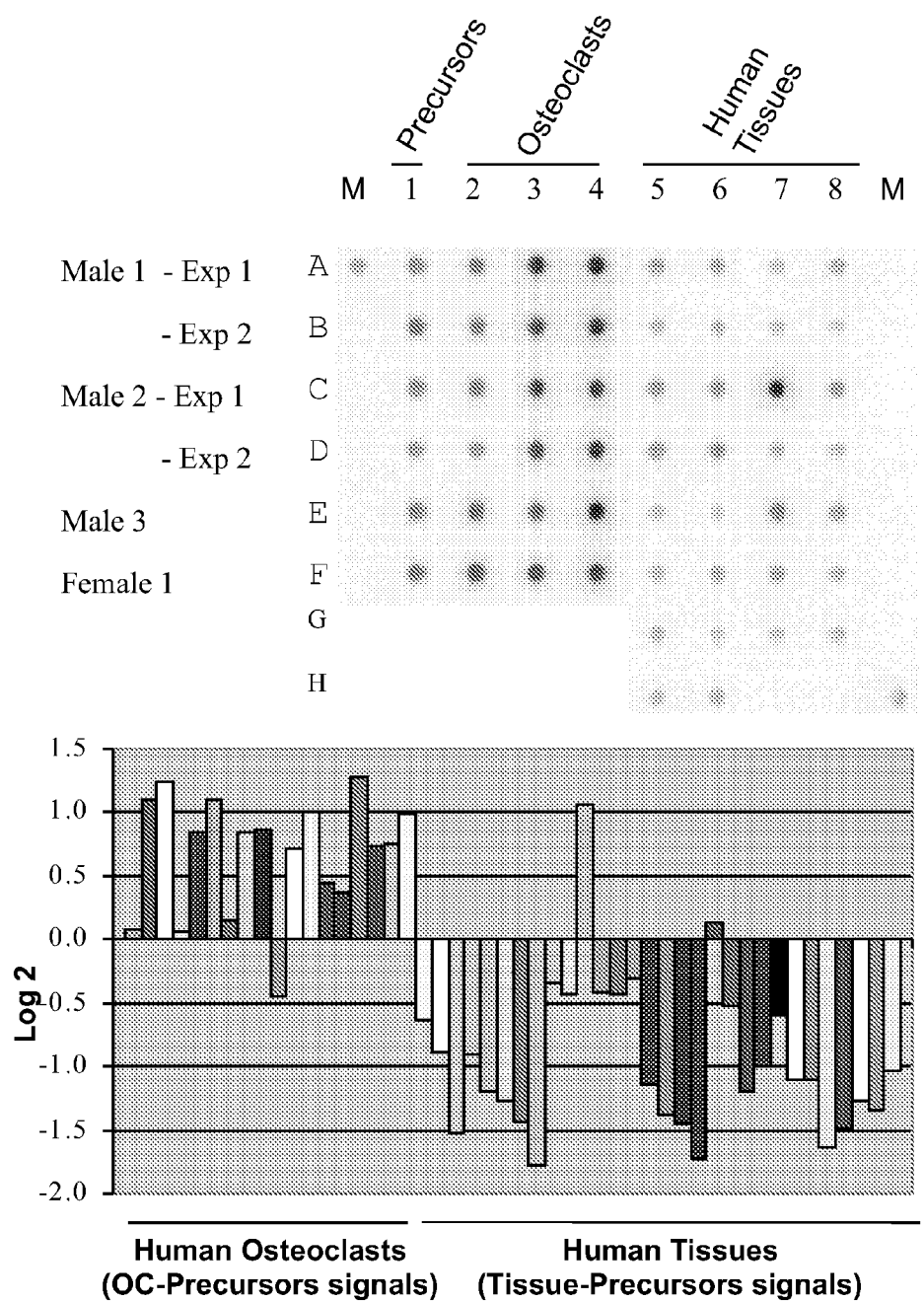
FIG. 21 is a picture of the macroarray hybridization results (upper panel) and quantitation of the signal intensities illustrated by a bar graph (lower panel) showing the differential expression data for STAR selected osteoclast-specific human SEQ. ID. NO. 21 (0638-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 22:
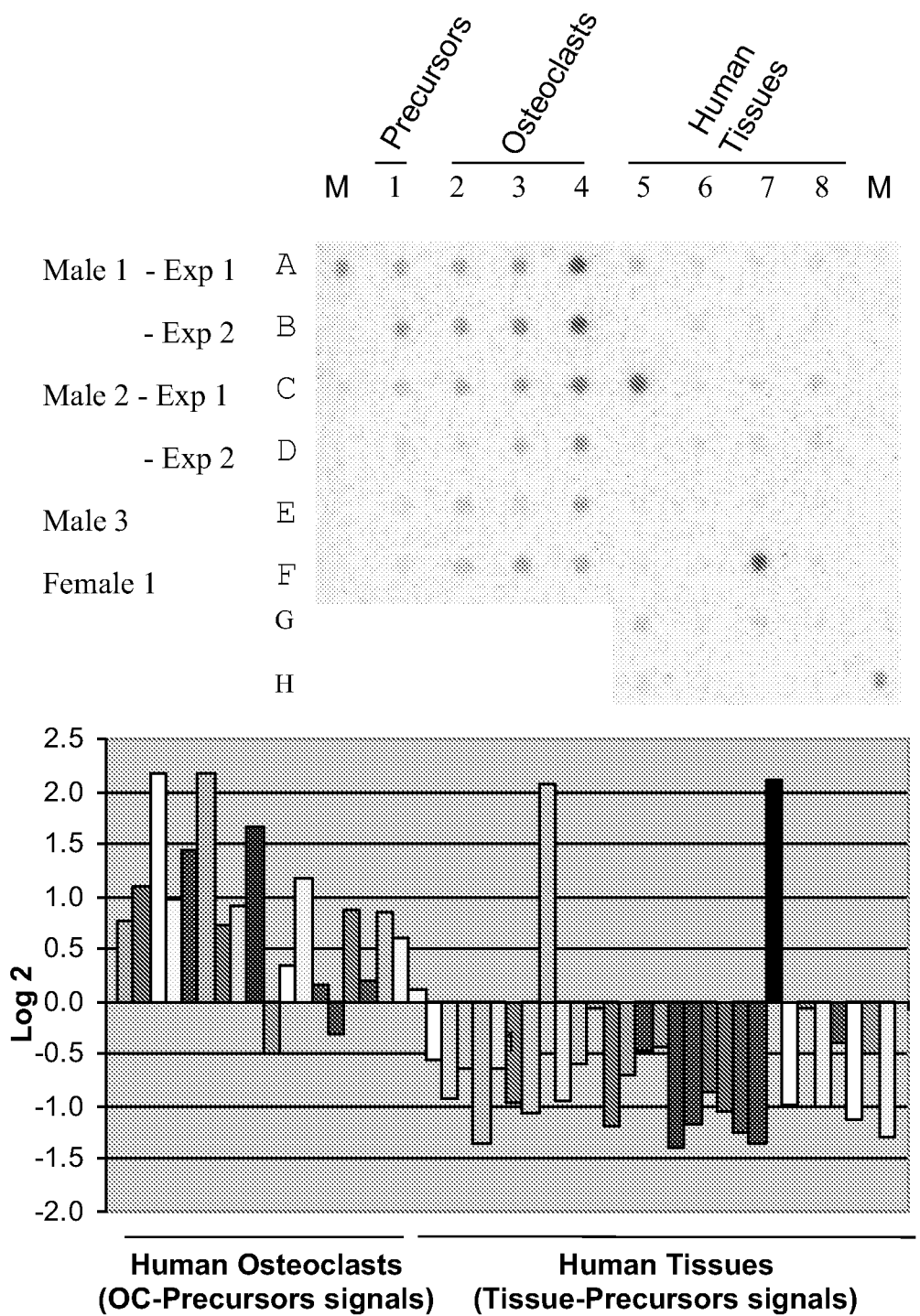
FIG. 22 is a picture of the macroarray hybridization results (upper panel) and quantitation of the signal intensities illustrated by a bar graph (lower panel) showing the differential expression data for STAR selected osteoclast-specific human SEQ. ID. NO. 22 (0902-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 23:
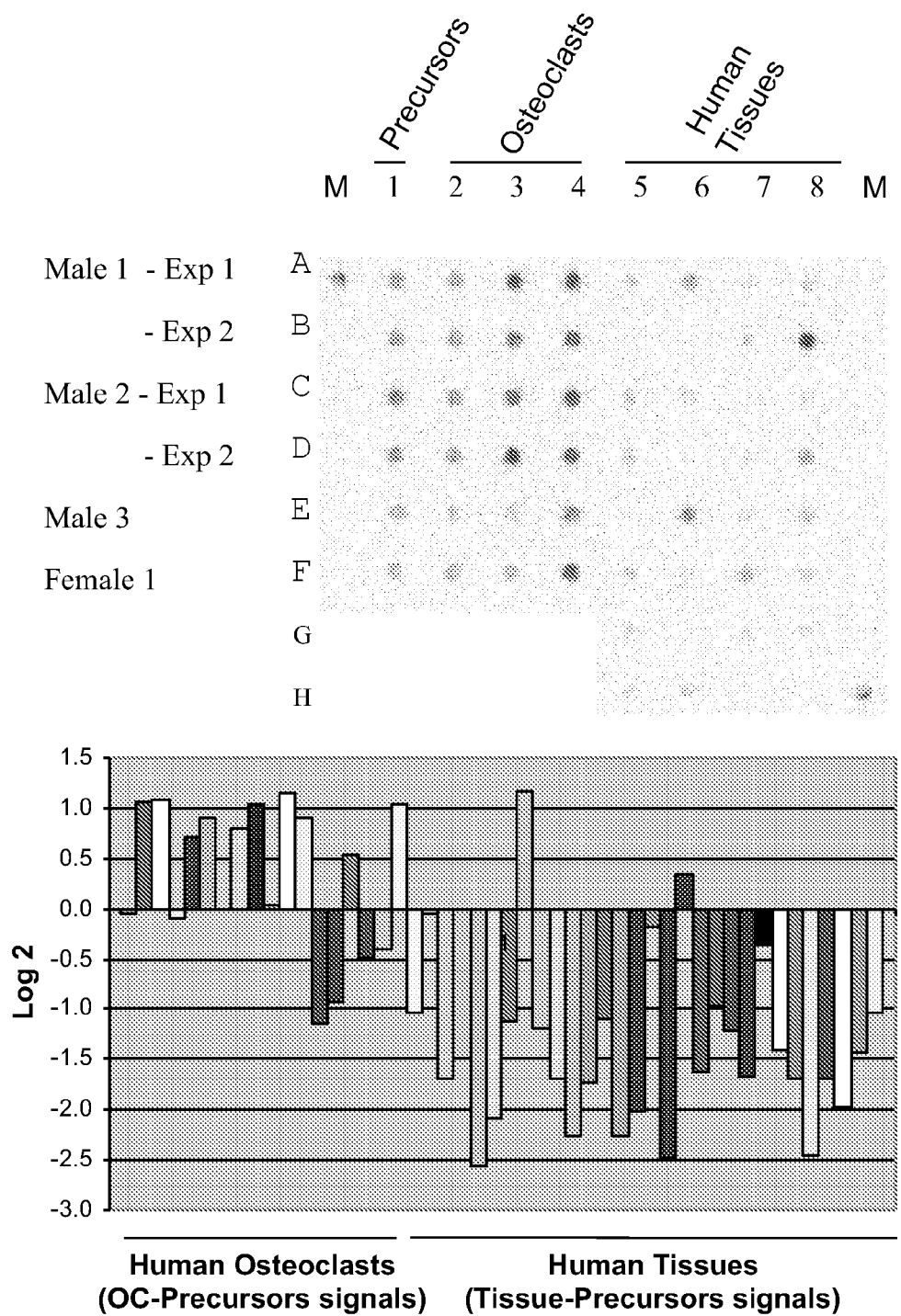
FIG. 23 is a picture of the macroarray hybridization results (upper panel) and quantitation of the signal intensities illustrated by a bar graph (lower panel) showing the differential expression data for STAR selected osteoclast-specific human SEQ. ID. NO. 23 (0103-SL109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 24:
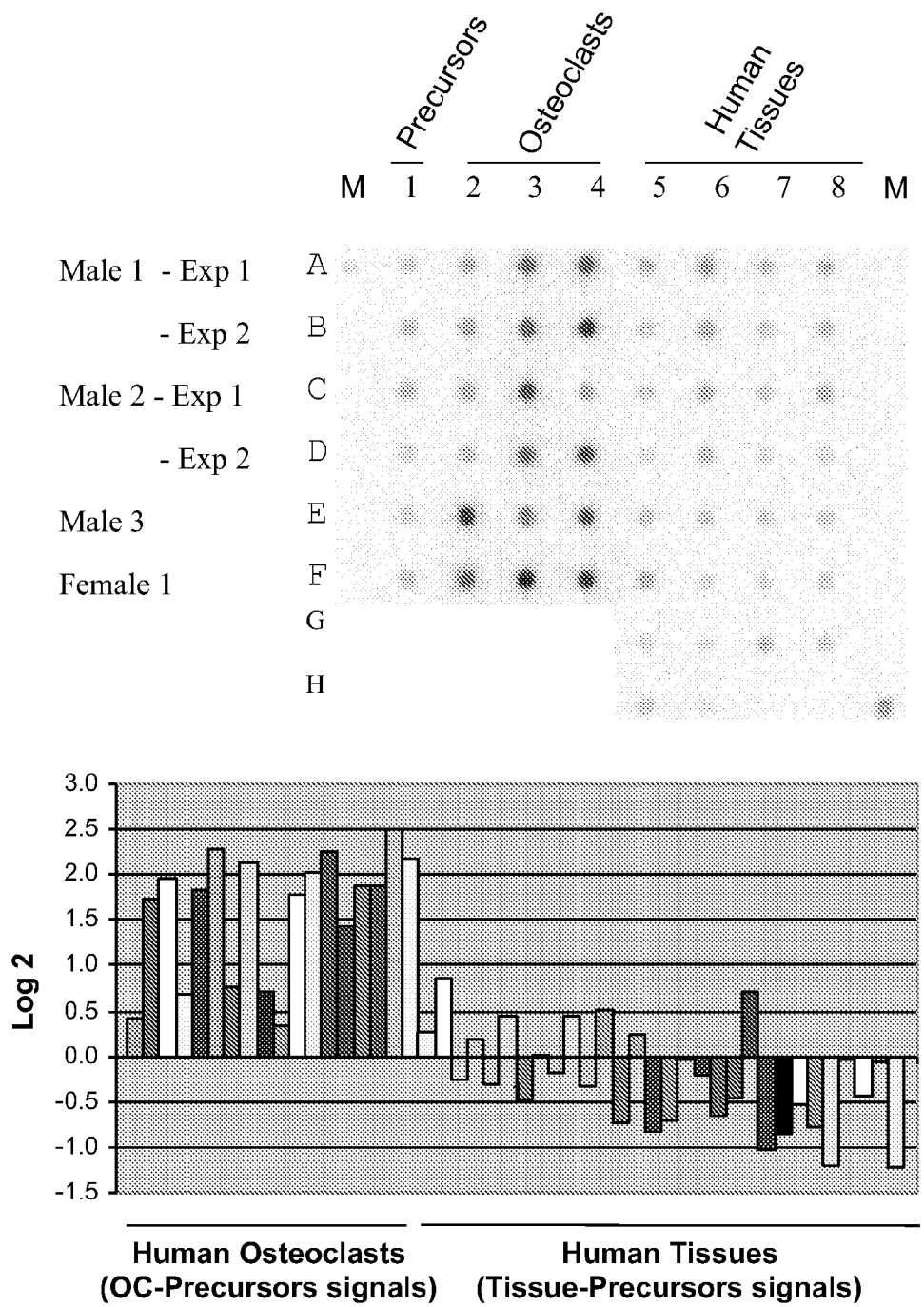
FIG. 24 is a picture of the macroarray hybridization results (upper panel) and quantitation of the signal intensities illustrated by a bar graph (lower panel) showing the differential expression data for STAR selected osteoclast-specific human SEQ. ID. NO. 24 (0139-SL86-1). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 25:
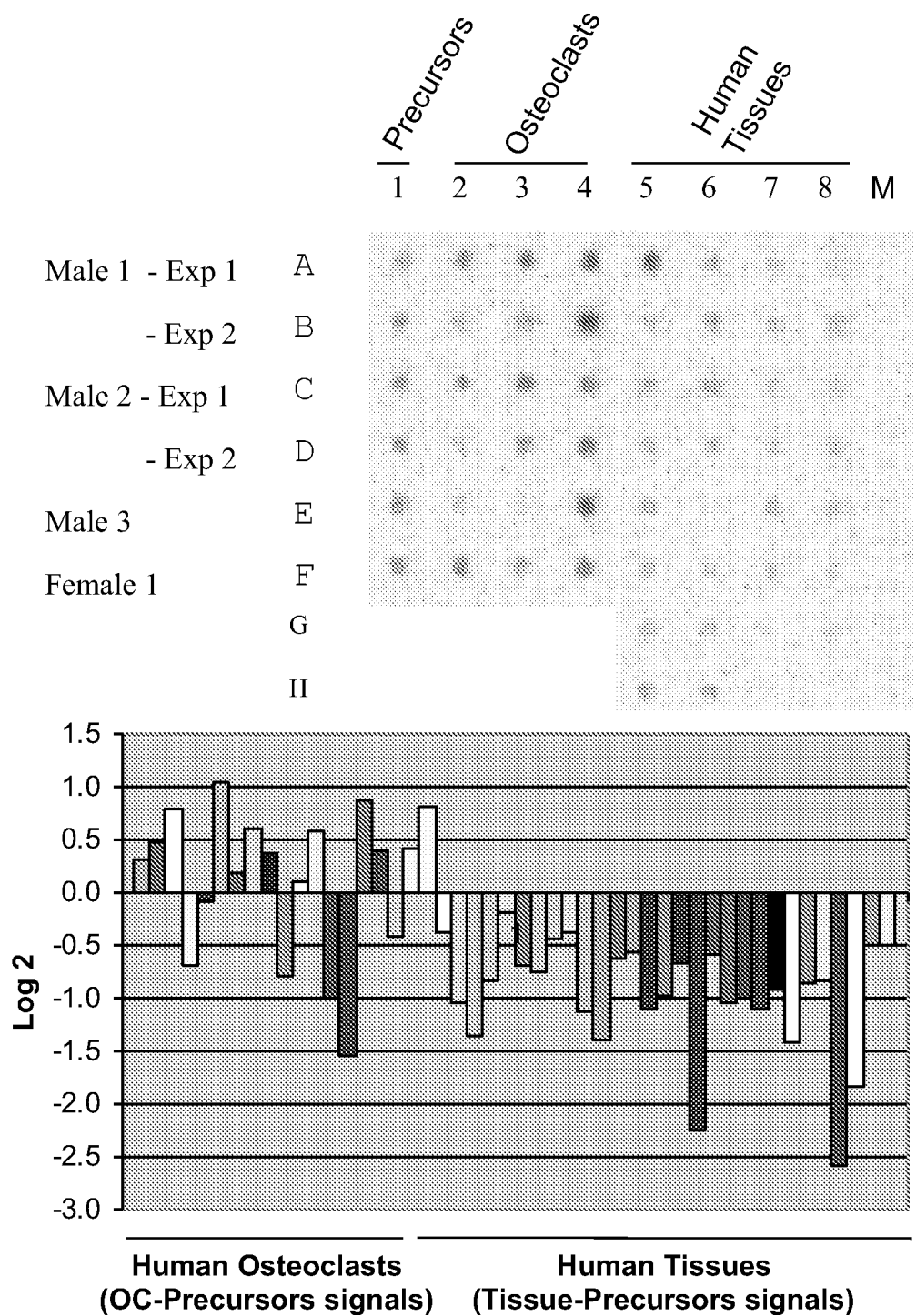
FIG. 25 is a picture of the macroarray hybridization results (upper panel) and quantitation of the signal intensities illustrated by a bar graph (lower panel) showing the differential expression data for STAR selected osteoclast-specific human SEQ. ID. NO. 25 (0636-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 26:
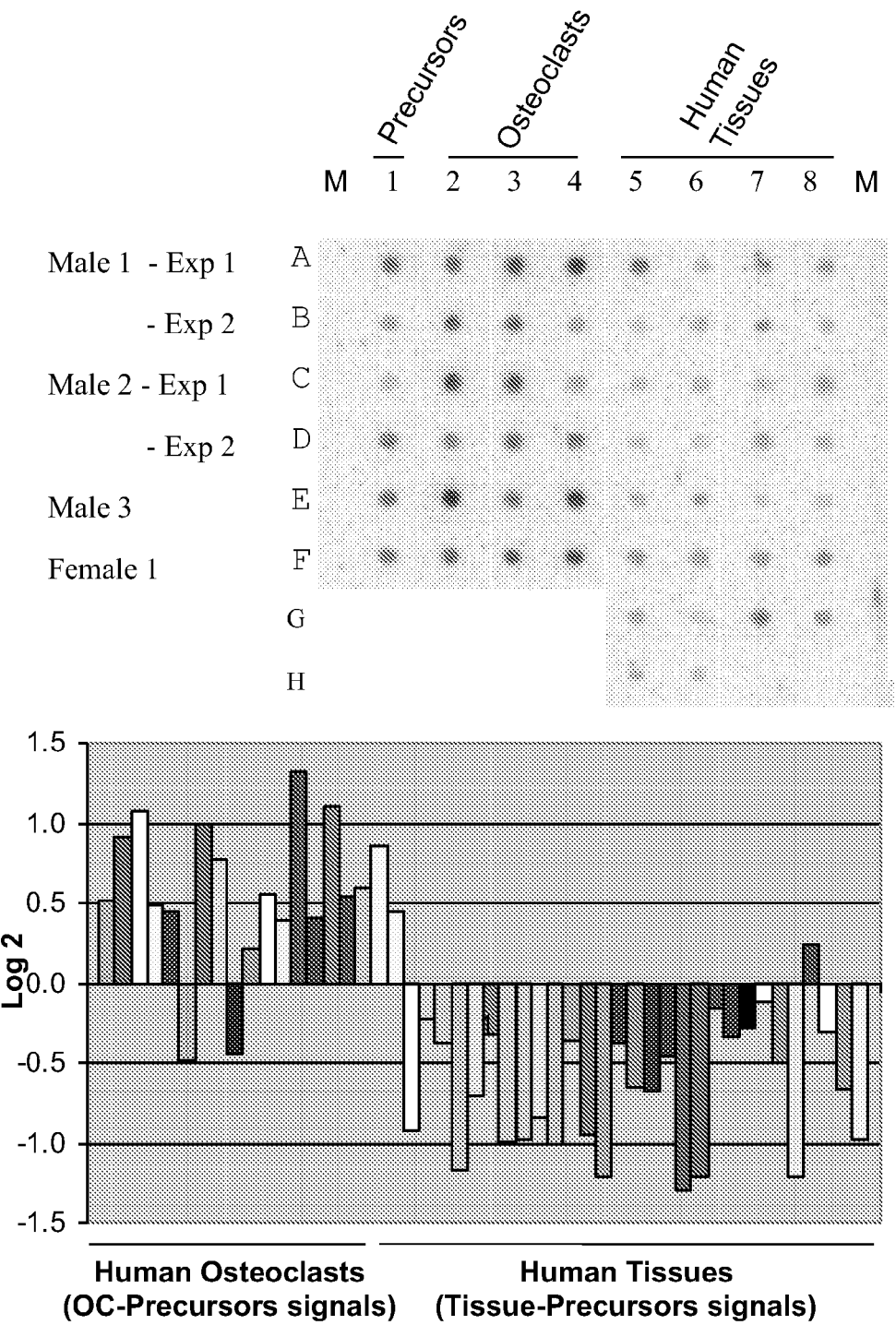
FIG. 26 is a picture of the macroarray hybridization results (upper panel) and quantitation of the signal intensities illustrated by a bar graph (lower panel) showing the differential expression data for STAR selected osteoclast-specific human SEQ. ID. NO. 26 (0747-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 27:
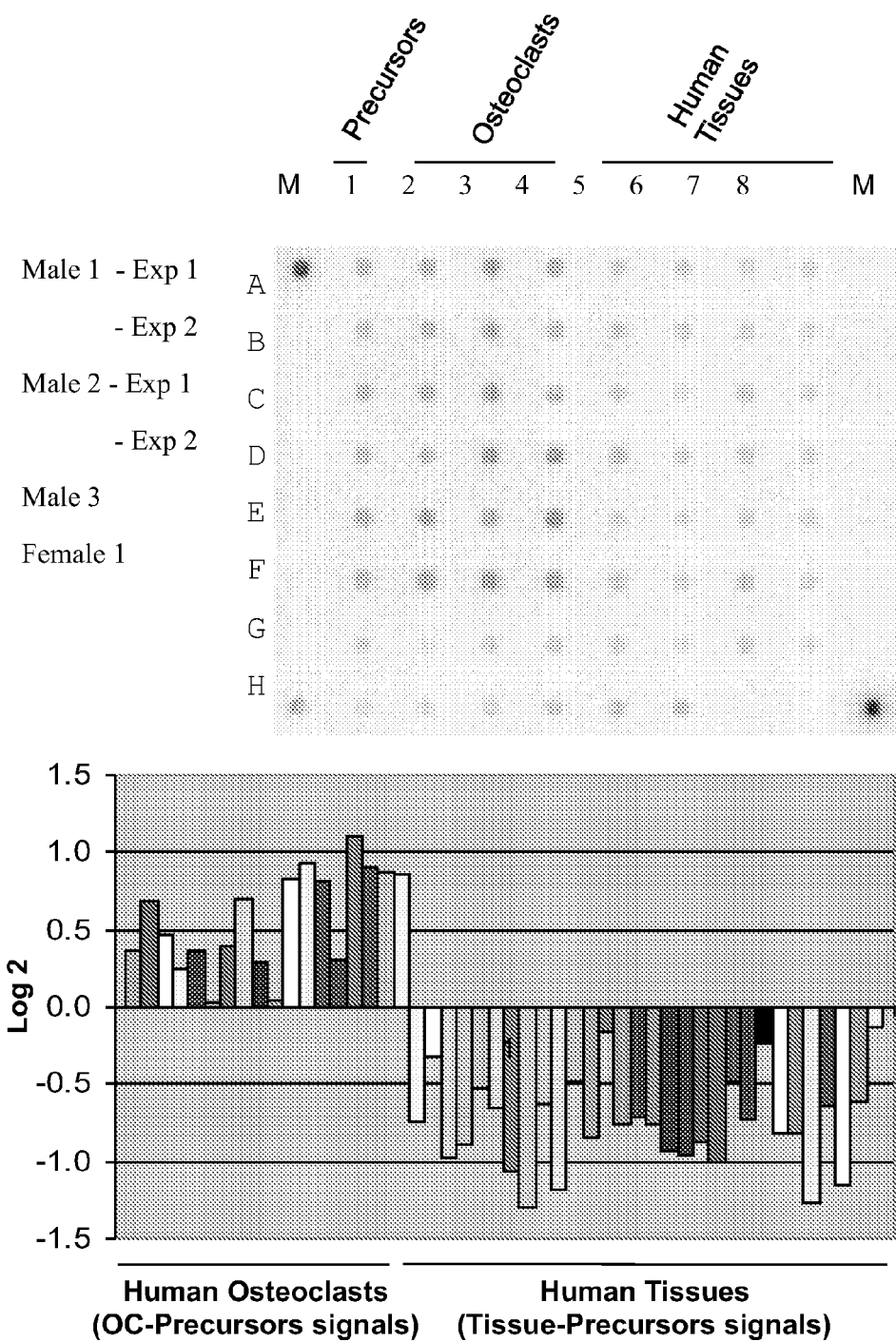
FIG. 27 is a picture of the macroarray hybridization results (upper panel) and quantitation of the signal intensities illustrated by a bar graph (lower panel) showing the differential expression data for STAR selected osteoclast-specific human SEQ. ID. NO. 27 (0763-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 28:
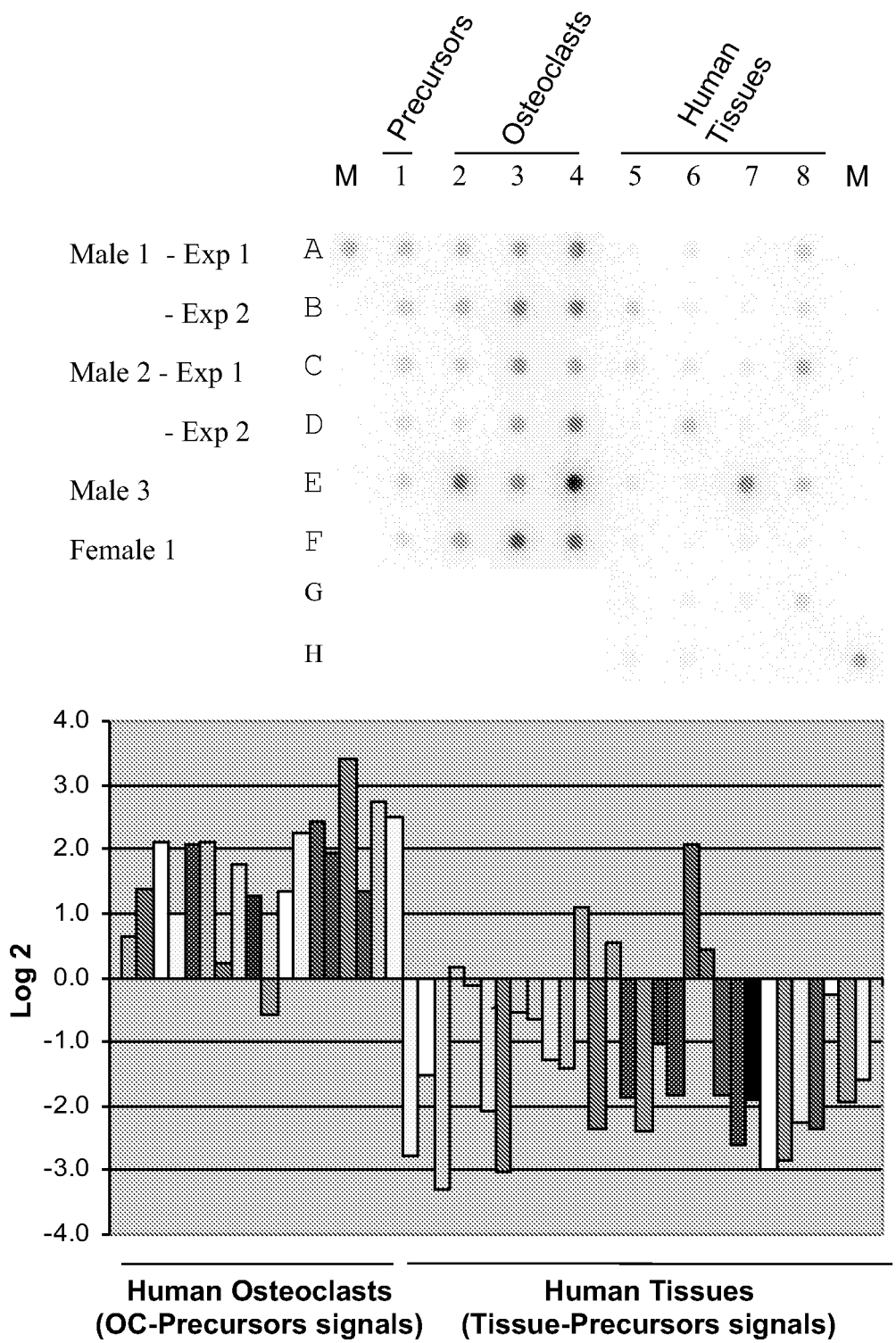
FIG. 28 is a picture of the macroarray hybridization results (upper panel) and quantitation of the signal intensities illustrated by a bar graph (lower panel) showing the differential expression data for STAR selected osteoclast-specific human SEQ. ID. NO. 28 (0198-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 29:
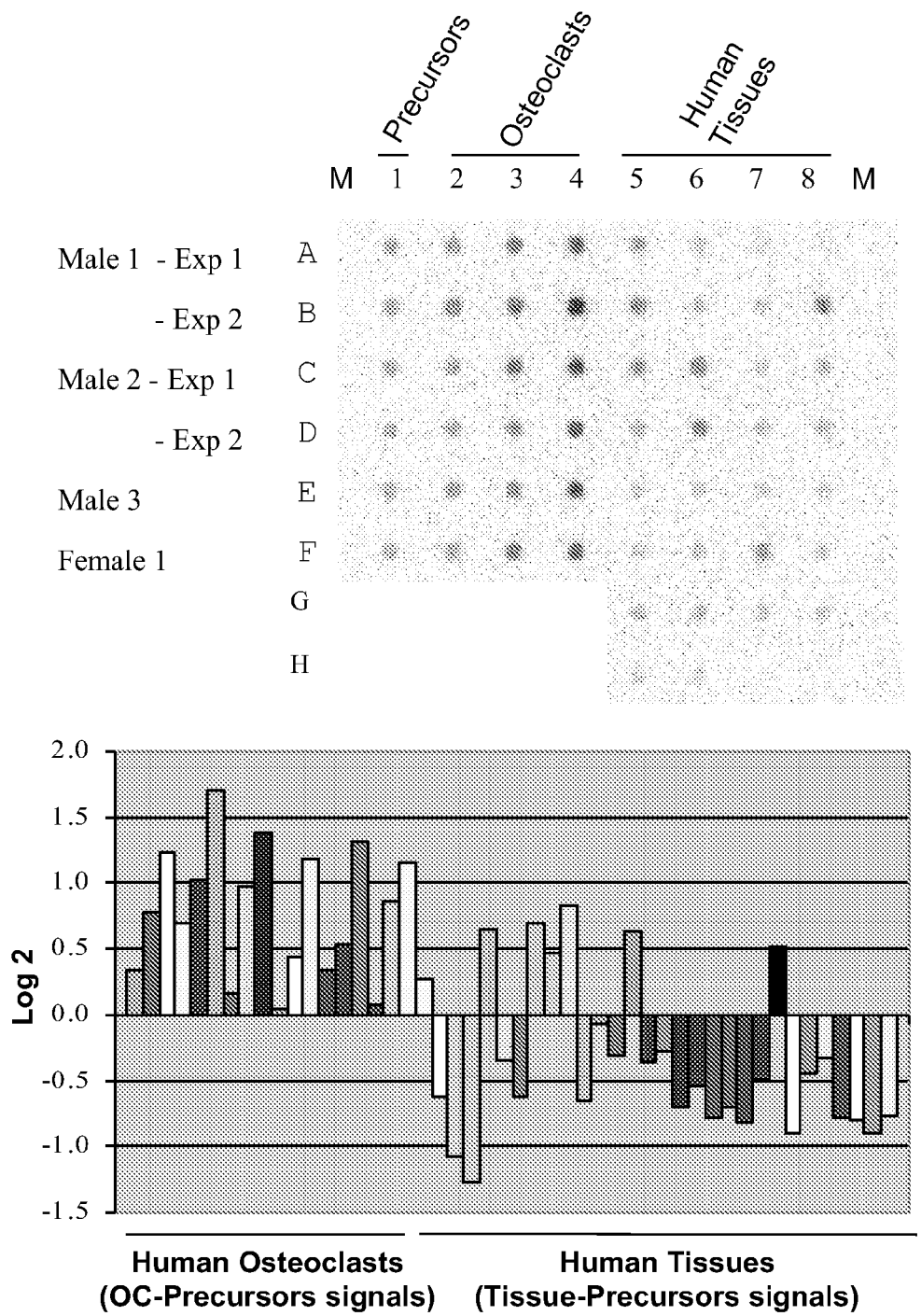
FIG. 29 is a picture of the macroarray hybridization results (upper panel) and quantitation of the signal intensities illustrated by a bar graph (lower panel) showing the differential expression data for STAR selected osteoclast-specific human SEQ. ID. NO. 29 (0662-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 30:
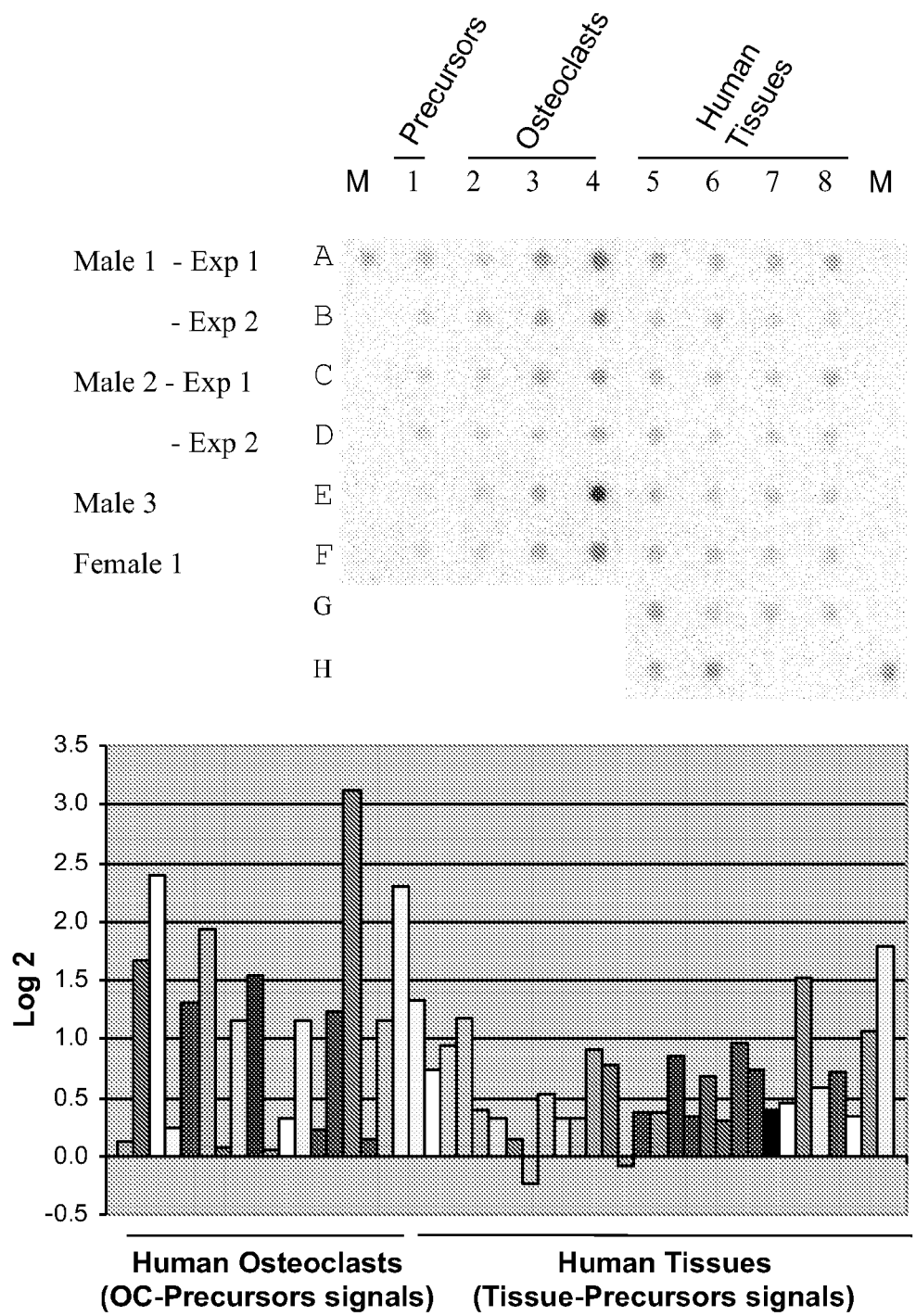
FIG. 30 is a picture of the macroarray hybridization results (upper panel) and quantitation of the signal intensities illustrated by a bar graph (lower panel) showing the differential expression data for STAR selected osteoclast-specific human SEQ. ID. NO. 30 (0269-SL86-1). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 31:
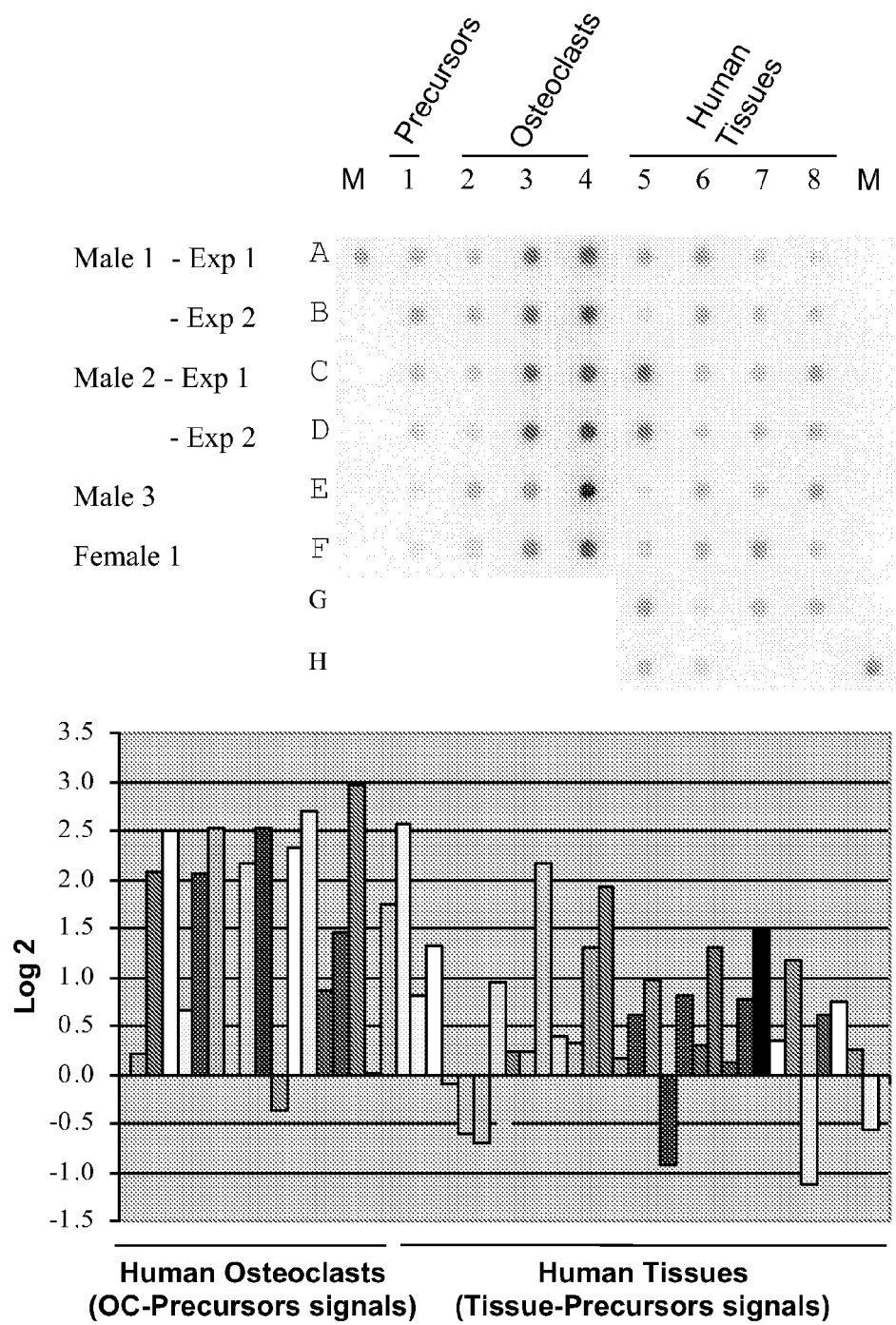
FIG. 31 is a picture of the macroarray hybridization results (upper panel) and quantitation of the signal intensities illustrated by a bar graph (lower panel) showing the differential expression data for STAR selected osteoclast-specific human SEQ. ID. NO. 31 (0685-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 32:
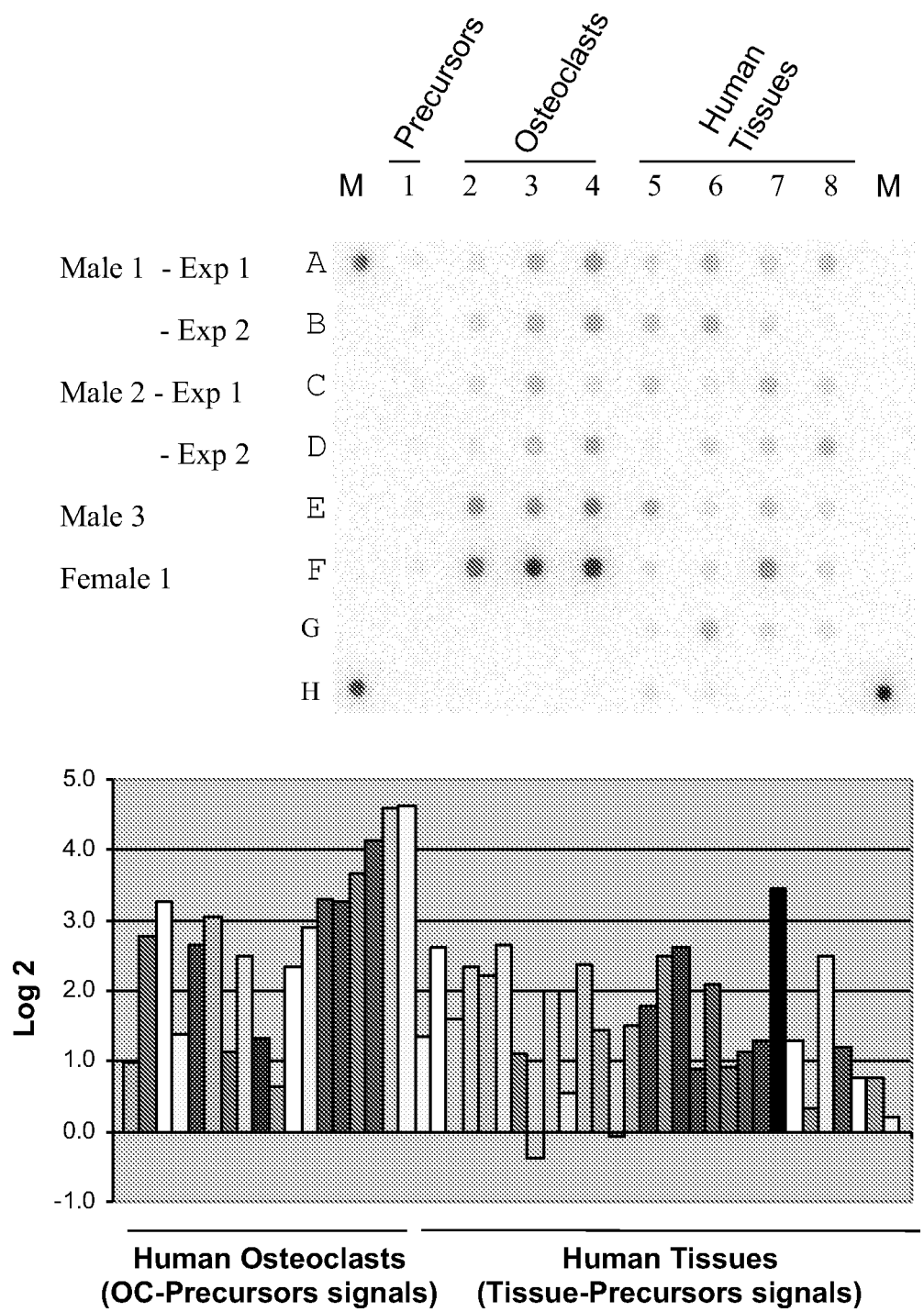
FIG. 32 is a picture of the macroarray hybridization results (upper panel) and quantitation of the signal intensities illustrated by a bar graph (lower panel) showing the differential expression data for STAR selected osteoclast-specific human SEQ. ID. NO. 32 (0315-SL109). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)
Figure 33:
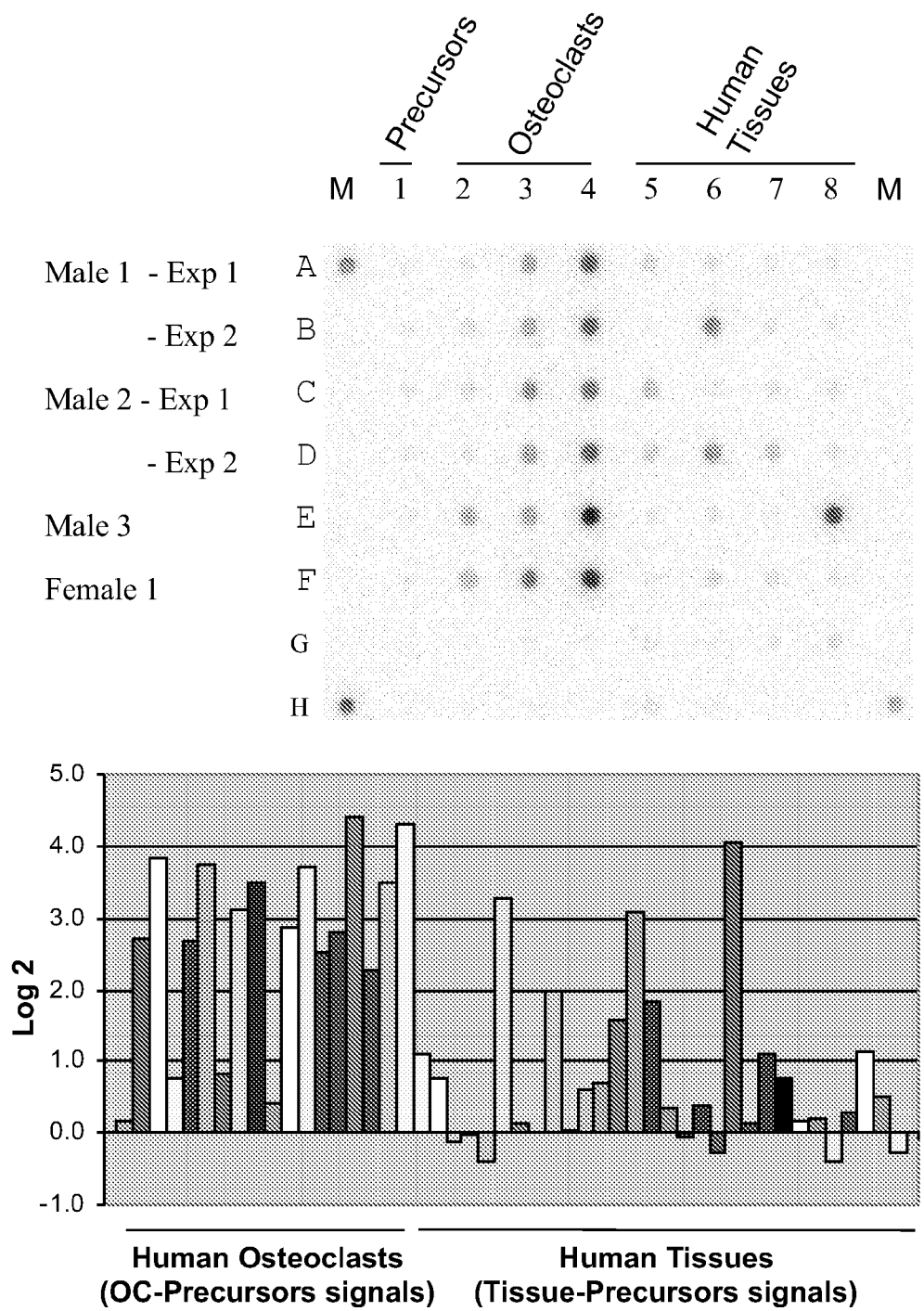
FIG. 33 is a picture of the macroarray hybridization results (upper panel) and quantitation of the signal intensities illustrated by a bar graph (lower panel) showing the differential expression data for STAR selected osteoclast-specific human SEQ. ID. NO. 33 (0551-SL110). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)

The applicant employed a carefully planned strategy to identify and isolate genetic sequences involved in osteoclastogenesis and bone remodeling. The process involved the following steps: 1) preparation of highly representative cDNA libraries using mRNA isolated from precursors and differentiated intermediate and mature osteoclasts of human origin; 2) isolation of sequences upregulated during osteoclastogenesis; 3) identification and characterization of upregulated sequences; 4) selection of upregulated sequences for tissue specificity; and 5) determination of knock-down effects on osteoclastogenesis. The results discussed in this disclosure demonstrate the advantage of targeting osteoclast genes that are specific to this differentiated cell type and provide a more efficient screening method when studying the genetic basis of diseases and disorders. Genes that are known to have a role in other areas of biology have been shown to play a critical role in osteoclastogenesis and osteoclast function. Genes that are known but have not had a role assigned to them until the present disclosure have also been isolated and shown to have a critical role in osteoclastogenesis and osteoclast function. Finally, novel genes have been identified and play a role, however, applicant reserves their disclosure until further study has been completed.

The present invention is illustrated in further details below in a non-limiting fashion.

A—Material and Methods

Commercially available reagents referred to in the present disclosure were used according to supplier's instructions unless otherwise indicated. Throughout the present disclosure certain starting materials were prepared as follows:

B—Preparation of Osteoclast Differentiated Cells

The RAW 264.7 (RAW) osteoclast precursor cell line and human precursor cells (peripheral blood mononuclear cells or CD34+ progenitors) are well known in the art as murine and human models of osteoclastogenesis. These murine and human osteoclasts are therefore excellent sources of materials for isolating and characterizing genes specialized for osteoclast function.

Human primary osteoclasts were differentiated from G-CSF-mobilized peripheral blood mononuclear cells (Cambrex, East Rutherford, N.J.) as described by the supplier in the presence of 35 ng/ml M-CSF and 100 ng/ml RANK ligand. Multinucleated TRAP-staining osteoclasts were visible by 11-14 days. Osteoclasts were also derived from human osteoclasts precursor cells (CD34+ progenitors) (Cambrex, East Rutherford, N.J.) and cultured as described by the supplier. In the latter case, osteoclasts were obtained after 7 days.

RAW cells were purchased from American Type Culture Collection and maintained in high glucose DMEM containing 10% fetal bovine serum and antibiotics. The cells were sub-cultured bi-weekly to a maximum of 10-12 passages. For osteoclast differentiation experiments, RAW cells were seeded in 96-well plates at a density of $4 \times 10^3$ cells/well and allowed to plate for 24 h. Differentiation was induced in high glucose DMEM, 10% charcoal-treated foetal bovine serum (Hyclone, Logan, Utah), 0.05% BSA, antibiotics, 10 ng/ml macrophage colony stimulating factor (M-CSF), and 100 ng/ml receptor activator of NF-kB (RANK) ligand. The plates were re-fed on day 3 and osteoclasts were clearly visible by day 4. Typically, the cells were stained for tartrate-resistant acid phosphatase (TRAP) on day 4 or 5 unless otherwise indicated. For TRAP staining, the cells were washed with PBS and fixed in 10% formaldehyde for 1 h. After two PBS washes, the cells were rendered lightly permeable in 0.2% Triton X-100 in PBS for 5 min before washing in PBS. Staining was conducted at 37° C. for 20-25 min in 0.01% Naphtol AS-MX phosphate, 0.06% Fast Red Violet, 50 mM sodium tartrate, 100 mM sodium acetate, pH 5.2. Cells were visualized microscopically.

C—Method of Isolating Differentially Expressed mRNA

Key to the discovery of differentially expressed sequences unique to osteoclasts is the use of the applicant's patented STAR technology (Subtractive Transcription-based Amplification of mRNA; U.S. Pat. No. 5,712,127 Malek et al., issued on Jan. 27, 1998). In this procedure, mRNA isolated from intermediate and mature osteoclasts is used to prepare "tester RNA", which is hybridized to complementary single-stranded "driver DNA" prepared from osteoclast precursor mRNA and only the un-hybridized "tester RNA" is recovered, and used to create cloned cDNA libraries, termed "subtracted libraries". Thus, the "subtracted libraries" are enriched for differentially expressed sequences inclusive of rare and novel mRNAs often missed by micro-array hybridization analysis. These rare and novel mRNA are thought to be representative of important gene targets for the development of better diagnostic and therapeutic strategies.

The clones contained in the enriched "subtracted libraries" are identified by DNA sequence analysis and their potential function assessed by acquiring information available in public databases (NCBI and GeneCard). The non-redundant clones are then used to prepare DNA micro-arrays, which are used to quantify their relative differential expression patterns by hybridization to fluorescent cDNA probes. Two classes of cDNA probes may be used, those which are generated from either RNA transcripts prepared from the same subtracted libraries (subtracted probes) or from mRNA isolated from different osteoclast samples (standard probes). The use of subtracted probes provides increased sensitivity for detecting the low abundance mRNA sequences that are preserved and enriched by STAR. Furthermore, the specificity of the differentially expressed sequences to osteoclast is measured by hybridizing radio-labeled probes prepared from each selected sequence to macroarrays containing RNA from different osteoclast samples and different normal human tissues. Additionally, Northern blot analysis is performed so as to confirm the presence of one or more specific mRNA species in the osteoclast samples. Following this, the full-length cDNAs representative of the mRNA species and/or spliced variants are cloned in E. coli DH10B.

A major challenge in gene expression profiling is the limited quantities of RNA available for molecular analysis. The amount of RNA isolated from many osteoclast samples or human specimens (needle aspiration, laser capture microdissection (LCM) samples and transfected cultured cells) is often insufficient for preparing: 1) conventional tester and driver materials for STAR; 2) standard cDNA probes for DNA micro-array analysis; 3) RNA macroarrays for testing the specificity of expression; 4) Northern blots and; 5) full-length cDNA clones for further biological validation and characterization etc. Thus, the applicant has developed a proprietary technology called RAMP (RNA Amplification Procedure) (U.S. patent application Ser. No. 11/000,958 published under No. US 2005/0153333A1 on Jul. 14, 2005 and entitled "Selective Terminal Tagging of Nucleic Acids"), which linearly amplifies the mRNA contained in total RNA samples yielding microgram quantities of amplified RNA sufficient for the various analytical applications. The RAMP RNA produced is largely full-length mRNA-like sequences as a result of the proprietary method for adding a terminal sequence tag to the 3'-ends of single-stranded cDNA molecules, for use in linear transcription amplification. Greater than 99.5% of the sequences amplified in RAMP reactions show <2-fold variability and thus, RAMP provides unbiased RNA samples in quantities sufficient to enable the discovery of the unique mRNA sequences involved in osteoclastogenesis.

D—Preparation of Human Osteoclasts Subtracted Library

Two human primary precursor cells from two different donors (Cambrex, East Rutherford, N.J.), and the corresponding intermediate (day 3 and day 7) and mature (days 11-14) osteoclasts were prepared as described above. Isolation of cellular RNA followed by mRNA purification from each was performed using standard methods (Qiagen, Mississauga, ON). Following the teachings of Malek et al. (U.S. Pat. No. 5,712,127), 2 μg of poly A+ mRNA from each sample were used to prepare highly representative (>2×10$^6$ CFU) cDNA libraries in specialized plasmid vectors necessary for preparing tester and driver materials. In each case, first-strand cDNA was synthesized using an oligo dT$_{11}$ primer with 3' locking nucleotides (e.g., A, G or C) and containing a Not I recognition site. Next, second-strand cDNA synthesis was performed according to the manufacturer's procedure for double-stranded cDNA synthesis (Invitrogen, Burlington, ON) and the resulting double-stranded cDNA ligated to linkers containing an Asc I recognition site (New England Biolabs, Pickering, ON). The double-stranded cDNAs were then digested with Asc I and Not I restriction enzymes (New England Biolabs, Pickering, ON), purified from the excess linkers using the cDNA fractionation column from Invitrogen (Burlington, ON) as specified by the manufacturer and each ligated into specialized plasmid vectors-p14 (SEQ. ID. NO:36) and p17+ (SEQ. ID. NO:37) used for preparing tester and driver materials respectively. Thereafter, the ligated cDNAs were transformed into *E. coli* DH10B resulting in the desired cDNA libraries (RAW 264.7-precursor-p14, RAW 264.7-precursor-p17+, RAW 264.7-osteoclasts-p14 and RAW 264.7-osteoclasts-p17+). The plasmid DNA pool for each cDNA library was purified and a 2-μg aliquot of each linearized with Not I restriction enzyme. In vitro transcription of the Not I digested p14 and p17+ plasmid libraries was then performed with T7 RNA polymerase and sp6 RNA polymerase respectively (Ambion, Austin, Tex.).

Next, in order to prepare 3'-represented tester and driver libraries, a 10-μg aliquot of each of the in vitro synthesized RNA was converted to double-stranded cDNA by performing first-strand cDNA synthesis as described above followed by primer-directed (primer OGS 77 for p14 (SEQ. ID. NO:40) and primer OGS 302 for p17+ (SEQ. ID. NO:41)) second-strand DNA synthesis using Advantage-2 Taq polymerase (BD Biosciences Clontech, Mississauga, ON). The sequences corresponding to OGS 77 and OGS 302 were introduced into the in vitro synthesized RNA by way of the specialized vectors used for preparing the cDNA libraries. Thereafter, 6×1-μg aliquots of each double-stranded cDNA was digested individually with one of the following 4-base recognition restriction enzymes Rsa I, Sau3A1, Mse I, Msp I, MinPI I and Bsh 1236I (MBI Fermentas, Burlington, ON), yielding up to six possible 3'-fragments for each RNA species contained in the cDNA library. Following digestion, the restriction enzymes were inactivated with phenol and the set of six reactions pooled. The restriction enzymes sites were then blunted with T4 DNA polymerase and ligated to linkers containing an Asc I recognition site. Each linker-adapted pooled DNA sample was digested with Asc I and Not I restriction enzymes, desalted and ligated to specialized plasmid vectors, p14 and p17 (p17 plasmid vector is similar to the p17+ plasmid vector except for the sequence corresponding to SEQ. ID. NO:41), and transformed into *E. coli* DH10B. The plasmid DNA pool for each p14 and p17 3'-represented library was purified (Qiagen, Mississauga, ON) and a 2-μg aliquot of each digested with Not I restriction enzyme, and transcribed in vitro with either T7 RNA polymerase or sp6 RNA polymerase (Ambion, Austin, Tex.). The resulting p14 3'-represented RNA was used directly as "tester RNA" whereas, the p17 3'-represented RNA was used to synthesize first-strand cDNA as described above, which then served as "driver DNA". Each "driver DNA" reaction was treated with RNase A and RNase H to remove the RNA, phenol extracted and desalted before use.

The following 3'-represented libraries were prepared:

Tester 1 (donor 1—day 3)—human intermediate osteoclast—3' in p14

Tester 2 (donor 1—day 7)—human intermediate osteoclast)—3' in p14

Tester 3 (donor 1—day 11—human mature osteoclast)—3' in p14

Tester 4 (donor 2—day 3)—human intermediate osteoclast)—3' in p14

Tester 5 (donor 2—day 7)—human intermediate osteoclast)—3' in p14

Tester 6 (donor 2—day 13—human mature osteoclast)—3' in p14

Driver 1 (donor 1—day 3)—human precursor—3' in p17

Driver 2 (donor 2—day 3)—human precursor—3' in p17

The tester RNA samples were subtracted following the teachings of U.S. Pat. No. 5,712,127 with the corresponding driver DNA in a ratio of 1:100 for either 1- or 2-rounds following the teachings of Malek et al. (U.S. Pat. No. 5,712, 127). Additionally, control reactions containing tester RNA and no driver DNA, and tester RNA plus driver DNA but no RNase H were prepared. The tester RNA remaining in each reaction after subtraction was converted to double-stranded DNA, and a volume of 5% removed and amplified in a standard PCR reaction for 30-cycles for analytical purposes. The remaining 95% of only the driver plus RNase H subtracted samples were amplified for 4-cycles in PCR, digested with Asc I and Not I restriction enzymes, and one half ligated into the pCATRMAN (SEQ. ID. NO:38) plasmid vector and the other half, into the p20 (SEQ. ID. NO:39) plasmid vector. The ligated materials were transformed into *E. coli* DH10B and individual clones contained in the pCATRMAN libraries were picked for further analysis (DNA sequencing and hybridization) whereas, clones contained in each p20 library were pooled for use as subtracted probes. Each 4-cycles amplified cloned subtracted library contained between 25,000 and 40,000 colonies.

The following cloned subtracted libraries were prepared:

SL90—tester 1 (day 3 osteoclast) minus driver 1 (precursor) (1-round) in pCATRMAN;

SL91—tester 2 (day 7 osteoclast) minus driver 1 (precursor) (1-round) in pCATRMAN;

SL92—tester 3 (day 11 osteoclast) minus driver 1 (precursor) (1-round) in pCATRMAN;

SL108—tester 1 (day 3 osteoclast) minus driver 1 (precursor) (2-rounds) in pCATRMAN;

SL109—tester 2 (day 7 osteoclast) minus driver 1 (precursor) (2-rounds) in pCATRMAN;

SL110—tester 3 (day 11 osteoclast) minus driver 1 (precursor) (2-rounds) in pCATRMAN;

SL93—tester 4 (day 3 osteoclast) minus driver 2 (precursor) (1-round) in pCATRMAN;

SL94—tester 5 (day 7 osteoclast) minus driver 2 (precursor) (1-round) in pCATRMAN;
SL95—tester 6 (day 13 osteoclast) minus driver 2 (precursor) (1-round) in pCATRMAN;
SL87—tester 4 (day 3 osteoclast) minus driver 2 (precursor) (2-rounds) in pCATRMAN;
SL88—tester 5 (day 7 osteoclast) minus driver 2 (precursor) (2-rounds) in pCATRMAN;
SL89—tester 6 (day 11 osteoclast) minus driver 2 (precursor) (2-rounds) in pCATRMAN A 5-μL aliquot of the 30-cycles PCR amplified subtracted materials described above were visualized on a 1.5% agarose gel containing ethidium bromide and then transferred to Hybond N+ (Amersham Biosciences, Piscataway, N.J.) nylon membrane for Southern blot analysis. Using radiolabeled probes specific to the CTSK (cathepsin K; NM_000396.2) gene, which is known to be upregulated in osteoclasts, and GAPDH (glyceraldehyde-3-phosphate dehydrogenase; M32599.1), which is a non-differentially expressed house-keeping gene, it was evident that there was subtraction of GAPDH but not CTSK. Based on these results, it was anticipated that the subtracted libraries would be enriched for differentially expressed upregulated sequences.

E—Sequence Identification and Annotation of Clones Contained in the Subtracted Libraries:

A total of 6,912 individual colonies contained in the pCATRMAN subtracted libraries (SL87-95 and SL108-110) described above were randomly picked using a Qbot (Genetix Inc., Boston, Mass.) into 60 μL of autoclaved water. Then, 42 μL of each was used in a 100-μL standard PCR reaction containing oligonucleotide primers, OGS 1 and OGS 142 and amplified for 40-cycles (94° C. for 10 minutes, 40× (94° C. for 40 seconds, 55° C. for 30 seconds and 72° C. for 2 minutes) followed by 72° C. for 7 minutes) in 96-wells microtitre plates using HotStart™ Taq polymerase (Qiagen. Mississauga, ON). The completed PCR reactions were desalted using the 96-well filter plates (Corning) and the amplicons recovered in 100 μL 10 mM Tris (pH 8.0). A 5-μL aliquot of each PCR reaction was visualized on a 1.5% agarose gel containing ethidium bromide and only those reactions containing a single amplified product were selected for DNA sequence analysis using standard DNA sequencing performed on an ABI 3100 instrument (Applied Biosystems, Foster City, Calif.). Each DNA sequence obtained was given a Sequence Identification Number and entered into a database for subsequent tracking and annotation.

Each sequence was selected for BLAST analysis of public databases (e.g. NCBI). Absent from these sequences were the standard housekeeping genes (GAPDH, actin, most ribosomal proteins etc.), which was a good indication that the subtracted library was depleted of at least the relatively abundant non-differentially expressed sequences.

Once sequencing and annotation of the selected clones were completed, the next step involved identifying those sequences that were actually upregulated in osteoclasts compared to precursors.

F—Hybridization Analysis for Identifying Upregulated Sequences

The PCR amplicons representing the annotated sequences from the pCATRMAN libraries described above were used to prepare DNA microarrays. The purified PCR amplicons contained in 70 μL of the PCR reactions prepared in the previous section was lyophilized and each reconstituted in 20 μL of spotting solution comprising 3×SSC and 0.1% sarkosyl. DNA micro-arrays of each amplicon in triplicate were then prepared using CMT-GAP2 slides (Corning, Corning, N.Y.) and the GMS 417 spotter (Affymetrix, Santa Clara, Calif.).

The DNA micro-arrays were then hybridized with either standard or subtracted cy3 and cy5 labelled cDNA probes as recommended by the supplier (Amersham Biosciences, Piscataway, N.J.). The standard cDNA probes were synthesized using RAMP amplified RNA prepared from the different human osteoclast samples and the corresponding precursors. It is well known to the skilled artisan that standard cDNA probes only provide limited sensitivity of detection and consequently, low abundance sequences contained in the cDNA probes are usually missed. Thus, the hybridization analysis was also performed using cy3 and cy5 labelled subtracted cDNA probes prepared from subtracted libraries representing the different tester and driver materials. These subtracted libraries may be enriched for low abundance sequences as a result of following the teachings of Malek et al., and therefore, may provide increased detection sensitivity.

All hybridization reactions were performed using the dye-swap procedure as recommended by the supplier (Amersham Biosciences, Piscataway, N.J.) and approximately 500 putatively differentially expressed upregulated (>2-fold) sequences were selected for further analysis.

G—Determining Osteoclast Specificity of the Differentially Expressed Sequences Identified:

The differentially expressed sequences identified in Section F for the different human osteoclast subtracted libraries were tested for osteoclast specificity by hybridization to nylon membrane-based macroarrays. The macroarrays were prepared using RAMP amplified RNA from human precursors and osteoclasts (intermediate and mature) of six independent experiments from 4 different donors (3 males and 1 female), and 30 normal human tissues (adrenal, liver, lung, ovary, skeletal muscle, heart, cervix, thyroid, breast, placenta, adrenal cortex, kidney, vena cava, fallopian tube, pancreas, testicle, jejunum, aorta, esophagus, prostate, stomach, spleen, ileum, trachea, brain, colon, thymus, small intestine, bladder and duodenum) purchased commercially (Ambion, Austin, Tex.). Because of the limited quantities of mRNA available for many of these samples, it was necessary to first amplify the mRNA using the RAMP methodology. Each amplified RNA sample was reconstituted to a final concentration of 250 ng/μL in 3×SSC and 0.1% sarkosyl in a 96-well microtitre plate and 1 μL spotted onto Hybond N+ nylon membranes using the specialized MULTI-PRINT™ apparatus (VP Scientific, San Diego, Calif.), air dried and UV-cross linked. A total of 400 different sequences selected from SL87-95 and SL108-110 were individually radiolabeled with $\alpha$-$^{32}$P-dCTP using the random priming procedure recommended by the supplier (Amersham, Piscataway, N.J.) and used as probes on the macroarrays. Hybridization and washing steps were performed following standard procedures well known to those skilled in the art.

Of the 500 sequences tested, approximately 85% were found to be upregulated in all of the osteoclast RNA samples that were used to prepare the macroarrays. However, many of these sequences were also readily detected in a majority of the different normal human tissues. Based on these results, those sequences that appeared to be associated with experimental variability and those that were detected in many of the other human tissues at significantly elevated levels were eliminated. Consequently, only 35 sequences, which appeared to be upregulated and highly osteoclast-specific, were selected for biological validation studies. Included in this set of 35 genes were 4 (SEQ. ID. NOs. 30-33) where there was a significant upregulation in mature osteoclasts compared to most normal tissues but because the expression of these genes were overall lower in the precursor cells, they appeared to be elevated in the normal tissues after quantitation FIG. 30-33;

bar graph). However, their expression in the normal tissues was still relatively lower than that of the mature osteoclasts. Thus, these genes may still be important regulators in osteoclastogenesis and bone resorption and were therefore selected for biological validation. This subset of 35 sequences does not included genes also identified such as, CTSK, TRAP, MMP9, CST3 and CKB amongst others since these were previously reported in the literature to be upregulated in osteoclasts. The macroarray data for CST3 (SEQ. ID. NO. 34) is included to exemplify the hybridization pattern and specificity of a gene that is already known to be a key regulator of the osteoclast resorption process. One gene (ANKH; SEQ. ID. NO. 17) was included in the subset of 35 genes although it was previously reported in the database (NCBI-Gene) to play a role in bone mineralization. However, the observed bone phenotype resulting from mutations in the ANKH gene was not specifically linked to its upregulation in osteoclasts. Thus our data suggests the important role for ANKH may be associated with osteoclast activity during bone remodeling.

FIGS. 1-33, 38 and 39 show the macroarray patterns and quantitation of the hybridization signals of the osteoclasts and normal human tissues relative to precursor cells for the 35 sequences selected for biological validation. Amongst the 35 selected sequences were 24 genes with functional annotation 9 genes with no functional annotation and 2 novel sequences (genomic hits). The identification of gene products involved in regulating osteoclast differentiation and function has thus led to the discovery of novel targets for the development of new and specific therapies of disease states characterized by abnormal bone remodeling. Representative sequences summarized in Table 1 are presented below and corresponding sequences are illustrated in Table 5.

SEQ. ID. NO:1:
SEQ. ID. NO:1 (Table 5) corresponds to a previously identified gene that encodes a hypothetical protein, LOC284266 with an unknown function (see Table 1). We have demonstrated that this gene is markedly upregulated in intermediate and mature osteoclast compared to precursor cells and other normal human tissues (FIG. 1), which have not been previously reported. Thus, it is believed that this gene may be required for osteoclastogenesis and/or bone remodeling.

SEQ. ID. NO:2:
SEQ. ID. NO:2 (Table 5) corresponds to a previously identified gene that encodes a predicted open reading frame, C6 or f82 with an unknown function (see Table 1). We have demonstrated that this gene is markedly upregulated in intermediate and mature osteoclast compared to precursor cells and other normal human tissues (FIG. 2), which have not been previously reported. At least 5 transcript variants of this gene coding for 3 protein isoforms has been identified so far (NCBI). Thus, it is believed that this gene may be required for osteoclastogenesis and/or bone remodeling.

SEQ. ID. NO:3:
SEQ. ID. NO:3 (Table 5) corresponds to a previously identified gene that encodes a hypothetical protein, LOC133308 with an unknown function (see Table 1) but may be involved in the process of pH regulation. We have demonstrated that this gene is markedly upregulated in intermediate and mature osteoclast compared to precursor cells and other normal human tissues (FIG. 3), which have not been previously reported. Thus, it is believed that this gene may be required for osteoclastogenesis and/or bone remodeling.

SEQ. ID. NO:4:
SEQ. ID. NO:4 (Table 5) corresponds to a previously identified gene that encodes a hypothetical protein, LOC116211 with an unknown function (see Table 1). We have demonstrated that this gene is markedly upregulated in intermediate and mature osteoclast compared to precursor cells and other normal human tissues (FIG. 4), which have not been previously reported. Thus, it is implied that this gene may be required for osteoclastogenesis and/or bone remodeling.

SEQ. ID. NO:5
SEQ. ID. NO:5 (Table 5) corresponds to a previously identified gene that encodes a predicted protein, LOC151194 (similar to hepatocellular carcinoma-associated antigen HCA557b), with unknown function (see Table 1). We have demonstrated that this gene is markedly upregulated in intermediate and mature osteoclast compared to precursor cells and other normal human tissues (FIG. 5), which have not been previously reported. Thus, it is believed that this gene may be required for osteoclastogenesis and/or bone remodeling.

SEQ. ID. NO:6:
SEQ. ID. NO:6 (Table 5) corresponds to a previously identified gene that encodes a protein, chemokine (C—X—C motif) ligand 5 (CXCL5), which is an inflammatory chemokine that belongs to the CXC chemokine family (see Table 1). We have demonstrated that this gene is significantly upregulated in mature osteoclast compared to precursor cells and other normal human tissues (FIG. 6), which have not been previously reported. Thus, it is believed that this gene may be required for osteoclastogenesis and/or bone remodeling.

SEQ. ID. NO:7:
SEQ. ID. NO:7 (Table 5) corresponds to a previously identified gene that encodes a protein, ATPase, H+ transporting, lysosomal accessory protein 2 (ATP6AP2), which is associated with adenosine triphosphatases (ATPases). Proton-translocating ATPases have fundamental roles in energy conservation, secondary active transport, acidification of intracellular compartments, and cellular pH homeostasis (see Table 1). We have demonstrated that this gene is markedly upregulated in mature osteoclast compared to precursor cells and other normal human tissues (FIG. 7), which have not been previously reported. Thus, it is believed that this gene may be required for osteoclastogenesis and/or bone remodeling.

SEQ. ID. NO:8
SEQ. ID. NO:8 (Table 5) corresponds to a previously identified gene that encodes a protein, ubiquitin-specific protease 12-like 1 (USP12), which is associated with ubiquitin-dependent protein catabolism (see Table 1). We have demonstrated that this gene is markedly upregulated in intermediate and mature osteoclast compared to precursor cells and other normal human tissues (FIG. 8), which have not been previously reported. Thus, it is believed that this gene may be required for osteoclastogenesis and/or bone remodeling.

SEQ. ID. NO:9
SEQ. ID. NO:9 (Table 5) corresponds to a previously identified gene that encodes a protein, Ubiquitin-conjugating enzyme E2E 1 (UBC4/5 homolog, yeast) (UBE2E1), which is associated with ubiquitin-dependent protein catabolism (see Table 1). So far, there are 2 transcript variants and protein isoforms reported for this gene. We have demonstrated that this gene is significantly upregulated in mature osteoclast compared to precursor cells and other normal human tissues (FIG. 9), which have not been previously reported. Thus, it is believed that this gene may be required for osteoclastogenesis and/or bone remodeling.

SEQ. ID. NO:10
SEQ. ID. NO:10 (Table 5) corresponds to a previously identified gene that encodes a protein, Emopamil binding protein-like (EBPL), which may have cholestenol delta-isomerase activity (see Table 1). We have demonstrated that this gene is markedly upregulated in intermediate and mature osteoclast compared to precursor cells and other normal human tissues (FIG. 10), which have not been previously reported. Thus, it is believed that this gene may be required for osteoclastogenesis and/or bone remodeling.

SEQ. ID. NO:11

SEQ. ID. NO:11 (Table 5) corresponds to a previously identified gene that encodes a protein, development and differentiation enhancing factor 1 (DDEF1), which may be involved in cell motility and adhesion (see Table 1). We have demonstrated that this gene is markedly upregulated in intermediate and mature osteoclast compared to precursor cells and other normal human tissues (FIG. 11), which have not been previously reported. Thus, it is believed that this gene may be required for osteoclastogenesis and/or bone remodeling.

SEQ. ID. NO:12

SEQ. ID. NO:12 (Table 5) corresponds to a previously identified gene that encodes a protein, member 7 of the SLAM family (SLAM7), which may have receptor activity and involved in cell adhesion but still not fully characterized (see Table 1). We have demonstrated that this gene is markedly upregulated in mature osteoclast compared to precursor cells and other normal human tissues (FIG. 12), which have not been previously reported. Thus, it is believed that this gene may be required for osteoclastogenesis and/or bone remodeling.

SEQ. ID. NO:13

SEQ. ID. NO:13 (Table 5) corresponds to a previously identified gene that encodes a protein, Ubiquitin-conjugating enzyme E2E 3 (UBC4/5 homolog, yeast) (UBE2E3), which is associated with ubiquitin-dependent protein catabolism (see Table 1). There are 2 transcript variants documented so far, which code for the same protein isofrom. We have demonstrated that this gene is markedly upregulated in mature osteoclast compared to precursor cells and other normal human tissues (FIG. 1), which have not been previously reported. Thus, it is believed that this gene may be required for osteoclastogenesis and/or bone remodeling.

SEQ. ID. NO:14

SEQ. ID. NO:14 (Table 5) corresponds to a previously identified gene that encodes a protein, Galanin (GAL), which is associated with neuropeptide hormone activity (see Table 1). We have demonstrated that this gene is markedly upregulated in intermediate and mature osteoclast compared to precursor cells and other normal human tissues except for colon (FIG. 14), which have not been previously reported. Thus, it is believed that this gene may be required for osteoclastogenesis and/or bone remodeling.

SEQ. ID. NO:15

SEQ. ID. NO:15 (Table 5) corresponds to a previously identified gene that encodes a protein, Cytokine-like nuclear factor n-pac (N-PAC), which may have oxireductase activity (see Table 1). We have demonstrated that this gene is markedly upregulated in intermediate and mature osteoclast compared to precursor cells and other normal human tissues (FIG. 15), which have not been previously reported. However, some overexpression of this gene but still way below that of mature osteoclasts were seen in heart, fallopian tube, spleen and cervix. Thus, it is believed that this gene may be required for osteoclastogenesis and/or bone remodeling.

SEQ. ID. NO:16

SEQ. ID. NO:16 (Table 5) corresponds to a previously identified gene that encodes a protein, Integrin alpha X (antigen CD11C (p150), alpha polypeptide) (ITGAX), which is involved in cell adhesion and ion binding (see Table 1). We have demonstrated that this gene is markedly upregulated in intermediate and mature osteoclast compared to precursor cells and other normal human tissues (FIG. 16), which have not been previously reported. Minimal expression but much lower than mature osteoclasts is observed for this gene in adrenal, lung and spleen amongst the normal tissues. Thus, it is believed that this gene may be required for osteoclastogenesis and/or bone remodeling.

SEQ. ID. NO:17

SEQ. ID. NO:17 (Table 5) corresponds to a previously identified gene that encodes a protein, Ankylosis, progressive homolog (mouse) (ANKH), which is involved in regulating pyrophosphate levels, suggested as a possible mechanism regulating tissue calcification (see Table 1). We have demonstrated that this gene is markedly upregulated in intermediate and mature osteoclast compared to precursor cells and other normal human tissues (FIG. 17), which have not been previously reported. However, this gene has been reported to be involved in bone mineralization but without evidence of its upregulation in osteoclasts (Malkin et al., 2005). Thus, it is believed that this gene may be required for osteoclastogenesis and/or bone remodeling.

SEQ. ID. NO:18

SEQ. ID. NO:18 (Table 5) corresponds to a previously identified gene that encodes a protein, ATPase, H+ transporting, lysosomal 70 kD, V1 subunit A, which is involved in hydrogen-transporting ATPase activity, rotational mechanism (see Table 1). We have demonstrated that this gene is markedly upregulated in mature osteoclast compared to precursor cells and other normal human tissues (FIG. 18), which have not been previously reported. Thus, it is believed that this gene may be required for osteoclastogenesis and/or bone remodeling.

SEQ. ID. NO:19

SEQ. ID. NO:19 (Table 5) corresponds to a previously identified gene that encodes a predicted open reading frame coding for protein, FLJ10874 (chromosome 1 open reading frame 75), which has no known function (see Table 1). We have demonstrated that this gene is significantly upregulated in mature osteoclast compared to precursor cells and other normal human tissues (FIG. 19), which have not been previously reported. Thus, it is believed that this gene may be required for osteoclastogenesis and/or bone remodeling.

SEQ. ID. NO:20

SEQ. ID. NO:20 (Table 5) corresponds to a previously identified gene that encodes a protein, Integrin beta 1 binding protein 1 (ITGB1BP1), which has an important role during integrin-dependent cell adhesion (see Table 1). Two transcript variants and protein isoforms for this gene has been isolated. We have demonstrated that this gene is significantly upregulated in mature osteoclast compared to precursor cells and other normal human tissues (FIG. 20), which have not been previously reported. Thus, it is believed that this gene may be required for osteoclastogenesis and/or bone remodeling.

SEQ. ID. NO:21

SEQ. ID. NO:21 (Table 5) corresponds to a previously identified gene that encodes a protein, Thioredoxin-like 5 (TXNL5), which has no known function (see Table 1). We have demonstrated that this gene is significantly upregulated in intermediate and mature osteoclast compared to precursor cells and other normal human tissues with the exception of esophagus (FIG. 21), which have not been previously reported. Thus, it is believed that this gene may be required for osteoclastogenesis and/or bone remodeling.

SEQ. ID. NO:22

SEQ. ID. NO:22 (Table 5) corresponds to a previously identified gene that encodes a protein, C-type lectin domain family 4, member E (CLECSF9), which has no known specific function (see Table 1). Members of this family share a common protein fold and have diverse functions, such as cell adhesion, cell-cell signaling, glycoprotein turnover, and roles in inflammation and immune response. We have demonstrated that this gene is significantly upregulated in mature osteoclast compared to precursor cells and other normal human tissues with the exception of lung and spleen (FIG. 22), which have not been previously reported. At this point, we cannot rule out cross hybridization to family members in lung and spleen. Thus, it is believed that this gene may be required for osteoclastogenesis and/or bone remodeling.

SEQ. ID. NO:23

SEQ. ID. NO:23 (Table 5) corresponds to a previously identified gene that encodes a protein, RAB33A, member RAS oncogene family (RAB33A), which has GTPase activity (see Table 1). We have demonstrated that this gene is significantly upregulated in intermediate and mature osteoclast compared to precursor cells and other normal human tissues with the exception of brain (FIG. 23), which have not been previously reported. Thus, it is believed that this gene may be required for osteoclastogenesis and/or bone remodeling.

SEQ. ID. NO:24

SEQ. ID. NO:24 (Table 5) corresponds to a previously identified gene that encodes a protein, Down syndrome critical region gene 1 (DSCR1), which interacts with calcineurin A and inhibits calcineurin-dependent signaling pathways, possibly affecting central nervous system development (see Table 1). There are 3 transcript variants and protein isoforms isolated so far. We have demonstrated that this gene is markedly upregulated in intermediate and mature osteoclast compared to precursor cells and other normal human tissues (FIG. 24), which have not been previously reported. Thus, it is believed that this gene may be required for osteoclastogenesis and/or bone remodeling.

SEQ. ID. NO:25

SEQ. ID. NO:25 (Table 5) corresponds to a previously identified gene that encodes a protein, SNARE protein Ykt6 (YKT6), which is one of the SNARE recognition molecules implicated in vesicular transport between secretory compartments (see Table 1). We have demonstrated that this gene is significantly upregulated in mature osteoclast compared to precursor cells and other normal human tissues (FIG. 25), which have not been previously reported. Thus, it is believed that this gene may be required for osteoclastogenesis and/or bone remodeling.

SEQ. ID. NO:26

SEQ. ID. NO:26 (Table 5) corresponds to a previously identified gene that encodes a protein, Actinin, alpha 1 (ACTN1), which is cytoskeletal, and involved in actin binding and adhesion (see Table 1). We have demonstrated that this gene is significantly upregulated in intermediate and mature osteoclast compared to precursor cells and other normal human tissues (FIG. 26), which have not been previously reported. Thus, it is believed that this gene may be required for osteoclastogenesis and/or bone remodeling.

SEQ. ID. NO:27

SEQ. ID. NO:27 (Table 5) corresponds to a previously identified gene that encodes a protein, ClpX caseinolytic peptidase X homolog (*E. coli*) (CLPX), which may be involved in protein turnover (see Table 1). We have demonstrated that this gene is significantly upregulated in intermediate and mature osteoclast compared to precursor cells and other normal human tissues (FIG. 27), which have not been previously reported. Thus, it is believed that this gene may be required for osteoclastogenesis and/or bone remodeling.

SEQ. ID. NO:28

SEQ. ID. NO:28 (Table 5) corresponds to a previously identified gene that encodes a protein, Carbonic anhydrase II (CA2), which has carbonate dehydratase activity (see Table 1). Defects in this enzyme are associated with osteopetrosis and renal tubular acidosis (McMahon et al., 2001) and have been shown to be upregulated in mature osteoclasts under induced acidic pH conditions (Biskobing and Fan, 2000). We have demonstrated that this gene is markedly upregulated in intermediate and mature osteoclast compared to precursor cells independent of induced acidic pH conditions and other normal human tissues (FIG. 28), which have not been previously reported. However, elevated expression of this gene was also observed in colon and stomach but still significantly below the levels of mature osteoclasts. Thus, it is believed that this gene may be required for osteoclastogenesis and/or bone remodeling.

SEQ. ID. NO:29

SEQ. ID. NO:29 (Table 5) corresponds to a previously identified gene that encodes a protein, Sorting nexin 10 (SNX10), whose function has not been determined (see Table 1). We have demonstrated that this gene is markedly upregulated in mature osteoclast compared to precursor cells and most normal human tissues (FIG. 29), which have not been previously reported. However, elevated expression of this gene was also observed in liver, brain, lung, adrenal cortex, kidney and spleen but still significantly below the levels of mature osteoclasts. Thus, it is believed that this gene may be required for osteoclastogenesis and/or bone remodeling.

SEQ. ID. NO:30

SEQ. ID. NO:30 (Table 5) corresponds to a previously identified gene that encodes a protein, Tudor domain containing 3 (TDRD3), whose function has not been determined but may be involved in nucleic acid binding (see Table 1). We have demonstrated that this gene is markedly upregulated in mature osteoclast compared to precursor cells and most normal human tissues (FIG. 30), which have not been previously reported. However, above baseline expression of this gene was observed in the normal human tissues because of a lower than normal precursor level but it was still significantly below the levels of mature osteoclasts. Thus, this gene was still selected. Thus, it is believed that this gene may be required for osteoclastogenesis and/or bone remodeling.

SEQ. ID. NO:31

SEQ. ID. NO:31 (Table 5) corresponds to a previously identified gene that encodes a protein, Selenoprotein P, plasma, 1 (SEPP1), which has been implicated as an oxidant defense in the extracellular space and in the transport of selenium (see Table 1). This gene encodes a selenoprotein that contains multiple selenocysteines. Selenocysteine is encoded by the usual stop codon UGA. The unusual amino acids are indicated as 'U' in the amino acid sequence in SEQ. ID. NO:78 (Table 5) or by Xaa in the sequence listing. We have demonstrated that this gene is markedly upregulated in intermediate and mature osteoclast compared to precursor cells and most normal human tissues (FIG. 31), which have not been previously reported. However, above baseline expression of this gene was observed in the normal human tissues because of a lower than normal precursor level but it was still significantly below the levels of mature osteoclasts. Thus, this gene was still selected. Thus, it is believed that this gene may be required for osteoclastogenesis and/or bone remodeling.

SEQ. ID. NO:32

SEQ. ID. NO:32 (Table 5) corresponds to a previously identified gene that encodes a hypothetical protein, KIAA0040, which has no known function (see Table 1). We have demonstrated that this gene is markedly upregulated in intermediate and mature osteoclast compared to precursor cells and most normal human tissues (FIG. 32), which have not been previously reported. However, above baseline expression of this gene was observed in the normal human tissues because of a lower than normal precursor level but it was still significantly below the levels of mature osteoclasts. Thus, this gene was still selected. Thus, it is believed that this gene may be required for osteoclastogenesis and/or bone remodeling.

SEQ. ID. NO:33

SEQ. ID. NO:33 (Table 5) corresponds to a previously identified gene that encodes a protein, Dipeptidylpeptidase 4 (CD26, adenosine deaminase complexing protein 2) (DPP4), which is an intrinsic membrane glycoprotein and a serine exopeptidase that cleaves X-proline dipeptides from the N-terminus of polypeptides (see Table 1). We have demonstrated that this gene is markedly upregulated in intermediate and mature osteoclast compared to precursor cells and most normal human tissues (FIG. 33), which have not been previously reported. However, above baseline expression of this gene was observed in the normal human tissues except for placenta, lung, ovary, kidney, prostate and small intestine because of a lower than normal precursor level but it was still significantly below the levels of mature osteoclasts. Thus, this gene was still selected. Thus, it is believed that this gene may be required for osteoclastogenesis and/or bone remodeling.

Figure 34:
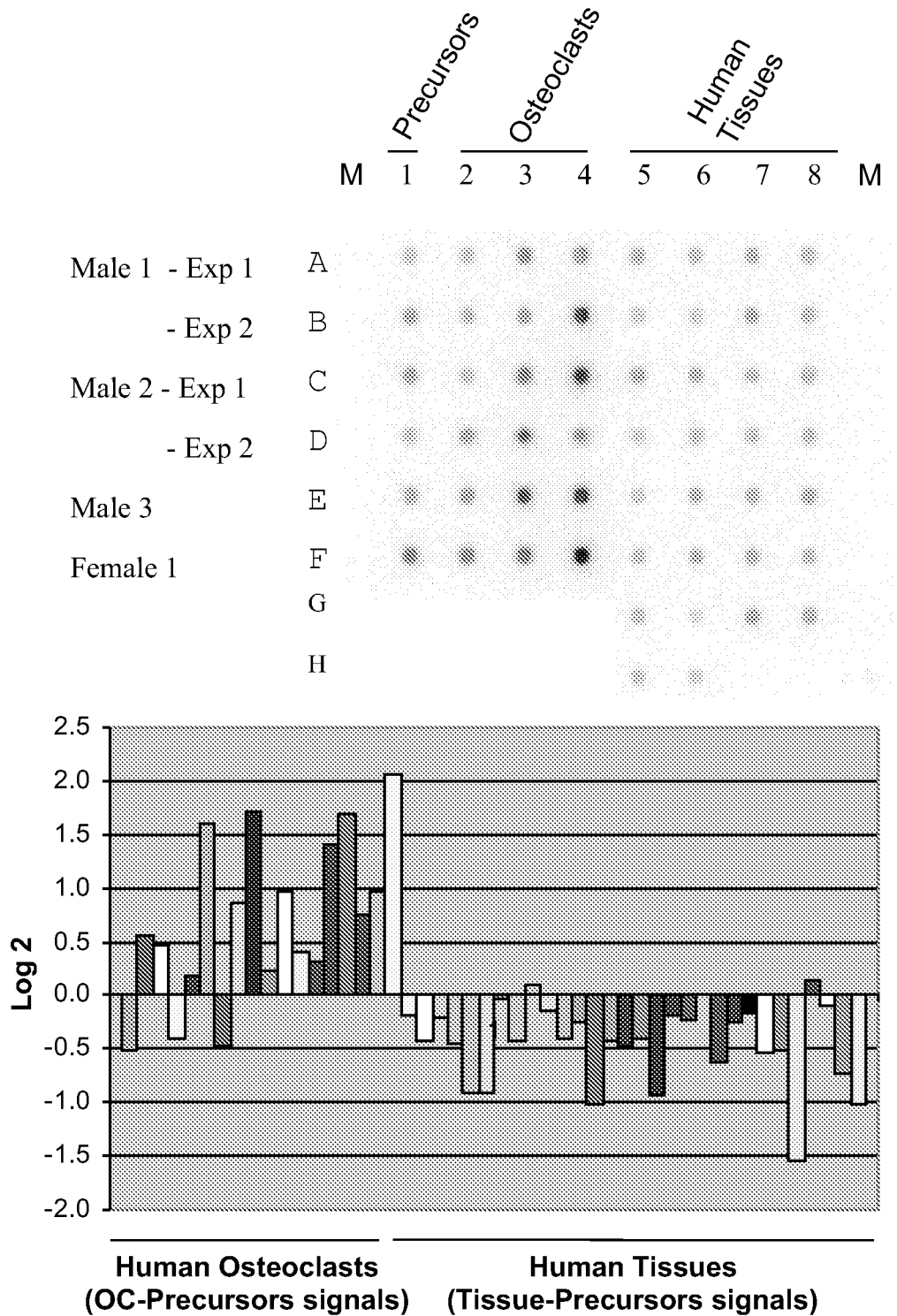
FIG. 34 is a picture of the macroarray hybridization results (upper panel) and quantitation of the signal intensities illustrated by a bar graph (lower panel) showing the differential expression data for STAR selected osteoclast-specific human SEQ. ID. NO. 34 (0017-SL92-1). The hybridization results obtained confirms its upregulation in all of the human osteoclast samples with generally higher expression in the more mature osteoclasts (A-F 2-4) compared to the precursors (A-F 1) and little or no expression in all or most normal tissues (A-H 5-6 and A-G 7-8)

SEQ. ID. NO:34:

SEQ. ID. NO:34 (Table 5) corresponds to a previously identified gene that encodes a protein, cystatin C precursor, with members of the cystatin family known to be inhibitor of cysteine proteases (see Table 1). We have demonstrated that this gene is markedly upregulated in intermediate and mature osteoclast compared to precursor cells and other normal human tissues (FIG. 34), which have not been previously reported. However, it is well documented that cystatin C plays a critical role in inhibiting bone resorption due to osteoclasts (Brage et al., 2005). Thus, the hybridization profile for this gene is an excellent example of highly upregulated and specific sequences related to osteoclasts.

SEQ. ID. NO:85

SEQ. ID. NO:85 (Table 5) encodes an unknown protein found on chromosome 1 (clone RP11-344F13), which contains a novel gene (see Table 1). We have demonstrated that this gene is markedly upregulated in intermediate and mature osteoclast compared to precursor cells and other normal human tissues (FIG. 38), which have not been previously reported. Thus, it is implied that this gene may be required for osteoclastogenesis and/or bone remodeling.

SEQ. ID. NO:86

SEQ. ID. NO:86 (Table 5) encodes no known protein. Unknown gene with matching Est sequence in the data base corresponding to BQ182670 isolated from an osteoarthritic cartilage sample (see Table 1). We have demonstrated that this gene is significantly upregulated in intermediate and mature osteoclast compared to precursor cells and other normal human tissues (FIG. 39), which have not been previously reported. Thus, it is implied that this gene may be required for osteoclastogenesis and/or bone remodeling.

H—Cloning of Full-Length cDNAs of Selected Sequences from Osteoclast mRNA:

It was necessary to obtain full-length cDNA sequences in order to perform functional studies of the expressed proteins. Spliced variants are increasingly being implicated in tissue specific functions and as such, it is important to work with cDNA clones from the system under study. Applicant also recognizes that spliced variants may not always be involved. Thus, the applicant's approach has been to isolate the relevant full-length cDNA sequences directly from osteoclasts in order to identify variants and their potential role with respect to specificity.

Coding cDNA clones were isolated using both a 5'-RACE strategy (Invitrogen, Burlington, ON) and a standard two-primer gene specific approach in PCR. The 5'-RACE strategy used cDNA prepared from cap-selected osteoclast RNA and/or RAMP amplified osteoclast RNA. For amplification using gene specific primers, either cDNA prepared from RAMP RNA or total RNA was used. All cDNAs were synthesized following standard reverse transcription procedures (Invitrogen, Burlington, ON). The cDNA sequences obtained were cloned in E. coli DH10B and the nucleotide sequences for multiple clones determined. Thereafter, the cDNA sequences for each set were aligned and the open reading frame(s) (ORF) identified using standard software (e.g. ORF Finder-NCBI). Table 2 shows the consensus sequence of the cDNA clones for the coding region for SEQ. ID. NO.1 (SEQ. ID. NO. 83) and SEQ. ID. NO.2 (SEQ. ID. NO. 84) obtained from a human osteoclast sample, which were identical to that of the published sequences corresponding to Accession #NM_213602 and NM_001014433 (NCBI), respectively.

I—RNA Interference Studies

RNA interference is a recently discovered gene regulation mechanism that involves the sequence-specific decrease in a gene's expression by targeting the mRNA for degradation and although originally described in plants, it has been discovered across many animal kingdoms from protozoans and invertebrates to higher eukaryotes (reviewed in Agrawal et al., 2003). In physiological settings, the mechanism of RNA interference is triggered by the presence of double-stranded RNA molecules that are cleaved by an RNAse III-like protein active in cells, called Dicer, which releases the 21-23 bp siRNAs. The siRNA, in a homology-driven manner, complexes into a RNA-protein amalgamation termed RISC (RNA-induced silencing complex) in the presence of mRNA to cause degradation resulting in attenuation of that mRNA's expression (Agrawal et al., 2003).

Current approaches to studying the function of genes, such as gene knockout mice and dominant negatives, are often inefficient, and generally expensive, and time-consuming. RNA interference is proving to be a method of choice for the analysis of a large number of genes in a quick and relatively inexpensive manner. Although transfection of synthetic siRNAs is an efficient method, the effects are often transient at best (Hannon G. J., 2002). Delivery of plasmids expressing short hairpin RNAs by stable transfection has been successful in allowing for the analysis of RNA interference in longer-term studies (Brummelkamp et al., 2002; Elbashir et al., 2001). In addition, more recent advances have permitted the expression of siRNA molecules, in the form of short hairpin RNAs, in primary human cells using viral delivery methods such as lentivirus (Lee et al., 2004; Rubinson et al., 2003).

J—Determination of Knockdown Effects on Osteoclastogenesis

In order to develop a screening method for the human candidate genes, RNA interference was adapted to deliver shRNAs into human osteoclast precursor cells so that the expression of the candidate genes could be attenuated. This approach would then allow osteoclast differentiation to be carried out in cells containing decreased expression of these genes to determine their requirement, if any, in this process.

To this end, a commercial lentiviral shRNA delivery system (Invitrogen, Burlington, ON) was utilized to introduce specific shRNAs into human osteoclast precursor cells. The techniques used were as described by the manufacturer unless otherwise stated. In this example, the results obtained for two of the candidate genes, SEQ. ID. NO. 1 (AB0326) and SEQ. ID. NO. 2 (AB0369) tested so far, are presented. The proteins encoded by both of these two genes have no known function.

Figure 35:
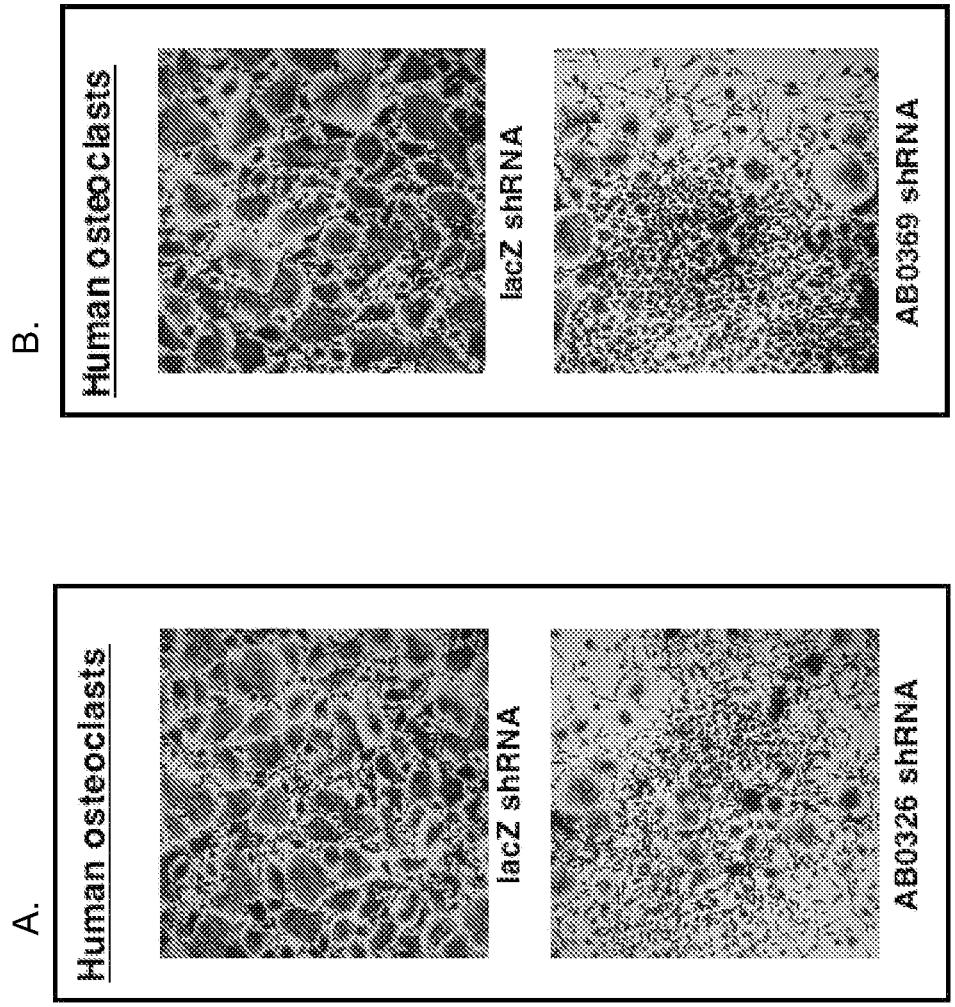

The shRNA sequences used to specifically target SEQ. ID. NO. 1 and SEQ. ID. NO. 2 were 5'-CAGGCCCAGGAGTC-CAATT-3' (SEQ. ID. NO. 42) and 5'-TCCCGTCTTTGGGT-CAAAA-3' (SEQ. ID. NO. 43) respectively. Briefly, a template for the expression of the shRNA was cloned into the lentiviral expression vector and co-transfected in 293FT cells with expression vectors for the viral structural proteins. After two days, supernatants containing the lentivirus were collected and stored at −80° C. Human osteoclast precursors purchased from Cambrex (East Rutherford. NJ) were seeded in 24-well plates and cultured in complete medium containing macrophage-colony stimulating factor and allowed to adhere for three days. After washing with PBS, the cells were infected with 20 MOIs (multiplicity of infection) of either lentiviral particles containing a shRNA specific for the bacterial lacZ gene as a control (IacZ shRNA) or SEQ. ID. NO. 1 (AB0326 shRNA) or SEQ. ID. NO. 2 (AB0369 shRNA). After 24 h, the infected cells were treated with same medium containing 100 ng/ml RANK ligand for 5-8 days to allow for differentiation of osteoclast from precursor cells. Mature osteoclasts were fixed with formaldehyde and stained for TRAP expression as follows: the cells were washed with PBS and fixed in 10% formaldehyde for 1 h. After two PBS washes, the cells were lightly permeabilized in 0.2% Triton X-100 in PBS for 5 min before washing in PBS. Staining was conducted at 37° C. for 20-25 min in 0.01% Naphtol AS-MX phosphate, 0.06% Fast Red Violet, 50 mM sodium tartrate, 100 mM sodium acetate, pH 5.2. The stained cells were visualized by light microscopy and photographed (magnification: 40×). A significant decrease in the number of multinucleated osteoclasts was observed from precursor cells infected with the AB0326 shRNA (FIG. 35A; bottom panel) and AB0369 shRNA (FIG. 35B; bottom panel) compared to those with the lacZ shRNA (FIGS. 35A and B; top panels). Therefore, in both cases, the respective lentiviral shRNA (SEQ. ID. NOs. 42 and 43, respectively) (Table 4) perturbed osteoclastogenesis. These results clearly indicated that expression of the gene encoding SEQ. ID. NO. 1 (AB0326) and SEQ. ID. NO. 2 (AB0369) are required for osteoclast differentiation.

Similar experimentations to those described above are carried out for other sequences (SEQ ID NO.3 to SEQ ID NO.: 33, SEQ ID NO.:85 or SEQ ID NO.:86).

K—Biological Validation of the Mouse Orthologue for AB0326 (SEQ. ID. NO. 35) in Osteoclastogenesis Using the RAW 264.7 Model As a means of developing a drug screening assay for the discovery of therapeutic molecules capable of attenuating human osteoclasts differentiation and activity using the targets identified, it was necessary to turn to another osteoclast differentiation model. The RAW 264.7 (RAW) osteoclast precursor cell line is well known in the art as a murine model of osteoclastogenesis. However, due to the difficulty in transiently transfecting RAW cells, stable transfection was used as an approach where shRNA are expressed in the RAW cells constitutively. This permitted long term studies such as osteoclast differentiation to be carried out in the presence of specific shRNAs specific to the mouse orthologues of the human targets identified.

RAW cells were purchased from American Type Culture Collection (Manassass, Va.) and maintained in high glucose DMEM containing 10% fetal bovine serum and antibiotics. The cells were sub-cultured bi-weekly to a maximum of 10-12 passages. For osteoclast differentiation experiments, RAW cells were seeded in 96-well plates at a density of $4 \times 10^3$ cells/well and allowed to plate for 24 h. Differentiation was induced in high glucose DMEM, 10% charcoal-treated foetal bovine serum (obtained from Hyclone, Logan, Utah), 0.05% BSA, antibiotics, 10 ng/ml macrophage colony stimulating factor (M-CSF), and 100 ng/ml RANK ligand. The plates were re-fed on day 3 and osteoclasts were clearly visible by day 4. Typically, the cells were stained for TRAP on day 4 or 5 unless otherwise indicated.

To incorporate the shRNA-expression cassettes into the RAW cell chromosomes, the pSilencer 2.0 plasmid (SEQ. ID. NO. 47) was purchased from Ambion (Austin, Tex.) and sequence-specific oligonucleotides were ligated as recommended by the manufacturer. Two shRNA expression plasmids were designed and the sequences used for attenuating the mouse ortholog of AB0326 (SEQ. ID. NO. 35) gene expression were 5'-GCGCCGCGGATCGTCAACA-3' (SEQ. ID. NO. 44) and 5'-ACACGTGCACGGCGGCCAA-3' (SEQ. ID. NO. 45). A plasmid supplied by Ambion containing a scrambled shRNA sequence with no known homology to any mammalian gene was also included as a negative control in these experiments. RAW cells were seeded in 6-well plates at a density of $5 \times 10^5$ cells/well and transfected with 1 μg of each plasmid using Fugene6 (Roche, Laval, QC) as described in the protocol. After selection of stable transfectants in medium containing 2 μg/ml puromycin, the cell lines were expanded and tested in the presence of RANK ligand for osteoclastogenesis.

The stably transfected cell lines were designated RAW-0326.1, RAW-0326.2 and RAW-ctl. In 96-well plates in triplicate, 4 000 cells/well were seeded and treated with 100 ng/ml RANK ligand. After 4 days, osteoclasts were stained for TRAP expression and visualized by light microscopy (magnification was 40× and 100× as depicted in the left and right panels, respectively).

Figure 36:
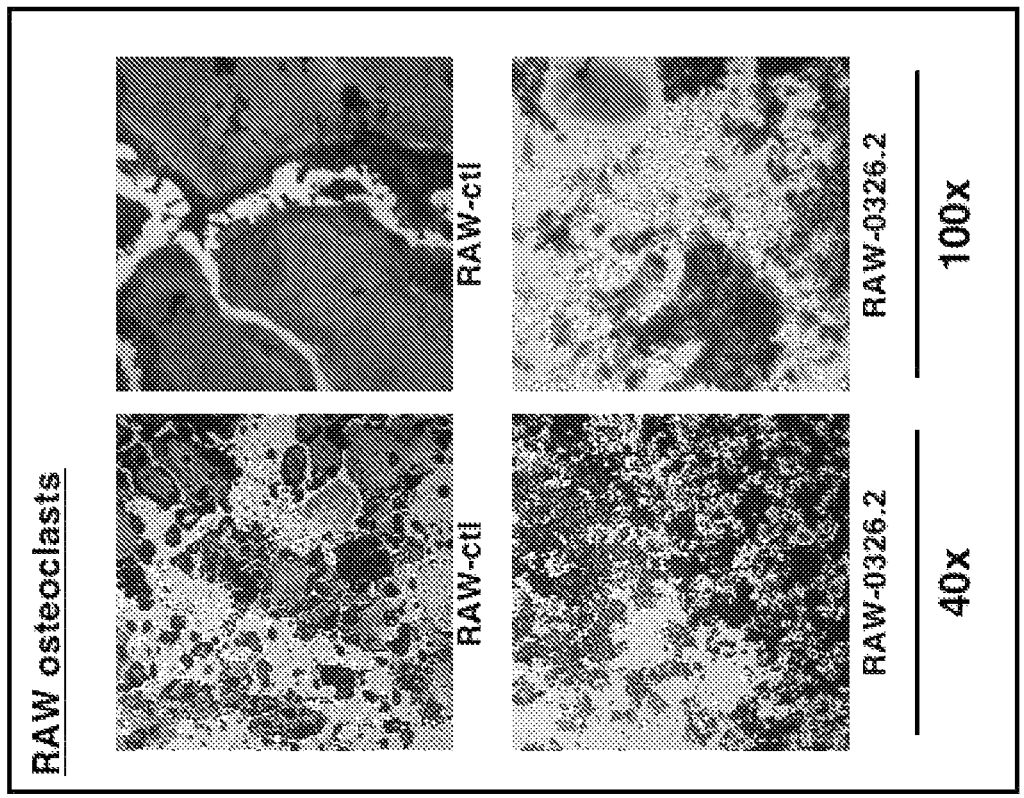

The representative results for the RAW-0326.2 line is shown in FIG. 36. The RAW-0326.2 cell line produced significantly less osteoclasts (FIG. 36; bottom panel) compared to the cell line containing the scrambled shRNA (FIG. 36; top panel). The RAW-0326.1 cell line also showed attenuation of the mouse ortholog of AB0326 but not as pronounced (data not shown). Therefore, as observed for SEQ ID NO.:42 and 43, siRNAs to the mouse orthologue (SEQ. ID. NOs. 44 and 45) (Table 4) appear to phenotypically perturb osteoclast differentiation in the mouse model as well. These results, coupled with that obtained in the human osteoclast precursor cells using the lentiviral shRNA delivery system (section J), demonstrate that in both human and mouse, AB0326 gene product is clearly required for osteoclastogenesis.

L—A Functional Complementation Assay for SEQ. ID. NO. 1 (AB0326) in RAW 264.6 Cells to Screen for Inhibitors of Osteoclastogenesis To establish a screening assay based on SEQ. ID. NO. 1 (AB0326) to find small molecules capable of attenuating osteoclast differentiation, the cDNA encoding human AB0326 was introduced into the RAW-0326.2 cell line. Thus, if the human AB0326 plays an identical functional role as the mouse orthologue in RAW 264.7 cells, it should restore the osteoclastogenesis capabilities of the RAW-0326.2 cell line.

Figure 37:
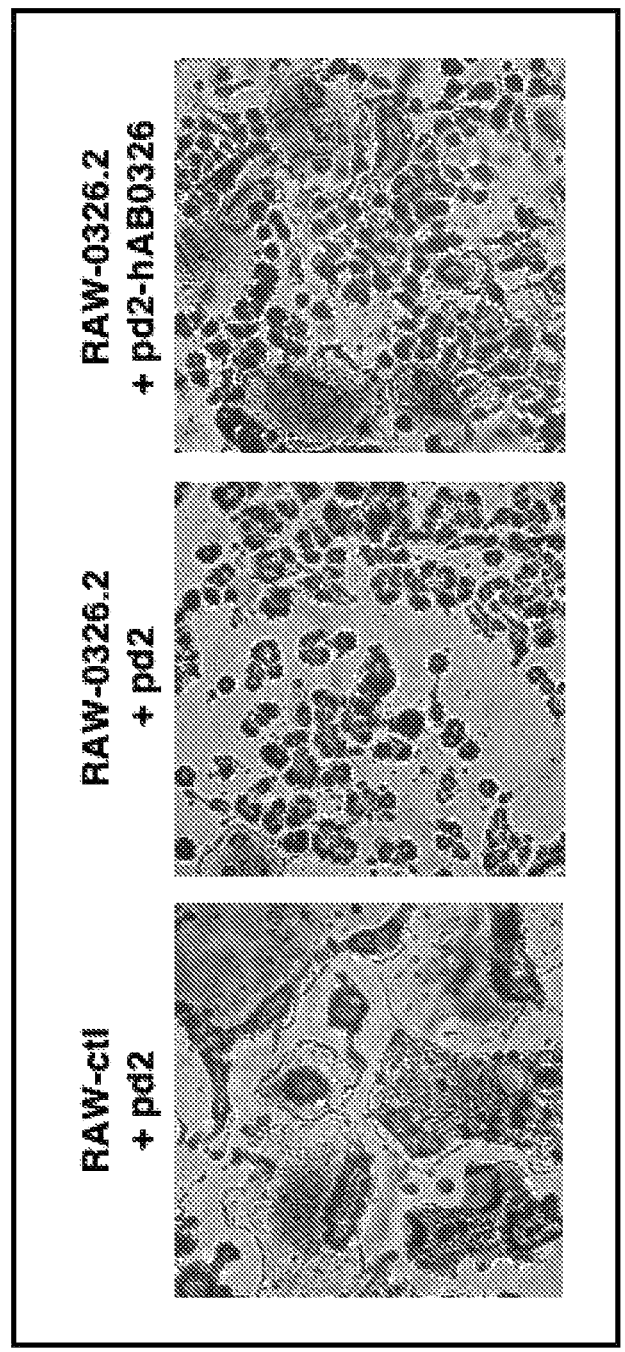
Figure 38:
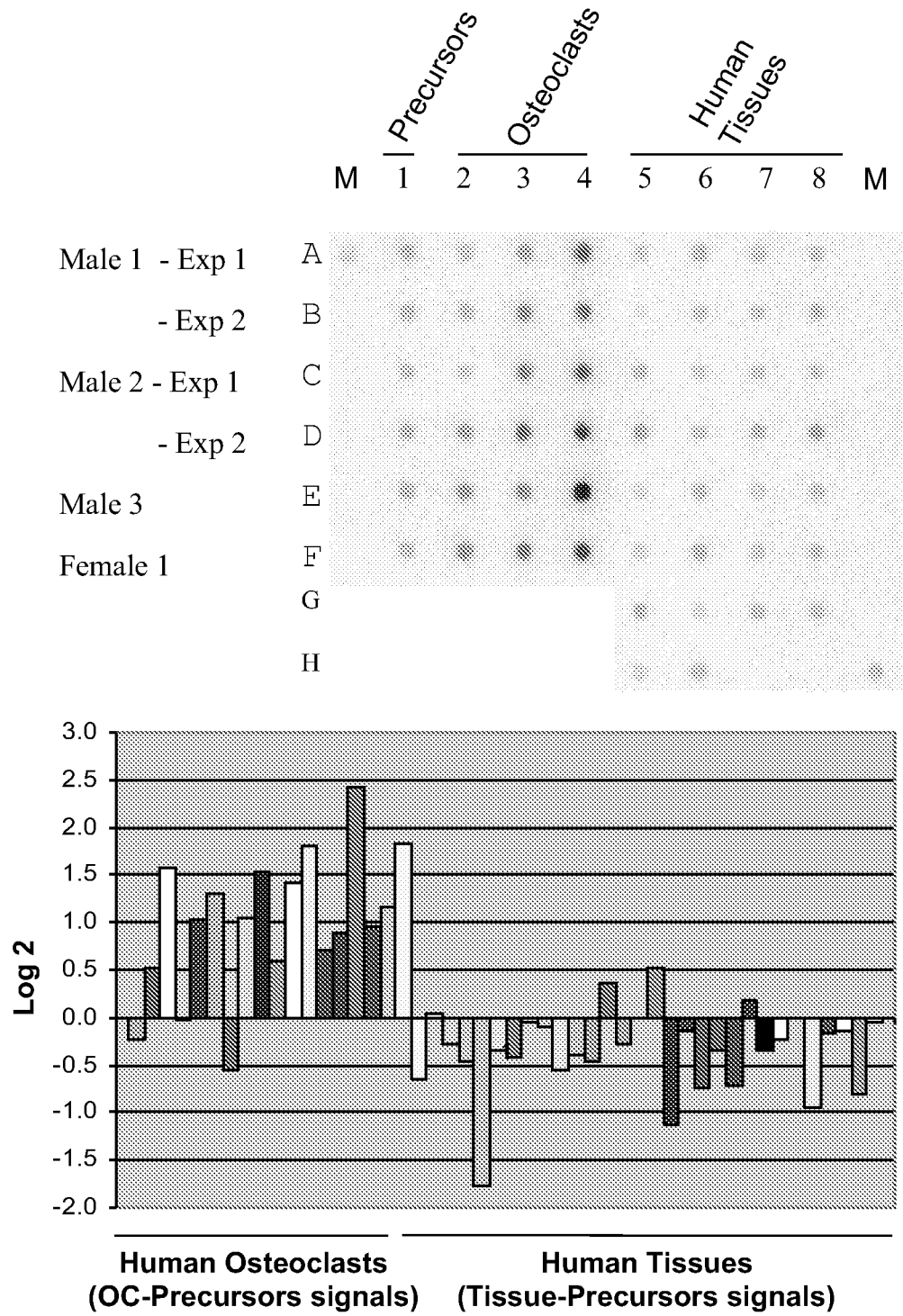
FIG. 38 is a picture of the macroarray hybridization results (upper panel) and quantitation of the signal intensities illustrated by a bar graph (lower panel) showing the differential Expression data for STAR selected osteoclast-specific human SEQ. ID. NO. 85 (0570-SL109). Macroarrays were prepared using RAMP amplified RNA from human precursor cells (A-F 1), and differentiated intermediate and mature osteoclasts for four human donors (A-F 2-4), and 30 different normal human tissues (adrenal, liver, lung, ovary, skeletal muscle, heart, cervix, thyroid, breast, placenta, adrenal cortex, kidney, vena cava, fallopian tube, pancreas, testicle, jejunum, aorta, esophagus, prostate, stomach, spleen, ileum, trachea, brain, colon, thymus, small intestine, bladder and duodenum (A-H 5-6 and A-G 7-8)). The STAR clone representing SEQ. ID. NO. 85 was labeled with $^{32}$P and hybridized to the macroarray. The hybridization results obtained confirms its upregulation in all of the human osteoclast samples with generally higher expression in the more mature osteoclasts (A-F 2-4) compared to the precursors (A1-F1) and little or no expression in all or most normal tissues (A-H 5-6 and A-G 7-8)
Figure 39:
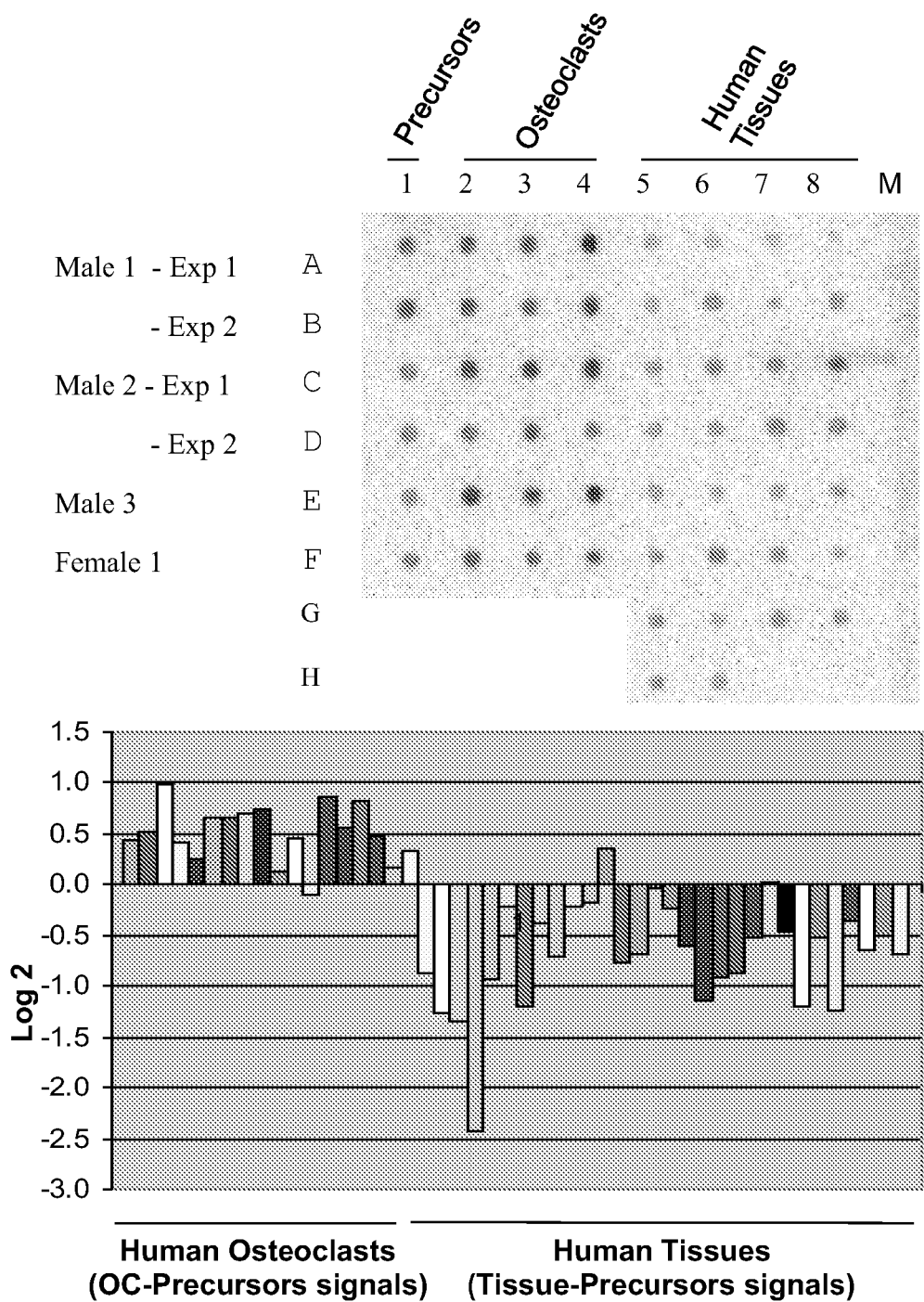
FIG. 39 is a picture of the macroarray hybridization results (upper panel) and quantitation of the signal intensities illustrated by a bar graph (lower panel) showing the differential Expression data for STAR selected osteoclast-specific human SEQ. ID. NO. 86 (0766-SL84-1). Macroarrays were prepared using RAMP amplified RNA from human precursor cells (A-F 1), and differentiated intermediate and mature osteoclasts for four human donors (A-F 2-4), and 30 different normal human tissues (adrenal, liver, lung, ovary, skeletal muscle, heart, cervix, thyroid, breast, placenta, adrenal cortex, kidney, vena cava, fallopian tube, pancreas, testicle, jejunum, aorta, esophagus, prostate, stomach, spleen, ileum, trachea, brain, colon, thymus, small intestine, bladder and duodenum (A-H 5-6 and A-G 7-8)). The STAR clone representing SEQ. ID. NO. 86 was labeled with $^{32}$P and hybridized to the macroarray. The hybridization results obtained confirms its upregulation in all of the human osteoclast samples with generally higher expression in the more mature osteoclasts (A-F 2-4) compared to the precursors (A1-F1) and little or no expression in all or most normal tissues (A-H 5-6 and A-G 7-8).

To accomplish this task, the RAW-0326.2 cell line was transfected with an eukaryotic expression vector encoding the full length cDNA for human AB0326, termed pd2-hAB0326. This expression vector (pd2; SEQ. ID. NO. 47) was modified from a commercial vector, pd2-EGFP-N1 (Clontech, Mountain View, Calif.) where the EGFP gene was replaced by the full length coding sequence of the human AB0326 cDNA. The AB0326 gene expression was driven by a strong CMV promoter. Stable transfectants were selected using the antibiotic, G418. This resulted in a RAW-0326.2 cell line that expressed the human AB0326 gene product in which, the mouse orthologue of AB0326 was silenced. As a control, RAW-0326.2 cells were transfected with the pd2 empty vector, which should not complement the AB0326 shRNA activity. Also, the pd2 empty vector was transfected into RAW 264.7 cells to serve as a further control. After selection of stable pools of cells, 4 000 cells/well were seeded in 96-well plates and treated for 4 days with 100 ng/ml RANK ligand. Following fixation with formaldehyde, the cells were stained for TRAP, an osteoclast-specific marker gene. As shown in FIG. 37, the RAW-0326.2 cells transfected with the empty pd2 vector are still unable to form osteoclasts in the presence of RANK ligand (center panel) indicating that the mouse AB0326 shRNA is still capable of silencing the AB0326 gene expression in these cells. Conversely, the cells transfected with human AB0326 (pd2-hAB0326) are rescued and thus, differentiate into more osteoclasts in response to RANK ligand (right panel). RAW 264.7 cells containing the empty vector (pd2) did not adversely affect the formation of osteoclasts in the presence of RANK ligand (left panel). These results confirm that the mouse and human orthologues of AB0326 are functionally conserved in osteoclast differentiation.

This particular type of cell-based assay can now serve as the basis for screening compounds capable of binding to and inhibiting the function of human AB0326. A compound library could be applied to this 'rescued' cell line in order to identify molecules (small molecule drugs, peptides, or antibodies) capable of inhibiting AB0326. Any reduction in osteoclast differentiation measured by a reduction in the expression of TRAP would be indicative of a decrease in human AB0326 activity. This assay is applicable to any gene required for proper osteoclast differentiation in RAW cells. A complementation assay can be developed for any human gene and used as the basis for drug screening.

Similar experimentation to those described above are carried out for other sequences (SEQ ID NO.3 to SEQ ID NO.:33 or SEQ ID NO.:85 or SEQ ID NO.:86). This type of assay may be used to screen for molecules capable of increasing or decreasing (e.g., inhibiting) the activity or expression of NSEQ or PSEQ.

In the NSEQs of the present invention, their methods, compositions, uses, its, assays or else, the polynucleotide may either individually or in group (collectively) more particularly be (or may comprise or consist in) either;

a translatable portion of either SEQ ID NO.:1, of SEQ ID NO.:2, of SEQ ID NO.:3, of SEQ ID NO.:4, of SEQ ID NO.:5, of SEQ ID NO.:6, of SEQ ID NO.:7, of SEQ ID NO.:8, of SEQ ID NO.:9, of SEQ ID NO.:10, of SEQ ID NO.:11, of SEQ ID NO.:12, of SEQ ID NO.:13, of SEQ ID NO.:14, of SEQ ID NO.:15, of SEQ ID NO.:16, of SEQ ID NO.:17, of SEQ ID NO.:18, of SEQ ID NO.:19, of SEQ ID NO.:20, of SEQ ID NO.:21, of SEQ ID NO.:22, of SEQ ID NO.:23, of SEQ ID NO.:24, of SEQ ID NO.:25, of SEQ ID NO.:26, of SEQ ID NO.:27, of SEQ ID NO.:28, of SEQ ID NO.:29, of SEQ ID NO.:30, of SEQ ID NO.:31, of SEQ ID NO.:32, of SEQ ID NO.:33, of SEQ ID NO.:85 or of SEQ ID NO.:86;

sequence substantially identical to a translatable portion of SEQ ID NO.:1, of SEQ ID NO.:2, of SEQ ID NO.:3, of SEQ ID NO.:4, of SEQ ID NO.:5, of SEQ ID NO.:6, of SEQ ID NO.:7, of SEQ ID NO.:8, of SEQ ID NO.:9, of SEQ ID NO.:10, of SEQ ID NO.:11, of SEQ ID NO.:12, of SEQ ID NO.:13, of SEQ ID NO.:14, of SEQ ID NO.:15, of SEQ ID NO.:16, of SEQ ID NO.:17, of SEQ ID NO.:18, of SEQ ID NO.:19, of SEQ ID NO.:20, of SEQ ID NO.:21, of SEQ ID NO.:22, of SEQ ID NO.:23, of SEQ ID NO.:24, of SEQ ID NO.:25, of SEQ ID NO.:26, of SEQ ID NO.:27, of SEQ ID NO.:28, of SEQ ID NO.:29, of SEQ ID NO.:30, of SEQ ID NO.:31, of SEQ ID NO.:32, of SEQ ID NO.:33, of SEQ ID NO.:85 or of SEQ ID NO.:86;

a sequence substantially complementary to a translatable portion of SEQ ID NO.:1, a fragment of a transcribable portion of SEQ ID NO.:1, of SEQ ID NO.:2, of SEQ ID NO.:3, of SEQ ID NO.:4, of SEQ ID NO.:5, of SEQ ID NO.:6, of SEQ ID NO.:7, of SEQ ID NO.:8, of SEQ ID NO.:9, of SEQ ID NO.:10, of SEQ ID NO.:11, of SEQ ID NO.:12, of SEQ ID NO.:13, of SEQ ID NO.:14, of SEQ ID NO.:15, of SEQ ID NO.:16, of SEQ ID NO.:17, of SEQ ID NO.:18, of SEQ ID NO.:19, of SEQ ID NO.:20, of SEQ ID NO.:21, of SEQ ID NO.:22, of SEQ ID NO.:23, of SEQ ID NO.:24, of SEQ ID NO.:25, of SEQ ID NO.:26, of SEQ ID NO.:27, of SEQ ID NO.:28, of SEQ ID NO.:29, of SEQ ID NO.:30, of SEQ ID NO.:31, of SEQ ID NO.:32, of SEQ ID NO.:33, of SEQ ID NO.:85 or of SEQ ID NO.:86;

a fragment of a sequence substantially identical to a translatable portion of SEQ ID NO.:1, of SEQ ID NO.:2, of SEQ ID NO.:3, of SEQ ID NO.:4, of SEQ ID NO.:5, of SEQ ID NO.:6, of SEQ ID NO.:7, of SEQ ID NO.:8, of SEQ ID NO.:9, of SEQ ID NO.:10, of SEQ ID NO.:11, of SEQ ID NO.:12, of SEQ ID NO.:13, of SEQ ID NO.:14, of SEQ ID NO.:15, of SEQ ID NO.:16, of SEQ ID NO.:17, of SEQ ID NO.:18, of SEQ ID NO.:19, of SEQ ID NO.:20, of SEQ ID NO.:21, of SEQ ID NO.:22, of SEQ ID NO.:23, of SEQ ID NO.:24, of SEQ ID NO.:25, of SEQ ID NO.:26, of SEQ ID NO.:27, of SEQ ID NO.:28, of SEQ ID NO.:29, of SEQ ID NO.:30, of SEQ ID NO.:31, of SEQ ID NO.:32, of SEQ ID NO.:33, of SEQ ID NO.:85 or of SEQ ID NO.:86;

a fragment of a sequence substantially complementary to a translatable portion of SEQ ID NO.:1, of SEQ ID NO.:2, of SEQ ID NO.:3, of SEQ ID NO.:4, of SEQ ID NO.:5, of SEQ ID NO.:6, of SEQ ID NO.:7, of SEQ ID NO.:8, of SEQ ID NO.:9, of SEQ ID NO.:10, of SEQ ID NO.:11, of SEQ ID NO.:12, of SEQ ID NO.:13, of SEQ ID NO.:14, of SEQ ID NO.:15, of SEQ ID NO.:16, of SEQ ID NO.:17, of SEQ ID NO.:18, of SEQ ID NO.:19, of SEQ ID NO.:20, of SEQ ID NO.:21, of SEQ ID NO.:22, of SEQ ID NO.:23, of SEQ ID NO.:24, of SEQ ID NO.:25, of SEQ ID NO.:26, of SEQ ID NO.:27, of SEQ ID NO.:28, of SEQ ID NO.:29, of SEQ ID NO.:30, of SEQ ID NO.:31, of SEQ ID NO.:32, of SEQ ID NO.:33, of SEQ ID NO.:85 or of SEQ ID NO.:86;

or a library comprising any of the above.

In the PSEQs of the present invention, their methods, compositions, uses, kits assays, or else, the polypeptide may either individually or in group (collectively) more particularly be (or may comprise or consist in) either;

SEQ ID NO.:48, SEQ ID NO.:49, SEQ ID NO.:50, SEQ ID NO.:51, SEQ ID NO.:52, SEQ ID NO.:53, SEQ ID NO.:54, SEQ ID NO.:55, SEQ ID NO.:56, SEQ ID NO.:57, SEQ ID NO.:58, SEQ ID NO.:59, SEQ ID NO.:60, SEQ ID NO.:61, SEQ ID NO.:62, SEQ ID NO.:63, SEQ ID NO.:64, SEQ ID NO.:65, SEQ ID NO.:66, SEQ ID NO.:67, SEQ ID NO.:68, SEQ ID NO.:69, SEQ ID NO.:70, SEQ ID NO.:71, SEQ ID NO.:72, SEQ ID NO.:73, SEQ ID NO.:74, SEQ ID NO.:75 SEQ ID NO.:76, SEQ ID NO.:77, SEQ ID NO.:78, SEQ ID NO.:79 or SEQ ID NO.:80;

a fragment of SEQ ID NO.:48, SEQ ID NO.:49, SEQ ID NO.:50, SEQ ID NO.:51, SEQ ID NO.:52, SEQ ID NO.:53, SEQ ID NO.:54, SEQ ID NO.:55, SEQ ID NO.:56, SEQ ID NO.:57, SEQ ID NO.:58, SEQ ID NO.:59, SEQ ID NO.:60, SEQ ID NO.:61, SEQ ID NO.:62, SEQ ID NO.:63, SEQ ID NO.:64, SEQ ID NO.:65, SEQ ID NO.:66, SEQ ID NO.:67, SEQ ID NO.:68, SEQ ID NO.:69, SEQ ID NO.:70, SEQ ID NO.:71, SEQ ID NO.:72, SEQ ID NO.:73, SEQ ID NO.:74, SEQ ID NO.:75 SEQ ID NO.:76, SEQ ID NO.:77, SEQ ID NO.:78, SEQ ID NO.:79 or SEQ ID NO.:80;

or a biologically active analog, variant or a non-human hortologue of SEQ ID NO.:48, SEQ ID NO.:49, SEQ ID NO.:50, SEQ ID NO.:51, SEQ ID NO.:52, SEQ ID NO.:53, SEQ ID NO.:54, SEQ ID NO.:55, SEQ ID NO.:56, SEQ ID NO.:57, SEQ ID NO.:58, SEQ ID NO.:59, SEQ ID NO.:60, SEQ ID NO.:61, SEQ ID NO.:62, SEQ ID NO.:63, SEQ ID NO.:64, SEQ ID NO.:65, SEQ ID NO.:66, SEQ ID NO.:67, SEQ ID NO.:68, SEQ ID NO.:69, SEQ ID NO.:70, SEQ ID NO.:71, SEQ ID NO.:72, SEQ ID NO.:73, SEQ ID NO.:74, SEQ ID NO.:75 SEQ ID NO.:76, SEQ ID NO.:77, SEQ ID NO.:78, SEQ ID NO.:79 or SEQ ID NO.:80.

One of skill in the art will readily recognize that orthologues for all mammals maybe identified and verified using well-established techniques in the art, and that this disclosure is in no way limited to one mammal. The term "mammal(s)" for purposes of this disclosure refers to any animal classified as a mammal, including humans, domestic and farm animals, and zoo, sports, or pet animals, such as dogs, cats, cattle, horses, sheep, pigs, goats, rabbits, etc. Preferably, the mammal is human.

The sequences in the experiments discussed above are representative of the NSEQ being claimed and in no way limit the scope of the invention. The disclosure of the roles of the NSEQs in osteoclastogenesis and osteoclast function satisfies a need in the art to better understand the bone remodeling process, providing new compositions that are useful for the diagnosis, prognosis, treatment, prevention and evaluation of therapies for bone remodeling and associated disorders.

The art of genetic manipulation, molecular biology and pharmaceutical target development have advanced considerably in the last two decades. It will be readily apparent to those skilled in the art that newly identified functions for genetic sequences and corresponding protein sequences allows those sequences, variants and derivatives to be used directly or indirectly in real world applications for the development of research tools, diagnostic tools, therapies and treatments for disorders or disease states in which the genetic sequences have been implicated.

Although the present invention has been described hereinabove by way of preferred embodiments thereof, it may be modified, without departing from the spirit and nature of the subject invention as defined in the appended claims.

TABLE 1

Differentially expressed sequences found in osteoclasts.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 1 | Hs.287692/ CD33L3/ 284266 | NM_213602 | 150-1136 encoding SEQ ID NO.: 48 | hypothetical protein LOC284266; membrane associated function unknown |
| SEQ ID NO. 2 | Hs.520070/ C6orf82/ 51596 | NM_001014433 | 104-700 encoding SEQ ID NO.: 49 | chromosome 6 open reading frame 82; membrane associated with unknown function |
| SEQ ID NO. 3 | Hs.546482/ LOC133308/ 133308 | NM_178833 | 633-2246 encoding SEQ ID NO.: 50 | hypothetical protein LOC133308 possibly involved in regulation of pH |
| SEQ ID NO. 4 | Hs.135997/ LOC116211/ 116211 | NM_138461 | 112-741 encoding SEQ ID NO.: 51 | transmembrane 4 L six family member 19; function unknown |
| SEQ ID NO. 5 | Hs.558655/ LOC151194/ 151194 | NM_145280 | 172-82 encoding SEQ ID NO.: 52 | hypothetical protein LOC151194 |
| SEQ ID NO. 6 | Hs.89714/ CXCL5/ 6374 | NM_002994 | 119-463 encoding SEQ ID NO.: 53 | chemokine (C-X-C motif) ligand 5 precursor; chemokine activity |
| SEQ ID NO. 7 | Hs.495960/ ATP6AP2/ 10159 | NM_005765 | 103-1155 encoding SEQ ID NO.: 54 | ATPase, H+ transporting, lysosomal accessory protein 2; receptor activity |
| SEQ ID NO. 8 | Hs.42400/ USP12/ 219333 | NM_182488 | 259-1371 encoding SEQ ID NO.: 55 | ubiquitin-specific protease 12-like 1; cysteine-type endopeptidase activity |
| SEQ ID NO. 9 | Hs.164853/ UBE2E1/ 7324 | NM_003341 | 175-756 encoding SEQ ID NO.: 56 | ubiquitin-conjugating enzyme E2E 1 isoform 1; ligase activity |
| SEQ ID NO. 10 | Hs.433278/ EBPL/ 84650 | NM_032565 | 53-673 encoding SEQ ID NO.: 57 | emopamil binding related protein, delta8-delta7; integral to membrane |
| SEQ ID NO. 11 | Hs.106015/ DDEF1/ 50807 | NM_018482 | 29-3418 encoding SEQ ID NO.: 58 | development and differentiation enhancing factor 1; membrane |

TABLE 1-continued

Differentially expressed sequences found in osteoclasts.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 12 | Hs.517265/ SLAMF7/ 57823 | NM_021181 | 16-1023 encoding SEQ ID NO.: 59 | SLAM family member 7; receptor activity |
| SEQ ID NO. 13 | Hs.470804/ UBE2E3/ 10477 | NM_006357 | 385-1008 encoding SEQ ID NO.: 60 | ubiquitin-conjugating enzyme E2E 3; ligase activity |
| SEQ ID NO. 14 | Hs.278959/ GAL/ 51083 | NM_015973 | 177-548 encoding SEQ ID NO.: 61 | galanin preproprotein; neuropeptide hormone activity |
| SEQ ID NO. 15 | NM_032569/ N-PAC/ 84656 | NM_032569 | 19-1680 encoding SEQ ID NO.: 62 | cytokine-like nuclear factor n-pac; 3-hydroxyisobutyrate dehydrogenase-like |
| SEQ ID NO. 16 | Hs.248472/ ITGAX/ 3687 | NM_000887 | 68-3559 encoding SEQ ID NO.: 63 | integrin alpha X precursor; cell-matrix adhesion |
| SEQ ID NO. 17 | Hs.156727/ ANKH/ 1827 | NM_054027 | 321 = 1799 encoding SEQ ID NO.: 64 | ankylosis, progressive homolog; regulation of bone mineralization |
| SEQ ID NO. 18 | Hs.477155/ ATP6V1A/ 523 | NM_001690 | 67-1920 encoding SEQ ID NO.: 65 | ATPase, H+ transporting, lysosomal 70 kD, V1 subunit A, isoform 1; proton transport; hydrolase activity |
| SEQ ID NO. 19 | Hs.445386/ FLJ10874/ 55248 | NM_018252 | 139-1191 encoding SEQ ID NO.: 66 | hypothetical protein LOC55248 |
| SEQ ID NO. 20 | Hs.467662/ ITGB1BP1/ 9270 | NM_004763 | 170-772 encoding SEQ ID NO.: 67 | integrin cytoplasmic domain-associated protein 1; cell adhesion |
| SEQ ID NO. 21 | Hs.408236/ TXNL5/ 84817 | NM_032731 | 77-448 encoding SEQ ID NO.: 68 | thioredoxin-like 5; function unknown |
| SEQ ID NO. 22 | Hs.236516/ CLECSF9/ 26253 | NM_014358 | 152-811 encoding SEQ ID NO.: 69 | C-type lectin, superfamily member 9; integral to membrane |
| SEQ ID NO. 23 | Hs.56294/ RAB33A/ 9363 | NM_004794 | 265-978 encoding SEQ ID NO.: 70 | Ras-related protein Rab-33A; small GTPase mediated signal transduction |
| SEQ ID NO. 24 | Hs.282326/ DSCR1/ 1827 | NM_004414 | 73-831 encoding SEQ ID NO.: 71 | calcipressin 1 isoform a; interacts with calcineurin A and inhibits calcineurin-dependent signaling pathways |
| SEQ ID NO. 25 | Hs.520794/ YKT6/ 10652 | NM_006555 | 158-754 encoding SEQ ID NO.: 72 | SNARE protein Ykt6; vesicular transport between secretory compartments |
| SEQ ID NO. 26 | Hs.509765/ ACTN1/ 87 | NM_001102 | 184-2862 encoding SEQ ID NO.: 73 | alpha-actinin 1; structural constituent of cytoskeleton; calcium ion binding |
| SEQ ID NO. 27 | Hs.113823/ CLPX/ 10845 | NM_006660 | 73-1974 encoding SEQ ID NO.: 74 | ClpX caseinolytic protease X homolog; energy-dependent regulator of proteolysis |
| SEQ ID NO. 28 | Hs.155097/ CA2/ 760 | NM_000067 | 66-848 encoding SEQ ID NO.: 75 | carbonic anhydrase II; carbonate dehydratase activity |
| SEQ ID NO. 29 | Hs.520714/ SNX10/ 29887 | NM_013322 | 216-821 encoding SEQ ID NO.: 76 | sorting nexin 10; function unknown |
| SEQ ID NO. 30 | Hs.525061/ TDRD3/ 81550 | NM_030794 | 258-2213 encoding SEQ ID NO.: 77 | tudor domain containing 3; nucleic acid binding |

TABLE 1-continued

Differentially expressed sequences found in osteoclasts.

| Nucleotide Sequence No. | NCBI Unigene #/Gene Symbol/Gene ID | Accession Number | ORF Nucleotide Positions/ Polypeptide sequence No. | Function |
|---|---|---|---|---|
| SEQ ID NO. 31 | Hs.275775/ SEPP1/ 6414 | NM_005410 | 101-1246 encoding SEQ ID NO.: 78 | selenoprotein P; extracellular space implicated in defense |
| SEQ ID NO. 32 | Hs.518138/ KIAA0040/ 9674 | NM_014656 | 921-1382 encoding SEQ ID NO.: 79 | KIAA0040; novel protein |
| SEQ ID NO. 33 | Hs.368912/ DPP4/ 1803 | NM_001935 | 562-2862 encoding SEQ ID NO.: 80 | dipeptidylpeptidase IV; aminopeptidase activity |
| SEQ ID NO. 34 | Hs.304682/ CST3/ 1471 | NM_000099 | 76-516 encoding SEQ ID NO.: 81 | cysteine protease inhibitor activity |
| SEQ ID NO. 85 | None/ none/ none | AL357873 | Novel | novel |
| SEQ ID NO. 86 | | AL645465/ BQ182670 | novel | novel |

TABLE 2

Shows the concensus sequences for SEQ. ID. NO. 1 and SEQ. ID. NO. 2 cloned from a mature human osteoclast sample.

| Sequence Identification | ORF Nucleotide Positions | Polypeptide sequence No. |
|---|---|---|
| SEQ ID NO. 83 | 1-987 | SEQ ID NO. 48 |
| SEQ ID NO. 84 | 1-471 | SEQ ID NO. 49 |

TABLE 3

List of mouse orthologue for AB0326

| Sequence Identification | NCBI Unigene Cluster | Accession Number | ORF Nucleotide Positions | Polypeptide sequence No. |
|---|---|---|---|---|
| SEQ ID NO. 35 | None/ LOC620235/ 620235 | XM_884636 | 122-1102/ similar to neural cell adhesion molecule 2/ unknown function | SEQ ID NO.: 82 |

TABLE 4 list of additional sequences identification of plasmids and shRNA oligonucleotides

| Sequence Identification | name | Description |
|---|---|---|
| SEQ. ID. NO. 36 | p14 | Vector for STAR |
| SEQ. ID. NO. 37 | p17+ | Vector for STAR |
| SEQ. ID. NO. 38 | pCATRMAN | Vector for STAR |
| SEQ. ID. NO. 39 | p20 | Vector for STAR |
| SEQ. ID. NO. 40 | OGS 77 | Primer used for STAR p14 vector |
| SEQ. ID. NO. 41 | OGS 302 | Primer used for STAR p17+ vector |
| SEQ. ID. NO: 42 | human 0326.1 | siRNA sequence for SEQ. ID. NO. 1 |
| SEQ. ID. NO: 43 | Human 0369.1 | shRNA sequence for SEQ. ID. NO. 2 |
| SEQ. ID. NO: 44 | mouse 0326.1 | shRNA sequence for SEQ. ID. NO. 35 |
| SEQ. ID. NO: 45 | mouse 0326.2 | shRNA sequence for SEQ ID NO. 35 |
| SEQ. ID. NO: 46 | | pSilencer2.0 vector |
| SEQ. ID. NO: 47 | | pd2 vector |

TABLE 5

| Nucleotide Sequence (5'-3') | ORFs |
|---|---|
| SEQ ID NO.: 1<br>TCCGGCTCCCGCAGAGCCCACAGGACCTGAGTGCCTGCCCACCCCGCCCTTCCTTCCCCACCACGCCTGGGA<br>GGGCCCTCACTGGGAGGTGCCGAGAACGGGTCTGGCCTGGGGTGTTCAGATGTCTCACAGCATGGAAAAGT<br>CCTGCTTGGCGTGGGTTCTCCCGACCAGGCTCATTTGTGAGAACTAAAATAGATACTCAAACAGAGAGTGCACA<br>GCTCGCCAGCGCAGCGCTGCTCATGCAGGTGCCAGTGCCGCTGAGTGCGGAGGCAGGCGACGTCGGCAGTGCTGCCCTGCACCTTCA<br>CGCACCCGCAGCGCTACGACGGCCGTGACGCCCATCTGGCGCGTGATGCCGGGAAGCCCTATGCGGGAGCCCCAGGTGTTCCGCTGCG<br>CTGCGCCGCGCGAGCGCTTCGGCCTGACGCCCTGGCACGCCGCTGGGACATCGGCAGGCGACGACCCTCATCGGGAACC<br>TCTCGCCGGGCGACGACGGGCGCTCGAGCGCGCTCGGTCCGGTGCACGTGACGAGCCGCGGCGGTCTGCCCAGTCCGGCTCACGCT<br>ACGAGCGCCACGGCGTCTGACTGGCCGAAGGGAGCCGCCGGCTACGTGCCGCCGCGCGACCAGCTTGGCAGCCGTGC<br>GGAGCCGTGAGGTCACGGCAACTGTCTGCCCGCAGCTGCCGCGCTACAGGCGCGCTGCTGCTGCACGCCGCTCTCTCCGCG<br>ACAGCCTGGGCCTGTCAAGGCGCTGCTGTCCGAGCGCCAGCTTCCCCGGACGAGAAGCGCCTCTCTCCGGG<br>CTCTCCGGCTTCAAGGCGCTGTCTGCTCGGGAGCTCCCGGGAGCTGCCACCGGCGCTCCGCCCGCCCAACGTGCTCAC<br>CGTCACCGCTCCCAGGCCCAGGATAGGTCCCAATTATGAAACTGGTGAAAATTTCGTAAAGCGTGAAACATCCAGTGTCAAC<br>CGTGGAGGAGGTCCCTGCAGCCCACCAGACCGCAGCTCCTGAAGGTCAAGACCCCTGCTCTCAAGGAGCTCATCTGGCT<br>GGTTCATGTGGACAACCATTTGGAGCAGGAGTACACGACGATCAAAGAAAAAAAAAAAAA<br>CAGACAGGAAACTGTTAAAAAAAAAAAAAAAAA | SEQ ID NO.: 48<br>MEKSIWLLACLAWVLPTGSFVRT<br>KIDTTENLLNTEVHSSPAQRWSM<br>QVPPEVSAEAGDAAVLPCTFTHP<br>HRHYDGPLTAIWRAGEPYAGPQV<br>FRCAAARGSELCQTALSLHGRFR<br>LLGNPRRNDLSLRVERLALADDR<br>RYPCRVEFAGDVHDRYESRHGVR<br>LHVTAAPRIVNLSVLPSPAHAFR<br>ALCTAEGEPPPALAWSGPALGNS<br>LAAVRSPREGHGHLVTAELPALT<br>HDGRYTCTAANSLGRSEASVYLF<br>RFHGASGASTVALLLGALGFKAL<br>LLLGVLAARAARRPEHLDTPDT<br>PPRSQAQESNYENLSQMNPRSPPATMCSP |
| SEQ ID NO.: 2<br>ACGAAACGGGCGTGCCATTTCCGCACGTCGCAGATGCGGTAGTCGATTGGTCAAGTCTCCATGGCTCCTTCATCAGGAG<br>GTGGGCAAACCGCGCCATGATAGGGCTCGGGATTGCGGTTGCGTCCGAGGCCAGGTGGTCTTCTACTGTCACATGGTGCGCCT<br>GTTTTCTAATCACGTGGCTGCACCCAGGCCTTCTGTCTTGTTGATGGGGCGTGCTGCTGCCCTGAGCATCTCCGGTGGGGCTCCCCT<br>TTTGTGCTACCCCGAGTCTTGCTCAGTCCTCTGCAGCCCTTCGACCCAGCCTCTGCCGACCCAGCCTCTCCGATTGCGAGCTTCCGGCCTGCTCCGGCTA<br>CGTTCCGGGCTCGCGGCGCTCTCTGCAGCTTTGTTACTTGCCCAACGAGAAGGTGCGCGCCAGGAAGATGAGATGGAGAAGCG<br>CCTAGCAGCCTGCGCTGACCTCATCCCTCAGATTCATCATCCAGATTTTGTTCGTTCTGTGCACCCTTTACCGAAGTGGCGAGTGAT<br>GATTAAAACCAAAGTTCCTTGGTCCCAGCTTTGCGTACCTCCGATCGGGTACCCGAGTCCAGTTTCGATCCTCATCACGATCTGC<br>ATTGCCTGGAACAGGGAACTTTCCTGCTCATGAAGAATCCCCGACATACTTCAAGCCTTCCAGCTGATGACTGGGCCCCCATAATCCCGTCT<br>ATGATGAGCCCTGTTCCTCCTCATGAAGAATCCCCGACATACTTCAAGCCTTCCAGGTGATGACTGGGCCCCCATAATCCCGTCT<br>TTGGGTCTCTCTGCCAAAAAAAAAAAAAAAAA | SEQ ID NO.: 49<br>MIGSGLAGSGAGGPSSTVTWCA<br>LFSNHVAATQASLLLSFVWMPAL<br>LPVASRLLLPRVLLTMASGSPP<br>TQPSPASDSGSGVPGSVSAAFV<br>TCPNEKVAKEIARAVVEKRLAAC<br>VNLIPQITSIYEMKGKIEEDSEV<br>LMMIKTQSSLVPALTDFVRSVHP<br>YEVAEVIALPVEQGNFPYLQWRQVTESVSDSITVLP |
| SEQ ID NO.: 3<br>CGGTCTGTCTCTCATCTCCGGAAGACTCGGCCGTCCGCGCTCTGGGTAAGCTTCCGGGAAGCTTTCCGGGAGCTCGCT<br>GGTCCTGCGTCCAGAAGCTGGCCTGCGACTCCGTCCCGCCGTCCGCGCCTCCGAGGCCCCGGGAGCGTC<br>GGGCCATGTGGCCTGGCGGCACCTTTCCGGGGAGAAGCCACCGGCAGCGCATCGGCAGCCGCTCCGAGCGCATGCTACTCCGGAGCCGCGGACG<br>GGTGAAACTCCCACTGCCTCCGCGGTTCGTCGCAGAGCCGGTTCGTGCGAAGAAGCCTACTCCGAGCTGTATCGGGGGAGACG<br>ATCTGCAGCAGTCAAGCGAGCCCCTTTCTGACCAGGTCCAGCCGTGGCTCCGAGATCTCGTTCTGTTCCCTG<br>GCCTCATCTTTAATTATAAATATGGGGATGAAGAAAGATTCAGAAGATTCGAAGATGAAGATCAGGAATGAATTACA<br>GGCGTCCATCATGAGAAGAGAGCAGTTATGCAGGCCTGTCATGATATGCCAAATGAACCAACAGAAGAAGTATTC<br>TTTGAAAGCGTTTTACTGAAGACAGTCATAACACAGTTACCATCACATTTGCTCGTTCGGTCGGGCTGTAGGTTGTCAATTACTGGCAGTGAAT<br>CACATGGTTCATCAGGCTACATTGGAATTATATAATCCTATTCTGTGCCATCATTGTGGTCGCAATTTGGGGCTTATTAAGTTACAG<br>CTACATAGCACAAGCTCCACTGCTCTCTTTGAAGAACTGTCTTCTCTGACATGCCCTGCTATCAATTCCAGTCACAAGCGATAATGCT<br>AGATCAAGCACAAGTTAAAGGCGGTTGTCTTCTCCATGGCAGATTCCATGGCGTAAGTCCTGTTATCATTGGAGGCGCTGCACACCTGCTCTGCTCGAGGCCCATTT<br>CCCTCGCCCGGCCCTAAATCTGTCTCATGGCAGTTTATTACTTGGGCAGTGATATAATTAACTGGCAGCTTGCGCAGCTCCTGATGACCATTCTGGCCCAT<br>ACCTGCTGGGGTTGCGAAAGCGCCTATGCTGTTGTGAAAGAGCGCTCCGAAGCCCAGCTTCGATGCCATTCTCGAC | SEQ ID NO.: 50<br>MGDEDKRITYEDSEPSTGMNYTP<br>SMHQEAQEETVMKLKGIDANEPT<br>EGSILLKSSEKKLQEPTEANHV<br>QRLRQMLACPPHGLLDRVITNVT<br>IIVLLWAVVWSITGSECLPGGNL<br>FGIIILFYCAIIGGKLLGLIKLP<br>TLPLPSLLGMLLAGFLIRNIPV<br>INDNVQIKHKWSSSLRSIALSII<br>LVRAGLGLDSKALKKLKGVCVRL<br>SMGPCIVEACTSALLAHYLLGLP<br>WQMGFILGFVLGAVSPAVVVPSM<br>LLQGGYGVEKGVPTLLMAAGS<br>FDDILAITGFNTCLGIAPSTGST<br>VFNVLRGVLEVVIGVATGSVLGF<br>FIQYFPSRDQDKLVCKRTFLVLG<br>LSVLAVFSSVHFGFPGSGGLCTL<br>VMAFLAGMGWTSEKAEVEKIIAV |

TABLE 5-continued

| Nucleotide Sequence (5'→3') | ORFs |
|---|---|
| TCACTGGCTTCAACACCATGCTTGGGCATAGCCTTTCCACAGGTCTACTGTCTTTAATGTCCTCCAGAGGAGTTTTGGAGGTGTGTAA<br>TTGGTGTGGCAACTGGATCTTGTTCTTGGGATTTTCATTCAGTACTTTCCAAGCCTGACCAGGACAAACTGTGTGTAAGAGAACAT<br>TCCTTCTGTTGGGTTGTCTGTCTAGCTGTGTTCAGCAGTGTGCATTTTGGTTTCCCTGGATCAGGAGGACTGTGCACGTTGGTCA<br>TGGCTTCCTTGGACTAATTGCAGCATGGAGCAGGAGGTATCTATTGCATCTCAGACACAGAAACTCTAGGCCTTGTGTTGCCACCGTAGGCATTG<br>TTCTTTTGGACTAATTGCAGCATGGAGCAGGAGGTATCTATTGCATCTCAGACACAGAAACTCTAGGCCTTGTGTTGCCACCGTAGGCATTG<br>CAGTATTGATACGAATTTTGACTACATTTCTGATGGTGTTTCTGGTTTTACTTAAAGAAAAGATATTTATTCTTTTGCAT<br>GGCTTCCAAAGGCCACAGTTCAGGTCATCAGGCTGCAATGGCTTCAGGACACAGCAAGGTCACATGGAAGAAACAATTAGAGGACT<br>ATGGAATGGGATGTGTTGCAGTTTGTCAGTCTGCATTTTGTTGCTCATCCTCATCAGACAAGCTCGTCTATTGGTTACTGGCCCCA<br>GGCTTCTGCAGAAGTTGAACATCAAAATAAAGATGAAGAAGTTCAAGGAGAAGTTCTGTGCAAGTTTAAGCTTAAAATGTAATAGAACC<br>TGCGAACATAATGTTTAGAAAGTGCTACTTTTTCAGCCCTTGCTCTTTCATGTGGTGTAATGATTCTATATCCCAAAAAAAAAAAAAAAAAAAA<br>AAAAGTAGCTGTTTCTTTTAAACAGCATTTTTAGCCCTTGCTCTTTCATGTGGTGTAATGATTCTATATCCCAAAAAAAAAAAAAAAAAAAA<br>AAAAA | AWDIFQPLLFGLIGAEVSIASLR<br>PETVGLCVATVGIAVLIRLTTF<br>LMVCFAGRNLKEKIFISFAWLPK<br>ATVQAAIGSVALDTARSHGEKQL<br>EDYGMDVLTVAFLSILITAPIGS<br>LLIGLLGPRLLQKVEHQNKDEVQGETSVQV |
| SEQ ID NO.: 4 | |
| GACAACCTTCAGGTCCAGCCTGGAGGAGTGGAGCCAGCCTTTCTCGTTCTGTCTCTCCCATT<br>CTGATTCTTGACACCAGATGCAGGATGGTGTCTCCTCCGTACACGGCCAAGCTGCTCCCGTATCCTGGGACTGAGC<br>GCCCTCGTCCTGATGCGCCATGCTGCTGGGGCCAACGTGGCACACTGGCCAACGTGGACCCCTCTTGAGGGCCTC<br>CTTGGCAGGCACATGCTGGGACTGCTGATGGGGCTCTCAGTGAGAGTGCTCATGGCTACTCACGCAGTATCCTCATCCTCCTTGAGGAGCC<br>TGGAGATACCGGCTGCTCAGTGAAGAGTGGGCTCTGTGGAAGATGGTCCTTTTGCATGTTTCATCCTCAGCAGGAACTCCT<br>CTGATTGCTTTGTCACTTCTGGAGTTGCTCTGAAAGATAGGAATTATCTGTATGAACCGTTCCGTTCCTGGAACTCCGTCTGCCTGAGCCC<br>TCTGCAGCCTGTCTGGCACGTGCTCCCCTCTCCGTGTGCATCACTCTGTAGACAACTCTGTAGCAATCACTCTGTGATTCTTTTAGCATGCCGATT<br>ATCAACAGCCTCCTGGGCTTCTCTACAAGGAGTGGGTTCAGCGCCTCAGTTTAAAGACTTTGCAGGCAGAACCTTCACTTGCTGTCTCAAGGAGGAACTGG<br>GCTCTTGAATATTCTCAGAAGAATATTATCCAGAATGCGGTCCAGTTTACAAGAAGATTAATGAACATTTATCAGAAAACATTAAGATAAATTAAAGGTAATCATGGTGAAAAAAAAAA<br>AAAAA | SEQ ID NO.: 51<br>MVSSPCTPASSRTCSRIILGLSLG<br>TAALFAAGANVALLLPNWDVTYL<br>LRGLLGRHAMLGTLMWGGLMVL<br>TAAILISLMGWRYGCFSKSGLCR<br>SVLTALLSGGLALLGALICFVTS<br>GVALKDGPFCMFDVSSFNQTQAW<br>KYGYPFKDLHSRNYLYDRSLWNS<br>VCLEPSAAVVWHVSLFSALLCIS<br>LLQLLLVVVHVINSLLGLFCSLCEK |
| SEQ ID NO.: 5 | |
| CCACGCGTCCGCCACTTCCAGGGTGCGGGAGGACGGAACTGCGGCAGGAACTGCGGCTAACACCCAGTCTAA<br>GGGCAGGTTCTGCCCATTGTTCCCATTGAGGAGAGCCAGGTCTGAGCAGAGGGGGAGGTTGGAGCTGAGTAGGCAGCAGCGGAATG<br>GCCCTCGTCCTTAGACTGCCAAATCTTAACAGATTTAATGAAATGTCTTACCTGTACAAAAAGTCTAAGCAAAAGTTCTCAGGGAGAAG<br>CACATGTCTTAGAGTTTAAACACAAAGCGCTTTGTCCCATGCGTGCTGATTTTAGTCAGACTTTACTCAGTCTGAAATGCAATTAAC<br>ATTAAAGAATTAAGTGTGAGATTTCGATTTGTGATATCCCATACTCTATTTGTGATATCCCCTTTAATAAACAGTTTCCACTGATGATA<br>TGAAGGGCCGGTATAAAGAAGAGTCTTAAAGTGAGTAAGCTTCTGGATGATTAAAGAATTGGTAAAACAAAAGTTTAATCTATTTCCTTGAGCTGTTAGTGCTATTT<br>AAATCTTTTGCCCCGTTAACAAACACTTTTAGTTAGATAAGAATAAAAAAAATTCAGTTACTTTTAAAAGACACCTGAAATCTGGCCGGA<br>TGCGGTGGCTCATGCCTGTAATCCCACCACTTTGGGAGGCCGAGGCCGGCCGTGGTGAGAATTCCAGCAGCCTGCCAGTCAGGAGG<br>CTGAGGCAGGGAATCGCTTGAACCTGGGAGGCGGAGGTTGCAGTGAGCTGAGAATGCCATTGTACTCCAGCCTGCCGGGACAGCGAGACTCCAT<br>CTCAAAAAAAAAAAAAAA | SEQ ID NO.: 52<br>MALVPYEETTEFGLQKPHKPLAT<br>FSFANHTIQIRQDWRHLGVAAVV<br>WDAAIVLSTYLEMGAVELRGRSA<br>VELGAGTGLVGIVAALLGAHVTI<br>TDRKVALEFLKSNVQANLPPHIQ<br>TKTVVKELTWGQNLGSFSPGEFD<br>LILGADIIYLEETFTDLLQTLEH<br>LCSNHSVILLACRIRYERDNNFL<br>AMLERQFIVRKVHYDPEKDVHIYEAQKRNQKEDL |
| <SEQ ID NO.: 6<br>CGCAGAAGGCACGGAGGAAGCCACAGTGCTCCAGTGTCTCCGATCCTCCTCCAATCTCCGCTCCTCCACCCAGTCCAGGAACC<br>CGCGTGGCTCCTCCTTGACCACTATGACCCTCCAGCCCGGCGAGCCCGTCCTCGAGGTCCTTGTG<br>CGGCGTCGTTGTCGCTGCTGCTGGAGGACTGGAAGATCGCTGACAGCAGGCCAGGGCCATGCAGCCAGCGCTTTCATCGTGTCCTGGTCTGCAAGCAGTGAGAGAGCTGCG | SEQ ID NO.: 53<br>MSLLSSRAARVPGPSSSLCALLV<br>LLLLLTQPGPIASAGPAAVLRE<br>LRCVCLQTTQGVHPKMISNLQVF |

TABLE 5-continued

| Nucleotide Sequence (5'-3') | ORFs |
|---|---|
| TTGCTTGTTTACAGACCACCGCAAGGAGTTCATCCCAAATGATTCAGTAATCTGCAAGTGTTCGCCATAGGCCCACAGTGCTCCAA GGTGGAAGTGGTAGCCTCCCTGAAGAACGGAAGAACTGATTAAGGAAATGAGCACGTCATTCCCAGTCTTCAGCAGAGAAGTTTCGG TTTGACGGTGGAAACAAGGAAACTGATTAAGGAAATGAGCACGTCATTCCCAGTCTTCAGCAGAGAAGTTTCTGG AGTCTCTGAACCCAGGAGAGTGTGAGGAAGACAAGAACCTATGTGTTTGTGTTTTATTTGTTTGTTGTTCCAGTGTTAGCTTTCTTGA TTCCTCACTTTGCTGTTATTTATCTGCATGCTATTGAAGTTTGGCAATTGCACTTGGCATATAGTGTGAGCCAGGAATCACTGGCTGTTAATCTT GCTATTGTCTTGAATTGTAGGTGACTATTATATATTCCTAAGATATTCCTTATATTTCACTTTAATTTCACTTTAAGAAGCTGAGTGTTTCACACCTT TCAAAGTGTCTGATTGTTCATAAGAATTATTTCTTGATGAAATCATGTGGGATACTATTTTAAGAAGCTGAGTGTTTCACACCTT GAAAATATGTTTCATAAGAATTATTTCTTGATGAAATCATGTGGGATACTATTTTAAGTTCTATGAGGCTAATATCTTATCTTCTATAATTTTAGA GGGGAATATGTTAGAGAATTATATTCCTTATTCAGAATTCTAAAAGTGCTCAAAAGTTTCTAAACTTGATTTTATACTTTATTATGAGCTATCTTCTATAATTTTAGA CATTCTTATCTTTTAGATATGGCAAACTGCCATCATTTACTTTAGAATTCTAAACTTGATTTTATACTTTATTATGAGCTATCTTCTATAATTTTAGA AGTACCATAATCTCGTAGCTAAATATATTTTAGATAGAAGAAGCAGTAGAAACAGGCAAATTCCTGACTCAGTTATATA GAAATGTATTCTTTTAGTTTTAAAGGCAAACTTGTACTGTACTCTGAAAGTTTTGAAACGTATTCAAACAATTT GAATAAAATTATCATTTTAGTTATAAACAAAGAAAAAAAATATTAGGCGACATCTCGAGGCCCTAGACATTTTCAATTTTTATCCTCTGTATTGGGT GCTTTGAGACCACTGGGGTTTGCCAAGTTGTCTCCAAGGATATGTCAGAATATATTGTCTCGGGAATATCCTTGATTGCTTTCAAGAGA TAGAGTTTATTTTAGGTAACATAATAAAGGCCAGCATTTATGGTGGAAGAAGCCAGCATATATATAAGGTGGCCACTGGGGCAAGT GTAAAGTTTATTTTTGAAAGCTAATATTCTTGTTTAAGCTATTTCACCTTGTTCTGAAAATCCTCCCTTTAAAGAGAAAATGTGACACT TCCCTCCCCACTGAAGCTCTGGGTTTTGGGGGTCTCTGGAAATGCCTGGTTAGTCGGGAAGATGCGGTTAGTCCGGGTAAAGCCTGTCTAGTGC GGGAGAAGCAGAGCCTGGGGTTTTAGCACGTGGGGTTTTTGGGGGAGATGCCTCTGGTAAGATGCCGGTTAGTCCGGGTAAAGCCTGTCTAGTGC TAGAGTTTATTTTGAAAGCTTACTGCCAAGATAATTCTCTTGTTTGAAAGCAATTAATCTTTCACCTTGTTTGAAAAGTCCCCATTATTCAAAACATTTCTAAAAGTCCTCTAAATGCTCAGAGCTGTACT TGTGAAAGGCTTGTAGGAAAGCTCCTGCTTTCTCAGAATGATGAACATTTGTTTCTCAGAATAGAGTCGTGATATTCTTTAACTTTAAATGACAAACATAAATAATATATAT ATTGACGGGAGAGATGACCCCATATTCCCAGACATATTTTTAACTTTTTAAAGGTTTGACCCATTTGTATGACTTTAAGTAGCTAATTACA TATATATTACATTCACATATATTAAAATTGTACTTTTAACATTGTCCATTGCTTTCTTTGTCCTTAACAATTAAACATTTAAAAGATTT CTAAACTTCAAAAAAAAAAAAAAAAAA SEQ ID NO.: 7 | SEQ ID NO.: 54 MAVFVLLALVAGVLGNEFSILK SPGSVVFRNGNWPIPGERIPDVA ALSMGFSVKEDLSWPGLAVGNLF HRPRATVMVKGVNKLALPPGS VISYPLENAVPPSLDSVANSIHS LFSEETPVVLQLAPSEERVYMVG KANSVFEDLSVTLRQLRNRLFQE NSVLSSLPLNSLSRNNEVDLLFL SELQVLHDISSLLSRHKHLAKDH SPDLYSLELAGLDEIGKRYGEDS EQPRDASKILVDALQKFADDMYS LYGGNAVVELVLVVKSFDTSLIRK TRTILEAKQAKNPASPYNLAYKY NFEYSVVFNMVLMIMIALALAVI ITSYNINNMDPGYDSIIYRMTNQKIRMD |
| CTGGACGAGTCCGAGCGCCAGCTGCACCTGCCGGCTGCCGCCCTTCGAGTTCCGATTCCGTTCCCCAGTGCTGC GGCCGCGCCGCCACCATGGCTGTGTTTGTCGTGCTCCTGGCCGTTGGGGAACGAGTTTAGTATATTAAAATCA CCAGGGTCTGTGTTTTCCGAAATGGAAATTGGCCTATACCAGGGAGCAGAACCTGTTTCCAGACGTGGCTGCATTGTCCATGGGCTTCT GTGAAGAAGACCTTTCTTGGCCAGGAGTCGCAGTTCATTTCGTACCCTTGGAGAATGCAGTTCCTTTAGTCTGACAGTGTGCAAAT GTCAACAATGGCTCTACCCAGGAGTGCATTCGGAGATCAGTTCCTTTAGTCTGACAGTGTGCAAAT TCCAGTCACTCCTTATTTTCGAGGAAACCTTTCAGTGATCCTTGGCTCCCAGTGAGGAAAGAGTGTATATGTAGGAGAGGCA AACTCAGTGTTTGAAGACCTTTCAGTGACAATGAAGTTGACCTGTCTCTAGGTACACTCAAGACACGAATGAGAAATGGATGAATCTAATGGATGAATCTAATGGATGAAT CTCAATTCTCGAGTAGGACACATGAAGTTGACCTGTCTCAGTGCTACATGACATCTCCAGTTGCTGCTGCTGTCT CGTCATAAGCATCTAGCCAAGGATCATTCTCTGATTTATATTTCACTGAGCTGTTGGATGAATTGGATGAATCTAATGGATGAATCTTATGGG GAAGACTTCAAATCCAGATCAATGAGATCATCTCTGCAAGATCACTGAGCTGTTGGATGAATTGGGAAGCCTTATGGG GAAGACTTCAAATTCCAGATCAAGTAGTTAGCACTGGGTCAAGTCATCACTGGGTAGTTGGATGAATTGGGAAGCCTTATGGG GAAGACTTCAAATTCCAGATCAAGTAGTTAGCACTGGGTCAAGTCATCACTGGGTAGTTGGATGAATTGGGAAGCCTTATGGG GCGGAGAACCCAGCAAGTCCTATACCTTGCATATAGTCCATATATTAATATAAAAATAATATAAAAATAAAATAAAAATAATATA CGAGAACAACCCAGCAAGTCCTATACCTTGCATATAGTCCATATATTAATATAAAAATAATATAAAAATAAAATAAAAATAATATA AACCAGAAGAATTCGAATGGATTGAATTACTGTCGCAGAATTGAATAAAGGGTCTGGAAAATTGCGTGGTTGTTTGTTAAATATCT TTTGCTGTCTAGAGTGAATAAGGGAATCATAATGATGGGTGAATCCACTGTGGATAAGATTCCATATTATTTGGGTGAATACTTGATGGATATACTGCATTA AAAGATGCCTGAATTTATTACAGAATCTTACGAACATCGAATCGATAAGTTGATTTTACACCAAGAGGACAGAGAAACATTGGGTGCATATGGAAA CTATGAACATTGCTTATATAATGGGGCGTTTAATTTTAAATGGCATCATGCTGAATCGATAAGCTTCTTTACCACAGCATAGGTGAAATGTTTTTATTCTTGACTATTGTATA TGACCTACTGAATTATTGCAGAAATGTTATGAATTGATCAATCATCATCGATCATCATTCGTCAGATAGAAAACATTCTCAATTGTTATGTTTCAT TATACAACAAAATCCCTGAAAAAATCCCTTGAGGGACACATTTGAGGCATGAATAATACATTAAAACATTTATTTATTCCCCCTGTAAGTTAC | |

TABLE 5-continued

| Nucleotide Sequence (5'-3') | ORFs |
|---|---|
| TATGTTTGTGTGGTACAACTTCATTCTATAGAATATTAAGTGGAAGTGGTGAATTCTACTTTTATGTTGGAGTGGACCAATGTCTATCAAGAGTGACAA ATAAAGTTAATGATGATTCCAAAAAAAAAA SEQ ID NO.: 8 AGCGGGCTAGCGGCTGCGCCCTGCCGGGGCGGAGCGCGGGGCGGGGCCCGGGA GTGCCTGAGCCGCCGGCGGACGACGGCAGCGCGGGCCGGCTCCGTGGTTCCGCGGAGCCTGGGCTGGAGCCCGGGGTCCGCCCGGGG TGCCGTGCCAGCGGCGGCCGGCTCCCTCCCCCGCCGCTGTGATTGGGTGGAAGATGGCGCTGCCGAGGCCGGATG GAAATCCTAATGACAGTCTCCAAATTGCCTCCATCGGCCATGGGCGCCAATGCTGTACCATGGCGCTGCGTCCGGCATTAGAGAGAGATTGGTCCAGAA CAGTTTCCGTCAATGACACTATTTGGATTGCAATTTGGAATACCTGCTACTGACGTTCCAGTTCGTACTGCAAGCACTTTATTT TGTCGTCCATTTCGGCGAAAAGTTCTGCCTATAGAAGAGTCAACCTGCCTCCAGCCTTCTTACATGCTTAGCAGATCTCTTC CATAGCATAGCCACTCAGAGAATGCCACGGAAAAAGGTTGGAGTAATACCCCCTAAGAAGTTCATCACAGAAGTTACGAAGAAAATGAGCTTTTT GACAACTACATGCACAAGATGCCCATGACGAATTCTTAAATTACTACTAATTACTGTGATATTTACAAAGAGAGAAGAAGCAG GAAAACAAAATGGCTGTCTATAATGGATAATATGAAATAATAACAGCCACCAGCCCACGATACGCTTTAGACTTCAGAGATT TTTCAGGGAACATTAACTAATGAAACCAGATGTCTTACTTGTGAAACTATGAAACTGCAGCAACTCTGTCAGTGAATACAAGTATTACTGT GACGTGGAACAAATATCATTCACTGCTTAAGGGGTTCAGCAACACAGAAAACTGCCATGATTCTAGCTCTCACACCTGAAGACATTT AAGGTGTCCAGCAAATGCATAACAATTGGAAGTCATAACTCTGTTCAGTATGATTTCTTCGGGTATATCAGTTGGTCGTGTCTTTTAACACTTCAGGT AAATATATGATCATGCCTTATTCATGAAAATCAGAATACAAAATCCGGTTCAGCAATACTGCCCATGATTCTCCTTTGAGAACCTCTCTTAACACTCTGT GATGCCACCAATCCAGACAGATTTTGGTTGTGCTGATGACGAACATTGTAGAAAATAGATGCACAAGCTATTGAAGAAATCTACGGG ATAGTTAAGACATCAGATATCCTCAAAGAACTCTGAGTCTGTACATCCTTTTCTATCAGTCCGGACTCGAGAGGGACGAACCTGATGAAGACAA CACTTTCTCTGCCTCATTCTCTGGTTATTTCTGTGATTTTTCAAGAAAGACACTGATTTTCTTCAAGAAAGAAATGCAGGAAGCTCAGGG GGCAGTAGCACCTTTGCACACGACGATAAAGCAAAGCGATGGATTGTTATTGTGC ATCATGTCTCTGCTACAGTTCCAATCACAAGGAGGTGAAATCAGAGATGCTTGAATTCCTTGGGGGTGCAGTAGAACATCCGGAATCTGCGTCGTATTGA ACGCATTTCTTTCTTTATTATTGCACCAATAATGCTCCATAAATGCTCATAAATTTGCCTGTTGCCTTCTGATGAAGCATAATCCAGTGGTCTCTTTTCAACTTCAGGT TAAGGACATGAGTTGAACAACTCTGACAAAAGCATTCTCATCAAATTGCGTCCGTTGCACTTGGCTTTCTCCTGTATGGGAAGAGACAAAGA AGAGAAGGAGAGAGATTAGGGGCAAGTAAGTGCAGTCAGCATGAGCAAAAACTCAGCAGCCATGTGGACAGCGATGAATTCAGACGAGCAAAAACATGTGTCTTCCACCAGCCAAGAGGAGCTCGGACAAGTCTCGACC AGAGAGAAGGAGAGATTAGCCAGTCAGTAAGTACAAAACTCGACCGATCCTCTTCCACCGACAAGGAGCGGAGCTGGCGAC ATCACTTAGACCCTCACCTAATTGCAGCTTAAGGACATGAATCATCATGATGGAGAATCATGAAAAGCTTCAAGCTCTAGGGCCTCG GGATCCGTGATGAGGGTGGTAGTTCTTGGATATCGTTATTCTGGTATCAGTCAAGGTGTATTCTTGGATCAAGTCTTGATACTTCGG ACAAGAATCTATCATTGTAATATTGACAGATCCTTACAGAGTCGAGCATTGTCTTGGAAGATAATTGGAAGATATTGGGCACATTTCCCACCATT TCTAAAGTCTGTCAGAGACAACAGCTGCTCTAGGGGCAATTTGAAGGCTTGCTCATAAATTTGGGTTCAACATCTTACATTAT ACCAACAGAGCAGAACATACTGGAAGAGCAGAGATACGCTACAGAATCCGCTACATAAATGGGGTTTGAAGGGTCAGCAACAATCTTACAATTAT TGCTCGTCACAGAGCTCTATTTCCAGAGAGATTTGAAGGTCAGGAGGCTAGGAGCATACATCATCATCATCAACTTTTAAA ATATTATTCAGTCTTAATTGTGTACAGTTACATTAGGATATCATGAGGGAGTCCCCCTAGCATAGTCTCATTGCGAACTCCTAAGCAGGAGGATGAGT ATTGCTCATTTAAAATCAGCTGCATATTGCTCGAGGTTAATTGGTACAGATTCTGAGAAATGGTACAGAAATTAAGGTCATTCTCATATATAAA ACAAATTGAAATTGTTTCCCCCTGAGAAGGAACTATGGCCATTTATGTAACCTATGAAGATAAAACAGAGTTTTAAGAGTTTTATGCCAATCCAATTCAAAAACCGTGTTTGTCTCAATTCTTTGGTGTTTGTTT TGGACACGTGCTATAAACACCATATAGAAGATATCCTTAAGCTTTGATAACTGTAAGCGCGGAATAGAATACCCTGAATTAGGAGAGTTGCTCAGTGAATATAGGTCTGA ATCAGGACTTGTGAAACCTGTAGTGAAATACCTTGCTAATGCTCTAATACATTTAACTAACTATTTAAACAATCAATTGAAACAAAA TGGACTACTTAAGCTCTGCATTGTTTACTGCTGTAACTATTTAAAAAATCTATGTGAATTAAGAGCAGTGCTCGTCAGTGATTGGTTCTATGTTG | SEQ ID NO.: 55 MEILMTVSKFASICTMGANASAL EKEIGPEQFPVNEHYFGLVNFGN TCYCNSVLQALYFCRPPREKVLA YKSQPRKKESLLTCLADLFHSIA TQKKKVGVIPPKKFITRLRKENE LFDNYMQQDAHEPLNYLLNTIAD ILQEERKQEKQNGRLPNGNIDNE NNNSTPDPTWVDEIFQGTLTNET RCLTCETISSKDEDFLDLSVDVE QNTSITHCLRGFSNTETLCSEYK YYCEECRSKQEAHKRMKVKKLPM ILALHLKRFKYMDQLHRYTKLSY RVVFPLELRLFNTSGDATNPDRM YDLVAVVHCGSPNRGHYIAIV KSHDFWLLFDDDIVEKIDAQAIE EFYGLTSDISKNSESGYILFYQSRD |
| SEQ ID NO.: 9 GGAAGCCATTGCCTCTGTTTAATAGTTGCTGTTGCTGCACTTCCGCTTCTCCCAGCGCGAGAGAGACACAGTGCCAGCCAGCC GCAGCCCGGCAGCAGCAGCCGCCGGGCAGCGACGAGGAGCCAGAGCAGACACATCCGTCTTCCAACCAGCAACCGAGAAAGAAACAACACCCCCT ATGTCCGATGACGATTCGAGGGCCAGAGTAAGTGCCATGAGCAAGAATGGAATTCAGATGAGGAAGGAGCTGGCGAC AAGAGAAGAGGAGATTGAGACCCCTCCACCTAATTGCAGCTAAGCATGGAGGATCTTCGTGATGCTACTAACAATCTGCTACTTTGTTCTTTAAA ATCACTTAGACCCTCACCTAATTGCAGCTTAAGGACATGAATCATCATGATGGAGAATCATGAAAAGCTTCAAGCTCTAGGGCCTCG GGATCCGTGATGAGGGTGGTAGTTCTTGGATATCGTTATTCTGGTATCAGTCAAGGTGTATTCTTGGATCAAGTCTTGATACTTCGG ACAAGAATCTATCATTGTAATATTGACAGATCCTTACAGAGTCGAGCATTGTCTTGGAAGATAATTGGAAGATATTGGGCACATTTCCCACCATT TCTAAAGTCTGTCAGAGACAACAGCTGCTCTAGGGGCAATTTGAAGGCTTGCTCATAAATTTGGGTTCAACATCTTACATTAT ACCAACAGAGCAGAACATACTGGAAGAGCAGAGATACGCTACAGAATCCGCTACATAAATGGGGTTTGAAGGGTCAGCAACAATCTTACAATTAT TGCTCGTCACAGAGCTCTATTTCCAGAGAGATTTGAAGGTCAGGAGGCTAGGAGCATACATCATCATCATCAACTTTTAAA ATATTATTCAGTCTTAATTGTGTACAGTTACATTAGGATATCATGAGGGAGTCCCCCTAGCATAGTCTCATTGCGAACTCCTAAGCAGGAGGATGAGT ATTGCTCATTTAAAATCAGCTGCATATTGCTCGAGGTTAATTGGTACAGATTCTGAGAAATGGTACAGAAATTAAGGTCATTCTCATATATAAA ACAAATTGAAATTGTTTCCCCCTGAGAAGGAACTATGGCCATTTATGTAACCTATGAAGATAAAACAGAGTTTTAAGAGTTTTATGCCAATCCAATTCAAAAACCGTGTTTGTCTCAATTCTTTGGTGTTTGTTT TGGACACGTGCTATAAACACCATATAGAAGATATCCTTAAGCTTTGATAACTGTAAGCGCGGAATAGAATACCCTGAATTAGGAGAGTTGCTCAGTGAATATAGGTCTGA ATCAGGACTTGTGAAACCTGTAGTGAAATACCTTGCTAATGCTCTAATACATTTAACTAACTATTTAAACAATCAATTGAAACAAAA TGGACTACTTAAGCTCTGCATTGTTTACTGCTGTAACTATTTAAAAAATCTATGTGAATTAAGAGCAGTGCTCGTCAGTGATTGGTTCTATGTTG | SEQ ID NO.: 56 MSDDDSRASTSSSSSSSSNQQTE KETNTPKKKESKVSMSKNSKLLS TSAKRIQKELADITLDPPNCSA GPKGDNIYEWRSTILGPPGSVYE GGVFFLDITFTPEYPFKPPKVTF RTRIYHCNINSQGVICLDILKDN WSPALTISKVLLSICSLLTDCNP ADPLVGSIATQYMTNRAEHDRMARQWTKRYAT |

TABLE 5-continued

| Nucleotide Sequence (5'-3') | ORFs |
|---|---|
| SEQ ID NO: 10<br>TTGCTTTCCTCTGCCGCCATGGTCCTTGGGCCGTTGCGTCGGAAGCCTGAAGCATGGGCCGCTGAAGTGGGAGGAGCTGGGGGCCTGAGGCTGG<br>CGGTTCGCTCGCTGCGCCGCCTGCGGCGCGGCTGGCCCCTGGGCCTTGTCTGCACTTGCAGGCGCCGGCAGGGGCGCGGGAACCG<br>CGGGGGCCATCTGGCCTCTGATTGCTTCTTTATGGAAGAATATCGGGTCCTGTGCACTGTCAAGCTGATGCAAGATGGGTTCTTATTTGATCGAACGT<br>TGCAAATTCCGATGGCTTCGATGGCTTCTTTATGGAGGTCTCTGGCATTGTTCCTCATTATGCCATAGTCAAAGATATCCGGCA<br>GTTCTGTGGAATTCTGACCCGTCCGTTTGCCGTCCAGATCGAGATCAGAGGGACTTCCACCCAGAAGCCTCAACCCT<br>TTTCCTGCAGATCACCCTGTCGTGGAAGCTGGACACTTGTTCCTCTCTCAATATCACCAGAAGCCTCAACCCT<br>CAACACCATGCTGCTTACTGTTGCTGTAGTCGGTGTGGGTTGTTCACGGCTGCTCGCTGGAAGTGCACCTAGTCAGGCTTGCTCTGAAAA<br>CTCATGGCTAGATCTCAAGAACAAATGCATCAGAGAAAATGCATCAGGAAGAACCAGTTCAGTGAAGAAGTTTCAGTGAACCTTCAAAACCATAAACCAT<br>TATCTAACTTCATGAACAACCTGTTTCAAATTGGTTTAAGGCGACCAGTTTCCTGATGTTGTTCAATTAAATGGTGATATAGGGGAAAAGAGAACAA<br>ATTTGAATTGTAATAATTAAAATAATGTTTAATTATACAAAAAAAAAAA | SEQ ID NO: 57<br>MGAEWELGAEAGGSLLLCAALLA<br>AGCALGLRLGRGQGAADRGALIW<br>LCYDALVHFALEGPFVYLSLVGN<br>VANSDGLIASLWKEYGKADARWV<br>YFDPTIVSVEILTVALDGSLALF<br>LIYAIVEKEKYYRHFLQITLCVE<br>LYGCWMTFLPEWLTRSPNLNTSN<br>WLYCWLYLFFNGVWVLIPGLLL<br>WQSWLELKKMHQKETSSVKKFQ |
| SEQ ID NO: 11<br>GGTCGTTTCTGATGTGACGGCTGAGACATGAGACATCTTCAGCTGAGATCTTCGTCGAGAGATTCACTATGGAATCG<br>GATGCCGGACCAGATCTCGTCCGAGTTCATCGCAGAGTTCATCGCCAGAAGCCCAGCTTCACCACCG<br>GCTGCAACTGCAGGAACACCTGTCTAGAACCAAGATTGACACTTTCTGATGAAAGTGAAGAAGTTCTT<br>AAAAGCAATATATATATTCTGCTCAAGATCATGTCAAAATGAAGAAAACATGGAGTAATTTTT<br>AAGTCGAGACAACCCGACCTTGGCACCGCGTTTGTCAAGTTTCTACTCTTACACTGTCCACACTGCTGAAAAATCTGCT<br>CCAGGGTTTGAGCCACAATGTGATCTCACCTTGGATTCTTTGTTAAAGGAGAGCTCAAAGGAGTCAAAGGAGAGTCTCAAGAAGCC<br>ATTTGAACAAAGATTATGAGACAAAGTTTACAAAAATGAGAAAGAGAGAGCACGCAAACACCAAACATCGGGATGAT<br>GTCGACAGAGATAACAGGGACTGAGAGTGCGGAAGAAAGGGTGCTGAATCTGCTGCTAGAGCATTACCATGGCACAGTGCAATTTTCTTCA<br>TAAAGTTAATGAAATCCAAGAGCTGATAAGTTGAAACAGCTGGATACCATTGAAAAATCTGCGCAGACAGT<br>AGATGCTTGAAAACAGCTAACTCCGAGTTCCCAAGGAGCTGATAACAGTACATGCCAAAAATAGGAACTTCTGAGGAAGAG<br>AGAAAAGACTTGACTGTAACTGCCACCCTAGACGCGTCTAATAAAATCCTCTCAACTTCACGAAAGAATTCTCAGACCTGTTGAGGCCAT<br>AGGATAAAGACCGCATCAGTCTCAGGGAATAAGGAATATGGCAGTCAGTCAAGGGGTACCTGCTAAAGAAAGTGACGGATCCG<br>GAAAGTATGGCAGAGGAAGAGTGCTCAGTCAAGAGAAGTGTTGAGTCCTAACACATATCAACCAGCCACAGTTTCA<br>GAACCTTCTCACCTGCCAAGTAAGAAAATCCTTAATCGGAAGACAAAAATCTTTGACCACTGATATCACATATAGAACATAATCATCACTTTCA<br>GGCAGAAGATGCAGGAGAACCTGAAGCTGTGACATGCATGCTACTAGACGACCATGGCCTCTACAGTGTGAGA<br>GCAGAGTGCGGGAGAAGAACACCTGGAAGCCTCTTCGAAAGCCATTATTGAGGATGCTCAGGAGATATGCTCCAGGAGATAGAGAGCAT<br>CGATTGTGGCTCATCAGAAGCTCATCAGTCTTCGACTCTTCTTTGGAACTAGACAAATTAGGAACTCGGCGATCAACCAACA<br>GGGGTTCATATTTCGATGGATGCAAGGACAAAATGTTTCAGATGTCTTCTCAAGTGATATGACTGTACGAAAAGAATA<br>TAGTTTTAATGATATATGGAAGCAAATTTACCGAAGCCACCCCTTCAAGGAACTCAAGGCACAAAACCATGGCACAGAGCT<br>TATCACTGCAAAGTATGTAGATCATAGGTTTTCAAGGAAGACCTGGCAACACATCTCTTCGACATGAATTGCTTGAGGCCAT<br>CAAATCCAGGAGATTTACTTGCACTATTGCAAGTCTATGCAGAGGGTAGAGCTATGCAGAAGACTATGCTATGGGAACCTGCTGGGAGAGCT<br>GTCCACAAACAAGAGCCCCTTCACCTTGCCGTCCAACCTCAGATCAGACATCTCTCTCCATTTGGTTGACTTCTTGTACAAAACTGTGGGAA<br>CCTGGATAAGCACAGGCAGAGAAACACAGTTCTACAGTTCTACACTGTATATGCAGTAAGCCTGAGCTTTGAGCTTTGCTCAG<br>GAGCAAGCCTGTGATTAGTTAACACATTGAGAGACATAGCAAAGAACTACCTCGTTTCATACCAGTGTAGAAA<br>TCTGCTTCCCAAGGCTAAATCGGAAAGTTCAATCTGAAAGTTCAATCGAACGTAGAATTCTTCGACAGAGGAGATAGATGA<br>GAGCGATGATCGATGGATGACAAGCCTGATCTGACGCTCACAAGAAGAGCGCTCACCAGAGCTGCCACTCCTCACCAACCAG<br>CTTCGTTTCCACAGACAGACCTGCCCACAACCAAGGAGCACTTCCAGGATTCAGCACTTCCTCCTCTAGGAAGAGCCGGGAAAGGTCCAAT<br>TGGCCCCACCTTCAACACTCCCTATCCGACCCTCTAAGCACCTCCACTACCTACGTGGCCCCAGCACACAAGTGGAGGACTACTCCATGGCCAGCATAGTTCCAGGCCCAGAGGCAGTTCGTCAAAGACCATCAGATGG<br>CGGACACAGAACCTCATCCCTATCGACCTCTAAGCACCTCCACTACCTAGTGGCCAGCATATCCCCAGCAGTGGAGGACTACTCCATGGCCAGCTTCGCTCCGTGGTAACGATGG<br>GGGTCCATCTTCTCCAAGTAAGACTCTCCTAACTACCTCAGAAAGGTTGCACAAAAGATCATCTCTCCTAGAAAATGCGCCACCATCCCCCGA<br>CCCAAGATTCTTCTCTAAACTACCTCAGAAAGGTTGCACAAAAGATCATCTCTCCCTAGAAAATGCGCCACCATCCCCCGA<br>AATCTTTCAGAAATCATCATCGAGAATTGCGCCTAAGCAGATTGCGCCAAGCAGATGCCAAAGAACTGCCCCCCAAACCACAGCTGGGAAGGCTGCTAGCAAAATGCCCAACCCCAACT<br>CAAGCCCCAAATTGCCTCCCAAACCAGATGAAGACTCTGAGGTCACATGAGATCATCTTCTCCAAGAAGTGCAGTCCAGACTGAAGA<br>TGTCTCACCCAAGGCTAAGCAGAAGCATCTGAAGAACTTCAGGACTCCAACGACTAACTGCAGAGACGCCCGTACCACCTGCAGAGACGC<br>CATCCAAAAGCAAGCATCATCGAAGACTCCAACGACTAACTGCAGAGACGCCCGTACCACCTGCAGAGATCAATAC | SEQ ID NO: 58<br>MRSSASRLSSFSSRDSLWNRMPD<br>QISVSEFIAETTEDYNSPTTSSF<br>TTRLHNCRNTVTLLEEALDQDRT<br>ALQKVKKSVKAIYNSGQDHVQNE<br>ENYAQVLDKFGSNFLSRDNPDLG<br>TAFVKFSTLITKELSTLLKNLLQG<br>LSHNVIFTLDSLLKGDLKGVKGD<br>LKKPFDKAWKDYETKFTKIEKEK<br>REHAKQHGMIRTEITGAEIAEEM<br>EKERRLFQLQMCEYLIKVNEIKT<br>KKGVDLLQNLIKYYHAQCNFFQD<br>GLKTADKLKQYIEKLAADLYNIK<br>QTQDEERKQLTALRDLLIKSSLQL<br>DQKEDSQRQGGYSMHQLQGNKE<br>YGSEKKGYLLKKSDGIRKVWQRR<br>KCSVKNGLLTISHATSNRQPAKL<br>NLLTCQVKPNAEDKKSFDLISHN<br>RTYHFQAEDEQDYVAWLSVLTNS<br>KEEALTMAFRGBQSAGENSLEDL<br>TKAIIEDVQRLPGNDICCDCGSS<br>EPTWLSTNLGILTCIECSGIHRE<br>MGVHISRIQSLELDKLGTSELLL<br>AKNVGNNSFNDIMEANLPSPSPK<br>PTPSSDMTVRKEYITAKYVDHRF<br>SRKTCSTSSAKLNELLEAIKSRD<br>LLALIQYYAEGVELMEPLLEPGQ<br>ELGETALHLAVRTADQTSLHLVD<br>FLVQNCGNLDKQTALGNTVLHYC<br>SMYSKPECLKLLLRSKPTVDIVN<br>QAGETALDIAKRLKATQCEDLLS<br>IDESDDLLDDKPSPIKKERSPRP<br>QSFCHSSSISPQDKLALPGFSTP<br>RDKQRLSYGAFTNQIFVSTSTDS<br>PTSPTTRAPPLPPRNAGKGPTGP<br>PSTLPLSTQTSSGSSTLSKKRPP<br>PPPGHKRTLSDPPSPLPHGPPN |

TABLE 5-continued

| Nucleotide Sequence (5'-3') | ORFs |
|---|---|
| GGGGAAAATAAAGTGAGGCGAGTGAAGACCCATTTATGACTGCCAGGCAGACAACGATGACGAGCTCACATTCATCGAGGAGAAGT<br>GATTATCGTCACAGGGAAGAGGACCAGGAGTGGTGGATTGGCCACATCGAAGGACCACCTGAAAGGAAGGAGGGTCTTTCCAGTGTC<br>CTTTGTTCATATCCTGTCTGACTAGCTGTGTTCACCAGTATGAGGGTAGCCTGCAAACAAACAAAATAGGAGTAGACAGCAATGCAGTATTCTAACAATGCAACAATTGACTCTGTTCTACAAGCAACAAAATAGGAGTAGACAGCAATGCAATAGTCAATCTGTCATGTAGCCTGCAAAATGCAACATTA<br>GTCTCCAGCAACCGTTGAAAGGCATAGAATTCAGTATTTCCAGGTGAAACTTTAGCTCCATGAGAACCAGCCTGTAGTTATCTGTACACAGTTACAGCT<br>GCAAAAGGTGGGTTCTGTTTTCCAGGTGAAACTTTAGCTCCATGAGAACCAGCCTGTAGTTATCTGTACACAGTTACAGCT<br>ACAAAACCTACTTTGTATTTATTACAGAAAAGTGCTCAGTTAAGTGTTATTCCTTCAGCAAAATATTCACTGACCCCAAAA<br>CTCTTATGCATTTTACAATGCACCAGCCTCATGCAAGTTTAGACAAGTGGATTTATACTGTCTTATGAGTGCCCGCCCCTGATA<br>TATTACCTCATTATGCCAAAAATAACATATCTTTCATGACATATTTTGAAACACATATGAAGTTCAAATTTCAGGAC<br>CAAGGACTGCCAGAAATATAGCCTCTAATTAGAAAGTCTTACCTGCAATAATAATTTCCAG<br>GATAAGTGGATTGTACATTTTTAAACTTGATTGCCATTTAAAGCAGAATATATAAGGTTGCAACAATATTGTTCTAATCACTGG<br>CTTTCTCAAGATGTATGGATTGGTTGTTTGGACAATATTTTAAAGATTATTCAAGATGTGTTGAAGCATCCCATGAAGCCTACCTCTCAACAAGTTTCCAC<br>CTACTGTATGTAGAATCCAGGGCCTGAGCTGTTCTTCTTTTGACAATTCTTTTAAACCCCATAATAATAATTTTCCAG<br>CCTTAAGCCTCTGCTGCTTCCAAGCCATGGTTCAATTCATAACCAAGTTTTGAACCCTGTCATGATCTTTACATCAGTGTGAAAGGACTCTTCCCTC<br>TCAGTTTCTCTTTCATTCATCCAGCCATGGTTTACTCCACAGTTGTATTCTGGCAATCTGTTCCATGGTCATGTAGCGCCACTACCATTTCTGGAATTTGCTTAAAT<br>TGCTATTTTGCAACAGCAGAAAACTAATAATTTTTAAGCAGAAATTCTGACGAGAATGTTAAATTCACAGAAGCAC<br>AACTCCCAATTAGGAAAAAGCCCCTCTTAGGACACCTTTGCTCATGAATATACAAACCTTCATCTGATCTGATAAGGCTTATTGCT<br>ATACAACATTGCTTCCTCAGGTCAATGTGAATTTCCAATCACAGAGCCATGAGGAACCAGTTGACATGCTGGGTTGTGA<br>TAAGCAATTGCTTCCTCAGGTCAATGTGAATTTCCAATCACAGAGCCATGAGGAACCAGTTGACATGCTGGGTTGTGA<br>TGGCCAGTTAGCAGCCTGGGTACTGCGGATCGTTCCCGATGGAAGTCTGAGGTTCAGTGTCCCGGTCATT<br>CATTTTACACATTCACATTTGCATTAAACTTGACTCCCCCCCCGGCCCGCCCGCCCCCCCCCCCCCCCCCCCCGCCCCTTCTATTCTTTTCCC<br>CCTTTTGCAGCAACTTACCCCCCGGCATTTCAACATTTGGTGGAATCCAGTGAGAAATACCCTTTGTCTGAGATCAGTGTGTTAAGTCTGATCTGATC<br>CTCTCTGTGGCCAGCTACTGTGGAATCCAGTGAGAAATACCCTTTGTCTGAGATCAGTGTGTTAAGTCTGATCTGATC<br>TTAACTCAGTAAGCCACTATCTGCAATTTGTACATTATAGAATATTTGAAGATATGGAACAGCCTGTGAACAAGTAATCAAGTCAATCAATT<br>AGTTCTTTTTCCCCAGAGGGGAAAGTTATGTTCTGCAAAGTATGTTCTCTAAATTACATGAGAGTTAGTCTATTCTATCTCCC<br>TTTATGCCTAGAACTTCAACATGTGTCATTTCACATGTGTTAATGCACGGTTTCACAGTTACCAGTTGTATGTGTATATTTATTCTACTTTATTTAATATTATAAAATTGCTT<br>AACATCAGTACACTTGTCATTTCACATGTGTTAATGCACGGTTTCACAGTTACCAGTTGTATGTGTATATTTATTCTACTTTATTTAATATTATAAAATTGCTT<br>TTAAATAAACATATTCTCAGTTGATCCC | KGAVPWGNDGPSSSSKTTNKFE<br>GLSQQSSTSSAKTALGPRVLPKL<br>PQKVALRKTDHLSLDKATIPPEI<br>FQKSSQLAELPQKPPGDLPPKP<br>TELAPKPQIGDLPPKPGELPPKP<br>QLGDLPPKPQLSDLPPKPQMKDL<br>PPKPQLGDLLAKSQTGDVSPKAQ<br>QPSEVTLKSHPLDLSPNVQSRDA<br>IQKQASEDSNDLTPTLPETPVPL<br>PRKINTGKNKVRRVKTIYDCQAD<br>NDDELFIEGEVIIVTGEEDQEWWIGHIEGQP<br>ERKGVFPVSFVHILSD |
| SEQ ID NO.: 12<br>CTTCAGAGAGCAATATGGCTAATGGCTGGTCTCCCAACATGCCTCACACCCCCTCATCTATATCCTTTGGCAGCTCAAGAGGTCAGCAGCCTCTGGA<br>CCGTCGAAGAAGCTCCGTTCGGTTCCGTTCCTGTGGGCCCGTGACAAACTTTCCCCCTGAAGTCCAAAGAAAGCAAGTTGACTCTATTCTGG<br>ACCTTGCAACAACCCCCTCTGTCATCCATTACACGAAGTGACCTGTTTGTCTGTCCAAAATCGTAATAGGAGAGAGAGCTGG<br>TTCCCAGTGAGGCTACTCACCCAGGAGTAGCTGCAAGCTCAGCGAATCTGTCAAAGCTCAAGGGATCTACTAAGTGCACATGGTCCTGCAGCCAAT<br>CTCAGCAGCCTCACCCAGTGAGCTGTGTCATGTCCATGGAAGACATGGGAAGGATGTGATTTATACCGTGAAGCCCTGGGGCAA<br>AAGAATGGCACTTGTGTGCACAATAATGGGTCCATCCTCCCATCTTCCCCAATCTTCCAGTCTCTTTTGTCCAGGAGATGATAACCTTCATCTGCCGGTTGCCAGG<br>GCAACCAATGACTGCCATAATGGGTCCATCCTCCCATCTTCCCCAATCTTCCAGTCTCTTTTGTCCAGGAGATGATAACCTTCATCTGCCGGTTGCCAGG<br>CTCTGTGTCTCCTGTTGGTGCCCCTCCTGCTCAGTCATTGTCGGAAACTTGTCCGGAAGAGCTCTGTGGGCTATTTCTGTACTGGGAAATATGCCCTGATGCCTGATGGTC<br>ACAATTGTTGAAAGAGAACAATCCTAAAGGAGATCTTGCAAGAGATTCCATCCACCCATTGCCCATTGCCCATCGCTGGAGAAGAAAACCAGAGTACGAC<br>AATCCCCACTCACACTATAGAACATTTCCGCCAGACAAAGGCTATTTTGCCTTATGAGAATGTATCTAGACACAGCAGTGCACTCCCCTAAG<br>TCTCTGCTCAAAATGACTTTTTCAAAGGTTAATTATCATGTCCTAGAAATGGGAGTTCATCAGCAAACTCAGAAAATCTGAAGTCTGAGAAATC<br>CCCAAACCAGAAGGTTGACTTTTTCATCCCAAATGAATGCAGCCTTGTCAGCAACGATTGTCAGCAACATTCATAATTCATCCACTCCTTCATCGAGAAGAGTATT<br>CCTATAGAAATGTAACATGTCAAGGTCACACATATTAATGACAGCTGTTGTATTATGATGCCTCCAGGTGCTCCAGGTGTCTCCAGGTGTATTATGATGCCTTCAT | SEQ ID NO.: 59<br>MAGSPTCLTLIYILWQLTGSAAS<br>GPVKELVGSVGGAVTFPLKSKVK<br>QVDSIVWTFNTTPLVTIQPEGGT<br>IIVTQNRNRERVDFPDGGYSLKL<br>SKLKKNDSGIYYVGIYYSSSLQQP<br>STQEYVLHVYEHLSKPKVTMGLQ<br>SNKNGTCVTNLTCCMEHGEEDVI<br>YTWKALGQAANESHNGSILPISW<br>RWGESDMTFICVARNPVSRNFSS<br>PILARKLCEGADDPDSSMVLLC<br>LLLVPLLLSLFVLGLFLWFLKRE<br>RQPEYIEKKRVDICRETPNICP<br>HSGENTEYDTIPHTNRTILKEDP<br>ANTVYSTVEIPKKMENPHSLLTMPDTPRL<br>FAYENVI |

TABLE 5-continued

| Nucleotide Sequence (5'-3') | ORFs |
|---|---|
| TCCATCCCAGGGCTTGGATGTAAGGATTATACCAAGAGTTCTTGCTACCAGGAGGGCAAGAAGACCAAAACAGACAGACAAGTCCAGC AGAAGCAGATGCACCTGACAAAAATGGATGTATTAATTGGCTCATAAACTATGTGCCCAGCACTATGTGAGCTTACACTCAATTGG TCAGACGTGCTGCTTGCCCCTGACAATGAAATTGGCTCCAAATGAACTACTTTCATGAGCAGTTGTAGCAGGCCTGACCACGATTC CCAGAGGCCAGTGTGGATCCACAGACTTGAAGTCAAAGTTCAAAGTGACAAGGTAGCTAGCTGACCATGTTTGGCAGAT ACTATAATGAGACAGACAGAAGGTGTGCCAGAACCCATCCAATAAAGAGACCGAGTCTGAAGCTTCATTTATGCATGCTGTCGAAGAAA AGTCTAGGTTTTAAGGCTGTGCCAGAACCCATCCAATAAAGAGACCGAGTCTGAAGCTTGTAAACCTTTAAAGATGGTTAATTCATTCAATAGATATTTA GAGTCAGGCAGTGAGACTGTGGGGGCAGTGGATACTTGTAAACCTTGGAGCCAGTGGGTTCATCTGAGGTCA TTAAGAACCTATGCGGTCCGGCAGTGGCTGACCACCTGTAATCCCAGCACTTTGGGAGCCGAGGTGGCCATCTGAGGTCA GGAGTTCAAGACCAGCCTGGCCAGCCATGGTGAAACCCCATCTCTTACTAAAGATACAAAAATTTGCTGAGCGTGTGGTGCACCTG TAATCCCAGCTACTCGAGGAGGCCAAGGCATGAGAATCGCTTGAACCTGGGAGGTGGAGTTGCAGTGAGCCGAGATGCACCACTGC ACTCCCAGCCTGGGCAACAAGAGCGAAACTCCATCAATACAAACAAACAAACAAACACCTGTGCTAGGTCAGTCTGGCACGTAAGATGAAC ATCCC ACCAACACAGAGCTCACATCTCTATACTTAAGTGAAAAACATGGGAGGGAAAGGGAATGGCTTGTTTGTATATGT TCCCTGACACATATCTTGAATGGAGACCTCCCTACCAAGTGTGAAAGTGTTGAAAAACTTAATAACAAATGCTTGTTGGGCAAGAA TGGGATTGAGGATTATCTTCTCTCAGAAGGCATTGTGAAGGAATTGAGCCAGATCTCTCCTACTGCAAATCCTATTGTAGTAAAAAGTCTT CTTTACTATCTTAATAAAACAGATATTGTGAGATTCAAAAATAAAAAAAAAAA | SEQ ID NO.: 60<br>MSSDRQRSDDESPSTSSGSSDAD QRDPAAPEPEEQDEERKPSATQQK KNTKLSSKTTAKLSTSAKRIQKE LAEITLDPPPNCSAGPKGDNIYE WRSTILGPPGSVEGGVFFLDIT FSSDYPFKPPKVTFRTRIYHCNI NSQGVICLDILKDNWSPALTISK VLLSICSLLTDCNPADPLVGSIATQYLTNRA EHDRIARQWTKRYAT |
| SEQ ID NO.: 13<br>GACTGCGCGGCCGGGAGGAGCCGAGCCCGGCCAGCCGAGCTTTTCCGAAGGCGCTGGGCGCTGCACACCTCCCGAGCCCGG GGGAGCTCGCGCTCGCGCCAGCCAGCTTCAATGTTCCACACTCCCGGCCCAGAGCCTCCCTCCTTTTTTCCCCGCCCCCTTTCCC CCCCCGGCCTCCCTTCCATTTCTTAAGGAAGGGGTTTTTTCTCCTCTCCCCCCACCGTAGCGGCGCGCGGCGGCCGGGCCGGCC GGGCGCCGGAGTTTTCCAAGAGATAACTTCACCAAGAAGTGTCCAGTGATAGGCAAAGTCGATGATGAGAGAAACTTCTGCCACCCAGCAGAGT GCAGTTCAGATGCGACGAGACCCAGCCCTCCAGAGCCTCTAAGTTATCCACTAGTGCTAAGTAGTGCTAAAGAATTCAGAAGGAGTCAGAATAACCCTT AAAACCCCCTAATTGCAGTGCTGGGCTAAAGGAGAATAACATTTAGAATGAATGCAACAACTATACTTGGTCCACCGGGTTCTGTA GATCTCCCTCCTAATTGCAGTGCTGGGCTAAAGGAGAATAACATTTCATCAGATTATCCATTTAAGCCACAGAAGGTTACTTTCTGGTTAACAGTTCCGACTATTTGACCAACAGA TATGAGGTGTGTGTTTTTCTGGAGTCAGGGAGTCATCTGTCTGGACATCCTTAAAGACAACTGGAGTCCCCGCTTGACTATTTCAAAGGTT TTGCTGTCTATTTGTTCCCTTTGACAGATAGCCACAGGATGGACCAAGAATAGCCAACCTGGTTGGAAGACAGCAGAA GCAGAACACAGGATAGCCACAGGATGGACCAAGGAACATAAGCCATATTCCAGAAATGTGATGCAGTGATGCAGTGGAGCAGAAG GCATCTTCTCACTGTGCTGCAAATTTTATAGCTTACAATACGGACTTCTGTATATGTATAAATTCAGCACAGCGCCACTCTTATTTTT CCCTTTGGAGCCTGGGAGACTCCCCAAAAAGTAAATGCATCAAGAGTAAATGTTTTACCTTTGTCAGTTGTAATGAGAGATTTTATTGTATTGTTTAAAACGCC TACTTGCAAGTCTTGCTTTCTTTGGATATCAAAATGATTATTTTGTGATGATACTGGTCTCGAAGTCATGCATTGTATTAAACCCAG GCAATCATTGAGTTCTGCATCTGAAGCAGGGTCTGTCCCGGATCCTCCCGCCTGCAGCCT ATCTATTTCTGAGTATGTCATGCTGTTGTGAAAATGTTTTACCTTTGTCAGTTGATAATGAGGATTCCTTTGCCTTTTACCCTTTGTAG CTCAGAGACCACCTGATGTATCATCTCAAACACCAATAAACATGCTCCTGAAGGAAAAAAAAAAAAAAAAAAAA | SEQ ID NO.: 61<br>MARGSALLLASLLLAAALSASAG LWSPAKEKRGWTLNSAGYLLGPH AVGNHRSFSDKNGLTSKRELRPE DDMKPGSFDRSIPENNIMRTIIE FLSFLHLKEAGALDRLLDLPAAASSEDIERS |
| SEQ ID NO.: 15<br>CGGTGGTTGGGTGGTAAGATGGCGCTGTGAGTCTGCGGCTCGGCGACTTGGTGTGTGGGGGAAACTCGGCCGATATCCTCCTTGGCCA GGAAAGATTGTTAATCCACCAAAGGACTTGAAGAAACCTCGCGAGAAATGCTTCTTTGTGAAATTTTTGAACACAGAAGATCAT GCCTGATCAAAGTGCAAAGTGGAAGTTCCTCAGGAAGCCAAAGTGAAATGATAATGATAAATTAACAAGGTAAACGATTCCAGCAA GCCGTAGAATGCGTCAGAAGAAGTTCCTCAGGAAGCCAAAGTGAAGAAGCCAGAGCTTCATCCCACCCAAAGTGTTCTCTGATGACAAGATCGA CGTAATTCCAGTGACGAGTAGGCCAAACTCAGGTGATGAGAGAAGCCAAACTTAGCCTGTCGTGAAGGAAGGTGAAGAAGAAC | SEQ ID NO.: 62<br>MAAVSLRLGDLVWGKLGRYPPWP GKIVNPPKDLKKPRGKKCFFVKF FGTEDHAWIKVEQLKPYHAHKEE MIKINKGKRFQQAVDAVEEFLRR AKGKDQTSHNSSDDKNRRNSSE |

TABLE 5-continued

| Nucleotide Sequence (5'-3') | ORFs |
|---|---|
| ATGGGAGAAGGAAAGAGGGGTGTCTTCAGGCTCTCTTCAGAGAGAGGCTCCAAATCCCCTCTGAAAAGAGCCCAAGAGCAAAGTCCC<br>CGGAGCGGGGTCGGCCCCAAAGGATGAGAAGGATCTCACCATCCGGAGTCTAGTACCGTGAAGGGATGATGGCCGACCGATG<br>GCCGCGTTTAAATGCCGAAGCCAACCGGCAGCCGAGCTCGTTAAAGATGCAGATCCTCATTTCCATCATTTCCTGCTAAGCCAAACAGAG<br>AAGCCAGCTGCTCTGTTACCAGGCAATCACACCCACAGCATCGAAGAAGTTGAAGAGGAAACTGGCTCACCTCCATCCAGGCAGCTGAC<br>AGCCAGCCGGTGAATGGCCAGCATCCACAGTGACTGTCTGAAACCGACTTTCAGAGAAATTTTTGGCCTTGGTCTCATGGGAAGTGGAATCGTCTCC<br>AACTTGCTAAAAATGGGTCACAAGTGTCTCAACCTGACTCTGCAGATCATTTGCTGCCGGTGATCTCCAAGGACGCGCCAAGGACCTGGTGCTG<br>GGAAGACACCCCGTGTCTGCAAGGGATCCGCTGGGGAGTGCTACGTGGACATGTCAACAGTGGACACTGTCACACTGGCCGTCACTGAGCTG<br>GCCCCAGTGGTGATTGTGTCAGGAGGGCCCTTTCAGGAGAATCAGCAGCTGTCTAATGACGGATGTTGGTG<br>ATCTTAGCGGCTAGCAGCCAAGATGATGGTGAACATGTCCAGGGAAGACATCCTTCTTCCAGGTGAA<br>GTGCTGCAATGCAGCCAGTGTGGACATCCTAATCAGCGACCACCTTCCTGGACGTGGCCACTATTGCCAGGGGCTCATTGCCTGCC<br>CAGGTGACAGGCCAGTCCCAGTGGACATCTTGGACACTGTGCGGCGCTTCCTGGAGGCCCTGTCGGGAATGCCAA<br>AATATCCTGCAAGGAAACTTTAAGCCTGATTTCTACCTGAAATACATTCAGAGGATCTCCGCTTAGCCATTGCCGCTGGGGATGTCG<br>GTCAACCATCCGACTCCATGGCAGCTGCAGCTGAGCAAATGAGGTGTACAAAGAGCCACCGCCATCTCCTTCTGACCACCGTCTCCACATG<br>GGGGTCGGGGCCTACATACACTAAGCTGTCCGACCACTTCATTTCCTTTTATACAGACTTGAGCTTGCCATCGAGAGCTG<br>CACACAGCAGCAGGCCTTCCCTGAGCGGTGTGTGTCACAGGACCAAGTGTCAGCAGGATTGCGTGTGGAAAGCTCTTGAGCTGGGCA<br>CTGGCCCCCCAGAGAGGTGGCTGTGCCTGGCTTGTTTTTCCTGGCTGTCAGTGGAACTGTATCTCAAAACCCTTGTATCTGAAGGAACTAGAATCAGCA<br>ACGAGAGTTGAAGCTCTTCCCCAGAGCGTGTAGTCATGTCCCCACTGATTCCTCTACAAGGA<br>GAGGGCCTTGGGCCTCTAAGCGTCCAGTGTGCACCCAGCGCTCAGTGCAGCCGGCCTGCAGGTGAGCATGGCAGCGCTCACCGCTCGAAGCCATGC<br>GGGGCCCTGGCCTTCCAGGGAGTGCAGCAGCCGCTCCTCCGGCCGGCGCCTTCCTCTCCAGCAGCGGAGCATGATAAGAGACTGGCACCGCGGGAAGCCGG<br>CCAGAGCCACTGCCCTCGCTGAGCCAAGCTGTTTTAGTATTTGGATTTGCATTCCATCTCGCTGGGGAGGAGCCATCCTAGAGGCTC<br>TCAGGGCCACTAGTGATGAGCCAAGAACTGGGCTGACTACCTGACGTGTAATGGAGCTCCTCCTGGGTGCTGGTCTGGACACCAAGGCTG<br>CTGAAGAGCACTCCTCCCCTCGGTCCCCCTCCAGTGGAGACACAGTATTTCTTGCTGTCTGCCCCAGACCCAGCTGACCAACG<br>TCCATCCTCCTCCTCCCCTGATACGGAAACGAGCTGTCTAGTCATGTCCCCCATCGCTTCGGTGCTCCGGCCCC<br>ATGACATTTCTTAGGCTGCAGCTCTGATAGCCAAGAGGTCTTTAGCAATGCTTGAAGCTTCTGTTCCAAAGCTGCTTAGACAAGCTG<br>GGGGTCTGTCGGGAGGAAGAACTGGGCTGACTACCTGACGTCAGTTCATTTCTACTGAGCATTTCTGTCTGAACACAAGGCTG<br>TACATTTGTCCTGGATAGGGGCGAACACACTGGGGTGGGGGGGAAGAGTGGGGGAATGCGGTAAGAAGGAAGTTACCAGAGGATGTCAGTTTTTTATCCCT<br>TGCATGGGTGGATTTTCAAAATCATATTTGTAAGAAGATATCGTTTGGAAGAAGGCCCCCTTCAGAACCGTTGTGAACACGAGTGG<br>CACTAGGGCGGGTCCTTCCCCCTGAGGATTTCACTGAGATTTTACTGAGCATTTCTGTCTGAACACAAGCTG<br>GGGGAGGGTGGAAGAGACTGGGGGTGGGGGGGAAGAGTGCGGTAATGAACCCGTTAGTAGATTCTCACTTGAAGGTTTAAGTTGT<br>GACAATTCTGTGAAAGCTTCTTTGTAAGAAGTCGTTTGAAGACAATTGTCTTCAGAATAGGATGTGTGATAAATGTTAATTGGCAAAACAAACATGATTTTGTGCA<br>GAATTTTTATTTTGTGTTTTGTAAATGAACACTTTGGTAACACAAAATAAAACAATAAAAAAAAAAAAAAAA<br>ATTAACAAAGCTACTGCAAGAAAATAAAACACTTCTTTGGTAACACAAAATAAAACAATAAAAAAAAAAAAA<br>SEQ ID NO.: 16 | ERSRPNSGDEKRKLSLSEGKVKK<br>NMGEGKKRVSSGSSERGSKSPLK<br>RAQEQSPRKRGRPPKDEKDLTIP<br>ESSTVKGMMAGPMAAFKWQPTAS<br>EPVKDADPHFHHFLLSQTEKPAV<br>CYQAITKKLKICEEETGSTSIQA<br>ADSTAVNGSITPTDKKIGFLGLG<br>LMGSGIVSNLLKMGHTVTVWNRT<br>ABKCDLFIQEGARLGRTPAEVVS<br>TCDITFACVSDPKAAKDLVLGPS<br>GVLQGIRPGKCYVDMSTVDADTV<br>TELAQVIVSRGGRFLEAPVSGNQ<br>QLSNDGMLVILAAGDRGLYEDCS<br>SCFQAMGKTSFFLGEVGNAAKMM<br>LIVNMVQQSFMATIAEGLTLAQV<br>TQSQQTLLDILNQGQLASIFLD<br>QKCQNILQGNFKPDFYLKYIQKD<br>LRLAIALGDAVNHPTMAAAANE<br>VYKRAKALDQSDNDMSAVYRAYIH |
| AGTACCTTGGTCCAGCTCTTCCTGCAACGGCCCAGGAGCTCCAGGAGCTCCATCTGACCTTCTAGTCATGACCAGGCCCGGAGC<br>ACTCCTGCTGTCTCACGACTGCCTAGCACTTGCCTGCAGCACTTGGACACCAGAGGAGCTGACGACCTTCGTCTGGACACGCTGG<br>GTTTGGAGACAGCAGCGTGGTCACTCCTGGGTGGTGGAGCCCCCAAAAGATAACAGCTGCCAACCAAACGGGTGG<br>CCTCTACCAGCTCACTGCCATCCACAGCCTGGTGCTGCCATCGGCTGCGGCCGGTGAACATCTCCTTGCCAGCAGCCTCTGCCCCT<br>GGGLSASTTSPSQLLACGPTVHHE<br>CGGAGCCTGGGCTCCTCCTCCCAGGGCCCCCGTGTCAGCCAGGACCAAGTGGGGGAGGGACCAGAGGTACGTACACAT<br>TGTGTTCCCGATCGATGGCTCAGGCAGCATCCCTTCCCCCGGACTTCACACGTCGTAGGACTGTGATAGCAGTT<br>CCAAAGCCCAGCACCAGGTTTCCCGATGCAGGTTCTCCAACAATTTCAAAACATTCCACCCGCATCCAAAATGTCGCATAAAAGTGG<br>AACCCCCTCAGCTCTTGGCTTCTTGTTCACCAGCTGCAGGATGCCCGCAAGGGTTTACATACAGGCTTCATCAATGCAGCGAGGAAGGCACTAAT<br>GTTCCATGCCATGATGGCCGGTGAGCATGCAGCAGCAGTCCGCCATCGCCATCCCTATGCATGCAATTGGGGTTGGATTAGCTTTCAAAACAGAAATTC<br>TTATAAGATGATTCATCCCCATGGCTGATGCAGCAGCAGTCCGCCATCCGCTACGACCGATCAAGCTTGGAATGCATTAGCTTTCAAAACAGAAATTC | SEQ ID NO.: 63<br>MTRTRAALLLFTALATSLGFNLD<br>TEELTAPFVDSAGFGDSVVQYAN<br>SWVVGAPKITAANQTGLYQC<br>GYSTGACEPIGLQVPPEAVNMSL<br>GLSLASTTSPSQLLACGPTVHHE<br>CGRNMYLTGLCFLLGPTQLTQRL<br>PVSRQECPRQEQDIVFLIDGSGS<br>ISSRNFATMMNFVRAVLSQFQRP<br>STQFSLMQFSNKFQTHFTFEEFR<br>RSSNPLSLLASVHQLQGFTYTAT<br>AIQNVVHRLFHASYGARRDAAKI |

TABLE 5-continued

| Nucleotide Sequence (5'-3') | ORFs |
|---|---|
| TTGGAAAGAATTAAATGACATTGCATCGAAGCCCTCCCAGGAACACATATTTAAAGTGAAGGACTTTGATGCTCTGAAAGATATTCA AACCAACTGAAGGAGAAAGATCTTTGCCATTGAGGGTACGGAGGACAGTAGCTTCCTTCGAATTGAGATGGCACAGGAGGG CTTCAGCCGTGTCTTCACACCTGATGCCCGTTCTGGGCGTGTGGGAGCTTCACCTGGTTCACCTACCGTGGGCCTACCCCC AAATATGAGCCGTCTTCATCAACATGTCTGCTGGGGACTGTCCTGGGGCACTTCTCACCCAGTGTCCACCGAGCTGCCCTC CTGAAGGGGGTGCAGAGGCCGAAGCTCACGGGGACTGTTCTTCTACAGGACAGCACCCCAGGGCCCCTGGTGTGTCCCTTGCCCAGGCA ATGAGGGATGAAGCCGAAGCTCCTATTCTACGAGGACTGTGTGCTCCGTGACGTAGACAGCGACGG CAGCCGACCTGGTTCCCTCATTCAGGGGTGTTCGTGATGGTGTCTTTCTACGGGGCACCCACCCCTGGCCCCAGGGG GTGGAGAAGGTGGTGTGTGATGTCTTCCTCACAGGACGTGCCTCCCTCTCCAGGAGAACGTGCTCTTGACCAGTGTTG GGATGTGAATGGACAAGCTGACACCCTCACCCAGGATGCCCTGGACTGACCTGGACTGCTGTGTGACCCTGTGTCAGACCACAG AGTCTTGGACCCCAGCATGCAAGAACCTCAAGCCAGGATGAGCCCGCCGATCGCGGCTCTCCCCAGCTCCTCGTGCTCTCGC ACCTGGCTCTGGGTGGAGGCATGGCTGCCGAGATCCTACCGTCTGGGATGTCGAGCCAGTCCTGAGCCAGCCAG TGAGCAGAGACCCTGGTACAGTCCAATCTGCCTTTACATTGACACAAGTTCTAAGAACCGTTCTGCCAGTGCCGTGACCCTCCAAAGCTC TGTGACCTTGGACCTTGGCCCTCGACCCTGGCCCTGAGTCCCTGCTCCCCGCTGAGTCCAGAGTCTGTGACCCCCATTACTTT CCGAGTCCTCGGGCTTGAAGGCACATGGATGGCTCGAAAGAGGAGACTCTGTGACCATCTACCCCAGATTACCT GCGTCTGAAACTCTACGGTGGTGAGCCCTGGACCCTGAGATCTTCTCGTGGGCGGCCGCCAGATCGACAATGGC CACGGCTCCAGGTACTGTTGACGTCTCCCAAGCGTGTTCTCTGGAGCTCTCCCCCAGCTGGAGCTGGACTGTGTCTCTACACTGTGGTTACGCAGCCAGCGACGCCGGA GAAGTCCCTGCTGTGGGGACTCGTTCTCCCAACCCCGCAGAACTTCTCAGAGTCTGGAGAAGCACAACTTGGGACACAGAGGA CAAATACCCTCCAACTTCTCAGAGTCTGGAGAAGCTGAAAACGCAGTCAATAACCTGGGACAGAGGACAATTGGGAGGAGGA ATTCAGTCTCTCTGGGTCCTCAGAGTCAGGGCAGTTGAACCAGAGCTGTGTGATGCATTCCGATGCATCAGCTGACTCCCCAGAA CCATCCCTTCCTGCTGCTGGGTCCGGTTCCGTGAGTTCGGGCTCGTGAGCCGCACATTCACCGTGAAGATCCACCTCCACCT CCAGTTCAGCTCCAGTATATTGACGACGAGATTTATGAGAGGACTATCAAGAAGCGGTGCACTCAACAAGTGTGCTCCCGCCTCACCAT CCAGAGCTCCCATTATGGAGAGCCAAATGCCCGAGTTTTCCCTCGAGTCCCACTCAGGAGAAACGGGACAGAGGCCTAACTT TGGCCTTGGACTTTTCTCCCCGCAGTTTCCTTTGGGAGAAAACGGTTGCTTGGAGAACCACTGCACACAG CGAGAGGAGGCCATGGGGATGGCCTGCTCTGCTTGAACCAACCCTTTGCTTGGAAGGGCCCTTGTCCTGTCAAAGGTTCCAAC TGGAAACCTTGGAGACTTAGGACGAGGGCTCCTGTGATCCCTCCCAAAGACTCTCAATGCTACTAGAAATACAAAGGAACATAACCC AGGCCTCAGTGCCGAGTCCGCTTCCTCCAGCCTTGGCACTCGAGCGAATGACTCCCAAAACATCGTCGTAGCCTTTGAATAA GAGAGGAGTGCCGGTTCCCTGCTCCCGTGTCATTCCCCAGGCTGACAGGGCTTCGTCTCTTGTCTTGCAAGGTCCAACCTC ATGTCGCTGCTGTCACATTCGCTGTTCAACACCCTCCCCCATTACCTCCAGGACTCCTTTAGCCAGCTGCCAGCGCTCGTCCAGTTGAAT TTCCATCCAGAGAGGTGGGTTTCAGGGGTGCCACAGCAGGCTCCAGTTCCGAATTTCGGCCCTTCGTGTCCCCATCCTCTTCTGTCCATG TCAGCATCAGCTCAGGCCTCAGGGTTTCCCATGGGGACCAGCCTTCATGCCCGATTCGAATGGAGATGCCGGGCTGCATCGTCGGTTCCATTGGGTGCTG CAGCCACCCCAGCCCCAGGCCTGCCTTGGACTTGGGAGACAAGCATGGATCGATCAGCATCTATTTTAGAGCTATGAATAATTTTGAGGCCTAGTAATATATGACCAAAAAAATGTCAAGAC ATGATTATTTTTTCAAAAATAATTTAAAGTTTGTGTAATGTTGTGTTAAATTAAAATGCACAAAAAAATGTCTTGGGAAAATGTCAAA GGTCTAAAAAATAAATAAAAAAGCCTTCTGTGAAAAAAAAA SEQ ID NO.: 17 | LIVITDGKKEGDSLDYKDVIPMA DAAGIIRYAIGVGLAFQNRNSWK ELNDIASKPSQBHIFKVEDFDAL KDIQNQLKEKIFAIEGTETTSSS SFELEMAQEGFSAVFTPDGPVLG AVGSFTWSGGAPLYPPNMSPTFI NMSQENVDMRDSYLGSTELALW KGVQSLVLGAPRYQHTGKAVIFT QVSRQWRMKAEVTGTQIGSYFGA SLCSVDVDSDGSTDLVLIGAPHY YEQTRGGQVSVCPLPRGWRRWNC DAVLYGEQGHPWGRFGAALTVLG DVNGDKLTDVIGAPGEENRGA VVLFHGVLGPSISPSHSQRIAGS QLSSRLQYFGQALSGGQDLTQDG LVDLAVGARGQVLLLRTRPVLWV GVSMQFIPAEIPRSAFECREQVV SEQTLVQSNICLYIDKRSKNLLG SRDLQSSVTLDLALDPGRLSPRA TFQETKNRSLSRVRVLGLKAHCE NFNLLLPSCVEDSVTPITLRLNF TLVGKPLLAFRNLRPMLAADAQR YFTASLPFEKNCGADHICQDNLG ISFSFPGLKSLLVGSNLELNAEV MVWNDGEDSYGTTITFSHPAGLS YRYVAEGQKQGQLRSLHLTCDSA PVGSQGTWSTSCRINHLIFRGGA QITFLATFDVSPKAVLGDRLLLI ANVSSENNTPRTSKTTFQLELPV KYAVYTVVSSHEQFTKYLNFSES EEKEBSHVAMHRYQVNNLGQRDLP VSINFWVPVELNQEAVWMDVEVS HPQNPSLRCSSEKIAPPASDFLA HIQKNPVLDCSIAGCLRPRCDVP SFSVQEELDFTLKGNLSFGWVRQ ILQKKVSVVSVAEITFDTSVYSQ LPGQEAFMRAQTTVLEKYKVHN PTPLIVGSSIGGLLLALITAVL YKVGFFKRQYKEMMEERANGQIAPENGTQTPS PPSEK |
| SEQ ID NO.: 17 AATGAGCCCGTCTGCAGCAGAACCTTCTGCCGTCGAACCTGGACGCCGCCTCTGCCTCTGCGATCTTGTGT TGGGAGGGCAGCAGGGATGGCAGCTTGAGCTTGCGCAGTCCCTGCTCTAGAGACAGCCCGCGCAGCCGCGAGGAGGA GCCGCCGCCCCCGACAGTCTCCCTCGCGGCACAGATGTGGTGGATCAGCCCACGACTATGGTGAATCCCGGCCGCTCACGACT ATGTCGCCGCCCATGCTCGATCCGTTCTGGTCCCCTGGGCATCACCAACATAGCCATTCGCACTGGGACTCCACTG CTGCTCGTCAAGGACATGCAGTCGGAGATGCTGGCCAGTACGGGCTGGCCAGTCTTCCATCGATGCAGAGCACT | SEQ ID NO.: 64 MVKFPALTHYWPLIRFLVPLGIT NIAIDFGQALNRGIAAVKEDAV EMLASYGLAYSLMKFFTGPMSDF KNVGLVFVNSKDRTKAVLCMVV AGAIAAVFHTLIAYSDLGYYIIN KLHHVDEVGSKTRRAFLYLAAF |

TABLE 5-continued

| Nucleotide Sequence (5'-3') | ORFs |
|---|---|
| ACTTCAAAAATGTGGCCTCGTGTTTGTGAACAGCAAGAGAGACAAGGACCAAAGCCGTCCTGTATGGTGGTGCAGGGGCCATCG<br>GCGCCGTCTTTCACACATGTAGTTAGATACATTAGATTGAGTATACATTCAATAAACTGCACCATGGACAGTCGGTGGGGA<br>GCAAGACGAAGGGCCTTCCTGGTGGGATGCCTCAATCTCAGATGTCAGTTCAGGTTGTTTTGTAGCCATTTGCTTCACAGTCT<br>ACAAATACAGTTCCGGAGCCCCTGCTCATCCCGACATCCCTGTACATGGGCCACTTGTGCCTGTCCACCACCCCTGTGCCTGGCTACT<br>TGGAATGCCGGGAGCCCCCTGCTCATCCCGACATCCCTGTACATGGGCCACTTGTGCCTGTCCACCACCCTGTGCCTGGCTACT<br>ACAGAACATTCGGCTCTAATTCTGCCACACAGAAGTGGCCCGGAGTCAGTCGGGGGAGTGCAACATAAGAAAGATGCTGAGCTTCTGT<br>GGCCTTTGGCTCTAATTCTGCCACACAGAAGTGGCCCGGAGTCAGTCGGCTATTGTCAACCTTTGTTCCCGGACAGCTTTGACGCTCTGT<br>CAGCCAGAGGCTGCCGCGATTTTGAACGAATAACCCAGCACGAGCAACAAACAGTGTGTGATGTTTGACAGGAAATCGTGCTGT<br>ATCCTGCTTCGCAAGAATAACCCAGCACGAGCAACAAACAGTGTGTGATGTTTTGACAGGAAATCTGATAGACATCATCG<br>TCGTCTGCATGGCTCTGACTCAGCCTCTGTTCTGCTTCCAGTTCCACTCACAGTGAGGGGCATCC<br>GAGTGGACTTTGCCTTTGCAGAACTCTGTGTTCCTTGTGCGATTCTCTCCCAGTTCCAGTCACAGTGAGGGGCATC<br>TCACCGGTGCGATGACATCGAAGAAAACCTTGCCTCGTGCTGCCATCCTGTCCATCGCAATG<br>TGGCCTACCCTACCCGTGCACGGTGCACGGTGCCACCCTGGGCGTGGAGCTGCAGCGTGGCGTGTGTGAGCCTGGCCTTTGTGGAGATCCATCCACCATGGTCG<br>CCATCGCTGCGTGTATGTCACCGGAAGCAGACATATCGTGGAAGCAGATCATCTCGTGAACATAGGCAGGACATGTGGGGACCATGTGCCATGACAG<br>ACAGTCAGTCGAGAGACACATCATCTCGTGTCAATTCTGTAAGCAGCAGACCACATCCTGTGCCATCAGCAGTGGGGGACCTAGTGAATGGTCTTT<br>AAGAGGCCTTGATTTGAAAGGTTCGTGTCATATGTCACCTGACTTCATACCCCTGGAACCAAAGGACTGGTGTGCCATCTGCCATCCTGCACAGCAG<br>CGTTGTCGTCCCCTGGACACAATCTCCTCTTGGAACATCTCCACGACCAGCAGCGGTTTAAAGGTCCACCAAAACTCGGCTTCTCCTTGATTTGCTTCCAGTCACATG<br>GCCGTACAAAGAGATGGAGCCCGGTGGGCCCTCTTTAAATTCCGTTGGGCATCTGGAGCTGGCAACGCATGGACAGCAGCAGGCTGACCAGGCAGGCAATTCTCGTTTCTAGA<br>GCCGGTGAGGGTGCCAGCCTGGGTTGGTTTGAAATGCCCGGGGACGGCAATGGTGCAGCAACATGACAGAATTGGTTGAATGATAAGGCAGTGATATAGCAGGCACGGCAATTCTCGGCATCCAGATTC<br>TCTGGCAACGGCATCTCCCCCCACCGTGGCCTGCTCTTCAAGGTTCACAGCTCTTGCATGGTCAATTCTGAAGAATTGTCCTCCAGAAGCGCAACCAGATTC<br>CAGACCCTGCCGCATGACTTTGTTTGTACAGTGGCTTGCTTCAAGCTTTAAGGTTCACGATCTCATCCAGCATTCTAATGCTGAAGATGTACAGTGTGTACTAGGTAACTTTT<br>CTAACTTTGCATTTTAGTTTACAGTAGGCTAACTACCTGGGTCTCTTAGTCCTTATCTTGTTAACCACTAATCAAGTCCAGGATGAGAATGTACACGATTCGAAATCCATGCA<br>AACACCATAGATATGGAAGATTTGGGAAGCCGATATTTTATAACGATTAACACCATCCGAAATCCATGCA<br>GTGCAGTATTTTTTCATTATGGTGTACTGGCAGCAGTTTTATATTTAAAGTGCACCATGGCTATTCAGTTCACAAAAGGCAGTGGGCAATATAGCAGA<br>ATTCCTAGACTGAAAGAACCTAAACAAAAAAATATTTAAGGTCATTCAGTGCCATGAATATGCTAATGTTTATGCTCAACATACCTGCAGTGAA<br>AATACATTGTATCAATGAACATGTACCATTTCGCATTTCTTATTGGCAGCAGTTTTATATTTAAAGTGCAGCAGTTTCATTGAATGTAAGGCTCAGTAAATG<br>ACGATTATGATTGTAACATGTACCATTTCGCATTTCTTATTGGCAGCAGTTTCATTTAAGCAGGACCATCGTGTGTCATTGAATGTAAGGCTCAGTAAATG<br>ACAGAACTATTTTCATTTATGGGATTACTAGGGCTGGATACCTCAGAGAAAAAACATCAATTATACCAGGGAATAGAAAGCATTAGAAAATTAAACAATTATT<br>TCAGAGGCAGATCAAGATATTAAAAAAAATCCAATGTATCAGTTTTTTAAAGAACATTACTAAGAATTAACAATGGAA<br>TTAACATGTGTGACTTTCATGCTTCTCTGGGGTTGAGCTAGAGCAGGAGAGGGGGCATGGAGAGGCAGGCAGGGGGCTGGCCAACATGGCCAACAACCCTGT<br>AATCCCAACATTTAAAAACATAAAAATTAGCTGCCGAGATCCCCCATGGAGTCGAGGGGACTTAAGGTTAGCAGATCTCACACATACCTGATCCAGCCTGTAATCCCAGCCTGGGTGACAGAGCAAAACTCCATCTC<br>AGGCAGAGGTTGTAGTGAGCCGAGATGCGCCCCATGCAGCTCCAGCCTGGGTGACAGAGCAAAACTCCATCTC | PFMDAMWTHAGILLKHKYSFLV<br>GCASISDVIAQVVFVAILLHSHL<br>ECREPLLIPILSLYMGALVRCTT<br>LCLGYYKNIHDIIPDRSGPELGG<br>DATIRKMLSFWWPLALILATQRI<br>SRPIVNLFVSRDLGGSSAATEAV<br>AILTATYPVGHMPYGWLTEIRAV<br>YPAFDKNNPSNKLVSTSNTVTAA<br>HIKKFTFVCMALSLTLCFVMFWT<br>PNVSEKILIDIIGVDFAFAELCV<br>VPLRIFSFPVTVRAHLTGWL<br>MTLKKTFVLAPSSVLRIIVLIAS<br>LVVLPYLGVHGATLGVGSLLAGF<br>VGESTMVAIAACYVYRKQKKME<br>NESATEGEDSAMTDMPPTEEVTDIVEMREENE |
| SEQ ID NO.: 18<br>GACAGCCCTCGGGTCCTCGGTCGGTACAGTTCTGCAGTTCTCTCGCACCTCTGACTCTGGTATTGTCACACTCTAATTGATTTGTTTCAAGCTACCC<br>AAAATACTCCGATGAAGAATAAAGAAAGCACATTTGGTTATGTGCATGGGTCTCAGGGAGCTCTGAGCCTGTGACCTGGCGGT<br>GCAGCCATGTATGAGCTGGTGGAGCGGGCCACACGACATTGTTGGAGAGATTATTGATTGAGGCGGTGACACTACTATTCAG<br>GTGTATGAAGAACCTTCTGATGTGTCTGTATTCCAAAGACCTTTGCACTGGTAAACCCTCTCGTAGACTGTCGCTGAGCAGTGGTCTGGCATT<br>ATGGGAGCCCATTTTGACAGAGATATCAATGGGACTTACCTTGCAAAAACCTAGGTGGTAGTCATATCACGGCAGGACATT<br>TATGAATTGTCAGTGAGCTGGTTACCCCCAGACAAATCATGTTACCGGGAGAACTTAACTACATGCTGAAGGAAGTTCACCATGGTCAAGTATGGCCT<br>CCTGGGAATTATGATACCTCTGATGTTGTCTTGGAGCTTGAAGTGAAGGTAAAGGAAGTAAAGGAAGTTCACCATGGTCAAGTATGGCCT | SEQ ID NO.: 65<br>MDFSKLPKILDEDKESTFGYVHG<br>VSGPVVTACDMAGAAMYELVRVG<br>HSELVGEIIRLRGDMAFIQVYEE<br>TSVSVGDPVLRTGKPLSVELGP<br>GIMGAIFDGIQRPLSDISSQTQS<br>IYIPRGVNVSALSRDIKWDFTPC<br>KNLRVGSHITGGDIYGIVSENSL<br>IKHKIMLPPRNRGTVTYIAPPGN |

TABLE 5-continued

| Nucleotide Sequence (5'-3') | ORFs |
|---|---|
| GTACTCAAGTCTGACCCTGTCACTGAGAAGCTGCCAGCCAATCATCCTGTTGACTGGCCAGAGAGTCCTTGATGCCCTTTTCCG TGTGTCCAGGGAGGAACTACTGCTATCCCTTGGCTGTGAAGACAGTGATATCACAGTTCTATCCAAGTATTCTAAC AGTGATGTAATCATCTATGTAGAGATGTGTGAAAGAGGAAATAGAGATGTCTGAAGTCCTCCGAGGACTTCCCAATGGGAG GTTGATGGTAAGGTAGAGTCAATTATGAAGAGGACAGCTTTGGTAGCCAATACCTCGTGTCGTGACTGACTCTAGAGAGCCTCT ATTATACTGGAATCACACTCTCAGAGTACTTCCGTGAGTAATGCCTGAGAATGGCTATCATGTGAGTACTCAGCAGCCTATGATGGCT GAGGCCCTTAGAGAATCTTGGTCGTTTAGCTGAAGATCCTGAAAATCCTGAAAGAGGATGCAGCATTGTAGGAGCAGTTCTCACCT TTTTATGAACGAGCAGGGTGAAATCCATCCACCTCTTGTGGCTATCCACAGAAATGCTGCCTTAGGATGAAGAACTAGCTCAACGT GGTGGTGATTTTCTGATCCAGTTACATCTTCAACACCTTCCATTGCGAGTGCCTTGATGGTATCCCTCTGCCTTAAGGCATAAGGC AAGCATTTCCCCTCTGAGACAGAACAGTTATGGCTCAATTGCTCAAGGAAGAATCCTTGACGGCTCAAGTGACGCAGTGGAAAGA TTCGTTCCTGCCCATTCTACAAGACAGTAGGGATGTCGTCCAACATGATTGCTCATTGTATGCATCTGGTGTTGAACAACACT AGGTTCTGCCCATTCTACAAGACAGTAGGGATGTCGTCCAACATGATTGCTCATTGTATGCATCTGGTGTTGAACAACACT GCCCAGTGACAATAAATACATCATTGTCGAGCACATGGTCCATTATTCGTGAGCACATGGAGAACATTCCTGAAATTCAAG GATCCACTGAAAGATTGGTGAGGCAAAGATTACAACTGTGATTTCCTTTCCTATGGACATGCAAAGATCATTCCGTAGCCTTGAA CCCTTGCTTCTTATTGGTGCAGCTTGAAGGCTCTAGCATTTGTCCCTGGCTGTCCAGAGAAAAATTGCTTGGCAGAAATGCAAAGT CAAACATTCCTTTTGTCTAGTGTGTAGGGTGATGACATTTGGAATTGGAAGGCCAGGTTTCTATAACTTTGAACAGGACTA ACTGATACTTCTTTTGACTGAATTTGAATGCAGTTGGAATGGGACCAGGTCCTATAACTTTGGAACAGGACTA ATGTTCAATTATGTTTATTTTTATTCCATATATCATCTGGACAGGTCTCCCTGTGTGCCCAGCTGGAGTGCAATGGCGTGATCTTGGCTCA GCTAGCCCTTCGCTTCCCGGTTCAAGTGATTCTCTGCGCAGTGCCAACCTTCACCATGCCAACCTCAGGCATGCTGAATGTGAAG GCTAATTTTTTAGTAGAAACGGGTTTCAGATGAGATGGTTCAGCCTGGTCTGAACTGTGAACAGCCTCAGGTCATGCCGGG TCGGCCTCTATTGAGGAAGAAGTATTCTTCTATACAACTTGTTTACCCTTGCAGAACATTGACAACGATTGGTCAATGGTTGTTGAG ATACGGACTTGATGGTGCTGTTTAACTCAGTTTGCTTGTTAATCAGTTGAGACAGTCAGAAATGCTGTTTCTCAAGCAACTAAAGACACTTAAA TCAAAACTCTTATTCCTTTCCTTGTCAATGAAAATTGATCGTACCCCACACCACCCTGTTATTCCCATGGAATGGAATGCAAAATAAATAATCA AATCATTTATCCTCTTTAAGTATATGTTTAAAATAAATATTTGTCAATATTGCAGAACAGTCTGGCTCACATGGCA AACAGCCAGTTGACCAATCAGTCCAAAGTGTATACCTTTCCATCCAATAGTGCTGGCACCAGTTGCAGGATGACATAGAATATCTA AAATCATTTTATCCTCTTTAAGTATATGTTTAAAAATATGTGCTGCAGTTTATGACAGCAACAGTCGCCAGCAAACAGT ATTCCCATTAACTCTTTTGACCAATAGTGCTGGCACCGTTGCTGCTCCATTTAATATATGTCTGAAGAATCTGGCTCACATGAAA TCTCTTGGTCTATTGAGGAAGAACGGCGTTTACCATCAGAAGTAGTTGTTTAATCTTTGCAGATTACATGTTTACAGT GGCCCTGCTATTGAGGAAGAAGTATTCTTCTATAACAACTTGTTTACCCTTGCAGAACATTGACAACGATTGGTCAATGGTTGTTGAG ATACGGACTTGATGGTGCTGTTTAACTCAGTTTGCTTGTTAATCAGTGAGACAGTCAGAAATGCTGTTTCTCAAGCAACTAAAGACATTT TCAAAACTCTTATTCCTTTCCTTGTCAATGAAAATTGATCGTACCCCACACCACCTGTTATTCCCATGAATGGAATGCAATAAATAATCA ATTGTTTTTATCTTCCTTTCCATGAAGTTCAAGGATTTTCAGTGTTGCTTGGAATTTGAAAGATAATATCAAGTGAATGAT AGCGAACCTATGCTCAGATTATCATCGTAAGTCCTTCCCTTACCTGTACAGAGTTTCAGATCGGTCACTGAGAGTATGATGTAAGT AGTAAGACATGTATTAAACAAGTGTAAAAGATTTCATTATGTGGCCCCTCCTTAAATCAGTTGCTTCAAATTTCAGTGTGAATCCACACCTTTATTATTGTCAAATTCTCCATCCGAACGAAT AGAAGGCCATATATAATTTGCCTCCTTAATCCTTGAGATTTCACTACCTTTATGTGAAATGCTGTATAATTCGTGAAAGAATAAAA GTGGATTTAAATTAAAAAAAAAAAAAAAAAA SEQ ID NO.:19 | YDTSDVVLELEFEGVKEKFTMVQ VNPVRQVRPVTEKLPANHPLLTG QRVLDALFPCVQGGTTAIPGAFG CGKTVISQSLSKYSNSDVIIYVG CGERGNEMSEVLRDFPELTMEVD GKVESIMKRTALVANTSNMPVAA REASIYTGITLSEYFRDMGYHVS MMADSTSRWAEALREISGRLAEM PADSGYPAYLGARLASFYERAGR VKCLGNPEREGSVSIVGAVSPPG GDFSDPVTSATLGIVQVFWGLDK KLAQRKHPSVNWLISYSKYMRA LDEYDKHFTEFVPLRTKAKEIL QEEEDLAEIVQLVGKASLAETDK ITLEVAKLIKDDFLQQNGYTPYD RFCPFYKTVGMLSNMIAPYDMAR RAVETTAQSDNKITWSIIREHMG DILYKLSSMKFDPLKDGEAKIKSDYAQLLED MQNAFRSLED |
| ACGCCTGGTCTCTGGGACGCCCCCTTCGCCTCGGACCCGTTTCGCCTCGGAGCCCGGTAGGTCCAGGTGCCAGCCGGCCAGTGCTGCTCCG TGCGCCGCGGCCGGTCGGGGCGGCGGTCCAGGTGCGGTCCAGTGCCATGATCCGGCAGGAGCCGCTCCACATCCTACCAGGAG CTGAGTGAAGAGTTGGTCCGCAGATTCGAGAGTGTGCAGGGGTCAGGACGGAGCAGAAGGGGCAGCCGGAACTGCAGAAGCTCCGGT ATCTTACCAGGCCTGACACGAGTCCGCCCTCCACAGCATCCGCTTCAGCAAGCCTGCTCGAAGACGCTCTTCCGGTCCTACTC SEQ ID NO.:66 | MIRQERSTYQELSEELVQVVES SELADEQDKETVRVQGPGILPGL DSESASSSIRFSKACLKNVFSVL LIFIYLLMAVFLVYRTITDF |

TABLE 5-continued

| Nucleotide Sequence (5'-3') | ORFs |
|---|---|
| ATCTTCATCTACCTGCTGCTCATGCTCTGTGCCGTCTTCCTGGTCTACCGGACCATCACAGACTTTCTGTGAGAAACTCAAGCACCCT<br>GTCATGTCTGTGTCTTACAAGGAAGTGGATCGCTATGACGCCCCAGGTATTGCCCTTGTACCCCGTCAGCCCCAGTTGCTCAGCTGT<br>GACCACCATTACGAGGTCATTCCTCCTGACAACGTCTGCCTCTGAAATCTGCCTGAATTGCACCACCAGAGATCAACTACACG<br>TTCCGCCTGAACAAGAGTAGTGAGGACTTCAGCGCCATTGATTACCTCCTCTTCTCTTCCAGGAGTTCCTGCAAAGCCCAAAC<br>AGGGTAGGGCTTCATGCAGGCCTGTGAGAGTGGGCAGGAGGAGTCTGTTAACATTGACCAAGGCCAGCT<br>GTAAAGACCTGTCAATTGTTTTTGTCTTTGAATGGAAAGATCCTTTCATCCAGAAAGTTCCAAGTATAGTCACTGCCAAT<br>GCCAAAAAGTGCTCAATTGCTCTTCTCTGTGCGCCTTCTTGGCCATTATTTAAAGAAGAGTCAGGCAACGAGCCAGCAGCAGCAGCTGAA<br>CCTTGAACACAATTGCTCTCTTCGTGCGCCTTCTTGGCCATTATTTAAAGAAGAGTCAGGCAACGAGCCAGCAGCAGCTGAAAATGATG<br>ATCAAAATTAGAAAGAGATACCTTAAAAGAGAGTCAGGCAACGAGCTATCAACAATCGTGACTACCTCACTTGAAGAAATGGGGCTTGC<br>TCCATCAATGGACGCATGTAAAACTGTAAAACTGTCCAATAATAGAAGAGGCTAATAGTAAGACGTATGATAAA<br>TGGGAGGAACGACATGTAAAACTGTAACCCGTCCCAAAAGAGTGTAGAGCAGCCGTATATGAGCTAATGACTATAAA<br>CCTACAAGTTATTTAAATATTTAAATTATTATAGGTTAAGCTCCTAGTATCAAGACGTGCAGGTCAGTTTCTACTTTAAAGTGAC<br>TTTCTCCTGTTGTTCATTGTATTTATTCATTTTTCCAAAATTCCTGAGTATCAAGACGTGCAGTTCACTCTTTAAAGTGGAC<br>AAAAGAGTGTGATTTTCTTTTCCAAAATTCCTGAGTATCAAGACGTGCAGGTCAGTGCTCTTTGATTTGTTAAATGTTAAATGAGACTTTA<br>CAAAACCCCTATGACTTGGCATCATCTGACATCGCTGAGGCTGTCTCAGGCTGCTCATGATGTCTTAATAATGTTAATAATGAGACTTTTA<br>AGGCTACTAGAGAAACTCAAAAGCACTAGACAGATGTACATAGAAGGTGCCTACTCATGTATTTTGATGATTTCATTGGTGACTTCCAAGGA<br>TAGATTAATACACTCAAAAGCACTAGACAGATGTACATAGAATATCTGCTCAATCATCGGGCACAATTACTTTCATTTGGTGACTTCCAAGGA<br>CAAAAAGTATGATGCTGGACTCCCAAGACTAACTCTCAAGTATGTTCTAACTGCTTCCAGGAAGGGTTGTTAGGC<br>ATGGCAACTGATGGAGCAGGTGTCCAGAAGAGTGACCTGTGACCCCTCAAAAAGTCTTAGCAGAGTTTTAAGCCTTTGGGTATTATGTGCCTGTTGAAAGAGCATTGGTGTA<br>CCATCATATGAGGAAGGGTATACGAGTGACCCTCAAAAAGTCTTAGCAGTGTTCACATTAAGGTAAATTGTTCAGAGAATTGTTCCAGAGAATGAGTATGGTA<br>AGTCTATTTCACATTAAGTTCAGTAATCTCGCTTCCGATAATCCAAAGGAATAATCAAATGTATGAATAGGCATTTAAATGGGAAGAAACTGTTTTTTGGAT<br>GAATGATTAAAGTGAACTGTATAAAG<br>SEQ ID NO.: 20<br>GCGGACGTGGGCAGGAGGGCTGGAAAAGCCGGCTGGAGGCGCCGGCGTGGAAACAGAGGTTATCCCCCAAAGGCCGCCGCACTCCCA<br>CGCGAGAAGCGCGGAAGCGATGCCAACCCGGAAGCGACCGCAGGAGTTCGAGGAGGATCTTCTCTGACATCAAGCAATGGTGGTGAAAAATGTT<br>TCGCAAGGGCAAAAACGACACAGTAGCAGTTCCACAGTAGCGAAATCAGTACTAAGAGCAAGTCTGTGATTCTAGCCTTGG<br>GGGTCTTTCACGATCCAGCAGTGTGCCAGCCTCGACAGTTCCACAGAACGAATTCAAGAAGGTCAACAATAATTCAGATACCTG<br>TGCAATTTGTGAATAAATATGTTGGTGCCAGCATCTGGAAAGTGCCTTTGTTCCTCCGAGGGAAGAATTATAGGGGAGTTTCCAAGTATGG<br>AAATTATATGAGGGTGCCCAGCAACATCAGAATGATCGTTTTGCACAGACCACAGCACACCGCTTTATCATCTGAAGAATCCTGAATCCAATC<br>CATAAAAGTATCAAGATCAGAATCAGATACATCGTGCTCTAATAGCCGATGTGTTACAGTACGATCAGCC<br>TCTGGGGCGGGAAAAGCACAACGCCAAAGCCATTTCAGGTTTCATCCAAGCAATGACGAAGCAATGACTCTGAGAAATCCCTGAATCCTGAATCGCAATC<br>CCTGAACAAGCAAGCACAAGTCACTTCATCTGAAGGTTTCAGCTGTTCAATGCTCATGCCGAAATTGAATATATGACTGACATAGAAGTTATCTTCCTTGCTC<br>CTAGATTTTCTGAAGAAATGGATTTGTGATCATTGTATCATTGTCATAAAATGCTTACAAGGTGCTCAGTGAGTTAACTCTCA<br>ATGAAGTCATCTATTTTCTGGGCTAAAACTTCATTGTCTTTTTCAACTTCTAATAAGCTTAACCTAAGGTGTCACGAAGACGAGA<br>TGTCACAGAGGTCCACTCAGTGACAGTGATCTGAGCATCTGAGGGAAGACATGGGCCTCAGTGGCCTGGCTTCCAGTCA<br>TGTATCACGTTGGCATGGACCTTCGTCGTCGGCCAGGAGTGTGGAAACATGCATGCATGCATCATGCATCATGCCAAC<br>TTAAGACACACAAGACAGATTTCGCTGTGAACAAAAATCCATGTCTGGAAGATAGAACAGAGATAATGATGAGAACCTTAA<br>AAGAATTACCCGCTCATAATGCTAAAAGTATGTAAAGATCCATGAGCTGGAACATGTACTTTTTTTTAAAGGACTGTCAATTACAAAACTTTAAAGAT<br>TAAAAAACATTAAGTAACATTAAAAAAAA<br>SEQ ID NO.: 21<br>CCTCGCCCCCTACGCGGGAACCCAACCCGGACCGACCTGCCACTCCTCCAGTAGCGCTGCACGTCGTCGTCAATGGCCGCTA<br>TGAGGAGGTGAGCGTGTCCGGCTTCGAGGAGTTCACCGGGCCGTGAACAGCAATGCAAGACCATTTCGCTCACTTACGGG<br>TTCTAAGGACGCGCGGGGAAAAGCTGGTGCCCGGACTCGTCGAGCCTGGAACAGCGAAGACCATTAGTGAGGGGCATACTGA<br>AGGAGTGCTGCTCGCCAACTACTGCCATGGGAACAGCTCAAATAATGATCTCAGGCCAACCTGTGAGAATGTTGTT<br>CTCGAAGATTAAGGATTTTAGGATGCCAATCATGTCTTGATTGTCTTGATTTGTTGTTAGTATCAATAAACTGTATATCTGCTTTGAAT | SEQ ID NO.: 67<br>MFRKGKRHSSSSSQSSEISTKS<br>KSVDSSLGGLSRSSTVASLDTDS<br>TKSSGQSNNNSDTCAEFRIKYVG<br>AIEKLKLSEGKGLEGPLDLINYI<br>DVAQQDGKLPFVPPEEEFIMGVS<br>KYGIKVSTSDQYDVLHRHALYLI<br>IRMVCYDDGLGAGKSLLALKTTD<br>ASNEEYSLWVYQCNSLEQAQAICKVLSTAFD<br>SVLTSEKP<br><br>SEQ ID NO.: 68<br>MARYEEVSVSGFEEFHRAVEQHN<br>GKTIFAYPTGSKDAGGKSWCPDC<br>VQAEPVVREGLKHISEGCVFIYC<br>QVGEKPYWKDPNNDFRKNLKVTA<br>VPTLLKYGTPQKLVESECLQANLVEMLFSED |
| | REKLKHPVMSVSYKEVDRYDAPG<br>IALYPGQAQLLSCKHHYEVIPPL<br>TSPGQPGDMNCTTQRINYTDPFS<br>NQTVKSALIVQGPREVKKRELVF<br>LQFRLNKSSEDFSAIDYLLFSSF<br>QEFLQSPNRVGFMQACESACSSW<br>KFSGGFRTWVKMSLVKTKEEDGR<br>EAVEFRQETSVVNYIDQRPAAKK<br>SAQLFVVFEWKDPFIQKVQDIV<br>TANPWNTIALLCGAFLALFKAAE<br>FAKLSIKWMIKIRKRYLKRRGQATSHIS |

TABLE 5-continued

| Nucleotide Sequence (5'-3') | ORFs |
|---|---|
| TCATGTTAGCACTTAACAATAATGATGTTAAAAAAACTGGCATGTGTCTAAACAATAGAGTGCTATTAAAATGCCCATGAACCTTTAGTTGC CTGTAATACATGGATATTTTAAAGATATAAGAAGTCTTCAGAAATAGCAGTAAGGCTCAAAGGAACGTGATTCTTGAAGGTGACGGTAATACCTA AAAACTTCCTAAAGGTGCAGAGC<br>SEQ ID NO.: 22<br>TCGGAGCTGAACTTCTCCTAAAAGACAAAGTGTTTATCTTTCAAGATTCATTTCCCTGAATCTTACCAACAAAACACTCCTGAGGAGA AAGAAAGAGAGGGAGGAGGAGAGAAAGAACAAAAGCAAAGAGAGAGAGAAAAATGAATTCATCTAAATCATCGA AACACAATGCACAGAGAAGACTGTTCTGCTCCTCCAAATGTTCTTGTGGATCCCATCCTATTTCTCAGTGCCTG TTTCATCACCAGAGTCGTGTGACATTTCGACATCTTCAAACCTGTACCTACCGAGAATTTCAGAGT CTCCTGCTACAATTGATCAGTTCAGTCGAGATCAATTGTGTCCATTGAACTGTGTTATCAACCAGCTGCTACTTCTTTTC TACTGACACATTTCCTGGGCGTTAAGTTTAAAGAACTGGTTTATTGGACTGCTCACCTGGTGCTCAGAGGAGGACA GGAATTCCTTTCCTACAAGAAACCTAAAATGAGAGAGTTTTTATTGGACCTGAGCAACCTCAGTGGCAATGGAT GGACGGCACACCTTTGACAAAGTCTCAGGCTTGGGATGTAGGGGAGCCAACAACATAGCTACCCTGGAGACTGTGCACATAT GAGAGACTCTTCAAACCCAAGGCAAAATTGGAATGATGTAACCTGTTTCCTCAATTATTTTCGAGTTGTGAAATGGTAGGAATAAA TCCTTTGAACAAGGAAAATCTCTTAAGAACAGAAGGCACAACTCAATGTGTAAAGAAGGAAGAGCAAGAACATGGCCACACCA CCGCCCCACACGAGAAATTTCTGCCTGAACTTCATAAGGTTCTAGTCTCCTCCAGATTTCACAAGCAATTC AAATGTATAATTCATGTTACTGCTGAAGTGCATTCTCCTCAGGTCCTTAGTCTCAGCCAATTTCAAAGAAACAATC ATACCTTTGCTACATTTGCCTCCAAAATCTCTGAATCCGGGCTCATTTTCCTGCCTAGTCGTCTTCTTTATCTGAGTAAGAAGCTTCTTCA GATTTTGGAAGGTGCCTTCATACCCGTTCATTGTGCTGCTCTATATCGTCTCTTTATCTCCCGTATAATGAGTAAGAAGCTTCTTCA AGTCATGAAACTTATTCCTGCTCAGAATACCGTGTGGCCTTTCTGCTGTCCCTGCACTTTCCTGTCGCAGGCCTTCTTAGGGAAGGCATGCC AGCCATCAGTCCAAACAGGCTGTACCAAGTCCACCATCCCTGGGCTTCCTTTGCTCTCCGGGTCTCAATGACTCACACTTC TCTACCAGATTTGTATCTATTGCATATTTCCAATTATTTTCTAACTTTAGCTTTCGGGGACTTTAGTCCGAATAGTTAGGGCATAGTAGGTAAACTCATG TCGTGGAGGTTGTTGCTACGAATACCGTGTGGCCTTTCTGCGTCTACAGGCCTCCATGCACTTTCCTGTTTTTCGGCCTGTCCTCCCCT CCTACTTCCGCCTCAAAGCTATTTGTTCTGTTCCCATGTTGCTTATTGCCCAGTCTTTTATGATTTCCCAATTATCAGTTCCACTTATAA GTGAGGACATGCAGTATTGTTTTTAAGCGTCTAGTATTGTGAATAGTGCTGCAATGAACATTCTGTCAGTGTCTTATGGTAGAAAGATTATATTCTCTGAGTATGTATCCA AATTTTTCTTCATGTTTCTATTGCTATTGTGAATAGTGCTGCAATGAACATTCGTTGCATGTCTTATGGTAGAAAGATTATATTTCCTGAGTATCCA TTGATTCCATGGTCTATTGTGAATAGTGCTGCAATGAACATTCGTGCATGTCTTATGGTAGAAAGATTATATTTTCTCTGAGTATGTATCCA GTAATAGCCCATTCATTATTGCATAAAATTCTACCAATAC | SEQ ID NO.: 69<br>MNSSKSSETQCTERGCFSSQMFL WTVAGIPILFLSACFITRCVVTF RIPQTCDEKKFQLPENFTELSCY NYGSGSVKNCCPLNWEYFQSSCY FFSTDTISWALSLKNCSAMGAHL VVINSQEEQEFLSYKKPKMREFF IGLSDQVVEGQWQWVDGTPLTKS LSFWDVGEPNNIATLEDCATMRD SSNPRQNWNDVTCFLNYFRICEMVGINPLNK GKSL |
| SEQ ID NO.: 23<br>CCTCTCTCCCTGGCTTTGTGTTGGTGCCTCCGAGCTGCAAGGAGGGTGCGCTCAAGGAGGAGGAGGGGGGCCGGAGTGAGAGGC ACCCCCTTCACGCGCGGCGGCCCCTGCCCGGCCGACCACACACACCACGCGCGCACACACACCAGCGGC GAGCTCGGCCTGCCGCGAACGTGACGTTCTCTTGTTGGAGCCCTCAAGCGGCGTTGGGGCCGTCCGTCCGGG GAGATGGCGCAGCCATCCGGGGAGCCATGGAGCTGCAGATTCGAGAAATAATCGTGATTGGGGACTCCAACGTCGGGCAAGACCTGCTTCTGC GACCAGTACCTTCCAGACAAGACTGAAGACCTGCTGACATCGTGATTGGGGACCATCCGGCGGAATTCAGGGAGAAATCAGGGGCGAGAAGATCAAG GTTCAGGTGTGGACGACCAGGACGTTCCGCAAGACATGTCGAGCATTACTACCGCAACATGCCGTGGTCTTC GTCTATGACGTCACCAAGATGACATCTTTCACCAACTGGATCAATGGATGCCCTCCAACTAGCCTGCAAATGTTGCTATGCCCAC CCCAAGTCGCTTGTTGTTGGACCATCAGCACATCGGCACGAAGACCCCAAGGAGTGAGGGAAGGTGCCACATCGAGTTCCAGCCAGCGAGCTAACAT AAGGCCCAGAAATCCCTGCTGTATCGTGATGTGAGGAGGCAGCAGCAGGGAAGGTGCCAGAAACTGGAGTCCCACAGAAAGCTAACATGT AAAACTTCCTGTTTCCATAGAATCAATATCCAAACCAAACGATATATATTGTATAGATTAACTTAAACAATTGATCACTTAG CCTGCTTGTTTCCATAGAATTGATATCAAATAAATTTGTATAGATTAAAAGATTTAAAATGAAAAAAAAAAAAAAAAA | SEQ ID NO.: 70<br>MAQPILGHGSLQPASAAGLASLE LDSSLDQYVQIRIFKIIVIGDSN VGKTCLTFRFCGGTFPDKTEATI GVDFREKTVEIEGEKIKVQVWDT AQGERFRKSMVEHYYRNVHAVVF VIDVTKMTSFTNLKMWIQECNGH AVPPLVPKVLVGNKCDLREQIQV PSNLALKPADAHNMLLFETSAKD PKESQNVESIFMCLACRLKAQKS LLYRDABRQQGKVQKLFPPQEANSKTSCPC |
| SEQ ID NO.: 24<br>GGAGCCGCGTGAGGCTCCGGCCGCGCAAGCCCGGAGCAGCCCGTCGGGCGCCGCAGCGGTCGCGGCGATGGAGGACGGCGTG CCCGGTCCCCAGCTCGGGGCGGCCGCGGAGGCGGAAGAGGCGCGGCCCGGGTGTCTGCGGCCCTTCCG CCCCTCTCGGGCGCCCAGGCGCGGCCAGGAGGGCGGACTGACTGCGAGATGCAGGAGCTGCAGGAGGAGCTGCAGGAC GGGATGAGCTTTATCGACTGCATGGAGGAGGTGGATCTGCCCCTGTCAGCCACCATCGCGCTGTCACCTGACGCCGCGGCAAAATTTGAGTCCCCTTTAGG ACGTATGACAAGGACATCACTTTCAGTATTTAAGAGCTTCAAGAGTCGAATAACTTCAGCAACCCCCTTCCCCAGCAGAT GCCAGCTCCAGCTGCATAAGACTGAGTTTCTGGGAAAGGAAATGAAGTTATATTTTTGCCTACAGACCTTACACATAGGAAGCTCACAC | SEQ ID NO.: 71<br>MEDGVAGPQLGAAAEAEAAEAR ARPGVTLRPFAPLSGAEBADEGG GDWSFIDCEMEEVDLQDLPSATI ACHLDPRVFVDGLCRAKFESLFR TYDKDITFQYFKSFKVRINFSN PFSAADARLQLHKTEFLGKEMKL |

TABLE 5-continued

| Nucleotide Sequence (5'-3') | ORFs |
|---|---|
| CTGGCTCCGCCAAATCCAGACAAGCAGTTTCTGATCTCCCCTCCCGCCTCTCCGCCAGTGGATGGAAACAAGTGGAAGATGCGACC<br>CCAGTCATAAACTATGATCTTATATGCCATCTCCAAGCTGGGGCTCAGGGGAAAAGTATGAATTGAATTGCACGCAGCGACTGACACCACT<br>CCCAGCCGTGGTCCATCGTATGTGAGAGTGACACGGAAATGGAAGAAGAGGAAATGGAAGACAGAAGAGGACCTAAGCCAAA<br>ATTATCCAGACAGGAGGCCGGAGTACACGCGAGTCAGTGACTTCTCCGAGTGGATGGCAGCCAGATCGGGGTGGCAGACGCGATTCCAAATCATACTCAC<br>GGGAGGAATCTTTACTGTGGAGGAGAATCAAGGCCGTGTCCCCTGTTCATGTCCACACCAGTTACTGTTCATGGCACCCGGAATGACTTGGGC<br>TGTGCTCAGAAGAGAATCAAGGCCGTGTCCCCTGTTCATGTCCACACCAGTTACTGTTCATGGCACCCGGAATGACTTGGGC<br>CAATCACTGAGTTGTCTGGTGATCGCACAAGGACATTTGGGACTGTCTTGAGAAAACAGATAATGATAGTGTTTGTACTTGTTCTTT<br>TCTGTGGATCAGGTTGTCTCTGTAAGGAGAGTACCCACAGAGAAGCCCCTAGTGCAGAGAGGTTGTGAAAACAGCAGCAATGTGAAATTGTAG<br>CGTTTCCTTTCTTTCTCCATGTTCTCATGTTTGTGCATGAAACGTATTACCAAGACTAACCTTTCCCAGATTCTCGAGATCTCTT<br>CCGTTGTTGTTTACATCTTGCGAACCTGCTTGCGAACTCTCTCTGAATGCATTCACTGCGAATGCTGTAACTTGTCTTTGCAA<br>AGAAGTTGATCTGAAATTCCTCTGTAGAATTAGCTTATACAATTCAGAGAATACAGTTTCACTGCAGTTTTTAGTGGGTGAGAA<br>ATTTTAGTTAGGTGTTTGGGATCGGACTCAGTTTCTGTTGTTCTTTACCCCACGAAGACATCAAGATACACTTGTAAATAAAGCTGATAGCATAT<br>TTTTTGGAAACTGTTGTTGTACACTGGGTGAAGATATGCCAGTGCAGTGATTAACCTACCTGTGAATCATATGTTGTAGGA<br>ATTCATACCTGTACCTGGATGGGTGAAGAATATGCCAGTCAGTGATTAACCTACCTGTGAATCATATGTTGTAGGA<br>AAAGCTGTTCCCATGTCTAACAGGAATTGTTATACTAGGTTCAAAGCATGTCAAGTGGATATAGAATCTGTGCGATAATGAGGGATGCAGTGC<br>CTTTCCCATTCATTCCTGATGGAATTGTTATACCGTAACAATGTTTGTCATTTTGAAATATCCTAATGCCAAGTAACAATGCATGCTTTGGAAAT<br>GGTATTATATTTTGGCTTCTACAATACCGTAACAATGTTTGTCATTTTGAAATATCCTAATGCCAAGTAACAATGCATGCTTTGGAAAT<br>TTGGAAGAGATGTTTATTCTTGAAGACAAATATGTTTTGCATTAAATGCTTTGATTGTTCATATTCAAGAAATGTTGAACGTTCT<br>CAAACCCTGTTTACGTACTTGGTAAGAGGGAGCCGGTTTGGTAAGAATATTTTTTTAACTGCATTCTATAATAAATGCACAGTATGCTCCTTACAGAAAAAAAAAAAAAAAAAAAAA<br>TAAACTGGAGAGGCTAACCTCAAAATATTTTTTAACTGCATTCTATAATAAATGCACAGTATGCTCCTTACAGAAAAAAAAAAAAAAAAAA<br>AAAAAA | YFAQTLHIGSSHLAPPNPDKQFL<br>ISPPASPPVGWKQVEDATPVINY<br>DLLYAISKLGPGEKYELHAATDI<br>TPSVVHVCESDQEKEEEEMRMRPKPKIIQ<br>TRRPEYTPIHLS |
| SEQ ID NO.: 25 | |
| GATTGCGAGCCAGGAGGAGGAAGCGGCCGGTCGGTGGCCCCGTCAGCAGCCGGCTGCTGAGAGGCCGGTAGGCGGCGGGTCCGAGGG<br>CGGCGGCCGCGTCCTCGAGAACGGCCAAGGTGGCGGCCTGAGCCAGGGGCGCGGAGCCATGAAGCTCTACAGCCTGTACAGCCT<br>CAGCTCCTCTCAAGGCGAGGCCAAGGTGCTGCTCAACTGGTGTCTTCCTTCCAGCTTTTCCAGAGATCCAGACTA<br>CGTTCAGGAATTCATGACCTTCAGTCAGCTTGTGGTCATCGCAGATAATGAGTACCCATCCCGGGTGCCTTTACCTT<br>TCTGGAGAAGGTACTGGACGGAATTCCAAGGACGTGACCAAGCAAGTGCAGACCCCTGCTACAATCCATTACCCAGC<br>GCTGAGAAGAGTACCTCAGTAGAATACCAGAACCACGAAGAAGTCAATGATGCAGGCCGAACTAGATGAGACCAAAAT<br>CATTCTGCACAACAACATGGAGTCTCTGTTAGAGCGAGGTAGAGTGCTGCAGGGCCAATGCTGTGGAACACA<br>GTCAGCCTTCTATAAAACTGCCCGGAAACAAAACTCATGCTGTCCATCATGTGATGCAGGGCCAATGCTGGAA<br>TGGCACCATCATTCACATCGAACAGAACTGCAGCCCTGCGAAAAGAAGACAGCAAGAGGCCAAGAGTTCAATATGTGTAGTGATTCTTGGAAAG<br>TTTTATTTTGAAGTTCTGCGAGAAATGAATGGTGGAAGGTGGCAATGTGAAGGCAATCAATTCATGTGTAGTGATTCTTGGAAAG<br>AATTTGAGTCTCCCGAAGGTCGTATTTTGGGCAAAATGAAAACCATAAACTGGCTTTCTCGACTGGCTTCTGTATATCTTTGATCTATATTGTACATT<br>GCTAACTTCCTGGAAGGCTCTGTGGGGAGGTGAGGAGCCAGCTGGTCTTTCCCAAGGCAGAATATAACTTGGGAGTTTTGAAGACTCTTGGAAAGCCTC<br>AATGATATTAACACTCCAGTGGGTGGGGTGGAGTGGAGCTCAGAACTGTTGGTTAGGCTGAGCTGTGGGAGCAGCCCCAAGGCTCCGGAGGCGGG<br>TCCTGGGGCCACTGTTGGGTCCAGTCCACAGAGCTCAGAACTGTTTTAGCTAGCTTCCCCCAGGGTCAAGCGGGGGCTCAGGGCCAT<br>CCTAGGAGCAGCTTCCACCAAGTCCACAAGGTGGCTTTGTGGGAGGAGCCTCATTGTGGGCGGGAGTGTGTGCTGGTTGGGT<br>CGTACCAGCAAGATCAAACAGGTGCACTCAGCTGAGCTCAGCTTGCCCAGGATGTTTCCTGGTGCTTCAACATGCCTTGCAACATCACGA<br>CAGGGAAGATCAAACAGGTGCACTCAGCTGAGCTCAGCTTGCCCAGGATGTTTCCTGGTGCTTCAACATGCCTTGCAACATCACGA<br>GCATCAGCAGGTGGGTCTTCCCTTGAGCACCCAAGCAGTCAATTGATTTTATTGACCTGCCTTAAGACTCTTGCCTTCCACCCCACCCACTATGGTCTT<br>GCCAGCATAGGCTTGCTAGTTCTTCTCTGCCCAAGTCATGCAACAGGCTGAGCAGGTAGCTGCAGAGGATAGGCCTAAAATGTTCTGATCCCTTG<br>CCTGCCAGGAGGGCCACCTGCTAGTTTCTTCTCTGCCCAAGTCATGCAACAGGCTGAGCAGCTGAGCAGCCAAGGGTTTGGTTAAGCTGTGCCTGCA<br>GGTCACCTATGGTTCAGTGGTCTCAGTAGGCGGTCAGTGACGTCAGGTTAGGGCTTTATTTGAACCAGGTGTGGCCTTGGTCGCCCCACACTGTGCCACCCATGGAAGCCATTATGGAACAGACCACTGTCC<br>TGACCAGAGTTCAGTGGTCTCAGTGACCCCCAATGTGGGCAGGGGCCATGGGGCCATGGGCACCATGGGCACCATGGGCATCGGGTGCTGCTGTGGGTTCAGAGGACTCCAC | SEQ ID NO.: 72<br>MKLYSLSVLYKGEAKVLLKAAY<br>DVSSFSFFQRSSVQEFMTFTSQL<br>IVERSSKGTRASVKEQDYLCHVY<br>VRNDSLAGVVIADNEYPSRVAFT<br>LLEKVLDEFSKQVDRIDWPVGSP<br>ATIHYPALDGHLSRYQNPREADP<br>MTKVQAELDETKIILHNTMESLL<br>ERGEKLDDLIVSKSEVLGTQSKAFYKTARK<br>QNSCCAIM |

TABLE 5-continued

| Nucleotide Sequence (5'-3') | ORFs |
|---|---|
| CTCCTGGCTGGTTACCTGCTGCTGCCCATTTTCTCTGGGTACTGCTGGCCAGAGGACTTTAGCCTACCCCTGAAGAGCCTGTCCAT GTCATTTTCCTACTGCCATAGATACCCTGAGGCCCAGAGCCCAGCCTCAGCCTGCCCACTGGTGCCGGAGACGGAGTG GAGTGGGCCTGGATCCGAGGGATGCTACCTCCCTTCCACTTGAGAGAGGGGAGATGGGGGCGGAAAATGGAGTAT GAATTTGGGGTAAGAGAGGATGAGATCTCCGACCCACCCACCGACCGCCCTGCCTTGCAGGTCAGGTCAGCCCTGTCAGGCCCTGTGAG ATAGAGGGGCCAGCCAGCCCACCCACCGGCCGCTGTCTCGATAAGTGTCTTGAAATTTCAAAAAAAAAAAAAAAAA | SEQ ID NO.: 73 MDHYDSQTNDYMQPEEDWRDL LLDPAWEKQQRKTFTAWCNSHLR KAGTQIENIEEDFRDGLKLMLL EVISGERLAKPERGKMRVHKISN VNKALDFIASKGVKLVSIGAEEI VDGNVKMTLGMIWTIILRFAIQD ISVEETSAKEGLLLWCQRKTAPY KNVNIQNPHISWKDGLGFCALIH RHRPELIDYGKLRKDDPLTNLNT AFDVAEKYLDIPKMLDAEDIVGT ARPDEKAIMTYVSSFYHAFSGAQ KAETAANRICKVLAVNQENEQLM EDYEKLASDLLEWIRRTIPWLEN RVPENTMHAMQQKLEDFRDYRRL HKPPKVQEKCQLEINFNTLQTKL RLSNRPAFMPSEGRMVSDINNAW GCLEQVEKGYEEWLLNEIRRLER LDHLAEKFRQKASIHEAWTDGKE AMLRQKDYETATLSEIKALLKKH EAFESDLAAHQDRVEQIAAIAQE LNELDYYDSPSVNARCQKICDQW DNLGALTQKRREALERTEKLLET IDQLYLEYAKRAAPFNNWMEGAM EDLQDTFIVHTIEEIQGLTTAHE QFKATLPDADKERLAILGIHNEV SKIVQTYHVNMAGTNPYTTITPQ EINGKWDHVRQLVPRDQALTEE HARQQHNERLRKQFGAQANVIGP WIQTKMEEIGRLSIEMHGTLEDQ LSHLRQYEKSIVNYKPKIDQLEG DHQLIQEALIFDNKHTNYTMEHI RVGWEQLLTTIARTINEVENQIL TRDAKGISQEQMNEFRASFNHFD RDHSGTLGPEEFKACLLSLGYDI GNDPQGEAFARIMSIVDPNRLG VVTFQAFIDFMSRETADTDTADQ VMASFKILAGDKNYITMDELRRE LPPDQAEYCIARMAPYTGPDSVPGALLDYMS FSTALYGESDL |
| SEQ ID NO.: 26 CGCTCGCGCCAGTAGCAGCCTTCGCCGCAGCGACCTTCGCCGCGGCCGAAACCGGGCGGCCGGAGCAGCGAGAGCAGCCCGCCCCAGCC CAGCCAGCCCTACTTCCCTCCCCAGGGCCAGCAGCAGCCGTTGCTCAGAGAGAAGAAGAAGTGGAGGAAGAAATCCAGACCTAGCACGCG CGCACACATGACCATTATGATTCTCAGCAACCAACGATTACTGAAGGACTGGAGCCGGAGATGGGGGGGCGGGAAAATGGAGTAT CCGGGGCTGGGAGAAGCAGCAGAGAAGACATTCACGGCATGGTAACTCCACCTCCGAAGGCGGGACACAGATCGAGAACATC GAAGAGGACTTCCGAGATGCCTGAGGTCATGCTCAGTGAGGTCATTCAGTGAAGTCAGCCCTGCTTGCAAGCCAGGATCAAGGCC ATGAGAGTGCACAAGATCTCAACGTCAAGGCCCTGGATTTCATAGCCAGCAAGGGCGTCAAACTGTGTCCATCGAGCCGAA GAAATCGTGATGGGAATGGTGAAGATGACCCTGGGTGGTCTGTCAGAGAAGACAGCCCTTGCCATCCAGAACATTCCACATA AGCTGGAAGATGGCCCTGGCTTCTGCGCTCTGATCCACCGCCCCGAGCTGATTGACTATGGCAAGCTGAGAAAGGATGATGAT CCACTCACAAATCTGAATACGGCCTTTGACGTGCAGAAGTACCTGGACATCCCCAAGATGCTGGATGCCGAAGACATCGTTGAA ACTGCCCGACCGATGAGAAGGCCATCATGACTTACGTGTCAGCAGTTCTACCACGCAGAACGAGCAGCTGATGGAAGAACCTGTTG GCCAATCTGCAAGGTGTTGGCCGTCAACCAGGAGACGAGCAGTTTTATGGAAGACTACGAAGCTGGCCAGTGATCTGTTG GAGTGGATCCGCCGCACAATCCCTGGCTGAGAACGCGGGTGCCCAGGACACCATGGCCATGCAACAGAAGCTGGAGGACTTC CGGGACTACCGGCCTGCACAAGCCGCTGGGTGCACCGAAGGTGCAGGACTGCCGAGGATCAACAACGCTGAGGTCAAGAGC CGGACTCAAGAAGCATGAGAAGCAGAGGGCCATGGAGCATAGAGGCCAAGATATGAGGCAGAAGACTGCACCATGAAGAAGGATCACT AATTGTCCAGACTACCACGTCAATATGCGGGACCCAAGCTCTGACGGAGGAGCATGCCGAGGAGCAGCAGCAATGCCGACACCAGTTT GTGCCGAGGAGGTGTGCCTGCCGAGGGAGTCATCGGGCCTGAATCGAGAAGCCATGGGCTGTACTTGAGCTACTGGAAGAGCATGGGAGCCAGTTT GCAACAGATCATCGGCAGGACCATCAATGAGTGGAGGAACAGATCTGGAGGCAGACATCACTCCGGACACATTTCAAAGCCTGCATCAGCTTGGTTAT ACCGGCTCCCTTGACCGGAGATCACTCCGGACACATTTCAAAGCCTGCATCAGCTTTGGTTAT CCGGCCCGGCCTCCGTCTGTTGCCCTGCCCTCTGCAGGCTTGAGGCCATCCGCCGTTCCCCCGGTTTCCCCATGGGGGCCCAAGACCCCG CCTCCCACCGGGTGAGCATGGCCACGTGGCATCACTACATATTTATTAGAGAAAAGATATTTCCACCAGACAAATGGAAATGAAAAAAG GAAAAAGGAATTAGTAGTGTAGGGCCACCCGAAATGTCTGGTTGTTGCCACCCGAAGACCCAAAGTATTAATTATTCATCCTTTT TACTGATTTTGTTTCCTAATTGTCTTCCCATTCCTATTCATTTCTCGTGTCCAAGGCCCTTTGGTGGCGGAGGCGGAGGTCAAG GGGTACTCTTGTCAAAGGCACATTGGTGCGTGTGTTTGTCTAGCTCACTTGTCATGAAATATTTTTATGATTATTAAGAAAATCTTTTG | |
| SEQ ID NO.: 27 GCTTGTACTTCGGCGGCGGCCCTTGGGACTTCAGGGATCTTGAAACTCAGATTCTGAAACTCAGATTTGAAACTAAAGCTGTCGAAATTCTGTCATCGAAGTTTGAAATCTTTTAGATCTTTTAGATCTTTAGACACACATTACACAAGAGCTCTCTTTAGGCTCTGCCAAAAGAGCTCTCTTTAGATCTTTTAGACAAGAGATAC | SEQ ID NO.: 74 MPSCGACTCGAAAVRLITSSLAS AQRGISGGRIHMSVLGRLGTFET QIIQRAPLRSFTFTPAYFASKDG |

TABLE 5-continued

| Nucleotide Sequence (5'-3') | ORFs |
|---|---|
| TTTGCCTCAAAGATGGGATAAGTAAGATGGTTCTCGAGATGAAATAAGAAATCAGCAAGTCAGCAAGTGAGGGAAGTAGTAAGAAATCAGGC<br>TCTGGGAATTCTGGGAAAGGTGGAAACCAGCTGCGCTGTTCCAAATGTGCGACTTGTGCACACATGTAGAGACCTTTGTATCATCC<br>ACCCGTTTTGTCAAGTCTGTGAAAAGTTGCATCATTTTTTGTGTCATCTGAAGCAGTCAAAGAAAAGCATAATTAAAGAACCT<br>GAATCAGCAGCAGAAGCTGTAAAATGGCATTCCAACAGAAACCACCTCCCCTAAGCAGTTATAACTACCTCGACAAGTAT<br>GTTGTTGGCCAGTCATTTGCTAAGAAGTGCTTTCAGTTGCTGTGTACAATCATTAATAAGAGAATATATATAAGATCCCAGCTAAT<br>CTGAGACAGCAGCAAGCAGAGGTTGAAGCAGACATCATTAACACCAAGAGTTAGGAGCACAGTGAGGATGAATCAACAAATACCT<br>ACAAAATTGCTTCAGATTGCTGGAATTAGCCCAGATGTTCTTCATGATGACTAAGAAATACTGAAAAAGTAATATATTTGCTGTTGACTT<br>CAGGAAAACAGGAGGTGAAGTATTGGATTCTTCTCATGATGCAAAACCTGGCACAAACCCTGAATGCCTTGATGTCCCTTTGCTATCTGTGACTACAACTT<br>GGGTCAGGTAAGATATAGCCGGCAAGATATTGAATCTGTGATTGCAAAACTACTCCAGGATGCAATTACGGATGTAGGTCGAGAAGGCTTCAGCAA<br>ATTGCTCTTTCTGGATGAAGTAGGATAGATTGAAGAAGGTGCCAGCCAATTATGAATTACCGGCATGTAGGTGGAGAAAGCACACAAGGA<br>GGCTTATTAAAACTACTAGAAGCCACAATATGTCTTCCAGAAAGAATTCCTGGAAGAAAACAGTTCAAGTTGAT<br>ACAACAAACATCCTGTTTGTGGCCATCTGGTGCTTTTCAATGGCTTCCACAGAATCATCAGCAGGAGCAGAAAAATGAAAAGTATCTTGA<br>TTTGAACACCATCCTAATCTGGGAAAAAGATCGGTTATTGCGTCATGTGGAAGCCAGAGATCATGCTGTAATGACGTTGCATGAGCTGAGTT<br>CAAGAGATTGAAAAGATAAAGATCTGTATGTCCATTGTGCTTATGGCCATAGATCCTGATTGAGTTTGCATGATGAAGTGTGGGA<br>CGGTTGCCCTGTGCGTGACCATTGCAATGAGAAGAAACTGTGTTGTACAAATATTAACTTACCGACCAAGATGTCTGTTATTCCT<br>AGCTTTCCTCTTTTTCAGGAGAATGTCTTACCGAGTCGACATTGTATTTGATTGGAACAAATAAATCAGCTAGAA<br>CAGTACCAGGCCTTATTCAGCATGGATAAGTGTGACTGAATGTGAAAGCTATAGCCAGATTGGCACTAGAA<br>CGAAAATCAGGTGCACGAGGTTGACAAAGAAGTAGTAGAAGAACCAGGATACATCCGGGCTCCAACAAGAATCCTCAAGAGGAG<br>TATGTGTGGAGGTTGCAAAGATGGCAAAATCCGCATGGAACGATTCAAAACGCTAAATGAAAGCCTAAAATGAAAAGAAAGAGAAAATTGCCTGTCTGTAATAC<br>AGCTTTTCCTTTTTGTTTTGTAAAAGAGCTTAGGAGAGAAGAAGCAATTGCATCAATCATGGATCATAAATGTTTAAC<br>TAAGCAGAAGCCTTTAGGAGGTATTGCCGATAAGTGCTAGATTTACAATAATGTTAACTGGAAAATAAATTCTTTAAAATTGAATTCTT<br>SEQ ID NO.: 28 | ISKDGSDGNKKSASEGSSKKSG<br>SGNSGKGGNQLRCPKCGDLCTHV<br>ETFVSSTRFVKCEKCHHFFVLS<br>EADSKKSIKEPSAAEAVKLAF<br>QQKPPPPKKIYNYLDKYVVGQS<br>FAKKVLSVAVYNHYKRIYNNIPA<br>NLRQQAEVEKQTSLTPRELEIRR<br>REDEYRFTKLLQIAGISPHGNAL<br>GASMQQVNQQIPQEKRGGEVLD<br>SSHDDIKLEKSNILLLGPTGSGK<br>TLLAQTLAKCLDVPFAICDCTTL<br>TQAGYVGEDIESVIAKLLQDANY<br>NVEKAQQGIVFLDEVDKIGSVPG<br>IHQLRDVGGEGVQOGLLKLLEGT<br>IVNVPEKNSRKLRGETVQVDTTN<br>ILFVASGAFNGLDRIISRRKNEK<br>YLGFGTPSNLGKGRRAAAAADLA<br>NRSGESNTHQDIEEKDRLLRHVE<br>ARDLIEFGMIPEFVGRLPVVVPL<br>HSLDEKTLVQILTEPRNAVIPQY<br>QALFSMDKCELNVTEDALKAIAR<br>LALERKTGARGLRSIMEKLLEP<br>MFEVPNSDIVCVEVDKEVVEGKK<br>EPGYIRAPTKESSEEEYDSGVEEEGWPRQADAANS<br>SEQ ID NO.: 75 |
| GGCCCCAAGCCGCCGCCGAGATCGGTGCCGATTCCTGCCCCGACCCGCCAGCCATGTCCCATCACTGGGGTACG<br>GCAAACACCAACGACCTGAGCACTTGCATAAGGACTCCCATTGCCAAGGGAGAGCGCCAGTCCCCGTTGACATCGACACTCATA<br>CAGCCAAGTAGCAGCCCTTCCTGAGGCTCTCGTCTTCCTATGATCAGCAACTTCCCTGAGATCCTCAAGATGATCAGTCATGCTT<br>TCAACCTGGAGTTTGATGACTCTCAGGACACAAGCAGTGCTCAAGGGAGGCCCCTGATCGCACTTACAGATTGATTCAGTTCACT<br>TTCACTCGGGTCACTGATGGACAAGGTTCAGAGCACATACTGTGGATAAAAAGAATTTGAAATAATCGTGGATGCAGCCATAGAGCCTA<br>ACACCAAAATATGGGGATTTTGGAAGTTGTGATGCTGGATTCCATTAAAACAAAGGGCAATGGCCGTTCTAGGTATTTTTGAAGGTTGGCAGCCGTA<br>AACCGGGCCTTGAAATCCTGGATTACTGACGTCAGCGAGCAGGTGTTGAAATTCCGTAAACTTAACTTCCTTCCAAATAAGATGTGCCATAGTCTGTATCC<br>GCCTCCTTCGAATCAGCGTCAGCAGCTCAGCCACTGCAGCGAGCAGGTGTTGAAATTCCGTAAACTTAACTTCCTTCCAAATAAGATGTGCCATAGTCTGTATCC<br>TGGTGGACAACTGCGCCGCCAGCTCCCTTAGCTAAGAATTGCCCCCCCACACAGATCTGAAGACATTTGGACACATGATGCTTTGCTTGTCTACACACCTGTGCTGGCTG<br>AAATAATGAATCTTCATCCTTACTTTGATTAGAAGTATTACTAATAAAATAATCTGCTTTTAAACATAGGTAAAATGCCATTTTAAACATAGGAAAGTTGAGTGACATCCAT<br>GTTGGTGCTTGTTTTATGGTAGTAGTTTTCGTATAACACGAAATGTAACTAAATAGGATAAAGAAATGGAGAAAGGTGAGTGCAAATCAT<br>GCATGGTAGGTGATGAGCACTCACATGTTGACATAAATGTCTTTTTAAAGCATGAATCATGATATCATGGTAAAATAGTTCA<br>AGCAAGATAAATAAATTGAATCTAGTTAAGGACAAATCTTTAAAAAATTTAAAAATTTATGAAATTTATAGCAAGTAAACAATTTAAAATGAATTGTGTGTAA<br>TGATTTCAAGAGTCTATATTAAGAAGAAAACTTAAAAAATTATTAAAATTTATGCACAGTATTATCTAAAAAATTGTATATAGAGTTGTGATACAGAGTATTTCCATTCAGACA<br>TTTAATGACTTTTGAATTACAGAGATAAATGAAGTATTATCTCTAATAAAATTCAGAATTCT<br>ATATATCATAAACTTAAAACTTAGATATTTGTATTTTAGATAATTTAGATAATTTAGATAATTCAGAATTCT<br>SEQ ID NO.: 29 | MSHHWGYGKHNGPEHWHKDFPIA<br>KGERQSPVDIDTHTAKYDPSLKP<br>LSVSYDQATSLRILNNGHAFNVE<br>FDDSQDKAVLKGGPLDGTYRLIQ<br>FHPHWGSLDGQGSEHTVDKKKYA<br>AEHLVHWNTKYGDFGKAVQQPD<br>GLAVLGIFLKVGSAKPGLQKVVD<br>VLDSIKTKGKSADFTNFDPRGLL<br>PESLDYWTYPGSLTTPPLLECVT<br>WIVLKEPISVSSEQVLKFRKLNF<br>NGEGEPELMVDNWRPAQPLKNRQIKASFK |
| GCTGAGCGCGGGCGCCGCTACGTGCGGGGAGCCGCGGAGCCGCGCCTCGTGTCGCGCTCCTCGGGC<br>GCTCGCCGCCGCGTCGCCCCGCCCTTTGAGTCAGCAGCTTTGAGTCAGCAGCAAACTCCGCGGCAAAGATGTTCCGGACAACAGAAGAGAATTTGTAAGTGTCTGGGTTC<br>TGCCCGGAGGACCCCCATTGACTGCGTCTCGTGCTGAAGATGTTCCGGACAACAGAAGAGAATTTGTAAGTGTCTGGGTTC<br>AGATCCTAGGATTCAGAAGGAGGACTTCTGGCATTCTTACATTGACTATGAGAGATAATGTATTCATACTAATAGCATGTGTTTACAA<br>TGAAAACATCCGTGTGTACAGAATATAGAAGAATTTGTGGCTGAGGCAGGACTCCAAAGTAATGCGTTCGTGGTACAACTGC<br>CAGAAACTCCATCAGAATTCCATCAAAACCTGTGTTTTTCAACATGAACAATCGCCAGCAGCACACGTGGATCAGCGTCGCAGGTCGCCAGGGTCTGGAAGATTTCCTCA | SEQ ID NO.: 76<br>MPPEQQKEEFVSWVRDPRIQKE<br>DFWHSYIDYEICIHTNSMCFTMK<br>TSCVRRRYREFVWLRQRLQSNAL<br>LVQLPELPSKNLFFNMNRQHVD<br>QRRQGLEDFLRKVLQNALLSDS<br>SLHLFLQSHLNSEDIEACVSGQT |

TABLE 5-continued

| Nucleotide Sequence (5'-3') | ORFs |
|---|---|
| GAAAAGTCTACAGAATGACACTTTTGCTTTCAGATAGCAGCCTTCACCTCTTCTTACAGAGCCATCTGAATTCAGAAGACATTGAGG<br>CGTGTGTTTCTGGGCAGACTAAGTACTCTGTGGAAGAAGCAATCAAGTTCACAAGTTGCCTTAATGAATAGACGTTTCCTGAAGAAGATG<br>AAGAGCAAAAAGAAAATGATATAGATGATTGAGAAATTCAGAAAGTTCATCCTCTGGCTTGGACACAGTGTGATGACAGCAGTTCAC<br>ATGGATGAAGTAAAGCAAAGCTTCATAATAATACATTCTTACCTAAAGCTCTGAATTCATGATGTCTAAGCTACATCTTAGGTAAGCA<br>ATAGAAGAAGAAAGCTTCATAATAATACATTCTTACCTAAAGCTCTGAATGATGTCTGTAATTATGTCCAGTC<br>TGTTTATTAGTGGACATTATTGTAAACAAGATCTTGCCCTGCCAATGAAATGAGCTACATGTTTTAAAAACCTGTGAATACAATACTCCTTT<br>ACAGGCAGACATTATTGTAAACAAGATCTTGCCCTGCCAATGAAATGAGCTACATGTTTTAAAAACCAGTTGGTTTTATTGAATT<br>TAAAAAGATAGGTAACTAAGTAGCATTTAAAATCAAGATAGAGCATTCCTTCTTCTGTATCAGTGGGCAGTTGTACTAAACACGGT<br>GTATATGTGTTAAACCCTATGAAGAGTAACAGTGTAGACCAGACTGAAACTGAAATATTTTAAGCTCCTGATATTTGTGGATACCTCC<br>CCTGCACTGGCAAAACATATGCTTTTGGGTGTTAGACTGAAATATTTAAAATATGTTTACATCTTAGAAAAAAACATAGATAGTGCTAGTAATATTACTT<br>AGATGGAAATGTATCTTATGAATAGAAGAGACATTTCTCAATAATATCCAAATGAGCTTCAACAAATGGTTCTGAGACAACATTTTGTT<br>ATAACTGTATATATATAGATTCAGAAATACATTTTCTTAATTGATAATAAACTATTTCAGATTTCTGAGAGAGGCAACATTTTCTT<br>TCATTATCATTGTATAATACTTAGTCCGAGGAAGGATTTATTTTCATTTTAAAGATCTGAATCTACTTACGAGATTGGTATAATTT<br>TGGTTACTTATTACTTGCTAATTCAGAAATAATAATTCATTTTTAAAAGCATCTACTTGAGATTGGTATAATTT<br>AGGATGTCGACTTGCTAATTTCAGAAATAATAATTCATTTTTAAAAGCATCTACTTGAGATTGGTATAATTT<br>CATAAAATGCTTTTTTTTTTTAGTGTCCAAAGACATATCTTTAGATAACTATTTCAGATTTGCAGATGAGGCAACATTTTCTT<br>GAGATAATTACCCAAGTTCATCCATGTGAATGGTACAAAAATATTTCTGAAACTAACAACAACCTTTCCATTTTCACTAAGAGTTTAAA<br>AACTTGTTGCTTGTTACCCAGCCATTAAAATCATTTGAATGGTACAAAAATATTTCTGAAACTAACAACAACCTTTCATTCACTAAGAGTTTAAA<br>AGCTATTGTATATTAAAATAGACCTTGTTCAAAGAACCTGTAATTTCAAAGAACCAACAGAAAAAGCTAAGAACAACCTGAGAACTTAAACATTA<br>AAAAAATTAGAATAAGAATGATCTTCTTTAATTTGTCCTTTTTTTCTTGGTCTAAAACATTAATAAATTTTGTAAAATATT<br>TTGATTAAATGTGTCTTTAGATCCTTCATTATTTTAATACAGGAAGAAATTTAGTAATTTCTGTTTTACAGCAGTTTGA<br>CATGCCATCCAGGCATTTAAAGACGCATCCTCACCCAATTGCATATATTTAGATGATGTAACATAGCCATCAAATTAATATATTATGTAATGCCTAATACTTAGTATGTAAATG<br>TCACGAGATCATTTTTACATTAAACGTGAAAAAAATCAAAAATAAAAA | KYSVERAIHKFALMNRRFPEEDE<br>EGKKENDIDYDESSSSGLGHSSDDSSSH<br>GCKVNTAPQES |
| SEQ ID NO.: 30 | |
| GAACCTCCCGCGACTTCCAAGTGTATCTTCAAGTGAAGGCATTGAAGCTTGCACAAGCTCTCCAGACAAAGTCAATGTAAATGAC<br>ATCATCCTGATTGCTTCCAATATTCGAAAACTCAAGATTGGCAAGAAATTCCTCCCAGTGACATCAATAGTGAAAGGTAGAAAAGCTCG<br>AAGGTCCATGTTCTTGCAAATGTTGCAATGTTGCTGCCAATATAATGAAGATCTGTCACCAAGGATGC<br>TGCGATTACGAATGACTGATCTCTCAGGCATTGCTCATATTAAGTTGCACAGCAGAATTAGTTATATGTCAAAATAAGCTGACACACACCTG<br>GAACTAAAGTTAAGCTCTCAGGCATGTCATATTAAGTTGCACAGCAGAATTAGTTATATGTCAAAATAAGCTGACACACACCTG<br>CGCCTTTTGCCTTATTGGAAATGGAGTTACAGAAGTGTTGGAGTTACAGAAGACAGAACAAAACATTGCAAGTTA<br>CAATGCCTGTCAAACCTACAAATGATAATGATAATGATATTGAAAAGCAAAGAGCGGCTGCTATTGCTGAAGTGCAAAGAGCCAAGAAA<br>CCAAGACATTTGGAGGAGGTGGTGTGCTAGAAGTAATCCATATGAATGCTGCTGGTAACCGAAATAGGGAAGTTTTACAGA<br>AGGAAAAGTCAACCAAATCAGAGGGAAAACATGAAGGGTCTATAGAGAACTGTTGATGAGAAAGCTCTGAACGTACTTCTTACAAGCA<br>TGGGCTTCAGTAAGGAAGCATCGAGGCAAGCTCTTATGGATAATGGCAACAACTTAGAAGCAGCACAACAACTTCTTACAAGCA<br>ATAAACGAAAACCTGTTATGGTCCTCTCCAGGACACAGTTCTGAAGATAGATCTGAAGATGAAGGCACAGAATCAAGATGATA<br>GAAATCAAGGCATCAGCACCAGCTCATCAGGCAGCAGCACAATACAGAATCATCATCAAATACAACCCGTCTGTTTTGAATGTGGAAGAACCTAAATCAC<br>AGCCACAGCAGCTCATCAGGCAGCAGCACAATACAGAATGAAAATGGAGTAAAGAGACTCCAAAATTCAAAGTCAGTTTTAGAAGGCA<br>GTGGATTACCTAGGAAGCAGCAGGTGTTGCAAGATATCTCAGTATCTCTTCAGTATTCTCAGTACAAGTGAGAAGCAGTTTTAGAAGGCA<br>GACCGTATTCCTAGATATGACAGAACATAGGAAGGTCTCTGCAATCCTTCATCATCTTGCAGAGGCAAAAGAGAGATGAGAATTATAATA<br>ACTCTATGCAAAGCAGATCAGGAAAAGAGGAAAAGCCAAACATTTTAAGATATTTTATGCAGGGAAATCACAAACATAATAATGAAGCTT<br>TCAGTGGTATATAAAATTGAAAAATGCCACTGGGCCCAAACGAAGAATAGGAACTCGGGCCAATTAAGCCAGAGACCATATTAAGCCCAGAAAAATACTAGAATCATCATCTATTCCTGTGATGATA<br>ATGGAGAAGTAGAAATTTACAATAGTGGGCCCCAAACGAAGAATCTGGGCCAATTAAGCCAGAGAACAACAAGTTTTACCGGCAGCAGAGTCAAGCACCTCATT<br>AATTTACAATAGTGGGCCCCAAACGAAGAATCTGGGCCAATTAAGCCAGAGAACAACAAGTTTTACCGGCAGCAGAGTCAAGCACCTCATT<br>CTTCGGGTATGACAGCAGTTGTTAAATTCATTGACTACGAAACATGAAGAGGTGCTACTAGACAATATCAAGCCACTCAAACAG<br>AGGCATGGGAGGAAGGCACCTACGATCAAACTTGGAGTTCCGTAGGGAGTGAGCAGCCAAGCACATATCAAGCCACTCAAACAG | SEQ ID NO.: 77<br>MLRLQMTDGHISCTAVEFSYMSK<br>ISLNTPPGTKVKLSGIVDIKNGF<br>LLLNDSNTTVLGGEVEHLIEKWE<br>LQRSLSKHNRSNIGTEGGPPFV<br>PFGQKCVSHVQVDSRELDRRKTL<br>QVTMPVKPTNDNDEFEKQRTAAI<br>AEVAKSKETKTFPGGGGGARSNL<br>NMNAAGNRNREVLQKEKSTKSEG<br>KHEGVYRELVDEKALKHITEMGF<br>SKEASRQALMDNGNNLEAALNVL<br>LTSNKQPVMGPPLRGRGKGRGR<br>IRSEDEEDLGNARPSAPSTLFDF<br>LESKMGTLNVEEPKSQPQQLHQG<br>QYRSSNTEQNGVKDNNHLRHPPR<br>NDTRQPRNEKPPRFQRDSQNSKS<br>VLEGSGLPRNRGSERPSTSSVSE<br>VWAEDRIKCDRPYSRYDRTKDTS<br>YPLGSQHSDGAFKKRDNSMQSRS<br>GKGPSFABAKENPLPQGSVDYNN<br>QKRGKRESQTSIPDYFYDRKSQT<br>INNEAFSGIKIEKHFNVNTDYQN<br>PVRSNSFIGVPNGEVEMPLKGRR<br>IGPIKPAGPVTAVPCDDKIFYNS<br>GPKRRSGPIKPKEILESSIPMEY<br>AKMWKPGDECFALYWEDNKFYRA |

TABLE 5-continued

| Nucleotide Sequence (5'-3') | ORFs |
|---|---|
| CCCACAAGTTTTACCAACAGCCCCGGGCTCGGAACTAATAGGAAAAGAGACTCTTTGTGAAGAAAACGAGCCAGTGACTGAAACACCCTG<br>GACAAGCCTGTTGACAGAACCTTGCACTTCTCTTCAGATAAGTAGCTGGGTGGATATTATTTGAGAAAGAAAAACAGAT<br>TTTAGGGTGGAAAAAACAGTCAACTCACACAAGAATGGAAAAAATACTGAGTTAAATTAAGCAAATACCTTTTACAAGTGAAAGGAAGAATTTTCTTC<br>TGCCGTCAATAAAACCATTGTGCTATTATGTTTAAAAAAAAAAAAA<br>SEQ ID NO.: 31<br>ATAAATATCAGAGTGTGCTGCTGGCTTTGTGAGCTGCCAGAGTCAAGCAAGTAAAGCAGAGAAAGGAAGCAAGAGAAGGACTCTTGGAAGTGGTGT<br>GACAAACCCCAGCAATGTGGAGAAGCCTGGGGCTTGCCTGGCCTCTGTCCATCGGAGTAAAGCAAGAGAGCCAGGACCAAAG<br>CTCCTTATGTAAGCAACCCCCAGGCTGGAGCATAAGAATCTAAATCCAATGGTTCAGTGCTGTGTGTGTCT<br>TCTTCAAGCCAGCTGATACCTGTGCATACTGCAGGCATCTCTTCTGCAGAGACCTGCGAGTAAAACTGAAGAAGAGATATTCTAA<br>TATTTCTTATATTGTTGTTAATCATCAAGGAATTCTCTCTGGACTCTTTTAAAATACACATCTTAAGAATAAGGTTTCAGAGAATATCC<br>TGTTTATCAACAAGAAGAAAACCAAACAGATTGTTGCATTTGGAAGCAAGAGCATGACTTTCCTCATATATGATAGATGTGG<br>CCGTCTTGTATATCATCTTGGTTGCACGACTTCTCAAAGATGAAGAACGTGTATCTTTGCGTACTGTGATAAACAGTTGA<br>GAAATGTGGAAACTGCTCTTCTCAAGATGAAGACTTTTGTAAACGTGATCTTTGCAGCAGTGAGCTTTCAGAGAATCAGCA<br>AACTCCATGCCTCATTACCATCATGAGCATCACAATCAGCACCTTCATCACCACAAGGCTCAGCATAAGCACAAGGCAGGGTCA<br>ACCAGAGACGCCAGGTCACCCTCAAAATGCCCCAGCAAGATTTACAAAGAAGATTTACGACAACATATACTTGTCTTTC<br>CTGTAAATTGCCCACAGATTCAGAGAAAACTCAGGTGCCTGACAAATAAGTCAGCAGGACTTCGGGCAGAGAATCAGGGC<br>AATCACCTGACAGTTGCCTCCAGCTGCCTGACAAATAAGTCAGCAGGACTTCGGGCAGAGAATCAGGGCAGCCAATCAGGG<br>AAAAAGTGACAGAGAATGACCCTGAACACTAGTAAGATAACACCAATTTAAGAAGACATCACTGAATTCTCAGCATT<br>GTATCTTCTATTCTTTCTCTAAGTATTTGTATCATACTCTTAAAACTTGAGTGCTGTTAATAGGTAAACCAAATATAGAATATGTC<br>TTAATACTATTAAGCAAGAATGCAGTACAGTACGAATTTGTCAAATAAATCAATAAAAACCTTAAAGCTGAAAAAAAAAAAA<br>AAAAAAAAAAAAAAAA<br>AAATTTATGTCATAGAATATTGACTCAAACCATATTTTGCTTAATGAGAATAAGAACTATGACCTAGGGGTTTCTGTTGGATAATTAG<br>CAGTTTAGAATGGAGGAAGACAAAGACCTTTCCATTTTTCTTAAGATCTCAGAAATACATTATACTTCTGCTCTTTC<br>AATTCTACTTTTAACTAATAATAGTGGATTTGTATTTTAAGATCTAAGAATACTTAAGAGTCGTGATATTTGCTAAAAAG<br>CATATATAACTATTTTAAATATCCATTTATCTTCTAAACTTGAGTGCTGTTAATAGGGAAGATATATTGTC<br>TGTCTTTCTATATGTTTTGCTTAGTAAGTATCATACTCTTCCATAGTCAATGATGTTTAATAGGTAAACCAAATATAGAATATGTC<br>TTAATACTATTAAGCAAGAATGCAGTACAGTACGAATTTGTCAAATAAATCAATAAAAACCTTAAAGCTGAAAAAAAAAAAA<br>AAAAAAAAAAAAAAAA | SEQ ID NO.: 78<br>MWRSLGLALALCLLPSGGTESQD<br>QSSLCKQPPAWSIRDQDPMLNSN<br>GSVTVVALLQASUYLCILQASKL<br>EDLRVKLKKEGYSNISYIVVNHQ<br>GISSRLKYTHLKNKVSEHIPVYQ<br>QEENQTDVWTLLNGSKDDFLIYD<br>RCGRLVYHLGLPFSFLTFPYVEE<br>AIKIAYCEKKCGNCSLITLKDED<br>FCKRVSLATVDKTVETPSPHYHH<br>EHHNNHGHQHLGSSELSENQQPG<br>APNAPTHPAPPGLHHHKHKGQH<br>RQGHPENRDMPASEDLQDLQKKL<br>CRKRCINQLLCKLPTDSELAPRS<br>UCCHCRHLIFEKTGSAITUQCKE<br>NLPSLCSUQGLRAEENITESCQU<br>RLPPAAUQISQQLIPTEASASURUKNQAKKU<br>EUPSN |
| SEQ ID NO.: 32<br>CGGGGCCCTACACCCCAGAGCTGGCTCGGGGTGGAGTGCAGAGTGCAGAGCAACCAAAAAAGGAACCCCACCCTTCCCCTGCCAGGCCCGGGC<br>GCTGTGCAAGCAGCAGCTCAAAGCAGCAGCAGAGATTCCCTGGGCCTGCAGGAAGCCTTCCGCGACGAAGTGTTCCCCATTTTGGAGA<br>TGAAGAACTGAGACTTCAAAGCAGTCGAAGACTCCCAAGGCTGAGTGACCTTCCCAAGGACACACACAGAGTTCTGGCCGACAGTCTGATCAGATCCAGGG<br>CGGGTGTTCAGCGATTGTTTACTACGTTGAACGTGACCTCCAAGGAAAGCAGTTCTGGCCGACATCGACACGCAAAGCAAGAA<br>GTAACGTGGAAGGAGGCATCATCCAAGCTGGCTGGCCATTTGTGCTGCTGGGCATGCCCAAGCGGGTTCTCGGCCTCA<br>TGGAGAGGATAAATTACAACATGGGAGAATCAGTGCCTCTTCTCAGCTGTCATCCTTTGCCAGGACACACCTTCGGACAACACACAAGAAGGCATCTAC<br>AACACCATCCAAGCATGCCTGGGAGTCCTCGGGACTCCAGCAGCATGAAGAAGACAAGAAGAAGGACAATGAAGAAGAGGACTTCGGATC<br>CACCAGGCAACCCAAGCTTCTCCAGATGCAGCCAGGCAAGACCATCACTCGCCTGTTAGTTAGGCAGGAAGCAGAGGATGAAGAAGACCTTCTTCTTTGGG<br>GCTAAGCCTTCCTTCTGACCACAGAGACATTTCAGGAACCCCTGAAATAATGCACACACCACGTGGACCAATTCCTTGGATACTGTCTTGGCAGCTA<br>CAAGGAACAAACCTCAGATAGCAATGCTCAGCAGCAGGCATGCCTCTCCAAGTGGACATCTGCTCTGGACATACCCCAAGCACCAAGAAC<br>ATTTATCCATAACTCAATATGGTTCCCAAGGTCGTGCACATGCAAGAAGACACATCAACTTCAGGTAGCCAGTGTCATG<br>CAAGTATATTCTGCCAGATTCAGACAATATACACATTTGGCTATGTTACCTTGTGCACACCAAGTTTTTCTGTCCTGAAGTTTCTGACCCAAGATCATTCAGTGCCAGATACTCAGG<br>GGAAAGCCTTGCACCCTTGACCTCCATCCATCCAAGGACACCCTCAAGTTTCTGTGCCTCGACCCCTCACCTGCCCAAGATGTTTAAAGTGA<br>AGTCCCACCCTGTGTGTCTGATACAGACAGACACACAAGTTCTGTGACACATGACATTCCAGCAACCTGCTAC<br>TGGTTCAAATTCATTGAAGCTCTTTTCTTGTCTAACTCATGACAAAGTCCGTCCCATTGCACCAAGTCCACTGAGAGTGTTAATGATCCA | SEQ ID NO.: 79<br>MHYVHVRVTTQPRNKPQTKCPS<br>GGQSQGPRGQFLDTVLAAMCPIA<br>MLLTADPGMPPTCLWHTPHAKHK<br>EHLSIHLNMVPKCVHMVTHTHT<br>NSGSRYVGKYILLIKWSLAMYFV<br>QGSTLSTVTKMSHGKALPDSDTYIQFPNQQ<br>GPHTPSIP |

TABLE 5-continued

| Nucleotide Sequence (5'-3') | ORFs |
|---|---|
| AGACCTCTGTGAAGACATTACCCCGCAAACCACTCAGCAAAGTGCCTTTCTCCAAGCAAGAACAAAGAGCTCTTGGTGGTGACTG CTAGAAATTATGGAAGCCACTGTATCTCCTATATACGAAGTTCAGTGGACTGCAATGCTGTGTACCTGTGAATGTTTACAGATGGAAAGGTGAAGAG ATGCTACACCTGAGCTGATGTCCTATATAACCAAAGTTCCAGCAGGAACTAGAACATCAGTGCAGTCTCACAGAA GGCAACACTGAAGTGATGTCATAAAGAGGTTTATTTATATTTATAATTGAAGCTGTAATACCTCCCCAGTTCTCCCGAGTGATCTTCTTCTAAGTGA GTAGGATGAAGCTATTGGATATGTGATGTGTTAAGGGTAAGCTTGTAATACTGAGAGGACATGTAGTTGGAAGCATGTCCCTTGAGGTATGTGAGG GCCCACTAATTGCTCAGATGATGAAATTGGGTGTTAATGCTGAAGAGAGTTAATCACTATAGGATG ACATGTAAATTAGATGCACAGATGAGCTCAGAAGGTCCAGAGTGGGAAGCAGAGTTATCATCACTTATAGGATG AACTGCTTGGTATTTTTATTGTGACTGTATTACAAAGATGGACAATTCACTCCTTGGGAGCAAGTTATGCTCTAGAAGTTTA TTTACAAAATGCTGGGCAGCTCTTCTTGAATATTTTCCCAAGGAAGCTATTCTACACAGTGGCAAAATTGCTATCTAATTAATAAT GTAGCTGTTTGTACTCACCTGCCTCCACCACGAATGATTTAGCCTGTGACCCTTGCAGCATTAGTGCTGACCCTGCACCAGGGTTTC TAACAGATGACCCCTGTGAATCATATAATTTAAACCTCCATATATTTTATAGCCAGTCACATTTGCCCTCTCCACCCTATATGGCCATAAA CTGCCTAAGCACTCAGGCCTCTCGGCTGTCGCCCTTCACATAACAGAATGACTTGCCATCTGCCCAAACCCAGGATGTGAAGACA AGTTTGTCATGGGGCCTTCGGCTGTCGCCCTTCACCCTGTCCCATCTGCCCAAACCCAGGATGTGAAGACA TCTCCCCACACATGCACTGCCACTGCTCCTCTTTCCCCATCCAACAGACTCCCTGACAACCTTTCTGGCGTATAGAGAGT GGTGGAGGCTTGACAGCTGAGACGTAGTGTCAGAATGATGAGAGCGAGTCAGTGTCATTGTGAATAAACAGGCTGAAGCCTAAGGTCCATGAAAGGAGCAATGTCC TCCATGGCAACTGCTCTGCTTCCTTTGAATTAAGACAGACAGTCAGTCGTGATCATTGCCCCATCTGCCTGAAACCTACTTTCCACAGCCGATG ACTCAGAAGAGCCACAACCCAGAAGTGGGACTCTCTCTTTTTCCCATCACAACCTTTCTGGCGTAACTAGAGAGT CCCAGTGCAGAGATAGCCCTAAACGTTTGTTAAAATAAACAGGTCCATGAATGAAAGGAGCCTAAGGCATTGTTGATAATATCCACTCTCTC TTTCACTTCCTCCCATTTTTCACTCCTTTTCTCAGCCTCTTGCCCACTGCCTGTCCCACAGACCCCTCAGGACCTGCTGACT CATCTCGGGGAGGTAAGTTCACAGACATTTCCTAGAACGACACCCCATGCTCCCTAGAACGCAGGCTCGAGAAAGACAT CCCCTAGGCCCTGGACTTCTGAGCAGCTTAGCAGCTCCTCCCGGGAGGAGAGGAGAAAAATGCAGCCACCCTTTCCCCATTG CCAATGGATTTCCATGTTCTATAGTGTTCAGTAGTTGATGTAGTCAGATGATTTTTGTAAAATCAAAACACACAAAAGAAAAATTATTTAATAAAATA CTTTGAAATGAAAGTTCTCTGATGGCCTGCAACAAATGGGCAAAAAAATAGTTCCCCAGCATCCTTTAACATTTCTGCTCACCACTCAGAATGA GAGGAAATGCGTGTCTCACCCTTGCTGCAAACAGATGCCCTTCATCAATGAGGTCCATCAATGGGGATCAAAAACCTCTATAGTAGCCACTAGGC TACTGATGTTCTTCGGCAACACTTACAGACTTCCATCAATGGAGCTCCATCAATGGCTTCTTAAAGGAAAAACCTCTATAGTAGCCACTAGGC AAACACTGTATGGTGTGTAAGTGTTGTACACGTTCAATATGTTCAATATGTTAAATTCATTGCAA TGAAATAAAATTAAAAGGTATAAGGTATACTC | SEQ ID NO.: 80<br>MKTPWKVLLGLLGAAALVTIITV<br>PVVLLNKGTDDATADSRKTYTLT<br>DYLKNTYRLKLYSLRWISDHEYL<br>YKQENNILVFNAEYGNSSVFLEN<br>STPDEFGHSINDYSISPDGQFIL<br>LEYNYVKQWRHSYTASYDIYDLN<br>KRQLITERIPNNTQWVTWSPVG<br>HKLAYVWNNDIVKIEPNLPSYR<br>ITWTGKEDIIYNGITDWVYEEEV<br>FSAYSALWWSPNGTFLAYAQFND<br>TEVPLIEYSFYSDESLQYPKTVR<br>VPYPKAGAVNPTVKFFVVNTDSL<br>SSVTNATSIQITAPASMLIGDHY<br>LCDVTWATQERISLQWLRRIQNY<br>SVMDICDYDESSGRWNCLVARQH |
| SEQ ID NO.: 33<br>CTTTCACTGCAGCAAGACGAGTCCTGGGTTTCAGTTGCCTCAGTTGCCTGCCTGTGTGAGTTGCCAAAGTCCTGTGAGTTGCCAAAGTCCCCCTCCT<br>CTGGGCTTCTCGTTCCCTGCGCTCGCCGATCCAACGCACGGTGAGGTTGAACGCCGACTCATTTTAGCTAAGAGGACCAGGGTCCC<br>GAGTCCCCGGCCCAGGGCTCTCGCATCCGAGGCCGCGCCCTTCCCCACGGCTCCTCGGGGCCCCACTCTGCGCCCC<br>GGCTCCCGCCAGCGCCTACACCCTGCAGCCTGCAGCTGCAGGGGCCCTCGCAGGGACGCCCTCGGGATGCCAGTGCCCAGTGCCAGCGCGC<br>GAAACTTCCAGCGGCCGAGTGACTGACTTCACCCCGCAGTGAGCCTCCGCCGAGCGTCTCCGCCGCGGACTGTTTAACTCGGAGCC<br>CTTCTCTCGACCATCATCACCGTGCCCGTGGTTCGTGCCGGTCGCTGAACAAAGGCACAGATGATGCTACGACTCGCACAGTCGCAAAACTTACACTCTA<br>ACTGATTACTTTAAAAATACTTATGACTGAAGTTATACTGTAGAAGTTGATATTTCAGATCATGAATATCTTCCAAGATGAAAT<br>AATATTCAATATTCCTGATATAAAGCCAGTGGGAGTTTATTCTTTAGAATACAACATACTGTGACAATGAGCATCCTCACAGCTTCATAT<br>GACATTTATGCATATATTGGAATAACGAGACAGCATTAACAGAAGACCAGGAGACCATCAAGATCAGTGGTCAGCATCAGTGCTTCATAT<br>GAAGATATATATATAATGAATAACGACACAGAAGTCCCCACTTATTGAATACTCTTCTACTCTGATGAGTCACTGCAGTAC<br>GGCACTTTTTAGCATATGCCAATTTAACGACACAGAAGTCCCCACTTATTGAATACTCTTCTACTCTGATGAGTCACTGCAGTAC | |

TABLE 5-continued

| Nucleotide Sequence (5'-3') | ORFs |
|---|---|
| CCAAAGACTGTACGGTTCCATATCCAAAGGCAGGAGCTGTGAATCCAACTGTAAAGTTCTTTGTTGTAAATACAGACTCTCTCAGC<br>TCAGTCACCAATGCAACTTCCATAGACAAATCACTCGCTTCCTTCTATGTTGATAGGGATCACTACTTGTGTGATGTGACATGGCA<br>ACACCAAGAAGAATTTCTTTGCAGTGGGCTCAGGAGGATTCAGAACTATTCGGTCAGATGATATTGTGACTATGATGAAATCCAGTGGA<br>AGATGAACTGCTTAGTGCACGGCAACAGATGCAATCATCAGCAATGGGATAGAAGCTGGAAGTTACAGACACATTGTGATTCCAAAGAC<br>ACCCTTGATGGTAATAGCTTCTACAAAGGCACCTGGGGATAGAAGCTCATCGGGATAGAAGCTCAACCAGTGACATTACTATATCTACATAGTAATGAATTAT<br>TGCACATTTATTACAAGGATGCCAAGGAGAAATCTTTATAAAATCCAACTAGTGACTTATCATCCCCAGTGCTTGAGCTGAATCCG<br>AAAGGAATGCCAGACCAGCCAAGGAATCTTTATAAAATCCAACTAGTGACTTATCAGCTGAGTGTTCCGGTCTGCCCCTCTAT<br>GAAAGTGTCAGTACTATTCTGTGATCAAAAGGGCTGAAGAGTCCTGAAGACAATTCAGCTTTTGGATAAAATGCTCAGAAGTCCAGATG<br>ACTCTACCACAGCAGCTGAATTGCCTAATTATATTTTGAATGAAGAACAAAATTTGGTATCAGATGATCTTGCCTCCTCATTTGATAAATCCAAG<br>CCCTCCAAAAACTGGACTTCATTATTTGGTGATGCAGCCCATGTAGTCAAAAGCAGAACACTGTCTTCAGACTGAACTGGGCCACTTACCTT<br>GCAAGCACAGAAGACATTATAGTAGCTTGTGTGACGAAGAAGTTGTTCTCCCAAATTTGTCTCCTGACCAAATTCATCTTAAGTAGGGACTTCTGTCTTCACAAC<br>AGACTCGGAACATTTGAAGTTGAAGATCAAATTGAAGCAGCAGCCCAGAACAATTTTCAAAATGGGATTTGTGACAACAAACCAATTTCA<br>ATTTGGGGCTGGTCATATGAGGGGTACGTAACCTCAGTGACTCAGGTGTTCAAGTGTGAATAGCCGTGGCG<br>CCTGTATCCCGGTGGAGTCAGTGCTATGACTCAGTGTACACAGAACAGTTCATGGCTCCTCTTATTCATGAAGACAACCTTGACCATTAC<br>AGAAATTCAACAGTCATGAGGGAAGAATTTTAACCTATGAGTAATGGACTTGAGTAACGTGATAACGTTGAA<br>TTTCAGCAGTCAGTCCAGATCTCAAAGCCCTGGTCGATGTTGGAGCTTCAAGTCAGTATCAGTCTGATTACTGATGAAGACACCTCAAA<br>ATAGCTAGACACAGCACACAATATACCAACACATATAAAACTGCACTGTCAAGATGATGATCTTAAAA<br>TACCATGCCAATCCAAATCAAGAAACTTAAGGTTCACTTTTGTTTCATTATCTCAAGATGATGATCTTAAAA<br>AGATTATTACCTTACACAGAAGTTTGATTAAACCTTATTGTTTAAATCATTTCTGCAACTGACTGGTTCAAATGTTGTCTCT<br>GAATTGTTTAAAGGATGGCAAGATGTGGGCAGTGATGTCACTGGGCAGGATAAGGACAGGCCTGTTCACCAGCCA<br>TGGCTGGGAACCCAAGCTACCACAGCACCAGGCTGTCAGAGTGTCAGCTGTGTCACCAGCCAGCCAGCCAGCCA<br>ACAGTTTCTGAGAAGACTATTTCAAACAGTCAGGAGCTTCTCAGAGAATCAAATCAAATCAATCAATGGAAAGAAATGCCAAGGCAGTTGAA<br>AAGACTCCAAAGAATGTAAGGGAACATTGTGCCTTTTAAAAAGATGTCTTCCTAAGCTTAGCGGTTCCTTGAAACTGAAGATGAAGATGATGAA<br>AGGGTATGGGAAGCCCTGCCATGGCCTCGCTGTTAAAGAGAACAATTGTTCCCCCAACTTCCAACCTCTTTATTT<br>ACACATCAGCTTGGTGTCTTGTTAATTAAGAAAGATGAAAATATTTTGTATCACAAATTTAAAAATGCACTCTTAAAAATGCAATGTTATGTATTATTATTCCCA<br>CATTTCTTTGAGTGTCTTAATTAAGAATTTCTCCAGTCATTAATAAATGTGCCTTCATTTTTTCAGAAAAAAAAAAAAAAAAAAAA<br>TTCTACATACTATGGAATTTCTCCCAGTCATTAATAAATGTGCCTTCATTTTTTCAGAAAAAAAAAAAAAAAAAAAA | IEMSTTGWVGRFRPSEPHFTLDG<br>NSFYKIISNEEGYRHICYFQIDK<br>KDCTFITKGTWEVIGIRALTSDY<br>LYYISNEYKGMPGGRNLYKIQLS<br>DYTKVTCLSCELNPERCQYYSVS<br>FSKEAKYYQLRCSGPGLPLYTLH<br>SSVNDKGLRVLEDNSALDKMLQN<br>VQMPSKKLDFIILNETKFWYQMI<br>LPPHFDKSKKYPLLLDVYAGPCS<br>QKADTVFRLNWATYLASTENIIV<br>ASFDGRGSGYQGDKIMHAINRRL<br>GTPEVEDQIEAARQFSKMGFVDN<br>KRIAIWGWSYGYGVTSMVLGSGS<br>GVFKCGIAVAPVSRWEYYDSVYT<br>ERYMGLPTPEDNLDHYRNSTVMS<br>RAENFKQVEYLLIHGTADDNVHF<br>QQSAQISKALVDVGVDFQAMWYT<br>DEDHGIASSTAHQHITYHMSHFIKQCFSLP |
| SEQ ID NO.: 34<br>CGCAGCGCGGTCCTCTCATCTAGCTCCTGCGCCTCTGCCTCCGGTCCCGACCATGGCCGCGGCCC<br>CTGCGCCCCGCACTGCTCCTCTGCCTGCGCTCCTCGGCCGTCCGCGGCCCGGTGCCCAGTCCCGGCAAGCCGCCG<br>CGCCTCGTGGGAGGCCCCATGGACGCCAGCGTGGAGGAGGGTGCGCGCTGACGACCGGCGAGTACAACAAA<br>GCCAGCAACGACATGTACCACAGCGCATGGCTCTGCAAGCAGATCGTAGCTGGGGTGAACTACTTCTTGGAC<br>GTGGAGCTGGGCCGAACCACGTGCTACCAAGACCGCTGTACAAGACTGCCCCATCTGAAAAAGGAAA<br>GCATTCTGCTCTTTGCCAGATCAGCTGTCAGGAGCAACATGCACCTGTCAGGAGCCCATCTGCGCCCTTGG<br>GTACCCGGCTGGCCTGGCCTGCCTATCCATGTGCCATCCTTATGCACACGCTGGCCCCTTGG<br>GAAGGTCTCCCATGGCCCTGCCACCAGGACAGAGGCAGAGGACAGCCGCGTTCTGTGCTCAGCAAGCGG<br>GGACCTTCCCTTGCTTCTCATAGCCCGCGTCGCCGGGGCCCATAGAGTAGCATCGGCAAAAAATAGCACA<br>AAAAAAAAAAAAAAAAAAAAAA | SEQ ID NO.: 81<br>MAGPLRAPLLLLAILAVALAVSP<br>AAGSSPGKPPRLVGGPMDASVEE<br>EGVRRALDFAVGEYNKASNDMYH<br>SRALQVVRARKQIVAGVNYFLDV<br>ELGRTTCTKTQPNLDNCPFHDQP<br>HLKRKAFCSFQIYAVPWQGTMTLSKSTCQDA |
| SEQ ID NO.: 35<br>CCCAGCGCGGCCCTGCCAGCTTGGCACAGAGCACACCCACCTGCCTTTGTCACAGACACACTAAGAAGGTTCTCTGTGGTGACCAGCTG<br>GGTGAGGGGTCTGGGTCTGCAGGGGAGGCATGGCAGGCGTCAGGAGGAGCATGGCCTGGCCTGCTGCCAGCCTGTCCCATGCA<br>ATCCCTTGTGAGAAACTAGAAGAGACCTTCGGGAGGATCTGCTCACAGAGACGAAGCTCCCCGGCCGCACCCGACACGACGGGCC<br>GGTGGCCCCGCCCGCCGGAGGTGAACGCGAGCTCGGCGAGCCTGCGGCGCGAGCCCGGCGCTGCTCCCTGCCCACTACGACGGGCC<br>GCTGAGCGCCATCTGAGCCTTGCACTTCTGCCTGTGGGCAACCCGGCCCTGTCCCTGCCGCGCAACGACTCGTCCCTGGAGCCTGTGCCA<br>GCGGCGCTGAGCAGCGGCCCTACTTCTGCCGCGTGGAGTTCACCGGCGACGCACGACCGCACGAGGACTCCGCGTGCG<br>GGCGACAGCGGCGACCTCCTGCCCGGCGATCGTCAACATCGTGCTGCCGGCACATCCGTCCGCGCTCAGTCATCCGGCACCCCCAGGGGGA | SEQ ID NO.: 82<br>MEGSLQLLACLACVLQMGSLVKT<br>RRDASGDLLNTEAHSAPAQRWSM<br>QVPAEVNAEAGDAAVLPCTFTHP<br>HRHYDGPLTAINRSGEPYAGPQV<br>FRCTAAPGSELCQTALSLHGRFR<br>LLGNPRNDLSLRVERLALADSG<br>RYFCRVEFTGDAHDRYESRHGVR<br>LRVTAAPRIVNISVLPGPAHAFR |

TABLE 5-continued

| Nucleotide Sequence (5'-3') | ORFs |
|---|---|
| GCCCCCGCCGCCCTCGCCTGGTCGGTCCGCCCCAGGCAACAGCTCCGCCTGCCCTGAGGGCCAGGGTCACGGCTACCAGGTGAC<br>CGCCGAGTTGCCCGCGCTGACCCGGCAGACGCCGCTACACTGCACGGCCGCCAATAGCCTGGGCCGCGCCGAGGCCAGCGTCTACCT<br>GTTCCGCTTCCACGGAGCGCCTCCACCCGACCTCGAACCTGACCTGTGACCTGAGCCTGGGCGCCGTTGCAAGGCCTTGCTGCTTGGCAT<br>TCTGGGAGCGCGGTGCACGCAGCGCCGACTAGATCCTGTCCCCCAGGACACCTGCAGCGTGCGACCAGGACACTTCACCTATCTGGGGC<br>TCAGCTGAAGAAATAGAAGATCTGAAAGACCTGATAAACTCCAACGCTAG | ALCTAEGEPPPALAWSGPAPGNS<br>SAALQGGQHGYQVTAELPALTRD<br>GRYTCTAANSLGRAEASVYLFRF<br>HGAPGTSTLALLGALGLKALLL<br>LGILGARATRRRLDHLVPQDTPP<br>RADQDTSPIWGSAEEIEDLKDLHKLQR |

SEQ ID NO.: 36
TTTTCCAGTCACGACGTTGTAAAACGACGGCCAGTGAATTCTAATACGACTCACTATAGGGAGACGAGAGCACTGGATAGGTTCG
CGTGGCGCCGCCATGCGTCGAGTCGTCGAGTGACCGATCCTGAGAACTTCAGGCTCTGGGCAACGCTGCTGGTTATTGTCGTCTCATCATTTTGGC
AAAGAATTCACTCCTGCAGGCTGCCTATCAGAAGGTGGTGCTGGTGCCAATGCCCTGGCTCACAAATACCACTGAGAT
CTTTTTCCCTCTGCCAAAATTATGGGACATCATGAAGCCCTTGAGCATCTGACTTCTGGCTAATAAGAGAAATTTATTTTCATT
GCAAAAAAAAAGCGCCTAACTATGTGCACAAGGCCTCGGACGCCTAGCTGTGCTAATCATGGTCATAGCTGTTTCCTGT
GAAATTGTATCCGCTCACAATTCCACACATACGAGCCGGAAGCATAAAGTGTAAAGCCTGGGGGTGCCTAATGAGTGAGCTAAC
TCACATTAATTGCGTTGCGCTCACTGCCCGCTTTCCAGTCGGGGAAACTGTCGTGCCAGCTGCATTAATGAATCGGCAACGCGCGG
GGAGAGGCGGGTTGCGTATTGGGCGCTCTTCCGCTTCCTCGCTCACTGACTCGCTGCGCTCGGTCGTTCGGCTGCGGCGAGCGGTAT
CAGCTCACTCAAAGGCGGTAATACGGTTATCCACAGAATCAGGGGATAACGCAGGAAAGAACATGTGAGCAAAAGGCCAGCAAAAGG
CCAGGAACCGTAAAAAGGCCGCGTTGCTGGCGTTTTTCCATAGGCTCCGCCCCCCTGACGAGCATCACAAAAATCGACGCTCAAGTC
AGAGGTGGCGAAACCCGACAGGACTATAAAGATACCAGGCGTTTCCCCCTGGAAGCTCCCTCGTGCGCTCTCCTGTTCCGACCCTGC
CGCTTACCGGATACCTGTCCGCCTTTCTCCCTTCGGGAAGCGTGGCGCTTTCTCAATGCTCACGCTGTAGGTATCTCAGTTCGGTGT
AGGTCGTTCGCTCCAAGCTGGGCTGTGTGCACGAACCCCCCGTTCAGCCCGACCGCTGCGCCTTATCCGGTAACTATCGTCTTGAGT
CCAACCCGGTAAGACACGACTTATCGCCACTGGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCTGCGCTCTGCTGAAGCCAGTTACCTTCGGAA
AAAGAGTTGGTAGCTCTTGATCCGGCAAACAAACCACCGCTGGTAGCGGTGGTTTTTTTGTTTGCAAGCAGCAGATTACGCGCAGAA
AAAAAGGATCTCAAGAAGATCCTTTGATCTTTTCTACGGGGTCTGACGCTCAGTGGAACGAAAACTCACGTTAAGGGATTTTGGTCA
TGAGATTATCAAAAAGGATCTTCACCTAGATCCTTTTAAATTAAAATGAAGTTTTAAATCAATCTAAAGTATATATGAGTAAACTT
GGTCTGACAGTTACCAATGCTTAATCAGTGAGGCACCTATCTCAGCGATCTGTCTATTTCGTTCATCCATAGTTGCCTGACTCCCCG
TCGTGTAGATAACTACGATACGGGAGGGCTTACCATCTGGCCCCAGTGCTGCAATGATACCGCGAGACCCACGCTCACCGGCTCCAG
ATTTATCAGCAATAAACCAGCCAGCCGGAAGGGCCGAGCGCAGAAGTGGTCCTGCAACTTTATCCGCCTCCATCCAGTCTATTAATT
GTTGCCGGGAAGCTAGAGTAAGTAGTTCGCCAGTTAATAGTTTGCGCAACGTTGTTGCCATTGCTACAGGCATCGTGGTGTCACGCT
CGTCGTTTGGTATGGCTTCATTCAGCTCCGGTTCCCAACGATCAAGGCGAGTTACATGATCCCCCATGTTGTGCAAAAAAGCGGTTA
GCTCCTTCGGTCCTCCGATCGTTGTCAGAAGTAAGTTGGCCGCAGTGTTATCACTCATGGTTATGGCAGCACTGCATAATTCTCTTA
CTGTCATGCCATCCGTAAGATGCTTTTCTGTGACTGGTGAGTACTCAACCAAGTCATTCTGAGAATAGTGTATGCGGCGACCGAGTT
GCTCTTGCCCGGCGTCAATACGGGATAATACCGCGCCACATAGCAGAACTTTAAAAGTGCTCATCATTGGAAAACGTTCTTCGGGGC
GAAAACTCTCAAGGATCTTACCGCTGTTGAGATCCAGTTCGATGTAACCCACTCGTGCACCCAACTGATCTTCAGCATCTTTTACTT
TCACCAGCGTTTCTGGGTGAGCAAAAACAGGAAGGCAAAATGCCGCAAAAAAGGGAATAAGGGCGACACGGAAATGTTGAATACTCA
TACTCTTCCTTTTTCAATATTATTGAAGCATTTATCAGGGTTATTGTCTCATGAGCGGATACATATTTGAATGTATTTAGAAAAATA
AACAAATAGGGGTTCCGCGCACATTTCCCCGAAAAGTGCCACCTGACGTCTAAGAAACCATTATTATCATGACATTAACCTATAAAA
ATAGGCGTATCACGAGGCCCTTTCGTCTTCAAG

SEQ ID NO.: 37
TTTTCCAGTCACGACGTTGTAAAACGACGGCCAGTCAGTTCGAGCTCACATACGATTAGGTGACACTATAGGCCTGCACCACAG
TTAACACGCGCACCATCCGTCGCCAGTAGCGTCCTGCCCGACGCTGAGGAAACTTCAGGTCTGGCGGCTCTCTTCTCAACCTTCGATAACTCGTCTGGCTCGCTCATCATTTGGCAAGAATTCACTCCCTGCCACCTGTCCTGCCAGGCAGGCTGCAGGCTGCCTATCAGAAGGTGGTGCTGGCCAATGCCCTGGCTCACAAATACCACTG
AGATCTTTTTCCCTCTGCCAAAATTATGGGACATCATGAAGCCCTTGAGCATCTGACTTCTGGCTAATAAGGAAATTTATTTT
CATTGCAAAAAAAAAGCGGCCGCTAGCTTCATCGGCGTAAAGGTCATCATCATGCTTAAAGCCTGGCTAATGCCCTAATGAGTGAAA
ATGCGCCATTGCCCATTGCTTCCACACATACGAGCCGGAAGCATAAAGTGTAAAGCCTGGGGTGCCTAATGAGTGAGCTAACTCAC
ATTAATTGCGTTGCGCTCACTGCCCGCTTTCCAGTCGGGAAACCTGTCGTGCCAGCTGCATTAATGAATCGGCCAACGCGCGGGGAG
AGGCGGTTTGCGTATTGGGTAACCGCCAGGG

TABLE 5-continued

| Nucleotide Sequence (5'-3') | ORFs |
|---|---|
| AGGCGGTTTGCGTATTGGGCGCTCTTCCGCTTCTCGCTCACTGACTCGCTGCGCTCGGTCGTTCGGCTGCGGCGAGCGGTATCAGC<br>TCACTCAAAGGCGGTAATACGGTTATCCACAGAATCAGGGGATAACGCAGGAAAGAACATGTGAGCAAAAGGCCAGCAAAAGGCCAG<br>GAACCGTAAAAAGGCCGCGTTGCTGGCGTTTTTCCATAGGCTCCGCCCCCCTGACGAGCATCACAAAAATCGACGCTCAAGTCAGAG<br>GTGGCGAAACCCGACAGGACTATAAAGATACCAGGCGTTTCCCCCTGGAAGCTCCCTCGTGCGCTCTCCTGTTCCGACCCTGCCGCT<br>TACCGGATACCTGTCCGCCTTTCTCCCTTCGGGAAGCGTGGCGCTTTCTCAAAGCTCACGCTGTAGGTATCTCAGTTCGGTGTAGGT<br>CGTTCGCTCCAAGCTGGGCTGTGTGCACGAACCCCCCGTTCAGCCCGACCGCTGCGCCTTATCCGGTAACTATCGTCTTGAGTCCAA<br>CCCGGTAAGACACGACTTATCGCCACTGGCAGCAGCCACTGGTAACAGGATTAGCAGAGCGAGGTATGTAGGCGGTGCTACAGAGTT<br>CTTGAAGTGGTGGCCTAACTACGGCTACACTAGAAGAACAGTATTTGGTATCTGCGCTCTGCTGAAGCCAGTTACCTTCGGAAAAAG<br>AGTTGGTAGCTCTTGATCCGGCAAACAAACCACCGCTGGTAGCGGTGGTTTTTTTGTTTGCAAGCAGCAGATTACGCGCAGAAAAAA<br>AGGATCTCAAGAAGATCCTTTGATCTTTTCTACGGGGTCTGACGCTCAGTGGAACGAAAACTCACGTTAAGGGATTTTGGTCATGAG<br>ATTATCAAAAAGGATCTTCACCTAGATCCTTTTAAATTAAAAATGAAGTTTTAAATCAATCTAAAGTATATATGAGTAAACTTGGTC<br>TGACAGTTACCAATGCTTAATCAGTGAGGCACCTATCTCAGCGATCTGTCTATTTCGTTCATCCATAGTTGCCTGACTCCCCGTCGT<br>GTAGATAACTACGATACGGGAGGGCTTACCATCTGGCCCCAGTGCTGCAATGATACCGCGAGACCCACGCTCACCGGCTCCAGATTT<br>ATCAGCAATAAACCAGCCAGCCGGAAGGGCCGAGCGCAGAAGTGGTCCTGCAACTTTATCCGCCTCCATCCAGTCTATTAATTGTTG<br>CCGGGAAGCTAGAGTAAGTAGTTCGCCAGTTAATAGTTTGCGCAACGTTGTTGCCATTGCTACAGGCATCGTGGTGTCACGCTCGTC<br>GTTTGGTATGGCTTCATTCAGCTCCGGTTCCCAACGATCAAGGCGAGTTACATGATCCCCCATGTTGTGCAAAAAAGCGGTTAGCTC<br>CTTCGGTCCTCCGATCGTTGTCAGAAGTAAGTTGGCCGCAGTGTTATCACTCATGGTTATGGCAGCACTGCATAATTCTCTTACTGT<br>CATGCCATCCGTAAGATGCTTTTCTGTGACTGGTGAGTACTCAACCAAGTCATTCTGAGAATAGTGTATGCGGCGACCGAGTTGCTC<br>TTGCCCGGCGTCAATACGGGATAATACCGCGCCACATAGCAGAACTTTAAAAGTGCTCATCATTGGAAAACGTTCTTCGGGGCGAAA<br>ACTCTCAAGGATCTTACCGCTGTTGAGATCCAGTTCGATGTAACCCACTCGTGCACCCAACTGATCTTCAGCATCTTTTACTTTCAC<br>CAGCGTTTCTGGGTGAGCAAAAACAGGAAGGCAAAATGCCGCAAAAAAGGGAATAAGGGCGACACGGAAATGTTGAATACTCATACT<br>CTTCCTTTTTCAATATTATTGAAGCATTTATCAGGGTTATTGTCTCATGAGCGGATACATATTTGAATGTATTTAGAAAAATAAACA<br>AATAGGGGTTCCGCGCACATTTCCCCGAAAAGTGCCACCTGACGTCTAAGAAACCATTATTATCATGACATTAACCTATAAAAATAG<br>GCGTATCACGAGGCCCTTTCGTCTTCACCTCGA | |

SEQ ID NO.: 38

TTTTCCCAGTCACGACGTTGTAAAACGACGGCCAGTGAATTCTAATACGACTCACTATAGGGAGAATGGAGAAAAAAATCACTGGACG
CGTGGCGCGCCATTAATTAATGCGGCCGCTAGCTCGAGTCGAGTGATAATAAGCGGATGAATGGCTGCAGGCATGCAAGCTTGGCGTAATCA
TGGTCATAGCTGTTTCCTGTGTGAAATTGTTATCCGCTCACAATTCCACACAACATACGAGCCGGAAGCATAAAGTGTAAAGCCTGG
GGTGCCTAATGAGTGAGCTAACTCACATTAATTGCGTTGCGCTCACTGCCCGCTTTCCAGTCGGGAAACCGTCTGCCAGCTGCAT
TAATGAATCGGCCAACGCGCGGGGAGAGGCGGTTTGCGTATTGGGCGCTCTTCCGCTTCCTCGCTCACTGACTCGCTGCGCTCGGTC
GTTCGGCTGCGGCGAGCGGTATCAGCTCACTCAAAGGCGGTAATACGGTTATCCACAGAATCAGGGGATAACGCAGGAAAGAACATG
TGAGCAAAAGGCCAGCAAAAGGCCAGGAACCGTAAAAAGGCCGCGTTGCTGGCGTTTTTCCATAGGCTCCGCCCCCCTGACGAGCAT
CACAAAAATCGACGCTCAAGTCAGAGGTGGCGAAACCCGACAGGACTATAAAGATACCAGGCGTTTCCCCCTGGAAGCTCCCTCGTG
CGCTCTCCTGTTCCGACCCTGCCGCTTACCGGATACCTGTCCGCCTTTCTCCCTTCGGGAAGCGTGGCGCTTTCTCATAGCTCACGC
TGTAGGTATCTCAGTTCGGTGTAGGTCGTTCGCTCCAAGCTGGGCTGTGTGCACGAACCCCCCGTTCAGCCCGACCGCTGCGCCTTA
TCCGGTAACTATCGTCTTGAGTCCAACCCGGTAAGACACGACTTATCGCCACTGGCAGCAGCCACTGGTAACAGGATTAGCAGAGCG
AGGTATGTAGGCGGTGCTACAGAGTTCTTGAAGTGGTGGCCTAACTACGGCTACACTAGAAGGACAGTATTTGGTATCTGCGCTCTG
CTGAAGCCAGTTACCTTCGGAAAAAGAGTTGGTAGCTCTTGATCCGGCAAACAAACCACCGCTGGTAGCGGTGGTTTTTTTGTTTGC
AAGCAGCAGATTACGCGCAGAAAAAAAGGATCTCAAGAAGATCCTTTGATCTTTTCTACGGGGTCTGACGCTCAGTGGAACGAAAAC
TCACGTTAAGGGATTTTGGTCATGAGATTATCAAAAAGGATCTTCACCTAGATCCTTTTAAATTAAAAATGAAGTTTTAAATCAATC
TAAAGTATATATGAGTAAACTTGGTCTGACAGTTACCAATGCTTAATCAGTGAGGCACCTATCTCAGCGATCTGTCTATTTCGTTCA
TCCATAGTTGCCTGACTCCCCGTCGTGTAGATAACTACGATACGGGAGGGCTTACCATCTGGCCCCAGTGCTGCAATGATACCGCGA
GACCCACGCTCACCGGCTCCAGATTTATCAGCAATAAACCAGCCAGCCGGAAGGGCCGAGCGCAGAAGTGGTCCTGCAACTTTATCC
GCCTCCATCCAGTCTATTAATTGTTGCCGGGAAGCTAGAGTAAGTAGTTCGCCAGTTAATAGTTTGCGCAACGTTGTTGCCATTGCT
ACAGGCATCGTGGTGTCACGCTCGTCGTTTGGTATGGCTTCATTCAGCTCCGGTTCCCAACGATCAAGGCGAGTTACATGATCCCCC
ATGTTGTGCAAAAAAGCGGTTAGCTCCTTCGGTCCTCCGATCGTTGTCAGAAGTAAGTTGGCCGCAGTGTTATCACTCATGGTTATG

TABLE 5-continued

| Nucleotide Sequence (5'-3') | ORFs |
|---|---|

GCAGCACTGCATAATTCTCTTACTGTCATGCCATCCGTAAGATGCTTTTCTGTGACTGTGAGTACTCAACCAAGTCATTCTGAGAA
TAGTGTATGCGGGCACCGAGTTGCTCTTGCCCGAGTTCTCAAGGATCTTCAAGGATATAACGCGCCACATAGCAGAACTTTAAAAGTGCTCATC
ATTGGAAAACGTTCTCGGGCGAAAACTCTCAAGGATCTTACCGCTGTTGAGATCCAGTTGCTGATGTGACCCTGTGCACCCAAC
TGATCTTCAGCATCTTTACTTTCACCAGCGTTCTGGGTGAGCAAACAGGAGGCAAAATGCGACAAAAAGGGAATAAGGCG
ACACGGAAATGTTGAATACTCATACTCTTCCTTTTTCAATATATTGAAGCATTTATCAGGGTTATTGTCTCATGAGCGATACATA
TTTGAATGTATTAGAAAATATAAACAAATAGGGGTTCCGGCACATTTCCCGAAAGTCCACCTGACGTCTAAGAACCTTCGACAC
ATCATGACATTAACCTATAAAAATAGGCTATCAGAGGCCTATCACGAGGCTGTCTGTAAGCGCGATGACCGTGTAAAACCTGAC
ATGCAGCTCCCGGACGCTGCAGCTTGTCTGTAAGCGGATAGCCGGAGCACAAGCCGTCAGGCGTCAGCGGGGTGTTGGC
GGGTGTCGGGGCTGGCTTAACTATCGCCATCAGGCCGATTGTACTGAGAGTGCACCATATGCGGTGAAATACCGCACAGATGC
CGAAAGGGGGATGTCGCAAGGCGATTAAGTTGGGTAACGCCAGGG

SEQ ID NO.: 39

TTTTCCCAGTCACGACGTGTAAAACGACGGCCAGTGAATTCAATTAACCCTCACTAAAGGGAGACTTGTTCCAAATGTGTTAGGcg
CGCCGCATGCGTCGACGGATCCTGAGGACTTCAGGCTCTGGGCAACGTGCTGGTTATTGCTGTCTCATCATTTTGGCAAAGAAT
TCACTCCTCAGGTGCAGGCTCCTATCAGAAGGTGCTGGGTGCAAATGCCCTGCGTCACAAATGGAAATACCACTGAGATCTTTTTC
CCTCTGCCAAAATATGGGACATCATGGAGCCCTTGACTTCTGCTAATAAGGAAATTATTTTCATTGCAAAA
AAAAAAGCGGCCGCTTCTCTATAGTGTCACCTACATCCCAGCGGCCTTGGCGTAAGCGTTGGGCGGTCATAGCTGTTCCTGTGTG
AAATTGTTATCCGCTCACAATTCCACACACACGCGGTTCACTGCGTTGCGTTCGTTCAGCCTGAAGCATTAATGAATCGCGCAACGCGCGG
GAGAGGCGGTTTTGCGTTATTGGGCTCGTCTTCCGCTTCCTCCGCTCACTGACTCGCTGCGCTCGGTCGTTCGGCTGCGGCGAGCGGTATC
AGCTCACTCAAAGCGGTAATACGGTTATCCACAGAATCAGGGGATAACGCAGGAAAGAACATGTGAGCAAAAGGCCAGCAAAAGGC
CAGGAACCGTAAAAAGCCCGCGTTGCTGGCGTTTTTCCCATAGGCTCCGCCCCCCTGAACGATCGACATCACAAAATCGACGCTCAAGTCA
GAGGTGGCGAAACCCGACAGGACTATAAAGATACCAGGCGTTCCCCCCTGGAAGCTCCCTCGTGCGCTCTCCTGTTCCGACCCTGCC
GCTTACCGGATACCTGTCCGCCTTTTCTCCCTTCGGGAAGCGTGGCGCTTTTCTCAAAGCTCACGCTGTAGGTATCTCAGTTCGGTGTA
GGTCGTTCGCTCCAAGCTGGGCTGTGTGCACGAACCCCCGTTCAGCCCGACCGCTGCGCCTTATCCGGTAACTATCGTCTTGAGT
CAACCCGGTAAGACACGACTTATCGCCACTGGCAGCAGCCACTGGTAACAGGATTAGCAGAGCGAGGTATGTAGGCGGTGCTACAGA
GTTCTTGAAGTGGTGGCCTAACTACGGCTACACTAGAAGAACAGTATTTGGTATCTGCGCTCTGCTGAAGCCAGTTACCTTCGGAAA
AAGAGTTGGTAGCTCTTGATCCGGCAAACAAACCACCGCTGGTAGCGGTGGTTTTTTTGTTTGCAAGCAGCAGATTACGCGCAGAAA
AAAAGGATCTCAAGAAGATCCTTTGATCTTTTCTACGGGGTCTGACGCTCAGTGGAACGAAAACTCACGTTAAGGGATTTTGGTCAT
GAGATTATCAAAAAGGATCTTCACCTAGATCCTTTTAAATTAAAAATGAAGTTTTAAATCAATCTAAAGTATATATGAGTAAACTTG
GTCTGACAGTTACCAATGCTTAATCAGTGAGGCACCTATCTCAGCGATCTGTCTATTTCGTTCATCCATAGTTGCCTGACTCCCCGT
CGTGTAGATAACTACGATACGGGAGGGCTTACCATCTGGCCCCAGTGCTGCAATGATACCGCGAGACCCACGCTCACCGGCTCCAGA
TTTATCAGCAATAAACCAGCCAGCCGGAAGGGCCGAGCGCAGAAGTGGTCCTGCAACTTTATCCGCCTCCATCCAGTCTATTAATTG
TTGCCGGGAAGCTAGAGTAAGTAGTTCGCCAGTTAATAGTTTGCGCAACGTTGTTGCCATTGCTACAGGCATCGTGGTGTCACGCTC
GTCGTTTGGTATGGCTTCATTCAGCTCCGGTTCCCAACGATCAAGGCGAGTTACATGATCCCCCATGTTGTGCAAAAAAGCGGTTAG
CTCCTTCGGTCCTCCGATCGTTGTCAGAAGTAAGTTGGCCGCAGTGTTATCACTCATGGTTATGGCAGCACTGCATAATTCTCTTAC
TGTCATGCCATCCGTAAGATGCTTTTCTGTGACTGGTGAGTACTCAACCAAGTCATTCTGAGAATAGTGTATGCGGCGACCGAGTTG
CTCTTGCCCGGCGTCAATACGGGATAATACCGCGCCACATAGCAGAACTTTAAAAGTGCTCATCATTGGAAAACGTTCTTCGGGGCG
AAAACTCTCAAGGATCTTACCGCTGTTGAGATCCAGTTCGATGTAACCCACTCGTGCACCCAACTGATCTTCAGCATCTTTTACTTT
CACCAGCGTTTCTGGGTGAGCAAAAACAGGAAGGCAAAATGCCGCAAAAAAGGGAATAAGGGCGACACGGAAATGTTGAATACTCAT
ACTCTTCCTTTTTCAATATTATTGAAGCATTTATCAGGGTTATTGTCTCATGAGCGGATACATATTTGAATGTATTTAGAAAAATAAAC
AAATAGGGGTTCCGCGCACATTTCCCCGAAAAGTGCCACCTGACGTCTAAGAAACCATTATTATCAGTGACATTAACCTATAAAA
TAGGCGTATCACGAGGCCCTTTCGTCTCGCGCGTTTCGGTGATGACGGTGAAAACCTCTGACACATGCAGCTCCCGGAGACGGTCAC
AGCTTGTCTGTAAGCGGATGCCGGGAGCAGACAAGCCCGTCAGGGCGCGTCAGCGGGTGTTGGCGGGTGTCGGGGCTGGCTTAACTA
TGCGGCATCAGAGCAGATTGTACTGAGAGTGCACCATATGCGGTGTGAAATACCGCACAGATGCGTAAGGAGAAAATACCGCATCAG
GCGCCATTCGCCATTCAGGCTGCGCAACTGTTGGGAAGGGCGATCGGTGCGGGCCTCTTCGCTATTACGCCAGCTGGCGAAAGGGGGATGTGCTGCAAG
GCGATTAAGTTGGGTAACGCCAGGG

SEQ ID NO.: 40

AATTCTAATACGACTCACTATAGGGAGAGAGAGAGCACCTGGATAGGTT

TABLE 5-continued

| Nucleotide Sequence (5'-3') | ORFs |
|---|---|
| SEQ ID NO.: 41<br>GCCTGCACCAACAGTTAACA | |
| SEQ ID NO.: 42<br>CAGGCCCAGGAGTCCAATT | |
| SEQ ID NO.: 43<br>TCCCCGTCTTTGGGTCAAAA | |
| SEQ ID NO.: 44<br>GCGCCGCGGATCGTCAACA | |
| SEQ ID NO.: 45<br>ACACGTGCACGGCGGCCAA | |
| SEQ ID NO.: 46<br>TCGCGCCGTTTCGGTGATGACGGTGAAAACCTCTGCACATGCAGCTCCCGGAGACGGTCACAGCTTGTCTGTAAGCGATGCCGGGA<br>GCAGAAGCCCGTCAGGGCGCGTCAGGGTGTTGGCGGGTGTCGGGGCTTAACTATGCCGCATCAGAGCAGATTGTACTGA<br>GAGTGCACCATATGCGGTGCTGTGAAATACCGCACAGTGCTAAGGAGAAATACCATCAGGCGCCATTCGCATTCAGGCTGCGCA<br>ACTGTTGGGAAGGGCGATCGGTGCGGGCCCTTCCTGCCAGCTGGCCAGCTGGCGAAAGGCGCATTGCTGCAAGGCGATTAAGTTGGG<br>TAACGCAGGGTTTTCCAGTCACGACGTGTAAAACGACGGCCAGTGCCAAGCTTTTCCAAAAAACTACCGTTGTTATAGGTCGT<br>CTTGAACACCTATAACAACGGTAGTGGATCCCGCCTCCTTTCCACAAGATATATTAAACCAAGAAATTATTACTTTCACGTTACG<br>GTAAGCATATGATAGTCCATTTTAAAACATAATTTTAAAACTGCAAACTATCTCTAACAGCCTTGTATCGTATATGCAAATGAAGGAATCATG<br>ACTAATATCTTTGTGTTACAGTCAAATTAATTCTAATAGCTTGGTGTTCCTGCCCCGACCTTGGCGCGCCTCGGCGCGTCTTGCCCTGTTGCCTGCGCGTCT<br>GGAAATAGGCCCTCTCTCTGCCCGACCTTGGCCGCCTCGGCGCCGCGCCGCGCTGGCGCGCGCCGCCCCCGCCCGCCCGCGCGTCTT<br>TTCCACTGGGGAATTCATGCTTGCGGTTCTCCCCTTTAGTGAGGGTAATTCTCTCTCCTCCTCTCCCTATAGTGAGTCGTATTAATTCCTTCT<br>TCTATAGTGTCACCTAAATCGTTGCAATTCGTAATCATGTCATAGCTGTTTCTCGTGTGAAATGTATCCGCTCACAATTCCACAC<br>AACATACGAGCCGGAAGCATAAAGTGTAAAGCCTGGGGTGCCCTAATGAGTGAGCTAACTCACATTAATTGCGTTGCGCTCACTGCCC<br>GCTTTCCAGTCGGGAAACCTGTCGTGCCAGCTGCATTAATGAATCGGCCAACGCGCGGGGAGAGGCGGTTTGCGTATTGGGCGCTCT<br>TCCGCTTCCTCGCTCACTGACTCGCTGCGCTCGGTCGTTCGGCTGCGGCGAGCGGTATCAGCTCACTCAAAGGCGGTAATACGGTTA<br>TCCACAGAATCAGGGGATAACGCAGGAAAGAACATGTGAGCAAAAGGCCAGCAAAAGGCCAGGAACCGTAAAAAGGCCGCGTTGCTG<br>GCGTTTTTCCATAGGCTCCGCCCCCCTGACGAGCATCACAAAAATCGACGCTCAAGTCAGAGGTGGCGAAACCCGACAGGACTATAA<br>AGATACCAGGCGTTTCCCCCTGGAAGCTCCCTCGTGCGCTCTCCTGTTCCGACCCTGCCGCTTACCGGATACCTGTCCGCCTTTCTC<br>CCTTCGGAAGCGTGGCGCTTTCTCATAGCTCACGCTGTAGGTATCTCAGTTCGGTGTAGGTCGTTCGCTCCAAGCTGGGCTGTGTG<br>CACGAACCCCCCGTTCAGCCCGACCGCTGCGCCTTATCCGGTAACTATCGTCTTGAGTCCAACCCGGTAAGACACGACTTATCGCCA<br>CTGGCAGCAGCCACTGGTAACAGGATTAGCAGAGCGAGGTATGTAGGCGGTGCTACAGAGTTCTTGAAGTGGTGGCCTAACTACGGC<br>TACACTAGAAGAACAGTATTTGGTATCTGCGCTCTGCTGAAGCCAGTTACCTTCGGAAAAAGAGTTGGTAGCTCTTGATCCGGCAAA<br>CAAACCACCGCTGGTAGCGGTGGTTTTTTTGTTTGCAAGCAGCAGATTACGCGCAGAAAAAAAGGATCTCAAGAAGATCCTTTGATC<br>TTTTCTACGGGGTCTGACGCTCAGTGGAACGAAAACTCACGTTAAGGGATTTTGGTCATGAGATTATCAAAAGGATCTTCACCTAG<br>ATCCTTTTAAATTAAAAATGAAGTTTTAAATCAATCTAAAGTATATATGAGTAAACTTGGTCTGACAGTTACCAATGCTTAATCAGT<br>GAGGCACCTATCTCAGCGATCTGTCTATTTCGTTCATCCATAGTTGCCTGACTCCCCGTCGTGTAGATAACTACGATACGGGAGGGC<br>TTACCATCTGGCCCCAGTGCTGCAATGATACCGCGAGACCCACGCTCACCGGCTCCAGATTTATCAGCAATAAACCAGCCAGCCGGA<br>AGGGCCGAGCGCAGAAGTGGTCCTGCAACTTTATCCGCCTCCATCCAGTCTATTAATTGTTGCCGGGAAGCTAGAGTAAGTAGTTCG<br>CCAGTTAATAGTTTGCGCAACGTTGTTGCCATTGCTACAGGCATCGTGGTGTCACGCTCGTCGTTTGGTATGGCTTCATTCAGCTCC<br>GGTTCCCAACGATCAAGGCGAGTTACATGATCCCCCATGTTGTGCAAAAAAGCGGTTAGCTCCTTCGGTCCTCCGATCGTTGTCAGA<br>AGTAAGTTGGCCGCAGTGTTATCACTCATGGTTATGGCAGCACTGCATAATTCTCTTACTGTCATGCCATCCGTAAGATGCTTTTCT<br>GTGACTGGTGAGTACTCAACCAAGTCATTCTGAGAATAGTGTATGCGGCGACCGAGTTGCTCTTGCCCGGCGTCAATACGGGATAAT<br>ACCGCGCCACATAGCAGAACTTTAAAAGTGCTCATCATTGGAAAACGTTCTTCGGGGCGAAAACTCTCAAGGATCTTACCGCTGTTG<br>AGATCCAGTTCGATGTAACCCACTCGTGCACCCAACTGATCTTCAGCATCTTTTACTTTCACCAGCGTTTCTGGGTGAGCAAAAACA<br>GGAAGGCAAAATGCCGCAAAAAAGGGAATAAGGGCGACACGGAAATGTTGAATACTCATACTCTTCCTTTTTCAATATTATTGAAGC<br>ATTTATCAGGGTTATTGTCTCATGAGCGGATACATATTTGAATGTATTTAGAAAAATAAACAAATAGGGGTTCCGCGCACATTTCCC<br>CGAAAAGTGCCACCTATTGTGTGGAAAGTCCCCAGGCTCCCCAGCAGGCAGAAGTATGCAAAGCATGCATCTCAATTAGTCAGCAA<br>CCAGGTGTGGAAAGTCCCCAGGCTCCCCAGCAGGCAGAAGTATGCAAAGCATGCATCTCAATTAGTCAGCAACCATAGTCCCGCCCC<br>TAACTCCGCCCATCCCGCCCCTAACTCCGCCCAGTTCCGCCCATTCTCCGCCCCATGGCTGACTAATTTTTTTATTTATGCAGAGG<br>CCGAGGCCGCCTCGGCCTCTGAGCTATTCCAGAAGTAGTGAGGAGGCTTTTTTGGAGGCCTAGGCTTTTGCAAAAAGCTAGCTTGCA | |

TABLE 5-continued

| Nucleotide Sequence (5'-3') | ORFs |
|---|---|
| TGCCTGCAGTCGGCCGCCACGACCGGTGCCGCCACCATCCCTGACCCACCGCCCCCTGACCCCTCACAAGGAGACGACCTTCCATGA<br>CCGAGTACAAGCCCACCGTGCGCTCGCCACCCGGACGACGTCCCCCGGCCGTACGACCTCGCCCTCGCCGTTCGCGACTACC<br>CCGCCACCGCGCCACACCCGTCGACGCTGACCATCGAGCGGGTCACCGAGCTCGAAGAACTTCCTCACCGCGTCGGGCTCG<br>ACATCGCAAGGTGTGGGTCGCGGACGACGGCCCGCCCGGTGGCGTCTGACCACGCCGAGAGCCTCGGCGAGGGCCGTGTTCG<br>CCGAGATCGGCCCGCCGGTGGTTCCTGGCGGTCCGCGTCGCCGACCAGGGCAACAGATGGAAGGCCTCCTGGCCGCCACCGGC<br>CCAAGGAGCCCGCCGGTGGTTCCTGGCCACCGGCCGGTTGGGCCAGCGCCAACCTCCCCTTCTACGAGCCGCTCGGCT<br>GAGTGGAGGCCGCCACCGTCGAGGTGCCGCCGACTTCGCATGACCGCGATGACCGAAGCCCCGCCGACTCGTGACGCCCACG<br>TCACCGTCACCGCCACGCTCGAGGTGCCGCACCTGTCCATGACCCGAAGCCCATTCGCTTCCGGCCACCCTCCCACACTC<br>ACCCGCAGCCCACCGACTCTAGAGGATCATAATCAGCCATACACATTTGTGTGTGTGTAACAACCTCCCCACACTC<br>CCCTGAACCTGAAACATAAAATAAAGCATTTTTCACTGCAATCTAAGAAACCATTATATCAGCATTAACTATAAATGGGCTATCACGAGGCCCT<br>ATCACAAATTCACAAATAAAGCATTTTTCACTGCAATCTAAGAAACCATTATATCAGCATTAACTATAAATGGGCTATCACGAGGCCCT<br>TCGTC<br>SEQ ID NO.: 47<br>TAGTTATTAATAGTAATCAATTACGGGTCATTAGTTCATAGCCCATATAGGAGTTCCGCTTACATAACTTACGGTAAATGCCC<br>GCCTGGCCTGACCGGCCAACGACCCCGCGCCCATTGCGCCCCCGGCGCCATAGTAACGCATTGCCCCCTATTGGAACCCCATATAGGGACTTCCATTG<br>ACGTCAATGGGTGGAGTATTTACGGTAAACTGCCCACTTGGCAGTACATCAAGTGTATCATATGCCAAGTACGCCCCCTATTGACGT<br>CAATGACGGTAAATGGCCCGCCTGGCATTATGCCCAGTACATGACCTTATGGGACTTCCTACTTGGCAGTACATCTACGTATTAGT<br>CATCCCATTATGACCATGGTGATGCGGTTTTGGCAGTACATCAATGGGCGTGGATAGCGGTTTGACTCACGGGGATTTCCAAGTCTCA<br>CCCCATTGACGTCAATGGGAGTTTGTTTTGGCACCAAAATCAACGGGACTTTCCAAAATGTCGTAACAACTCCGCCCATTGACGCA<br>AATGGGCGGTAGGCGTGTACGGTGGGAGGTCTATATAAGCAGAGCTCTCTGGCTAACTCCGCTAGCGCTACCGGACTCA<br>GATCTCGAGCTCAAGCTTCGAATTCGCAGTGACGCGGTACCGGGGATCCACCGGTCGCCACCATGGTGAGCAAGGGCGAGGAGCTGT<br>GTTGTTAACAACTGTTGATTCACCGCCGTCCATATATATCAGCACACCTCCGAACCTGAAACATAAAATGAATGCAATGTT<br>CATTCAGTGTGGTTGTCCAAACTCATCATCAATGTATCTTTAAGGGTCAATGTGTCCAAAATTGTAAGCGTTAATATTTTGTTAAAATTCGCTTAAA<br>TTTTTGTTTAAATCAGCTCATTTTTTTAAACCAATAGGCCGAAATGCCCTATTAACCAATAGGCCGAAATCAATCAAAGAATAGACCGTCTATCAGGGCGA<br>GAGTGTTGTTCCAGTTTGGAACAAGAGTCCACTATTAACAAGAGTCCACTATTAACGAAGCTGGACTCCAACGTCGTGACTGGGAAAACCGTCTATCAGGGCGA<br>TGGCCCAGCATCACCCATGGTGACCTTTGAACCATCAAGTTTTTGGGGGTCGAGGTGCCGTAAAGCACTAAATCGAACCTAAAGGAGCCC<br>CCGATTTAGAGCTTGACGGGGCTTGTCTGCTCCCGGCGTTGGGTCGCTTTGCCCTTCGCCCTCAGACGAGCCGGACGCTATCACGACAATGAACTGCC<br>AAGTGTAGCGGTCACGCTGCGCGTAACCACCACAACCCGCCGCGCTTAATGCGCCGCTACAGGGCGCGTCAGGTGGCACTTTCGGG<br>AAATGTGCGCGGAACCCCTATTTGTTTATTTTTCTAAATACATTCAAATATGTATCGCGTGTCAGTTAGGGTGTGGAAAGTCCCCAGGC<br>TCAATAATATTGAAAAGAAGAGCTCCAGGAAGATGAACCAGCTGTGGAATGTGTGTCAGTTAGGGTGTGGAAAGTCCCCAGGC<br>TCCCAGCAGAAGTATGCAAAGCATCGCATCTCAATTAGTCAGCAACCAGGTGTGGAAAGTCCCCAGCCTCCCCAGCAGGACAGA<br>AGTATGCAAAGCATGCATCTCAATTAGTCAGCAACCATAGGTCCCCGCCCATTCTCCGCCCATCCCGCCCTAACTCCGCCCATCCCGCCCAGTTCC<br>GCCCATTCTCCGCCCCATCATGGCTGACTAATTTTTTATTTTATGCAGAGGCCGGAGGCGCTTGCAATGCAGAAGATAG<br>GGAGAGGAGCTTTTTGGAGGCCTAGGCTTTTGCAAAGATCGATCAGAACATACAGGATGGAGCATCGTTTGCATGATTGAACAAGATGG<br>ATTGCACGCAGGTTCTCCGGCCGCTTGGGTGGAGAGGCTATTCGGCTATGACTGGGCACAACAGACAATCGGCTGCTCTGATGCCGC<br>CGTGTTCCGGCTGTCAGCGCAGGGGCGCCCGGTTCTTTTTGTCAAGACCGACCTGTCCGGTGCCCTGAATGAACTGCAAGACGAGGC<br>AGCGCGGCTATCGTGGCTGGCCACGACGGGCGTTCCTTGCGCAGCTGTGCTCGACGTTGTCACTGAAGCGGGAAGGGACTGGCTGCT<br>ATTGGGCGAAGTGCCGGGGCAGGATCTCCTGTCATCTCACCTGCTCCGTCGAGAAGTAGTCATGGCTGATGCAATGCGGCGG<br>CTGCATACGCTTGATCCGGCTACCTGCCCATTCGACCACCAAGCGAAACATCGCATCGAGCGAGCACGTACTCGGATGGAAGCCGG<br>TCTTGTCGATCAGGATGGATCTGGACGAAGAGCATCAGGGGCTCGCGCCAGCCGAACTGTTCGCCAGGCTCAAGGCGAGCATGCCCGA<br>CGGCGAGGATCTCGTCGTGACCCATGGCGATGCCTGCTTGCCGAATATCATGGTGGAAAATGGCCGCTTTTCTGGATTCATCGACTG<br>TGGCCGGCTGGGTGTGGCGGACCGCTATCAGGACATAGCGTTGGCTACCCGTGATATTGCTGAAGAGCTTGGCGGCGAATGGGCTGA<br>CCGCTTCCTCGTGCTTTACGGTATCGCCGCTCCCGATTCGCAGCGCATCGCCTTCTATCGCCTTCTTGACGAGTTCTTCTGAGCGGGA<br>CTCTGGGGTTCGAAATGACCGACCAAGCGACGCCCAACCTGCCATCACGAGATTTCGATTCCACCGCCGCCTTCTATGAAAGGTTG<br>GGCTTCGGAATCGTTTTCCGGGACGCCGGCTGGATGATCCTCCAGCGCGGGGATCTCATGCTGGAGTTCTTCGCCCACCCCAACTTGTT<br>TATTGCAGCTTATAATGGTTACAAATAAAGCAATAGCATCACAAATTTCACAAATAAAGCATTTTTTTCACTGCATTCTAGTT<br>GTGGTTTGTCCAAACTCATCAATGTATCTTATCATGTCTGGATCAACTGGATAACCGGTATCGCCGCCCATGGGGTT<br>AGGCTGGCCGTAAAGCGGGTTCGAATAATGACCGGTTCGCCCACGGTGGACGACCCGCTGCAACTCGCCGGTT<br>CGCGGTTTCTTCCTTTCGCGCTTCCCCAAGTTCGGGTGAAGGCCCAACGCTGCGGGGCGGCCCTGCC |  |

TABLE 5-continued

| Nucleotide Sequence (5'-3') | ORFs |
|---|---|
| ATAGCCTCAGGTTACTCATATATACTTTAGATTGATTTAAAACTTCATTTTTAATTTAAAAGGATCTAGGTGAAGATCCTTTTGAT AATCTCATGACCAAAATCCCTTAACGTGAGTTTCGTTCCACTGAGCGTCAGACCCCGTAGAAAAGATCAAAGGATCTTCTTGAGAT CCTTTTTTTCTGCGCGTAATCTGCTGCTTGCAAACAAAAAAACCACCGCTACCAGCGGTGGTTTGTTTGCCGGATCAAGAGCTACCA ACTCTTTTTCCGAAGGTAACTGGCTTCAGCAGAGCGCAGATACCAAATACTGTCCTTCTAGTGTAGCCGTAGTTAGGCCACCACTTC AAGAACTCTGTAGCACCGCCTACATACCTCGCTCTGCTAATCCTGTTACCAGTGGCTGCTGCCAGTGGCGATAAGTCGTGTCTTACC GGGTTGGACTCAAGACGATAGTTACCGGATAAGGCGCAGCGGTCGGGCTGAACGGGGGGTTCGTGCACACAGCCCAGCTTGGAGCGA ACGACCTACACCGAACTGAGATACCTACAGCGTGAGCTATGAGAAAGCGCCACGCTTCCCGAAGGGAGAAAGGCGGACAGGTATCCG GTAAGCGGCAGGGTCGGAACAGGAGAGCGCACGAGGGAGCTTCCAGGGGGAAACGCCTGGTATCTTTATAGTCCTGTCGGGTTTCGC CACCTGACTTGAGCGTCGATTTTTGTGATGCTCGTCAGGGGGGCGGAGCCTATGGAAAAACGCCAGCAACGCGGCCTTTTTACGG TTCCTGGCCTTTTGCTGGCCTTTTGCTCACATGTTCTTTCCTGCGTTATCCCCTGATTCTGTGGATAACCGTATTACCGCCATGCAT SEQ ID NO.: 83
ATGGAAAAGTCCATCTGGCTCCTGGCCTGTGGGTTCTCCGACAGGTCATTTGTGAGAACTAAATAGATACTACGAG AACTTCTCAACACAGAGTGCACAGTTCCCCAGCCAGCCAGCTCCCGAGGTGTCATGCAGGTGCCGTCAGGTGACGCGAGGCAGGCGAC GCGCAGTGCCTGCCCTGCCACCTTCACGCACCACCCGGACACTGGAGCCTCGACGGCCATCTGGCGGCGCAGGCCCTAT GCGGGCCCAGGTCCCCAGGTGTCCGGCTGGCTCTCCAGACGCGGACGACGAGCTCTGGCCGCTGAGCCTGCACGGCCGCTTCCGGCTG CTGGGCAACCGTCTCGCTGCCGCGTCGAGCGCCGCTACTTCTGCCGTGAGG TTCGCCGGGCGACGTCGGCTCCATGACAAGCCGCCGCTCCGCCTCTCCGGAGAGCCCGCCGCTCGTCACATCTCG GTGCTGCCCAGTCCGGCTCACGCTTGGGAAGCCGTCTGCAGGGAGCCCCCGCTCCCGGGAGAGCCTGCGCGTAGGACGCACCTAGTGAGGTCACGGCCAACAGCTGCAGCCCGTGTCCCCGGATGCCCCGGATGAC GGCCCTACACGTGTACGGCGCCCAACAGCCTGGCGCCTCCCGAGGCGTCCTGGCCTGTTCCGCTTCTCCATGGCCGTCAGCGAGGGCC TCGACGGTCGCGCCTCTCGTCGGCCTTCAAGGCGCTCCTCGGCTTCCAATTATGAAAATTGAGCCCAGATGAACCCCCGAGACCCCACCCAG CCAGAGCATCTGGACACCCCGGACACCCCGGAAACCTGAAAATTTGAGGCCCAGATGAACCCAGCAGATGAACCCCGAGGCCCAG CCACCATGTGCTCACCGTGA SEQ ID NO.: 84
ATGCCGGCGGCTGCTGCCTGTGGGCCTCCCCGCTTTGTTGCTACCCCGAGTCTTGCTGACCATGGCCTTGAAGCCTCCGACCCAG CCCTCGCCGGCCGGATTCCGGCTCGGCCCTCGGCTACGTTCCGGGTCTCGTCTCCAGCCTTTGTTACTTGCCCAACGAGAGGGTCCGC AAGGAGAGATCCGCAGGGCCGTGGTGGAGAAGCGCCTAGCAGCCTGCGCTCAACCTCAGATTACATCCATCTATGAGTGAAA GGGGAAGATCGAGGAAGACAGTGAGGTGCTGATGATGATAAAACCCAAAGTTCTTGGTCCCAGCTTTGACAGATTTGTTCGTTCT GTGCACCCCTTACGAAGTGGCCGAAGTGGCCGAAGTCCTGTGAACAGGGGAACTTCCGTCAGTGGGTGCGCCAGGTCACA GAGTCAGTTTCTGACTCTATCACAGTCCTGCCATGA SEQ ID NO.: 85:
CATGTGCCACCTGCCAGGTTTGCTCTCATATNTATACTTTGCTGTGCTGCACCCATTAACTCCGCTCATTAGCATTAGTA TATTCTTAATGCTATCCCCTCCCCCCACCCACAACAGTCCCGCTGTGTGATGTCCCCAAATTTTTTTTCTCAT CANCATTATCNCTAAACAACATTGAATGAACAACATTGAAGAGATCGAACAAAAAAATAAAAAATACAAAATAAACA TTTTAAAAATACAGTGTAAACAACTATTTACATAGAATTTTACAGTCTATTAGGTATTGNANGTAATCTAGAGTTGATTTAAAGGAGGG GNGTCCAAACTTTTTGCTTCCCTGGGCCACACTGAAANAANAATTGTCTTGGGCTACCCATAAATAATACACTAACAATAGCTGATAACGA SEQ ID NO.: 86
GCTGATTACAGAGTTTCCTCCCTTATAAATATTCAATAACGTCCATTTCAATGTCAAATGTCTATAACAGCAACAAACTACAAAGAAACTACAAAGAAGGAAGAAGTATGGTCTACTCACAGA |

REFERENCES

Patents

U.S. Pat. No. 5,712,127 Malek et al., Jan. 27, 1998
U.S. Pat. No. 6,498,024, Malek et al., Dec. 24, 2002
U.S. patent application Ser. No. 11/000,958 field on Dec. 2, 2003 published under No. US 2005/0153333A1 on Jul. 14, 2005 and entitled "Selective Terminal Tagging of Nucleic Acids"
U.S. Pat. No. 6,617,434 Duffy, Sep. 9, 2003
U.S. Pat. No. 6,451,555 Duffy, Sep. 17, 2002

Other References

1. Frost H. M., 1964 Dynamics of Bone Remodeling. In: Bone Biodynamics, Little and Brown, Boston, Mass., USA pp. 315;
2. Baron, R., Anatomy and Biology of Bone Matrix and Cellular Elements, In: Primer on the Metabolic Bone Diseases and Disorders of Mineral Metabolism, Fifth Edition 2003, American Society for Bone and Mineral Research, Washington D.C., pp. 1-8;
3. Jilka, R. L. et al., "Increased Osteoclast Development After Estrogen Loss: Mediation by Interleukin-6", Science 257: 88-91 (1992).
4. Poli, V. et al., "Interleukin-6 deficient mice are protected from bone loss caused by estrogen depletion", EMBO J 13: 1189-1196 (1994).
5. Srivastava, S. et al., "Estrogen Blocks M-CSF Gene Expression and Osteoclast Formation by Regulating Phosphorylation of Egr-1 and Its Interaction with Sp-1", J Clin Invest 102: 1850-1859 (1998).
6. de Vernejoul, M. C., "Dynamics of Bone Remodeling: Biochemical and Pathophysiological Basis", Eur J Clin Chem Clin Biochem 34: 729-734 (1996).
7. Netzel-Arnett, S., J. D. Hooper, et al. (2003). "Membrane anchored serine proteases: a rapidly expanding group of cell surface proteolytic enzymes with potential roles in cancer." Cancer Metastasis Rev 22(2-3): 237-58.
8. Shan, J., L. Yuan, et al. (2002). "TSP50, a possible protease in human testes, is activated in breast cancer epithelial cells." CancerRes 62(1): 290-4.
9. Yuan, L., J. Shan, et al. (1999). "Isolation of a novel gene, TSP50, by a hypomethylated DNA fragment in human breast cancer." Cancer Res 59(13): 3215-21.
10. Nishi, T. and M. Forgac (2002). "The vacuolar (H+)-ATPases—nature's most versatile proton pumps." Nat Rev Mol Cell Biol 3(2): 94-103.
11. Nishi, T., S. Kawasaki-Nishi, et al. (2003). "Expression and function of the mouse V-ATPase d subunit isoforms." J Biol Chem 278(47): 46396-402.
12. Morello, R., L. Tonachini, et al. (1999). "cDNA cloning, characterization and chromosome mapping of Crtap encoding the mouse cartilage associated protein." Matrix Biol 18(3): 319-24.
13. Tonachini, L., R. Morello, et al. (1999). "cDNA cloning, characterization and chromosome mapping of the gene encoding human cartilage associated protein (CRTAP)." Cytogenet Cell Genet 87(3-4): 191-4.
14. Kawai, J., A. Shinagawa, et al. (2001). "Functional annotation of a full-length mouse cDNA collection." Nature 409(6821): 685-90.
15. Strausberg, R. L., E. A. Feingold, et al. (2002). "Generation and initial analysis of more than 15,000 full-length human and mouse cDNA sequences." Proc Natl Acad Sci USA 99(26): 16899-903.
16. Janssen, E., M. Zhu, et al. (2003). "LAB: a new membrane-associated adaptor molecule in B cell activation." Nat Immunol 4(2): 117-23.
17. Kawaida, R., T. Ohtsuka, et al. (2003). "Jun dimerization protein 2 (JDP2), a member of the AP-1 family of transcription factor, mediates osteoclast differentiation induced by RANKL." J Exp Med 197(8): 1029-35.
18. Agrawal, N., P. V. Dasaradhi, et al. (2003). "RNA interference: biology, mechanism, and applications." Microbiol Mol Biol Rev 67(4): 657-85.
19. Hannon, G. J. (2002). "RNA interference." Nature 418 (6894): 244-51.
20. Brummelkamp, T. R., R. Bernards, et al. (2002). "A system for stable expression of short interfering RNAs in mammalian cells." Science 296(5567): 550-3.
21. Elbashir, et al. (2001). "Duplexes of 21-nucleotide RNAs mediate RNA interference in cultured mammalian cells." Nature 411(6836): 494-8.
22. Lee, J. S., Z. Hmama, et al. (2004). "Stable gene silencing in human monocytic cell lines using lentiviral-delivered small interference RNA. Silencing of the p110alpha isoform of phosphoinositide 3-kinase reveals differential regulation of adherence induced by 1alpha,25-dhydroxycholecalciferol and bacterial lipopolysaccharide." J Biol Chem 279(10): 9379-88.
23. Rubinson, D. A., C. P. Dillon, et al. (2003). "A lentivirus-based system to functionally silence genes in primary mammalian cells, stem cells and transgenic mice by RNA interference." Nat Genet 33(3): 401-6.
24. Boyle, W. J., W. S. Simonet, et al. (2003). "Osteoclast differentiation and activation." Nature 423(6937): 337-42.
25. Gee et al. In: Huber and Carr (1994) Molecular and Immunologic Approaches, Futura Publishing Co., Mt. Kisco N.Y., pp. 163-177.
26. Smith, A. N., F. Jouret, et al. (2005). "Vacuolar H+-ATPase d2 subunit: molecular characterization, developmental regulation, and localization to specialized proton pumps in kidney and bone." J Am Soc Nephrol 16(5): 1245-56
27. Smith, A. N., J. Skaug, et al. (2000). "Mutations in ATP6N1B, encoding a new kidney vacuolar proton pump 116-kD subunit, cause recessive distal renal tubular acidosis with preserved hearing." Nat Genet 26(1): 71-5.
28. Stehberger, P. A., N. Schulz, et al. (2003). "Localization and regulation of the ATP6V0A4 (a4) vacuolar H+-ATPase subunit defective in an inherited form of distal renal tubular acidosis." J Am Soc Nephrol 14(12): 3027-38.
29. Malkin I, Dahm S, Suk A, Kobyliansky E, Toliat M, Ruf N. Livshits G, Nurnberg P. Association of ANKH gene polymorphisms with radiographic hand bone size and geometry in a Chuvasha population. Bone. 2005 February; 36(2):365-73.
30. McMahon C, Will A, Hu P, Shah G N, Sly W S, Smith O P. Bone marrow transplantation corrects osteopetrosis in the carbonic anhydrase II deficiency syndrome. Blood. 2001 Apr. 1; 97(7):1947-50.
31. Biskobing D M, Fan D. Acid pH increases carbonic anhydrase II and calcitonin receptor mRNA expression in mature osteoclasts. Calcif Tissue Int. 2000 August; 67(2): 178-83.
32. Brage M, Abrahamson M, Lindstrom V, Grubb A, Lerner U H. Different cysteine proteinases involved in bone resorption and osteoclast formation. Calcif Tissue Int. 2005 June; 76(6):439-47. Epub 2005 May 19.

What is claimed is:

1. An antibody or antigen binding fragment capable of specific binding to a polypeptide consisting of SEQ ID NO.:48 or SEQ ID NO.:82 wherein said antibody or antigen binding fragment inhibits osteoclast differentiation or bone resorption activity of osteoclasts.

2. The antibody or antigen binding fragment of claim 1, wherein said antibody or antigen binding fragment inhibits osteoclastogenesis.

3. The antibody or antigen binding fragment of claim 1, wherein the antibody is a polyclonal antibody, a monoclonal antibody, a chimeric antibody, a humanized antibody or a human antibody.

4. The antibody or antigen binding fragment of claim 1, wherein the antigen binding fragment is a FV, a Fab, a Fab' or a (Fab')$_2$.

5. A pharmaceutical composition comprising:
a. an antibody or antigen binding fragment capable of specific binding to a polypeptide consisting of SEQ ID NO.:48 or SEQ ID NO.:82 wherein said antibody or antigen binding fragment inhibits osteoclast differentiation or bone resorption activity of osteoclasts and;
b. a pharmaceutically acceptable carrier.

6. The pharmaceutical composition of claim 5, wherein the antibody or antigen binding fragment inhibits osteoclastogenesis.

7. The pharmaceutical composition of claim 5, wherein the antibody is a polyclonal antibody, a monoclonal antibody, a chimeric antibody, a humanized antibody or a human antibody.

8. The pharmaceutical composition of claim 5, wherein the antigen binding fragment is a FV, a Fab, a Fab' or a (Fab')$_2$.

9. The pharmaceutical composition of claim 5, further comprising a drug or an hormone.

10. The pharmaceutical composition of claim 9, wherein the drug is an antiresorptive drug or a drug increasing bone mineral density.

11. An antibody or antigen binding fragment capable of specific binding to a polypeptide consisting of SEQ ID NO.:48 or SEQ ID NO.:82, wherein said antibody or antigen binding fragment is characterized with its ability to inhibit osteoclast differentiation in an in vitro assay, said assay comprising the steps of:
contacting a cell expressing said polypeptide with an antibody or antigen binding fragment thereof capable of specific binding to said polypeptide,
measuring osteoclast differentiation, and
selecting an antibody or antigen binding fragment that inhibits osteoclast differentiation.

12. The antibody or antigen binding fragment of claim 11, wherein the contacting step is performed in the presence of an inducer of osteoclast differentiation.

13. The antibody or antigen binding fragment of claim 12, wherein the inducer is RANKL.

14. The antibody or antigen binding fragment of claim 11, wherein the antibody is a polyclonal antibody, a monoclonal antibody, a chimeric antibody, a humanized antibody or a human antibody.

15. The antibody or antigen binding fragment of claim 11, wherein the antigen binding fragment is a FV, a Fab, a Fab' or a (Fab')$_2$.

16. An antibody or antigen binding fragment which specifically binds to a polypeptide consisting of SEQ ID NO:48 or SEQ ID NO:82 and is produced by a process including a characterization step indicative of its ability to inhibit osteoclast differentiation activity or inhibit bone resorption.

17. The antibody or antigen binding fragment of claim 16, wherein the inhibition of osteoclast differentiation activity comprises inhibition of differentiation of osteoclast precursors into differentiated osteoclasts in an in vitro assay.

18. The antibody or antigen binding fragment of claim 16, wherein the antibody is a polyclonal antibody, a monoclonal antibody, a chimeric antibody, a humanized antibody or a human antibody.

19. The antibody or antigen binding fragment of claim 16, wherein the antigen binding fragment is a FV, a Fab, a Fab' or a (Fab')$_2$.

* * * * *